US007385034B2

(12) United States Patent
Edwards et al.

(10) Patent No.: US 7,385,034 B2
(45) Date of Patent: Jun. 10, 2008

(54) COMPLEMENTARY DNAS ENCODING PROTEINS WITH SIGNAL PEPTIDES

(75) Inventors: Jean-Baptiste Dumas Milne Edwards, Paris (FR); Lydie Bougueleret, Vanves (FR); Severin Jobert, Paris (FR)

(73) Assignee: Serono Genetics Institute S.A., Evry (FR)

( * ) Notice: Subject to any disclaimer, the term of this patent is extended or adjusted under 35 U.S.C. 154(b) by 796 days.

(21) Appl. No.: 10/315,664

(22) Filed: Dec. 9, 2002

(65) Prior Publication Data
US 2003/0203377 A1 Oct. 30, 2003

Related U.S. Application Data

(60) Division of application No. 09/599,360, filed on Jun. 21, 2000, now Pat. No. 6,548,633, which is a continuation-in-part of application No. 09/469,099, filed on Dec. 21, 1999, now abandoned.

(60) Provisional application No. 60/141,032, filed on Jun. 25, 1999, provisional application No. 60/113,686, filed on Dec. 22, 1998.

(51) Int. Cl.
*A61K 38/00* (2006.01)
*A61K 38/16* (2006.01)
(52) U.S. Cl. .......................................... 530/350; 514/2
(58) Field of Classification Search ................. 530/350; 514/2
See application file for complete search history.

(56) References Cited

U.S. PATENT DOCUMENTS

| 5,527,896 A | 6/1996 | Wigler et al. |
| 5,536,637 A | 7/1996 | Jacobs |
| 2004/0203106 A1* | 10/2004 | Tang et al. ................. 435/69.1 |

FOREIGN PATENT DOCUMENTS

| EP | 0 625 572 | | 11/1994 |
| EP | 0 625572 A1 | | 11/1994 |
| EP | 0 756 006 A2 | | 1/1997 |
| EP | 0786519 A2 | | 7/1997 |
| EP | 1 130 094 | | 9/2001 |
| EP | 1 396 543 | | 3/2004 |
| WO | WO 99/51727 A2 | | 10/1977 |
| WO | WO 90/14432 A1 | | 11/1990 |
| WO | WO 96/17925 A1 | | 6/1996 |
| WO | WO 96/33276 A1 | | 10/1996 |
| WO | WO 96/34981 A2 | | 11/1996 |
| WO | WO 96/34981 A3 | | 11/1996 |
| WO | WO 96/41624 A1 | | 12/1996 |
| WO | WO 97/04097 A2 | | 2/1997 |
| WO | WO 97/07198 A2 | | 2/1997 |
| WO | WO 97/07198 A3 | | 2/1997 |
| WO | WO 98/31818 A2 | | 7/1998 |
| WO | WO 98/31818 A3 | | 7/1998 |
| WO | WO 99/06439 A2 | | 7/1998 |
| WO | WO 99/06552 A2 | | 7/1998 |
| WO | WO 98/41624 A1 | | 9/1998 |
| WO | WO 98/45437 A2 | | 10/1998 |
| WO | WO 98/45437 A3 | | 10/1998 |
| WO | WO 99/06548 A2 | | 2/1999 |
| WO | WO 99/06549 A2 | | 2/1999 |
| WO | WO 99/06550 A2 | | 2/1999 |
| WO | WO 99/51727 A2 | | 10/1999 |
| WO | WO 99/51727 A3 | | 10/1999 |
| WO | WO 00/03013 A2 | | 1/2000 |
| WO | WO 00/55350 | | 9/2000 |

OTHER PUBLICATIONS

Attwood et al. Science 2000; 290:471-473.*
Skolnick et al. Trends in Biotech. 2000; 18(1):34-39.*
Bloomston, M. et al. "Identification of Molecular Markers Specific for Pancreatic Neuroendocrine Tumors by Genetic Profiling of Core Biopsies" *Annals of Surgical Oncology*, Apr. 2004, pp. 413-419, vol. 11, No. 4.
Qu X. et al. "Characterization and Tissue Expression of a Novel Human Gene *npdc1*" *Gene*, Feb. 7, 2001, pp. 37-44, vol. 264, No. 1.
UniProtKB/Swiss-Prot Accession No. Q9NQX5.
UniProtKB/Swiss-Prot Accession No. Q64322.
Tashiro, et al.; "Signal Sequeince Trap: A Cloning Strategy for Secreted Proteins and Type I Membrane Proteins"; Science, vol. 281, Jul. 30, 1993; pp. 600-603; XP000673204.
Yan, et al.; "Membrane-anchored aspartyl protease with Alzheimer's disease B-secretaseactivity"; Nature, vol. 402; Dec. 2, 1999; pp. 533-538.
Hussain, et al.; "Identificationof a Novel Aspartic Protease (Asp2) as B-Secretase"; Molecular and Cellular Neuroscience 14, 419-427 (1999).
Yokoyama-Kobayahsi et al.; "A signal sequence detection system using secreted protease activity as an indicator"; Gene, 163 (1995), 193-196; 1995 Elsevier Science B.V.; XP002053953.
Lockhart, et al.; "Expression monitoring by hybridization to high-density oligonucleotide arrays"; Bio/Technology, vol. 14; Dec. 14, 1996; pp. 1675-1680; XP002074420.
Von Heline, G.; "A new method for predicting signal sequence cleavage sites"; Nucleic Acids Research, vol. 14, No. 11; 1986; pp. 4663-4690; XP002053954.
Kato, et al.; "Construction of a human full-length cDNA bank"; Gene; vol. 150, 1994; pp. 243-250; XP002081364.
Carninci, et al.; "High-Efficiency Full-Length cDNA Cloning by Biothylated CAP Trapper"; Genomics; vol. 37, No. 3; Nov. 1, 1996; pp. 327-336; XP002081729.

(Continued)

*Primary Examiner*—Michael Borin
(74) *Attorney, Agent, or Firm*—Saliwanchik, Lloyd & Saliwanchik

(57) ABSTRACT

The sequences of cDNAs encoding secreted proteins are disclosed. The cDNAs can be used to express secreted proteins or fragments thereof or to obtain antibodies capable of specifically binding to the secreted proteins. The cDNAs may also be used in diagnostic, forensic, gene therapy, and chromosome mapping procedures. The cDNAs may also be used to design expression vectors and secretion vectors.

10 Claims, 9 Drawing Sheets

OTHER PUBLICATIONS

Sinha, et al.; "Purification and cloning of amyloid precursor protein B-secretase fromhuman brain"; Nature, vol. 402; Dec. 2, 1999; pp. 537-540.

Vassar, et al.; "B-Secretase Cleavage of Alzheimer's Amyloid Precursor Protein by the Transmembrane Aspartic Protease BACE"; Science, vol. 286, Oct. 22, 1999; pp. 735-741.

Lin, et al.; "Human aspartic protease memapsin 2 cleaves the B-Secretase site of B-Amyloid precursor protein"; PNAS Online, vol. 97, Issue 4, pp. 1456-1460; Feb. 15, 2000.

Abraham, E.; "Tissue factor inhibition and clinical trail results of tissue factor pathway inhibitor in sepsis"; Crit Care Med 2000, vol. 28; No. 9 (Suppl.); pp. S31-S33.

Wolfsberg, et al.; "Adam, a Novel Family of Membrane Proteins Containing A Disintegrin And Metalloprotease Domain: Multipotential Functions in Cell-Cell and Cell-Matrix Interactions"; The Rockefeller University Press; 0021-9525/95/10/275/4; The Journal of Cell Biology; vol. 131, No. 2; Oct. 1995; pp. 275-278.

Jacobs, et al.; "A genetic selection for isolating cDNAs encoding secreted proteins"; Gene, 198 (1997) 289-296; 1997 Elsevier Science B.V.; 0378-1119/97; XP002045919.

Shirozu, et al.; "Characterizationof Novel Secreted and Membrane Proteins Isolated by the Signal Sequence Trap Method"; Genomics; 37, 273-280 (1996); Article No. 0560; Academic Press, Inc.; 0888-7543/96; XP002054773.

Jacobs, K., et al.; "A novel method for isolating Eukaryotic cDNA clones encoding secreted proteins"; Journal of Cellular Biocshemistry—Supplement; vol. 21A, Mar. 10, 1995; p. 19; XP002027246.

Hillier, et al.; "Generation and Analysis of 280,000 Human Expressed Sequence Tags"; Genome Research; 6:807-828; 1996 Cold Spring Harbor Laboratory Press; 1054-9803/96.

Nomura, et al.; "Prediction of the Coding Sequences of Unidentified Human Genes. I. The Coding Sequences of 40 New Genes (KIAA0001-KIAA0040) Deducted by Analysis of Randomly Sampled cDNA Clones from Human Immature Myeloid Cell Line KG-1"; DNA Research, vol. 1, 27-35 (1994).

Accession No. Y08617; Hall, L, et al.; "Macaque MDC family of proteins: sequence analysis, tissue distribution and processing in the male reproductive tract"; XP002069695.

Adams, et al. (1995) "initial Assessment of Human Gene Diversity and Expression Patterns Based Upon 83 Million Nucleotides of cDNA Sequence," *Nature*, 377:3-17.

Caminci, et al. (1996). "High-Efficiency Full-Length cDNA Cloning by Biotinylated CAP Trapper" *Genomics*, 37:327-36.

Hillier, et al. (1996). "Generation and Analysis of 280,000 Human Expressed Sequence Tags," *Genome Res*, 6:807-28.

Jacobs, et al. (1995). "A Novel Method for Isolating Eukaryotic cDNA Clones Encoding Secreted Proteins," *J. Cell Biochem.*, 10:19.

Jacobs, et al. (1997). "A Genetic Selection for Isolating cDNAs Encoding Secreted Proteins," *Gene*, 198:289-296.

Kato, et al. (1994). "Construction of a Human Full-Length cDNA Bank," *Gene*, 150:243-50.

Nomura, et al. (1994). "Prediction of the Coding Sequences of Unidentified Human Genes. I. The Coding Sequences of 40 New Genes (KIAA0001-KIAA0040) Deduced by Analysis of Randomly Sampled cDNA Clones from Human Immature Myeloid Cell Line KG-1," *DNA Res*, 1:27-35.

Shirozu, et al. (1996). "Characterization of Novel Secreted and Membrane Proteins Isolated by the Signal Sequence Trap Method," *Genomics*, 37:273-280.

Von Heijne (1986). "A New Method for Predicting Signal Sequence Cleavage Sites," *Nucleic Acids Res*, 14:46383-90.

Wells, et al., "The chemokine information source: identification and characterization of novel chemokines using the World Wide Web and Expressed Sequence Tag Databases", J. Leukocyte Biol. (1997), 61:5(545-550).

Gerhold, et al., "Its the genes! EST access to human genome content", BioEssays (1996), 18(12):973-981.

Russell, et al., "Structural Features can be Unconserved in Proteins with Similar Folds," J. Mol. Biol. (1994), 244:332-350.

\* cited by examiner

| Step | Search characteristic | | | Selection Characteristics | | |
|---|---|---|---|---|---|---|
| | Program | Strand | Parameters | Identity (%) | Length (bp) | Comments |
| miscellanaeous | FASTA | both | - | 90 | 15 | |
| tRNA | FASTA | both | - | | 60 | |
| rRNA | BLASTN | both | S=108 | 80 | 40 | |
| mtRNA | BLASTN | both | S=108 | 80 | 40 | |
| Procaryotic | BLASTN | both | S=144 | 90 | 40 | |
| Fungal | BLASTN | both | S=144 | 90 | 40 | |
| Alu | BLASTN | both | S=72, B=5 | 70 | 40 | max 5 matches, masking |
| L1 | BLASTN | both | S=72, B=5 | 70 | 40 | max 5 matches, masking |
| Repeats | BLASTN | both | S=72 | 70 | 40 | masking |
| PolyA | BLAST2N | top | W=6, S=10, E=1000, N=-12 | 90 | 10 | in the last 100 nucleotides |
| Polyadenylation signal | - | top | AATAAA allowing 1 mismatch | | | in the 50 nucleotides preceding the 5' end of the polA |
| Vertebrate | BLASTN then FASTA | both | | 90 then 70 | 30 | first BLASTN and then FASTA on maching sequences |
| ESTs | BLAST2N | both | | 90 | 30 | |
| Geneseq | BLASTN | both | W=8, B=10 | 90 | 30 | |
| ORF | BLASTP | top | W=8, B=10 | - | - | on ORF proteins, max 10 matches |
| Proteins | BLASTX | top | E = 0.001 | 70 | 30 | |

Parameters Used For Each Step of cDNA Analysis

Figure 1

| Minimum signal peptide score | false positive rate | false negative rate | proba(0.1) | proba(0.2) |
|---|---|---|---|---|
| 3.5 | 0.121 | 0.036 | 0.467 | 0.664 |
| 4 | 0.096 | 0.06 | 0.519 | 0.708 |
| 4.5 | 0.078 | 0.079 | 0.565 | 0.745 |
| 5 | 0.062 | 0.098 | 0.615 | 0.782 |
| 5.5 | 0.05 | 0.127 | 0.659 | 0.813 |
| 6 | 0.04 | 0.163 | 0.694 | 0.836 |
| 6.5 | 0.033 | 0.202 | 0.725 | 0.855 |
| 7 | 0.025 | 0.248 | 0.763 | 0.878 |
| 7.5 | 0.021 | 0.304 | 0.78 | 0.889 |
| 8 | 0.015 | 0.368 | 0.816 | 0.909 |
| 8.5 | 0.012 | 0.418 | 0.836 | 0.92 |
| 9 | 0.009 | 0.512 | 0.856 | 0.93 |
| 9.5 | 0.007 | 0.581 | 0.863 | 0.934 |
| 10 | 0.006 | 0.679 | 0.835 | 0.919 |

Figure 2

| Description of Transcription Factor Binding Sites Present on Promoters Isolated From SignalTag Sequences ||||| 
|---|---|---|---|---|
| Promoter sequence P13H2 (546 bp): |||||
| Matrix | Position on SEQ ID NO:17 | Orientation | Score | Length |
| CMYB_01 | 17 to 25 | + | 0.983 | 9 |
| MYOD_Q6 | 18 to 27 | - | 0.961 | 10 |
| S8_01 | 75 to 85 | - | 0.960 | 11 |
| S8_01 | 94 to 104 | + | 0.966 | 11 |
| DELTAEF1_01 | 129 to 139 | - | 0.960 | 11 |
| GATA_C | 155 to 165 | - | 0.964 | 11 |
| CMYB_01 | 170 to 178 | + | 0.958 | 9 |
| GATA1_02 | 176 to 189 | + | 0.959 | 14 |
| GATA_C | 180 to 190 | + | 0.953 | 11 |
| TAL1ALPHAE47_01 | 284 to 299 | + | 0.973 | 16 |
| TAL1BETAE47_01 | 284 to 299 | + | 0.983 | 16 |
| TAL1BETAITF2_01 | 284 to 299 | + | 0.978 | 16 |
| MYOD_Q6 | 287 to 296 | - | 0.954 | 10 |
| GATA1_04 | 302 to 314 | - | 0.953 | 13 |
| IK1_01 | 393 to 405 | + | 0.963 | 13 |
| IK2_01 | 393 to 404 | + | 0.985 | 12 |
| CREL_01 | 396 to 405 | + | 0.962 | 10 |
| GATA1_02 | 423 to 436 | + | 0.950 | 14 |
| SRY_02 | 478 to 489 | - | 0.951 | 12 |
| E2F_02 | 486 to 493 | + | 0.957 | 8 |
| MZF1_01 | 514 to 521 | - | 0.975 | 8 |
| Promoter sequence P15B4 (861bp) : |||||
| Matrix | Position on SEQ ID NO:20 | Orientation | Score | Length |
| NFY_Q6 | 60 to 70 | - | 0.956 | 11 |
| MZF1_01 | 70 to 77 | + | 0.962 | 8 |
| CMYB_01 | 124 to 132 | + | 0.994 | 9 |
| VMYB_02 | 126 to 134 | - | 0.985 | 9 |
| STAT_01 | 135 to 143 | + | 0.968 | 9 |
| STAT_01 | 135 to 143 | - | 0.951 | 9 |
| MZF1_01 | 252 to 259 | - | 0.956 | 8 |
| IK2_01 | 357 to 368 | + | 0.965 | 12 |
| MZF1_01 | 384 to 391 | + | 0.986 | 8 |
| SRY_02 | 410 to 421 | - | 0.955 | 12 |
| MZF1_01 | 592 to 599 | + | 0.960 | 8 |
| MYOD_Q6 | 618 to 627 | + | 0.981 | 10 |
| DELTAEF1_01 | 632 to 642 | + | 0.958 | 11 |
| S8_01 | 813 to 823 | - | 0.992 | 11 |
| MZF1_01 | 824 to 831 | - | 0.986 | 8 |
| Promoter sequence P29B6 (555 bp) : |||||
| Matrix | Position on SEQ ID NO:23 | Orientation | Score | Length |
| ARNT_01 | 191 to 206 | + | 0.964 | 16 |
| NMYC_01 | 193 to 204 | + | 0.965 | 12 |
| USF_01 | 193 to 204 | + | 0.985 | 12 |
| USF_01 | 193 to 204 | - | 0.985 | 12 |
| NMYC_01 | 193 to 204 | - | 0.956 | 12 |
| MYCMAX_02 | 193 to 204 | - | 0.972 | 12 |
| USF_C | 195 to 202 | + | 0.997 | 8 |
| USF_C | 195 to 202 | - | 0.991 | 8 |
| MZF1_01 | 210 to 217 | - | 0.968 | 8 |
| ELK1_02 | 397 to 410 | + | 0.963 | 14 |
| CETS1P54_01 | 400 to 409 | + | 0.974 | 10 |
| AP1_Q4 | 460 to 470 | - | 0.963 | 11 |
| AP1FJ_Q2 | 460 to 470 | - | 0.961 | 11 |
| PADS_C | 547 to 555 | + | 1.000 | 9 |

Figure 5

COMPLEMENTARY DNAS ENCODING PROTEINS WITH SIGNAL PEPTIDES

RELATED APPLICATION

This application is a divisional of U.S. application Ser. No. 09/599,360, filed Jun. 21, 2000 now U.S. Pat. No. 6,548,633, which is a continuation-in-part of U.S. application Ser. No. 09/469,099 filed Dec. 21, 1999 now abandoned, and claims priority from U.S. Provisional Patent Application Ser. No. 60/113,686, filed Dec. 22, 1998, and U.S. Provisional Patent Application Ser. No. 60/141,032, filed Jun. 25, 1999, the disclosures of which are incorporated herein by reference in their entireties (including all references, figures, sequences, and formulae).

BACKGROUND OF THE INVENTION

The disclosures of all references cited throughout this application are incorporated herein in their entireties.

The estimated 50,000-100,000 genes scattered along the human chromosomes offer tremendous promise for the understanding, diagnosis, and treatment of human diseases. In addition, probes capable of specifically hybridizing to loci distributed throughout the human genome find applications in the construction of high resolution chromosome maps and in the identification of individuals.

In the past, the characterization of even a single human gene was a painstaking process, requiring years of effort. Recent developments in the areas of cloning vectors, DNA sequencing, and computer technology have merged to greatly accelerate the rate at which human genes can be isolated, sequenced, mapped, and characterized.

Currently, two different approaches are being pursued for identifying and characterizing the genes distributed along the human genome. In one approach, large fragments of genomic DNA are isolated, cloned, and sequenced. Potential open reading frames in these genomic sequences are identified using bio-informatics software. However, this approach entails sequencing large stretches of human DNA which do not encode proteins in order to find the protein encoding sequences scattered throughout the genome. In addition to requiring extensive sequencing, the bio-informatics software may mischaracterize the genomic sequences obtained, i.e., labeling non-coding DNA as coding DNA and vice versa.

An alternative approach takes a more direct route to identifying and characterizing human genes. In this approach, complementary DNAs (cDNAs) are synthesized from isolated messenger RNAs (mRNAs) which encode human proteins. Using this approach, sequencing is only performed on DNA which is derived from protein coding fragments of the genome. Often, only short stretches of the cDNAs are sequenced to obtain sequences called expressed sequence tags (ESTs). The ESTs may then be used to isolate or purify cDNAs which include sequences adjacent to the EST sequences. The cDNAs may contain all of the sequence of the EST which was used to obtain them or only a fragment of the sequence of the EST which was used to obtain them. In addition, the cDNAs may contain the full coding sequence of the gene from which the EST was derived or, alternatively, the cDNAs may include fragments of the coding sequence of the gene from which the EST was derived. It will be appreciated that there may be several cDNAs which include the EST sequence as a result of alternate splicing or the activity of alternative promoters.

In the past, these short EST sequences were often obtained from oligo-dT primed cDNA libraries. Accordingly, they mainly corresponded to the 3' untranslated region of the mRNA. In part, the prevalence of EST sequences derived from the 3' end of the mRNA is a result of the fact that typical techniques for obtaining cDNAs, are not well suited for isolating cDNA sequences derived from the 5' ends of mRNAs (Adams et al., *Nature* 377:3-174, 1996, Hillier et al., *Genome Res.* 6:807-828, 1996). In addition, in those reported instances where longer cDNA sequences have been obtained, the reported sequences typically correspond to coding sequences and do not include the full 5' untranslated region (5'UTR) of the mRNA from which the cDNA is derived. Indeed, 5'UTRs have been shown to affect either the stability or translation of mRNAs. Thus, regulation of gene expression may be achieved through the use of alternative 5'UTRs as shown, for instance, for the translation of the tissue inhibitor of metalloprotease mRNA in mitogenically activated cells (Waterhouse et al., *J Biol Chem.* 265:5585-9. 1990). Furthermore, modification of 5'UTR through mutation, insertion or translocation events may even be implied in pathogenesis. For instance, the fragile X syndrome, the most common cause of inherited mental retardation, is partly due to an insertion of multiple CGG trinucleotides in the 5'UTR of the fragile X mRNA resulting in the inhibition of protein synthesis via ribosome stalling (Feng et al., *Science* 268:731-4, 1995). An aberrant mutation in regions of the 5'UTR known to inhibit translation of the proto-oncogene c-myc was shown to result in upregulation of c-myc protein levels in cells derived from patients with multiple myelomas (Willis et al., *Curr Top Microbiol Immunol* 224:269-76, 1997). In addition, the use of oligo-dT primed cDNA libraries does not allow the isolation of complete 5'UTRs since such incomplete sequences obtained by this process may not include the first exon of the mRNA, particularly in situations where the first exon is short. Furthermore, they may not include some exons, often short ones, which are located upstream of splicing sites. Thus, there is a need to obtain sequences derived from the 5' ends of mRNAs.

Moreover, despite the great amount of EST data that large-scale sequencing projects have yielded (Adams et al., *Nature* 377:174, 1996, Hillier et al., *Genome Res.* 6:807-828, 1996), information concerning the biological function of the mRNAs corresponding to such obtained cDNAs has revealed to be limited. Indeed, whereas the knowledge of the complete coding sequence is absolutely necessary to investigate the biological function of mRNAs, ESTs yield only partial coding sequences. So far, large-scale full-length cDNA cloning has been achieved only with limited success because of the poor efficiency of methods for constructing full-length cDNA libraries. Indeed, such methods require either a large amount of mRNA (Ederly et al., 1995), thus resulting in non representative full-length libraries when small amounts of tissue are available or require PCR amplification (Maruyama et al., 1994; CLONTECHniques, 1996) to obtain a reasonable number of clones, thus yielding strongly biased cDNA libraries where rare and long cDNAs are lost. Thus, there is a need to obtain full-length cDNAs, i.e. cDNAs containing the full coding sequence of their corresponding mRNAs.

While many sequences derived from human chromosomes have practical applications, approaches based on the identification and characterization of those chromosomal sequences which encode a protein product are particularly relevant to diagnostic and therapeutic uses. Of the 50,000-100,000 protein coding genes, those genes encoding proteins which are secreted from the cell in which they are synthesized, as well as the secreted proteins themselves, are particularly valuable as potential therapeutic agents. Such proteins are often involved in cell to cell communication and may be responsible for producing a clinically relevant response in their target cells. In fact, several secretory proteins, including tissue plasminogen activator, G-CSF, GM-CSF, erythropoietin, human growth hormone, insulin, interferon-α, interferon-β, interferon-γ, and interleukin-2, are currently in clinical use. These proteins are used to treat a wide range of conditions, including acute myocardial infarction, acute ischemic stroke, anemia, diabetes, growth hormone deficiency, hepatitis, kidney carcinoma, chemotherapy induced neutropenia and multiple sclerosis. For these reasons, cDNAs encoding secreted proteins or fragments thereof represent a particularly valuable source of therapeutic agents. Thus, there is a need for the identification and characterization of secreted proteins and the nucleic acids encoding them.

In addition to being therapeutically useful themselves, secretory proteins include short peptides, called signal peptides, at their amino termini which direct their secretion. These signal peptides are encoded by the signal sequences located at the 5' ends of the coding sequences of genes encoding secreted proteins. Because these signal peptides will direct the extracellular secretion of any protein to which they are operably linked, the signal sequences may be exploited to direct the efficient secretion of any protein by operably linking the signal sequences to a gene encoding the protein for which secretion is desired. In addition, fragments of the signal peptides called membrane-translocating sequences, may also be used to direct the intracellular import of a peptide or protein of interest. This may prove beneficial in gene therapy strategies in which it is desired to deliver a particular gene product to cells other than the cells in which it is produced. Signal sequences encoding signal peptides also find application in simplifying protein purification techniques. In such applications, the extracellular secretion of the desired protein greatly facilitates purification by reducing the number of undesired proteins from which the desired protein must be selected. Thus, there exists a need to identify and characterize the 5' fragments of the genes for secretory proteins which encode signal peptides.

Sequences coding for secreted proteins may also find application as therapeutics or diagnostics. In particular, such sequences may be used to determine whether an individual is likely to express a detectable phenotype, such as a disease, as a consequence of a mutation in the coding sequence for a secreted protein. In instances where the individual is at risk of suffering from a disease or other undesirable phenotype as a result of a mutation in such a coding sequence, the undesirable phenotype may be corrected by introducing a normal coding sequence using gene therapy. Alternatively, if the undesirable phenotype results from overexpression of the protein encoded by the coding sequence, expression of the protein may be reduced using antisense or triple helix based strategies.

The secreted human polypeptides encoded by the coding sequences may also be used as therapeutics by administering them directly to an individual having a condition, such as a disease, resulting from a mutation in the sequence encoding the polypeptide. In such an instance, the condition can be cured or ameliorated by administering the polypeptide to the individual.

In addition, the secreted human polypeptides or fragments thereof may be used to generate antibodies useful in determining the tissue type or species of origin of a biological sample. The antibodies may also be used to determine the cellular localization of the secreted human polypeptides or the cellular localization of polypeptides which have been fused to the human polypeptides. In addition, the antibodies may also be used in immunoaffinity chromatography techniques to isolate, purify, or enrich the human polypeptide or a target polypeptide which has been fused to the human polypeptide.

Public information on the number of human genes for which the promoters and upstream regulatory regions have been identified and characterized is quite limited. In part, this may be due to the difficulty of isolating such regulatory sequences. Upstream regulatory sequences such as transcription factor binding sites are typically too short to be utilized as probes for isolating promoters from human genomic libraries. Recently, some approaches have been developed to isolate human promoters. One of them consists of making a CpG island library (Cross et al., *Nature Genetics* 6: 236-244, 1994). The second consists of isolating human genomic DNA sequences containing SpeI binding sites by the use of SpeI binding protein. (Mortlock et al., *Genome Res.* 6:327-335, 1996). Both of these approaches have their limits due to a lack of specificity and of comprehensiveness. Thus, there exists a need to identify and systematically characterize the 5' fragments of the genes.

cDNAs including the 5' ends of their corresponding mRNA may be used to efficiently identify and isolate 5'UTRs and upstream regulatory regions which control the location, developmental stage, rate, and quantity of protein synthesis, as well as the stability of the mRNA (Theil et al., *BioFactors* 4:87-93, (1993). Once identified and characterized, these regulatory regions may be utilized in gene therapy or protein purification schemes to obtain the desired amount and locations of protein synthesis or to inhibit, reduce, or prevent the synthesis of undesirable gene products.

In addition, cDNAs containing the 5' ends of secretory protein genes may include sequences useful as probes for chromosome mapping and the identification of individuals. Thus, there is a need to identify and characterize the sequences upstream of the 5' coding sequences of genes encoding secretory proteins.

SUMMARY OF THE INVENTION

The present invention relates to purified, isolated, or recombinant cDNAs which encode secreted proteins or fragments thereof. Preferably, the purified, isolated or recombinant cDNAs contain the entire open reading frame of their corresponding mRNAs, including a start codon and a stop codon. For example, the cDNAs may include nucleic acids encoding the signal peptide as well as the mature protein. Such cDNAs will be referred herein as "full-length" cDNAs. Alternatively, the cDNAs may contain a fragment of the open reading frame. Such cDNAs will be referred herein as "ESTs" or "5'ESTs". In some embodiments, the fragment may encode only the sequence of the mature protein. Alternatively, the fragment may encode only a fragment of the mature protein. A further aspect of the present invention is a nucleic acid which encodes the signal peptide of a secreted protein.

The term "corresponding mRNA" refers to the mRNA which was the template for the cDNA synthesis which produced the cDNA of the present invention.

As used herein, the term "purified" does not require absolute purity; rather, it is intended as a relative definition. Purification of starting material or natural material is at least one order of magnitude, preferably two or three orders, and more preferably four or five orders of magnitude is expressly contemplated. As an example, purification from 0.1% concentration to 10% concentration is two orders of magnitude.

To illustrate, individual cDNA clones isolated from a cDNA library have been conventionally purified to electrophoretic homogeneity. The sequences obtained from these clones could not be obtained directly either from the library or from total human DNA. The cDNA clones are not naturally occurring as such, but rather are obtained via manipulation of a partially purified naturally occurring substance (messenger RNA). The conversion of mRNA into a cDNA library involves the creation of a synthetic substance (cDNA) and pure individual cDNA clones can be isolated from the synthetic library by clonal selection. Thus, creating a cDNA library from messenger RNA and subsequently isolating individual clones from that library results in an approximately $10^4$-$10^6$ fold purification of the native message.

The term "purified" is further used herein to describe a polypeptide or polynucleotide of the invention which has been separated from other compounds including, but not limited to, polypeptides or polynucleotides, carbohydrates, lipids, etc. The term "purified" may be used to specify the separation of monomeric polypeptides of the invention from oligomeric forms such as homo- or hetero-dimers, trimers, etc. The term "purified" may also be used to specify the separation of covalently closed polynucleotides from linear polynucleotides. A polynucleotide is substantially pure when at least about 50%, preferably 60 to 75% of a sample exhibits a single polynucleotide sequence and conformation (linear versus covalently close). A substantially pure polypeptide or polynucleotide typically comprises about 50%, preferably 60 to 90% weight/weight of a polypeptide or polynucleotide sample, respectively, more usually about 95%, and preferably is over about 99% pure. Polypeptide and polynucleotide purity, or homogeneity, is indicated by a number of means well known in the art, such as agarose or polyacrylamide gel electrophoresis of a sample, followed by visualizing a single band upon staining the gel. For certain purposes higher resolution can be provided by using HPLC or other means well known in the art. As an alternative embodiment, purification of the polypeptides and polynucleotides of the present invention may be expressed as "at least" a percent purity relative to heterologous polypeptides and polynucleotides (DNA, RNA or both). As a preferred embodiment, the polypeptides and polynucleotides of the present invention are at least; 10%, 20%, 30%, 40%, 50%, 60%, 70%, 80%, 90%, 95%, 96%, 96%, 98%, 99%, or 100% pure relative to heterologous polypeptides and polynucleotides, respectively. As a further preferred embodiment the polypeptides and polynucleotides have a purity ranging from any number, to the thousandth position, between 90% and 100% (e.g., a polypeptide or polynucleotide at least 99.995% pure) relative to either heterologous polypeptides or polynucleotides, respectively, or as a weight/weight ratio relative to all compounds and molecules other than those existing in the carrier. Each number representing a percent purity, to the thousandth position, may be claimed as individual species of purity.

As used herein, the term "recombinant polynucleotide" means that the cDNA is adjacent to "backbone" nucleic acid to which it is not adjacent in its natural environment. Additionally, to be "enriched" the cDNAs will represent 5% or more of the number of nucleic acid inserts in a population of nucleic acid backbone molecules. Backbone molecules according to the present invention include nucleic acids such as expression vectors, self-replicating nucleic acids, viruses, integrating nucleic acids, and other vectors or nucleic acids used to maintain or manipulate a nucleic acid insert of interest. Preferably, the enriched cDNAs represent 15% or more of the number of nucleic acid inserts in the population of recombinant backbone molecules. More preferably, the enriched cDNAs represent 50% or more of the number of nucleic acid inserts in the population of recombinant backbone molecules. In a highly preferred embodiment, the enriched cDNAs represent 90% or more (including any number between 90 and 100%, to the thousandth position, e.g., 99.5%) # of the number of nucleic acid inserts in the population of recombinant backbone molecules.

Unless otherwise specified, nucleotides and amino acids of polynucleotide and polypeptide fragments (respectively) of the present invention are contiguous and not interrupted by heterologous sequences.

The term "isolated" requires that the material be removed from its original environment (e. g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment. Specifically excluded from the definition of "isolated" are: naturally occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies, and/or further wherein the polynucleotide of the present invention makes up less than 5% (or alternatively 1%, 2%, 3%, 4%, 10%, 25%, 50%, 75%, or 90%, 95%, or 99%) of the number of nucleic acid inserts in the vector molecules. Further specifically excluded are whole cell genomic DNA or whole cell RNA preparations (including said whole cell preparations which are mechanically sheared or enzymaticly digested). Further specifically excluded are the above whole cell preparations as either an in vitro preparation or as a heterogeneous mixture separated by electrophoresis (including blot transfers of the same) wherein the polynucleotide of the invention have not been further separated from the heterologous polynucleotides in the electrophoresis medium (e.g., further separating by excising a single band from a heterogeneous band population in an agarose gel or nylon blot).

Thus, cDNAs encoding secreted polypeptides or fragments thereof which are present in cDNA libraries in which one or more cDNAs encoding secreted polypeptides or fragments thereof make up 5% or more of the number of nucleic acid inserts in the backbone molecules are "enriched recombinant cDNAs" as defined herein. Likewise, cDNAs encoding secreted polypeptides or fragments thereof which are in a population of plasmids in which one or more cDNAs of the present invention have been inserted such that they represent 5% or more of the number of inserts in the plasmid backbone are "enriched recombinant cDNAs" as defined herein. However, cDNAs encoding secreted polypeptides or fragments thereof which are in cDNA libraries in which the cDNAs encoding secreted polypeptides or fragments thereof constitute less than 5% of the number of nucleic acid inserts in the population of backbone molecules, such as libraries in which backbone molecules having a cDNA insert encoding a secreted polypeptide are extremely rare, are not "enriched recombinant cDNAs."

The term "polypeptide" refers to a polymer of amino acids without regard to the length of the polymer; thus, "peptides," "oligopeptides", and "proteins" are included within the definition of polypeptide and used interchangeably herein. This term also does not specify or exclude chemical or post-expression modifications of the polypeptides of the invention, although chemical or post-expression modifications of these polypeptides may be included or excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. The natural or other chemical modifications, such as those listed in examples above can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12, 1983; Seifter et al., Meth Enzymol 182:626-646, 1990; Rattan et al., Ann NY Acad Sci 663:48-62, 1992). Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring. The term "polypeptide" may also be used interchangeably with the term "protein".

As used interchangeably herein, the terms "nucleic acid molecule", "oligonucleotides", and "polynucleotides" include RNA or, DNA (either single or double stranded, coding, non-coding, complementary or antisense), or RNA/DNA hybrid sequences of more than one nucleotide in either single chain or duplex form (although each of the above species may be particularly specified). The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one modifications (a) an alternative linking group, (b) an analogous form of purine, (c) an analogous form of pyrimidine, or (d) an analogous sugar; for examples of analogous linking groups, purine, pyrimidines, and sugars see for example PCT publication No. WO 95/04064. Preferred modifications of the present invention include, but are not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v) ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and diaminopurine. Methylenemethylimino linked oligonucleosides as well as mixed backbone compounds having, may be prepared as described in U.S. Pat. Nos. 5,378,825; 5,386,023; 5,489,677; 5,602,240; and 5,610,289. Formacetal and thioformacetal linked oligonucleosides may be prepared as described in U.S. Pat. Nos. 5,264,562 and 5,264,564. Ethylene oxide linked oligonucleosides may be prepared as described in U.S. Pat. No. 5,223,618. Phosphinate oligonucleotides may be prepared as described in U.S. Pat. No. 5,508,270. Alkyl phosphonate oligonucleotides may be prepared as described in U.S. Pat. No. 4,469,863. 3'-Deoxy-3'-methylene phosphonate oligonucleotides may be prepared as described in U.S. Pat. Nos. 5,610,289 or 5,625,050. Phosphoramidite oligonucleotides may be prepared as described in U.S. Pat. No. 5,256,775 or U.S. Pat. No. 5,366,878. Alkylphosphonothioate oligonucleotides may be prepared as described in published PCT applications WO 94/17093 and WO 94/02499. 3'-Deoxy-3'-amino phosphoramidate oligonucleotides may be prepared as described in U.S. Pat. No. 5,476,925. Phosphotriester oligonucleotides may be prepared as described in U.S. Pat. No. 5,023,243. Borano phosphate oligonucleotides may be prepared as described in U.S. Pat. Nos. 5,130,302 and 5,177,198.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 10 kb, 7.5 kb, 5 kb, 2.5 kb, 2 kb, 1.5 kb, or 1 kb in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 75, 50, 25, 20, 15, 10, 5, 4, 3, 2, or 1 genomic flanking gene(s).

The polynucleotide sequences of the invention may be prepared by any known method, including synthetic, recombinant, ex vivo generation, or a combination thereof, as well as utilizing any purification methods known in the art.

The terms "comprising", "consisting of" and "consisting essentially of" may be interchanged or one another throughout the instant application". The term "having" has the same meaning as "comprising" and may be replaced with either the term "consisting of" or "consisting essentially of".

"Stringent", "moderate," and "low" hybridization conditions are as defined below.

A sequence which is "operably linked" to a regulatory sequence such as a promoter means that said regulatory element is in the correct location and orientation in relation to the nucleic acid to control RNA polymerase initiation and expression of the nucleic acid of interest. As used herein, the term "operably linked" refers to a linkage of polynucleotide elements in a functional relationship. For instance, a promoter or enhancer is operably linked to a coding sequence if it affects the transcription of the coding sequence.

The terms "base paired" and "Watson & Crick base paired" are used interchangeably herein to refer to nucleotides which can be hydrogen bonded to one another be virtue of their sequence identities in a manner like that found in double-helical DNA with thymine or uracil residues linked to adenine residues by two hydrogen bonds and cytosine and guanine residues linked by three hydrogen bonds (See Stryer, L., Biochemistry, $4^{th}$ edition, 1995).

The terms "complementary" or "complement thereof" are used herein to refer to the sequences of polynucleotides which are capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide," "complementary nucleic acid" and "complementary nucleotide sequence". These terms are applied to pairs of polynucleotides based solely upon their sequences and not any particular set of conditions under which the two polynucleotides would actually bind. Preferably, a "complementary" sequence is a sequence which an A at each position where there is a T on the opposite strand, a T at each position where there is an A on the opposite strand, a G at each position where there is a C on the opposite strand and a C at each position where there is a G on the opposite strand.

The term "allele" is used herein to refer to variants of a nucleotide sequence. A biallelic polymorphism has two forms. Diploid organisms may be homozygous or heterozygous for an allelic form. Unless otherwise specified, the polynucleotides of the present invention encompass all allelic variants of the disclosed polynucleotides.

The term "upstream" is used herein to refer to a location that is toward the 5' end of the polynucleotide from a specific reference point.

As used herein, the term "non-human animal" refers to any non-human vertebrate animal, including insects, birds, rodents and more usually mammals. Preferred non-human animals include: primates; farm animals such as swine, goats, sheep, donkeys, cattle, horses, chickens, rabbits; and rodents, more preferably rats or mice. As used herein, the term "animal" is used to refer to any species in the animal kingdom, preferably vertebrates, including birds and fish, and more preferable a mammal. Both the terms "animal" and "mammal" expressly embrace human subjects unless preceded with the term "non-human".

The terms "vertebrate nucleic acid" and "vertebrate polypeptide" are used herein to refer to any nucleic acid or polypeptide respectively which are derived from a vertebrate species including birds and more usually mammals, preferably primates such as humans, farm animals such as swine, goats, sheep, donkeys, and horses, rabbits or rodents, more preferably rats or mice. As used herein, the term "vertebrate" is used to refer to any vertebrate, preferably a mammal. The term "vertebrate" expressly embraces human subjects unless preceded with the term "non-human"

"Stringent", "moderate," and "low" hybridization conditions are as defined below.

The term "capable of hybridizing to the polyA tail of said mRNA" refers to and embraces all primers containing stretches of thymidine residues, so-called oligo(dT) primers, that hybridize to the 3' end of eukaryotic poly(A)+ mRNAs to prime the synthesis of a first cDNA strand. Techniques for generating said oligo(dT) primers and hybridizing them to mRNA to subsequently prime the reverse transcription of said hybridized mRNA to generate a first cDNA strand are well known to those skilled in the art and are described in *Current Protocols in Molecular Biology*, John Wiley and Sons, Inc. 1997 and Sambrook et al., *Molecular Cloning: A Laboratory Manual*, Second Edition, Cold Spring Harbor Laboratory Press, 1989, the entire disclosures of which are incorporated herein by reference. Preferably, said oligo(dT) primers are present in a large excess in order to allow the hybridization of all mRNA 3' ends to at least one oligo(dT) molecule. The priming and reverse transcription step are preferably performed between 37° C. and 55° C. depending on the type of reverse transcriptase used. Preferred oligo(dT) primers for priming reverse transcription of mRNAs are oligonucleotides containing a stretch of thymidine residues of sufficient length to hybridize specifically to the polyA tail of mRNAs, preferably of 12 to 18 thymidine residues in length. More preferably, such oligo(T) primers comprise an additional sequence upstream of the poly(dT) stretch in order to allow the addition of a given sequence to the 5' end of all first cDNA strands which may then be used to facilitate subsequent manipulation of the cDNA. Preferably, this added sequence is 8 to 60 residues in length. For instance, the addition of a restriction site in 5' of cDNAs facilitates subcloning of the obtained cDNA. Alternatively, such an added 5' end may also be used to design primers of PCR to specifically amplify cDNA clones of interest.

In particular, the present invention relates to cDNAs which were derived from genes encoding secreted proteins. As used herein, a "secreted" protein is one which, when expressed in a suitable host cell, is transported across or through a membrane, including transport as a result of signal peptides in its amino acid sequence. "Secreted" proteins include without limitation proteins secreted wholly (e.g. soluble proteins), or partially (e.g. receptors) from the cell in which they are expressed. "Secreted" proteins also include without limitation proteins which are transported across the membrane of the endoplasmic reticulum.

cDNAs encoding secreted proteins may include nucleic acid sequences, called signal sequences, which encode signal peptides which direct the extracellular secretion of the proteins encoded by the cDNAs. Generally, the signal peptides are located at the amino termini of secreted proteins. Polypeptides comprising these signal peptides (as delineated in the sequence listing), and polynucleotides encoding the same, are preferred embodiments of the present invention.

Secreted proteins are translated by ribosomes associated with the "rough" endoplasmic reticulum. Generally, secreted proteins are co-translationally transferred to the membrane of the endoplasmic reticulum. Association of the ribosome with the endoplasmic reticulum during translation of secreted proteins is mediated by the signal peptide. The signal peptide is typically cleaved following its co-translational entry into the endoplasmic reticulum. After delivery to the endoplasmic reticulum, secreted proteins may proceed through the Golgi apparatus. In the Golgi apparatus, the proteins may undergo post-translational modification before entering secretory vesicles which transport them across the cell membrane.

The cDNAs of the present invention have several important applications. For example, they may be used to express the entire secreted protein which they encode. Alternatively, they may be used to express fragments of the secreted protein. The fragments may comprise the signal peptides encoded by the cDNAs or the mature proteins encoded by the cDNAs (i.e. the proteins generated when the signal peptide is cleaved off). The cDNAs and fragments thereof also have important applications as polynucleotides. For example, the cDNAs of the sequence listing and fragments thereof, may be used to distinguish human tissues/cells from non-human tissues/cells and to distinguish between human tissues/cells that do and do not express the polynucleotides comprising the cDNAs. By knowing the tissue expression pattern of the cDNAs, either through routine experimentation or by using the instant disclosure, the polynucleotides of the present invention may be used in methods of determining the identity of an unknown tissue/cell sample. As part of determining the identity of an unknown tissue/cell sample, the polynucleotides of the present invention may be used to determine what the unknown tissue/cell sample is and what the unknown sample is not. For example, if a cDNA is expressed in a particular tissue/cell type, and the unknown tissue/cell sample does not express the cDNA, it may be inferred that the unknown tissue/cells are either not human or not the same human tissue/cell type as that which expresses the cDNA. These methods of determining tissue/cell identity are based on methods which detect the presence or absence of the mRNA (or corresponding cDNA) in a tissue/cell sample using methods well know in the art (e.g., hybridization or PCR based methods).

In other useful applications, fragments of the cDNAs encoding signal peptides as well as degenerate polynucleotides encoding the same, may be ligated to sequences encoding either the polypeptide from the same gene or to sequences encoding a heterologous polypeptide to facilitate secretion.

Antibodies which specifically recognize the entire secreted proteins encoded by the cDNAs or fragments thereof having at least 6 consecutive amino acids, 8 consecutive amino acids, 10 consecutive amino acids, at least 15 consecutive amino acids, at least 25 consecutive amino acids, or at least 40 consecutive amino acids may also be obtained as described below. Antibodies which specifically recognize the mature protein generated when the signal peptide is cleaved may also be obtained as described below. Similarly, antibodies which specifically recognize the signal peptides encoded by the cDNAs may also be obtained.

In some embodiments, the cDNAs include the signal sequence. In other embodiments, the cDNAs may include the full coding sequence for the mature protein (i.e. the protein generated when the signal polypeptide is cleaved off). In addition, the cDNAs may include regulatory regions upstream of the translation start site or downstream of the stop codon which control the amount, location, or developmental stage of gene expression. As discussed above, secreted proteins are therapeutically important. Thus, the proteins expressed from the cDNAs may be useful in treating or controlling a variety of human conditions. The cDNAs may also be used to obtain the corresponding genomic DNA. The term "corresponding genomic DNA" refers to the genomic DNA which encodes mRNA which includes the sequence of one of the strands of the cDNA in which thymidine residues in the sequence of the cDNA are replaced by uracil residues in the mRNA.

The cDNAs or genomic DNAs obtained therefrom may be used in forensic procedures to identify individuals or in diagnostic procedures to identify individuals having genetic diseases resulting from abnormal expression of the genes corresponding to the cDNAs. In addition, the present invention is useful for constructing a high resolution map of the human chromosomes.

The present invention also relates to secretion vectors capable of directing the secretion of a protein of interest. Such vectors may be used in gene therapy strategies in which it is desired to produce a gene product in one cell which is to be delivered to another location in the body. Secretion vectors may also facilitate the purification of desired proteins.

The present invention also relates to expression vectors capable of directing the expression of an inserted gene in a desired spatial or temporal manner or at a desired level. Such vectors may include sequences upstream of the cDNAs such as promoters or upstream regulatory sequences.

In addition, the present invention may also be used for gene therapy to control or treat genetic diseases. Signal peptides may also be fused to heterologous proteins to direct their extracellular secretion.

One embodiment of the present invention is a purified or isolated nucleic acid comprising the sequence of one of SEQ ID NOs: 24-73 or a sequence complementary thereto, allelic variants thereof, and degenerate variants thereof. In one aspect of this embodiment, the nucleic acid is recombinant.

Another embodiment of the present invention is a purified or isolated nucleic acid comprising at least 8 consecutive bases of the sequence of one of SEQ ID NOs: 24-73 or one of the sequences complementary thereto, allelic variants thereof, and degenerate variants thereof. In one aspect of this embodiment, the nucleic acid comprises at least 10, 12, 15, 18, 20, 25, 28, 30, 35, 40, 50, 75, 100, 150, 200, 300, 400, 500, 1000 or 2000 consecutive bases of one of the sequences of SEQ ID NOs: 24-73 or one of the sequences complementary thereto, allelic variants thereof, and degenerate variants thereof. The nucleic acid may be a recombinant nucleic acid.

In addition to the above preferred nucleic acid sizes, further preferred sub-genuses of nucleic acids comprise at least 8 nucleotides, wherein "at least 8" is defined as any integer between 8 and the integer representing the 3' most nucleotide position as set forth in the sequence listing or elsewhere herein. Further included as preferred polynucleotides of the present invention are nucleic acid fragments at least 8 nucleotides in length, as described above, that are further specified in terms of their 5' and 3' position. The 5' and 3' positions are represented by the position numbers set forth in the sequence listing below. For allelic and degenerate variants, position 1 is defined as the 5' most nucleotide of the ORF, i.e., the nucleotide "A" of the start codon with the remaining nucleotides numbered consecutively. Therefore, every combination of a 5' and 3' nucleotide position that a polynucleotide fragment of the present invention, at least 8 contiguous nucleotides in length, could occupy is included in the invention as an individual species. The polynucleotide fragments specified by 5' and 3' positions can be immediately envisaged and are therefore not individually listed solely for the purpose of not unnecessarily lengthening the specifications.

It is noted that the above species of polynucleotide fragments of the present invention may alternatively be described by the formula "a to b"; where "x" equals the 5" most nucleotide position and "y" equals the 3" most nucleotide position of the polynucleotide; and further where "x" equals an integer between 1 and the number of nucleotides of the polynucleotide sequence of the present invention minus 8, and where "y" equals an integer between 9 and the number of nucleotides of the polynucleotide sequence of the present invention; and where "x" is an integer smaller then "y" by at least 8.

The present invention also provides for the exclusion of any species of polynucleotide fragments of the present invention specified by 5' and 3' positions or sub-genuses of polynucleotides specified by size in nucleotides as described above. Any number of fragments specified by 5' and 3' positions or by size in nucleotides, as described above, may be excluded.

Another embodiment of the present invention is a vertebrate purified or isolated nucleic acid of at least 15, 18, 20, 23, 25, 28, 30, 35, 40, 50, 75, 100, 200, 300, 500 or 1000 nucleotides in length which hybridizes under stringent conditions to the sequence of one of SEQ ID NOs: 24-73 or a sequence complementary to one of the sequences of SEQ ID NOs: 24-73. In one aspect of this embodiment, the nucleic acid is recombinant.

Another embodiment of the present invention is a purified or isolated nucleic acid comprising the full coding sequences of one of SEQ ID NOs: 24-73, or an allelic variant thereof, wherein the full coding sequence optionally comprises the sequence encoding signal peptide as well as the sequence encoding mature protein. In one aspect of this embodiment, the nucleic acid is recombinant.

A further embodiment of the present invention is a purified or isolated nucleic acid comprising the nucleotides of one of SEQ ID NOs: 24-73, or an allelic variant thereof which encode a mature protein. In one aspect of this embodiment, the nucleic acid is recombinant. In another aspect of this embodiment, the nucleic acid is an expression vector wherein said nucleotides of one of SEQ ID NOs: 24-73, or an allelic variant thereof which encode a mature protein, are operably linked to a promoter.

Yet another embodiment of the present invention is a purified or isolated nucleic acid comprising the nucleotides of one of SEQ ID NOs: 24-73, or an allelic variant thereof, which encode the signal peptide. In one aspect of this embodiment, the nucleic acid is recombinant. In another aspect of this embodiment, the nucleic acid is an fusion vector wherein said nucleotides of one of SEQ ID NOs: 24-73, or an allelic variant thereof which encode the signal peptide, are operably linked to a second nucleic acid encoding an heterologous polypeptide.

Another embodiment of the present invention is a purified or isolated nucleic acid encoding a polypeptide comprising the sequence of one of the sequences of SEQ ID NOs: 74-123, or allelic variant thereof. In one aspect of this embodiment, the nucleic acid is recombinant.

Another embodiment of the present invention is a purified or isolated nucleic acid encoding a polypeptide comprising the sequence of a mature protein included in one of the sequences of SEQ ID NOs: 74-123, or allelic variant thereof. In one aspect of this embodiment, the nucleic acid is recombinant.

Another embodiment of the present invention is a purified or isolated nucleic acid encoding a polypeptide comprising the sequence of a signal peptide included in one of the sequences of SEQ ID NOs: 74-123, or allelic variant thereof. In one aspect of this embodiment, the nucleic acid is recombinant. In another aspect it is present in a vector of the invention.

Further embodiments of the invention include isolated polynucleotides that comprise, a nucleotide sequence at least 70% identical, more preferably at least 75% identical, and still more preferably at least 80%, 85%, 90%, 95%, 96%, 97%, 98%, or 99% identical to any of the polynucleotides of the present invention. Methods of determining identity include those well known in the art and described herein.

Yet another embodiment of the present invention is a purified or isolated protein comprising the sequence of one of SEQ ID NOs: 74-123, or allelic variant thereof.

Another embodiment of the present invention is a purified or isolated polypeptide comprising at least 5 or 8 consecutive amino acids of one of the sequences of SEQ ID NOs: 74-123. In one aspect of this embodiment, the purified or isolated polypeptide comprises at least 10, 12, 15, 20, 25, 30, 35, 40, 50, 60, 75, 100, 150 or 200 consecutive amino acids of one of the sequences of SEQ ID NOs: 74-123.

In addition to the above polypeptide fragments, further preferred sub-genuses of polypeptides comprise at least 8 amino acids, wherein "at least 8" is defined as any integer between 8 and the integer representing the C-terminal amino acid of the polypeptide of the present invention including the polypeptide sequences of the sequence listing below. Further included are species of polypeptide fragments at least 8 amino acids in length, as described above, that are further specified in terms of their N-terminal and C-terminal positions. Preferred species of polypeptide fragments specified by their N-terminal and C-terminal positions include the signal peptides delineated in the sequence listing below. However, included in the present invention as individual species are all polypeptide fragments, at least 8 amino acids in length, as described above, and may be particularly specified by a N-terminal and C-terminal position. That is, every combination of a N-terminal and C-terminal position that a fragment at least 8 contiguous amino acid residues in length could occupy, on any given amino acid sequence of the sequence listing or of the present invention is included in the present invention The present invention also provides for the exclusion of any fragment species specified by N-terminal and C-terminal positions or of any fragment sub-genus specified by size in amino acid residues as described above. Any number of fragments specified by N-terminal and C-terminal positions or by size in amino acid residues as described above may be excluded as individual species.

The above polypeptide fragments of the present invention can be immediately envisaged using the above description and are therefore not individually listed solely for the purpose of not unnecessarily lengthening the specification. Moreover, the above fragments need not be active since they would be useful, for example, in immunoassays, in epitope mapping, epitope tagging, as vaccines, and as molecular weight markers. The above fragments may also be used to generate antibodies to a particular portion of the polypeptide. These antibodies can then be used in immunoassays well known in the art to distinguish between human and non-human cells and tissues or to determine whether cells or tissues in a biological sample are or are not of the same type which express the polypeptide of the present invention. Preferred polypeptide fragments of the present invention comprising a signal peptide may be used to facilitate secretion of either the polypeptide of the same gene or a heterologous polypeptide using methods well known in the art.

Another embodiment of the present invention is an isolated or purified polypeptide comprising a signal peptide of one of the polypeptides of SEQ ID NOs: 74-123.

Yet another embodiment of the present invention is an isolated or purified polypeptide comprising a mature protein of one of the polypeptides of SEQ ID NOs: 74-123.

Yet another embodiment of the present invention is an isolated or purified polypeptide comprising a full length polypeptide, mature protein, or signal peptide encoded by an allelic variant of the polynucleotides of the present invention.

A further embodiment of the present invention are polypeptides having an amino acid sequence with at least 70% similarity, and more preferably at least 75%, 80%, 85%, 90%, 95%, 96%, 97%, 98%, or 99% similarity to a polypeptide of the present invention, as well as polypeptides having an amino acid sequence at least 70% identical, more preferably at least 75% identical, and still more preferably 80%, 85%, 90%, 95%, 96%, 97%, 98%, or 99% identical to a polypeptide of the present invention. Further included in the invention are isolated nucleic acid molecules encoding such polypeptides. Methods for determining identity include those well known in the art and described herein.

A further embodiment of the present invention is a method of making a protein comprising one of the sequences of SEQ ID NO: 74-123, comprising the steps of obtaining a cDNA comprising one of the sequences of sequence of SEQ ID NO: 24-73, inserting the cDNA in an expression vector such that the cDNA is operably linked to a promoter, and introducing the expression vector into a host cell whereby the host cell produces the protein encoded by said cDNA. In one aspect of this embodiment, the method further comprises the step of isolating the protein.

Another embodiment of the present invention is a protein obtainable by the method described in the preceding paragraph.

Another embodiment of the present invention is a method of making a protein comprising the amino acid sequence of the mature protein contained in one of the sequences of SEQ ID NO: 74-123, comprising the steps of obtaining a cDNA comprising one of the nucleotides sequence of sequence of SEQ ID NO: 24-73 which encode for the mature protein, inserting the cDNA in an expression vector such that the cDNA is operably linked to a promoter, and introducing the expression vector into a host cell whereby the host cell produces the mature protein encoded by the cDNA. In one aspect of this embodiment, the method further comprises the step of isolating the protein.

Another embodiment of the present invention is a mature protein obtainable by the method described in the preceding paragraph.

Another embodiment of the present invention is a host cell containing the purified or isolated nucleic acids comprising the sequence of one of SEQ ID NOs: 24-73 or a sequence complementary thereto described herein.

Another embodiment of the present invention is a host cell containing the purified or isolated nucleic acids comprising the full coding sequences of one of SEQ ID NOs: 24-73, wherein the full coding sequence comprises the sequence encoding the signal peptide and the sequence encoding the mature protein described herein.

Another embodiment of the present invention is a host cell containing the purified or isolated nucleic acids comprising the nucleotides of one of SEQ ID NOs: 24-73 which encode a mature protein which are described herein.

Another embodiment of the present invention is a host cell containing the purified or isolated nucleic acids comprising the nucleotides of one of SEQ ID NOs: 24-73 which encode the signal peptide which are described herein.

Another embodiment of the present invention is a purified or isolated antibody capable of specifically binding to a protein comprising the sequence of one of SEQ ID NOs: 74-123. In one aspect of this embodiment, the antibody is capable of binding to a polypeptide comprising at least 6 consecutive amino acids, at least 8 consecutive amino acids, or at least 10 consecutive amino acids of the sequence of one of SEQ ID NOs: 74-123.

Another embodiment of the present invention is an array of cDNAs or fragments thereof of at least 15 nucleotides in length which includes at least one of the sequences of SEQ ID NOs: 24-73, or one of the sequences complementary to the sequences of SEQ ID NOs: 24-73, or a fragment thereof of at least 15 consecutive nucleotides. In one aspect of this embodiment, the array includes at least two of the sequences of SEQ ID NOs: 24-73, the sequences complementary to the sequences of SEQ ID NOs: 24-73, or fragments thereof of at least 15 consecutive nucleotides. In another aspect of this embodiment, the array includes at least five of the sequences of SEQ ID NOs: 24-73, the sequences complementary to the sequences of SEQ ID NOs: 24-73, or fragments thereof of at least 15 consecutive nucleotides.

A further embodiment of the invention encompasses purified polynucleotides comprising an insert from a clone deposited in an ECACC deposit, which contains the sequences of SEQ ID NOs. 25-40 and 42-46, having an accession No. 99061735 and named SignalTag 15061999 or deposited in an ECACC deposit having an accession No. 98121805 and named SignalTag 166-191, which contains SEQ ID NOs.: 47-73, or a fragment of these nucleic acids comprising a contiguous span of at least 8, 10, 12, 15, 18, 20, 25, 28, 30, 35, 40, 50, 75, 100, 150, 200, 300, 400, 500, 1000 or 2000 nucleotides of said insert. In one aspect of this embodiment, the purified polynucleotide is recombinant.

An additional embodiment of the invention encompasses purified polypeptides which comprise, consist of, or consist essentially of an amino acid sequence encoded by the insert from a clone deposited in an ECACC deposit, which contains the sequences of SEQ ID NOs. 25-40 and 42-46, having an accession No. 99061735 and named SignalTag 15061999 or deposited in an ECACC deposit having an accession No. 98121805 and named SignalTag 166-191, which contains SEQ ID NOs.: 47-73, as well as polypeptides which comprise a fragment of said amino acid sequence consisting of a signal peptide, a mature protein, or a contiguous span of at least 5, 8, 10, 12, 15, 20, 25, 30, 35, 40, 50, 60, 75, 100, 150 or 200 amino acids encoded by said insert.

An additional embodiment of the invention encompasses purified polypeptides which comprise a contiguous span of at least 5, 8, 10, 12, 15, 20, 25, 30, 35, 40, 50, 60, 75, 100, 150 or 200 amino acids of SEQ ID NOs: 74-123, wherein said contiguous span comprises at least one of the amino acid positions which was not shown to be identical to a public sequence in the instant application. Also encompassed by the invention are purified polynucleotides encoding said polypeptides.

Another embodiment of the present invention is a computer readable medium having stored thereon a sequence selected from the group consisting of a cDNA code of SEQ ID NOs. 24-73 and a polypeptide code of SEQ ID NOs. 74-123.

Another embodiment of the present invention is a computer system comprising a processor and a data storage device wherein the data storage device has stored thereon a sequence selected from the group consisting of a cDNA code of SEQ ID NOs. 24-73 and a polypeptide code of SEQ ID NOs. 74-123. In some embodiments the computer system further comprises a sequence comparer and a data storage device having reference sequences stored thereon. For example, the sequence comparer may comprise a computer program which indicates polymorphisms. In other aspects of the computer system, the system further comprises an identifier which identifies features in said sequence.

Another embodiment of the present invention is a method for comparing a first sequence to a reference sequence wherein the first sequence is selected from the group consisting of a cDNA code of SEQ ID NOs. 24-73 and a polypeptide code of SEQ ID NOs. 74-123 comprising the steps of reading the first sequence and the reference sequence through use of a computer program which compares sequences and determining differences between the first sequence and the reference sequence with the computer program. In some aspects of this embodiment, said step of determining differences between the first sequence and the reference sequence comprises identifying polymorphisms.

Another aspect of the present invention is a method for determining the level of identity between a first sequence and a reference sequence, wherein the first sequence is selected from the group consisting of a cDNA code of SEQ ID NOs. 24-73 and a polypeptide code of SEQ ID NOs. 74-123, comprising the steps of reading the first sequence and the reference sequence through the use of a computer program which determines identity levels and determining identity between the first sequence and the reference sequence with the computer program.

Another embodiment of the present invention is a method for identifying a feature in a sequence selected from the group consisting of a cDNA code of SEQ ID NOs. 24-73 and a polypeptide code of SEQ ID NOs. 74-123 comprising the steps of reading the sequence through the use of a computer program which identifies features in sequences and identifying features in the sequence with said computer program. In one aspect of this embodiment, the computer program comprises a computer program which identifies open reading frames. In a further embodiment, the computer program comprises a program that identifies linear or structural motifs in a polypeptide sequence.

BRIEF DESCRIPTION OF THE DRAWINGS

FIG. 1 is a table with all of the parameters that can be used for each step of cDNA analysis.

FIG. 2 is an analysis of the 43 amino terminal amino acids of all human SwissProt proteins to determine the frequency of false positives and false negatives using the techniques for signal peptide identification described herein.

FIG. 5 describes the transcription factor binding sites present in each of these promoters.

BRIEF DESCRIPTION OF THE TABLES

Figure 3:
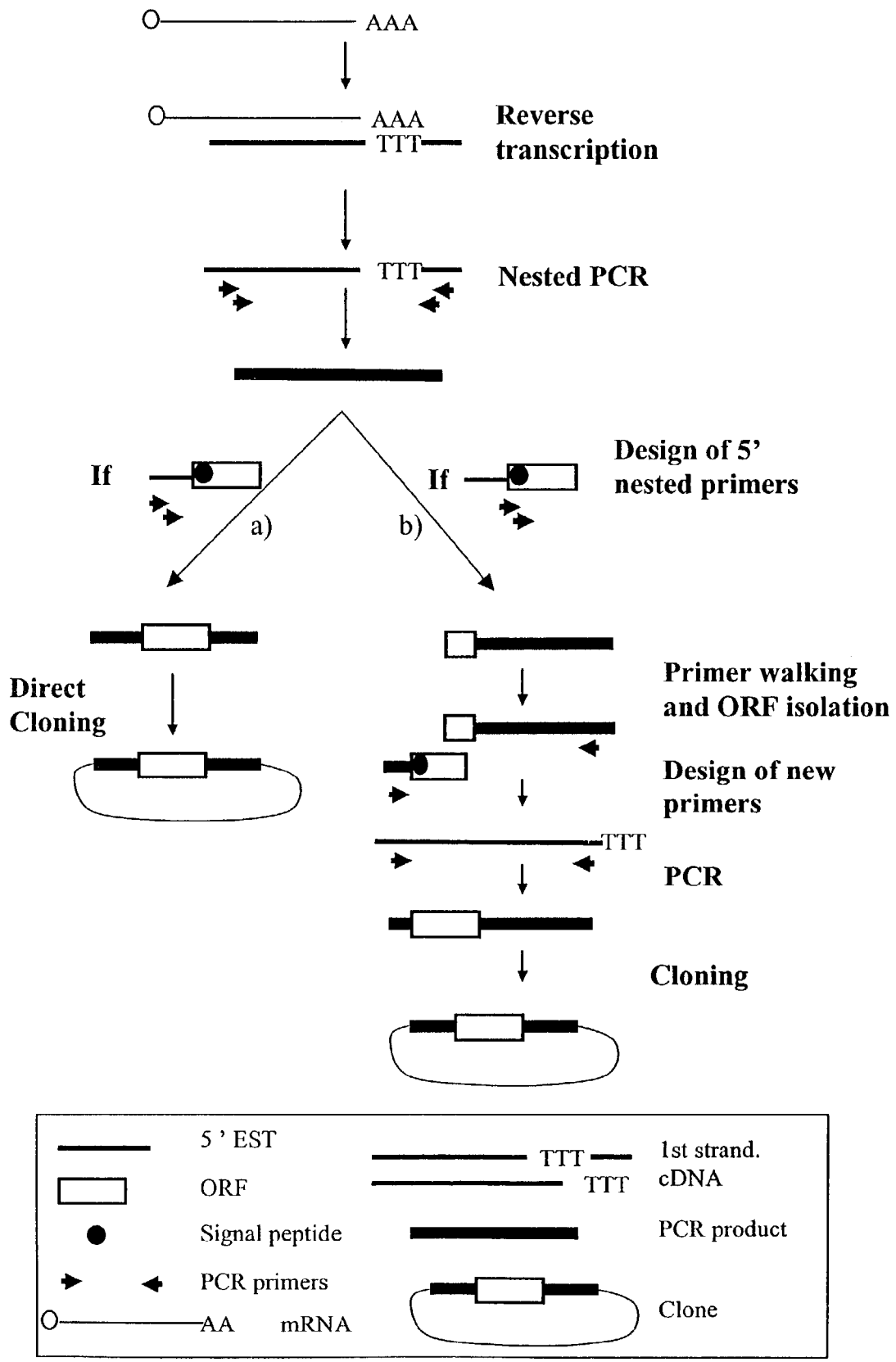
FIG. 3 provides a diagram of a RT-PCR-based method to isolate cDNAs containing sequences adjacent to 5'ESTs used to obtain them FIG. 4 provides a schematic description of the promoters isolated and the way they are assembled with the corresponding 5' tags.

Table I provides structural features of each cDNAs of SEQ ID NOs: 24-73, i.e., the locations of the full coding sequences, the locations of the nucleotides which encode the signal peptides, the locations of nucleotides which encode the mature proteins generated by cleavage of the signal peptides, the locations of stop codons, the locations of the polyA signals and the locations of polyA sites.

Table II provides structural features for each polypeptide of SEQ ID NOs: 74-123, i.e; the locations of the full length polypeptide, the locations of the signal peptides, and the locations of the mature polypeptide created by cleaving the signal peptide from the full length polypeptide.

Table III lists the positions of preferred fragments, defined as fragments not sharing more than 90% identity with any public sequence over at least 30 nucleotides in length, for some cDNAs of SEQ ID NOs:74-123.

Table IVa provides the positions of fragments which are preferably included in the present invention while Table IVb provides the positions of fragments which are preferably excluded from the present invention. Tables IVa and IVb provides for the inclusion and exclusion of polynucleotides in addition to those described elsewhere in the specification and is therefore, not meant as limiting description.

Table V provides the applicant's internal designation number assigned to each sequence identification number and indicates whether the sequence is a nucleic acid sequence or a polypeptide sequence.

Table VI list the Genset's libraries of tissues and cell types examined that express the polynucleotides of the present invention.

Table VII relates to the bias in spatial distribution of the polynucleotide sequences of the present invention.

Table VIII relates to the spatial distribution of the polynucleotide sequences of the sequence listing using information from public databases.

Table IX lists known biologically structural and functional domains for the cDNA of the present invention.

Table X lists antigenic peaks of predicted antigenic epitopes for cDNAs or the present invention.

Table XI lists the putative chromosomal location of the polynucleotides of the present invention.

DETAILED DESCRIPTION OF THE PREFERRED EMBODIMENT

I. Obtaining cDNA Libraries Including the 5'Ends of their Corresponding mRNAs

The cDNAs of the present invention may include the entire coding sequence of the protein encoded by the corresponding mRNA, including the authentic translation start site, the signal sequence, and the sequence encoding the mature protein remaining after cleavage of the signal peptide. Such cDNAs are referred to herein as "full length cDNAs." Alternatively, the cDNAs may include only the sequence encoding the mature protein remaining after cleavage of the signal peptide, or only the sequence encoding the signal peptide.

The methods explained therein can also be used to obtain cDNAs which encode less than the entire coding sequence of the secreted proteins encoded by the genes corresponding to the cDNAs. In some embodiments, the cDNAs isolated using these methods encode at least 5 amino acids of one of the proteins encoded by the sequences of SEQ ID NOs: 24-73. In further embodiments, the cDNAs encode at least 10, 12, 15, 20, 25, 30, 35, 40, 50, 60, 75, 100, 150 or 200 consecutive amino acids of the proteins encoded by the sequences of SEQ ID NOs: 24-73. In a preferred embodiment, the cDNAs encode a full length protein sequence, which includes the protein coding sequences of SEQ ID NOs: 24-73.

The cDNAs of the present invention were obtained from cDNA libraries derived from mRNAs having intact 5' ends as described in Examples 1 to 5 using either a chemical or enzymatic approach.

EXAMPLE 1

Preparation of mRNA

Total human RNAs or polyA+ RNAs derived from different tissues were respectively purchased from LABIMO and CLONTECH and used to generate cDNA libraries as described below. The purchased RNA had been isolated from cells or tissues using acid guanidium thiocyanate-phenol-chloroform extraction (Chomczyniski and Sacchi, *Analytical Biochemistry* 162:156-159, 1987). PolyA+ RNA was isolated from total RNA (LABIMO) by two passes of oligo dT chromatography, as described by Aviv and Leder, *Proc. Natl. Acad. Sci. USA* 69:1408-1412, 1972) in order to eliminate ribosomal RNA.

The quality and the integrity of the polyA+ RNAs were checked. Northern blots hybridized with a probe corresponding to an ubiquitous mRNA, such as elongation factor 1 or elongation factor 2, were used to confirm that the mRNAs were not degraded. Contamination of the polyA$^+$ mRNAs by ribosomal sequences was checked using Northern blots and a probe derived from the sequence of the 28S rRNA. Preparations of mRNAs with less than 5% of rRNAs were used in library construction. To avoid constructing libraries with RNAs contaminated by exogenous sequences (prokaryotic or fungal), the presence of bacterial 16S ribosomal sequences or of two highly expressed fungal mRNAs was examined using PCR.

EXAMPLE 2

Methods for Obtaining mRNAs having Intact 5' Ends

Following preparation of the mRNAs from various tissues as described above, selection of mRNA with intact 5' ends and specific attachment of an oligonucleotide tag to the 5' end of such mRNA is performed using either a chemical or enzymatic approach. Both techniques take advantage of the presence of the "cap" structure, which characterizes the 5' end of intact mRNAs and which comprises a guanosine generally methylated once, at the 7 position.

The chemical modification approach involves the optional elimination of the 2',3'-cis diol of the 3' terminal ribose, the oxidation of the 2',3', -cis diol of the ribose linked to the cap of the 5' ends of the mRNAs into a dialdehyde, and the coupling of the dialdehyde to a derivatized oligonucleotide tag. Further detail regarding the chemical approaches for obtaining mRNAs having intact 5' ends are disclosed in International Application No. WO96/34981, published Nov. 7, 1996, the disclosure of which is incorporated herein by reference in its entirety.

The enzymatic approach for ligating the oligonucleotide tag to the 5' ends of mRNAs with intact 5' ends involves the removal of the phosphate groups present on the 5' ends of uncapped incomplete mRNAs, the subsequent decapping of mRNAs with intact 5' ends and the ligation of the phosphate present at the 5' end of the decapped mRNA to an oligonucleotide tag. Further detail regarding the enzymatic approaches for obtaining mRNAs having intact 5' ends are disclosed in Dumas Milne Edwards J. B. (Doctoral Thesis of Paris VI University, Le clonage des ADNc complets: difficultes et perspectives nouvelles. Apports pour l'etude de la regulation de l'expression de la tryptophane hydroxylase de rat, 20 Dec. 1993), EP0 625572 and Kato et al., *Gene* 150:243-250 (1994), the disclosures of which are incorporated herein by reference in their entireties.

In either the chemical or the enzymatic approach, the oligonucleotide tag has a restriction enzyme site (e.g. EcoRI sites) therein to facilitate later cloning procedures. Following attachment of the oligonucleotide tag to the mRNA, the integrity of the mRNA was then examined by performing a Northern blot using a probe complementary to the oligonucleotide tag.

EXAMPLE 3 cDNA Synthesis Using mRNA Templates having Intact 5' Ends

For the mRNAs joined to oligonucleotide tags using either the chemical or the enzymatic method, first strand cDNA synthesis was performed using reverse transcriptase with an oligo-dT primer or random nonamer. In some instances, this oligo-dT primer contained an internal tag of at least 4 nucleotides which is different from one tissue to the other. In order to protect internal EcoRI sites in the cDNA from digestion at later steps in the procedure, methylated dCTP was used for first strand synthesis. After removal of RNA by an alkaline hydrolysis, the first strand of cDNA was precipitated using isopropanol in order to eliminate residual primers.

The second strand of the cDNA was then synthesized with a Klenow fragment using a primer corresponding to the 5' end of the ligated oligonucleotide. Preferably, the primer is 20-25 bases in length. Methylated dCTP was also used for second strand synthesis in order to protect internal EcoRI sites in the cDNA from digestion during the cloning process.

EXAMPLE 4

Cloning of cDNAs Derived from mRNA with Intact 5' Ends into BlueScript

Following second strand synthesis, the cDNAs were cloned into the phagemid pBlueScript II SK-vector (Stratagene). The ends of the cDNAs were blunted with T4 DNA polymerase (Biolabs) and the cDNA was digested with EcoRI. Since methylated dCTP was used during cDNA synthesis, the EcoRI site present in the tag was the only hemimethylated site, hence the only site susceptible to EcoRI digestion. In some instances, to facilitate subcloning, an HindIII adaptor was added to the 3' end of cDNAs.

The cDNAs were then size fractionated using either exclusion chromatography (AcA, Biosepra) or electrophoretic separation which yields 3 or 6 different fractions. The cDNAs were then directionally cloned either into pBlueScript using either the EcoRI and SmaI restriction sites or the EcoRI and HindIII restriction sites when the HindIII adaptor was present in the cDNAs. The ligation mixture was electroporated into bacteria and propagated under appropriate antibiotic selection.

EXAMPLE 5

Selection of Clones having the Oligonucleotide Tag Attached Thereto

Clones containing the oligonucleotide tag attached to cDNAs were then selected as follows.

The plasmid DNAs containing cDNA libraries made as described above were purified (Qiagen). A positive selection of the tagged clones was performed as follows. Briefly, in this selection procedure, the plasmid DNA was converted to single stranded DNA using gene II endonuclease of the phage F1 in combination with an exonuclease (Chang et al., *Gene* 127:95-8, 1993) such as exonuclease III or T7 gene 6 exonuclease. The resulting single stranded DNA was then purified using paramagnetic beads as described by Fry et al., *Biotechniques*, 13: 124-131, 1992. In this procedure, the single stranded DNA was hybridized with a biotinylated oligonucleotide having a sequence corresponding to the 3' end of the oligonucleotide tag described in example 2. Preferably, the primer has a length of 20-25 bases. Clones including a sequence complementary to the biotinylated oligonucleotide were captured by incubation with streptavidin coated magnetic beads followed by magnetic selection. After capture of the positive clones, the plasmid DNA was released from the magnetic beads and converted into double stranded DNA using a DNA polymerase such as the ThermoSequenase obtained from Amersham Pharmacia Biotech. Alternatively, protocols such as the Gene Trapper kit (Gibco BRL) may be used. The double stranded DNA was then electroporated into bacteria. The percentage of positive clones having the 5' tag oligonucleotide was estimated to typically rank between 90 and 98% using dot blot analysis.

Following electroporation, the libraries were ordered in 384-microtiter plates (MTP). A copy of the MTP was stored for future needs. Then the libraries were transferred into 96 MTP.

II. Characterization of the 5' Ends of Clones

In order to sequence only cDNAs which contain the 5' ends of their corresponding mRNA, a first round of sequencing was performed on the 5' end of clones as described in example 6. In some instances, only a partial sequence of the clone, therein referred to as "5'EST" was obtained. In other instances, the complete sequence of the clone, herein referred to as a "cDNA" is obtained. A computer analysis was then performed on the 5' ESTs or cDNAs as described in Examples 7 and 8 in order to evaluate the quality of the cDNA libraries and in order to select clones containing sequences of interest among cDNAs which contain the 5' ends of their corresponding mRNA.

EXAMPLE 6

Sequencing of the 5' End of cDNA Clones

The 5' ends of cloned cDNAs were then sequenced as follows. Plasmid inserts were first amplified by PCR on PE 9600 thermocyclers (Perkin-Elmer, Applied Biosystems Division, Foster City, Calif.) using standard SETA-A and SETA-B primers (Genset SA), AmpliTaqGold (Perkin-Elmer), dNTPs (Boehringer), buffer and cycling conditions as recommended by the Perkin-Elmer Corporation.

PCR products were then sequenced using automatic ABI Prism 377 sequencers (Perkin Elmer). Sequencing reactions were performed using PE 9600 thermocyclers with standard dye-primer chemistry and ThermoSequenase (Amersham Pharmacia Biotech). The primers used were either T7 or 21M13 (available from Genset SA) as appropriate. The primers were labeled with the JOE, FAM, ROX and TAMRA dyes. The dNTPs and ddNTPs used in the sequencing reactions were purchased from Boehringer. Sequencing buffer, reagent concentrations and cycling conditions were as recommended by Amersham.

Following the sequencing reaction, the samples were precipitated with ethanol, resuspended in formamide loading buffer, and loaded on a standard 4% acrylamide gel. Electrophoresis was performed for 2.5 hours at 3000V on an ABI 377 sequencer, and the sequence data were collected and analyzed using the ABI Prism DNA Sequencing Analysis Software, version 2.1.2.

The sequence data obtained from the sequencing of 5' ends of all cDNA libraries made as described above were transferred to a proprietary database, where quality control and validation steps were performed. A proprietary base-caller, working using a Unix system automatically flagged suspect peaks, taking into account the shape of the peaks, the inter-peak resolution, and the noise level. The proprietary base-caller also performed an automatic trimming. Any stretch of 25 or fewer bases having more than 4 suspect peaks was considered unreliable and was discarded. Sequences corresponding to cloning vector or ligation oligonucleotides were automatically removed from the sequences. However, the resulting sequences may contain 1 to 5 nucleotides belonging to the above mentioned sequences at their 5' end. If needed, these can easily be removed on a case by case basis.

Following sequencing as described above, the sequences of the cDNA clones were entered in a database for storage and manipulation as described below. Before searching the cDNA clones in the database for sequences of interest, cDNAs derived from mRNAs which were not of interest were identified and eliminated, namely, endogenous contaminants (ribosomal RNAs, transfert RNAs, mitochondrial RNAs) and exogenous contaminants (prokaryotic RNAs and fungal RNAs) using software and parameters described in FIG. 1. In addition, cDNA sequences showing showing identity to repeated sequences (Alu, L1, THE and MER repeats, SSTR sequences or satellite, micro-satellite, or telomeric repeats) were identified and masked in further processing.

EXAMPLE 7

Determination of Efficiency of 5' End Selection

To determine the efficiency at which the above selection procedures isolated cDNAs which include the 5' ends of their corresponding mRNAs, the sequences of 5'ESTs or cDNAs were aligned with a reference pool of complete mRNA/cDNA extracted from the EMBL release 57 using the FASTA algorithm. The reference mRNA/cDNA starting at the most 5' transcription start site was obtained, and then compared to the 5' transcription start site position of the 5'EST or cDNA. More than 75% of 5'ESTs or cDNAs had their 5' ends close to the 5' ends of the known sequence. As some of the mRNA sequences available in the EMBL database are deduced from genomic sequences, a 5' end matching with these sequences will be counted as an internal match. Thus, the method used here underestimates the yield of 5'ESTs or cDNAs including the authentic 5' ends of their corresponding mRNAs.

EXAMPLE 8

Identification of Open Reading Frames Coding for Potential Signal Peptides

The obtained nucleic acid sequences were then screened to identify those having uninterrupted open reading frames (ORF) with a good coding probability using proprietary software. When the full-length cDNA was obtained, only complete ORFs, namely nucleic acid sequences beginning with a start codon and ending with a stop codon, longer than 150 nucleotides were considered. When only 5'EST sequences were obtained, both complete ORFS longer than 150 nucleotides and incomplete ORFs, namely nucleic acid sequences beginning with a start codon and extending up to the end of the 5'EST, longer than 60 nucleotides were considered.

The retrieved ORFs were then searched to identify potential signal motifs using slight modifications of the procedures disclosed in Von Heijne, *Nucleic Acids Res.* 14:4683-4690, 1986, the disclosure of which is incorporated herein by reference. Those 5'ESTs or cDNA sequences encoding a polypeptide with a score of at least 3.5 in the Von Heijne signal peptide identification matrix were considered to possess a signal sequence. Those 5'ESTs or cDNAs which matched a known human mRNA or EST sequence and had a 5' end more than 30 nucleotides downstream of the known 5' end were excluded from further analysis.

EXAMPLE 9

Confirmation of Accuracy of Identification of Potential Signal Sequences in 5' ESTs The accuracy of the above procedure for identifying signal sequences encoding signal peptides was evaluated by applying the method to the 43 amino acids located at the N terminus of all human SwissProt proteins. The computed Von Heijne score for each protein was compared with the known characterization of the protein as being a secreted protein or a non-secreted protein. In this manner, the number of non-secreted proteins having a score higher than 3.5 (false positives) and the number of secreted proteins having a score lower than 3.5 (false negatives) could be calculated.

Using the results of the above analysis, the probability that a peptide encoded by the 5' region of the mRNA is in fact a genuine signal peptide based on its Von Heijne's score was calculated based on either the assumption that 10% of human proteins are secreted or the assumption that 20% of human proteins are secreted. The results of this analysis are shown in FIG. 2.

Using the above method of identification of secretory proteins, 5' ESTs of the following polypeptides known to be secreted were obtained: human glucagon, gamma interferon induced monokine precursor, secreted cyclophilin-like protein, human pleiotropin, and human biotinidase precursor. Thus, the above method successfully identified those 5' ESTs which encode a signal peptide.

To confirm that the signal peptide encoded by the 5' ESTs or cDNAs actually functions as a signal peptide, the signal sequences from the 5' ESTs or cDNAs may be cloned into a vector designed for the identification of signal peptides. Such vectors are designed to confer the ability to grow in selective medium only to host cells containing a vector with an operably linked signal sequence. For example, to confirm that a 5' EST or cDNA encodes a genuine signal peptide, the signal sequence of the 5' EST or cDNA may be inserted upstream and in frame with a non-secreted form of the yeast invertase gene in signal peptide selection vectors such as those described in U.S. Pat. No. 5,536,637, the disclosure of which is incorporated herein by reference. Growth of host cells containing signal sequence selection vectors with the correctly inserted 5' EST or cDNA signal sequence confirms that the 5' EST or cDNA encodes a genuine signal peptide.

Alternatively, the presence of a signal peptide may be confirmed by cloning the 5'ESTs or cDNAs into expression vectors such as pXT1 as described below, or by constructing promoter-signal sequence-reporter gene vectors which encode fusion proteins between the signal peptide and an assayable reporter protein. After introduction of these vectors into a suitable host cell, such as COS cells or NIH 3T3 cells, the growth medium may be harvested and analyzed for the presence of the secreted protein. The medium from these cells is compared to the medium from control cells containing vectors lacking the signal sequence or cDNA insert to identify vectors which encode a functional signal peptide or an authentic secreted protein.

EXAMPLE 10

Evaluation of Expression Levels and Patterns of mRNAs Corresponding to 5' ESTs or cDNAs The spatial and temporal expression patterns of the mRNAs corresponding to the 5' ESTs or cDNAs, as well as their expression levels, may be determined. Characterization of the spatial and temporal expression patterns and expression levels of these mRNAs is useful for constructing expression vectors capable of producing a desired level of gene product in a desired spatial or temporal manner, as will be discussed in more detail below.

In addition, cDNAs or 5' ESTs whose corresponding mRNAs are associated with disease states may also be identified. For example, a particular disease may result from lack of expression, over expression, or under expression of an mRNA corresponding to a cDNA or 5' EST. By comparing mRNA expression patterns and quantities in samples taken from healthy individuals with those from individuals suffering from a particular disease, cDNAs and 5' ESTs responsible for the disease may be identified.

Expression levels and patterns of mRNAs corresponding to 5' ESTs or cDNAs may be analyzed by solution hybridization with long probes as described in International Patent Application No. WO 97/05277, the entire contents of which are hereby incorporated by reference. Briefly, a 5' EST, cDNA, or fragment thereof corresponding to the gene encoding the mRNA to be characterized is inserted at a cloning site immediately downstream of a bacteriophage (T3, T7 or SP6) RNA polymerase promoter to produce antisense RNA. Preferably, the 5' EST or cDNA is 100 or more nucleotides in length. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridizations are performed under standard stringent conditions (40-50° C. for 16 hours in an 80% formamide, 0.4 M NaCl buffer, pH 7-8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

The 5' ESTs, cDNAs, or fragments thereof may also be tagged with nucleotide sequences for the serial analysis of gene expression (SAGE) as disclosed in UK Patent Application No. 2 305 241 A, the entire contents of which are incorporated by reference. In this method, cDNAs are prepared from a cell, tissue, organism or other source of nucleic acid for which it is desired to determine gene expression patterns. The resulting cDNAs are separated into two pools. The cDNAs in each pool are cleaved with a first restriction endonuclease, called an "anchoring enzyme," having a recognition site which is likely to be present at least once in most cDNAs. The fragments which contain the 5' or 3' most region of the cleaved cDNA are isolated by binding to a capture medium such as streptavidin coated beads. A first oligonucleotide linker having a first sequence for hybridization of an amplification primer and an internal restriction site for a "tagging endonuclease" is ligated to the digested cDNAs in the first pool. Digestion with the second endonuclease produces short "tag" fragments from the cDNAs.

A second oligonucleotide having a second sequence for hybridization of an amplification primer and an internal restriction site is ligated to the digested cDNAs in the second pool. The cDNA fragments in the second pool are also digested with the "tagging endonuclease" to generate short "tag" fragments derived from the cDNAs in the second pool. The "tags" resulting from digestion of the first and second pools with the anchoring enzyme and the tagging endonuclease are ligated to one another to produce "ditags." In some embodiments, the ditags are concatamerized to produce ligation products containing from 2 to 200 ditags. The tag sequences are then determined and compared to the sequences of the 5' ESTs or cDNAs to determine which 5' ESTs or cDNAs are expressed in the cell, tissue, organism, or other source of nucleic acids from which the tags were derived. In this way, the expression pattern of the 5' ESTs or cDNAs in the cell, tissue, organism, or other source of nucleic acids is obtained.

Quantitative analysis of gene expression may also be performed using arrays. As used herein, the term array means a one dimensional, two dimensional, or multidimensional arrangement of full length cDNAs (i.e. cDNAs which include the coding sequence for the signal peptide, the coding sequence for the mature protein, and a stop codon), cDNAs, 5' ESTs or fragments of the full length cDNAs, cDNAs, or 5' ESTs of sufficient length to permit specific detection of gene expression. Preferably, the fragments are at least 15 nucleotides in length. More preferably, the fragments are at least 100 nucleotides in length. More preferably, the fragments are more than 100 nucleotides in length. In some embodiments the fragments may be more than 500 nucleotides in length.

For example, quantitative analysis of gene expression may be performed with full length cDNAs, cDNAs, 5' ESTs, or fragments thereof in a complementary DNA microarray as described by Schena et al. (*Science* 270:467-470, 1995; *Proc. Natl. Acad. Sci. U.S.A*. 93:10614-10619, 1996). Full length cDNAs, cDNAs, 5' ESTs or fragments thereof are amplified by PCR and arrayed from 96-well microtiter plates onto silylated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 cm² microarrays under a 14×14 mm glass coverslip for 6-12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of the expression of genes may also be performed with full length cDNAs, cDNAs, 5' ESTs, or fragments thereof in complementary DNA arrays as described by Pietu et al. (Genome Research 6:492-503, 1996). The full length cDNAs, cDNAs, 5' ESTs or fragments thereof are PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis of the 5' ESTs or cDNAs can be done through high density nucleotide arrays as described by Lockhart et al. (Nature Biotechnology 14: 1675-1680, 1996) and Sosnowsky et al. (Proc. Natl. Acad. Sci. 94:1119-1123, 1997). Oligonucleotides of 15-50 nucleotides corresponding to sequences of the 5' ESTs or cDNAs are synthesized directly on the chip (Lockhart et al., supra) or synthesized and then addressed to the chip (Sosnowski et al., supra). Preferably, the oligonucleotides are about 20 nucleotides in length.

cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., Proc. Natl. Acad. Sci. 94:1119-1123.), the dyes or labeling compounds are detected and quantified. Duplicate hybridizations are performed. Comparative analysis of the intensity of the signal originating from cDNA probes on the same target oligonucleotide in different cDNA samples indicates a differential expression of the mRNA corresponding to the 5' EST or cDNA from which the oligonucleotide sequence has been designed.

III. Characterization of cDNAs Including the 5'End of their Corresponding mRNA

EXAMPLE 11

Characterization of the Complete Sequence of cDNA Clones

Clones which include the 5' end of their corresponding mRNA and which encode a new protein with a signal peptide as determined in the aforementioned procedure were then fully sequenced as follows.

First, both 5' and 3' ends of cloned cDNAs were sequenced twice in order to confirm the identity of the clone using a Die Terminator approach with the AmpliTaq DNA polymerase FS kit available from Perkin Elmer. Second, primer walking was performed if the full coding region had not been obtained yet using software such as OSP to choose primers and automated computer software such as ASMG (Sutton et al., *Genome Science Technol*. 1: 9-19, 1995) to construct contigs of walking sequences including the initial 5' tag. Contigation was then performed using 5' and 3' sequences and eventually primer walking sequences. The sequence was considered complete when the resulting contigs included the full coding region as well as overlapping sequences with vector DNA on both ends. In addition, clones were entirely sequenced in order to obtain at least two sequences per clone. Preferably, the sequences were obtained from both sense and antisense strands. All the contigated sequences for each clone were then used to obtain a consensus sequence which was then submitted to the computer analysis described below.

Alternatively, clones which include the 5' end of their corresponding mRNA and which encode a new protein with a signal peptide, as determined in the aforementioned procedure, may be subcloned into an appropriate vector such as pED6dpc2 (DiscoverEase, Genetics Institute, Cambridge, Mass.) before full sequencing.

EXAMPLE 12

Determination of Structural and Functional Features

Following identification of contaminants and masking of repeats, structural features, e.g. polyA tail and polyadenylation signal, of the sequences of cDNAs were subsequently determined using the algorithm, parameters and criteria defined in FIG. 1. Briefly, a polyA tail was defined as a homopolymeric stretch of at least 11 A with at most one alternative base within it. The polyA tail search was restricted to the last 100 nt of the sequence and limited to stretches of 11 consecutive A's because sequencing reactions are often not readable after such a polyA stretch. To search for a polyadenylation signal, the polyA tail was clipped from the full-length sequence. The 50 bp preceding the polyA tail were searched for the canonic polyadenylation AAUAAA signal allowing one mismatch to account for possible sequencing errors as well as known variation in the canonical sequence of the polyadenylation signal.

Functional features, e.g. ORFs and signal sequences, of the sequences of cDNAs were subsequently determined as follows. The 3 upper strand frames of cDNAs were searched for ORFs defined as the maximum length fragments beginning with a translation initiation codon and ending with a stop codon. ORFs encoding at least 80 amino acids were preferred. Each found ORF was then scanned for the presence of a signal peptide using the matrix method described in example 10.

Sequences of cDNAs were then compared, on a nucleotidic or proteic basis, to public sequences available at the time of filing.

EXAMPLE 13

Selection of Full Length Sequences cDNAs that had already been characterized by the aforementioned computer analysis were then submitted to an automatic procedure in order to preselect cDNAs containing sequences of interest.

a) Automatic Sequence Preselection

All cDNAs clipped for vector on both ends were considered. First, a negative selection was performed in order to eliminate sequences which resulted from either contaminants or artifacts as follows. Sequences matching contaminant sequences were discarded as well as those encoding ORF sequences exhibiting identity to repeats. Sequences lacking polyA tail were also discarded. Those cDNAs which matched a known human mRNA or EST sequence and had a 5' end more than 30 nucleotides downstream of the known 5' end were also excluded from further analysis. Only ORFs ending before the polyA tail were kept.

Then, for each remaining cDNA containing several ORFs, a preselection of ORFs was performed using the following criteria. The longest ORF was preferred. If the ORF sizes were similar, the chosen ORF was the one which signal peptide had the highest score according to Von Heijne method as defined in Example 10.

Sequences of cDNA clones were then compared pairwise with BLAST after masking of the repeat sequences. Sequences containing at least 90% identity over 30 nucleotides were clustered in the same class. Each cluster was then subjected to a clustal analysis that detects sequences resulting from internal priming or from alternative splicing, identical sequences or sequences with several frameshifts. This automatic analysis served as a basis for manual selection of the sequences.

b) Manual Sequence Selection

Manual selection was carried out using automatically generated reports for each sequenced cDNA clone. During the manual selection procedure, a selection was performed between clones belonging to the same class as follows. ORF sequences encoded by clones belonging to the same class were aligned and compared. If the identity between nucleotidic sequences of clones belonging to the same class was more than 90% over 30 nucleotide stretches or if the identity between amino acid sequences of clones belonging to the same class was more than 80% over 20 amino acid stretches, then the clones were considered as being identical. The chosen ORF was either the one exhibiting matches with known amino acid sequences or the best one according to the criteria mentioned in the automatic sequence preselection section. If the nucleotide and amino acid homologies were less than 90% and 80% respectively, the clones were said to encode distinct proteins which can be both selected if they contain sequences of interest.

Selection of full length cDNA clones encoding sequences of interest was performed using the following criteria. Structural parameters (initial tag, polyadenylation site and signal, eventually matches with public ESTs in 5' or 3' of the sequence) were first checked in order to confirm that the cDNA was complete in 5' and in 3'. Then, homologies with known nucleic acids and proteins were examined in order to determine whether the clone sequence matched a known nucleic acid or protein sequence and, in the latter case, its covering rate and the date at which the sequence became public. If there was no extensive match with sequences other than ESTs or genomic DNA, or if the clone sequence included substantial new information, such as encoding a protein resulting from alternative splicing of an mRNA coding for an already known protein, the sequence was kept. Examples of such cloned full length cDNAs containing sequences of interest are described in Example 14. Sequences resulting from chimera or double inserts as assessed by identity to other sequences were discarded during this procedure.

EXAMPLE 14

Characterization of Full-length cDNAs

The procedure described above was used to obtain or full length cDNAs derived from a variety of tissues. The following list provides a few examples of thus obtained cDNAs.

Using this procedure, the full length cDNA of SEQ ID NO:1 (internal identification number 108-005-5-0-F9-FLC) was obtained. This cDNA encodes a potentially secreted protein (SEQ ID NO:2) with a signal peptide having a von Heijne score of 4.1.

Using this procedure, the full length cDNA of SEQ ID NO:3 (internal identification number 108-004-5-0-G10-FLC) was obtained. This cDNA encodes a potentially secreted protein (SEQ ID NO:4) with a signal peptide having a von Heijne score of 5.3.

Using this procedure, the full length cDNA of SEQ ID NO:5 (internal identification number 108-004-5-0-B12-FLC) was obtained. This cDNA encodes a potentially secreted protein (SEQ ID NO:6) with a signal peptide having a von Heijne score of 7.0.

Using this procedure, the full length cDNA of SEQ ID NO:7 (internal identification number 108-013-5-0-G5-FLC) was obtained. This cDNA encodes a potentially secreted protein (SEQ ID NO:8) with a signal peptide having a von Heijne score of 9.4.

Furthermore, the polypeptides encoded by the extended or full-length cDNAs may be screened for the presence of known structural or functional motifs or for the presence of signatures, small amino acid sequences which are well conserved amongst the members of a protein family. Some of the results obtained for the polypeptides encoded by full-length cDNAs that were screened for the presence of known protein signatures and motifs using the Proscan software from the GCG package and the Prosite database are provided below.

The protein of SEQ ID NO:10 encoded by the full-length cDNA SEQ ID NO:9 (internal designation 108-013-5-O-H9-FLC) shows homologies with a family of lysophospholipases conserved among eukaryotes (yeast, rabbit, rodents and human). In addition, some members of this family exhibit a calcium-independent phospholipase A2 activity (Portilla et al., *J. Am. Soc. Nephro.*, 9:1178-1186 (1998)). All members of this family exhibit the active site consensus GXSXG motif of carboxylesterases that is also found in the protein of SEQ ID NO:10 (position 54 to 58). In addition, this protein may be a membrane protein with one transmembrane domain as predicted by the software TopPred II (Claros and von Heijne, *CABIOS applic. Notes*, 10:685-686 (1994)). Taken together, these data suggest that the protein of SEQ ID NO:10 may play a role in fatty acid metabolism, probably as a phospholipase. Thus, this protein or part therein, may be useful in diagnosing and/or treating several disorders including, but not limited to, cancer, diabetes, and neurodegenerative disorders such as Parkinson's and Alzheimer's diseases. It may also be useful in modulating inflammatory responses to infectious agents and/or to suppress graft rejection.

The protein of SEQ ID NO: 12 encoded by the full-length cDNA SEQ ID NO:11 (internal designation 108-004-5-0-D10-FLC) shows remote identity to a subfamily of beta4-alactosyltransferases widely conserved in animals (human, rodents, cow and chicken). Such enzymes, usually type II membrane proteins located in the endoplasmic reticulum or in the Golgi apparatus, catalyze the biosynthesis of glycoproteins, glycolipid glycans and lactose. Their characteristic features defined as those of subfamily A in Breton et al., *J. Biochem.*, 123:1000-1009 (1998) are pretty well conserved in the protein of SEQ ID NO: 12, especially the region I containing the DVD motif (positions 163-165) thought to be involved either in UDP binding or in the catalytic process itself. In addition, the protein of SEQ ID NO: 12 has the typical structure of a type II protein. Indeed, it contains a short 28-amino-acid-long N-terminal tail, a transmembrane segment from positions 29 to 49 and a large 278-amino-acid-long C-terminal tail as predicted by the software TopPred II (Claros and von Heijne, *CABIOS applic. Notes*, 10:685-686 (1994)). Taken together, these data suggest that the protein of SEQ ID NO: 12 may play a role in the biosynthesis of polysaccharides, and of the carbohydrate moieties of glycoproteins and glycolipids and/or in cell-cell recognition. Thus, this protein may be useful in diagnosing and/or treating several types of disorders including, but not limited to, cancer, atherosclerosis, cardiovascular disorders, autoimmune disorders and rheumatic diseases including rheumatoid arthritis.

The protein of SEQ ID NO: 14 encoded by the extended cDNA SEQ ID NO: 13 (internal designation 108-004-5-0-E8-FLC) exhibits the typical PROSITE signature for amino acid permeases (positions 5 to 66) which are integral membrane proteins involved in the transport of amino acids into the cell. In addition, the protein of SEQ ID NO: 14 has a transmembrane segment from positions 9 to 29 as predicted by the software TopPred II (Claros and von Heijne, CABIOS applic. Notes, 10:685-686 (1994)). Taken together, these data suggest that the protein of SEQ ID NO: 14 may be involved in amino acid transport. Thus, this protein may be useful in diagnosing and/or treating several types of disorders including, but not limited to, cancer, aminoacidurias, neurodegenerative diseases, anorexia, chronic fatigue, coronary vascular disease, diphtheria, hypoglycemia, male infertility, muscular and myopathies.

Bacterial clones containing plasmids containing the full length cDNAs described above are presently stored in the inventor's laboratories under the internal identification numbers provided above. The inserts may be recovered from the deposited materials by growing an aliquot of the appropriate bacterial clone in the appropriate medium. The plasmid DNA can then be isolated using plasmid isolation procedures familiar to those skilled in the art such as alkaline lysis minipreps or large scale alkaline lysis plasmid isolation procedures. If desired the plasmid DNA may be further enriched by centrifugation on a cesium chloride gradient, size exclusion chromatography, or anion exchange chromatography. The plasmid DNA obtained using these procedures may then be manipulated using standard cloning techniques familiar to those skilled in the art. Alternatively, a PCR can be done with primers designed at both ends of the cDNA insertion. The PCR product which corresponds to the cDNA can then be manipulated using standard cloning techniques familiar to those skilled in the art.

The above procedure was also used to obtain the cDNAs of the invention comprising the sequences of SEQ ID NOs: 24-73. Table I provides the sequence identification numbers of the cDNAs of the present invention, the locations of the first and last nucleotides of the full coding sequences in SEQ ID NOs: 24-73 (i.e. the nucleotides encoding both the signal peptide and the mature protein, listed under the heading FCS location in Table I), the locations of the first and last nucleotides in SEQ ID NOs: 24-73 which encode the signal peptides (listed under the heading SigPep Location in Table I), the locations of the first and last nucleotides in SEQ ID NOs: 24-73 which encode the mature proteins generated by cleavage of the signal peptides (listed under the heading Mature Polypeptide Location in Table I), the locations in SEQ ID NOs: 24-73 of stop codons (listed under the heading Stop Codon Location in Table I), the locations of the first and last nucleotides in SEQ ID NOs: 24-73 of the polyA signals (listed under the heading Poly A Signal Location in Table I) and the locations of the first and last nucleotides of the polyA sites (listed under the heading Poly A Site Location in Table I).

Table II lists the sequence identification numbers of the polypeptides of SEQ ID NOs: 74-123, the locations of the first and last amino acid residues of SEQ ID NOs: 74-123 in the full length polypeptide (second column), the locations of the first and last amino acid residues of SEQ ID NOs: 74-123 in the signal peptides (third column), and the locations of the first and last amino acid residues of SEQ ID NOs: 74-123 in the mature polypeptide created by cleaving the signal peptide from the full length polypeptide (fourth column).

The nucleotide sequences of the sequences of SEQ ID NOs: 24-73 and the amino acid sequences encoded by SEQ ID NOs: 24-73 (i.e. amino acid sequences of SEQ ID NOs: 74-123) are provided in the appended sequence listing. In some instances, the sequences are preliminary and may include some incorrect or ambiguous sequences or amino acids. All instances of the symbol "n" in the nucleic acid sequences mean that the nucleotide can be adenine, guanine, cytosine or thymine. For each amino acid sequence, Applicants have identified what they have determined to be the reading frame best identifiable with sequence information available at the time of filing. In some instances the polypeptide sequences in the Sequence Listing contain the symbol "Xaa." These "Xaa" symbols indicate either (1) a residue which cannot be identified because of nucleotide sequence ambiguity or (2) a stop codon in the determined sequence where applicants believe one should not exist (if the sequence were determined more accurately). Thus, "Xaa" indicates that a residue may be any of the twenty amino acids. In some instances, several possible identities of the unknown amino acids may be suggested by the genetic code.

The sequences of SEQ ID NOs: 24-73 can readily be screened for any errors therein and any sequence ambiguities can be resolved by resequencing a fragment containing such errors or ambiguities on both strands. Nucleic acid fragments for resolving sequencing errors or ambiguities may be obtained from the deposited clones or can be isolated using the techniques described herein. Resolution of any such ambiguities or errors may be facilitated by using primers which hybridize to sequences located close to the ambiguous or erroneous sequences. For example, the primers may hybridize to sequences within 50-75 bases of the ambiguity or error. Upon resolution of an error or ambiguity, the corresponding corrections can be made in the protein sequences encoded by the DNA containing the error or ambiguity. The amino acid sequence of the protein encoded by a particular clone can also be determined by expression of the clone in a suitable host cell, collecting the protein, and determining its sequence.

EXAMPLE 15A

Categorization of cDNAs of the Present Invention

The nucleic acid sequences of the present invention (SEQ ID NOs. 24-73) were grouped based on their identity to known sequences as follows. All sequences were compared to public sequences available at the time of filing the priority applications.

In some instances, the cDNAs did not match any known vertebrate sequence nor any publicly available EST sequence, thus being completely new.

All sequences exhibiting more than 90% of identity to known sequences over at least 30 nucleotides were retrieved and further analyzed. For these cDNAs referred to by their sequence identification numbers (first column), Table III gives the positions of preferred fragments within these sequences (second column entitled "Positions of preferred fragments"). Each fragment is represented by x-y where x and y are the start and end positions respectively of a given preferred fragment. Preferred fragments are separated from each other by a coma. As used herein the term "polynucleotide described in Table III" refers to the all of the preferred polynucleotide fragments defined in Table III in this manner.

In addition, Table IVa provides for preferred fragments of the polynucleotides of the invention while Table Ivb provides for For each polynucleotide referred to by its sequence identification number (first column), the second column of Table IVa provides the positions of fragments which are preferably included in the present invention (column 2) while the second column of IVb provides the positions of fragments which are preferably excluded from the present invention. Each fragment is represented by x-y where x and y are the start and end positions respectively of a given fragment. Fragments are separated from each other by a semi-column. Tables IVa and IVb provides for the inclusion and exclusion of polynucleotides in addition to those described elsewhere in the specification and is therefore, not meant as limiting description. As used herein the terms "polynucleotide described in Table IVa" and "polynucleotide described in Table IVb" refers to the all of the polynucleotide fragments defined in the second column of Tables IVa or IVb respectively in this manner.

The present invention encompasses isolated, purified, or recombinant nucleic acids which consist of, consist essentially of, or comprise a contiguous span of one of the sequences of SEQ ID Nos. 24-73 or a sequence complementary thereto, said contiguous span comprising at least 8, 10, 12, 15, 18, 20, 25, 28, 30, 35, 40, 50, 75, 100, 150, 200, 300, 400, 500, 1000 or 2000 nucleotides of the sequence of SEQ ID Nos. 24-73 or a sequence complementary thereto, to the extent that a contiguous span of these lengths is consistent with the lengths of the particular sequence, wherein the contiguous span comprises at least 1, 2, 3, 5, 10, 15, 18, 20, 25, 28, 30, 35, 40, 50, 75, 100, 150, 200, 300, 400 or 500 of a polynucleotide described in Table III or of a polynucleotide described in Table IVa, or a sequence complementary thereto. The present invention also encompasses isolated, purified, or recombinant nucleic acids comprising, consisting essentially of, or consisting of a contiguous span of at least 8, 10, 12, 15, 18, 20, 25, 28, 30, 35, 40, 50, 75, 100, 150, 200, 300, 400, 500, 1000 or 2000 nucleotides of a polynucleotide described in Table III or of a polynucleotide described in Table IVa or a sequence complementary thereto, to the extent that a contiguous span of these lengths is consistent with the length of the particular sequence described in Table III. The present invention also encompasses isolated, purified, or recombinant nucleic acids which comprise, consist of or consist essentially of a polynucleotide described in Table III or of a polynucleotide described in Table IVa, or a sequence complementary thereto. The present invention further encompasses any combination of the nucleic acids listed in this paragraph.

Cells containing the cDNAs (SEQ ID NOs: 24-73) of the present invention in the vector pBluescriptII SK-(Stratagene) are maintained in permanent deposit by the inventors at Genset, S. A., 24 Rue Royale, 75008 Paris, France.

Pool of cells containing the cDNAs of SEQ ID NOs: 24-73, from which the cells containing a particular polynucleotide is obtainable, were deposited with the European Collection of Cell Cultures (ECACC), Vaccine Research and Production Laboratory, Public Health Laboratory Service, Centre for Applied Microbiology and Reasearch, Porton Down, Salisbury, Wiltshire SP4 OJG, United Kingdom. Each cDNA clone has been transfected into separate bacterial cells (*E-coli*) for these composite deposits. In particular, cells containing the sequences of SEQ ID NOs: 25-40 and 42-46 were deposited on Jun., 17, 1999 in the pool having ECACC Accession No. 99061735 and designated SignalTag 15061999. In addition, cells containing the sequences of SEQ ID Nos: 47-73 were deposited on Dec. 18, 1998, in the pool having ECACC Accession No. 98121805 and designated SignalTag 166-191. Table IV provides the internal designation number assigned to each SEQ ID NO. and indicates whether the sequence is a nucleic acid sequence or a protein sequence.

Each cDNA can be removed from the Bluescript vector in which it was deposited by performing a BsH II double digestion to produce the appropriate fragment for each clone provided the cDNA clone sequence does not contain this restriction site. Alternatively, other restriction enzymes of the multicloning site of the vector may be used to recover the desired insert as indicated by the manufacturer.

Bacterial cells containing a particular clone can be obtained from the composite deposit as follows:

An oligonucleotide probe or probes should be designed to the sequence that is known for that articular clone. This sequence can be derived from the sequences provided herein, or from a combination of those sequences. The design of the oligonucleotide probe should preferably follow these parameters:

(a) It should be designed to an area of the sequence which has the fewest ambiguous bases ("N's"), if any;

(b) Preferably, the probe is designed to have a $T_m$ of approx. 80° C. (assuming 2 degrees for each A or T and 4 degrees for each G or C). However, probes having melting temperatures between 40° C. and 80° C. may also be used provided that specificity is not lost.

The oligonucleotide should preferably be labeled with γ-[$^{32}$P]ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantified by measurement in a scintillation counter. Preferably, specific activity of the resulting probe should be approximately $4 \times 10^6$ dpm/pmole.

The bacterial culture containing the pool of full-length clones should preferably be thawed and 100 μl of the stock used to inoculate a sterile culture flask containing 25 ml of sterile L-broth containing ampicillin at 100 μg/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 μg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them.

The filter is then preferably incubated at 65° C. for 1 hour with gentle agitation in 6×SSC (20×stock is 175.3 g NaCl/liter, 88.2 g Na citrate/liter, adjusted to pH 7.0 with NaOH) containing 0.5% SDS, 100 pg/ml of yeast RNA, and 10 mM EDTA (approximately 10 ml per 150 mm filter). Preferably, the probe is then added to the hybridization mix at a concentration greater than or equal to $1 \times 10^6$ dpm/ml. The filter is then preferably incubated at 65° C. with gentle agitation overnight. The filter is then preferably washed in 500 ml of 2×SSC/0.1% SDS at room temperature with gentle shaking for 15 minutes. A third wash with 0.1×SSC/0.5% SDS at 65° C. for 30 minutes to 1 hour is optional. The filter is then preferably dried and subjected to autoradiography for sufficient time to visualize the positives on the X-ray film. Other known hybridization methods can also be employed.

The positive colonies are picked, grown in culture, and plasmid DNA isolated using standard procedures. The clones can then be verified by restriction analysis, hybridization analysis, or DNA sequencing.

The plasmid DNA obtained using these procedures may then be manipulated using standard cloning techniques familiar to those skilled in the art. Alternatively, a PCR can be done with primers designed at both ends of the cDNA insertion. The PCR product which corresponds to the cDNA can then be manipulated using standard cloning techniques familiar to those skilled in the art.

Tissue expression of the cDNAs of the present invention was also examined. Table VI list the Genset's libraries of tissues and cell types examined that express the polynucleotides of the present invention. The tissues and cell types examined for polynucleotide expression were: brain, fetal brain, fetal kidney, fetal liver, pituitary gland, liver, placenta, prostate, salivary gland, stomach/intestine, and testis. For each cDNA referred to by its sequence identification number (first column), the number of proprietary 5'ESTs expressed in a particular tissue referred to by its name is indicated in parentheses (second column). In addition, the bias in the spatial distribution of the polynucleotide sequences of the present invention is indicated in Table VII. The expression of these sequences were examined by comparing the relative proportions of the biological polynucleotides of a given tissue using the following statistical analysis. The under- or over-representation of a polynucleotide of a given cluster in a given tissue was performed using the normal approximation of the binomial distribution. When the observed proportion of a polynucleotide of a given tissue in a given consensus had less than 1% chance to occur randomly according to the chi2 test, the frequency bias was reported as "preferred". The results are given in Table VII as follows. For each polynucleotide showing a bias in tissue distribution as referred to by its sequence identification number in the first column, the list of tissues where the polynucleotides are over-represented is given in the second column entitled "preferential expression".

In addition, the spatial distribution of the polynucleotide sequences of the present invention was investigated using information from public databases. The expression of the sequences of SEQ ID NOs:24-73 was examined by comparing them to the polynucleotide sequences in public databases. Table VIII lists tissues and cell types which express the polynucleotides of the sequence listing. Column one lists the sequence identification number and column two lists the corresponding tissues and cell types that were found to express the polynucleotide sequences using information from public databases. The number to the right of the tissue or cell type in column two represents the number of entries in the databases listing that tissue or cell type as expressing the sequence of column 1.

In one embodiment, polynucleotides of the invention selectively expressed in tissues may be used as markers to identify these tissues using any technique known to those skilled in the art those skilled in the art such as in situ PCR. Such tissue-specific markers may then be used to identify tissues of unknown origin, for example, forensic samples, differentiated tumor tissue that has metastasized to foreign bodily sites, or to differentiate different tissue types in a tissue cross-section using immunochemistry. For example, polynucleotides of the invention preferentially expressed in given tissues as indicated in Table VII may be used for this purpose. In addition, the polynucleotide of SEQ ID NO:39 may be used to selectively identify liver tissue. The polynucleotide of SEQ ID NO:52 may be used to selectively identify prostate tissue. The polynucleotides of SEQ ID NO:44, 46 and 72 may be used to selectively identify normal or diseased brain tissue.

EXAMPLE 15B

Functional Analysis of Predicted Protein Sequences

Following double-sequencing, contigated sequences were assembled for each of the cDNAs of the present invention and further reanalyzed. The following databases were used in sequence analyses: Genbank (release 117), EMBL (release 62), TrEmbl (release 13.4) Genseq (release 0011) Swissprot (release 38), PIR (release 64). In some cases, more preferred open reading frames differing from the ones previously selected in priority applications are indicated.

The polypeptides (SEQ ID NOs:74-123) encoded by the cDNAs were screened for the presence of known structural or functional motifs or for the presence of signatures, small amino acid sequences that are well conserved amongst the members of a protein family. The search was conducted on the Pfam 5.2 database using HMMER-2.1.1 (for info see Sonnhammer et Durbin, world wide web site: sanger.ac.uk/Pfam/), on the BLOCKSPLUS v 11.0 database using emotif (for info see Nevill-Manning et al., PNAS, 95, 5865-5871, (1998), world wide web site: motif.stanford/edu/EMOTIF) and on the Prosite 15.0 database using bla (Tatusov, R. L. & Koonin, E. V. CABIOS 10, No. 4) and pfscan (world wide web site: isrec.isb-sib.ch/cgi-bin/man.cgi?section=1&topic=pfscan).

It should be noted that, in the numbering of amino acids in the protein sequences discussed below, and in Table IX, the first methionine encountered is designated as amino acid number 1, i.e;, the leader sequence is not numbered negatively. In the appended sequence listing, the first amino acid of the mature protein resulting from cleavage of the signal peptide is designated as amino acid number 1 and the first amino acid of the signal peptide is designated with the appropriate negative number, in accordance with the regulations governing sequence listings. Each of the references cited in this example are hereby incorporated by reference in their entireties.

Table IX lists known biologically structural and functional domains for the cDNA of the present invention corresponding to the sequence identification number indicated in the first column. Column 2 lists the positions of the domains where each domain is represented by x-y where x and y are the start and end positions respectively of a given domain. Column 3 lists the domain designation. Column 4 lists the database from which the domain was identified.

Protein of SEQ ID NO: 93 (Internal Designation 117-007-2-0-C4-FLC)

The protein of SEQ ID NO: 93 encoded by the cDNA of SEQ ID NO:43 found in liver is homologous to a human protein thought to be transmembraneous (Genseq accession number W88491). In addition, this protein displays homology to alpha-2-HS glycoprotein precursors (fetuins) of human and pigs. The 382-amino-acid-long protein of SEQ ID NO: 93, which is similar in size to fetuins, displays pfam cystatin domains 1 and 2 from positions 37 to 104 and from positions 157 to 254. It also displays the 12 conserved cysteines of this family (positions 36, 93, 104, 117, 137, 151, 154, 216, 224, 237, 254 and 368) and a conserved region around the second cysteine (positions 89 to 96). In addition, the potential active site QxVxG is also present in the protein of the invention (positions 198 to 202).

Mammalian fetuins are secreted glycoproteins synthesized in liver and selectively concentrated in bone matrix. Their functions include control of endocytosis, cell proliferation and differentiation, immune response, bone formation and resorption, and apoptosis. More specifically, fetuin levels in human plasma are regulated in the manner of a negative acute phase reactant (Lebreton et al., J. Clin. Invest. 64:1118-29 (1979)) and serum levels decline in some cancer patients correlating with impaired cellular immune function (Baskies et al., Cancer 45:3050-58 (1980)). During mouse embryogenesis, fetuin mRNA is expressed in a number of developing organs and tissues including the heart, kidney, lung, nervous system and liver (Yang et al., Biochem. Biophysic. Acta 1130: 149-56 (1992)). Mammalian fetuin present in sub-populations of neurons in the developing central and peripheral nervous system is associated to cell survival (Saunders et al., Anat. Embryol 186:477-86 (1992)); Kitchener et al., Int J. Dev. Neurosci. 15:717-27 (1997)). Fetuin is able to promote growth in tissue culture (Puck et al. Proc. Natl. Acad. Sci. U.S.A., 59:192-99 (1968)), to enhance bone resorption (Coclasure et al., J. Clin. Endocrinol. Metab. 66:187-192 (1988)) and to stimulate adipogenesis in cell culture models (Cayatte et al., J. Biol. Chem. 265:5883-8 (1990)). Abnormal serum levels of fetuin are associated with alteration in cellular and biochemical properties of bone, Paget's disease, reduced bone quality and osteogenesis imperfecta (for a review see Binkert et al, J. Biol. Chem. 274:28514-20 (1999)). Part of the fetuin activities has been shown to depend upon their ability to inhibit the activity of TGF-beta cytokines and bone morphogenetic proteins (BMPs) through direct binding (Demetriou et al., J. Biol. Chem. 271:12755-61 (1996); Binkert et al., J. Biol. Chem. 274:28514-20 (1999)). These ligands are members of the TGF-beta superfamily comprising proteins belonging to the TGF-beta, activin/inhibin, DPP/VG1, and Mullerian Inhibiting Substance Family families mediating a wide range of biological processes in vertebrates and invertebrates, including regulation of cell proliferation, differentiation, recognition, and death, and thus play a major role in developmental processes, tissue recycling, and repair (J. Wrana and L. Attisano, "Mad-related Proteins in TGF-beta Signaling," TIG 12:493-496, 1996; U.S. Pat. No. 5,981,483). In addition, fetuins are members of the cystatin superfamily which contains evolutionarily related proteins with diverse functions such as cysteine protease inhibitors, stefins, fetuins and kininogens (see review by Brown and Dziegielewska, Prot. Science, 6:5-12 (1997)).

It is believed that the protein of SEQ ID NO: 93 or part thereof is a member of the cystatin superfamily and, as such, plays a role in cellular proteolysis, endocytosis, cell proliferation and differentiation, immune response, bone formation and resorption, and/or apoptosis. Preferred polypeptides of the invention are polypeptides comprising the amino acids of SEQ ID NO:93 from positions 37 to 104, 89 to 96, 157 to 254, 198 to 202, and 36 to 368. Other preferred polypeptides of the invention are fragments of SEQ ID NO:93 having any of the biological activity described herein.

An embodiment of the present invention relates to methods of using the protein of the invention or part thereof to identify and/or quantify cytokines of the TGF-beta superfamily, more preferably TGF-1beta, TGF-2beta and BMP-2, BMP-4 and BMP-6 in a biological sample, and thus used in assays and diagnostic kits for the quantification of such cytokines in bodily fluids, in tissue samples, and in mammalian cell cultures. The binding activity of the protein of the invention or part thereof may be assessed using the assay described in Demetriou et al., J. Biol. Chem. 271:12755-61 (1996) or any other method familiar to those skilled in the art. Preferably, a defined quantity of the protein of the invention or part thereof is added to the sample under conditions allowing the formation of a complex between the protein of the invention or part thereof and the cytokine to be identified and/or quantified. Then, the presence of the complex and/or or the free protein of the invention or part thereof is assayed and eventually compared to a control using any of the techniques known by those skilled in the art.

Another embodiment of the invention relates to compositions and methods using the protein of the invention or part thereof to modulate the activity of members of the TGF beta superfamily, preferably members of TGF beta family, members of actin/inhibin family, members of DPP/VG1 family, and members of Mullerian inhibiting substance family, more preferably TGF-1beta, TGF-2beta, BMP-2, BMP-4 and BMP-6, in contexts where the production of such proteins is undesirable.

In a preferred embodiment, the protein of the invention or part thereof is used to inhibit and/or attenuate the effects of cytokines belonging to the TGF beta family, such as TGF-1beta, TGF-2beta and BMP-2, BMP-4 and BMP-6, by blocking the binding of endogenous cytokines to its natural receptor, thereby blocking cell proliferative or inhibitory signals generated by the ligand-receptor binding event. The protein of the invention or part thereof would thereby stimulate immune responses and reduce the deposition of extracellular matrix. Accordingly, the protein of the invention or part thereof, would be particularly suitable for the treatment of conditions such as fibrosis including pulmonary fibrosis, fibrosis associated with chronic liver disease, hepatic veno-occlusive and idiopathic interstitial pneumonitis, kidney disease, and radiotherapy or radiation accidents; proliferative vitreoretinopathy; systemic sclerosis; autoimmune disorders such as rheumatoid arthritis, Graves disease, systemic lupus erythematosus, Wegener's granulomatosis, sarcoidosis, polyarthritis, pemphigus, pemphigoid, erythema multiform, Sjogren's syndrome, inflammatory bowel disease, multiple sclerosis, myasthenia gravis keratitis, scleritis, Type I diabetes, insulin-dependent diabetes mellitus, Lupus Nephritis, and allergic encephalomyelitis; proliferative disorders including various forms of cancer such as leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, atherosclerosis, angiogenesis, and viral infections, in particular HIV infections. The protein of the invention or part thereof may also be used, as an antagonist of cytokines of the TGF-beta family, to elevate blood pressure through the inhibition of hypotension induced by TGF-beta. Methods which lower and/or maintain the level of circulating TGF-beta in a subject may result in a similar pressor effect and may prevent excessive hypotensive signal generation and resulting hypotension.

In another preferred embodiment, the protein of the invention or part thereof is used to block the normal interaction between activin and its receptor. The protein of the invention or part thereof would thereby stimulate the release of FSH. Accordingly, the protein of the invention or part thereof can be applied to the control of fertility in humans, domesticated animals, and animals of commercial interest. The action of activin on erythropoiesis can also be modulated by administering a modulating effective amount of the protein of the invention or part thereof. Thus, the protein of the invention or part thereof may be used in the diagnosis and/or treatment of activin-dependent tumors or for enhancing the survival of brain neurons.

In still another preferred embodiment, the protein of the invention or part thereof is used to modulate bone formation and bone cell differentiation through binding to bone morphogenetic proteins and/or to TGF-beta proteins. Therefore, the protein of the invention or part thereof may be used to repair or heal fractures, treat osteoporosis, address dental problems, and with implants to encourage bone growth. In addition, the protein of the invention or part thereof may be used in disorders where there is too much bone formation (for example, achondroplasia, Paget's disease, and osteoporosis). The utility of the protein of the invention or part thereof may be further confirmed using binding assays and animal models described in Demetriou et al., J. Biol. Chem. 271:12755-61 (1996) and in U.S. Pat. No. 5,981,483.

In still another embodiment, the invention relates to methods and compositions containing the protein of the invention or part thereof to treat and/or prevent the ill-effects of bacterial infection during pregnancy in mammals, such as spontaneous abortion and maternal death. In a preferred embodiment, the protein of the invention may be used to counteract the effects of the bacterial endotoxin lipopolysaccharide (LPS). The method to use such compositions is described in Dziegielewska and Andersen, Biol. Neonate, 74:372-5 (1998).

In another series of embodiments, the protein of the invention, or part thereof may be used to inhibit proteases, preferably cysteine proteases. Examples of cysteine proteases that may be inhibited by the protein of the invention or part thereof include, but are not limited to, the plant cysteine proteases such as papain, ficin, aleurain, oryzain and actinidin; mammalian cysteine proteases such as cathepsins B, H, J, L, N, S, T, O, O2 and C, (cathepsin C is also known as dipeptidyl peptidase I), interleukin converting enzyme (ICE), calcium-activated neutral proteases, calpain I and II; bleomycin hydrolase, viral cysteine proteases such as picomian 2A and 3C, aphthovirus endopeptidase, cardiovirus endopeptidase, comovirus endopeptidase, potyvirus endopeptidases I and II, adenovirus endopeptidase, the two endopeptidases from chestnut blight virus, togavirus cysteine endopeptidase, as well as cysteine proteases of the polio and rhinoviruses; and cysteine proteases known to be essential for parasite life-cycles, such as the proteases from species of Plasmodia, Entamoeba, Onchocera, Trypanosoma, Leishmania, Haemonchus, Dictyostelium, Therileria, and Schistosoma, such as those associated with malaria (*P. falciparum*), trypanosomes (*T. cruzi*, the enzyme is also known as cruzain or cruzipain), murine *P. vinckei*, and the *C. elegans* cysteine protease. For an extensive listing of cysteine proteases that may be inhibited by the protein or part thereof of the present invention, see Rawlings et al., Biochem. J. 290:205-218 (1993). Assays for testing the inhibitory activities of cysteine protease inhibitors are presented in the U.S. Pat. No. 5,973,110, using methods for determining inhibition constants well known to those skilled in the art (see Fersht, ENZYME STRUCTURE AND MECHANISM, 2nd ed., W. H. Freeman and Co., New York, (1985)).

Since proteases play an important role in the regulation of many biological processes in virtually all living organisms as well as a major role in diseases, the protein of the invention or part thereof are useful in a wide variety of applications, such as those described in U.S. Pat. No. 6,004,933.

An embodiment of the present invention further relates to methods of using the protein of the invention or part thereof to quantify the amount of a given protease in a biological sample, and thus used in assays and diagnostic kits for the quantification of proteases in bodily fluids or other tissue samples, in addition to bacterial, fungal, plant, yeast, viral or mammalian cell cultures. In a preferred embodiment, the sample is assayed using a standard protease substrate. A known concentration of protease inhibitor is added, and allowed to bind to a particular protease present. The protease assay is then rerun, and the loss of activity is correlated to the protease inhibitor activity using techniques well known to those skilled in the art.

In addition, the protein of the invention or part thereof may be useful to remove, identify or inhibit contaminating proteases in a sample. Compositions comprising the polypeptides of the present invention may be added to biological samples as a "cocktail" with other protease inhibitors to prevent degradation of protein samples. The advantage of using a cocktail of protease inhibitors is that one is able to inhibit a wide range of proteases without knowing the specificity of any of the proteases. Using a cocktail of protease inhibitors also protects a protein sample from a wide range of future unknown proteases which may contaminate a protein sample from a vast number of sources. Such protease inhibitor cocktails (see for example the ready to use cocktails sold by Sigma) are widely used in research laboratory assays to inhibit proteases susceptible of degrading a protein of interest for which the assay is to be performed. For example, the protein of the invention or part thereof is added to samples where proteolytic degradation by contaminating proteases is undesirable. Alternatively, the protein of the invention or part thereof may be bound to a chromatographic support, either alone or in combination with other protease inhibitors, using techniques well known in the art, to form an affinity chromatography column. A sample containing the undesirable protease is run through the column to remove the protease. Alternatively, the same methods may be used to identify new proteases.

In a preferred embodiment, the protein of the invention or part thereof may be used to inhibit proteases implicated in a number of diseases where cellular proteolysis occur. In particular, the protein of the invention or part thereof may be useful to inhibit lysosomal cysteine proteases, both in vivo or in vitro, implicated in a wide spectrum of diseases characterized by tissue degradation including but not limited to arthritis, muscular dystrophy, inflammation, tumor invasion, glomerulonephritis, parasite-borne infections, Alzheimer's disease, periodontal disease, and cancer metastasis.

In another preferred embodiment, the protein of the invention or part thereof may be used to inhibit exogenous proteases, both in vivo or in vitro, implicated in a number of infectious diseases including but not limited to gingivitis, malaria, leishmaniasis, filariasis, osteoporosis and osteoarthritis, and other bacterial, and parasite-borne or viral infections. In particular, the protein of the invention or part thereof may offer applications in viral diseases where the proteolysis of primary polypeptide precursors is essential to the replication of the virus, as for HIV and HCV.

In another preferred embodiment, the protein of the invention or part thereof is used to prevent cells to undergo apoptosis. In a preferred embodiment, the apoptosis active polypeptide is added to an in vitro culture of mammalian cells in an amount effective to reduce apoptosis. For example, inhibiting the activity of apopain, a cysteine protease member of the ICE/CED-3 subfamily involved in apoptosis, attenuates apoptosis in vitro (U.S. Pat. No. 5,798,442). Furthermore, the protein of the invention or part thereof may be useful in the diagnosis, the treatment and/or the prevention of disorders in which apoptosis is deleterious, including but not limited to immune deficiency syndromes (including AIDS), type I diabetes, pathogenic infections, cardiovascular and neurological injury, alopecia, aging, Parkinson's disease and Alzheimer's disease.

Additionally, the protein of the invention or part thereof offer application in the treatment of inflammation and immune based disorders of the lung, airways, central nervous system and surrounding membranes, eyes, ears, joints, bones, connective tissues, cardiovascular system including the pericardium, gastrointestinal and urogenital systems, the skin and the mucosal membranes. These conditions include infectious diseases where active infection exists at any body site, such as meningitis and salpingitis; complications of infections including septic shock, disseminated intravascular coagulation, and/or adult respiratory distress syndrome; acute or chronic inflammation due to antigen, antibody and/or complement deposition; inflammatory conditions including arthritis, chalangitis, colitis, encephalitis, endocarditis, glomerulonephritis, hepatitis, myocarditis, pancreatitis, pericarditis, reperfusion injury and vasculitis. Immune-based diseases include but are not limited to conditions involving T-cells and/or macrophages such as acute and delayed hypersensitivity, graft rejection, and graft-versus-host disease; autoimmune diseases including Type I diabetes mellitus and multiple sclerosis. Bone and cartilage reabsorption as well as diseases resulting in excessive deposition of extracellular matrix such as interstitial pulmonary fibrosis, cirrhosis, systemic sclerosis, and keloid formation may also be treated with the protein of the invention or part thereof.

Furthermore, the protein of the present invention or part thereof find use in drug potentiation applications. For example, therapeutic agents such as antibiotics or antitumor drugs can be inactivated through proteolysis by endogenous proteases, thus rendering the administered drug less effective or inactive. Accordingly, the protein of the invention or part thereof may be administered to a patient in conjunction with a therapeutic agent in order to potentiate or increase the activity of the drug. This co-administration may be by simultaneous administration, such as a mixture of the protease inhibitor and the drug, or by separate simultaneous or sequential administration.

In addition, protease inhibitors have been shown to inhibit the growth of microorganisms including human pathogenic bacteria. For example, protease inhibitors are able to inhibit growth of all strains of group A streptococci, including antibiotic-resistant strains (Merigan, T. et al (1996) Ann Intem Med 124:1039-1050; Stoka, V. (1995) FEBS. Lett 370:101-104; Vonderfecht, S. et al (1988) J Clin Invest 82:2011-2016; Collins, A. et al (1991) Antimicrob Agents Chemother 35:2444-2446). Accordingly, the protein of the invention may or part thereof be used as antibacterial agents to retard or inhibit the growth of certain bacteria either in vitro or in vivo. Particularly, the polypeptides of the present invention may be used to inhibit the growth of group A streptococci on non-living matter such as instruments not conducive to other methods of preventing or removing contamination by group A streptococci, and in culture of living plant, fungi, and animal cells.

Protein of SEQ ID NO: 86 (Internal Designation 116-054-3-0-G12-FLC)

The protein of SEQ ID NO: 86 encoded by the cDNA of SEQ ID NO:36 found in liver is homologous to the subunit 2 of NADH dehydrogenase (Genseq accession number Y14556) and to the MLRQ subunit of NADH dehydrogenase (NADH-ubiquinone oxidoreductase, NADH-D or complex I) of bovine, murine and human species (Genbank accession numbers X64897, U59509 and EMBL accession number U94586 respectively). In addition, the 83-amino-acid-long protein of SEQ ID NO: 86 has a size similar to those of known MLRQ subunits as well as an hydrophobic N-terminal region of 25-30 amino acids.

Complex I is the first of 3 multienzyme complexes located in the mitochondrial membrane that make up the mitochondrial electron transport chain. Complex I accomplishes the first step in this process by accepting electrons from NADH and passing them through a flavin molecule to ubiquinone which then transfers electrons to the second enzyme complex in the chain.

Complex I contains approximately 40 polypeptide subunits of widely varying size and composition and is highly conserved in a variety of mammalian species including rat, rabbit, cow, and human (Cleeter, M. W. J. and Ragan, C. I. (1985) Biochem. J. 230: 739-46). The best characterized complex I is from bovine heart mitochondria and is composed of 41 polypeptides (Walker, J. E. et al. (1992) J. Mol. Biol. 226: 1051-72). Seven of these polypeptides are encoded by mitochondrial DNA, while the remaining 34 are nuclear gene products that are imported into the mitochondria. Six of these imported polypeptides are characterized by N-terminal signal peptide sequences which target these polypeptides to the mitochondria and are then cleaved from the mature proteins. A second group of polypeptides lack N-terminal targeting sequences and appear to contain import signals which lie within the mature protein (Walker et al., supra). The functions of many of the individual subunits in NADH-D are largely unknown. The 24-, 51-, and 75-kDa subunits have been identified as being catalytically important in electron transport, with the 51-kDa subunit forming part of the NADH binding site and containing the flavin moiety that is the initial electron acceptor (Ali, S. T. et al. (1993) Genomics 18:435-39). The location of other functionally important groups, such as the electron-carrying iron-sulfate centers, remains to be determined. Many of the smaller subunits (<30 kDa) contain hydrophobic sequences that may be folded into membrane spanning alpha-helices. These subunits presumably are anchored into the inner membrane of the mitochondria and interact via more hydrophilic parts of their sequence with globular proteins in the large extrinsic domain of NADH-D. The remaining proteins are likely to be globular and form part of a domain outside the lipid bilayer. The MLRQ subunit is one of the small (9 kDa) subunits that is nuclear encoded and contains no N-terminal extension to direct the protein into the nitochondrion, thus implying that the import signal should lie into the mature protein (Walker et al. supra). A potential membrane-spanning alpha-helix presumably anchors the MLRQ subunit to the inner membrane of the mitochondria, but the precise function of the subunit is unknown.

Mitochondriocytopathies due to complex I deficiency are frequently encountered and affect tissues with a high-energy demand such as brain (mental retardation, convulsions, movement disorders), heart (cardiomyopathy, conduction disorders), kidney (Fanconi syndrome), skeletal muscle (exercise intolerance, muscle weakness, hypotonia) and/or eye (opthmaloplegia, ptosis, cataract and retinopathy). Complex I is also thought to play a role in the regulation of apoptosis and necrosis. For a review on complex I, see Smeitink et al., *Hum. Mol. Gent.*, 7: 1573-1579 (1998); Lenaz et al., Acta Biochem Pol 46:1-21 (1999); Lee and Wei, J Biomed Sci 7:2-15 (2000). In addition, defects and altered expression of complex I are associated with a variety of disease conditions in man, including neurodegenerative diseases, myopathies, and cancer (Singer, T. P. et al. (1995) Biochim. Biophys. Acta 1271:211-19; Selvanayagam, P. and Rajaraman, S. (1996) Lab. Invest. 74:592-99). Moreover, NADH-D reduction of the quinone moiety in chemotherapeutic agents such as doxorubicin is believed to contribute to the antitumor activity and/or mutagenicity of these drugs (Akman, S. A. et al. (1992) Biochemistry 31:3500-6).

It is believed that the protein of SEQ ID NO: 86 is a NADH-ubiquinone oxidoreductase MLRQ-like protein and/or plays a role in mitochondria electron transport. Preferred polypeptides of the invention are fragments of SEQ ID NO: 111 having any of the biological activities described herein An object of the present invention are compositions and methods of targeting heterologous compounds, either polypeptides or polynucleotides to mitochondria by recombinantly or chemically fusing a fragment of the protein of the invention to an heterologous polypeptide or polynucleotide. Preferred fragments are signal peptide, amphiphilic alpha helices and/or any other fragments of the protein of the invention, or part thereof, that may contain targeting signals for mitochondria including but not limited to matrix targeting signals as defined in Herrman and Neupert, Curr. Opinion Microbiol. 3:210-4 (2000); Bhagwat et al. J. Biol. Chem. 274:24014-22 (1999), Murphy Trends 25 Biotechnol. 15:326-30 (1997); Glaser et al. Plant Mol Biol 38:311-38 (1998); Ciminale et al. Oncogene 18:4505-14 (1999). Such heterologous compounds may be used to modulate mitochondria's activities. For example, they may be used to induce and/or prevent mitochondrial-induced apoptosis or necrosis. In addition, heterologous polynucleotides may be used for mitochondrial gene therapy to replace a defective mitochondrial gene and/or to inhibit the deleterious expression of a mitochondrial gene.

In another embodiment, the protein of the invention or part thereof is used to prevent cells to undergo apoptosis. In a preferred embodiment, the apoptosis active polypeptide is added to an in vitro culture of mammalian cells in an amount effective to reduce apoptosis. Furthermore, the protein of the invention or part thereof may be useful in the diagnosis, the treatment and/or the prevention of disorders in which apoptosis is deleterious, including but not limited to immune deficiency syndromes (including AIDS), type I diabetes, pathogenic infections, cardiovascular and neurological injury, alopecia, aging, degenerative diseases such as Alzheimer's Disease, Parkinson's Disease, Huntington's disease, dystonia, Leber's hereditary optic neuropathy, schizophrenia, and myodegenerative disorders such as "mitochondrial encephalopathy, lactic acidosis, and stroke" (MELAS), and "myoclonic epilepsy ragged red fiber syndrome" (MERRF).

The invention further relates to methods and compositions using the protein of the invention or part thereof to diagnose, prevent and/or treat several disorders in which mitochondrial respiratory electron transport chain is impaired, or needs to be impaired, including but not limited to mitochondriocytopathies, necrosis, aging, neurodegenerative diseases, myopathies, and cancer. For diagnostic purposes, the expression of the protein of the invention could be investigated using any of the Northern blotting, RT-PCR or immunoblotting methods described herein and compared to the expression in control individuals. For prevention and/or treatment purposes, the protein of the invention may be used to enhance electron transport and increase energy delivery using any of the gene therapy methods described herein or known to those skilled in the art.

Moreover, antibodies to the protein of the invention or part thereof may be used for detection of mitochondria organelles and/or mitochondrial membranes using any techniques known to those skilled in the art.

Protein of SEQ ID NO: 111 (Internal Designation 108-013-5-O-H9-FL)

The protein of SEQ ID NO: 111 encoded by the extended cDNA SEQ ID NO: 61 is homologous to the human IHLP lysophospholipase (Genseq accession number W88457) and to a family of lysophospholipases conserved among eukaryotes (yeast, rabbit, rodents and human). In addition, some members of this family (rat :Genbank accession number U97146, rabbit: Genbank accession number U97147) exhibit a calcium-independent phospholipase A2 activity (Portilla et al, *J. Am. Soc. Nephro.*, 9:1178-1186 (1998)). All members of this family exhibit the active site consensus GXSXG motif of carboxylesterases that is also found in the protein of the invention (position 54 to 58). The protein of the invention also exhibits an emotif alpha/beta hydrolase fold signature from positions 52 to 66. In addition, this protein may be a membrane protein with one transmembrane domain as predicted by the software TopPred II (Claros and von Heijne, *CABIOS applic. Notes*, 10:685-686 (1994)).

Lysophospholipids are found in very low concentrations in biological membranes. Higher concentrations of lysophospholipids have been shown to disturb membrane conformation, affect the activities of many membrane-bound enzymes and may even lead to cell lysis. In addition, increased lysophospholipid levels were observed in atherosclerosis, inflammation, hyperlipidemia, lethal dysrhythmias in myocardial ischemia and segmental demyelination of peripheral nerves. Some lysophospholipids, such as lysophosphatidylcholine, may act as lipid second messengers, transducing signals eliciting from membrane receptors. They may also potentiate immune responses and exhibit anti-tumor effects as bactericidal activities (for a review see Wang and Dennis, Biochim Biophys Acta; 1439:1-16 (1999)).

Lysophospholipase is a widely distributed enzyme which regulates the level of lysophospholipids and occurs in numerous isoforms. These isoforms vary in molecular mass, substrate metabolized, and optimum pH required for activity. Small isoforms, approximately 15-30 kDa, function as hydrolases; large isoforms, those exceeding 60 kDa function both as transacylases and hydrolases. Lysophospholipases are regulated by lipid factors such as acylcarnitine, arachidonic acid and phosphatidic acid. The expression of IHLP is associated with proliferation and differentiation of cells of the immune system.

The role of lysophospholipases in human tissues has been investigated in various research studies. Selle, H. et al. (1993; Eur. J. Biochem. 212:411-16) characterized the role of lysophopholipase in the hydrolysis of lysophosphatidylcholine which causes lysis in erythrocyte membranes. Similarly, Endresen, M. J. et al. (1993) Scand. J. Clin. Invest. 53:733-9 reported that the increased hydrolysis of lysophosphatidylcholine by lysophopholipase in pre-eclamptic women causes release of free fatty acids into the sera. In renal studies, lysophopholipase was shown to protect NA+, K+-ATPase from the cytotoxic and cytolytic effects of cyclosporin A (Anderson, R. et al. (1994) Toxicol. Appl. Pharmacol. 125: 176-83).

It is believed that the protein of SEQ ID NO: 111 or part thereof plays a role in fatty acid metabolism, probably as a phospholipase. Preferred polypeptides of the invention are polypeptides comprising the amino acids of SEQ ID NO: 111 from positions 54 to 58, and 52 to 66. Other preferred polypeptides of the invention are fragments of SEQ ID NO: 111 having any of the biological activities described herein. The hydrolytic activity of the protein of the invention or part thereof may be assayed using any of the assays known to those skilled in the art including those described in Portilla et al., J Am Soc Nephrol; 9:1178-1186 (1998) and in the U.S. Pat. No. 6,004,792.

The invention relates to methods and compositions using the protein of the invention or part thereof to hydrolyze one or several substrates, alone or in combination with other substances. Such substrates are glycerophospholipids, preferably containing an acyl ester bond at the sn-2 position, more preferably lysophosphatidylcholine, lysophosphatidylinositol, lysophosphatidylserine, 1-oleoyl-2-acetyl-sn-glycero-3-phosphocholine, lecithin and lysolecithin. For example, the protein of the invention or part thereof is added to a sample containing the substrate(s) in conditions allowing hydrolysis, and allowed to catalyze the hydrolysis of the substrate(s). In a preferred embodiment, the hydrolysis is carried out using a standard assay such as those described by Portilla et al., supra and in the U.S. Pat. No. 6,004,792.

In a preferred embodiment, the protein of the invention or part thereof may be used to hydrolyze undesirable phospholipids, both in vitro or in vivo. In particular, the protein of the invention or part thereof may be used as a food additive to improve fat digestibility and to promote growth in animals using methods described in U.S. Pat. No. 6,017,530. In another preferred embodiment, the protein of the invention or part thereof may be used to improve the filtration of starch syrup by hydrolyzing the turbidity consisting mainly from phospholipids and resulting from the production of highly concentrated solutions of glucose isomers using methods described in U.S. Pat. No. 5,965,422. In addition, the protein of the invention or part thereof may be used in an enzymatic degumming process to free vegetable oils from phospholipids in order to allow their refining using methods described in U.S. Pat. No. 6,001,640. In another preferred embodiment, compositions comprising the protein of the present invention or part thereof are added to samples as a "cocktail" with other hydrolytic enzymes, such as other phospholipases for example to improve feed utilization in animals (see U.S. Pat. No. 6,017,530). The advantage of using a cocktail of hydrolytic enzymes is that one is able to hydrolyze a wide range of substrates without knowing the specificity of any of the enzymes. Using a cocktail of hydrolytic enzymes also protects a sample from a wide range of future unknown contaminants from a vast number of sources. For example, the protein of the invention or part thereof is added to samples where contaminating substrates is undesirable. Alternatively, the protein of the invention or part thereof may be bound to a chromatographic support, either alone or in combination with other hydrolytic enzymes, using techniques well known in the art, to form an affinity chromatography column. A sample containing the undesirable substrate is run through the column to remove the substrate. Immobilizing the protein of the invention or part thereof on a support is particularly advantageous for those embodiments in which the method is to be practiced on a commercial scale. This immobilization facilitates the removal of the enzyme from the batch of product and subsequent reuse of the enzyme. Immobilization of the protein of the invention or part thereof can be accomplished, for example, by replacing the transmembrane region by a cellulose-binding domain in the protein. One of skill in the art will understand that other methods of immobilization could also be used and are described in the available literature. Alternatively, the same methods may be used to identify new substrates.

In another embodiment, the protein of the invention or part thereof may be used to identify or quantify the amount of a given substrate in a biological sample. In a preferred embodiment, the protein of the invention or part thereof is used in assays and diagnostic kits for the identification and quantification of substrates in a biological sample.

In still another embodiment, the protein of the invention or part thereof may be used to diagnose, treat and/or prevent disorders where the presence of substrates is undesirable or deleterious. Such disorders include but are not limited to, cancer, neurodegenerative disorders such as Parkinson's and Alzheimer's diseases, diabetes. In a preferred embodiment, the protein of the invention or part thereof may be administered to a subject to reduce immune response. Although the inventors do not wish to be limited to a particular mechanism of action, it is thought that reduction would at least protect against lysophospholipid toxicity, deacylate platelet activating factor, and hydrolyze lytic lysophospholipids such as lysophosphatidylcholine which contribute to immune response, and in particular hypersensitivity reactions and immune cell mediated injuries. Such injuries include, but are not limited to, adult respiratory distress syndrome, allergies, asthma, arteriosclerosis, bronchitis, emphysema, hypereosinophilia, myocardial or pericardial inflammation, rheumatoid arthritis, complications of heart attack, stroke, cancer, hemodialysis, infections, and trauma.

In addition, the protein of the invention or part thereof may be used to identify inhibitors for mechanistic and clinical applications. Such inhibitors may then be used to identify or quantify the protein of the invention in a sample, and to diagnose, treat or prevent any of the disorders where the protein's activity is undesirable and/or deleterious including but not limited to inflammation, disorders associated with cell proliferation, immune and inflammatory disorders. Disorders associated with cell proliferation include adenocarcinoma, sarcoma, lymphoma, leukemia, melanoma, myeloma, teratocarcinoma, and in particular, cancers of the adrenal gland, bladder, bone, brain, breast, gastrointestinal tract, heart, kidney, liver, lung, ovary, pancreas, paraganglia, parathyroid, prostate, salivary glands, skin, spleen, testis, thyroid, and uterus. Immune and inflammatory disorders include Addison's disease, AIDS, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polycystic kidney disease, polymyositis, rheumatoid arthritis, scleroderma, Sjogren's syndrome, autoimmune thyroiditis.

Moreover, antibodies to the protein of the invention or part thereof may be used for detection of the Golgi apparatus using any techniques known to those skilled in the art.

Protein of SEQ ID NO: 76 (Internal Designation 105-095-1-0-D10-FLC)

The protein of SEQ ID NO: 76 encoded by the cDNA of SEQ ID NO:26 is homologous to the human parotid secretory protein HPSP (Genseq accession number W60682 and SEQ ID NO: 124). PSPs are leucine-rich glycoproteins well conserved among the murine, rat, bovine and human species which belongs to the PSP multigenic family with gland specific members which common traits are early and abundant expression. Because it is extremely abundant in saliva, PSP has been proposed as a marker for tissue-specific protein production of salivary glands and appears coordinately regulated with salivary amylase. PSP is also expressed although to a lesser extent in murine lacrimal glands. Although its function remains unknown, it was shown to bind to bacteria in exocrine secretions and was proposed to have antibacterial activity (Robinson et al., *Am J Physiol* 272:G863-G871 (1997)). Antagonists of this protein may be used to treat cancer and autoimmune diseases particularly of secretory or gastrointestinal tissue.

It is believed that the protein of SEQ ID NO: 76 or part thereof plays a role in the defense against pathogens, preferably pathogens present in the oral and gastrointestinal tracts. Preferred polypeptides of the invention are fragments of SEQ ID NO: 76 having any of the biological activity described herein. The activity of the protein of the invention or part thereof on pathogens may be assessed using techniques well known to those skilled in the art including those described in Robinson et al, supra.

In one embodiment, the present invention relates to methods and compositions using the protein of the invention or part thereof to detect bacteria in biological fluids, foods, water, air, solutions and the like. For example, the protein of the invention or part thereof is added to a sample containing bacteria and allowed to bind to such bacteria using any method known to those skilled in the art including those described in Robinson et al, supra. Then, the protein may be detected using any method known to those skilled including using an antibody able to bind to the protein of the invention or part thereof, or using another polypeptide fused to the protein of the invention or part thereof that may be detected directly, such as the green fluorescent protein, or though binding to a specific antibody. In a preferred embodiment, the protein of the invention or part thereof is used in assays and diagnostic kits for the detection of exogenous pathogens in bodily fluids, tissue samples or cell cultures. In another preferred embodiment, the protein of the invention or part thereof may be used to decontaminate samples. For example, the protein of the invention or part thereof may be bound to a chromatographic support using techniques well known in the art, to form an affinity chromatography column. A sample containing the undesirable contaminant is run through the column in order to be removed. Immobilizing the protein of the invention or part thereof on a support advantageous is particularly for those embodiments in which the method is to be practiced on a commercial scale. This immobilization facilitates the removal of the protein of the invention from the batch of product and its subsequent reuse. Immobilization of the protein of the invention or part thereof can be accomplished, for example, by inserting a cellulose-binding domain in the protein. One of skill in the art will understand that other methods of immobilization could also be used and are described in the available literature.

In another embodiment, the invention related to methods and compositions using the protein of the invention or part thereof to retard and/or inhibit the growth of pathogens, preferably bacteria, more preferably Listeria and Streptococci, and *Actinobacilli*, either in vitro or in vivo using any methods and techniques known to those skilled in the art, alone or in combination with other antimicrobial substances. For example, the protein of the invention or part thereof may be used to disinfect aqueous samples or materials, or as a food preservative. In a preferred embodiment, compositions comprising the protein of the present invention or part thereof are added to samples or materials as a "cocktail" with other antimicrobial substances to decontaminate samples. The advantage of using such a cocktail is that one is able to decontaminate samples without knowing the specificity of any of the antimicrobial substances. Using such a cocktail also protects a sample or material from a wide range of future unknown contaminants from a vast number of sources.

In another embodiment, the invention relates to methods and compositions using the protein of the invention or part thereof as a marker protein to selectively identify tissues, preferably salivary glands and lacrimal glands. For example, the protein of the invention or part may be used to synthesize specific antibodies using any techniques known to those skilled in the art including those described therein. Such tissue-specific antibodies may then be used to identify tissues of unknown origin, for example, forensic samples, differentiated tumor tissue that has metastasized to foreign bodily sites, or to differentiate different tissue types in a tissue cross-section using immunochemistry.

Protein of SEQ ID NO: 120 (Internal Designation 108-019-5-0-F5-FLC)

The protein of SEQ ID NO: 120 encoded by the cDNA of SEQ ID NO: 70 is homologous to human proteins either thought to be a transmembrane proteolipid protein down regulated upon cell differentiation induced by sodium butyrate (Genbank accession number AF057306) or described as the alternatively spliced chemokine-like factor 2 (Genbank accession number AF135380).

Proteolipids are a class of hydrophobic membrane proteins characterized in part by their capacity to assume conformations compatible with solubility in organic solvents and in water (Sapirstein V. S. et al (1983) Biochemistry 22:3330-3335). This amphipathic character of proteolipids explains their participation in transmembrane ion movement. Proteolipids are components of ion channel and transport systems, such as $H^+$ channels (Arai H. et al (1987) J Biol Chem 262: 11006-11011), $Ca^{2+}$ channels (Eytan G. D. et al (1977) J Biol Chem 252: 3208-3213) and the C (membrane channel) subunit of the vacuolar $H^+$-ATPase (Nelson H. et al (1990) J Biol Chem 265: 20390-20393).

The latter proteolipid, also known as ductin, is also associated. with gap junctions. Gap junctions are the relatively large pores which allow free diffusion of ions across biological membranes (Finbow M. E. et al (1995) Bioessays 17:247-255). Altered gap-junction intercellular communication (GJIC) may play an essential role in cancer development. A lack of GJIC has been observed between transformed and neighboring normal cells (Trosko et al (1990) Radiation Res 123:241-251). A decrease in GJIC has also been observed within tumor cells (Krutovskikh et al (1991) Carcinogenesis 12:1701-1706).

Proteolipids are also involved in membrane vesicular trafficking. Due to their lipid-like properties, proteolipids destabilize lipid bilayers and promote membrane vesicle fusion. Such proteolipid-assisted events may include the fusions and fissions of the nuclear membrane, endoplasmic reticulum, Golgi apparatus, and various inclusion bodies (peroxisomes, lysosomes, etc).

Human T-lymphocyte maturation-associated protein (MAL), a 153 amino acid proteolipid, has been localized to the endoplasmic reticulum (ER) of T-lymphocytes, where it mediates the fusion of ER-derived vesicles and Golgi cisterna (Rancano C. et al (1994) J Biol Chem 269:8159-8164). A canine MAL homologue, VIP17, is involved in the sorting and targeting of proteins between the Golgi complex and the apical plasma membrane (Zacchetti D. et al (1995) FEBS Lett 377:465-469). A rat MAL homologue, rMAL, is expressed in the myelinating cells of the nervous system including oligodendrocytes and Schwann cells. The rMAL protein serves as a gap junction component and plays a role in myelin compaction (Schaeren-Wiemers N. et al (1995) J. Neurosci 5753-5764).

Plasmolipin from rat is a proteolipid localized to plasma membranes in kidney and brain. It has 157 amino acids and, based on hydropathy plots and secondary structure predictions, consists of four alpha-helical transmembrane domains (I through IV) of 20-22 amino acids in length. Transmembrane domains III and IV contain hydroxyl groups which may contribute to an aqueous channel. Domains I through III are connected by short hydrophilic segments of 9-11 amino acids in length, and domains III and IV are connected by a longer hydrophilic segment of 20 amino acids. The small size and high hydrophobicity of plasmolipin constrains the distribution of its transmembrane regions such that the four transmembrane alpha-helices form an antiparallel bundle, and both the amino- and carboxy-termini face the cytoplasm. This structural model defines the growing class of small hydrophobic transport-related proteolipids containing four-helix transmembrane segments, such as the MAL homologues (Rancano et al, supra), and the vacuolar $H^+$-ATPase C subunit (Nelson et al, supra).

In rat brain, plasmolipin is localized to myelinated nerve tracts, and its expression increases markedly with the onset of myelination (Fischer I. et al (1991) Neurochem Res 28:81-89). The distribution of plasmolipin within myelin appears to include regions active in membrane recycling. Endocytotic coated vesicles isolated from myelinated tracts are enriched with plasmolipin (Sapirstein V. S. (1994) J Neurosci Res 37:348-358). Incorporation of the purified rat plasmolipin protein into lipid bilayers induces voltage-dependent $K^+$ channel formation, suggesting it may function in vivo as a pore or channel (Tosteson M. T. et al (1981) J Membr Biol 63:77-84). Channel formation involved the trimerization of the plasmolipin molecule. The oligomerization model of the plasmolipin molecule portrays transmembrane domains III and IV as walls of the channel, consistent with the presence of hydroxyl groups in these domains (Sapirstein et al (1983) supra). The putative role of rat plasmolipin in transport suggests its function may be in the fluid volume regulation of the myelin complex (Fischer et al (1994), supra).

Proteolipids are involved in membrane trafficking, gap junction formation, ion transport and cellular fluid volume regulation. The selective modulation of their expression may provide a means for the regulation of vesicle trafficking or the formation of channels or gap junctions in normal as well as acute and chronic disease situations.

It is believed that the protein of SEQ ID NO: 120 or part thereof plays a role membrane trafficking, gap junction formation, ion transport and/or cellular fluid volume regulation. Preferred polypeptides of the invention are fragments of SEQ ID NO: 120 having any of the biological activity described herein. The ability of the protein of the invention or part thereof to form pore and/or to destabilize lipid bilayers may be assessed using techniques well known to those skilled in the art including those described in U.S. Pat. No. 5,843,714.

The invention relates to methods and compositions using the protein of the invention or part thereof to promote membrane vesicle fusion both in vitro and in vivo.

In an embodiment, the protein of the invention or part thereof is used to facilitate exocytosis. For example, the protein of the invention or part thereof may be used to increase the release of chemokines involved in cell migration, proteases which are active in inflammation or other similar activities involving endothelial cells, fibroblasts, lymphocytes, etc. Accordingly, the protein of the invention or part thereof may be used to diagnose, treat and/or prevent disorders associated with abnormal membrane trafficking including but not limited to viral or other infections, traumatic tissue damage, hereditary diseases such as arthritis or asthma, invasive leukemias and lymphomas.

In another embodiment, the protein of the invention or part thereof may be used to promote vesicle fusion for drug delivery. The protein of the invention or part thereof may be incorporated into liposomes or artificial vesicles with a drug of interest and then used to promote vesicle fusion for drug delivery.

In another embodiment, antibodies to the protein of the invention or part thereof may be used for detection of membranes and/or gap junctions using any techniques known to those skilled in the art. In a preferred embodiment, the protein of the invention or part thereof may be used to diagnose disorders associated with altered intercellular communication, more preferably altered gap-junction communication, including but not limited to cardiac arrhythmia.

Protein of SEQ ID NO: 74 (Internal Designation 105-016-3-0-E3-FLC)

The 325-amino-acid-long protein of SEQ ID NO: 74 encoded by the cDNA of SEQ ID NO: 24 shows homology over the whole length of the 332-amino-acid-long murine neural proliferation differentiation and control 1 protein or NPDC-1 (Genbank accession number X67209) which is thought to play an important role in the control of neural cell proliferation and differentiation as well as in cell survival by interacting with cell cycle regulators such as E2F-1 (Galiana et al., *Proc. Natl. Acad. Sci. USA* 92:1560-1564 (1995); Dupont et al., *J. Neurosci. Res*. 51:257-267 (1998)).

It is believed that the protein of SEQ ID NO: 74 or part thereof plays a role in cell proliferation and differentiation. Preferred polypeptides of the invention are polypeptides comprising the amino acids of SEQ ID NO: 74 from positions 1 to 81, and 129 to 308. Other preferred polypeptides of the invention are fragments of SEQ ID NO: 74 having any of the biological activity described herein. The activity of the protein of the invention or part thereof on cellular proliferation and differentiation may be assessed using techniques well known to those skilled in the art including those described in Galiana et al, supra.

In one embodiment, the invention related to methods and compositions using the protein of the invention or part thereof to inhibit cellular proliferation, preferably neuronal cell proliferation, using any methods and techniques known to those skilled in the art including those described in Galiana et al, supra.

In another embodiment, the protein of the invention or part thereof, may be used to diagnose, treat and/or prevent several disorders linked to cell proliferation and differentiation including, but not limited to cancer and neurodegenerative disorders such as Parkinson's or Alzheimer's diseases. For diagnostic purposes, the expression of the protein of the invention could be investigated using any of the Northern blotting, RT-PCR or immunoblotting methods described herein and compared to the expression in control individuals.

Protein of SEQ ID NO: 75 (Internal Designation 105-031-3-0-D6-FLC)

The protein of SEQ ID NO: 75 encoded by the cDNA of SEQ ID. NO:25 exhibits homology to a murine putative sialyltransferase protein (TREMBL accession number O88725). Although sialyltransferases have virtually no sequence homology, they display the features of type II transmembrane proteins with a short N-terminal cytoplasmic tail, a 16-20 amino acid signal-anchor domain, and an extended stem region which is followed by the large C-terminal catalytic domain (Weinstein, J. et al., J. Biol. Chem. 262, 17735-17743, 1987; Paulson, J. C. et al., J. Biol. Chem. 264,17615-17618, 1989).

The protein of SEQ ID NO: 75 displays the two conserved motifs of the sialyltransferase protein family, namely the centrally located sialylmotifl (positions 73 to 120) thought to be involved in the recognition of the sugar nucleotide donor common to all sialyltransferases and the sialylmotifs (positions 211 to 233) thought to be the catalytic site and located in the C-terminus of the protein. Furthermore, the 302-amino-acid long protein of SEQ ID NO: 75 has a size similar to the one of the members of the sialyltransferase family. In addition, the protein of the invention has a predicted transmembrane structure. Indeed, it contains 2 potential transmembrane segments (positions 7 to 27 and 206 to 226, underlined in FIG. 12) as predicted by the software TopPred II (Claros and von Heijne, *CABIOS applic. Notes*, 10:685-686 (1994)).

Sialyltransferases are glycosyl transferases found primarily in the Golgi apparatus and also in body fluids such as breast milk, colustrum and blood. They are responsible for the terminal sialylation of carbohydrate groups of glycoproteins, glycolipids and oligosaccharides widely distributed in animal tissues. Sialic acids play important roles in the biological functions of carbohydrate structures because of their terminal position. Sialyltransferases are indeed involved in a large variety of biological processes such as cell-cell communication, cell-matrix interactions, maintenance of serum glycoproteins in the circulation, and so on (Sjoberg et al., J. Biol. Chem. 271:7450-7459 (1996); Tsuji, J. Biochem. 120:1-13 (1996)). A variety of biological phenomena are associated with recognition of sialosides, including viral replication, escape of immune detection, and cell adhesion (Schauer, R. Trends Biochem. Sci. 1985, 10, 357-360; Biology of the Sialic Acids ed. A. Rosenberg, Plenum Press, New York, 1995). For example, suppressed antibody production was observed in alpha-2, 6-sialyltransferase knockout mice (Muramatsu, J. Biochem. 127:171-6 (2000). In addition, carbohydrate structures have been shown to influence proteins' stability, rate of in vivo clearance from blood stream, rate of proteolysis, thermal stability and solubility. Changes in the oligosaccharide portion of cell surface carbohydrates have been noted in cells which have become cancerous.

It is believed that the protein of SEQ ID NO: 75 or part thereof plays a role in the biosynthesis of sialyl-glycoconjugates, probably as a sialyltransferase. Thus, the protein of the invention or part thereof is thought to be involved in cell-cell communication, cell-matrix interactions, maintenance of serum glycoproteins in the circulation, viral replication, escape of immune detection, and cell adhesion. Preferred polypeptides of the invention are polypeptides comprising the amino acids of SEQ ID NO:75 from positions 73 to 120, and from position 211 to 233. Other preferred polypeptides of the invention are fragments of SEQ ID NO:75 having any of the biological activity described herein. The sialyltransferase activity of the protein of the invention or part thereof may be assayed using any other technique known to those skilled in the art including those described in Sadler et al., J. Biol. Chem., 254:4434-4443 (1979) or U.S. Pat. Nos. 5,827,714 and 6,017,743.

One object of the present invention are compositions and methods of targeting heterologous polypeptides to the Golgi apparatus by recombinantly or chemically fusing a fragment of the protein of the invention to an heterologous polypeptide. Preferred fragments are signal peptide, transmembrane domains, the proline-rich region comprised between positions 31 and 67, tyrosine containing regions and/or any other fragments of the protein of the invention, or part thereof, that may contain targeting signals for the Golgi apparatus including but not limited to proline-rich regions (Ugur and Jones, Mol Cell Biol 11:1432-32 (2000), Picetti and Borrelli, Exp Cell Res 255:258-69 (2000)), tyrosine-based Golgi targeting signal region (Zhan et al., Cancer Immunol Immunother 46:55-60 (1998); Watson and Pessin J. Biol. Chem. 275: 1261-8 (2000); Ward and Moss, J. Virol. 74:3771-80 (2000) or any other region as defined in Munro, Trends Cell Biol. 8:11-15 (1998); Luetterforst et al., J. Cell. Biol. 145:1443-59 (1999); Essl et al., FEBS Lett. 453:169-73 (1999).

Sialylated compounds have considerable potential both as therapeutics and as reagents for clinical assays. However, synthesis of glycosylated compounds of potential commercial and/or therapeutic interest is difficult because of the very nature of the saccharide subunits. A multitude of positional isomers in which different substituent groups on the sugars become involved in bond formation, along with the potential formation of different anomeric forms, are possible. As a result of these problems, large scale chemical synthesis of most carbohydrates is not possible due to economic considerations arising from the poor yields of desired products. Enzymatic synthesis using glycosyl transferases such as sialyltransferases provides an alternative to chemical synthesis of carbohydrates. Enzymatic synthesis using glycosidases, glycosyl transferases, or combinations thereof, have been considered as a possible approach to the synthesis of carbohydrates. As a matter of fact, enzyme-mediated catalytic synthesis would offer dramatic advantages over the classical synthetic organic pathways, producing very high yields of carbohydrates economically, under mild conditions in aqueous solutions, and without generating notable amounts of undesired side products. To date, such enzymes are however difficult to isolate, especially from eukaryotic, e.g., mammalian sources, because these proteins are only found in low concentrations, and tend to be membrane-bound. In addition to being difficult to isolate, the acceptor (peptide) specificity of glycosyl transferases is poorly understood. Thus, there is a need for obtaining recombinant glycosyl transferase, including sialyltransferases, that could be produced in very large amounts.

Thus, the invention related to methods and compositions using the protein of the invention or part thereof to synthesize glycosylated compounds, either glycoproteins, glycoplipids, or oligosaccharides, more particularly sialylated compounds. If necessary, the protein of the invention or part thereof may be produced in a soluble form by removing its transmembrane domains and/or its Golgi retention signal using any of the methods skilled in the art including those described in U.S. Pat. No. 5,776,772. For example, the protein of the invention or part thereof is added to a sample containing sialic acid and a substrate compound in conditions allowing glycosylation, more particularly sialylation and allowed to catalyze the glycosylation of this compound. In a preferred embodiment, the enzymatic reaction carried out by the protein of the invention is part of a series of other chemical and/or enzymatic reactions aiming at the synthesis of complex glycosylated compounds, such as the ones described in U.S. Pat. Nos. 5,409,817 and 5,374,541. In another preferred embodiment where the method is to be practiced on a commercial scale, it may be advantageous to immobilize the glycosyl transferase on a support. This immobilization facilitates the removal of the enzyme from the batch of product and subsequent reuse of the enzyme. Immobilization of glycosyl transferases can be accomplished, for example, by removing from the transferase its membrane-binding domain, and attaching in its place a cellulose-binding domain. One of skill in the art will understand that other methods of immobilization could also be used and are described in the available literature.

In another embodiment, the present invention relates to processes and compositions for producing glycosylated compounds, preferably sialylated compounds, wherein a cell is genetically engineered to produce the protein of the invention or part thereof and used in combination with one or several other cells able to produce the donor substrate for the protein of the invention. Preferably, a bacteria is engineered to express the protein of the invention and used with recombinant bacteria expressing enzymes able to synthesize cytidine 5'-monophospho-N-acetyl neuramininc acid (CMP-NeuAc). The methods for performing the above bacterial coupling process and making the above compositions are carried using the methods known in the art and described in Endo et al., Appl. Microbiol. Biotechnol. 53:257-61, (2000).

Another embodiment of the present invention relates to a process and compositions for controlling the glycosylation of proteins in a cell wherein an insect, plant, or animal cell is genetically engineered to produce one or more enzymes which provide internal control of the cell's glycosylation mechanism. Preferably, the invention relates to a Chinese hamster ovary (CHO) cell line that is genetically engineered to produce a sialyltransferase of the present invention either alone or in combination with other sialyltransferases. This supplemental sialyltransferase modifies the CHO glycosylation machinery to produce glycoproteins having carbohydrate structures which more closely resemble naturally occurring human glycoproteins. The methods for performing the above process and making the above compositions are carried using the methods known in the art and described in U.S. Pat. No. 5,047,335.

The invention further relates to glycosylated compounds, preferably sialylated compounds, obtained using any of the processes described herein using the protein of the invention or part thereof. Such compounds may be used in the diagnosing, prevention and/or treating of disorders in which the recognition of such compounds is impaired or needs to be impaired. These disorders include, but are not limited to, cancer, cystic fibrosis, ulcer, inflammation and immune based disorders, including autoimmune disorders such as arthritis, fertility disorders, and hypothyroidism. These conditions include infectious diseases where active infection exists at any body site, such as meningitis and salpingitis; complications of infections including septic shock, disseminated intravascular coagulation, and/or adult respiratory distress syndrome; acute or chronic inflammation due to antigen, antibody and/or complement deposition; inflammatory conditions including arthritis, chalangitis, colitis, encephalitis, endocarditis, glomerulonephritis, hepatitis, myocarditis, pancreatitis, pericarditis, reperfusion injury and vasculitis. Immune-based diseases include but are not limited to conditions involving T-cells and/or macrophages such as acute and delayed hypersensitivity, graft rejection, and graft-versus-host disease; auto-immune diseases including Type I diabetes mellitus and multiple sclerosis. In a preferred embodiment, these glycosylated compounds or derivatives thereof may be used as pharmacological agents to trap pathogens or endogenous ligands thus reducing the binding of pathogens or endogenous ligands to the endogenous glycosylated compounds. For example, such compounds may be used to prevent and/or inhibit the adhesion of cancer cells to inner wall of blood vessel or aggregation between cancer cells and platelets, thus reducing cancer metastasis, to prevent and/or inhibit the adhesion of neutrophils to blood vessels endothelial cells, thus reducing inflammation. Other disorders include infections in which recognition of a glycosylated product is essential to the development of the infection. Such infections include, but are not limited to, those caused by *Vibrio cholerae, Escherichia Coli, Salmonella*, and the influenza virus. In a preferred embodiment, such compounds, preferably sialyl lactose, are used as neutralizers for enterotoxins from bacteria such as *Vibrio cholerae, Escherichia Coli*, and *Salmonella* as described in U.S. Pat. No. 5,330,975. In another preferred embodiment, such compounds, preferably galactose oligosaccharides, are used to diagnose, identify and inhibit the adherence of uropathogenic bacteria to red blood cells (U.S. Pat. No. 4,657,849). In another preferred embodiment, such compound, preferably oligosaccharides, are used as gram positive antibiotics and disinfectants (U.S. Pat. Nos. 4,851,338 and 4,665,060). In another embodiment, such compounds, preferably sialyl lactose, may be used for the treatment of arthritis and related autoimmune diseases (see, U.S. Pat. No. 5,164,374). In another embodiment, such compounds, preferably sialylalpha(2,3)galactosides, sialyl lactose and sialyl lactosamine, may be used for the treatment of ulcers. Phase I clinical trials have begun for the use of the former compound in this capacity. (Balkonen, et al., FEMS Immunology and Medical Microbiology 7:29 (1993) and BioWorld Today, p. 5, Apr. 4, 1995). In addition, such compounds, preferably sialyl lactose, may be used as food supplement, for instance in baby formula.

In addition, the protein of the invention or part thereof may be used in the development of inhibitors of glycosyl transferase, more particularly inhibitors of sialyltransferases and sialidases, for mechanistic and clinical applications (Taylor, G. Curr. Opin. Struc. Biol. 1996, 6, 830-837; Colman, P. M., Pure Appl. Chem. 1995, 67, 1683-1688; Bamford, M. J. J Enz. Inhib. 1995, 10, 1-16; Khan, S. H. & Matta, K. L. In Glycoconjugates, Composition, Structure, and Function. pp361-378. ed., Allen, H. J. & Kisailus, E. C. Marcel Dekker, Inc. New York, 1992, Thome-Tjomsland et al., Transplantation 69:806-8, (2000); Basset et al, Scand. J. Immunol. 51:307-11 (2000)).

The invention further relates to methods and compositions using the protein of the invention or part thereof to diagnose, prevent and/or treat several disorders in which recognition of glycosylated compounds, preferably of sialylated compounds, is impaired or needs to be impaired. For diagnostic purposes, the expression of the protein of the invention could be investigated using any of the Northern blotting, RT-PCR or immunoblotting methods described herein and compared to the expression in control individuals. For prevention and/or treatment purposes, inhibiting the endogenous expression of the protein of the invention using any of the antisense or triple helix methods described herein may be used to reduce the production of glycosylated compounds detrimental to the organism in any of the disorders described above.

Protein of SEQ ID NOs: 104 (Internal Designation 108-008-5-O-C5-FL)

The protein of SEQ ID NO: 104 encoded by the cDNA of SEQ ID NO: 54 exhibits homology over the whole length to the murine recombination activating gene 1 inducing protein found in stromal cell (Genbank accession number X96618). The amino acid residues are identical except for the positions 6, 7, 10-13, 17, 25, 34-35, 42, 51, 56, 62, 68, 71, 74, 78, 91, 93, 95-96, 106, 121-122, 151-152, 159, 162-163, 170-171, 176-177, 188, 190, 192, 196, 199, 202-203, 206, 210, 215 and 217 of the 221 amino acid long matched protein. This protein with 4 potential transmembrane segments facilitates gene activation of RAG-1 which is involved in the recombination of V(D)J segments in T cells (Tagoh et al., *Biochem Biophysic Res Comm* 221:744-749 (1996); Muraguchi et al, *Leuk Lymphoma*, 30:73-85 (1998)).

It is believed that the protein of SEQ ID NO: 104 may play a role in lymphocyte repertoire formation. Preferred polypeptides of the invention are fragments of SEQ ID NO: 74 having any of the biological activity described herein. The activity of the protein of the invention or part thereof on the induction of RAG expression may be assessed using techniques well known to those skilled in the art including those described in Tagoh et al, supra.

In an embodiment, antibodies to the protein of the invention or part thereof may be used as markers for haematopoietic precursors, preferably precursors for B and T cells.

In another embodiment, the protein of the invention or part thereof, may be used to diagnose, treat and/or prevent immunological disorders including, but not limited to Ommen'syndrome, acute and delayed hypersensitivity, graft rejection, and graft-versus-host disease; auto-immune diseases including Type I diabetes mellitus and multiple sclerosis, lymphoid neoplasia including non Hodgkins' lymphoma, ALL and CLL. For diagnostic purposes, the expression of the protein of the invention could be investigated using any of the Northern blotting, RT-PCR or immunoblotting methods described herein and compared to the expression in control individuals. In another embodiment, the protein of the invention or part thereof may also be used to modulate the immune response to pathogens.

Protein of SEQ ID NO: 87 (Internal Designation 116-073-4-0-C8-FLC)

The protein of SEQ ID NO: 87 encoded by the cDNA of SEQ ID NO:37 shows homology over the whole length of the widely conserved family of lysozyme C precursors (fish, bird, and mammals). In particular, the protein of the invention displays 17 out of the 20 amino acids conserved among all known lysozyme C proteins at positions 115, 117, 123, 137, 141, 144, 146, 150, 151, 162, 166, 180, 181, 194, 197, 201 and 213 (Prager and Jollès, Lysozymes: model enzymes in biochemistry and biology, ed. Jollès, 9-321 (1996)). In addition, this protein displays the characteristic signature of the family 22 of glysosyl hydrolases (PROSITE signature from positions 162 to 185, eMotif signatures from positions 183 to 202 and from positions 111 to 120), which contain the evolutionary related alpha-lactalbumin, the regulatory subunit of lactose synthetase, and the bacteriolytic defensive enzymes lysozyme C (Qasba and Kumar, *Crit. Rev. Biochem. Mol. Biol.* 32:255-306 (1997)). Furthermore, the cDNA of SEQ ID NO:37 seems to be preferentially expressed in testis (Table VII) and in germ cells tumors (Table VIII).

Lysozyme, an ubiquitous protein secreted in most body secretions, is defined as 1,4-beta-N-acetylmuramidases which cleave the glycoside bond between the C-1 of N-acetyl-muramic acid and the C-4 of N-acetylglucosamine in the peptidoglycan of bacteria. It has various therapeutic properties, such as antiviral, antibacterial, anti-inflammatory and antihistaminic effects. The activity of the lysozyme as an anti-bacterial agent appears to be based on both its direct bacteriolytic activity and also on stimulatory effects in connection with phagocytosis of polymorphonuclear leucocytes and macrophages (Biggar and Sturgess, J. M. Infect Immunol. 16: 974-982 (1977); Thacore and Willet, Am. Rev. Resp. Dis. 93: 786-790 (1966); Klockars and Roberts, P. Acta Haematol 55: 289-292 (1976)). Lysozyme has proven to be not only a selective factor but also an effective factor against microorganisms of the mouth (Iacono et al, J. J. Infect. Immunol. 29: 623-632 (1980)). Lysozyme can also kill pathogens by acting synergistically with other proteins such as complement or antibody to lyse pathogenic cells. Lysozyme, also inhibits chemotaxis of polymorphonuclear leukocytes and limits the production of oxygen free radicals following an infection. This limits the degree of inflammation, while at the same time enhances phagocytosis by these cells. Other postulated functions of lysozyme include immune stimulation (Jolles, P. Biomedicine 25: 275-276 (1976) Ossermann, E. F. Adv. Pathobiol 4: 98-102 (1976)) and immunological and non-immunological monitoring of host membranes for any neoplastic transformation (Jolles, P. Biomedicine 25: 275-276 (1976); Ossermann, E. F. Adv. Pathobiol 4: 98-102 (1976)). Lysozyme may thus be used in a wide spectrum of applications (see U.S. Pat. No. 5,618,712). Determination of the lysozymes from serum and/or urine is used to diagnose various diseases or as an indicator for their development. In acute lymphoblastic leukaemia the lysozyme serum level is significantly reduced, whereas in chronic myelotic leukaemia and in acute monoblastic and myelomonocytic leukaemia the lysozyme concentration in the serum is greatly increased. The therapeutically effective use of lysozyme is possible in the treatment of various bacterial and virus infections (Zona, Herpes zoster), in colitis, various types of pain, in allergies, inflammation and in pediatrics (the conversion of cows milk into a form suitable for infants by the addition of lysozyme).

It is believed that the protein of SEQ ID NO: 87 or part thereof plays a role in glycoprotein and/or peptidoglycan metabolism, probably as a glycosyl hydrolase of family 22. Thus, the protein of the invention or part thereof may be involved in immune and inflammatory responses and may have antiviral, antibacterial, anti-inflammatory and/or antihistaminic functions. Preferred polypeptides of the invention are polypeptides comprising the amino acids of SEQ ID NO:87 from positions 70 to 215, 111 to 120, 183 to 202, and 162 to 185. Other preferred polypeptides of the invention are fragments of SEQ ID NO: 87 having any of the biological activities described herein. The glycolytic activity of the protein of the invention or part thereof may be assayed using any of the assays known to those skilled in the art including those described in Gold and Schweiger, M. Methods in Enzymology, Vol. XX, Part C pp. 537-542, Ed. Moldave, Academic Press, New York and London, 1971 and in the U.S. Pat. No. 4,255,517.

The invention relates to methods and compositions using the protein of the invention or part thereof to hydrolyze one or several substrates, alone or in combination with other substances, preferably antiviral, antifungal and/or antibacterial substances including but not limited to immunoglobulins, lactoferrin, betalysin, fibronectin, and complement components. Such substrates are glycosylated compounds, preferably containing beta-1-4-glycoside bonds, more preferably containing beta-1-4-glycoside bonds between n-acetylomuraminic acid and n-acetyloglucosamine. For example, the protein of the invention or part thereof is added to a sample containing the substrate(s) in conditions allowing hydrolysis, and allowed to catalyze the hydrolysis of the substrate(s). In a preferred embodiment, the hydrolysis is carried out using a standard assay such as those described by Gold and Schweiger, supra, and U.S. Pat. Nos. 5,871,477 and 4,255,517. In a preferred embodiment, the protein of the invention or part thereof may be used to lyze recombinant bacteria in order to recover the recombinant DNA, the recombinant protein of interest, or both using, for example, any of the assays described in Sambrook, et al., Molecular Cloning: A Laboratory Manual, Second Edition, Cold Spring Harbor Laboratory Press (1989).

In an embodiment, the protein of the invention or part thereof is used to hydrolyze contaminating substrates in an aqueous sample or onto a material, preferably glassware and plasticware. In particular, the protein of the invention or part thereof may be used as a disinfectant in dental rinse, in protection of aqueous systems or in preparing material for medical applications using any of the methods and compositions described in U.S. Pat. Nos. 5,069,717, 4,355,022 and 5,001,062. In a preferred embodiment, the protein of the invention is used as a host resistance factor in infants' formulas to convert cow's milk into a form more suitable for infants as described in U.S. Pat. No. 6,020,015. In another preferred embodiment, the protein of the invention or part thereof may be used as a food preservative (see Hayashi et al., Agric. Biol. Chem. (European Edition of Japanese Journal of Agriculture, Biochemistry and Chemistry), Vol. 53, pp. 3173-3177, 1989). In addition, the protein of the invention or part thereof may be used to clarify xanthan gum fermented broth for applications in food and in cosmetic industries using the method described in U.S. Pat. No. 5,994,107. In another preferred embodiment, compositions comprising the protein of the present invention or part thereof are added to samples or materials as a "cocktail" with other antimicrobial substances, preferably antibiotics or hydrolytic enzymes such as those described in U.S. Pat. Nos. 5,458,876 and 5,041,326 to decontaminate the samples. For example, the protein of the invention or part thereof may be used in place or in combination with antibiotics in cell cultures. The advantage of using a cocktail of hydrolytic enzymes is that one is able to hydrolyze a wide range of substrates without knowing the specificity of any of the enzymes. Using a cocktail of hydrolytic enzymes also protects a sample or material from a wide range of future unknown contaminants from a vast number of sources. For example, the protein of the invention or part thereof is added to samples where contaminating substrates is undesirable. Alternatively, the protein of the invention or part thereof may be bound to a chromatographic support, either alone or in combination with other hydrolytic enzymes, using techniques well known in the art, to form an affinity chromatography column. A sample containing the undesirable substrate is run through the column to remove the substrate. Immobilizing the protein of the invention or part thereof on a support advantageous is particularly for those embodiments in which the method is to be practiced on a commercial scale. This immobilization facilitates the removal of the enzyme from the batch of product and subsequent reuse of the enzyme. Immobilization of the protein of the invention or part thereof can be accomplished, for example, by inserting a cellulose-binding domain in the protein. One of skill in the art will understand that other methods of immobilization could also be used and are described in the available literature. Alternatively, the same methods may be used to identify new substrates.

In addition, the protein of the invention or part thereof may be useful to identify or quantify the amount of a given substrate in biological fluids, foods, water, air, solutions and the like. In a preferred embodiment, the protein of the invention or part thereof is used in assays and diagnostic kits for the identification and quantification of exogenous substrates in bodily fluids including blood, lymph, saliva or other tissue samples, in addition to bacterial, fungal, plant, yeast, viral or mammalian cell cultures. In a preferred embodiment, the protein of the invention or part thereof is used to detect, identify, and or quantify eubacteria using reagents and assays described in U.S. Pat. No. 5,935,804. Briefly, the protein of the invention of part thereof is catalytically inactivated, i.e. capable of binding but not cleaving a peptidoglycan comprising NAc-muramic acid in the eubacteria, using any of the methods known to those skilled in the art including those which produce a mutant enzyme, a recombinant-enzyme, or a chemically inactivated enzyme. The catalytically inactive protein of the invention is then incubated with an aliquot of a biological sample under conditions suitable for binding of the inactive enzyme to the peptidoglycan substrate. Then, the bound enzyme is detected to assess the presence or amount of the eubacteria in the biological sample.

In another embodiment, the nucleic acid of the invention or part thereof may be used to increase disease resistance of plants to bacterial, fungal and/or viral infections. A polynucleotide containing the nucleic acid of the invention or part thereof is introduced into the plant genome in conditions allowing correct expression of the transgenic protein using any methods known to those skilled in the art including those disclosed in U.S. Pat. Nos. 5,349,122 and 5,850,025.

In another preferred embodiment, the protein of the invention or part thereof may be useful to treat and/or prevent bacterial, fungal and viral infections in humans or in animals caused by various agents including but not limited to *Streptococcus*, *Veillonella alcalescens*, *Actinomyces*, Herpes simplex, *Candida albicans, Micrococcus lysodeikticus* and HIV by hydrolyzing the glycosylated compounds contained in such micro-organisms. In still a preferred embodiment, the protein of the invention or part thereof is used to prevent and/or treat bacterial, fungal and viral infections in immuno-compromised individuals who lack fully functional immune systems, such as neonates or geriatric patients or HIV-infected individuals, or who suffer from a disease affecting the respiratory tract such as cystic fibrosis or the gastrointestinal tract such as ulcerative colitis or sprue.

In still another embodiment, the protein of the invention or part thereof may be used as a growth factor for in vitro cell culture, preferably for T cells and T cell lines, as described in U.S. Pat. No. 5,468,635.

In addition, the protein of the invention or part thereof may be used to identify inhibitors for mechanistic and clinical applications. Such inhibitors may then be used to identify or quantify the protein of the invention in a sample, and to diagnose, treat or prevent any of the disorders where the protein's hydrolytic, immunostimulatory and/or inflammatory activities is/are undesirable and/or deleterious including but not limited to amyloidosis, colitis, lysosomal diseases, inflammatory and immune disorders including allergies and leukaemia. The protein of the invention may also be used to monitor host cell membranes for neoplastic transformation.

In still another embodiment, the invention relates to methods and compositions using the protein of the invention or part thereof as a marker protein to selectively identify tissues, preferably germ cells, more preferably testis. For example, the protein of the invention or part may be used to synthesize specific antibodies using any techniques known to those skilled in the art including those described therein. Such tissue-specific antibodies may then be used to identify tissues of unknown origin, for example, forensic samples, differentiated tumor tissue that has metastasized to foreign bodily sites, or to differentiate different tissue types in a tissue cross-section using immunochemistry.

Protein of SEQ ID NO:101 (Internal Designation 108-005-5-O-F9-FL)

The protein of SEQ ID NO:101 encoded by the extended cDNA SEQ ID NO: 51 shows homology with the *Drosophila* rhythmically expressed gene 2 protein (Genbank accession number U65492) and with a 2-haloalkanoic acid dehalogenase (Embl accession number AJ248288). In addition, the protein of SEQ ID NO:71 exhibits the pfam signature for haloacid dehalogenase-like hydrolase family from positions 7 to 214.

Expression of the mRNA coding for Dreg-2 is dependent on the interplay between light-dark cycle, feeding conditions and expression of the per gene which is essential to the function of the endogenous circadian pacemaker (Van Gelder et al., *Curr. Biol.*, 5:1424-1436 (1995)). The matched pfam hydrolase family include proteins which are structurally different from the alpha/beta hydrolase family and which include L-2-haloacid dehalogenase, epoxide hydrolases and phosphatases (see Pfam accession number PF00702).

Organohalogen compounds are by-products in several industrial processes that are considered as environmental pollutants. The detection of trihalomethanes, halogenated acetic acids, halogenated acetonitriles and halogenated ketones in city water has become a great problem because of their liver toxicity and mutagenicity. Halogenated organic acids, for example halogenated acetic acids such as chloroacetic acid, dichloroacetic acid, trichloroacetic acid and bromoacetic acid have been designated as environment surveillance items in Japan since 1993. Increasing environmental concerns have created a demand for products that are free from such environmentally unsound byproducts. Physical methods of decontaminating aqueous reaction products containing unwanted nitrogen-free organohalogen byproducts are known, such as solvent extraction with a water-immiscible solvent, or adsorption on a solid adsorbent, such as charcoal. However, such known methods can result in depletion of the reaction product, as well as requiring costly measures to recover and purify the solvent or adsorbent. Furthermore, such methods still leave the problem of how to ultimately dispose of the contaminants such as undesired halogenated oxyalkylene compounds. As one of the countermeasures, for example, biodegradation treatment such as a bioreactor is very useful because treatment can be conducted under mild conditions and is relatively low in cost. The conversion of nitrogen-free organohalogen compounds with microorganisms containing a dehalogenase is also known. For example, C. E. Castro, et al. ("Biological Cleavage of Carbon-Halogen Bonds Metabolism of 3-Bromopropanol by *Pseudomonas* sp.", Biochimica et Biophysica Acta, 100, 384-392, 1965) describe the use of *Pseudomonas* sp. isolated from soil that metabolizes 3-bromopropanol in sequence to 3-bromopropionic acid, 3-hydroxypropionic acid and $CO_2$. Various U.S. Patents also describe the use of microorganisms for dehalogenating halohydrins, e.g. U.S. Pat. Nos. 4,452,894; 4,477,570; and 4,493,895.

Epoxide hydrolases are a family of enzymes which hydrolyze a variety of exogenous and endogenous epoxides to their corresponding diols. Compounds containing the epoxide functionality have become common environmental contaminants because of their wide use as pesticides, sterilants, and industrial precursors. Such compounds also occur as products, by-products, or intermediates in normal metabolism and as the result of spontaneous oxidation of membrane lipids (i.e. see, Brash, et al., Proc. Natl. Acad. Sci., 85:3382-3386 (1988), and Sevanian, A., et al., Molecular Basis of Environmental Toxicology (Bhatnager, R. S., ed.) pp. 213-228, Ann Algor Science, Michigan (1980)). As three-membered cyclic ethers, epoxides are often very reactive and have been found to be cytotoxic, mutagenic and carcinogenic (i.e. see Sugiyama, S., et al., Life Sci. 40:225-231 (1987)). Cleavage of the ether bond in the presence of electrophiles often results in adduct formation. As a result, epoxides have been implicated as the proximate toxin or mutagen for a large number of xenobiotics. Reactions of detoxification using epoxide hydrolases typically decrease the hydrophobicity of a compound, resulting in a more polar and thereby excretable substance. In addition to degradation of potential toxic epoxides, dehalogenases are believed to play a role in the formation or degradation of endogenous chemical mediators (see U.S. Pat. No. 5,445,956).

Many eukaryotic cell functions, including signal transduction, cell adhesion, gene transcription, RNA splicing, apoptosis and cell proliferation, are controlled by protein posphorylation which is in turn regulated by the dynamic relationship between kinases and phosphatases (see U.S. Pat. No. 6,040,323 for a short review). Thus, the protein phosphatases represent unique and attractive targets for small-molecule inhibition and pharmacological intervention. In addition, hydrolytic enzymes such as alkaline phosphatase are frequently used as markers or labels in enzyme-linked assays for biological molecules and other analytes of interest such as drugs, hormones, steroids and cancer markers.

It is believed that the protein of SEQ ID NO: 101 or part thereof is an hydrolase, preferably a phosphatase, an ether hydrolase or an hydrolase acting on C-halide bonds. Preferred polypeptides of the invention are polypeptides comprising the amino acids of SEQ ID NO: 101 from positions 7 to 214. Other preferred polypeptides of the invention are fragments of SEQ ID NO: 101 having any of the biological activity described herein. The hydrolytic activity of the protein of the invention or part thereof may be assayed using any of the assays known to those skilled in the art including those described in U.S. Pat. Nos. 5,445,942; 5,445,956, 6,017,746 and 5,871,616.

The invention relates to methods and compositions using the protein of the invention or part thereof to hydrolyze one or several substrates, alone or in combination with other substances, either in vitro or in vivo. Such substrates are compounds containing phosphoric ester bonds, ether bonds or C-halide bonds. For example, the protein of the invention or part thereof is added to a sample containing the substrate(s) in conditions allowing hydrolysis, and allowed to catalyze the hydrolysis of the substrate(s). In a preferred embodiment, the hydrolysis is carried out using any assay known to those skilled in the art including those described by the U.S. Pat. Nos. 5,445,942; 5,445,956, 6,017,746 and 5,871,616. In a preferred embodiment, the protein of the invention is used to hydrolyze environmental pollutants, preferably organohalogen compounds and epoxide, such as those cited below using any of the methods and techniques described in U.S. Pat. Nos. 6,017,746 and 5,871,616.

The invention relates to methods and compositions using the protein of the invention or part thereof to diagnose, prevent and/or treat several disorders of the circadian rhythm including, but not limited to, insomnia, depression, stress, night work or jet lag. For diagnostic purposes, the overexpression or the improper temporal expression of the protein of the invention could be investigated using any of the Northern blotting, RT-PCR or immunoblotting methods described herein and compared to the expression in control individuals.

Protein of SEQ ID NO: 95 (Internal Designation 122-005-2-0-F11-FLC)

The protein of SEQ ID NO: 95 encoded by the cDNA of SEQ ID NO:45 exhibits homology with a fragment of NADH-cytochrome b5 reductases of rat, bovine and human species which are part of the mitochondrial electron transport chain (Genbank accession numbers J03867, M83104 and Y09501, respectively). This homology includes the flavin-adenine dinucleotide (FAD)-binding domain of this family of proteins from positions 118 to 148, and 157 to 192. Moreover, the 3 lysine residues shown to be implicated in the formation of charged ion pairs with carboxyl groups on NADH-cytochrome b5 reductase during interactions between the active sites of cytochrome b5 and NADH-cytochrome b5 reductase are conserved in the protein of the invention at positions 46, 112 and 150 (Strittmatter, P. et al. (1990) J. Biol. Chem. 265: 21709-13). In addition, the protein of the invention exhibits emotif signatures for cytochrome b5 reductase from positions 123 to 138, 163 to 180, and 256 to 265, emotif signatures for eukaryotic molybdopterin oxidoreductases from positions 256 to 266 and 256 to 268, and emotif signatures for flavoprotein pyridine nucleotide cytochrome reductases from positions 110 to 120, 163 to 177, and 163 to 179.

NADH-cytochrome b5 reductase proteins belong to a flavoenzyme family sharing common structural features and whose members (ferrodoxin-NADP+ reductase, NADPH-cytochrome P450 reductase, NADPH-sulfite reductase, NADH-cytochrome b5 reductase and NADH-nitrate reductase) are involved in photosynthesis, in the assimilation of nitrogen and sulfur, in fatty-acid oxidation, in the reduction of methemoglobin and in the metabolism of many pesticides, drugs and carcinogens (Karplus et al., Science, 251:60-6 (1991)). In addition, cytochrome b5 reductase is thought to play a role in the prevention of apoptosis following oxidative stress (see review by Villalba et al., Mol Aspects Med 18 Suppl1:S7-13 (1997)).

It is believed that the protein of SEQ ID NO: 95 may be an oxidoreductase. Thus it may play a role in electron transport and general aerobic metabolism and may be associated with mitochondrial membranes. In addition, the protein of the invention may be able to use FAD and/or molybdopterin as cofactors. It may be involved in photosynthesis, in the assimilation of nitrogen and sulfur, in fatty-acid oxidation, in the reduction of methemoglobin and in the metabolism of many pesticides, drugs and carcinogens. Preferred polypeptides of the SEQ ID NO: 95 from positions 118 to 148, 157 to 192, 123 to 138, 163 to 180, 256 to 265, 256 to 266, 256 to 268, 110 to 120, 163 to 177, and 163 to 179. Other preferred polypeptides of the invention are fragments of SEQ ID NO: 95 having any of the biological activity described herein. The oxidoreductase activity of the protein of the invention may be assayed using any technique known to those skilled in the art. The ability to bind a cofactor may also be assayed using any techniques well known to those skilled in the art including, for example, the assay for binding NAD described in U.S. Pat. No. 5,986,172.

An object of the present invention are compositions and methods of targeting heterologous compounds, either polypeptides or polynucleotides to mitochondria by recombinantly or chemically fusing a fragment of the protein of the invention to an heterologous polypeptide or polynucleotide. Preferred fragments are signal peptide, amphiphilic alpha helices and/or any other fragments of the protein of the invention, or part thereof, that may contain targeting signals for mitochondria including but not limited to matrix targeting signals as defined in Herrman and Neupert, Curr. Opinion Microbiol. 3:210-4 (2000); Bhagwat et al. J. Biol. Chem. 274:24014-22 (1999), Murphy Trends Biotechnol. 15:326-30 (1997); Glaser et al. Plant Mol Biol 38:311-38 (1998); Ciminale et al. Oncogene 18:4505-14 (1999). Such heterologous compounds may be used to modulate mitochondria's activities. For example, they may be used to induce and/or prevent mitochondrial-induced apoptosis or necrosis. In addition, heterologous polynucleotides may be used for mitochondrial gene therapy to replace a defective mitochondrial gene and/or to inhibit the deleterious expression of a mitochondrial gene.

In another embodiment, the protein of the invention or part thereof is used to prevent cells to undergo apoptosis. In a preferred embodiment, the apoptosis active polypeptide is added to an in vitro culture of mammalian cells in an amount effective to reduce apoptosis. Furthermore, the protein of the invention or part thereof may be useful in the diagnosis, the treatment and/or the prevention of disorders in which apoptosis is deleterious, including but not limited to immune deficiency syndromes (including AIDS), type I diabetes, pathogenic infections, cardiovascular and neurological injury, alopecia, aging, degenerative diseases such as Alzheimer's Disease, Parkinson's Disease, Huntington's disease, dystonia, Leber's hereditary optic neuropathy, schizophrenia, and myodegenerative disorders such as "mitochondrial encephalopathy, lactic acidosis, and stroke" (MELAS), and "myoclonic epilepsy ragged red fiber syndrome" (MERRF).

The invention further relates to methods and compositions using the protein of the invention or part thereof to diagnose, prevent and/or treat several disorders in which energy metabolism is impaired, or needs to be impaired, including but not limited to mitochondriocytopathies, necrosis, aging, neurodegenerative diseases, myopathies, methemoglobinemia, hyperlipidemia, obesity, cardiovascular disorders and cancer. For diagnostic purposes, the expression of the protein of the invention could be investigated using any of the Northern blotting, RT-PCR or immunoblotting methods described herein and compared to the expression in control individuals. For prevention and/or treatment purposes, the protein of the invention may be used to enhance electron transport and increase energy delivery using any of the gene therapy methods described herein.

Protein of SEO ID NO: 113 (Internal Designation 108-014-5-0-C7-FLC)

The protein of SEQ ID NO: 113 encoded by the extended cDNA SEQ ID NO: 63 shows homology with a fragment of a cold active protease isolated from Flavobacterium balustinum (Genseq accession number W23332) which degrades casein, gelatin, haemoglobin and albumin. This protease is able to degrade proteins at low temperatures or in presence of organic solvents that are volatile at normal processing temperature.

These data suggest that the protein of SEQ ID NO: 113 or part thereof is an hydrolase, preferably a protease. Preferred polypeptides of the invention are polypeptides comprising the amino acids of SEQ ID NO: 113 from positions 1 to 44. Other preferred polypeptides of the invention are fragments of SEQ ID NO: 113 having any of the biological activity described herein. The hydrolytic activity of the protein of the invention or part thereof may be assayed using any of the assays known to those skilled in the art including those described in U.S. Pat. No. 6,069,229.

The invention relates to methods and compositions using the protein of the invention or part thereof to hydrolyze one or several substrates, alone or in combination with other substances. Such substrates are compounds containing peptide bonds. For example, the protein of the invention or part thereof is added to a sample containing the substrate(s) in conditions allowing hydrolysis, and allowed to catalyze the hydrolysis of the substrate(s). In a preferred embodiment, the hydrolysis is carried out using a standard assay such as those described by the U.S. Pat. No. 6,069,229.

In a preferred embodiment, compositions comprising the protein of the present invention or part thereof are added to samples as a "cocktail" with other hydrolytic enzymes such as those described in U.S. Pat. Nos. 5,458,876 and 5,041,326. The advantage of using a cocktail of hydrolytic enzymes is that one is able to hydrolyze a wide range of substrates without knowing the specificity of any of the enzymes. Using a cocktail of hydrolytic enzymes also protects a sample from a wide range of future unknown protein contaminants from a vast number of sources. For example, the protein of the invention or part thereof is added to samples where contaminating substrates is undesirable. For example, the protein of the invention or part thereof may be used to remove protein contaminants from nucleic acid preparations, to remove cells from cultureware. Alternatively, the protein of the invention or part thereof may be bound to a chromatographic support, either alone or in combination with other hydrolytic enzymes, using techniques well known in the art, to form an affinity chromatography column. A sample containing the undesirable substrate is run through the column to remove the substrate. Immobilizing the protein of the invention or part thereof on a support is particularly advantageous for those embodiments in which the method is to be practiced on a commercial scale. This immobilization facilitates the removal of the enzyme from the batch of product and subsequent reuse of the enzyme. Immobilization of the protein of the invention or part thereof can be accomplished, for example, by inserting a cellulose-binding domain in the protein. One of skill in the art will understand that other methods of immobilization could also be used and are described in the available literature. Alternatively, the same methods may be used to identify new substrates.

The protease of the invention may be used in many industrial processes, including in detergents and cleaning products, e.g., to degrade protein materials such as blood and stains or to clean contact lenses, in leather production, e.g., to remove hair, in baking, e.g., to break down glutens, in flavorings, e.g., soy sauce, in meat tenderizing, e.g., to break down collagen, in gelatin or food supplement production, in the textile industry, in waste treatment, and in the photographic industry. See, e.g., Gusek (1991) Inform 1:14-18; Zamost, et al. (1996) J. Industrial Microbiol. 8:71-82; James and Simpson (1996) CRC Critical Reviews in Food Science and Nutrition 36:437-463; Teichgraeber, et al. (1993) Trends in Food Science and Technology 4:145-149; Tjwan, et al. (1993) J. Dairy Research 60:269-286; Haard (1992) J. Aquatic Food Product Technology 1:17-35; van Dijk (1995) Laundry and Cleaning News 21:32-33; Nolte, et al. (1996) J. Textile Institute 87:212-226; Chikkodi, et al. (1995) Textile Res. J. 65:564-569; and Shih (1993) Poultry *Science* 72:1617-1620; PCT publication WO9925848-A1.

In addition, the protein of the invention or part thereof may be used to identify inhibitors for mechanistic and clinical applications. Such inhibitors may then be used to identify or quantify the protein of the invention in a sample, and to diagnose, treat or prevent any of the disorders where the protein's hydrolytic activity is undesirable and/or deleterious such as disorders characterized by tissue degradation including but not limited to amyloidosis, colitis, lysosomal diseases, arthritis, muscular dystrophy, inflammation, tumor invasion, glomerulonephritis, parasite-borne infections, Alzheimer's disease, periodontal disease, and cancer metastasis.

Protein of SEQ ID NO: 81 (Internal Designation 116-047-3-0-B1-FLC)

The protein of SEQ ID NO: 81 encoded by the extended cDNA SEQ ID NO: 31 shows homology with the ribokinase rbsk (Embl accession number Q9X4M5) which is part of the pfkb family of kinases. In addition, the protein of the invention exhibits the pfam signature for this family of carbohydrate and purine kinases from positions 28 to 94.

The pfkb family of carbohydrate kinase is composed of evolutionary related kinases including fructokinases, ribokinase, adenosine kinase, inosine-guanosine kinase, and phosphotagatokinase (for a short review see Prosite entry N°PD0C00504).

It is believed that the protein of SEQ ID NO: 81 or part thereof is a carbohydrate or purine kinase. Preferred polypeptides of the invention are polypeptides comprising the amino acids of SEQ ID NO: 81 from positions 28 to 94, and from 1 to 94. Other preferred polypeptides of the invention are fragments of SEQ ID NO: 81 having any of the biological activity described herein. The kinase activity of the protein of the invention or part thereof may be assayed using any of the assays known to those skilled in the art including those described by the U.S. Pat. Nos. 5,756,315 and 5,861,294.

The invention relates to methods and compositions using the protein of the invention or part thereof to phosphorylate substrates, preferably carbohydrate or purine substrates. For example, the protein of the invention or part thereof is added to a sample containing the substrate(s) as well as a phosphate donor group in conditions allowing the transfer of the phosphorus group, and allowed to transfer the phosphorus group to the substrate(s). In a preferred embodiment, the kination is carried out using a standard assay including those described by the U.S. Pat. Nos. 5,756,315 and 5,861,294. Such phosphorylated purine substrates, such as 5'-IMP and 5'-GMP, have an enhanced flavor activity and may be used as seasoning agents.

In another embodiment, the present invention relates to processes and compositions for controlling the production of phosphorylated substrates, preferably carbohydrate and purine substrates, more preferably glucose, fructose, inosine, guanosine, adenosine, wherein a cell or an organism is an organism is genetically engineered either to produce the protein of the invention or part thereof or to inhibit the endogenous expression of the protein of the invention or part thereof using methods and techniques known to those skilled in the art including those described in U.S. Pat. No. 6,031,154. For example, a plant may be genetically engineered to express the protein of the invention or part thereof, thereby increasing the amount of phosphorylated carbohydrate substrates to be imported into plastids and ultimately enhancing starch biosynthesis. On the contrary, a fruit may also be genetically engineered to inhibit the endogenous expression of the protein of the invention in order to increase the concentration of non phosphorylated carbohydrates, ultimately leading to fruits with enhanced sweetness.

The invention further relates to methods and composition using the protein of the invention or part thereof to diagnose, prevent and/or treat disorders in which the availability of phosphorylated substrates, preferably carbohydrate and purine substrates, is impaired or needs to be impaired. In a preferred embodiment, the protein of the invention or part thereof may be used to activate pharmacologically active nucleosides including but not limited to tubercidin, formycin, ribavirin, pyrazofurin and 6-(methylmercapto)purine riboside which are antimetabolites with cytotoxic, anticancer and antiviral properties. In another preferred embodiment, the protein of the invention or part thereof may be used to compensate alterations observed in endogenous adenosine kinase activity observed in certain disorders including but not limited to hepatoma, hepatectomy, gout, and HIV infection. In still another preferred embodiment, the protein of the invention or part thereof may be used to modulate the concentration of adenosine which was shown to play important physiological roles. In the central nervous system, adenosine inhibits the release of certain neurotransmitters (Corradetti et al., Eur. J. Pharmacol. 1984, 104: 19-26), stabilizes membrane potential (Rudolphi et al., Cerebrovasc. Brain Metab. Rev. 1992, 4: 346-360), functions as an endogenous anticonvulsant (Dragunow, Trends Pharmacol. Sci. 1986, 7:128-130) and may have a role as an endogenous neuroprotective agent (Rudolphi et al., Trends Pharmacol. Sci. 1992, 13: 439-445). Adenosine has also been implicated in modulating transmission in pain pathways in the spinal cord (Sawynok et al., Br. J. Pharmacol. 1986, 88: 923-930), and in mediating the analgesic effects of morphine (Sweeney et al., J. Pharmacol. Exp. Ther. 1987, 243: 657-665). In the immune system, adenosine inhibits certain neutrophil functions and exhibits anti-inflammatory effects (Cronstein, J. Appl. Physiol. 1994, 76: 5-13). Adenosine also exerts a variety of effects on the cardiovascular system, including vasodilation, impairment of atrioventricular conduction and endogenous cardioprotection in myocardial ischemia and reperfusion (Mullane and Williams, in Adenosine and Adenosine Receptors 1990 (Williams, ed) Humana Press, New Jersey, pp. 289-334). The widespread actions of adenosine also include effects on the renal, respiratory, gastrointestinal and reproductive systems, as well as on blood cells and adipocytes. Endogenous adenosine release appears to have a role as a natural defense mechanism in various pathophysiologic conditions, including cerebral and myocardial ischemia, seizures, pain, inflammation and sepsis. While adenosine is normally present at low levels in the extracellular space, its release is locally enhanced at the site(s) of excessive cellular activity, trauma or metabolic stress. Once in the extracellular space, adenosine activates specific extracellular receptors to elicit a variety of responses which tend to restore cellular function towards normal (Bruns, Nucleosides Nucleotides, 1991, 10: 931-943; Miller and Hsu, J. Neurotrauma, 1992, 9:S563-S577). Adenosine has a half-life measured in seconds in extracellular fluids (Moser et al., Am. J. Physiol. 1989, 25:C799-C806), and its endogenous actions are therefore highly localized. The inhibition of adenosine kinase can result in augmentation of the local adenosine concentrations at foci of tissue injury, further enhancing cytoprotection. This effect is likely to be most pronounced at tissue sites where trauma results in increased adenosine production, thereby minimizing systemic toxicities. Pharmacological compounds directed towards adenosine kinase inhibition provide potential effective new therapies for disorders benefited by the site- and event-specific potentiation of adenosine.

Protein of SEQ ID NO: 107 (Internal Designation 108-011-5-O-C7-FLC)

The protein of SEQ ID NO: 107 encoded by the extended cDNA SEQ ID NO: 57 shows homology with the chicken ribonuclease A (Embl accession number X61192) which is part of the pancreatic ribonuclease family. In addition, the protein of the invention exhibits the pfam signature for this family of pancreatic ribonucleases from positions 17 to 67.

Ribonucleases are proteins which catalyze the hydrolysis of phosphodiester bonds in RNA chains. Pancreatic ribonucleases are pyrimidic-specific ribonucleases present in high quantity in the pancreas of a number of mammalia taxa and of a few reptiles. In addition to their function in hydrolysis of RNA, ribonucleases have evolved to support a variety of other physiological activities. Such activities include anti-parasite, anti-bacterium, anti-virus, anti-neoplastic activities, neurotoxicity, and angiogenesis. For example, bovine seminal ribonuclease is anti-neoplastic (Laceetti, P. et al. (1992) Cancer Res. 52: 4582-4586). Some frog ribonucleases display both anti-viral and anti-neoplastic activity (Youle, R. J. et al. (1994) Proc. Natl. Acad. Sci. USA 91: 6012-6016; Mikulski, S. M. et al. (1990) J. Natl. Cancer Inst. 82: 151-152; and Wu, Y.-N. et al. (1993) J. Biol. Chem. 268: 10686-10693). Angiogenin is a tRNA-specific ribonuclease which binds actin on the surface of endothelial cells for endocytosis. Endocytosed angiogenin is translocated to the nucleus where it promotes endothelial invasiveness required for blood vessel formation (Moroianu, J. and Riordan, J. F. (1994) Proc. Natl. Acad. Sci. USA 91: 1217-1221). Eosinophil-derived neurotoxin (EDN) and eosinophil cationic protein (ECP) are related ribonucleases which possess neurotoxicity (Beintema, J. J. et al. (1988) Biochemistry 27: 4530-4538; Ackerman, S. J. (1993) In Makino, S. and Fukuda, T., Eosinophils: Biological and Clinical Aspects. CRC Press, Boca Raton, Fla., pp 33-74). In addition, ECP exhibits cytotoxic, anti-parasitic, and anti-bacterial activities. A EDN-related ribonuclease, named RNase k6, is shown to express in normal human monocytes and neutrophils, suggesting a role for this ribonuclease in host defense (Rosenberg, H. F. and Dyer, K. D. (1996) Nuc. Acid. Res. 24: 3507-3513).

It is believed that the protein of SEQ ID NO: 107 or part thereof is a ribonuclease. Preferred polypeptides of the invention are polypeptides comprising the amino acids of SEQ ID NO: 107 from positions 17 to 67. Other preferred polypeptides of the invention are fragments of SEQ ID NO: 107 having any of the biological activity described herein. The ribonuclease activity of the protein of the invention or part thereof may be assayed using any of the assays known to those skilled in the art including those described in U.S. Pat. No. 5,866,119.

The invention relates to methods and compositions using the protein of the invention or part thereof to hydrolyze one or several substrates, preferably nucleic acids, more preferably RNA, alone or in combination with other substances. For example, the protein of the invention or part thereof is added to a sample containing the substrate(s) in conditions allowing hydrolysis, and allowed to catalyze the hydrolysis of the substrate(s).

In a preferred embodiment, the protein of the invention or part thereof may be used to remove contaminating RNA in a biological sample, alone or in combination with other nucleases. In a more preferred embodiment, the protein of the invention or part thereof may be used to purify DNA preparations from contaminating RNA, to remove RNA templates prior to second strand synthesis and prior to analysis of in vitro translation products. Compositions comprising the protein of the present invention or part thereof are added to biological samples as a "cocktail" with other nucleases. The advantage of using a cocktail of hydrolytic enzymes is that one is able to hydrolyze a wide range of substrates without knowing the specificity of any of the enzymes. Such cocktails of nucleases are commonly used in molecular biology assays, for example to remove unbound RNA in RNAse protection assays. Using a cocktail of hydrolytic enzymes also protects a sample from a wide range of future unknown RNA contaminants from a vast number of sources. For example, the protein of the invention or part thereof is added to samples where contaminating substrates is undesirable. Alternatively, the protein of the invention or part thereof may be bound to a chromatographic support, either alone or in combination with other hydrolytic enzymes, using techniques well known in the art, to form an affinity chromatography column. A sample containing the undesirable substrate is run through the column to remove the substrate. Immobilizing the protein of the invention or part thereof on a support is particularly advantageous for those embodiments in which the method is to be practiced on a commercial scale. This immobilization facilitates the removal of the enzyme from the batch of product and subsequent reuse of the enzyme. Immobilization of the protein of the invention or part thereof can be accomplished, for example, by inserting a cellulose-binding domain in the protein. One of skill in the art will understand that other methods of immobilization could also be used and are described in the available literature. Alternatively, the same methods may be used to identify new substrates.

In another embodiment, the protein of the invention or part thereof may be used to decontaminate or disinfect samples infected by undesirable parasite, bacteria and/or viruses using any of the methods known to those skilled in the art including those described in Youle et al, (1994), supra; Mikulski et al (1990) supra, Wu et al (1993) supra.

In another embodiment, the present invention relates to compositions and methods using the protein of the invention or part thereof to selectively kill cells. The protein of the invention or part thereof is linked to a recognition moiety capable of binding to a chosen cell, such as lectins, receptors or antibodies thus generating cytotoxic reagents using methods and techniques described in U.S. Pat. No. 5,955,073.

In another embodiment, the protein of the invention or part thereof may be used in the diagnosis, prevention and/or treatment of disorders associated with excessive cell proliferation such as cancer.

Protein of SEQ ID NO: 77 (Internal Designation 105-118-4-O-E6-FLC)

The protein of SEQ ID NO: 77 encoded by the extended cDNA SEQ ID NO: 27 is homologous to a hepatocellular carcinoma associated ring finger protein (Embl accession number AF247565) and homology with a putative anaphase-promoting complex subunit from Drosophila (Embl accession number AJ251510). In addition, the protein of the invention exhibits the pfam PHD zinc finger signature from positions 33 to 79.

Zinc finger domains are found in numerous zinc binding proteins which are involved in protein-nucleic acid interactions. They are independently folded zinc-containing mini-domains which are used in a modular repeating fashion to achieve sequence-specific recognition of DNA (Klug 1993 Gene 135, 83-92). Such zinc binding proteins are commonly involved in the regulation of gene expression, and usually serve as transcription factors (see U.S. Pat. Nos. 5,866,325; 6,013,453 and 5,861,495). PHD fingers are $C_4HC_3$ zinc fingers spanning approximately 50-80 residues and distinct from RING fingers or LIM domains. They are thought to be mostly DNA or RNA binding domain but may also be involved in protein-protein interactions (for a review see Aasland et al, Trends Biochem Sci 20:56-59 (1995)).

It is believed that the protein of SEQ ID NO: 77 or part thereof is a zinc binding protein, preferably able to bind nucleic acids, more preferably a transcription factor. Preferred polypeptides of the invention are polypeptides comprising the amino acids of SEQ ID NO: 77 from positions 33 to 79. Other preferred polypeptides of the invention are fragments of SEQ ID NO: 77 having any of the biological activity described herein. The nucleic acid binding activity of the protein of the invention or part thereof may be assayed using any of the assays known to those skilled in the art including those described in U.S. Pat. No. 6,013,453.

The invention relates to methods and compositions using the protein of the invention or part thereof to bind to nucleic acids, preferably DNA, alone or in combination with other substances. For example, the protein of the invention or part thereof is added to a sample containing nucleic acid in conditions allowing binding, and allowed to bind to nucleic acids. In a preferred embodiment, the protein of the invention or part thereof may be used to purify nucleic acids such as restriction fragments. In another preferred embodiment, the protein of the invention or part thereof may be used to visualize nucleic acids when the polypeptide is linked to an appropriate fusion partner, or is detected by probing with an antibody. Alternatively, the protein of the invention or part thereof may be bound to a chromatographic support, either alone or in combination with other DNA binding proteins, using techniques well known in the art, to form an affinity chromatography column. A sample containing nucleic acids to purify is run through the column. Immobilizing the protein of the invention or part thereof on a support advantageous is particularly for those embodiments in which the method is to be practiced on a commercial scale. This immobilization facilitates the removal of the protein from the batch of product and subsequent reuse of the protein. Immobilization of the protein of the invention or part thereof can be accomplished, for example, by inserting a cellulose-binding domain in the protein. One of skill in the art will understand that other methods of immobilization could also be used and are described in the available literature.

In another embodiment, the present invention relates to compositions and methods using the protein of the invention or part thereof, especially the zinc-binding domain, to alter the expression of genes of interest in a target cells. Such genes of interest may be disease related genes, such as oncogenes or exogenous genes from pathogens, such as bacteria or viruses using any techniques known to those skilled in the art including those described in U.S. Pat. Nos. 5,861,495; 5,866,325 and 6,013,453.

In still another embodiment, the protein of the invention or part thereof may be used to diagnose, treat and/or prevent disorders linked to dysregulation of gene transcription such as cancer and other disorders relating to abnormal cellular differentiation, proliferation, or degeneration, including hyperaldosteronism, hypocortisolism (Addison's disease), hyperthyroidism (Grave's disease), hypothyroidism, colorectal polyps, gastritis, gastric and duodenal ulcers, ulcerative colitis, and Crohn's disease.

Protein of SEQ ID NO: 114 (Internal Designation 108-014-5-O-D12-FLC)

The protein of SEQ ID NO: 114 encoded by the extended cDNA SEQ ID NO: 64 shows homology with zinc binding proteins (Embl accession number Q9QZQ6 and Genseq accession number W69602). In addition, the protein of the invention exhibits the pfam RING zinc finger signature from positions 258 to 298.

Zinc binding (ZB) domains are found in numerous proteins which are involved in protein-nucleic acid or protein-protein interactions. ZB proteins are commonly involved in the regulation of gene expression, and may serve as transcription factors and signal transduction molecules. A ZB domain is generally composed of 25 to 30 amino acid residues which form one or more tetrahedral ion binding sites. The binding sites contain four ligands consisting of the sidechains of cysteine, histidine and occasionally aspartate or glutamate. The binding of zinc allows the relatively short stretches of polypeptide to fold into defined structural units which are well-suited to participate in macromolecular interactions (Berg, J. M. et al. (1996) Science 271:1081-1085). Zinc binding domains which contain a $C_3HC_4$ sequence motif are known as RING domains (Lovering, R. et al. (1993) Proc. Natl. Acad. Sci. USA 90:2112-2116). The RING domain consists of eight metal binding residues, and the sequences that bind the two metal ions overlap (Barlow, P. N. et al. (1994) J. Mol. Biol. 237:201-211). Functions of RING finger proteins are mediated through DNA binding and include the regulation of gene expression, DNA recombination, and DNA repair (see Borden and Freemont, Curr Opin Struct Biol 6:395-401 (1996) and U.S. Pat. No. 5,861,495).

It is believed that the protein of SEQ ID NO: 114 or part thereof is a zinc binding protein, preferably able to bind nucleic acids or proteins, more preferably a transcription factor. Preferred polypeptides of the invention are polypeptides comprising the amino acids of SEQ ID NO: 114 from positions 258 to 298. Other preferred polypeptides of the invention are fragments of SEQ ID NO: 114 having any of the biological activity described herein. The nucleic acid binding activity of the protein of the invention or part thereof may be assayed using any of the assays known to those skilled in the art including those described in U.S. Pat. No. 6,013,453.

The invention relates to methods and compositions using the protein of the invention or part thereof to bind to nucleic acids, preferably DNA, alone or in combination with other substances. For example, the protein of the invention or part thereof is added to a sample containing nucleic acid in conditions allowing binding, and allowed to bind to nucleic acids. In a preferred embodiment, the protein of the invention or part thereof may be used to purify nucleic acids such as restriction fragments. In another preferred embodiment, the protein of the invention or part thereof may be used to visualize nucleic acids when the polypeptide is linked to an appropriate fusion partner, or is detected by probing with an antibody. Alternatively, the protein of the invention or part thereof may be bound to a chromatographic support, either alone or in combination with other DNA binding proteins, using techniques well known in the art, to form an affinity chromatography column. A sample containing nucleic acids to purify is run through the column. Immobilizing the protein of the invention or part thereof on a support advantageous is particularly for those embodiments in which the method is to be practiced on a commercial scale. This immobilization facilitates the removal of the protein from the batch of product and subsequent reuse of the protein. Immobilization of the protein of the invention or part thereof can be accomplished, for example, by inserting a cellulose-binding domain in the protein. One of skill in the art will understand that other methods of immobilization could also be used and are described in the available literature.

In another embodiment, the present invention relates to compositions and methods using the protein of the invention or part thereof, especially the zinc binding domain, to alter the expression of genes of interest in a target cells. Such genes of interest may be disease related genes, such as oncogenes or exogenous genes from pathogens, such as bacteria or viruses using any techniques known to those skilled in the art including those described in U.S. Pat. Nos. 5,861,495; 5,866,325 and 6,013,453.

In still another embodiment, the protein of the invention or part thereof may be used to diagnose, treat and/or prevent disorders linked to dysregulation of gene transcription such as cancer and other disorders relating to abnormal cellular differentiation, proliferation, or degeneration, including hyperaldosteronism, hypocortisolism (Addison's disease), hyperthyroidism (Grave's disease), hypothyroidism, colorectal polyps, gastritis, gastric and duodenal ulcers, ulcerative colitis, and Crohn's disease.

Protein of SEQ ID NO: 105 (Internal Designation 108-008-5-O-G5-FLC)

The protein of SEQ ID NO: 105 encoded by the extended cDNA SEQ ID NO: 55 shows homology with zinc binding proteins (Embl accession number Q9VZJ9). In addition, the protein of the invention exhibits the pfam RING zinc finger signature from positions 302 to 339.

Zinc binding (ZB) domains are found in numerous proteins which are involved in protein-nucleic acid or protein-protein interactions. ZB proteins are commonly involved in the regulation of gene expression, and may serve as transcription factors and signal transduction molecules. A ZB domain is generally composed of 25 to 30 amino acid residues which form one or more tetrahedral ion binding sites. The binding sites contain four ligands consisting of the sidechains of cysteine, histidine and occasionally aspartate or glutamate. The binding of zinc allows the relatively short stretches of polypeptide to fold into defined structural units which are well-suited to participate in macromolecular interactions (Berg, J. M. et al. (1996) Science 271:1081-1085). Zinc binding domains which contain a $C_3HC_4$ sequence motif are known as RING domains (Lovering, R. et al. (1993) Proc. Natl. Acad. Sci. USA 90:2112-2116). The RING domain consists of eight metal binding residues, and the sequences that bind the two metal ions overlap (Barlow, P. N. et al. (1994) J. Mol. Biol. 237:201-211). Functions of RING finger proteins are mediated through DNA binding and include the regulation of gene expression, DNA recombination, and DNA repair (see Borden and Freemont, Curr Opin Struct Biol 6:395-401 (1996) and U.S. Pat. No. 5,861,495).

It is believed that the protein of SEQ ID NO: 105 or part thereof is a zinc binding protein, preferably able to bind nucleic acids or proteins, more preferably a transcription factor. Preferred polypeptides of the invention are polypeptides comprising the amino acids of SEQ ID NO: 105 from positions 302 to 339. Other preferred polypeptides of the invention are fragments of SEQ ID NO: 105 having any of the biological activity described herein. The nucleic acid binding activity of the protein of the invention or part thereof may be assayed using any of the assays known to those skilled in the art including those described in U.S. Pat. No. 6,013,453.

The invention relates to methods and compositions using the protein of the invention or part thereof to bind to nucleic acids, preferably DNA, alone or in combination with other substances. For example, the protein of the invention or part thereof is added to a sample containing nucleic acid in conditions allowing binding, and allowed to bind to nucleic acids. In a preferred embodiment, the protein of the invention or part thereof may be used to purify nucleic acids such as restriction fragments. In another preferred embodiment, the protein of the invention or part thereof may be used to visualize nucleic acids when the polypeptide is linked to an appropriate fusion partner, or is detected by probing with an antibody. Alternatively, the protein of the invention or part thereof may be bound to a chromatographic support, either alone or in combination with other DNA binding proteins, using techniques well known in the art, to form an affinity chromatography column. A sample containing nucleic acids to purify is run through the column. Immobilizing the protein of the invention or part thereof on a support advantageous is particularly for those embodiments in which the method is to be practiced on a commercial scale. This immobilization facilitates the removal of the protein from the batch of product and subsequent reuse of the protein. Immobilization of the protein of the invention or part thereof can be accomplished, for example, by inserting a cellulose-binding domain in the protein. One of skill in the art will understand that other methods of immobilization could also be used and are described in the available literature.

In another embodiment, the present invention relates to compositions and methods using the protein of the invention or part thereof, especially the zinc binding domain, to alter the expression of genes of interest in a target cells. Such genes of interest may be disease related genes, such as oncogenes or exogenous genes from pathogens, such as bacteria or viruses using any techniques known to those skilled in the art including those described in U.S. Pat. Nos. 5,861,495; 5,866,325 and 6,013,453.

In still another embodiment, the protein of the invention or part thereof may be used to diagnose, treat and/or prevent disorders linked to dysregulation of gene transcription such as cancer and other disorders relating to abnormal cellular differentiation, proliferation, or degeneration, including hyperaldosteronism, hypocortisolism (Addison's disease), hyperthyroidism (Grave's disease), hypothyroidism, colorectal polyps, gastritis, gastric and duodenal ulcers, ulcerative colitis, and Crohn's disease.

Protein of SEQ ID NO: 106 (Internal Designation 108-011-5-O-B12-FL)

The protein of SEQ ID NO: 106 encoded by the extended cDNA SEQ ID NO: 56 shows homology to the predicted extracellular domain and part of transmembrane domain of interleukin-17 receptor of both human and murine species (Genbank accession numbers W04185 and W04184). These IL-17R proteins are thought to belong to a new family of receptors for cytokines which induce T cell proliferation, I-CAM expression and preferential maturation of haematopoietic precursors into neutrophils (Yao et al., *Cytokine.*, 9:794-8001 (1997)). It is also thought to play a proinflammatory role and to induce nitric oxide. The protein of the invention has a 21 amino acid transmembrane domain (positions 172 to 192) as predicted by the software TopPred II (Claros and von Heijne, *CABIOS applic. Notes*, 10:685-686 (1994)) matching the 21 amino acid putative transmembrane domain of human interleukin-17 receptor.

It is believed that the protein of SEQ ID NO: 106 plays a role in regulating immune and/or inflammatory responses. Preferred polypeptides of the invention are fragments of SEQ ID NO: 106 having any of the biological activities described herein.

The present invention relates to methods and compositions using the protein of the invention or part thereof to inhibit the proliferation and/or the differentiation of lymphocytes or lymphocytic cell lines, both in vitro and in vivo. For example, soluble forms of the protein of the invention or part thereof may be added to cell culture medium in an amount effective to inhibit the proliferation and/or the differentiation of lymphocytes and/or lymphocytic cell lines.

Another embodiment relates to methods and compositions using the protein of the invention or part thereof to diagnose, treat and/or prevent several disorders including, but not limited to, cancer, inflammatory and immune disorders, septic shock and impotence. Immune and inflammatory disorders include Addison's disease, AIDS, acute or chronic inflammation due to antigen, antibody and/or complement deposition, acute and delayed hypersensitivity, adult respiratory distress syndrome, allergies, anemia, arthritis, asthma, atherosclerosis, bronchitis, chalangitis, cholecystitus, Crohn's disease, ulcerative colitis, atopic dermatitis, dermatomyositis, diabetes mellitus, emphysema, encephalitis, endocarditis, atrophic gastritis, glomerulonephritis, gout, graft rejection, graft-versus-host disease, Graves' disease, hepatitis, hypereosinophilia, irritable bowel syndrome, lupus erythematosus, multiple sclerosis, myasthenia gravis, myocardial or pericardial inflammation, osteoarthritis, osteoporosis, pancreatitis, polycystic kidney disease, polymyositis, reperfusion injury, rheumatoid arthritis, scleroderma, Sjogren's syndrome, and autoimmune thyroiditis.

In addition, this protein may also be useful to modulate immune and/or inflammatory responses to infectious responses and/or to suppress graft rejection. For example, soluble forms of the protein of the invention or blocking antibodies, or antagonists may be used to inhibit and/or reduce immune and/or inflammatory responses.

Protein of SEQ ID NO: 97 (internal designation 108-004-5-O-B12-FLC)

The protein of SEQ ID NO: 97 encoded by the extended cDNA SEQ ID NO: 47 is homologous to a human protein either described as a maid-like gene (Embl accession number AF132000) or a human secreted protein (Geneseq accession number Y41330).

Maid is a maternally transcribed gene encoding a putative regulator of basic helix-loop-helix transcription factor in the mouse egg and zygote. In vitro, maid is able to bind to DNA. When transfected, maid reduces the transcription of a CAT-reporter regulated by an E12/MyoD enhancer (Hwang et al, Dev Dyn, 209:217-26 (1997)).

It is believed that the protein of SEQ ID NO: 97 or part thereof is involved in the regulation of gene transcription, probably through direct binding to DNA. Preferred polypeptides of the invention are fragments of SEQ ID NO: 97 having any of the biological activity described herein. The nucleic acid binding activity of the protein of the invention or part thereof may be assayed using any of the assays known to those skilled in the art including those described in U.S. Pat. No. 6,013,453.

The invention relates to methods and compositions using the protein of the invention or part thereof to bind to nucleic acids, preferably DNA, alone or in combination with other substances. For example, the protein of the invention or part thereof is added to a sample containing nucleic acid in conditions allowing binding, and allowed to bind to nucleic acids. In a preferred embodiment, the protein of the invention or part thereof may be used to purify nucleic acids such as restriction fragments. In another preferred embodiment, the protein of the invention or part thereof may be used to visualize nucleic acids when the polypeptide is linked to an appropriate fusion partner, or is detected by probing with an antibody. Alternatively, the protein of the invention or part thereof may be bound to a chromatographic support, either alone or in combination with other DNA binding proteins, using techniques well known in the art, to form an affinity chromatography column. A sample containing nucleic acids to purify is run through the column. Immobilizing the protein of the invention or part thereof on a support advantageous is particularly for those embodiments in which the method is to be practiced on a commercial scale. This immobilization facilitates the removal of the protein from the batch of product and subsequent reuse of the protein. Immobilizing the protein of the invention or part thereof on a support advantageous is particularly for those embodiments in which the method is to be practiced on a commercial scale. This immobilization facilitates the removal of the protein from the batch of product and subsequent reuse of the protein. Immobilization of the protein of the invention or part thereof can be accomplished, for example, by inserting a cellulose-binding domain in the protein. One of skill in the art will understand that other methods of immobilization could also be used and are described in the available literature.

In another embodiment, the present invention relates to compositions and methods using the protein of the invention or part thereof to alter the expression of genes of interest in a target cell. Such genes of interest may be disease related genes, such as oncogenes or exogenous genes from pathogens, such as bacteria or viruses using any techniques known to those skilled in the art including those described in U.S. Pat. Nos. 5,861,495; 5,866,325 and 6,013,453.

In still another embodiment, the protein of the invention or part thereof may be used to diagnose, treat and/or prevent disorders linked to dysregulation of gene transcription such as cancer and other disorders relating to abnormal cellular differentiation, proliferation, or degeneration, including hyperaldosteronism, hypocortisolism (Addison's disease), hyperthyroidism (Grave's disease), hypothyroidism, colorectal polyps, gastritis, gastric and duodenal ulcers, ulcerative colitis, and Crohn's disease.

Protein of SEQ ID NO: 122 (Internal Designation 108-020-5-O-D4-FLC)

The protein of SEQ ID NO: 122 encoded by the extended cDNA SEQ ID NO: 72 shows homology to a murine transmembrane protein (Genbank accession number BAA92746). When expressed in *E. Coli*, the matched which suppresses bacterial growth (Inoue et al, Biochem Biophys Res Commun 268:553-61 (2000)). In addition, a transmembrane domain is predicted for the protein of SEQ ID NO: 122 from positions 36 to 56 by the software TopPred II (Claros and von Heijne, *CABIOS applic. Notes*, 10:685-686 (1994).

It is believed that the protein of SEQ ID NO: 122 or part thereof is able to suppress bacterial growth. Preferred polypeptides of the invention are fragments of SEQ ID NO: 97 having any of the biological activity described herein. The growth inhibiting activity of the protein of the invention or part thereof may be assayed using any of the assays known to those skilled in the art including those described in Inoue et al, supra.

The invention relates to methods and compositions using the protein of the invention or part thereof to suppress bacterial growth. For example, the protein of the invention may be expressed in a bacteria, preferably *E. coli*, using recombinant DNA technology methods known to those skilled in the art. The bacterial growth may then be assessed using any methods or techniques known to those skilled in the art.

Protein of SEQ ID NO: 96 (Internal Designation 122-007-3-O-D10-FLC)

The protein of SEQ ID NO: 96 encoded by the extended cDNA SEQ ID NO: 46 shows homology to a human secreted protein highly expressed in testis (Genseq accession number Y06940). In addition, it exhibits an emotif signature for the flagellar biosynthetic protein fliR family from positions 7 to 27.

FliR is an integral membrane protein located in the flagellar basal body and thought to be a component of the type III export apparatus (Fan et al, Mol Microbiol 26:1035-46 (1997)).

It is believed that the protein of SEQ ID NO: 96 or part thereof plays a role in gametogenesis, maybe as a component of spermatozoids. Preferred polypeptides of the invention are polypeptides comprising the amino acids of SEQ ID NO:96 from positions 7 to 27. Other preferred polypeptides of the invention are fragments of SEQ ID NO: 96 having any of the biological activity described herein.

The invention relates to methods and compositions using the protein of the invention or part thereof to diagnose, treat and/or prevent fertility disorders. For diagnostic purposes, the expression of the protein of the invention could be investigated using any of the Northern blotting, RT-PCR or immunoblotting methods described herein and compared to the expression in control individuals. For prevention and/or treatment purposes, the protein of the invention may be used to enhance gametogenesis using any of the gene therapy methods described herein or known to those skilled in the art.

Moreover, antibodies to the protein of the invention or part thereof may be used for detection of gametes using any techniques known to those skilled in the art.

Protein of SEQ ID NO: 110 (Internal Designation 108-013-5-0-G5-FLC)

The protein of SEQ ID NO: 110 encoded by the extended cDNA SEQ ID NO: 60 displays the pfam signature for the N-terminus of the alpha-macroglobulin A2M family from positions 17 to 40. A2M-like proteins are able to inhibit all four classes of proteinases by a "trapping mechanism" (see Prosite entry PS00477 for a short review).

It is believed that the protein of SEQ ID NO: 110 or part thereof is a member of the alpha-2-macroglobulin family, more preferably a protease inhibitor. Preferred polypeptides of the invention are polypeptides comprising the amino acids of SEQ ID NO:110 from positions 17 to 40. Other preferred polypeptides of the invention are fragments of SEQ ID NO:93 having any of the biological activity described herein. The protease inhibitor activity of the protein of the invention or part thereof may be assessed using any techniques known to those skilled in the art.

The invention relates to compositions and methods using the protein of the invention or part thereof to inhibit proteases, both in vitro or in vivo. Since proteases play an important role in the regulation of many biological processes in virtually all living organisms as well as a major role in diseases, inhibitors of proteases are useful in a wide variety of applications.

In one embodiment, the protein of the invention or part thereof may be useful to quantify the amount of a given protease in a biological sample, and thus used in assays and diagnostic kits for the quantification of proteases in bodily fluids or other tissue samples, in addition to bacterial, fungal, plant, yeast, viral or mammalian cell cultures. In a preferred embodiment, the sample is assayed using a standard protease substrate. A known concentration of protease inhibitor is added, and allowed to bind to a particular protease present. The protease assay is then rerun, and the loss of activity is correlated to the protease inhibitor activity using techniques well known to those skilled in the art.

In addition, the protein of the invention or part thereof may be used to remove, identify or inhibit contaminating proteases in a sample. Compositions comprising the polypeptides of the present invention may be added to biological samples as a "cocktail" with other protease inhibitors to prevent degradation of protein samples. The advantage of using a cocktail of protease inhibitors is that one is able to inhibit a wide range of proteases without knowing the specificity of any of the proteases. Using a cocktail of protease inhibitors also protects a protein sample from a wide range of future unknown proteases which may contaminate a protein sample from a vast number of sources. For example, the protein of the invention or part thereof are added to samples where proteolytic degradation by contaminating proteases is undesirable. Such protease inhibitor cocktails (see for example the ready to use cocktails sold by Sigma) are widely used in research laboratory assays to inhibit proteases susceptible of degrading a protein of interest for which the assay is to be performed. Alternatively, the protein of the invention or part thereof may be bound to a chromatographic support, either alone or in combination with other protease inhibitor, using techniques well known in the art, to form an affinity chromatography column. A sample containing the undesirable protease is run through the column to remove the protease. Alternatively, the same methods may be used to identify new proteases.

In a preferred embodiment, the protein of the invention or part thereof may be used to inhibit proteases implicated in a number of diseases where cellular proteolysis occur such as diseases characterized by tissue degradation including but not limited to arthritis, muscular dystrophy, inflammation, tumor invasion, glomerulonephritis, parasite-borne infections, Alzheimer's disease, periodontal disease, and cancer metastasis.

In another preferred embodiment, the protein of the invention or part thereof may be useful to inhibit exogenous proteases, both in vivo and in vitro, implicated in a number of infectious diseases including but not limited to gingivitis, malaria, leishmaniasis, filariasis, osteoporosis and osteoarthritis, and other bacterial, and parasite-borne or viral infections. In particular, the protein of the invention or part thereof may offer applications in viral diseases where the proteolysis of primary polypeptide precursors is essential to the replication of the virus, as for HIV and HCV.

Furthermore, the protease inhibitors of the present invention find use in drug potentiation applications. For example, therapeutic agents such as antibiotics or antitumor drugs can be inactivated through proteolysis by endogenous proteases, thus rendering the administered drug less effective or inactive. Accordingly, the protease inhibitors of the invention may be administered to a patient in conjunction with a therapeutic agent in order to potentiate or increase the activity of the drug. This co-administration may be by simultaneous administration, such as a mixture of the protease inhibitor and the drug, or by separate simultaneous or sequential administration.

In addition, protease inhibitors have been shown to inhibit the growth of microorganisms including human pathogenic bacteria. For example, protease inhibitors are able to inhibit growth of all strains of group A streptococci, including antibiotic-resistant strains (Merigan, T. et al (1996) Ann Intern Med 124:1039-1050; Stoka, V. (1995) FEBS. Lett 370:101-104; Vonderfecht, S. et al (1988) J Clin Invest 82:2011-2016; Collins, A. et al (1991) Antimicrob Agents Chemother 35:2444-2446). Accordingly, the protease inhibitors of the present invention may be used as antibacterial agents to retard or inhibit the growth of certain bacteria either in vitro or in vivo. Particularly, the polypeptides of the present invention may be used to inhibit the growth of group A streptococci on non-living matter such as instruments not conducive to other methods of preventing or removing contamination by group A streptococci, and in culture of living plant, fungi, and animal cells.

The nucleic acid sequences of SEQ ID NOs: 24-73 or fragments thereof may also be used to construct fusion proteins in which the polypeptide sequences of SEQ ID NOs: 74-123 or fragments thereof are fused to heterologous polypeptides. For example, the fragments of the polypeptides of SEQ ID NOs. 74-123 which are included in the fusion proteins may comprise at least 5, 10, 15, 20, 25, 30, 35, 35 40, 50, 75, 100, or 150 consecutive amino acids of the polypeptides of SEQ ID NOs. 74-123 or may be of any length suitable for the intended purpose of the fusion protein. Nucleic acids encoding the desired fusion protein are produced by cloning a nucleic acid of SEQ ID NOs. 24-73 in frame with a nucleic acid encoding the heterologous polypeptide. The nucleic acid encoding the desired fusion protein is operably linked to a promoter in an appropriate vector, such as any of the vectors described above, and introduced into a host capable of expressing the fusion protein.

Antibodies against the polypeptides of SEQ ID NOs. 74-123 or fragments thereof may be used in immunoaffinity chromatography to isolate the polypeptides of SEQ ID NOs. 74-123 or fragments thereof or to isolate fusion proteins containing the polypeptides of SEQ ID NOs. 74-123 or fragments thereof.

The invention further relates to methods and compositions using the protein of the invention or part thereof to diagnose, prevent and/or treat several disorders in which the activity of the protein of the invention is deleterious. For diagnostic purposes, the expression of the protein of the invention could be investigated using any of the Northern blotting, RT-PCR or immunoblotting methods described herein and compared to the expression in control individuals. For prevention and/or treatment purposes, inhibiting the endogenous expression of the protein of the invention using any of the antisense or triple helix methods described herein may be used. Alternatively, inhibitors for the protein's activity may be developed and use to inhibit and/or reduce its activity using any methods known to those skilled in the art.

Chromosomal localization of the cDNA of the present invention were also determined using information from public and proprietary databases. Table XI lists the putative chromosomal location of the polynucleotides of the present invention. Column 1 lists the sequence identification number with the corresponding chromosomal location listed in column two.

The present invention also relates to methods and compositions using the chromosomal location of the polynucleotides of the invention to construct a human high resolution map or to identify a given chromosome in a sample using any techniques to those skilled in the art including those disclosed in Example 43.

Alternatively, the cDNA clone obtained by the process described in Examples 1 through 13 may not include the entire coding sequence of the protein encoded by the corresponding mRNA, although they do include sequences derived from the 5' ends of their corresponding mRNA. Such 5'EST can be used to isolate extended cDNAs which contain sequences adjacent to the 5' ESTs. Such obtained extended cDNAs may include the entire coding sequence of the protein encoded by the corresponding mRNA, including the authentic translation start site. Examples 16 and 17 below describe methods for obtaining extended cDNAs using 5' ESTs. Example 17 also describes methods to obtain cDNA, mRNA or genomic DNA homologous to cDNA, 5'ESTs, or fragment thereof.

The methods of Examples 16 and 17 can also be used to obtain cDNAs which encode less than the entire coding sequence of proteins encoded by the genes corresponding to the 5' ESTs. In some embodiments, the cDNAs isolated using these methods encode at least 5, 8, 10, 12, 15, 20, 25, 30, 35, 40, 50, 60, 75, 100, 150 or 200 consecutive amino acids of one of the proteins encoded by the sequences of SEQ ID NOs. 24-73.

EXAMPLE 16

General Method for Using 5' ESTs to Clone and Sequence cDNAs which Include the Entire Coding Region and the Authentic 5'EST of the Corresponding mRNA The following general method may be used to quickly and efficiently isolate cDNAs including sequence adjacent to the sequences of the 5' ESTs used to obtain them. This method, ilustrated in FIG. 3, may be applied to obtain cDNAs for any 5' EST.

The method takes advantage of the known 5' sequence of the mRNA. A reverse transcription reaction is conducted on purified mRNA with a poly dT primer containing a nucleotide sequence at its 5' end allowing the addition of a known sequence at the end of the cDNA which corresponds to the 3' end of the mRNA. Such a primer and a commercially-available reverse transcriptase enzyme are added to a buffered mRNA sample yielding a reverse transcript anchored at the 3' polyA site of the RNAs. Nucleotide monomers are then added to complete the first strand synthesis. After removal of the mRNA hybridized to the first cDNA strand by alkaline hydrolysis, the products of the alkaline hydrolysis and the residual poly dT primer can be eliminated with an exclusion column.

Subsequently, a pair of nested primers on each end is designed based on the known 5' sequence from the 5' EST and the known 3' end added by the poly dT primer used in the first strand synthesis. Software used to design primers is either based on GC content and melting temperatures of oligonucleotides, such as OSP (Illier and Green, *PCR Meth. Appl.* 1:124-128, 1991), or based on the octamer frequency disparity method (Griffais et al., *Nucleic Acids Res.* 19: 3887-3891, 1991) such as PC-Rare (world wide web site: bioinformatics.weizmann.ac.il/software/PC-Rare/doc/manuel.html). Preferably, the nested primers at the 5' end and the nested primers at the 3' end are separated from one another by four to nine bases. These primer sequences may be selected to have melting temperatures and specificities suitable for use in PCR.

A first PCR run is performed using the outer primer from each of the nested pairs. A second PCR run using the inner primer from each of the nested pairs is then performed on a small aliquot of the first PCR product. Thereafter, the primers and remaining nucleotide monomers are removed.

Due to the lack of position constraints on the design of 5' nested primers compatible for PCR use using the OSP software, amplicons of two types are obtained. Preferably, the second 5' primer is located upstream of the translation initiation codon thus yielding a nested PCR product containing the entire coding sequence. Such a cDNA may be used in a direct cloning procedure such as the one described in example 4.

However, in some cases, the second 5' primer is located downstream of the translation initiation codon, thereby yielding a PCR product containing only part of the ORF. For such amplicons which do not contain the complete coding sequence, intermediate steps are necessary to obtain both the complete coding sequence and a PCR product containing the full coding sequence. The complete coding sequence can be assembled from several partial sequences determined directly from different PCR products. Once the full coding sequence has been completely determined, new primers compatible for PCR use are then designed to obtain amplicons containing the whole coding region. However, in such cases, 3' primers compatible for PCR use are located inside the 3' UTR of the corresponding mRNA, thus yielding amplicons which lack part of this region, i.e. the polyA tract and sometimes the polyadenylation signal, as illustrated in FIG. 3. Such obtained cDNAs are then cloned into an appropriate vector using a procedure essentially similar to the one described in example 4.

Full-length PCR products are then sequenced using a procedure similar to the one described in example 11. Completion of the sequencing of a given cDNA fragment may be assessed by comparing the sequence length to the size of the corresponding nested PCR product. When Northern blot data are available, the size of the mRNA detected for a given PCR product may also be used to finally assess that the sequence is complete. Sequences which do not fulfill these criteria are discarded and will undergo a new isolation procedure.

Full-length PCR products are then cloned in an appropriate vector. For example, the cDNAs can be cloned into a vector using a procedure similar to the one described in example 4. Such full-length cDNA clones are then double-sequenced and submitted to computer analyses using procedure essentially similar to the ones described in Examples 11 through 13. However, it will be appreciated that full-length cDNA clones obtained from amplicons lacking part of the 3'UTR may lack polyadenylations sites and signals.

EXAMPLE 17

Methods for Obtaining cDNAs or Nucleic Acids Homologous to cDNAs or Fragments thereof In addition to PCR based methods for obtaining cDNAs, traditional hybridization based methods may also be employed. These methods may also be used to obtain the genomic DNAs which encode the mRNAs from which the cDNA is derived, mRNAs corresponding to the cDNAs, or nucleic acids which are homologous to cDNAs or fragments thereof. Indeed, cDNAs of the present invention or fragments thereof, including 5'ESTs, may also be used to isolate cDNAs or nucleic acids homologous to cDNAs from a cDNA library or a genomic DNA library as follows. Such cDNA libraries or genomic DNA libraries may be obtained from a commercial source or made using techniques familiar to those skilled in the art such as the one described in Examples 1 through 5. An example of such hybridization-based methods is provided below. Techniques for identifying cDNA clones in a cDNA library which hybridize to a given probe sequence are disclosed in Sambrook et al., *Molecular Cloning: A Laboratory Manual* 2d Ed., Cold Spring Harbor Laboratory Press, 1989, the disclosure of which is incorporated herein by reference. The same techniques may be used to isolate genomic DNAs.

Briefly, cDNA or genomic DNA clones which hybridize to the detectable probe are identified and isolated for further manipulation as follows. A probe comprising at least 10 consecutive nucleotides from the cDNA or fragment thereof is labeled with a detectable label such as a radioisotope or a fluorescent molecule. Preferably, the probe comprises at least 12, 15, or 17 consecutive nucleotides from the cDNA or fragment thereof. More preferably, the probe comprises 20 to 30 consecutive nucleotides from the cDNA or fragment thereof. In some embodiments, the probe comprises more than 30 nucleotides from the cDNA or fragment thereof.

Techniques for labeling the probe are well known and include phosphorylation with polynucleotide kinase, nick translation, in vitro transcription, and non radioactive techniques. The cDNAs or genomic DNAs in the library are transferred to a nitrocellulose or nylon filter and denatured. After blocking of non specific sites, the filter is incubated with the labeled probe for an amount of time sufficient to allow binding of the probe to cDNAs or genomic DNAs containing a sequence capable of hybridizing thereto.

By varying the stringency of the hybridization conditions used to identify cDNAs or genomic DNAs which hybridize to the detectable probe, cDNAs or genomic DNAs having different levels of identity to the probe can be identified and isolated as described below.

1. Isolation of cDNA or Genomic DNA Sequences having a High Degree of Identity to the Labeled Probe To identify cDNAs or genomic DNAs having a high degree of identity to the probe sequence, the melting temperature of the probe may be calculated using the following formulas:

For probes between 14 and 70 nucleotides in length the melting temperature (Tm) is calculated using the formula: $Tm = 81.5 + 16.6(\log(Na+)) + 0.41(\text{fraction } G+C) - (600/N)$ where N is the length of the probe.

If the hybridization is carried out in a solution containing formamide, the melting temperature may be calculated using the equation $Tm = 81.5 + 16.6(\log(Na+)) + 0.41(\text{fraction } G+C) - (0.63\% \text{ formamide}) - (600/N)$ where N is the length of the probe.

Prehybridization may be carried out in 6×SSC, 5×Denhardt's reagent, 0.5% SDS, 100 µg denatured fragmented salmon sperm DNA or 6×SSC, 5×Denhardt's reagent, 0.5% SDS, 100 µg denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 15-25° C. below the Tm. Preferably, for hybridizations in 6×SSC, the hybridization is conducted at approximately 68° C. Preferably, for hybridizations in 50% formamide containing solutions, the hybridization is conducted at approximately 42° C.

All of the foregoing hybridizations would be considered to be under "stringent" conditions.

Following hybridization, the filter is washed in 2×SSC, 0.1% SDS at room temperature for 15 minutes. The filter is then washed with 0.1×SSC, 0.5% SDS at room temperature for 30 minutes to 1 hour. Thereafter, the solution is washed at the hybridization temperature in 0.1×SSC, 0.5% SDS. A final wash is conducted in 0.1×SSC at room temperature.

cDNAs or genomic DNAs which have hybridized to the probe are identified by autoradiography or other conventional techniques.

2. Isolation of cDNA or Genomic DNA Sequences having Lower Degrees of Identity to the Labeled Probe The above procedure may be modified to identify cDNAs or genomic DNAs having decreasing levels of identity to the probe sequence. For example, to obtain cDNAs or genomic DNAs of decreasing identity to the detectable probe, less stringent conditions may be used. For example, the hybridization temperature may be decreased in increments of 5° C. from 68° C. to 42° C. in a hybridization buffer having a sodium concentration of approximately 1M. Following hybridization, the filter may be washed with 2×SSC, 0.5% SDS at the temperature of hybridization. These conditions are considered to be "moderate" conditions above 50° C. and "low" conditions below 50° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of identity to the probe. Following hybridization, the filter may be washed with 6×SSC, 0.5% SDS at 50° C. These conditions are considered to be "moderate" conditions above 25% formamide and "low" conditions below 25% formamide. cDNAs or genomic DNAs which have hybridized to the probe are identified by autoradiography or other conventional techniques.

3. Determination of the Degree of Identity between the Obtained cDNAs or Genomic DNAs and cDNAs or Fragments thereof Used as the Labeled Probe or between the Polypeptides Encoded by the Obtained cDNAs or Genomic DNAs and the Polypeptides Encoded by the cDNAs or Fragment thereof Used as the Labeled Probe To determine the level of identity between the hybridized cDNA or genomic DNA and the cDNA or fragment thereof from which the probe was derived, the nucleotide sequences of the hybridized nucleic acid and the cDNA or fragment thereof from which the probe was derived are compared. The sequences of the cDNA or fragment thereof from which the probe was derived and the sequences of the cDNA or genomic DNA which hybridized to the detectable probe may be stored on a computer readable medium as described below and compared to one another using any of a variety of algorithms familiar to those skilled in the art such as those described below.

To determine the level of identity between the polypeptide encoded by the hybridizing cDNA or genomic DNA and the polypeptide encoded by the cDNA or fragment thereof from which the probe was derived, the polypeptide sequence encoded by the hybridized nucleic acid and the polypeptide sequence encoded by the cDNA or fragment thereof from which the probe was derived are compared. The sequences of the polypeptide encoded by the cDNA or fragment thereof from which the probe was derived and the polypeptide sequence encoded by the cDNA or genomic DNA which hybridized to the detectable probe may be stored on a computer readable medium as described below and compared to one another using any of a variety of algorithms familiar to those skilled in the art such as those described below.

Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, *Proc. Natl. Acad. Sci. USA* 85(8):2444-2448; Altschul et al., 1990, *J. Mol. Biol.* 215(3): 403-410; Thompson et al., 1994, *Nucleic Acids Res.* 22(2): 4673-4680; Higgins et al., 1996, *Methods Enzymol.* 266:383-402; Altschul et al., 1990, *J. Mol. Biol.* 215(3):403-410; Altschul et al., 1993, *Nature Genetics* 3:266-272).

In a particularly preferred embodiment, protein and nucleic acid sequence homologies are evaluated using the Basic Local Alignment Search Tool ("BLAST") which is well known in the art (see, e.g., Karlin and Altschul, 1990, *Proc. Natl. Acad. Sci. USA* 87:2267-2268; Altschul et al., 1990, *J. Mol. Biol.* 215:403-410; Altschul et al., 1993, *Nature Genetics* 3:266-272; Altschul et al., 1997, *Nuc. Acids Res.* 25:3389-3402). In particular, five specific BLAST programs are used to perform the following task:

(1) BLASTP and BLAST3 compare an amino acid query sequence against a protein sequence database;
(2) BLASTN compares a nucleotide query sequence against a nucleotide sequence database;
(3) BLASTX compares the six-frame conceptual translation products of a query nucleotide sequence (both strands) against a protein sequence database;
(4) TBLASTN compares a query protein sequence against a nucleotide sequence database translated in all six reading frames (both strands); and
(5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992, *Science* 256:1443-1445; Henikoff and Henikoff, 1993, *Proteins* 17:49-61). Less preferably, the PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation)

The BLAST programs evaluate the statistical significance of all high-scoring segment pairs identified, and preferably selects those segments which satisfy a user-specified threshold of significance, such as a user-specified percent identity. Preferably, the statistical significance of a high-scoring segment pair is evaluated using the statistical significance formula of Karlin (see, e.g., Karlin and Altschul, 1990, *Proc. Natl. Acad. Sci. USA* 87:2267-2268).

The parameters used with the above algorithms may be adapted depending on the sequence length and degree of identity studied. In some embodiments, the parameters may be the default parameters used by the algorithms in the absence of instructions from the user.

In some embodiments, the level of identity between the hybridized nucleic acid and the cDNA or fragment thereof from which the probe was derived may be determined using the FASTDB algorithm described in Brutlag et al. Comp. App. Biosci. 6:237-245, 1990. In such analyses the parameters may be selected as follows: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the sequence which hybridizes to the probe, whichever is shorter. Because the FASTDB program does not consider 5' or 3' truncations when calculating identity levels, if the sequence which hybridizes to the probe is truncated relative to the sequence of the cDNA or fragment thereof from which the probe was derived the identity level is manually adjusted by calculating the number of nucleotides of the cDNA or fragment thereof which are not matched or aligned with the hybridizing sequence, determining the percentage of total nucleotides of the hybridizing sequence which the non-matched or non-aligned nucleotides represent, and subtracting this percentage from the identity level. For example, if the hybridizing sequence is 700 nucleotides in length and the cDNA or fragment thereof sequence is 1000 nucleotides in length wherein the first 300 bases at the 5' end of the cDNA or fragment thereof are absent from the hybridizing sequence, and wherein the overlapping 700 nucleotides are identical, the identity level would be adjusted as follows. The non-matched, non-aligned 300 bases represent 30% of the length of the cDNA or fragment thereof. If the overlapping 700 nucleotides are 100% identical, the adjusted identity level would be 100−30=70% identity. It should be noted that the preceding adjustments are only made when the non-matched or non-aligned nucleotides are at the 5' or 3' ends. No adjustments are made if the non-matched or non-aligned sequences are internal or under any other conditions.

For example, using the above methods, nucleic acids having at least 95% nucleic acid identity, at least 96% nucleic acid identity, at least 97% nucleic acid identity, at least 98% nucleic acid identity, at least 99% nucleic acid identity, or more than 99% nucleic acid identity to the cDNA or fragment thereof from which the probe was derived may be obtained and identified. Such nucleic acids may be allelic variants or related nucleic acids from other species. Similarly, by using progressively less stringent hybridization conditions one can obtain and identify nucleic acids having at least 90%, at least 85%, at least 80% or at least 75% identity to the cDNA or fragment thereof from which the probe was derived.

Using the above methods and algorithms such as FASTA with parameters depending on the sequence length and degree of identity studied, for example the default parameters used by the algorithms in the absence of instructions from the user, one can obtain nucleic acids encoding proteins having at least 99%, at least 98%, at least 97%, at least 96%, at least 95%, at least 90%, at least 85% at least 80% or at least 75% identity to the protein encoded by the cDNA or fragment thereof from which the probe was derived. In some embodiments, the identity levels can be determined using the "default" opening penalty and the "default" gap penalty, and a scoring matrix such as PAM 250 (a standard scoring matrix; see Dayhoff et al., in: Atlas of Protein Sequence and Structure, Vol. 5, Supp. 3 (1978)).

Alternatively, the level of polypeptide identity may be determined using the FASTDB algorithm described by Brutlag et al. Comp. App. Biosci. 6:237-245, 1990. In such analyses the parameters may be selected as follows: Matrix=PAM 0, k-tuple=2, Mismatch Penalty=1, Joining Penalty=20, Randomization Group Length=0, Cutoff Score=1, Window Size=Sequence Length, Gap Penalty=5, Gap Size Penalty=0.05, Window Size=500 or the length of the homologous sequence, whichever is shorter. If the homologous amino acid sequence is shorter than the amino acid sequence encoded by the cDNA or fragment thereof as a result of an N terminal and/or C terminal deletion the results may be manually corrected as follows. First, the number of amino acid residues of the amino acid sequence encoded by the cDNA or fragment thereof which are not matched or aligned with the homologous sequence is determined. Then, the percentage of the length of the sequence encoded by the cDNA or fragment thereof which the non-matched or non-aligned amino acids represent is calculated. This percentage is subtracted from the identity level. For example wherein the amino acid sequence encoded by the cDNA or fragment thereof is 100 amino acids in length and the length of the homologous sequence is 80 amino acids and wherein the amino acid sequence encoded by the cDNA or fragment thereof is truncated at the N terminal end with respect to the homologous sequence, the identity level is calculated as follows. In the preceding scenario there are 20 non-matched, non-aligned amino acids in the sequence encoded by the cDNA or fragment thereof. This represents 20% of the length of the amino acid sequence encoded by the cDNA or fragment thereof. If the remaining amino acids are 100% identical between the two sequences, the identity level would be 100%–20%=80% identity. No adjustments are made if the non-matched or non-aligned sequences are internal or under any other conditions.

In addition to the above described methods, other protocols are available to obtain homologous cDNAs using cDNA of the present invention or fragment thereof as outlined in the following paragraphs.

cDNAs may be prepared by obtaining mRNA from the tissue, cell, or organism of interest using mRNA preparation procedures utilizing polyA selection procedures or other techniques known to those skilled in the art. A first primer capable of hybridizing to the polyA tail of the mRNA is hybridized to the mRNA and a reverse transcription reaction is performed to generate a first cDNA strand.

The first cDNA strand is hybridized to a second primer containing at least 10 consecutive nucleotides of the sequences of SEQ ID NOs 24-73. Preferably, the primer comprises at least 10, 12, 15, 17, 18, 20, 23, 25, or 28 consecutive nucleotides from the sequences of SEQ ID NOs 24-73. In some embodiments, the primer comprises more than 30 nucleotides from the sequences of SEQ ID NOs 24-73. If it is desired to obtain cDNAs containing the full protein coding sequence, including the authentic translation initiation site, the second primer used contains sequences located upstream of the translation initiation site. The second primer is extended to generate a second cDNA strand complementary to the first cDNA strand. Alternatively, RT-PCR may be performed as described above using primers from both ends of the cDNA to be obtained.

cDNAs containing 5' fragments of the mRNA may be prepared by hybridizing an mRNA comprising the sequences of SEQ ID NOs. 24-73 with a primer comprising a complementary to a fragment of the known cDNA, genomic DNA or fragment thereof hybridizing the primer to the mRNAs, and reverse transcribing the hybridized primer to make a first cDNA strand from the mRNAs. Preferably, the primer comprises at least 10, 12, 15, 17, 18, 20, 23, 25, or 28 consecutive nucleotides of the sequences complementary to SEQ ID NOs. 24-73.

Thereafter, a second cDNA strand complementary to the first cDNA strand is synthesized. The second cDNA strand may be made by hybridizing a primer complementary to sequences in the first cDNA strand to the first cDNA strand and extending the primer to generate the second cDNA strand.

The double stranded cDNAs made using the methods described above are isolated and cloned. The cDNAs may be cloned into vectors such as plasmids or viral vectors capable of replicating in an appropriate host cell. For example, the host cell may be a bacterial, mammalian, avian, or insect cell.

Techniques for isolating mRNA, reverse transcribing a primer hybridized to mRNA to generate a first cDNA strand, extending a primer to make a second cDNA strand complementary to the first cDNA strand, isolating the double stranded cDNA and cloning the double stranded cDNA are well known to those skilled in the art and are described in *Current Protocols in Molecular Biology*, John Wiley & Sons, Inc. 1997 and Sambrook et al., Molecular Cloning: A Laboratory Manual, Second Edition, Cold Spring Harbor Laboratory Press, 1989.

Alternatively, other procedures may be used for obtaining full-length cDNAs or homologous cDNAs. In one approach, cDNAs are prepared from mRNA and cloned into double stranded phagemids as follows. The cDNA library in the double stranded phagemids is then rendered single stranded by treatment with an endonuclease, such as the Gene II product of the phage F1 and an exonuclease (Chang et al., Gene 127:95-8, 1993). A biotinylated oligonucleotide comprising the sequence of a fragment of a known cDNA, genomic DNA or fragment thereof is hybridized to the single stranded phagemids. Preferably, the fragment comprises at least 10, 12, 15, 17, 18, 20, 23, 25, or 28 consecutive nucleotides of the sequences of SEQ ID NOs. 24-73.

Hybrids between the biotinylated oligonucleotide and phagemids are isolated by incubating the hybrids with streptavidin coated paramagnetic beads and retrieving the beads with a magnet (Fry et al., *Biotechniques*, 13: 124-131, 1992). Thereafter, the resulting phagemids are released from the beads and converted into double stranded DNA using a primer specific for the cDNA or fragment thereof used to design the biotinylated oligonucleotide. Alternatively, protocols such as the Gene Trapper kit (Gibco BRL) may be used. The resulting double stranded DNA is transformed into bacteria. Homologous cDNAs or full length cDNAs containing the cDNA or fragment thereof sequence are identified by colony PCR or colony hybridization.

Using any of the above described methods, a plurality of cDNAs containing full-length protein coding sequences or fragments of the protein coding sequences may be provided as cDNA libraries for subsequent evaluation of the encoded proteins or use in diagnostic assays as described below.

cDNAs prepared by any method described therein may be subsequently engineered to obtain nucleic acids which include desired fragments of the cDNA using conventional techniques such as subcloning, PCR, or in vitro oligonucleotide synthesis. For example, nucleic acids which include only the full coding sequences (i.e. the sequences encoding the signal peptide and the mature protein remaining after the signal peptide peptide is cleaved off) may be obtained using techniques known to those skilled in the art. Alternatively, conventional techniques may be applied to obtain nucleic acids which contain only the coding sequence for the mature protein remaining after the signal peptide is cleaved off or nucleic acids which contain only the coding sequences for the signal peptides.

Similarly, nucleic acids containing any other desired fragment of the coding sequences for the encoded protein may be obtained. For example, the nucleic acid may contain at least 8, 10, 12, 15, 18, 20, 25, 28, 30, 35, 40, 50, 75, 100, 150, 200, 300, 400, 500, 1000 or 2000 consecutive bases of a cDNA.

Once a cDNA has been obtained, it can be sequenced to determine the amino acid sequence it encodes. Once the encoded amino acid sequence has been determined, one can create and identify any of the many conceivable cDNAs that will encode that protein by simply using the degeneracy of the genetic code. For example, allelic variants or other homologous nucleic acids can be identified as described below. Alternatively, nucleic acids encoding the desired amino acid sequence can be synthesized in vitro.

In a preferred embodiment, the coding sequence may be selected using the known codon or codon pair preferences for the host organism in which the cDNA is to be expressed.

IV. Use of cDNA or Fragments thereof to Express Proteins and Uses of those Expressed Proteins Using any of the above described methods, cDNAs containing the full protein coding sequences of their corresponding mRNAs or portions thereof, such as cDNAs encoding the mature protein, may be used to express the secreted proteins or portions thereof which they encode as described below. If desired, the cDNAs may contain the sequences encoding the signal peptide to facilitate secretion of the expressed protein. It will be appreciated that a plurality of extended cDNAs containing the full protein coding sequences or portions thereof may be simultaneously cloned into expression vectors to create an expression library for analysis of the encoded proteins as described below.

EXAMPLE 18

Expression of the Proteins Encoded by cDNAs or Fragments thereof

To express the proteins encoded by the cDNAs or fragments thereof, nucleic acids containing the coding sequence for the proteins or fragments thereof to be expressed are obtained as described above and cloned into a suitable expression vector. If desired, the nucleic acids may contain the sequences encoding the signal peptide to facilitate secretion of the expressed protein. For example, the nucleic acid may comprise the sequence of one of SEQ ID NOs: 24-73 listed in Table I and in the accompanying sequence listing. Alternatively, the nucleic acid may comprise those nucleotides which make up the full coding sequence of one of the sequences of SEQ ID NOs: 24-73 as defined in Table I above.

It will be appreciated that should the extent of the full coding sequence (i.e. the sequence encoding the signal peptide and the mature protein resulting from cleavage of the signal peptide) differ from that listed in Table I as a result of a sequencing error, reverse transcription or amplification error, mRNA splicing, post-translational modification of the encoded protein, enzymatic cleavage of the encoded protein, or other biological factors, one skilled in the art would be readily able to identify the extent of the full coding sequences in the sequences of SEQ ID NOs. 24-73. Accordingly, the scope of any claims herein relating to nucleic acids containing the full coding sequence of one of SEQ ID NOs. 24-73 is not to be construed as excluding any readily identifiable variations from or equivalents to the full coding sequences listed in Table I. Similarly, should the extent of the full length polypeptides differ from those indicated in Table II as a result of any of the preceding factors, the scope of claims relating to polypeptides comprising the amino acid sequence of the full length polypeptides is not to be construed as excluding any readily identifiable variations from or equivalents to the sequences listed in Table II.

Alternatively, the nucleic acid used to express the protein or fragment thereof may comprise those nucleotides which encode the mature protein (i.e. the protein created by cleaving the signal peptide off) encoded by one of the sequences of SEQ ID NOs: 24-73 as defined in Table I above.

It will be appreciated that should the extent of the sequence encoding the mature protein differ from that listed in Table I as a result of a sequencing error, reverse transcription or amplification error, mRNA splicing, post-translational modification of the encoded protein, enzymatic cleavage of the encoded protein, or other biological factors, one skilled in the art would be readily able to identify the extent of the sequence encoding the mature protein in the sequences of SEQ ID NOs. 24-73. Accordingly, the scope of any claims herein relating to nucleic acids containing the sequence encoding the mature protein encoded by one of SEQ ID NOs.24-73 is not to be construed as excluding any readily identifiable variations from or equivalents to the sequences listed in Table I. Thus, claims relating to nucleic acids containing the sequence encoding the mature protein encompass equivalents to the sequences listed in Table I, such as sequences encoding biologically active proteins resulting from post-translational modification, enzymatic cleavage, or other readily identifiable variations from or equivalents to the secreted proteins in addition to cleavage of the signal peptide. Similarly, should the extent of the mature polypeptides differ from those indicated in Table II as a result of any of the preceding factors, the scope of claims relating to polypeptides comprising the sequence of a mature protein included in the sequence of one of SEQ ID NOs. 74-123 is not to be construed as excluding any readily identifiable variations from or equivalents to the sequences listed in Table II. Thus, claims relating to polypeptides comprising the sequence of the mature protein encompass equivalents to the sequences listed in Table II, such as biologically active proteins resulting from post-translational modification, enzymatic cleavage, or other readily identifiable variations from or equivalents to the secreted proteins in addition to cleavage of the signal peptide. It will also be appreciated that should the biologically active form of the polypeptides included in the sequence of one of SEQ ID NOs. 74-123 or the nucleic acids encoding the biologically active form of the polypeptides differ from those identified as the mature polypeptide in Table II or the nucleotides encoding the mature polypeptide in Table I as a result of a sequencing error, reverse transcription or amplification error, mRNA splicing, post-translational modification of the encoded protein, enzymatic cleavage of the encoded protein, or other biological factors, one skilled in the art would be readily able to identify the amino acids in the biologically active form of the polypeptides and the nucleic acids encoding the biologically active form of the polypeptides. In such instances, the claims relating to polypetides comprising the mature protein included in one of SEQ ID NOs. 74-123 or nucleic acids comprising the nucleotides of one of SEQ ID NOs. 24-73 encoding the mature protein shall not be construed to exclude any readily identifiable variations from the sequences listed in Table I and Table II.

In some embodiments, the nucleic acid used to express the protein or fragment thereof may comprise those nucleotides which encode the signal peptide encoded by one of the sequences of SEQ ID NOs: 24-73 as defined in Table I above.

It will be appreciated that should the extent of the sequence encoding the signal peptide differ from that listed in Table I as a result of a sequencing error, reverse transcription or amplification error, mRNA splicing, post-translational modification of the encoded protein, enzymatic cleavage of the encoded protein, or other biological factors, one skilled in the art would be readily able to identify the extent of the sequence encoding the signal peptide in the sequences of SEQ ID NOs. 24-73. Accordingly, the scope of any claims herein relating to nucleic acids containing the sequence encoding the signal peptide encoded by one of SEQ ID NOs.24-73 is not to be construed as excluding any readily identifiable variations from the sequences listed in Table I. Similarly, should the extent of the signal peptides differ from those indicated in Table II as a result of any of the preceding factors, the scope of claims relating to polypeptides comprising the sequence of a signal peptide included in the sequence of one of SEQ ID NOs. 74-123 is not to be construed as excluding any readily identifiable variations from the sequences listed in Table II.

Alternatively, the nucleic acid may encode a polypeptide comprising at least 5 consecutive amino acids of one of the sequences of SEQ ID NOs: 74-123. In some embodiments, the nucleic acid may encode a polypeptide comprising at least 8, 10, 12, 15, 20, 25, 30, 35, 40, 50, 60, 75, 100, 150 or 200 consecutive amino acids of one of the sequences of SEQ ID NOs: 74-123.

The nucleic acids inserted into the expression vectors may also contain sequences upstream of the sequences encoding the signal peptide, such as sequences which regulate expression levels or sequences which confer tissue specific expression.

The nucleic acid encoding the protein or polypeptide to be expressed is operably linked to a promoter in an expression vector using conventional cloning technology. The expression vector may be any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence may be optimized for the particular expression organism in which the expression vector is introduced, as explained by Hatfield, et al., U.S. Pat. No. 5,082,767, incorporated herein by this reference.

The following is provided as one exemplary method to express the proteins encoded by the cDNAs or the nucleic acids described above. First, the methionine initiation codon for the gene and the poly A signal of the gene are identified. If the nucleic acid encoding the polypeptide to be expressed lacks a methionine to serve as the initiation site, an initiating methionine can be introduced next to the first codon of the nucleic acid using conventional techniques. Similarly, if the cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a fragment of the gag gene from Moloney Murine Leukemia Virus. The position of the LTRs in the construct allow efficient stable transfection. The vector includes the Herpes Simplex Thymidine Kinase promoter and the selectable neomycin gene. The cDNA or fragment thereof encoding the polypeptide to be expressed is obtained by PCR from the bacterial vector using oligonucleotide primers complementary to the cDNA or fragment thereof and containing restriction endonuclease sequences for PstI incorporated into the 5' primer and BglII at the 5' end of the corresponding cDNA 3' primer, taking care to ensure that the cDNA is positioned in frame with the poly A signal. The purified fragment obtained from the resulting PCR reaction is digested with PstI, blunt ended with an exonuclease, digested with BglII, purified and ligated to pXT1, now containing a poly A signal and digested with BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.). Preferably the expressed protein is released into the culture medium, thereby facilitating purification.

Alternatively, the cDNAs may be cloned into pED6dpc2 (DiscoverEase, Genetics Institute, Cambridge, Mass.). The resulting pED6dpc2 constructs may be transfected into a suitable host cell, such as COS 1 cells. Methotrexate resistant cells are selected and expanded. Preferably, the protein expressed from the cDNA is released into the culture medium thereby facilitating purification.

Proteins in the culture medium are separated by gel electrophoresis. If desired, the proteins may be ammonium sulfate precipitated or separated based on size or charge prior to electrophoresis.

As a control, the expression vector lacking a cDNA insert is introduced into host cells or organisms and the proteins in the medium are harvested. The secreted proteins present in the medium are detected using techniques such as Coomassie or silver staining or using antibodies against the protein encoded by the cDNA. Coomassie and silver staining techniques are familiar to those skilled in the art.

Antibodies capable of specifically recognizing the protein of interest may be generated using synthetic 15-mer peptides having a sequence encoded by the appropriate 5' EST, cDNA, or fragment thereof. The synthetic peptides are injected into mice to generate antibody to the polypeptide encoded by the 5' EST, cDNA, or fragment thereof.

Secreted proteins from the host cells or organisms containing an expression vector which contains the cDNA or a fragment thereof are compared to those from the control cells or organism. The presence of a band in the medium from the cells containing the expression vector which is absent in the medium from the control cells indicates that the cDNA encodes a secreted protein. Generally, the band corresponding to the protein encoded by the cDNA will have a mobility near that expected based on the number of amino acids in the open reading frame of the cDNA. However, the band may have a mobility different than that expected as a result of modifications such as glycosylation, ubiquitination, or enzymatic cleavage.

Alternatively, if the protein expressed from the above expression vectors does not contain sequences directing its secretion, the proteins expressed from host cells containing an expression vector containing an insert encoding a secreted protein or fragment thereof can be compared to the proteins expressed in host cells containing the expression vector without an insert. The presence of a band in samples from cells containing the expression vector with an insert which is absent in samples from cells containing the expression vector without an insert indicates that the desired protein or fragment thereof is being expressed. Generally, the band will have the mobility expected for the secreted protein or fragment thereof. However, the band may have a mobility different than that expected as a result of modifications such as glycosylation, ubiquitination, or enzymatic cleavage.

The protein encoded by the cDNA may be purified using standard immunochromatography techniques. In such procedures, a solution containing the secreted protein, such as the culture medium or a cell extract, is applied to a column having antibodies against the secreted protein attached to the chromatography matrix. The secreted protein is allowed to bind the immunochromatography column. Thereafter, the column is washed to remove non-specifically bound proteins. The specifically bound secreted protein is then released from the column and recovered using standard techniques.

If antibody production is not possible, the cDNA sequence or fragment thereof may be incorporated into expression vectors designed for use in purification schemes employing chimeric polypeptides. In such strategies the coding sequence of the cDNA or fragment thereof is inserted in frame with the gene encoding the other half of the chimera. The other half of the chimera may be β-globin or a nickel binding polypeptide encoding sequence. A chromatography matrix having antibody to β-globin or nickel attached thereto is then used to purify the chimeric protein. Protease cleavage sites may be engineered between the β-globin gene or the nickel binding polypeptide and the cDNA or fragment thereof. Thus, the two polypeptides of the chimera may be separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are published in methods texts such as Davis et al., (*Basic Methods in Molecular Biology*, L. G. Davis, M. D. Dibner, and J. F. Battey, ed., Elsevier Press, NY, 1986) and many of the methods are available from Stratagene, Life Technologies, Inc., or Promega. Polypeptide may additionally be produced from the construct using in vitro translation systems such as the In vitro Express™ Translation Kit (Stratagene).

Following expression and purification of the secreted proteins encoded by the 5' ESTs, cDNAs, or fragments thereof, the purified proteins may be tested for the ability to bind to the surface of various cell types as described below. It will be appreciated that a plurality of proteins expressed from these cDNAs may be included in a panel of proteins to be simultaneously evaluated for the activities specifically described below, as well as other biological roles for which assays for determining activity are available.

Alternatively, the polypeptide to be expressed may also be a product of transgenic animals, i.e., as a component of the milk of transgenic cows, goats, pigs or sheeps which are characterized by somatic or germ cells containing a nucleotide sequence encoding the protein of interest.

EXAMPLE 19

Analysis of Secreted Proteins to Determine Whether they Bind to the Cell Surface The proteins encoded by the cDNAs, or fragments thereof are cloned into expression vectors such as those described in the previous example. The proteins are purified by size, charge, immunochromatography or other techniques familiar to those skilled in the art. Following purification, the proteins are labeled using techniques known to those skilled in the art. The labeled proteins are incubated with cells or cell lines derived from a variety of organs or tissues to allow the proteins to bind to any receptor present on the cell surface. Following the incubation, the cells are washed to remove non-specifically bound protein. The labeled proteins are detected by autoradiography. Alternatively, unlabeled proteins may be incubated with the cells and detected with antibodies having a detectable label, such as a fluorescent molecule, attached thereto.

Specificity of cell surface binding may be analyzed by conducting a competition analysis in which various amounts of unlabeled protein are incubated along with the labeled protein. The amount of labeled protein bound to the cell surface decreases as the amount of competitive unlabeled protein increases. As a control, various amounts of an unlabeled protein unrelated to the labeled protein is included in some binding reactions. The amount of labeled protein bound to the cell surface does not decrease in binding reactions containing increasing amounts of unrelated unlabeled protein, indicating that the protein encoded by the cDNA binds specifically to the cell surface.

As discussed above, secreted proteins have been shown to have a number of important physiological effects and, consequently, represent a valuable therapeutic resource. The secreted proteins encoded by the cDNAs or fragments thereof made using any of the methods described therein may be evaluated to determine their physiological activities as described below.

EXAMPLE 20

Assaying the Proteins Expressed from cDNAs or Fragments thereof for Cytokine, Cell Proliferation or Cell Differentiation Activity As discussed above, secreted proteins may act as cytokines or may affect cellular proliferation or differentiation. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7c and CMK. The proteins encoded by the above cDNAs or fragments thereof may be evaluated for their ability to regulate T. cell or thymocyte proliferation in assays such as those described above or in the following references, which are incorporated herein by reference: *Current Protocols in Immunology*, Ed. by J. E. Coligan et al., Greene Publishing Associates and Wiley-Interscience; Takai et al. *J. Immunol*. 137:3494-3500, 1986. Bertagnolli et al. *J. Immunol*. 145:1706-1712, 1990. Bertagnolli et al., *Cellular Immunology* 133:327-341, 1991. Bertagnolli, et al. *J. Immunol*. 149:3778-3783, 1992; Bowman et al., *J. Immunol*. 152:1756-1761, 1994.

In addition, numerous assays for cytokine production and/or the proliferation of spleen cells, lymph node cells and thymocytes are known. These include the techniques disclosed in *Current Protocols in Immunology*. J. E. Coligan et al. Eds., Vol 1 pp. 3.12.1-3.12.14 John Wiley and Sons, Toronto. 1994; and Schreiber, R. D. *Current Protocols in Immunolog.*, supra Vol 1 pp. 6.8.1-6.8.8, John Wiley and Sons, Toronto. 1994.

The proteins encoded by the cDNAs may also be assayed for the ability to regulate the proliferation and differentiation of hematopoietic or lymphopoietic cells. Many assays for such activity are familiar to those skilled in the art, including the assays in the following references, which are incorporated herein by reference: Bottomly, K., Davis, L. S. and Lipsky, P. E., Measurement of Human and Murine Interleukin 2 and Interleukin 4, *Current Protocols in Immunology.*, J. E. Coligan et al. Eds. Vol 1 pp. 6.3.1-6.3.12, John Wiley and Sons, Toronto. 1991; deVries et al., *J. Exp. Med.* 173:1205-1211, 1991; Moreau et al., *Nature* 36:690-692, 1988; Greenberger et al., *Proc. Natl. Acad. Sci. U.S.A.* 80:2931-2938, 1983; Nordan, R., Measurement of Mouse and Human Interleukin 6 *Current Protocols in Immunology*. J. E. Coligan et al. Eds. Vol 1 pp. 6.6.1-6.6.5, John Wiley and Sons, Toronto. 1991; Smith et al., *Proc. Natl. Acad. Sci. U.S.A.* 83:1857-1861, 1986; Bennett, F., Giannotti, J., Clark, S. C. and Turner, K. J., Measurement of Human Interleukin 11 *Current Protocols in Immunology*. J. E. Coligan et al. Eds. Vol 1 pp. 6.15.1 John Wiley and Sons, Toronto. 1991; Ciarletta, A., Giannotti, J., Clark, S. C. and Turner, K. J., Measurement of Mouse and Human Interleukin 9 *Current Protocols in Immunology*. J. E. Coligan et al., Eds. Vol 1 pp. 6.13.1, John Wiley and Sons, Toronto. 1991.

The proteins encoded by the cDNAs may also be assayed for their ability to regulate T-cell responses to antigens. Many assays for such activity are familiar to those skilled in the art, including the assays described in the following references, which are incorporated herein by reference: Chapter 3 (In vitro Assays for Mouse Lymphocyte Function), Chapter 6 (Cytokines and Their Cellular Receptors) and Chapter 7, (Immunologic Studies in Humans) in *Current Protocols in Immunology*, J. E. Coligan et al. Eds. Greene Publishing Associates and Wiley-Interscience; Weinberger et al., *Proc. Natl. Acad. Sci. USA* 77:6091-6095, 1980; Weinberger et al., *Eur. J. Immun.* 11:405-411, 1981; Takai et al., *J. Immunol.* 137:3494-3500, 1986; Takai et al., *J. Immunol.* 140:508-512, 1988.

Those proteins which exhibit cytokine, cell proliferation, or cell differentiation activity may then be formulated as pharmaceuticals and used to treat clinical conditions in which induction of cell proliferation or differentiation is beneficial. Alternatively, as described in more detail below, genes encoding these proteins or nucleic acids regulating the expression of these proteins may be introduced into appropriate host cells to increase or decrease the expression of the proteins as desired.

EXAMPLE 21

Assaying the Proteins Expressed from cDNAs or Fragments thereof for Activity as Immune System Regulators The proteins encoded by the cDNAs may also be evaluated for their effects as immune regulators. For example, the proteins may be evaluated for their activity to influence thymocyte or splenocyte cytotoxicity. Numerous assays for such activity are familiar to those skilled in the art including the assays described in the following references, which are incorporated herein by reference: Chapter 3 (In vitro Assays for Mouse Lymphocyte Function 3.1-3.19) and Chapter 7 (Immunologic studies in Humans) in *Current Protocols in Immunology*, J. E. Coligan et al. Eds, Greene Publishing Associates and Wiley-Interscience; Herrmann et al., *Proc. Natl. Acad. Sci. USA* 78:2488-2492, 1981; Herrmann et al., *J. Immunol.* 128:1968-1974, 1982; Handa et al., *J. Immunol.* 135:1564-1572, 1985; Takai et al., *J. Immunol.* 137:3494-3500, 1986; Takai et al., *J. Immunol.* 140:508-512, 1988; Herrmann et al., *Proc. Natl. Acad. Sci. USA* 78:2488-2492, 1981; Herrmann et al., *J. Immunol.* 128:1968-1974, 1982; Handa et al., *J. Immunol.* 135:1564-1572, 1985; Takai et al., *J. Immunol.* 137: 3494-3500, 1986; Bowman et al., *J. Virology* 61:1992-1998; Takai et al., *J. Immunol.* 140:508-512, 1988; Bertagnolli et al., *Cellular Immunology* 133:327-341, 1991; Brown et al., *J. Immunol.* 153:3079-3092, 1994.

The proteins encoded by the cDNAs may also be evaluated for their effects on T-cell dependent immunoglobulin responses and isotype switching. Numerous assays for such activity are familiar to those skilled in the art, including the assays disclosed in the following references, which are incorporated herein by reference: Maliszewski, *J. Immunol.* 144: 3028-3033, 1990; Mond, J. J. and Brunswick, M Assays for B Cell Function: In vitro Antibody Production, Vol 1 pp. 3.8.1-3.8.16 in *Current Protocols in Immunology*. J. E. Coligan et al Eds., John Wiley and Sons, Toronto. 1994.

The proteins encoded by the cDNAs may also be evaluated for their effect on immune effector cells, including their effect on Th1 cells and cytotoxic lymphocytes. Numerous assays for such activity are familiar to those skilled in the art, including the assays disclosed in the following references, which are incorporated herein by reference: Chapter 3 (In vitro Assays for Mouse Lymphocyte Function 3.1-3.19) and Chapter 7 (Immunologic Studies in Humans) in *Current Protocols in Immunology*, J. E. Coligan et al. Eds., Greene Publishing Associates and Wiley-Interscience; Takai et al., *J. Immunol.* 137:3494-3500, 1986; Takai et al.; *J. Immunol.* 140:508-512, 1988; Bertagnolli et al., *J. Immunol.* 149:3778-3783, 1992.

The proteins encoded by the cDNAs may also be evaluated for their effect on dendritic cell mediated activation of naive T-cells. Numerous assays for such activity are familiar to those skilled in the art, including the assays disclosed in the following references, which are incorporated herein by reference: Guery et al., *J. Immunol.* 134:536-544, 1995; Inaba et al., *Journal of Experimental Medicine* 173:549-559, 1991; Macatonia et al., *Journal of Immunology* 154:5071-5079, 1995; Porgador et al., *Journal of Experimental Medicine* 182:255-260, 1995; Nair et al., *Journal of Virology* 67:4062-4069, 1993; Huang et al., *Science* 264:961-965, 1994; Macatonia et al., *Journal of Experimental Medicine* 169:1255-1264, 1989; Bhardwaj et al., *Journal of Clinical Investigation* 94:797-807, 1994; and Inaba et al., *Journal of Experimental Medicine* 172:631-640, 1990.

The proteins encoded by the cDNAs may also be evaluated for their influence on the lifetime of lymphocytes. Numerous assays for such activity are familiar to those skilled in the art, including the assays disclosed in the following references, which are incorporated herein by reference: Darzynkiewicz et al., *Cytometry* 13:795-808, 1992; Gorczyca et al., *Leukemia* 7:659-670, 1993; Gorczyca et al., *Cancer Research* 53:1945-1951, 1993; Itoh et al., *Cell* 66:233-243, 1991; Zacharchuk, *Journal of Immunology* 145:4037-4045, 1990; Zamai et al., Cytometry 14:891-897, 1993; Gorczyca et al., *International Journal of Oncology* 1:639-648, 1992.

Assays for proteins that influence early steps of T-cell commitment and development include, without limitation, those described in: Antica et al., Blood 84:111-117, 1994; Fine et al., Cellular immunology 155:111-122, 1994; Galy et al., Blood 85:2770-2778, 1995; Toki et al., Proc. Nat. Acad Sci. USA 88:7548-7551, 1991.

Those proteins which exhibit activity as immune system regulators activity may then be formulated as pharmaceuticals and used to treat clinical conditions in which regulation of immune activity is beneficial. For example, the protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases caused by viral, bacterial, fungal or other infection may be treatable using a protein of the present invention, including infections by HIV, hepatitis viruses, herpesviruses, mycobacteria, *Leishmania* spp., *malaria* spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to regulate immune responses, in a number of ways. Down regulation may be in the form of inhibiting or blocking an immune response already in progress or may involve preventing the induction of an immune response. The functions of activated T-cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789-792 (1992) and Turka et al., Proc. Natl. Acad. Sci USA, 89:11102-11105 (1992). In addition, murine models of GVHD (see Paul ed., Fundamental Immunology, Raven Press, New York, 1989, pp. 846-847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/pr/pr mice or NZB hybrid mice, murine autoimmuno collagen arthritis, diabetes mellitus in OD mice and BB rats, and murine experimental myasthenia gravis (see Paul ed., Fundamental Immunology, Raven Press, New York, 1989, pp. 840-856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory form of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. The infected cells would now be capable of delivering a costimulatory signal to T cells in vivo, thereby activating the T cells.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acids encoding all or a fragment of (e.g., a cytoplasmic-domain truncated fragment) of an MHC class I $\alpha$ chain protein and $\beta_2$ microglobulin protein or an MHC class II $\alpha$ chain protein and an MHC class II $\beta$ chain protein to thereby express MHC class I or MHC class II proteins on the cell surface. Expression of the appropriate class II or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject. Alternatively, as described in more detail below, genes encoding these proteins or nucleic acids regulating the expression of these proteins may be introduced into appropriate host cells to increase or decrease the expression of the proteins as desired.

EXAMPLE 22

Assaying the Proteins Expressed from cDNAs or Fragments thereof for Hematopoiesis Regulating Activity The proteins encoded by the cDNAs or fragments thereof may also be evaluated for their hematopoiesis regulating activity. For example, the effect of the proteins on embryonic stem cell differentiation may be evaluated. Numerous assays for such activity are familiar to those skilled in the art, including the assays disclosed in the following references, which are incorporated herein by reference: Johansson et al. *Cellular Biology* 15:141-151, 1995; Keller et al., *Molecular and Cellular Biology* 13:473-486, 1993; McClanahan et al., *Blood* 81:2903-2915, 1993.

The proteins encoded by the cDNAs or fragments thereof may also be evaluated for their influence on the lifetime of stem cells and stem cell differentiation. Numerous assays for such activity are familiar to those skilled in the art, including the assays disclosed in the following references, which are incorporated herein by reference: Freshney, M. G. Methylcellulose Colony Forming Assays, in *Culture of Hematopoietic Cells*. R. I. Freshney, et al. Eds. pp. 265-268, Wiley-Liss, Inc., New York, N.Y. 1994; Hirayama et al., *Proc. Natl. Acad. Sci. USA* 89:5907-5911, 1992; McNiece, I. K. and Briddell, R. A. Primitive Hematopoietic Colony Forming Cells with High Proliferative Potential, in *Culture of Hematopoietic Cells*. R. I. Freshney, et al. eds. Vol pp. 23-39, Wiley-Liss, Inc., New York, N.Y. 1994; Neben et al., *Experimental Hematology* 22:353-359, 1994; Ploemacher, R. E. Cobblestone Area Forming Cell Assay, In *Culture of Hematopoietic Cells*. R. I. Freshney, et al. Eds. pp. 1-21, Wiley-Liss, Inc., New York, N.Y. 1994; Spooncer, E., Dexter, M. and Allen, T. Long Term Bone Marrow Cultures in the Presence of Stromal Cells, in *Culture of Hematopoietic Cells*. R. I. Freshney, et al. Eds. pp. 163-179, Wiley-Liss, Inc., New York, N.Y. 1994; and Sutherland, H. J. Long Term Culture Initiating Cell Assay, in *Culture of Hematopoietic Cells*. R. I. Freshney, et al. Eds. pp. 139-162, Wiley-Liss, Inc., New York, N.Y. 1994.

Those proteins which exhibit hematopoiesis regulatory activity may then be formulated as pharmaceuticals and used to treat clinical conditions in which regulation of hematopoiesis is beneficial. For example, a protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantion, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy. Alternatively, as described in more detail below, genes encoding these proteins or nucleic acids regulating the expression of these proteins may be introduced into appropriate host cells to increase or decrease the expression of the proteins as desired.

EXAMPLE 23

Assaying the Proteins Expressed from cDNAs or Fragments thereof for Regulation of Tissue Growth The proteins encoded by the cDNAs or fragments thereof may also be evaluated for their effect on tissue growth. Numerous assays for such activity are familiar to those skilled in the art, including the assays disclosed in International Patent Publication No. WO95/16035, International Patent Publication No. WO95/05846 and International Patent Publication No. WO91/07491, which are incorporated herein by reference.

Assays for wound healing activity include, without limitation, those described in: Winter, *Epidermal Wound Healing*, pps. 71-112 (Maibach, H1 and Rovee, D T, eds.), Year Book Medical Publishers, Inc., Chicago, as modified by Eaglstein and Mertz, J. Invest. Dermatol 71:382-84 (1978) which are incorporated herein by reference.

Those proteins which are involved in the regulation of tissue growth may then be formulated as pharmaceuticals and used to treat clinical conditions in which regulation of tissue growth is beneficial. For example, a protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e., for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium) muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to generate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

Alternatively, as described in more detail below, genes encoding these proteins or nucleic acids regulating the expression of these proteins may be introduced into appropriate host cells to increase or decrease the expression of the proteins as desired.

EXAMPLE 24

Assaying the Proteins Expressed from cDNAs or Fragments thereof for Regulation of Reproductive Hormones or Cell Movement The proteins encoded by the cDNAs or fragments thereof may also be evaluated for their ability to regulate reproductive hormones, such as follicle stimulating hormone. Numerous assays for such activity are familiar to those skilled in the art, including the assays disclosed in the following references, which are incorporated herein by reference: Vale et al., *Endocrinology* 91:562-572, 1972; Ling et al., *Nature* 321:779-782, 1986; Vale et al., *Nature* 321:776-779, 1986; Mason et al., *Nature* 318:659-663, 1985; Forage et al., *Proc. Natl. Acad. Sci. USA* 83:3091-3095, 1986. Chapter 6.12 (Measurement of Alpha and Beta Chemokines) *Current Protocols in Immunology*, J. E. Coligan et al. Eds. Greene Publishing Associates and Wiley-Intersciece ; Taub et al. *J. Clin. Invest.* 95:1370-1376, 1995; Lind et al. *APMIS* 103:140-146, 1995; Muller et al. *Eur. J. Immunol.* 25:1744-1748; Gruber et al. *J. of Immunol.* 152:5860-5867, 1994; Johnston et al. *J. of Immunol.* 153:1762-1768, 1994.

Those proteins which exhibit activity as reproductive hormones or regulators of cell movement may then be formulated as pharmaceuticals and used to treat clinical conditions in which regulation of reproductive hormones or cell movement are beneficial. For example, a protein of the present invention may also exhibit activin- or inhibin-related activities. Inhibins are characterized by their ability to inhibit the release of follicle stimulating hormone (FSH), while activins are characterized by their ability to stimulate the release of folic stimulating hormone (FSH). Thus, a protein of the present invention, alone or in heterodimers with a member of the inhibin α family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-B group, may be useful as a fertility inducing therapeutic, based upon the ability of activin molecules in stimulating FSH release from cells of the anterior pituitary. See, for example, U.S. Pat. No. 4,798,885, the disclosure of which is incorporated herein by reference. A protein of the invention may also be useful for advancement of the onset of fertility in sexually immature mammals, so as to increase the lifetime reproductive performance of domestic animals such as cows, sheep and pigs.

Alternatively, as described in more detail below, genes encoding these proteins or nucleic acids regulating the expression of these proteins may be introduced into appropriate host cells to increase or decrease the expression of the proteins as desired.

EXAMPLE 25

Assaying the Proteins Expressed from cDNAs or Fragments thereof for Chemotactic/Chemokinetic Activity The proteins encoded by the cDNAs or fragments thereof may also be evaluated for chemotactic/chemokinetic activity. For example, a protein of the present invention may have chemotactic or chemokinetic activity (e.g., act as a chemokine) for mammalian cells, including, for example, monocytes, fibroblasts, neutrophils, T-cells, mast cells, cosinophils, epithelial and/or endothelial cells. Chemotactic and chmokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhension of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 6.12, Measurement of alpha and beta Chemokincs 6.12.1-6.12.28; Taub et al. J. Clin. Invest. 95:1370-1376, 1995; Lind et al. APMIS 103:140-146, 1995; Mueller et al Eur. J. Immunol. 25:1744-1748; Gruber et al. J. of Immunol. 152:5860-5867, 1994; Johnston et al. J. of Immunol, 153:1762-1768, 1994.

EXAMPLE 26

Assaying the Proteins Expressed from cDNAs or Fragments thereof for Regulation of Blood Clotting The proteins encoded by the cDNAs or fragments thereof may also be evaluated for their effects on blood clotting. Numerous assays for such activity are familiar to those skilled in the art, including the assays disclosed in the following references, which are incorporated herein by reference: Linet et al., *J. Clin. Pharmacol.* 26:131-140, 1986; Burdick et al., *Thrombosis Res.* 45:413-419, 1987; Humphrey et al., *Fibrinolysis* 5:71-79 (1991); Schaub, *Prostaglandins* 35:467-474, 1988.

Those proteins which are involved in the regulation of blood clotting may then be formulated as pharmaceuticals and used to treat clinical conditions in which regulation of blood clotting is beneficial. For example, a protein of the invention may also exhibit hemostatic or thrombolytic activity. As a result, such a protein is expected to be useful in treatment of various coagulations disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke)). Alternatively, as described in more detail below, genes encoding these proteins or nucleic acids regulating the expression of these proteins may be introduced into appropriate host cells to increase or decrease the expression of the proteins as desired.

EXAMPLE 27

Assaying the Proteins Expressed from cDNAs or Fragments thereof for Involvement in Receptor/Ligand Interactions The proteins encoded by the cDNAs or a fragment thereof may also be evaluated for their involvement in receptor/ligand interactions. Numerous assays for such involvement are familiar to those skilled in the art, including the assays disclosed in the following references, which are incorporated herein by reference: Chapter 7.28 (Measurement of Cellular Adhesion under Static Conditions 7.28.1-7.28.22) in *Current Protocols in Immunology*, J. E. Coligan et al. Eds. Greene Publishing Associates and Wiley-Interscience; Takai et al.,

*Proc. Natl. Acad. Sci. USA* 84:6864-6868, 1987; Bierer et al., *J. Exp. Med.* 168:1145-1156, 1988; Rosenstein et al., *J. Exp. Med.* 169:149-160, 1989; Stoltenborg et al., *J. Immunol. Methods* 175:59-68, 1994; Stitt et al., *Cell* 80:661-670, 1995; Gyuris et al., *Cell* 75:791-803, 1993.

For example, the proteins of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune respones). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

EXAMPLE 28

Assaying the Proteins Expressed from cDNAs or Fragments thereof for Anti-Inflammatory Activity The proteins encoded by the cDNAs or a fragment thereof may also be evaluated for anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusioninury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

EXAMPLE 29

Assaying the Proteins Expressed from cDNAs or Fragments thereof for Tumor Inhibition Activity The proteins encoded by the cDNAs or a fragment thereof may also be evaluated for tumor inhibition activity. In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or climination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

EXAMPLE 30

Identification of Proteins which Interact with Polypeptides Encoded by cDNAs

Proteins which interact with the polypeptides encoded by cDNAs or fragments thereof, such as receptor proteins, may be identified using two hybrid systems such as the Matchmaker Two Hybrid System 2 (Catalog No. K1604-1, Clontech). As described in the manual accompanying the Matchmaker Two Hybrid System 2 (Catalog No. K1604-1, Clontech), which is incorporated herein by reference, the cDNAs or fragments thereof, are inserted into an expression vector such that they are in frame with DNA encoding the DNA binding domain of the yeast transcriptional activator GAL4. cDNAs in a cDNA library which encode proteins which might interact with the polypeptides encoded by the cDNAs or fragments thereof are inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells which are positive in both the histidine selection and the lacZ assay contain plasmids encoding proteins which interact with the polypeptide encoded by the cDNAs or fragments thereof.

Alternatively, the system described in Lustig et al., Methods in Enzymology 283: 83-99 (1997), the disclosure of which is incorporated herein by reference, may be used for identifying molecules which interact with the polypeptides encoded by cDNAs. In such systems, in vitro transcription reactions are performed on a pool of vectors containing cDNA inserts cloned downstream of a promoter which drives in vitro transcription. The resulting pools of mRNAs are introduced into *Xenopus laevis* oocytes. The oocytes are then assayed for a desired acitivity.

Alternatively, the pooled in vitro transcription products produced as described above may be translated in vitro. The pooled in vitro translation products can be assayed for a desired activity or for interaction with a known polypeptide.

Proteins or other molecules interacting with polypeptides encoded by cDNAs can be found by a variety of additional techniques. In one method, affinity columns containing the polypeptide encoded by the cDNA or a fragment thereof can be constructed. In some versions, of this method the affinity column contains chimeric proteins in which the protein encoded by the cDNA or a fragment thereof is fused to glutathione S-transferase. A mixture of cellular proteins or pool of expressed proteins as described above and is applied to the affinity column. Proteins interacting with the polypeptide attached to the column can then be isolated and analyzed on 2-D electrophoresis gel as described in Ramunsen et al. Electrophoresis, 18, 588-598 (1997), the disclosure of which is incorporated herein by reference. Alternatively, the proteins retained on the affinity column can be purified by electrophoresis based methods and sequenced. The same method can be used to isolate antibodies, to screen phage display products, or to screen phage display human antibodies.

Proteins interacting with polypeptides encoded by cDNAs or fragments thereof can also be screened by using an Optical Biosensor as described in Edwards & Leatherbarrow, Analytical Biochemistry, 246, 1-6 (1997), the disclosure of which is incorporated herein by reference. The main advantage of the method is that it allows the determination of the association rate between the protein and other interacting molecules. Thus, it is possible to specifically select interacting molecules with a high or low association rate. Typically a target molecule is linked to the sensor surface (through a carboxymethl dextran matrix) and a sample of test molecules is placed in contact with the target molecules. The binding of a test molecule to the target molecule causes a change in the refractive index and/or thickness. This change is detected by the Biosensor provided it occurs in the evanescent field (which extend a few hundred manometers from the sensor surface). In these screening assays, the target molecule can be one of the polypeptides encoded by cDNAs or a fragment thereof and the test sample can be a collection of proteins extracted from tissues or cells, a pool of expressed proteins, combinatorial peptide and/or chemical libraries,or phage displayed peptides. The tissues or cells from which the test proteins are extracted can originate from any species.

In other methods, a target protein is immobilized and the test population is a collection of unique polypeptides encoded by the cDNAs or fragments thereof.

To study the interaction of the proteins encoded by the cDNAs or fragments thereof with drugs, the microdialysis coupled to HPLC method described by Wang et al., Chromatographia, 44, 205-208(1997) or the affinity capillary electrophoresis method described by Busch et al., J. Chromatogr. 777:311-328 (1997), the disclosures of which are incorporated herein by referenc can be used.

The system described in U.S. Pat. No. 5,654,150, the disclosure of which is incorporated herein by reference, may also be used to identify molecules which interact with the polypeptides encoded by the cDNAs. In this system, pools of cDNAs are transcribed and translated in vitro and the reaction products are assayed for interaction with a known polypeptide or antibody.

It will be appreciated by those skilled in the art that the proteins expressed from the cDNAs or fragments may be assayed for numerous activities in addition to those specifically enumerated above. For example, the expressed proteins may be evaluated for applications involving control and regulation of inflammation, tumor proliferation or metastasis, infection, or other clinical conditions. In addition, the proteins expressed from the cDNAs or fragments thereof may be useful as nutritional agents or cosmetic agents.

The proteins expressed from the cDNAs or fragments thereof may be used to generate antibodies capable of specifically binding to the expressed protein or fragments thereof as described below. The antibodies may capable of binding a full length protein encoded by one of the sequences of SEQ ID NOs. 24-73, a mature protein encoded by one of the sequences of SEQ ID NOs. 24-73, or a signal peptide encoded by one of the sequences of SEQ ID Nos. 24-73. Alternatively, the antibodies may be capable of binding fragments of the proteins expressed from the cDNAs which comprise at least 10 amino acids of the sequences of SEQ ID NOs: 74-123. In some embodiments, the antibodies may be capable of binding fragments of the proteins expressed from the cDNAs which comprise at least 15 amino acids of the sequences of SEQ ID NOs: 74-123. In other embodiments, the antibodies may be capable of binding fragments of the proteins expressed from the cDNAs which comprise at least 25 amino acids of the sequences of SEQ ID NOs: 74-123. In further embodiments, the antibodies may be capable of binding fragments of the proteins expressed from the cDNAs which comprise at least 40 amino acids of the sequences of SEQ ID NOs: 74-123.

EXAMPLE 31

Epitopes and Antibody Fusions

A preferred embodiment of the present invention is directed to eiptope-bearing polypeptides and epitope-bearing polypeptide fragments. These epitopes may be "antigenic epitopes" or both an "antigenic epitope" and an "immunogenic epitope". An "immunogenic epitope" is defined as a part of a protein that elicits an antibody response in vivo when the polypeptide is the immunogen. On the other hand, a region of polypeptide to which an antibody binds is defined as an "antigenic determinant" or "antigenic epitope." The number of immunogenic epitopes of a protein generally is less than the number of antigenic epitopes (See, e.g., Geysen, et al., 1983). It is particularly noted that although a particular epitope may not be immunogenic, it is nonetheless useful since antibodies can be made to both immunogenic and antigenic epitopes.

An epitope can comprise as few as 3 amino acids in a spatial conformation, which is unique to the epitope. Generally an epitope consists of at least 6 such amino acids, and more often at least 8-10 such amino acids. In preferred embodiment, antigenic epitopes comprise a number of amino acids that is any integer between 3 and 50. Fragments which function as epitopes may be produced by any conventional means (See, e.g., Houghten, R. A., 1985),also, further described in U.S. Pat. No. 4,631,211. Methods for determining the amino acids which make up an epitope include x-ray crystallography, 2-dimensional nuclear magnetic resonance, and epitope mapping, e.g., the Pepscan method described by Mario H. Geysen et al. (1984); PCT Publication No. WO 84/03564; and PCT Publication No. WO 84/03506. Epitopes may also be delineated using an algorithm, such as the algorithm of Jameson and Wolf, (Jameson and Wolf, Comp. Appl. Biosci. 4:181-186 (1988). The Jameson-Wolf antigenic analysis, for example, may be performed using the computer program PROTEAN, using default parameters (Version 4.0 Windows, DNASTAR, Inc., 1228 South Park Street Madison, Wis.

Table X lists antigenic peaks of predicted antigenic epitopes identified by the Jameson-Wolf algorithm. For each polypeptide referred to by its sequence identification number in the first column, the second column gives a list of antigenic peaks separated by a coma. Preferred antigenic epitopes of the present invention comprise an additional 6 amino acid residues both N-terminal and C-terminal to the positions listed in the Table. For example, for SEQ ID NO:74, the first preferred immunogenic epitope comprises amino acid residues 52 to 64. Note that for the purposes of this Table, position 1 is the N-terminal methionine residue, i.e., the leader sequence is not numbered negatively.

It is pointed out that the immunogenic epitope list describe only amino acid residues comprising epitopes predicted to have the highest degree of immunogenicity by a particular algorithm. Polypeptides of the present invention that are not specifically described as immunogenic are not considered non-antigenic. This is because they may still be antigenic in vivo but merely not recognized as such by the particular algorithm used. Alternatively, the polypeptides are probably antigenic in vitro using methods such a phage display. In fact, all fragments of the polypeptides of the present invention, at least 6 amino acids residues in length, are included in the present invention as being useful as antigenic epitope. Moreover, listed in Table IX are only the critical residues of the epitopes determined by the Jameson-Wolf analysis. Thus, additional flanking residues on either the N-terminal, C-terminal, or both N- and C-terminal ends may be added to the sequences listed to generate an epitope-bearing portion at least 6 residues in length. Amino acid residues comprising other immunogenic epitopes may be determined by algorithms similar to the Jameson-Wolf analysis or by in vivo testing for an antigenic response using the methods described herein or those known in the art.

The epitope-bearing fragments of the present invention preferably comprises 6 to 50 amino acids (i.e. any integer between 6 and 50, inclusive) of a polypeptide of the present invention. Also, included in the present invention are antigenic fragments between the integers of 6 and the full length polypeptide sequence of the sequence listing. All combinations of sequences between the integers of 6 and the full-length sequence of a polypeptide are included. The epitope-bearing fragments may be specified by either the number of contiguous amino acid residues (as a sub-genus) or by specific N-terminal and C-terminal positions (as species) as described above for the polypeptide fragments of the present invention. Any number of epitope-bearing fragments of the present invention may also be excluded in the same manner.

Antigenic epitopes are useful, for example, to raise antibodies, including monoclonal antibodies that specifically bind the epitope (See, Wilson et al., 1984; and Sutcliffe, J. G. et al., 1983). The antibodies are then used in various techniques such as diagnostic and tissue/cell identification techniques, as described herein, and in purification methods.

Similarly, immunogenic epitopes can be used to induce antibodies according to methods well known in the art (See, Sutcliffe et al., supra; Wilson et al., supra; Chow, M. et al.; (1985) and Bittle, F. J. et al., (1985)). The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.).

Epitope-bearing polypeptides of the present invention are used to induce antibodies according to methods well known in the art including, but not limited to, in vivo immunization, in vitro immunization, and phage display methods (See, e.g., Sutcliffe, et al., supra; Wilson, et al., supra, and Bittle, et al., 1985). If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as—maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of anti-peptide antibody, which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins (See, e.g., EPA 0,394,827; and Traunecker et al., 1988). Fusion proteins that have a disulfide-linked dimeric structure due to the IgG portion can also be more efficient in binding and neutralizing other molecules than monomeric polypeptides or fragments thereof alone (See, e.g., Fountoulakis et al., 1995). Nucleic acids encoding the above epitopes can also be recombined with a gene of interest as an epitope tag to aid in detection and purification of the expressed polypeptide.

Additonal fusion proteins of the invention may be generated through the techniques of gene-shuffling, motif-shuffling, exon-shuffling, or codon-shuffling (collectively referred to as "DNA shuffling"). DNA shuffling may be employed to modulate the activities of polypeptides of the present invention thereby effectively generating agonists and antagonists of the polypeptides. See, for example, U.S. Pat. Nos.: 5,605,793; 5,811,238; 5,834,252; 5,837,458; and Patten, P. A., et al., (1997); Harayama, S., (1998); Hansson, L. O., et al (1999); and Lorenzo, M. M. and Blasco, R., (1998). In one embodiment, one or more components, motifs, sections, parts, domains, fragments, etc., of coding polynucleotides of the invention, or the polypeptides encoded thereby may be recombined with one or more components, motifs, sections, parts, domains, fragments, etc. of one or more heterologous molecules.

Antibodies:

The present invention further relates to antibodies and T-cell antigen receptors (TCR), which specifically bind the polypeptides, and more specifically, the epitopes of the polyepeptides of the present invention. The antibodies of the present invention include IgG (including IgG, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen binding fragments thereof. In a preferred embodiment the antibodies are human antigen binding antibody fragments of the present invention include, but are not limited to, Fab, Fab' F(ab)2 and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies, which specifically bind the polypeptides of the present invention. The present invention further includes antibodies that are anti-idiotypic to the antibodies of the present invention.

The antibodies of the present invention may be monospecific, bispecific, and trispecific or have greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991); U.S. Pat. Nos. 5,573,920, 4,474,893, 5,601,819, 4,714,681, 4,925,648; Kostelny, S. A. et al. (1992).

Antibodies of the present invention may be described or specified in terms of the epitope(s) or epitope-bearing portion(s) of a polypeptide of the present invention, which are recognized or specifically bound by the antibody. In the case of proteins of the present invention secreted proteins, the antibodies may specifically bind a full-length protein encoded by a nucleic acid of the present invention, a mature protein (i.e., the protein generated by cleavage of the signal peptide) encoded by a nucleic acid of the present invention, a signal peptide encoded by a nucleic acid of the present invention, or any other polypeptide of the present invention. Therefore, the epitope(s) or epitope bearing polypeptide portion(s) may be specified as described herein, e.g., by N-terminal and C-terminal positions, by size in contiguous amino acid residues, or otherwise described herein (including the sequence listing). Antibodies which specifically bind any epitope or polypeptide of the present invention may also be excluded as individual species. Therefore, the present invention includes antibodies that specifically bind specified polypeptides of the present invention, and allows for the exclusion of the same.

Antibodies of the present invention may also be described or specified in terms of their cross-reactivity. Antibodies that do not specifically bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein, eg., using FASTDB and the parameters set forth herein) to a polypeptide of the present invention are also included in the present invention. Further included in the present invention are antibodies, which only bind polypeptides encoded by polynucleotides, which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples (See, e.g., Harlow et al., 1988).

The antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "antibody" refers to a polypeptide or group of polypeptides which are comprised of at least one binding domain, where a binding domain is formed from the folding of variable domains of an antibody molecule to form three-dimensional binding spaces with an internal surface shape and charge distribution complementary to the features of an antigenic determinant of an antigen, which allows an immunological reaction with the antigen. The term "monoclonal antibody" refers to an antibody that is derived from a single clone, including eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art (See, e.g., Harlow et al. 1988; Hammerling, et al, 1981). (Said references incorporated by reference in their entireties). Fab and F(ab')2 fragments may be produced, for example, from hybridoma-produced antibodies by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle, which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995); Ames, R. S. et al. (1995); Kettleborough, C. A. et al. (1994); Persic, L. et al. (1997); Burton, D. R. et al. (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743.

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' F(ab)2 and F(ab')2 fragments can also be employed using methods known in the art such as those disclosed in WO 92/22324; Mullinax, R. L. et al. (1992); and Sawai, H. et al. (1995); and Better, M. et al. (1988).

Examples of techniques which can be used to produce single-chain Fvs and antibodies include those described in U.S. Pat. Nos. 4,946,778 and 5,258,498; Huston et al. (1991); Shu, L. et al. (1993); and Skerra, A. et al. (1988). For some uses, including in vivo use of antibodies in humans and in vitro detection assays, it may be preferable to use chimeric, humanized, or human antibodies. Methods for producing chimeric antibodies are known in the art. See e.g., Morrison, (1985); Oi et al., (1986); Gillies, S. D. et al. (1989); and U.S. Pat. No. 5,807,715. Antibodies can be humanized using a variety of techniques including CDR-grafting (EP 0 239 400; WO 91/09967; U.S. Pat. Nos. 5,530,101; and 5,585,089), veneering or resurfacing, (EP 0 592 106; EP 0 519 596; Padlan E. A., 1991; Studnicka G. M. et al., 1994; Roguska M. A. et al., 1994), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; WO 98/46645; WO 98/50433; WO 98/24893; WO 96/34096; WO 96/33735; and WO 91/10741.

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art (See e.g., Harbor et al. supra; WO 93/21232; EP 0 439 095; Naramura, M. et al. 1994; U.S. Pat. No. 5,474,981; Gillies, S. O. et al., 1992; Fell, H. P. et al., 1991).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half-life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991); Zheng, X. X. et al. (1995); and Vil, H. et al. (1992).

The invention further relates to antibodies that act as agonists or antagonists of the polypeptides of the present invention. For example, the present invention includes antibodies that disrupt the receptor/ligand interactions with the polypeptides of the invention either partially or fully. Included are both receptor-specific antibodies and ligand-specific antibodies. Included are receptor-specific antibodies, which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies that bind the ligand and prevent binding of the ligand to the receptor, as well as antibodies that bind the ligand, thereby preventing receptor activation, but do not prevent the ligand from binding the receptor. Further included are antibodies that activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998); Chen, Z. et al. (1998); Harrop, J. A. et al. (1998); Zhu, Z. et al. (1998); Yoon, D. Y. et al. (1998); Prat, M. et al. (1998) J.; Pitard, V. et al. (1997); Liautard, J. et al. (1997); Carlson, N. G. et al. (1997) J.; Taryman, R. E. et al. (1995); Muller, Y. A. et al. (1998); Bartunek, P. et al. (1996).

As discussed above, antibodies of the polypeptides of the invention can, in turn, be utilized to generate anti-idiotypic antibodies that "mimic" polypeptides of the invention using techniques well known to those skilled in the art (See, e.g. Greenspan and Bona (1989); and Nissinoff (1991). For example, antibodies which bind to and competitively inhibit polypeptide multimerization or binding of a polypeptide of the invention to ligand can be used to generate anti-idiotypes that "mimic" the polypeptide multimerization or binding domain and, as a consequence, bind to and neutralize polypeptide or its ligand. Such neutralization anti-idiotypic antibodies can be used to bind a polypeptide of the invention or to bind its ligands/receptors, and therby block its biological activity, The invention also concerns a purified or isolated antibody capable of specifically binding to a mutated full length or mature polypeptide of the present invention or to a fragment or variant thereof comprising an epitope of the mutated polypeptide. In another preferred embodiment, the present invention concerns an antibody capable of binding to a polypeptide comprising at least 10 consecutive amino acids of a polypeptide of the present invention and including at least one of the amino acids which can be encoded by the trait causing mutations.

Non-human animals or mammals, whether wild-type or transgenic, which express a different species of a polypeptide of the present invention than the one to which antibody binding is desired, and animals which do not express a polypeptide of the present invention (i.e. a knock out animal) are particularly useful for preparing antibodies. Gene knock out animals will recognize all or most of the exposed regions of a polypeptide of the present invention as foreign antigens, and therefore produce antibodies with a wider array of epitopes. Moreover, smaller polypeptides with only 10 to 30 amino acids may be useful in obtaining specific binding to any one of the polypeptides of the present invention. In addition, the humoral immune system of animals which produce a species of a polypeptide of the present invention that resembles the antigenic sequence will preferentially recognize the differences between the animal's native polypeptide species and the antigen sequence, and produce antibodies to these unique sites in the antigen sequence. Such a technique will be particularly useful in obtaining antibodies that specifically bind to any one of the polypeptides of the present invention.

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The antibodies of the invention may be labeled by any one of the radioactive, fluorescent or enzymatic labels known in the art.

Consequently, the invention is also directed to a method for detecting specifically the presence of a polypeptide of the present invention according to the invention in a biological sample, said method comprising the following steps:

a) bringing into contact the biological sample with a polyclonal or monoclonal antibody that specifically binds a polypeptide of the present invention; and b) detecting the antigen-antibody complex formed.

The invention also concerns a diagnostic kit for detecting in vitro the presence of a polypeptide of the present invention in a biological sample, wherein said kit comprises:

a) a polyclonal or monoclonal antibody that specifically binds a polypeptide of the present invention, optionally labeled;

b) a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself.

A. Monoclonal Antibody Production by Hybridoma Fusion

Monoclonal antibody to epitopes of any of the peptides identified and isolated as described can be prepared from murine hybridomas according to the classical method of Kohler, G. and Milstein, C., *Nature* 256:495 (1975) or derivative methods thereof. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as Elisa, as originally described by Engvall, E., *Meth. Enzymol.* 70:419 (1980), and derivative methods thereof. Selected positive clones can be expanded and their monoclonal antibody product harvested for use. Detailed procedures for monoclonal antibody production are described in Davis, L. et al. *Basic Methods in Molecular Biology* Elsevier, New York. Section 21-2.

B. Polyclonal Antibody Production by Immunization

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J. Clin. Endocrinol. Metab.* 33:988-991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental Immunology* D. Wier (ed) Blackwell (1973). Plateau concentration of antibody is usually in the range of 0.1 to 0.2 mg/ml of serum (about 12 μM). Affinity of the antisera for the antigen is determined by preparing competitive binding curves, as described, for example, by Fisher, D., Chap. 42 in: *Manual of Clinical Immunology*, 2d Ed. (Rose and Friedman, Eds.) Amer. Soc. For Microbiol., Washington, D.C. (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

V. Use of cDNAs or Fragments thereof as Reagents

The cDNAs of the present invention may be used as reagents in isolation procedures, diagnostic assays, and forensic procedures. For example, sequences from the cDNAs (or genomic DNAs obtainable therefrom) may be detectably labeled and used as probes to isolate other sequences capable of hybridizing to them. In addition, sequences from the cDNAs (or genomic DNAs obtainable therefrom) may be used to design PCR primers to be used in isolation, diagnostic, or forensic procedures.

EXAMPLE 32

Preparation of PCR Primers and Amplification of DNA

The cDNAs (or genomic DNAs obtainable therefrom) may be used to prepare PCR primers for a variety of applications, including isolation procedures for cloning nucleic acids capable of hybridizing to such sequences, diagnostic techniques and forensic techniques. The PCR primers are at least 10 bases, and preferably at least 12, 15, or 17 bases in length. More preferably, the PCR primers are at least 20-30 bases in length. In some embodiments, the PCR primers may be more than 30 bases in length. It is preferred that the primer pairs have approximately the same G/C ratio, so that melting temperatures are approximately the same. A variety of PCR techniques are familiar to those skilled in the art. For a review of PCR technology, see Molecular Cloning to Genetic Engineering White, B. A. Ed. in Methods in Molecular Biology 67: Humana Press, Totowa 1997. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites.

EXAMPLE 33

Use of cDNAs as Probes

Probes derived from cDNAs or fragments thereof (or genomic DNAs obtainable therefrom) may be labeled with detectable labels familiar to those skilled in the art, including radioisotopes and non-radioactive labels, to provide a detectable probe. The detectable probe may be single stranded or double stranded and may be made using techniques known in the art, including in vitro transcription, nick translation, or kinase reactions. A nucleic acid sample containing a sequence capable of hybridizing to the labeled probe is contacted with the labeled probe. If the nucleic acid in the sample is double stranded, it may be denatured prior to contacting the probe. In some applications, the nucleic acid sample may be immobilized on a surface such as a nitrocellulose or nylon membrane. The nucleic acid sample may comprise nucleic acids obtained from a variety of sources, including genomic DNA, cDNA libraries, RNA, or tissue samples.

Procedures used to detect the presence of nucleic acids capable of hybridizing to the detectable probe include well known techniques such as Southern blotting, Northern blotting, dot blotting, colony hybridization, and plaque hybridization. In some applications, the nucleic acid capable of hybridizing to the labeled probe may be cloned into vectors such as expression vectors, sequencing vectors, or in vitro transcription vectors to facilitate the characterization and expression of the hybridizing nucleic acids in the sample. For example, such techniques may be used to isolate and clone sequences in a genomic library or cDNA library which are capable of hybridizing to the detectable probe as described in example 17 above.

PCR primers made as described in example 32 above may be used in forensic analyses, such as the DNA fingerprinting techniques described in Examples 34-38 below. Such analyses may utilize detectable probes or primers based on the sequences of the cDNAs or fragments thereof (or genomic DNAs obtainable therefrom).

EXAMPLE 34

Forensic Matching by DNA Sequencing

In one exemplary method, DNA samples are isolated from forensic specimens of, for example, hair, semen, blood or skin cells by conventional methods. A panel of PCR primers based on a number of the cDNAs (or genomic DNAs obtainable therefrom), is then utilized in accordance with example 32 to amplify DNA of approximately 100-200 bases in length from the forensic specimen. Corresponding sequences are obtained from a test subject. Each of these identification DNAs is then sequenced using standard techniques, and a simple database comparison determines the differences, if any, between the sequences from the subject and those from the sample. Statistically significant differences between the suspect's DNA sequences and those from the sample conclusively prove a lack of identity. This lack of identity can be proven, for example, with only one sequence. Identity, on the other hand, should be demonstrated with a large number of sequences, all matching. Preferably, a minimum of 50 statistically identical sequences of 100 bases in length are used to prove identity between the suspect and the sample.

EXAMPLE 35

Positive Identification by DNA Sequencing

The technique outlined in the previous example may also be used on a larger scale to provide a unique fingerprint-type identification of any individual. In this technique, primers are prepared from a large number of sequences from Table I and the appended sequence listing. Preferably, 20 to 50 different primers are used. These primers are used to obtain a corresponding number of PCR-generated DNA segments from the individual in question in accordance with example 32. Each of these DNA segments is sequenced, using the methods set forth in example 34. The database of sequences generated through this procedure uniquely identifies the individual from whom the sequences were obtained. The same panel of primers may then be used at any later time to absolutely correlate tissue or other biological specimen with that individual.

EXAMPLE 36

Southern Blot Forensic Identification

The procedure of example 35 is repeated to obtain a panel of at least 10 amplified sequences from an individual and a specimen. Preferably, the panel contains at least 50 amplified sequences. More preferably, the panel contains 100 amplified sequences. In some embodiments, the panel contains 200 amplified sequences. This PCR-generated DNA is then digested with one or a combination of, preferably, four base specific restriction enzymes. Such enzymes are commercially available and known to those of skill in the art. After digestion, the resultant gene fragments are size separated in multiple duplicate wells on an agarose gel and transferred to nitrocellulose using Southern blotting techniques well known to those with skill in the art. For a review of Southern blotting see Davis et al. (*Basic Methods in Molecular Biology*, 1986, Elsevier Press. pp 62-65).

A panel of probes based on the sequences of the cDNAs (or genomic DNAs obtainable therefrom), or fragments thereof of at least 10 bases, are radioactively or colorimetrically labeled using methods known in the art, such as nick translation or end labeling, and hybridized to the Southern blot using techniques known in the art (Davis et al., supra). Preferably, the probe comprises at least 12, 15, or 17 consecutive nucleotides from the cDNA (or genomic DNAs obtainable therefrom). More preferably, the probe comprises at least 20-30 consecutive nucleotides from the cDNA (or genomic DNAs obtainable therefrom). In some embodiments, the probe comprises more than 30 nucleotides from the cDNA (or genomic DNAs obtainable therefrom). In other embodiments, the probe comprises at least 40, at least 50, at least 75, at least 100, at least 150, or at least 200 consecutive nucleotides from the cDNA (or genomic DNAs obtainable therefrom).

Preferably, at least 5 to 10 of these labeled probes are used, and more preferably at least about 20 or 30 are used to provide a unique pattern. The resultant bands appearing from the hybridization of a large sample of cDNAs (or genomic DNAs obtainable therefrom) will be a unique identifier. Since the restriction enzyme cleavage will be different for every individual, the band pattern on the Southern blot will also be unique. Increasing the number of cDNA probes will provide a statistically higher level of confidence in the identification since there will be an increased number of sets of bands used for identification.

EXAMPLE 37

Dot Blot Identification Procedure

Another technique for identifying individuals using the cDNA sequences disclosed herein utilizes a dot blot hybridization technique.

Genomic DNA is isolated from nuclei of subject to be identified. Oligonucleotide probes of approximately 30 bp in length are synthesized that correspond to at least 10, preferably 50 sequences from the cDNAs or genomic DNAs obtainable therefrom. The probes are used to hybridize to the genomic DNA through conditions known to those in the art. The oligonucleotides are end labeled with $P^{32}$ using polynucleotide kinase (Pharmacia). Dot Blots are created by spotting the genomic DNA onto nitrocellulose or the like using a vacuum dot blot manifold (BioRad, Richmond Calif.). The nitrocellulose filter containing the genomic sequences is baked or UV linked to the filter, prehybridized and hybridized with labeled probe using techniques known in the art (Davis et al. supra). The $^{32}P$ labeled DNA fragments are sequentially hybridized with successively stringent conditions to detect minimal differences between the 30 bp sequence and the DNA. Tetramethylammonium chloride is useful for identifying clones containing small numbers of nucleotide mismatches (Wood et al., *Proc. Natl. Acad. Sci. USA* 82(6):1585-1588 (1985)) which is hereby incorporated by reference. A unique pattern of dots distinguishes one individual from another individual.

cDNAs or oligonucleotides containing at least 10 consecutive bases from these sequences can be used as probes in the following alternative fingerprinting technique. Preferably, the probe comprises at least 12, 15, or 17 consecutive nucleotides from the cDNA (or genomic DNAs obtainable therefrom). More preferably, the probe comprises at least 20-30 consecutive nucleotides from the cDNA (or genomic DNAs obtainable therefrom). In some embodiments, the probe comprises more than 30 nucleotides from the cDNA (or genomic DNAs obtainable therefrom). In other embodiments, the probe comprises at least 40, at least 50, at least 75, at least 100, at least 150, or at least 200 consecutive nucleotides from the cDNA (or genomic DNAs obtainable therefrom).

Preferably, a plurality of probes having sequences from different genes are used in the alternative fingerprinting technique. Example 38 below provides a representative alternative fingerprinting procedure in which the probes are derived from cDNAs.

EXAMPLE 38

Alternative "Fingerprint" Identification Technique 20-mer oligonucleotides are prepared from a large number, e.g. 50, 100, or 200, of cDNA sequences (or genomic DNAs obtainable therefrom) using commercially available oligonucleotide services such as Genset, Paris, France. Cell samples from the test subject are processed for DNA using techniques well known to those with skill in the art. The nucleic acid is digested with restriction enzymes such as EcoRI and XbaI. Following digestion, samples are applied to wells for electrophoresis. The procedure, as known in the art, may be modified to accommodate polyacrylamide electrophoresis, however in this example, samples containing 5 ug of DNA are loaded into wells and separated on 0.8% agarose gels. The gels are transferred onto nitrocellulose using standard Southern blotting techniques.

10 ng of each of the oligonucleotides are pooled and end-labeled with $P^{32}$. The nitrocellulose is prehybridized with blocking solution and hybridized with the labeled probes. Following hybridization and washing, the nitrocellulose filter is exposed to X-Omat AR X-ray film. The resulting hybridization pattern will be unique for each individual.

It is additionally contemplated within this example that the number of probe sequences used can be varied for additional accuracy or clarity.

The antibodies generated in Examples 18 and 31 above may be used to identify the tissue type or cell species from which a sample is derived as described above.

EXAMPLE 39

Identification of Tissue Types or Cell Species by Means of Labeled Tissue Specific Antibodies Identification of specific tissues is accomplished by the visualization of tissue specific antigens by means of antibody preparations according to Examples 18 and 31 which are conjugated, directly or indirectly to a detectable marker. Selected labeled antibody species bind to their specific antigen binding partner in tissue sections, cell suspensions, or in extracts of soluble proteins from a tissue sample to provide a pattern for qualitative or semi-qualitative interpretation.

Antisera for these procedures must have a potency exceeding that of the native preparation, and for that reason, antibodies are concentrated to a mg/ml level by isolation of the gamma globulin fraction, for example, by ion-exchange chromatography or by ammonium sulfate fractionation. Also, to provide the most specific antisera, unwanted antibodies, for example to common proteins, must be removed from the gamma globulin fraction, for example by means of insoluble immunoabsorbents, before the antibodies are labeled with the marker. Either monoclonal or heterologous antisera is suitable for either procedure.

A. Immunohistochemical Techniques

Purified, high-titer antibodies, prepared as described above, are conjugated to a detectable marker, as described, for example, by Fudenberg, H., Chap. 26 in: *Basic 503 Clinical Immunology*, 3rd Ed. Lange, Los Altos, Calif. (1980) or Rose, N. et al., Chap. 12 in: *Methods in Immunodiagnosis*, 2d Ed. John Wiley 503 Sons, New York (1980).

A fluorescent marker, either fluorescein or rhodamine, is preferred, but antibodies can also be labeled with an enzyme that supports a color producing reaction with a substrate, such as horseradish peroxidase. Markers can be added to tissue-bound antibody in a second step, as described below. Alternatively, the specific antitissue antibodies can be labeled with ferritin or other electron dense particles, and localization of the ferritin coupled antigen-antibody complexes achieved by means of an electron microscope. In yet another approach, the antibodies are radiolabeled, with, for example $^{125}$I, and detected by overlaying the antibody treated preparation with photographic emulsion.

Preparations to carry out the procedures can comprise monoclonal or polyclonal antibodies to a single protein or peptide identified as specific to a tissue type, for example, brain tissue, or antibody preparations to several antigenically distinct tissue specific antigens can be used in panels, independently or in mixtures, as required.

Tissue sections and cell suspensions are prepared for immunohistochemical examination according to common histological techniques. Multiple cryostat sections (about 4 μm, unfixed) of the unknown tissue and known control, are mounted and each slide covered with different dilutions of the antibody preparation. Sections of known and unknown tissues should also be treated with preparations to provide a positive control, a negative control, for example, pre-immune sera, and a control for non-specific staining, for example, buffer.

Treated sections are incubated in a humid chamber for 30 min at room temperature, rinsed, then washed in buffer for 30-45 min. Excess fluid is blotted away, and the marker developed.

If the tissue specific antibody was not labeled in the first incubation, it can be labeled at this time in a second antibody-antibody reaction, for example, by adding fluorescein- or enzyme-conjugated antibody against the immunoglobulin class of the antiserum-producing species, for example, fluorescein labeled antibody to mouse IgG. Such labeled sera are commercially available.

The antigen found in the tissues by the above procedure can be quantified by measuring the intensity of color or fluorescence on the tissue section, and calibrating that signal using appropriate standards.

B. Identification of Tissue Specific Soluble Proteins

The visualization of tissue specific proteins and identification of unknown tissues from that procedure is carried out using the labeled antibody reagents and detection strategy as described for immunohistochemistry; however the sample is prepared according to an electrophoretic technique to distribute the proteins extracted from the tissue in an orderly array on the basis of molecular weight for detection.

A tissue sample is homogenized using a Virtis apparatus; cell suspensions are disrupted by Dounce homogenization or osmotic lysis, using detergents in either case as required to disrupt cell membranes, as is the practice in the art. Insoluble cell components such as nuclei, microsomes, and membrane fragments are removed by ultracentrifugation, and the soluble protein-containing fraction concentrated if necessary and reserved for analysis.

A sample of the soluble protein solution is resolved into individual protein species by conventional SDS polyacrylamide electrophoresis as described, for example, by Davis, L. et al., Section 19-2 in: *Basic Methods in Molecular Biology* (P. Leder, ed), Elsevier, N.Y. (1986), using a range of amounts of polyacrylamide in a set of gels to resolve the entire molecular weight range of proteins to be detected in the sample. A size marker is run in parallel for purposes of estimating molecular weights of the constituent proteins. Sample size for analysis is a convenient volume of from 5 to 55 μl, and containing from about 1 to 100 μg protein. An aliquot of each of the resolved proteins is transferred by blotting to a nitrocellulose filter paper, a process that maintains the pattern of resolution. Multiple copies are prepared. The procedure, known as Western Blot Analysis, is well described in Davis, L. et al., (above) Section 19-3. One set of nitrocellulose blots is stained with Coomassie Blue dye to visualize the entire set of proteins for comparison with the antibody bound proteins. The remaining nitrocellulose filters are then incubated with a solution of one or more specific antisera to tissue specific proteins prepared as described in Examples 18 and 31. In this procedure, as in procedure A above, appropriate positive and negative sample and reagent controls are run.

In either procedure A or B, a detectable label can be attached to the primary tissue antigen-primary antibody complex according to various strategies and permutations thereof. In a straightforward approach, the primary specific antibody can be labeled; alternatively, the unlabeled complex can be bound by a labeled secondary anti-IgG antibody. In-other approaches, either the primary or secondary antibody is conjugated to a biotin molecule, which can, in a subsequent step, bind an avidin conjugated marker. According to yet another strategy, enzyme labeled or radioactive protein A, which has the property of binding to any IgG, is bound in a final step to either the primary or secondary antibody.

The visualization of tissue specific antigen binding at levels above those seen in control tissues to one or more tissue specific antibodies, prepared from the gene sequences identified from cDNA sequences, can identify tissues of unknown origin, for example, forensic samples, or differentiated tumor tissue that has metastasized to foreign bodily sites.

In addition to their applications in forensics and identification, cDNAs (or genomic DNAs obtainable therefrom) may be mapped to their chromosomal locations. example 40 below describes radiation hybrid (RH) mapping of human chromosomal regions using cDNAs. example 41 below describes a representative procedure for mapping a cDNA (or a genomic DNA obtainable therefrom) to its location on a human chromosome. example 42 below describes mapping of cDNAs (or genomic DNAs obtainable therefrom) on metaphase chromosomes by Fluorescence In Situ Hybridization (FISH).

EXAMPLE 40

Radiation Hybrid Mapping of cDNAs to the Human Genome

Radiation hybrid (RH) mapping is a somatic cell genetic approach that can be used for high resolution mapping of the human genome. In this approach, cell lines containing one or more human chromosomes are lethally irradiated, breaking each chromosome into fragments whose size depends on the radiation dose. These fragments are rescued by fusion with cultured rodent cells, yielding subclones containing different fragments of the human genome. This technique is described by Benham et al. (*Genomics* 4:509-517, 1989) and Cox et al., (*Science* 250:245-250, 1990), the entire contents of which are hereby incorporated by reference. The random and independent nature of the subclones permits efficient mapping of any human genome marker. Human DNA isolated from a panel of 80-100 cell lines provides a mapping reagent for ordering cDNAs (or genomic DNAs obtainable therefrom). In this approach, the frequency of breakage between markers is used to measure distance, allowing construction of fine resolution maps as has been done using conventional ESTs (Schuler et al., *Science* 274:540-546, 1996, hereby incorporated by reference).

RH mapping has been used to generate a high-resolution whole genome radiation hybrid map of human chromosome 17q22-q25.3 across the genes for growth hormone (GH) and thymidine kinase (TK) (Foster et al., *Genomics* 33:185-192, 1996), the region surrounding the Gorlin syndrome gene (Obermayr et al., *Eur. J. Hum. Genet.* 4:242-245, 1996), 60 loci covering the entire short arm of chromosome 12 (Raeymaekers et al., *Genomics* 29:170-178, 1995), the region of human chromosome 22 containing the neurofibromatosis type 2 locus (Frazer et al., *Genomics* 14:574-584, 1992) and 13 loci on the long arm of chromosome 5 (Warrington et al., *Genomics* 11:701-708, 1991).

EXAMPLE 41

Mapping of cDNAs to Human Chromosomes Using PCR Techniques cDNAs (or genomic DNAs obtainable therefrom) may be assigned to human chromosomes using PCR based methodologies. In such approaches, oligonucleotide primer pairs are designed from the cDNA sequence (or the sequence of a genomic DNA obtainable therefrom) to minimize the chance of amplifying through an intron. Preferably, the oligonucleotide primers are 18-23 bp in length and are designed for PCR amplification. The creation of PCR primers from known sequences is well known to those with skill in the art. For a review of PCR technology see Erlich, H. A., *PCR Technology; Principles and Applications for DNA Amplification.* 1992. W. H. Freeman and Co., New York.

The primers are used in polymerase chain reactions (PCR) to amplify templates from total human genomic DNA. PCR conditions are as follows: 60 ng of genomic DNA is used as a template for PCR with 80 ng of each oligonucleotide primer, 0.6 unit of Taq polymerase, and 1 μCu of a $^{32}$P-labeled deoxycytidine triphosphate. The PCR is performed in a microplate thermocycler (Techne) under the following conditions: 30 cycles of 94° C., 1.4 min; 55° C., 2 min; and 72° C., 2 min; with a final extension at 72° C. for 10 min. The amplified products are analyzed on a 6% polyacrylamide sequencing gel and visualized by autoradiography. If the length of the resulting PCR product is identical to the distance between the ends of the primer sequences in the cDNA from which the primers are derived, then the PCR reaction is repeated with DNA templates from two panels of human-rodent somatic cell hybrids, BIOS PCRable DNA (BIOS Corporation) and NIGMS Human-Rodent Somatic Cell Hybrid Mapping Panel Number 1 (NIGMS, Camden, N.J.).

PCR is used to screen a series of somatic cell hybrid cell lines containing defined sets of human chromosomes for the presence of a given cDNA (or genomic DNA obtainable therefrom). DNA is isolated from the somatic hybrids and used as starting templates for PCR reactions using the primer pairs from the cDNAs (or genomic DNAs obtainable therefrom). Only those somatic cell hybrids with chromosomes containing the human gene corresponding to the cDNA (or genomic DNA obtainable therefrom) will yield an amplified fragment. The cDNAs (or genomic DNAs obtainable therefrom) are assigned to a chromosome by analysis of the segregation pattern of PCR products from the somatic hybrid DNA templates. The single human chromosome present in all cell hybrids that give rise to an amplified fragment is the chromosome containing that cDNA (or genomic DNA obtainable therefrom). For a review of techniques and analysis of results from somatic cell gene mapping experiments. (See Ledbetter et al., *Genomics* 6:475-481 (1990).)

Alternatively, the cDNAs (or genomic DNAs obtainable therefrom) may be mapped to individual chromosomes using FISH as described in example 42 below.

EXAMPLE 42

Mapping of cDNAs to Chromosomes Using Fluorescence in Situ Hybridization

Fluorescence in situ hybridization allows the cDNA (or genomic DNA obtainable therefrom) to be mapped to a particular location on a given chromosome. The chromosomes to be used for fluorescence in situ hybridization techniques may be obtained from a variety of sources including cell cultures, tissues, or whole blood.

In a preferred embodiment, chromosomal localization of a cDNA (or genomic DNA obtainable therefrom) is obtained by FISH as described by Cherif et al. (*Proc. Natl. Acad. Sci. U.S.A.*, 87:6639-6643, 1990). Metaphase chromosomes are prepared from phytohemagglutinin (PHA)-stimulated blood cell donors. PHA-stimulated lymphocytes from healthy males are cultured for 72 h in RPMI-1640 medium. For synchronization, methotrexate (10 μM) is added for 17 h, followed by addition of 5-bromodeoxyuridine (5-BudR, 0.1 mM) for 6 h. Colcemid (1 μg/ml) is added for the last 15 min before harvesting the cells. Cells are collected, washed in RPMI, incubated with a hypotonic solution of KCl (75 mM) at 37° C. for 15 min and fixed in three changes of methanol: acetic acid (3:1). The cell suspension is dropped onto a glass slide and air dried. The cDNA (or genomic DNA obtainable therefrom) is labeled with biotin-16 dUTP by nick translation according to the manufacturer's instructions (Bethesda Research Laboratories, Bethesda, Md.), purified using a Sephadex G-50 column (Pharmacia, Upssala, Sweden) and precipitated. Just prior to hybridization, the DNA pellet is dissolved in hybridization buffer (50% formamide, 2×SSC, 10% dextran sulfate, 1 mg/ml sonicated salmon sperm DNA, pH 7) and the probe is denatured at 70° C. for 5-10 min.

Slides kept at −20° C. are treated for 1 h at 37° C. with RNase A (100 μg/ml), rinsed three times in 2×SSC and dehydrated in an ethanol series. Chromosome preparations are denatured in 70% formamide, 2×SSC for 2 min at 70° C., then dehydrated at 4° C. The slides are treated with proteinase K (10 μg/100 ml in 20 mM Tris-HCl, 2 mM CaCl$_2$) at 37° C. for 8 min and dehydrated. The hybridization mixture containing the probe is placed on the slide, covered with a coverslip, sealed with rubber cement and incubated overnight in a humid chamber at 37° C. After hybridization and post-hybridization washes, the biotinylated probe is detected by avidin-FITC and amplified with additional layers of biotinylated goat anti-avidin and avidin-FITC. For chromosomal localization, fluorescent R-bands are obtained as previously described (Cherif et al., supra.). The slides are observed under a LEICA fluorescence microscope (DMRXA). Chromosomes are counterstained with propidium iodide and the fluorescent signal of the probe appears as two symmetrical yellow-green spots on both chromatids of the fluorescent R-band chromosome (red). Thus, a particular cDNA (or genomic DNA obtainable therefrom) may be localized to a particular cytogenetic R-band on a given chromosome.

EXAMPLE 43

Use of cDNAs to Construct or Expand Chromosome Maps

Once the cDNAs (or genomic DNAs obtainable therefrom) have been assigned to particular chromosomes using the techniques described in Examples 40-42 above, they may be utilized to construct a high resolution map of the chromosomes on which they are located or to identify the chromosomes in a sample.

Chromosome mapping involves assigning a given unique sequence to a particular chromosome as described above. Once the unique sequence has been mapped to a given chromosome, it is ordered relative to other unique sequences located on the same chromosome. One approach to chromosome mapping utilizes a series of yeast artificial chromosomes (YACs) bearing several thousand long inserts derived from the chromosomes of the organism from which the cDNAs (or genomic DNAs obtainable therefrom) are obtained. This approach is described in Ramaiah Nagaraja et al. *Genome Research* 7:210-222, March 1997. Briefly, in this approach each chromosome is broken into overlapping pieces which are inserted into the YAC vector. The YAC inserts are screened using PCR or other methods to determine whether they include the cDNA (or genomic DNA obtainable therefrom) whose position is to be determined. Once an insert has been found which includes the cDNA (or genomic DNA obtainable therefrom), the insert can be analyzed by PCR or other methods to determine whether the insert also contains other sequences known to be on the chromosome or in the region from which the cDNA (or genomic DNA obtainable therefrom) was derived. This process can be repeated for each insert in the YAC library to determine the location of each of the cDNAs (or genomic DNAs obtainable therefrom) relative to one another and to other known chromosomal markers. In this way, a high resolution map of the distribution of numerous unique markers along each of the organisms chromosomes may be obtained.

As described in example 44 below cDNAs (or genomic DNAs obtainable therefrom) may also be used to identify genes associated with a particular phenotype, such as hereditary disease or drug response.

EXAMPLE 44

Identification of Genes Associated with Hereditary Diseases or Drug Response

This example illustrates an approach useful for the association of cDNAs (or genomic DNAs obtainable therefrom) with particular phenotypic characteristics. In this example, a particular cDNA (or genomic DNA obtainable therefrom) is used as a test probe to associate that cDNA (or genomic DNA obtainable therefrom) with a particular phenotypic characteristic.

cDNAs (or genomic DNAs obtainable therefrom) are mapped to a particular location on a human chromosome using techniques such as those described in Examples 40 and 41 or other techniques known in the art. A search of Mendelian Inheritance in Man (V. McKusick, *Mendelian Inheritance in Man* (available on line through Johns Hopkins University Welch Medical Library) reveals the region of the human chromosome which contains the cDNA (or genomic DNA obtainable therefrom) to be a very gene rich region containing several known genes and several diseases or phenotypes for which genes have not been identified. The gene corresponding to this cDNA (or genomic DNA obtainable therefrom) thus becomes an immediate candidate for each of these genetic diseases.

Cells from patients with these diseases or phenotypes are isolated and expanded in culture. PCR primers from the cDNA (or genomic DNA obtainable therefrom) are used to screen genomic DNA, mRNA or cDNA obtained from the patients. cDNAs (or genomic DNAs obtainable therefrom) that are not amplified in the patients can be positively associated with a particular disease by further analysis. Alternatively, the PCR analysis may yield fragments of different lengths when the samples are derived from an individual having the phenotype associated with the disease than when the sample is derived from a healthy individual, indicating that the gene containing the cDNA may be responsible for the genetic disease.

VI. Use of cDNAs (or Genomic DNAs Obtainable Therefrom) to Construct Vectors

The present cDNAs (or genomic DNAs obtainable therefrom) may also be used to construct secretion vectors capable of directing the secretion of the proteins encoded by genes inserted in the vectors. Such secretion vectors may facilitate the purification or enrichment of the proteins encoded by genes inserted therein by reducing the number of background proteins from which the desired protein must be purified or enriched. Exemplary secretion vectors are described below.

EXAMPLE 45

Construction of Secretion Vectors

The secretion vectors of the present invention include a promoter capable of directing gene expression in the host cell, tissue, or organism of interest. Such promoters include the Rous Sarcoma Virus promoter, the SV40 promoter, the human cytomegalovirus promoter, and other promoters familiar to those skilled in the art.

A signal sequence from a cDNA (or genomic DNA obtainable therefrom), such as one of the signal sequences in SEQ ID NOs: 24-73 as defined in Table I above, is operably linked to the promoter such that the mRNA transcribed from the promoter will direct the translation of the signal peptide. The host cell, tissue, or organism may be any cell, tissue, or organism which recognizes the signal peptide encoded by the signal sequence in the cDNA (or genomic DNA obtainable therefrom). Suitable hosts include mammalian cells, tissues or organisms, avian cells, tissues, or organisms, insect cells, tissues or organisms, or yeast.

In addition, the secretion vector contains cloning sites for inserting genes encoding the proteins which are to be secreted. The cloning sites facilitate the cloning of the insert gene in frame with the signal sequence such that a fusion protein in which the signal peptide is fused to the protein encoded by the inserted gene is expressed from the mRNA transcribed from the promoter. The signal peptide directs the extracellular secretion of the fusion protein.

The secretion vector may be DNA or RNA and may integrate into the chromosome of the host, be stably maintained as an extrachromosomal replicon in the host, be an artificial chromosome, or be transiently present in the host. Preferably, the secretion vector is maintained in multiple copies in each host cell. As used herein, multiple copies means at least 2, 5, 10, 20, 25, 50 or more than 50 copies per cell. In some embodiments, the multiple copies are maintained extrachromosomally. In other embodiments, the multiple copies result from amplification of a chromosomal sequence. Many nucleic acid backbones suitable for use as secretion vectors are known to those skilled in the art, including retroviral vectors, SV40 vectors, Bovine Papilloma Virus vectors, yeast integrating plasmids, yeast episomal plasmids, yeast artificial chromosomes, human artificial chromosomes, P element vectors, baculovirus vectors, or bacterial plasmids capable of being transiently introduced into the host.

The secretion vector may also contain a polyA signal such that the polyA signal is located downstream of the gene inserted into the secretion vector.

After the gene encoding the protein for which secretion is desired is inserted into the secretion vector, the secretion vector is introduced into the host cell, tissue, or organism using calcium phosphate precipitation, DEAE-Dextran, electroporation, liposome-mediated transfection, viral particles or as naked DNA. The protein encoded by the inserted gene is then purified or enriched from the supernatant using conventional techniques such as ammonium sulfate precipitation, immunoprecipitation, immunochromatography, size exclusion chromatography, ion exchange chromatography, and hplc. Alternatively, the secreted protein may be in a sufficiently enriched or pure state in the supernatant or growth media of the host to permit it to be used for its intended purpose without further enrichment.

The signal sequences may also be inserted into vectors designed for gene therapy. In such vectors, the signal sequence is operably linked to a promoter such that mRNA transcribed from the promoter encodes the signal peptide. A cloning site is located downstream of the signal sequence such that a gene encoding a protein whose secretion is desired may readily be inserted into the vector and fused to the signal sequence. The vector is introduced into an appropriate host cell. The protein expressed from the promoter is secreted extracellularly, thereby producing a therapeutic effect.

The cDNAs or 5' ESTs may also be used to clone sequences located upstream of the cDNAs or 5' ESTs which are capable of regulating gene expression, including promoter sequences, enhancer sequences, and other upstream sequences which influence transcription or translation levels. Once identified and cloned, these upstream regulatory sequences may be used in expression vectors designed to direct the expression of an inserted gene in a desired spatial, temporal, developmental, or quantitative fashion. The next example describes a method for cloning sequences upstream of the cDNAs or 5' ESTs.

EXAMPLE 46

Use of cDNAs or Fragments thereof to Clone Upstream Sequences from Genomic DNA

Sequences derived from cDNAs or 5' ESTs may be used to isolate the promoters of the corresponding genes using chromosome walking techniques. In one chromosome walking technique, which utilizes the GenomeWalker™ kit available from Clontech, five complete genomic DNA samples are each digested with a different restriction enzyme which has a 6 base recognition site and leaves a blunt end. Following digestion, oligonucleotide adapters are ligated to each end of the resulting genomic DNA fragments.

For each of the five genomic DNA libraries, a first PCR reaction is performed according to the manufacturer's instructions (which are incorporated herein by reference) using an outer adaptor primer provided in the kit and an outer gene specific primer. The gene specific primer should be selected to be specific for the cDNA or 5' EST of interest and should have a melting temperature, length, and location in the cDNA or 5' EST which is consistent with its use in PCR reactions. Each first PCR reaction contains 5 ng of genomic DNA, 5 µl of 10× Tth reaction buffer, 0.2 mM of each dNTP, 0.2 µM each of outer adaptor primer and outer gene specific primer, 1.1 mM of Mg(OAc)$_2$, and 1 µl of the Tth polymerase 50× mix in a total volume of 50 µl. The reaction cycle for the first PCR reaction is as follows: 1 min at 94° C./2 sec at 94° C., 3 min at 72° C. (7 cycles)/2 sec at 94° C., 3 min at 67° C. (32 cycles)/5 min at 67° C.

The product of the first PCR reaction is diluted and used as a template for a second PCR reaction according to the manufacturer's instructions using a pair of nested primers which are located internally on the amplicon resulting from the first PCR reaction. For example, 5 µl of the reaction product of the first PCR reaction mixture may be diluted 180 times. Reactions are made in a 50 µl volume having a composition identical to that of the first PCR reaction except the nested primers are used. The first nested primer is specific for the adaptor, and is provided with the GenomeWalker™ kit. The second nested primer is specific for the particular cDNA or 5' EST for which the promoter is to be cloned and should have a melting temperature, length, and location in the cDNA or 5' EST which is consistent with its use in PCR reactions. The reaction parameters of the second PCR reaction are as follows: 1 min at 94° C./2 sec at 94° C., 3 min at 72° C. (6 cycles)/2 sec at 94° C., 3 min at 67° C. (25 cycles)/5 min at 67° C.

The product of the second PCR reaction is purified, cloned, and sequenced using standard techniques. Alternatively, two or more human genomic DNA libraries can be constructed by using two or more restriction enzymes. The digested genomic DNA is cloned into vectors which can be converted into single stranded, circular, or linear DNA. A biotinylated oligonucleotide comprising at least 15 nucleotides from the cDNA or 5' EST sequence is hybridized to the single stranded DNA. Hybrids between the biotinylated oligonucleotide and the single stranded DNA containing the cDNA or EST sequence are isolated as described in example 17 above. Thereafter, the single stranded DNA containing the cDNA or EST sequence is released from the beads and converted into double stranded DNA using a primer specific for the cDNA or 5' EST sequence or a primer corresponding to a sequence included in the cloning vector. The resulting double stranded DNA is transformed into bacteria. DNAs containing the 5' EST or cDNA sequences are identified by colony PCR or colony hybridization.

Once the upstream genomic sequences have been cloned and sequenced as described above, prospective promoters and transcription start sites within the upstream sequences may be identified by comparing the sequences upstream of the cDNAs or 5' ESTs with databases containing known transcription start sites, transcription factor binding sites, or promoter sequences.

In addition, promoters in the upstream sequences may be identified using promoter reporter vectors as described below.

EXAMPLE 47

Identification of Promoters in Cloned Upstream Sequences

The genomic sequences upstream of the cDNAs or fragment thereof are cloned into a suitable promoter reporter vector, such as the pSEAP-Basic, pSEAP-Enhancer, pβgal-Basic, pβgal-Enhancer, or pEGFP-1 Promoter Reporter vectors available from Clontech. Briefly, each of these promoter reporter vectors include multiple cloning sites positioned upstream of a reporter gene encoding a readily assayable protein such as secreted alkaline phosphatase, β galactosidase, or green fluorescent protein. The sequences upstream of the cDNAs or 5' ESTs are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for augmenting transcription levels from weak promoter sequences. A significant level of expression above that observed with the vector lacking an insert indicates that a promoter sequence is present in the inserted upstream sequence.

Appropriate host cells for the promoter reporter vectors may be chosen based on the results of the above described determination of expression patterns of the cDNAs and ESTs. For example, if the expression pattern analysis indicates that the mRNA corresponding to a particular cDNA or fragment thereof is expressed in fibroblasts, the promoter reporter vector may be introduced into a human fibroblast cell line.

Promoter sequences within the upstream genomic DNA may be further defined by constructing nested deletions in the upstream DNA using conventional techniques such as Exonuclease III digestion. The resulting deletion fragments can be inserted into the promoter reporter vector to determine whether the deletion has reduced or obliterated promoter activity. In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into the cloning sites in the promoter reporter vectors.

EXAMPLE 48

Cloning and Identification of Promoters

Using the method described in example 47 above with 5' ESTs, sequences upstream of several genes were obtained. Using the primer pairs GGG AAG ATG GAG ATA GTA TTG CCT G (SEQ ID NO:15) and CTG CCA TGT ACA TGA TAG AGA GAT TC (SEQ ID NO:16), the promoter having the internal designation P13H2 (SEQ ID NO:17) was obtained.

Using the primer pairs GTA CCA GGGG ACT GTG ACC ATT GC (SEQ ID NO:18) and CTG TGA CCA TTG CTC CCA AGA GAG (SEQ ID NO:19), the promoter having the internal designation P15B4 (SEQ ID NO:20) was obtained.

Using the primer pairs CTG GGA TGG AAG GCA CGG TA (SEQ ID NO:21) and GAG ACC ACA CAG CTA GAC AA (SEQ ID NO:22), the promoter having the internal designation P29B6 (SEQ ID NO:23) was obtained.

Figure 4:
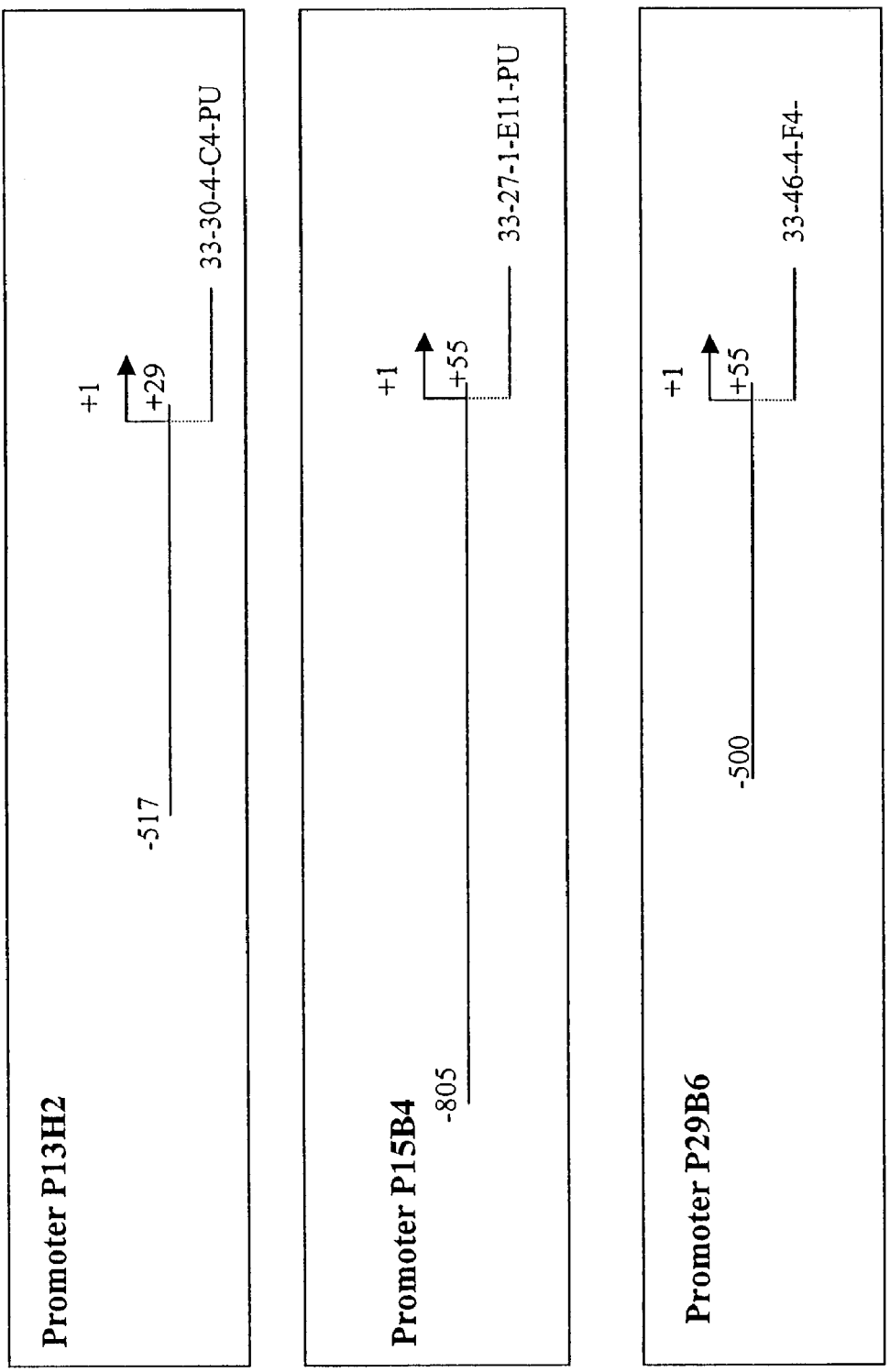

FIG. 4 provides a schematic description of the promoters isolated and the way they are assembled with the corresponding 5' tags. The upstream sequences were screened for the presence of motifs resembling transcription factor binding sites or known transcription start sites using the computer program MatInspector release 2.0, August 1996.

FIG. 5 describes the transcription factor binding sites present in each of these promoters. The columns labeled matrice provides the name of the MatInspector matrix used. The column labeled position provides the 5' postion of the promoter site. Numeration of the sequence starts from the transcription site as determined by matching the genomic sequence with the 5' EST sequence. The column labeled "orientation" indicates the DNA strand on which the site is found, with the + strand being the coding strand as determined by matching the genomic sequence with the sequence of the 5' EST. The column labeled "score" provides the MatInspector score found for this site. The column labeled "length" provides the length of the site in nucleotides. The column labeled "sequence" provides the sequence of the site found.

The promoters and other regulatory sequences located upstream of the cDNAs or 5' ESTs may be used to design expression vectors capable of directing the expression of an inserted gene in a desired spatial, temporal, developmental, or quantitative manner. A promoter capable of directing the desired spatial, temporal, developmental, and quantitative patterns may be selected using the results of the expression analysis described in example 10 above. For example, if a promoter which confers a high level of expression in muscle is desired, the promoter sequence upstream of a cDNA or 5' EST derived from an mRNA which is expressed at a high level in muscle, as determined by the method of example 10, may be used in the expression vector.

Preferably, the desired promoter is placed near multiple restriction sites to facilitate the cloning of the desired insert downstream of the promoter, such that the promoter is able to drive expression of the inserted gene. The promoter may be inserted in conventional nucleic acid backbones designed for extrachromosomal replication, integration into the host chromosomes or transient expression. Suitable backbones for the present expression vectors include retroviral backbones, backbones from eukaryotic episomes such as SV40 or Bovine Papilloma Virus, backbones from bacterial episomes, or artificial chromosomes.

Preferably, the expression vectors also include a polyA signal downstream of the multiple restriction sites for directing the polyadenylation of mRNA transcribed from the gene inserted into the expression vector.

Following the identification of promoter sequences using the procedures of Examples 46-48, proteins which interact with the promoter may be identified as described in example 49 below.

EXAMPLE 49

Identification of Proteins which Interact with Promoter Sequences, Upstream Regulatory Sequences, or mRNA Sequences within the promoter region which are likely to bind transcription factors may be identified by identity to known transcription factor binding sites or through conventional mutagenesis or deletion analyses of reporter plasmids containing the promoter sequence. For example, deletions may be made in a reporter plasmid containing the promoter sequence of interest operably linked to an assayable reporter gene. The reporter plasmids carrying various deletions within the promoter region are transfected into an appropriate host cell and the effects of the deletions on expression levels is assessed. Transcription factor binding sites within the regions in which deletions reduce expression levels may be further localized using site directed mutagenesis, linker scanning analysis, or other techniques familiar to those skilled in the art. Nucleic acids encoding proteins which interact with sequences in the promoter may be identified using one-hybrid systems such as those described in the manual accompanying the Matchmaker One-Hybrid System kit available from Clontech (Catalog No. K1603-1), the disclosure of which is incorporated herein by reference. Briefly, the Matchmaker One-hybrid system is used as follows. The target sequence for which it is desired to identify binding proteins is cloned upstream of a selectable reporter gene and integrated into the yeast genome. Preferably, multiple copies of the target sequences are inserted into the reporter plasmid in tandem.

A library comprised of fusions between cDNAs to be evaluated for the ability to bind to the promoter and the activation domain of a yeast transcription factor, such as GAL4, is transformed into the yeast strain containing the integrated reporter sequence. The yeast are plated on selective media to select cells expressing the selectable marker linked to the promoter sequence. The colonies which grow on the selective media contain genes encoding proteins which bind the target sequence. The inserts in the genes encoding the fusion proteins are further characterized by sequencing. In addition, the inserts may be inserted into expression vectors or in vitro transcription vectors. Binding of the polypeptides encoded by the inserts to the promoter DNA may be confirmed by techniques familiar to those skilled in the art, such as gel shift analysis or DNAse protection analysis.

VII. Use of cDNAs (or Genomic DNAs Obtainable Therefrom) in Gene Therapy

The present invention also comprises the use of cDNAs (or genomic DNAs obtainable therefrom) in gene therapy strategies, including antisense and triple helix strategies as described in Examples 50 and 51 below. In antisense approaches, nucleic acid sequences complementary to an mRNA are hybridized to the mRNA intracellularly, thereby blocking the expression of the protein encoded by the mRNA. The antisense sequences may prevent gene expression through a variety of mechanisms. For example, the antisense sequences may inhibit the ability of ribosomes to translate the mRNA. Alternatively, the antisense sequences may block transport of the mRNA from the nucleus to the cytoplasm, thereby limiting the amount of mRNA available for translation. Another mechanism through which antisense sequences may inhibit gene expression is by interfering with mRNA splicing. In yet another strategy, the antisense nucleic acid may be incorporated in a ribozyme capable of specifically cleaving the target mRNA.

EXAMPLE 50

Preparation and Use of Antisense Oligonucleotides

The antisense nucleic acid molecules to be used in gene therapy may be either DNA or RNA sequences. They may comprise a sequence complementary to the sequence of the cDNA (or genomic DNA obtainable therefrom). The antisense nucleic acids should have a length and melting temperature sufficient to permit formation of an intracellular duplex having sufficient stability to inhibit the expression of the mRNA in the duplex. Strategies for designing antisense nucleic acids suitable for use in gene therapy are disclosed in Green et al., *Ann. Rev. Biochem.*, 55:569-597 (1986) and Izant and Weintraub, *Cell*, 36:1007-1015 (1984), which are hereby incorporated by reference.

In some strategies, antisense molecules are obtained from a nucleotide sequence encoding a protein by reversing the orientation of the coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of the antisense nucleic acids in vivo by operably linking DNA containing the antisense sequence to a promoter in an expression vector.

Alternatively, oligonucleotides which are complementary to the strand normally transcribed in the cell may be synthesized in vitro. Thus, the antisense nucleic acids are complementary to the corresponding mRNA and are capable of hybridizing to the mRNA to create a duplex. In some embodiments, the antisense sequences may contain modified sugar phosphate backbones to increase stability and make them less sensitive to RNase activity. Examples of modifications suitable for use in antisense strategies include 2' O-methyl RNA oligonucleotides and Protein-nucleic acid (PNA) oligonucleotides. Further examples are described by Rossi et al., *Pharmacol. Ther.*, 50(2):245-254, (1991).

Various types of antisense oligonucleotides complementary to the sequence of the cDNA (or genomic DNA obtainable therefrom) may be used. In one preferred embodiment, stable and semi-stable antisense oligonucleotides described in International Application No. PCT WO94/23026, hereby incorporated by reference, are used. In these moleucles, the 3' end or both the 3' and 5' ends are engaged in intramolecular hydrogen bonding between complementary base pairs. These molecules are better able to withstand exonuclease attacks and exhibit increased stability compared to conventional antisense oligonucleotides.

In another preferred embodiment, the antisense oligodeoxynucleotides against herpes simplex virus types 1 and 2 described in International Application No. WO 95/04141, hereby incorporated by reference, are used.

In yet another preferred embodiment, the covalently cross-linked antisense oligonucleotides described in International Application No. WO 96/31523, hereby incorporated by reference, are used. These double- or single-stranded oligonucleotides comprise one or more, respectively, inter- or intra-oligonucleotide covalent cross-linkages, wherein the linkage consists of an amide bond between a primary amine group of one strand and a carboxyl group of the other strand or of the same strand, respectively, the primary amine group being directly substituted in the 2' position of the strand nucleotide monosaccharide ring, and the carboxyl group being carried by an aliphatic spacer group substituted on a nucleotide or nucleotide analog of the other strand or the same strand, respectively.

The antisense oligodeoxynucleotides and oligonucleotides disclosed in International Application No. WO 92/18522, incorporated by reference, may also be used. These molecules are stable to degradation and contain at least one transcription control recognition sequence which binds to control proteins and are effective as decoys therefor. These molecules may contain "hairpin" structures, "dumbbell" structures, "modified dumbbell" structures, "cross-linked" decoy structures and "loop" structures.

In another preferred embodiment, the cyclic double-stranded oligonucleotides described in European Patent Application No. 0 572 287 A2, hereby incorporated by reference are used. These ligated oligonucleotide "dumbbells" contain the binding site for a transcription factor and inhibit expression of the gene under control of the transcription factor by sequestering the factor.

Use of the closed antisense oligonucleotides disclosed in International Application No. WO 92/19732, hereby incorporated by reference, is also contemplated. Because these molecules have no free ends, they are more resistant to degradation by exonucleases than are conventional oligonucleotides. These oligonucleotides may be multifunctional, interacting with several regions which are not adjacent to the target mRNA.

The appropriate level of antisense nucleic acids required to inhibit gene expression may be determined using in vitro expression analysis. The antisense molecule may be introduced into the cells by diffusion, injection, infection or transfection using procedures known in the art. For example, the antisense nucleic acids can be introduced into the body as a bare or naked oligonucleotide, oligonucleotide encapsulated in lipid, oligonucleotide sequence encapsidated by viral protein, or as an oligonucleotide operably linked to a promoter contained in an expression vector. The expression vector may be any of a variety of expression vectors known in the art, including retroviral or viral vectors, vectors capable of extrachromosomal replication, or integrating vectors. The vectors may be DNA or RNA.

The antisense molecules are introduced onto cell samples at a number of different concentrations preferably between $1\times10^{-10}$M to $1\times10^{-4}$M. Once the minimum concentration that can adequately control gene expression is identified, the optimized dose is translated into a dosage suitable for use in vivo. For example, an inhibiting concentration in culture of $1\times10^{-7}$ translates into a dose of approximately 0.6 mg/kg bodyweight. Levels of oligonucleotide approaching 100 mg/kg bodyweight or higher may be possible after testing the toxicity of the oligonucleotide in laboratory animals. It is additionally contemplated that cells from the vertebrate are removed, treated with the antisense oligonucleotide, and reintroduced into the vertebrate.

It is further contemplated that the antisense oligonucleotide sequence is incorporated into a ribozyme sequence to enable the antisense to specifically bind and cleave its target mRNA. For technical applications of ribozyme and antisense oligonucleotides see Rossi et al, supra.

In a preferred application of this invention, the polypeptide encoded by the gene is first identified, so that the effectiveness of antisense inhibition on translation can be monitored using techniques that include but are not limited to antibody-mediated tests such as RIAs and ELISA, functional assays, or radiolabeling.

The cDNAs of the present invention (or genomic DNAs obtainable therefrom) may also be used in gene therapy approaches based on intracellular triple helix formation. Triple helix oligonucleotides are used to inhibit transcription from a genome. They are particularly useful for studying alterations in cell activity as it is associated with a particular gene. The cDNAs (or genomic DNAs obtainable therefrom) of the present invention or, more preferably, a fragment of those sequences, can be used to inhibit gene expression in individuals having diseases associated with expression of a particular gene. Similarly, a fragment of the cDNA (or genomic DNA obtainable therefrom) can be used to study the effect of inhibiting transcription of a particular gene within a cell. Traditionally, homopurine sequences were considered the most useful for triple helix strategies. However, homopyrimidine sequences can also inhibit gene expression. Such homopyrimidine oligonucleotides bind to the major groove at homopurine:homopyrimidine sequences. Thus, both types of sequences from the cDNA or from the gene corresponding to the cDNA are contemplated within the scope of this invention.

EXAMPLE 51

Preparation and Use of Triple Helix Probes

The sequences of the cDNAs (or genomic DNAs obtainable therefrom) are scanned to identify 10-mer to 20-mer homopyrimidine or homopurine stretches which could be used in triple-helix based strategies for inhibiting gene expression. Following identification of candidate homopyrimidine or homopurine stretches, their efficiency in inhibiting gene expression is assessed by introducing varying amounts of oligonucleotides containing the candidate sequences into tissue culture cells which normally express the target gene. The oligonucleotides may be prepared on an oligonucleotide synthesizer or they may be purchased commercially from a company specializing in custom oligonucleotide synthesis, such as GENSET, Paris, France.

The oligonucleotides may be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced gene expression using techniques such as Northern blotting, RNase protection assays, or PCR based strategies to monitor the transcription levels of the target gene in cells which have been treated with the oligonucleotide. The cell functions to be monitored are predicted based upon the homologies of the target gene corresponding to the cDNA from which the oligonucleotide was derived with known gene sequences that have been associated with a particular function. The cell functions can also be predicted based on the presence of abnormal physiologies within cells derived from individuals with a particular inherited disease, particularly when the cDNA is associated with the disease using techniques described in example 44.

The oligonucleotides which are effective in inhibiting gene expression in tissue culture cells may then be introduced in vivo using the techniques described above and in example 50 at a dosage calculated based on the in vitro results, as described in example 50.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al. (*Science*, 245:967-971 (1989), which is hereby incorporated by this reference).

EXAMPLE 52

Use of cDNAs to Express an Encoded Protein in a Host Organism

The cDNAs of the present invention may also be used to express an encoded protein in a host organism to produce a beneficial effect. In such procedures, the encoded protein may be transiently expressed in the host organism or stably expressed in the host organism. The encoded protein may have any of the activities described above. The encoded protein may be a protein which the host organism lacks or, alternatively, the encoded protein may augment the existing levels of the protein in the host organism.

A full length cDNA encoding the signal peptide and the mature protein, or a cDNA encoding only the mature protein is introduced into the host organism. The cDNA may be introduced into the host organism using a variety of techniques known to those of skill in the art. For example, the cDNA may be injected into the host organism as naked DNA such that the encoded protein is expressed in the host organism, thereby producing a beneficial effect.

Alternatively, the cDNA may be cloned into an expression vector downstream of a promoter which is active in the host organism. The expression vector may be any of the expression vectors designed for use in gene therapy, including viral or retroviral vectors.

The expression vector may be directly introduced into the host organism such that the encoded protein is expressed in the host organism to produce a beneficial effect. In another approach, the expression vector may be introduced into cells in vitro. Cells containing the expression vector are thereafter selected and introduced into the host organism, where they express the encoded protein to produce a beneficial effect.

EXAMPLE 53

Use of Signal Peptides to Import Proteins into Cells

The short core hydrophobic region (h) of signal peptides encoded by the cDNAs of the present invention or fragment thereof may also be used as a carrier to import a peptide or a protein of interest, so-called cargo, into tissue culture cells (Lin et al., *J. Biol. Chem.*, 270: 14225-14258 (1995); Du et al., *J. Peptide Res.*, 51: 235-243 (1998); Rojas et al., *Nature Biotech.*, 16: 370-375 (1998)).

When cell permeable peptides of limited size (approximately up to 25 amino acids) are to be translocated across cell membrane, chemical synthesis may be used in order to add the h region to either the C-terminus or the N-terminus to the cargo peptide of interest. Alternatively, when longer peptides or proteins are to be imported into cells, nucleic acids can be genetically engineered, using techniques familiar to those skilled in the art, in order to link the cDNA sequence or fragment thereof encoding the h region to the 5' or the 3' end of a DNA sequence coding for a cargo polypeptide. Such genetically engineered nucleic acids are then translated either in vitro or in vivo after transfection into appropriate cells, using conventional techniques to produce the resulting cell permeable polypeptide. Suitable hosts cells are then simply incubated with the cell permeable polypeptide which is then translocated across the membrane.

This method may be applied to study diverse intracellular functions and cellular processes. For instance, it has been used to probe functionally relevant domains of intracellular proteins and to examine protein-protein interactions involved in signal transduction pathways (Lin et al., supra; Lin et al, *J. Biol. Chem.*, 271: 5305-5308 (1996); Rojas et al., *J. Biol. Chem.*, 271: 27456-27461 (1996); Liu et al., *Proc. Natl. Acad. Sci. USA*, 93: 11819-11824 (1996); Rojas et al., *Bioch. Biophys. Res. Commun.*, 234: 675-680 (1997)).

Such techniques may be used in cellular therapy to import proteins producing therapeutic effects. For instance, cells isolated from a patient may be treated with imported therapeutic proteins and then re-introduced into the host organism.

Alternatively, the h region of signal peptides of the present invention could be used in combination with a nuclear localization signal to deliver nucleic acids into cell nucleus. Such oligonucleotides may be antisense oligonucleotides or oligonucleotides designed to form triple helixes, as described in examples 50 and 51 respectively, in order to inhibit processing and maturation of a target cellular RNA.

EXAMPLE 54

Computer Embodiments

As used herein the term "cDNA codes of SEQ ID NOs. 24-73" encompasses the nucleotide sequences of SEQ ID NOs. 24-73, fragments of SEQ ID NOs. 24-73, nucleotide sequences homologous to SEQ ID NOs. 24-73 or homologous to fragments of SEQ ID NOs. 24-73, and sequences complementary to all of the preceding sequences. The fragments include fragments of SEQ ID NOs. 24-73 comprising at least 8, 10, 12, 15, 18, 20, 25, 28, 30, 35, 40, 50, 75, 100, 150, 200, 300, 400, 500, 1000 or 2000 consecutive nucleotides of SEQ ID NOs. 24-73. Preferably, the fragments are novel fragments. Preferably the fragments include polynucleotides described in Table III or fragments thereof comprising at least 8, 10, 12, 15, 18, 20, 25, 28, 30, 35, 40, 50, 75, 100, 150, 200, 300, 400, 500, 1000 or 2000 consecutive nucleotides of the polynucleotides described in Table III. Homologous sequences and fragments of SEQ ID NOs. 24-73 refer to a sequence having at least 99%, 98%, 97%, 96%, 95%, 90%, 85%, 80%, or 75% identity to these sequences. Identity may be determined using any of the computer programs and parameters described in example 17, including BLAST2N with the default parameters or with any modified parameters. Homologous sequences also include RNA sequences in which uridines replace the thymines in the cDNA codes of SEQ ID NOs. 24-73. The homologous sequences may be obtained using any of the procedures described herein or may result from the correction of a sequencing error as described above. Preferably the homologous sequences and fragments of SEQ ID NOs. 24-73 include polynucleotides described in Table III or fragments comprising at least 8, 10, 12, 15, 18, 20, 25, 28, 30, 35, 40, 50, 75, 100, 150, 200, 300, 400, 500, 1000 or 2000 consecutive nucleotides of the polynucleotides described in Table III. It will be appreciated that the cDNA codes of SEQ ID NOs. 24-73 can be represented in the traditional single character format (See the inside back cover of Styer, Lubert. *Biochemistry*, 3$^{rd}$ edition. W. H Freeman & Co., New York.) or in any other format which records the identity of the nucleotides in a sequence.

As used herein the term "polypeptide codes of SEQ ID NOS. 74-123" encompasses the polypeptide sequences of SEQ ID NOs. 74-123 which are encoded by the cDNAs of SEQ ID NOs. 24-73, polypeptide sequences homologous to the polypeptides of SEQ ID NOS. 74-123, or fragments of any of the preceding sequences. Homologous polypeptide sequences refer to a polypeptide sequence having at least 99%, 98%, 97%, 96%, 95%, 90%, 85%, 80%, 75% identity to one of the polypeptide sequences of SEQ ID NOS. 74-123. Identity may be determined using any of the computer programs and parameters described herein, including FASTA with the default parameters or with any modified parameters. The homologous sequences may be obtained using any of the procedures described herein or may result from the correction of a sequencing error as described above. The polypeptide fragments comprise at least 5, 8, 10, 12, 15, 20, 25, 30, 35, 40, 50, 60, 75, 100, 150 or 200 consecutive amino acids of the polypeptides of SEQ ID NOS. 74-123. Preferably, the fragments are novel fragments. Preferably, the fragments include polypeptides encoded by the polynucleotides described in Table III, or fragments thereof comprising at least 5, 10, 15, 20, 25, 30, 35, 40, 50, 75, 100, or 150 consecutive amino acids of the polypeptides encoded by the polynucleotides described in Table III. It will be appreciated that the polypeptide codes of the SEQ ID NOS. 74-123 can be represented in the traditional single character format or three letter format (See the inside back cover of Starrier, Lubert. *Biochemistry*, 3$^{rd}$ edition. W. H Freeman & Co., New York.) or in any other format which relates the identity of the polypeptides in a sequence.

It will be appreciated by those skilled in the art that the cDNA codes of SEQ ID NOs. 24-73 and polypeptide codes of SEQ ID NOS. 74-123 can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the cDNA codes of SEQ ID NOs. 24-73, one or more of the polypeptide codes of SEQ ID NOS. 74-123. Another aspect of the present invention is a computer readable medium having recorded thereon at least 2, 5, 10, 15, 20, 25, 30, or 50 cDNA codes of SEQ ID NOs. 24-73. Another aspect of the present invention is a computer readable medium having recorded thereon at least 2, 5, 10, 15, 20, 25, 30, or 50 polypeptide codes of SEQ ID NOS. 74-123.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Figure 6:
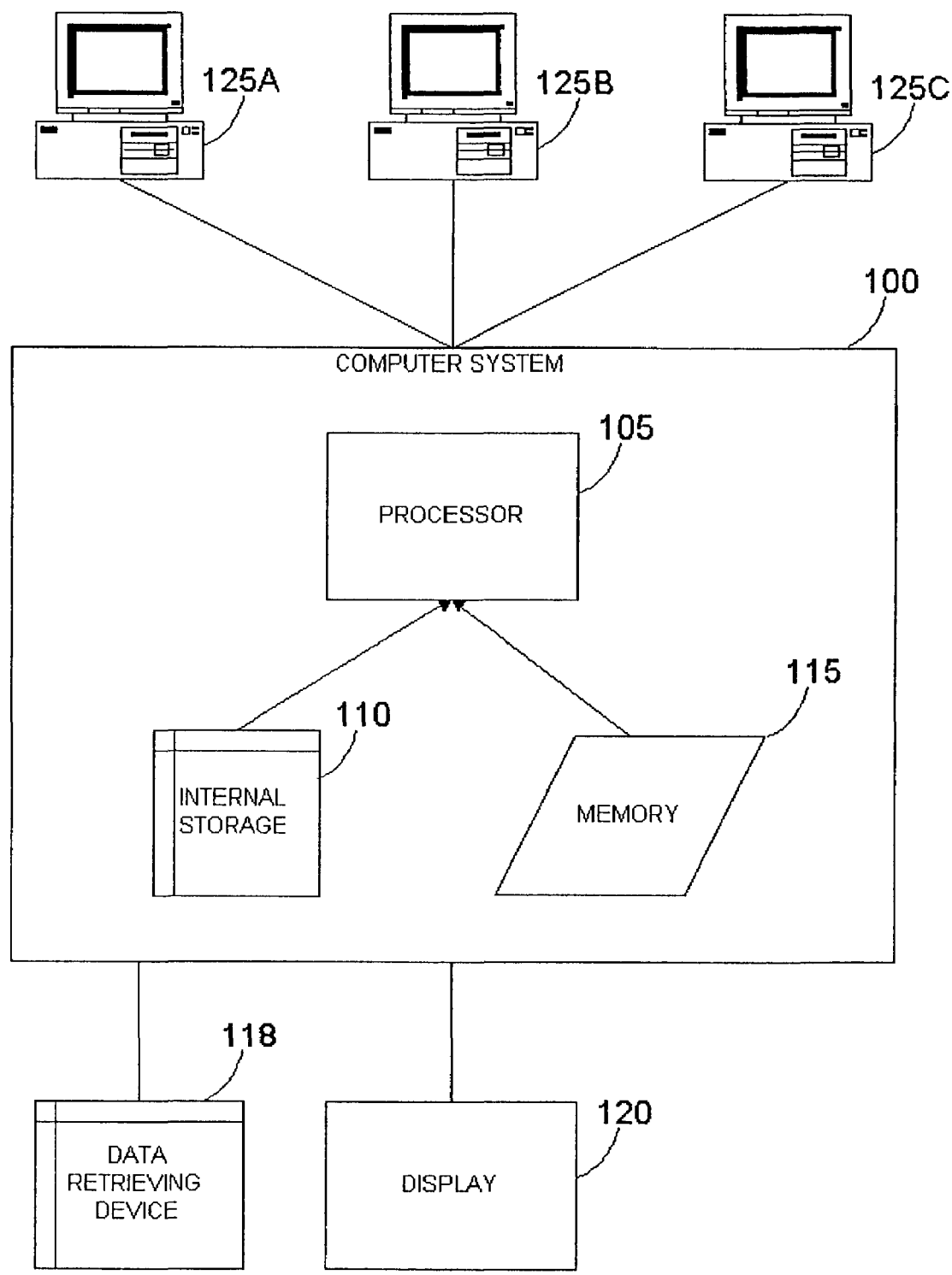
FIG. 6 is a block diagram of an exemplary computer system.

Embodiments of the present invention include systems, particularly computer systems which store and manipulate the sequence information described herein. One example of a computer system 100 is illustrated in block diagram form in FIG. 6. As used herein, "a computer system" refers to the hardware components, software components, and data storage components used to analyze the nucleotide sequences of the cDNA codes of SEQ ID NOs. 24-73, or the amino acid sequences of the polypeptide codes of SEQ ID NOS. 74-123. In one embodiment, the computer system 100 is a Sun Enterprise 1000 server (Sun Microsystems, Palo Alto, Calif.). The computer system 100 preferably includes a processor for processing, accessing and manipulating the sequence data. The processor 105 can be any well-known type of central processing unit, such as the Pentium III from Intel Corporation, or similar processor from Sun, Motorola, Compaq or International Business Machines.

Preferably, the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125*a-c* in a network or wide area network to provide centralized access to the computer system 100.

Software for accessing and processing the nucleotide sequences of the cDNA codes of SEQ ID NOs. 24-73, or the amino acid sequences of the polypeptide codes of SEQ ID NOS. 74-123 (such as search tools, compare tools, and modeling tools etc.) may reside in main memory 115 during execution.

In some embodiments, the computer system 100 may further comprise a sequence comparer for comparing the above-described cDNA codes of SEQ ID NOs. 24-73 or polypeptide codes of SEQ ID NOS. 74-123 stored on a computer readable medium to reference nucleotide or polypeptide sequences stored on a computer readable medium. A "sequence comparer" refers to one or more programs which are implemented on the computer system 100 to compare a nucleotide or polypeptide sequence with other nucleotide or polypeptide sequences and/or compounds including but not limited to peptides, peptidomimetics, and chemicals stored within the data storage means. For example, the sequence comparer may compare the nucleotide sequences of the cDNA codes of SEQ ID NOs. 24-73, or the amino acid sequences of the polypeptide codes of SEQ ID NOS. 74-123 stored on a computer readable medium to reference sequences stored on a computer readable medium to identify homologies, motifs implicated in biological function, or structural motifs. The various sequence comparer programs identified elsewhere in this patent specification are particularly contemplated for use in this aspect of the invention.

Figure 7:
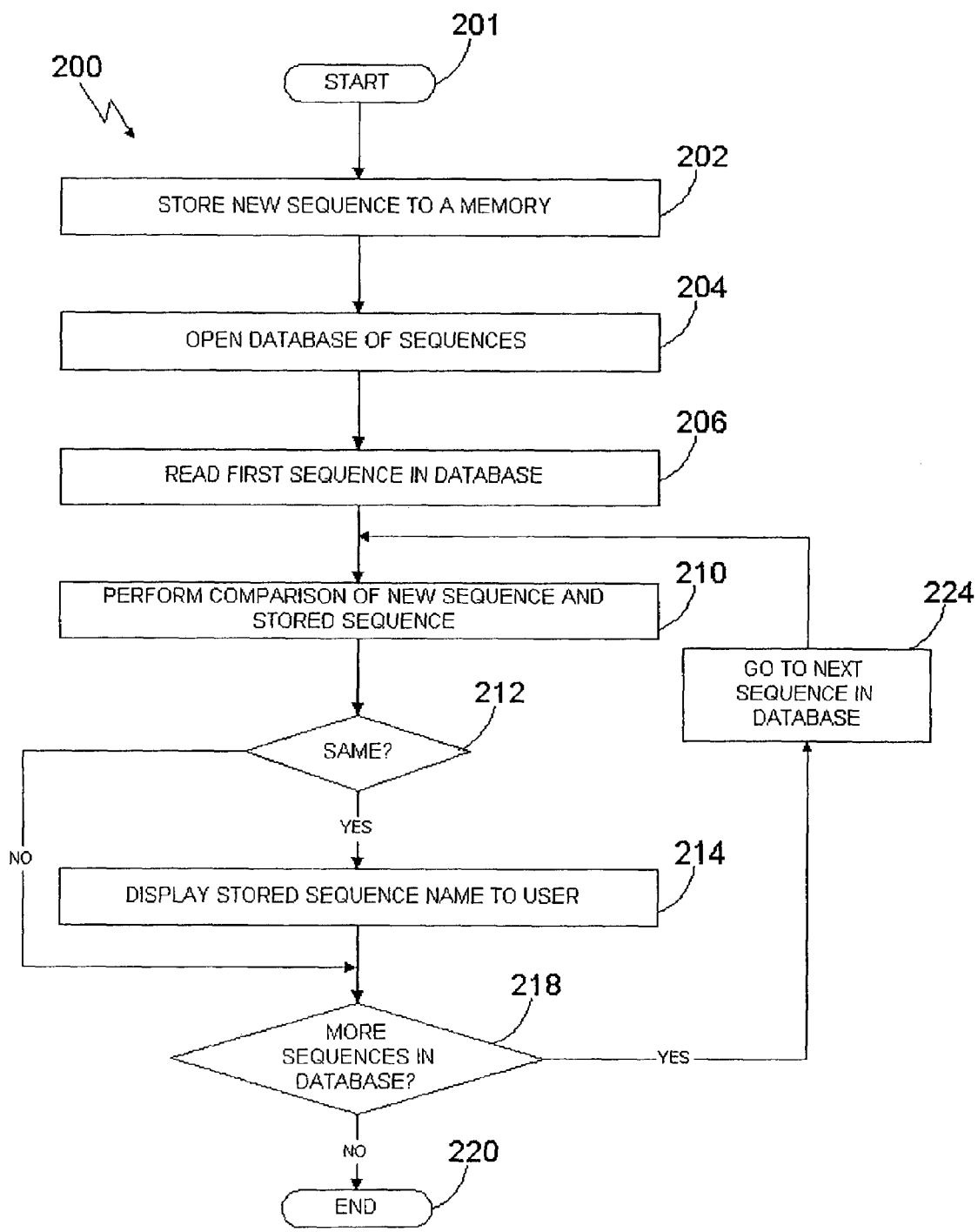
FIG. 7 is a flow diagram illustrating one embodiment of a process 200 for comparing a new nucleotide or protein sequence with a database of sequences in order to determine the identity levels between the new sequence and the sequences in the database.

FIG. 7 is a flow diagram illustrating one embodiment of a process 200 for comparing a new nucleotide or protein sequence with a database of sequences in order to determine the identity levels between the new sequence and the sequences in the database. The database of sequences can be a private database stored within the computer system 100, or a public database such as GENBANK, PIR or SWISSPROT that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the identity level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the identity parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the identity constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the present invention is a computer system comprising a processor, a data storage device having stored thereon a nucleic acid code of SEQ ID NOs. 24-73 or a polypeptide code of SEQ ID NOS. 74-123, a data storage device having retrievably stored thereon reference nucleotide sequences or polypeptide sequences to be compared to the nucleic acid code of SEQ ID NOs. 24-73 or polypeptide code of SEQ ID NOS. 74-123 and a sequence comparer for conducting the comparison. The sequence comparer may indicate a identity level between the sequences compared or identify structural motifs in the above described nucleic acid code of SEQ ID NOs. 24-73 and polypeptide codes of SEQ ID NOS. 74-123 or it may identify structural motifs in sequences which are compared to these cDNA codes and polypeptide codes. In some embodiments, the data storage device may have stored thereon the sequences of at least 2, 5, 10, 15, 20, 25, 30, or 50 of the cDNA codes of SEQ ID NOs. 24-73 or polypeptide codes of SEQ ID NOS. 74-123.

Another aspect of the present invention is a method for determining the level of identity between a nucleic acid code of SEQ ID NOs. 24-73 and a reference nucleotide sequence, comprising the steps of reading the nucleic acid code and the reference nucleotide sequence through the use of a computer program which determines identity levels and determining identity between the nucleic acid code and the reference nucleotide sequence with the computer program. The computer program may be any of a number of computer programs for determining identity levels, including those specifically enumerated herein, including BLAST2N with the default parameters or with any modified parameters. The method may be implemented using the computer systems described above. The method may also be performed by reading 2, 5, 10, 15, 20, 25, 30, or 50 of the above described cDNA codes of SEQ ID NOs. 24-73 through use of the computer program and determining identity between the cDNA codes and reference nucleotide sequences.

Figure 8:
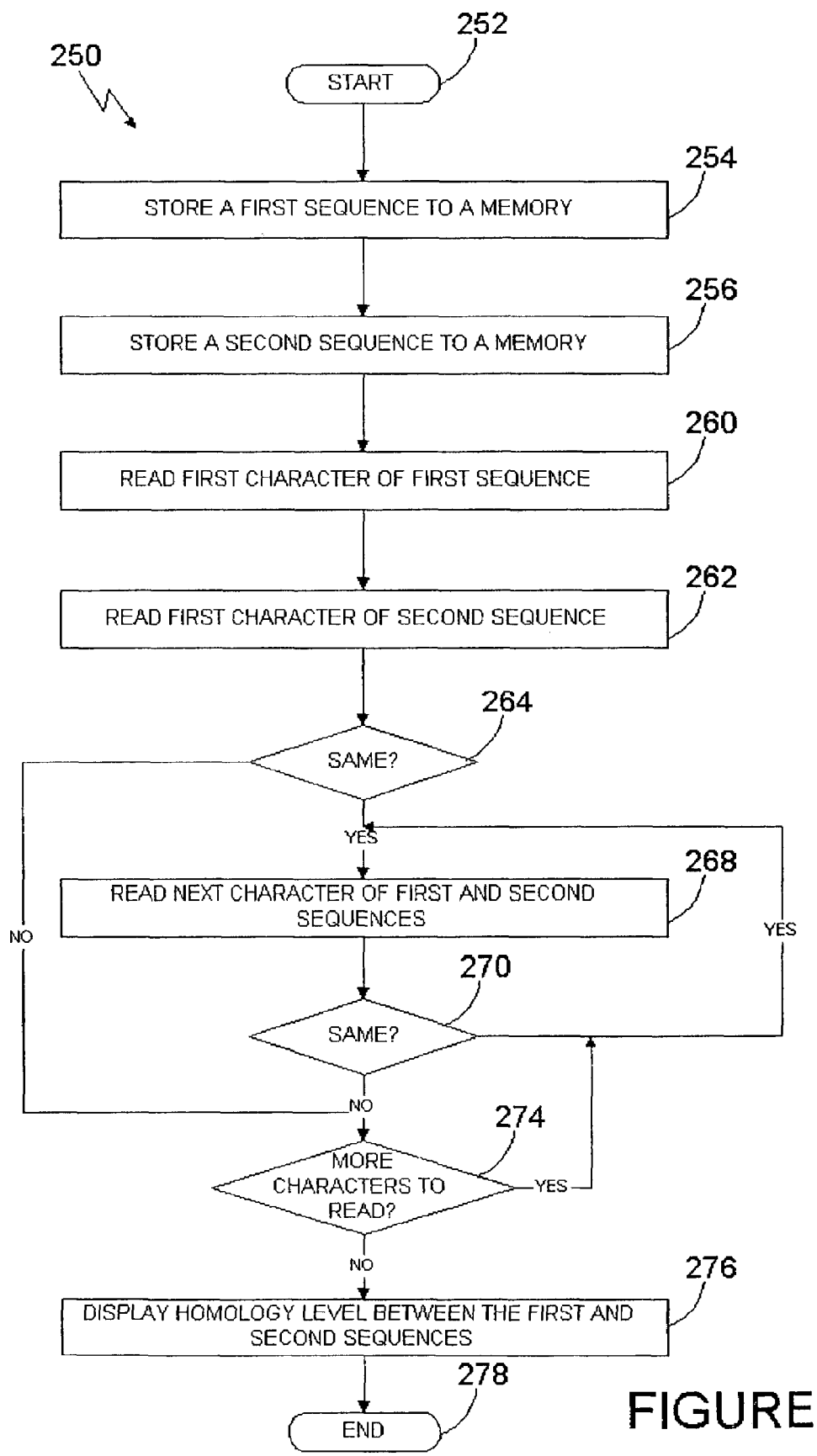
FIG. 8 is a flow diagram illustrating one embodiment of a process 250 in a computer for determining whether two sequences are homologous.

FIG. 8 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it should be in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there aren't any more characters to read, then the process 250 moves to a state 276 wherein the level of identity between the first and second sequences is displayed to the user. The level of identity is determined by calculating the profragment of characters between the sequences that were the same out of the total number of sequences in the first sequence. Thus, if every character in a first 100 nucleotide sequence aligned with a every character in a second sequence, the identity level would be 100%.

Alternatively, the computer program may be a computer program which compares the nucleotide sequences of the cDNA codes of the present invention, to reference nucleotide sequences in order to determine whether the nucleic acid code of SEQ ID NOs. 24-73 differs from a reference nucleic acid sequence at one or more positions. Optionally such a program records the length and identity of inserted, deleted or substituted nucleotides with respect to the sequence of either the reference polynucleotide or the nucleic acid code of SEQ ID NOs. 24-73. In one embodiment, the computer program may be a program which determines whether the nucleotide sequences of the cDNA codes of SEQ ID NOs. 24-73 contain a biallelic marker or single nucleotide polymorphism (SNP) with respect to a reference nucleotide sequence. This single nucleotide polymorphism may comprise a single base substitution, insertion, or deletion, while this biallelic marker may comprise about one to ten consecutive bases substituted, inserted or deleted.

Another aspect of the present invention is a method for determining the level of identity between a polypeptide code of SEQ ID NOS. 74-123 and a reference polypeptide sequence, comprising the steps of reading the polypeptide code of SEQ ID NOS. 74-123 and the reference polypeptide sequence through use of a computer program which determines identity levels and determining identity between the polypeptide code and the reference polypeptide sequence using the computer program.

Accordingly, another aspect of the present invention is a method for determining whether a nucleic acid code of SEQ ID NOs. 24-73 differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some embodiments, the computer program is a program which identifies single nucleotide polymorphisms. The method may be implemented by the computer systems described above and the method illustrated in FIG. 8. The method may also be performed by reading at least 2, 5, 10, 15, 20, 25, 30, or 50 of the cDNA codes of SEQ ID NOs. 24-73 and the reference nucleotide sequences through the use of the computer program and identifying differences between the cDNA codes and the reference nucleotide sequences with the computer program.

In other embodiments the computer based system may further comprise an identifier for identifying features within the nucleotide sequences of the cDNA codes of SEQ ID NOs. 24-73 or the amino acid sequences of the polypeptide codes of SEQ ID NOS. 74-123.

An "identifier" refers to one or more programs which identifies certain features within the above-described nucleotide sequences of the cDNA codes of SEQ ID NOs. 24-73 or the amino acid sequences of the polypeptide codes of SEQ ID NOS. 74-123. In one embodiment, the identifier may comprise a program which identifies an open reading frame in the cDNAs codes of SEQ ID NOs. 24-73.

Figure 9:
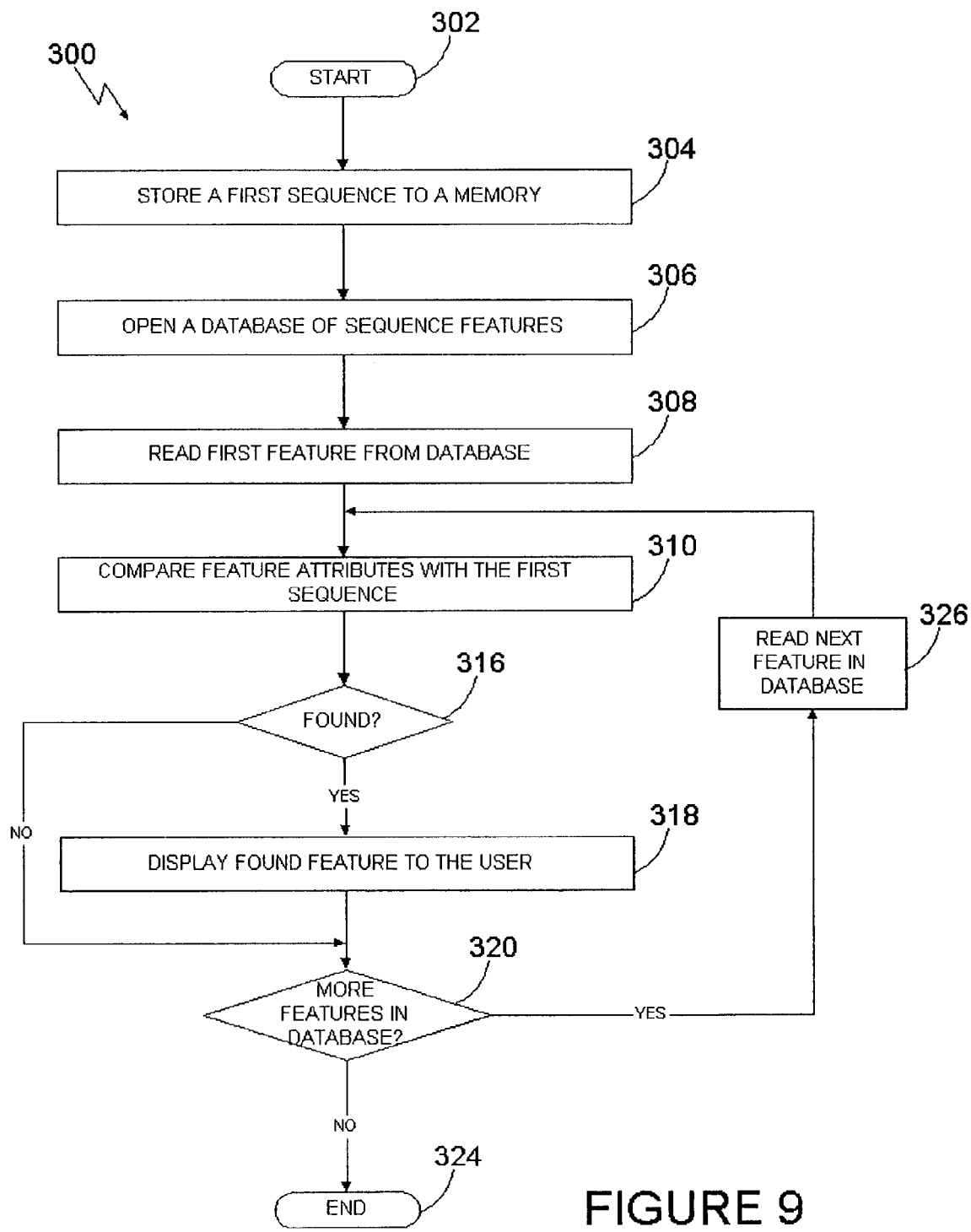
FIG. 9 is a flow diagram illustrating one embodiment of an identifier process 300 for detecting the presence of a feature in a sequence.

FIG. 9 is a flow diagram illustrating one embodiment of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group (world wide web site: gcg.com).

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence.

It should be noted, that if the feature attribute is not found in the first sequence at the decision state 316, the process 300 moves directly to the decision state 320 in order to determine if any more features exist in the database.

In another embodiment, the identifier may comprise a molecular modeling program which determines the 3-dimensional structure of the polypeptides codes of SEQ ID NOS. 74-123. In some embodiments, the molecular modeling program identifies target sequences that are most compatible with profiles representing the structural environments of the residues in known three-dimensional protein structures. (See, e.g., Eisenberg et al., U.S. Pat. No. 5,436,850 issued Jul. 25, 1995). In another technique, the known three-dimensional structures of proteins in a given family are superimposed to define the structurally conserved regions in that family. This protein modeling technique also uses the known three-dimensional structure of a homologous protein to approximate the structure of the polypeptide codes of SEQ ID NOS. 74-123. (See e.g., Srinivasan, et al., U.S. Pat. No. 5,557,535 issued Sep. 17, 1996). Conventional identity modeling techniques have been used routinely to build models of proteases and antibodies. (Sowdhamini et al., Protein Engineering 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence identity.

The recent development of threading methods now enables the identification of likely folding patterns in a number of situations where the structural relatedness between target and template(s) is not detectable at the sequence level. Hybrid methods, in which fold recognition is performed using Multiple Sequence Threading (MST), structural equivalencies are deduced from the threading output using a distance geometry program DRAGON to construct a low resolution model, and a full-atom representation is constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalencies obtained from the MST output are converted into inter-residue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (See e.g., Aszódi et al., Proteins: Structure, Function, and Genetics, Supplement 1:38-42 (1997)).

The results of the molecular modeling analysis may then be used in rational drug design techniques to identify agents which modulate the activity of the polypeptide codes of SEQ ID NOS. 74-123.

Accordingly, another aspect of the present invention is a method of identifying a feature within the cDNA codes of SEQ ID NOs. 24-73 or the polypeptide codes of SEQ ID NOS. 74-123 comprising reading the nucleic acid code(s) or the polypeptide code(s) through the use of a computer program which identifies features therein and identifying features within the nucleic acid code(s) or polypeptide code(s) with the computer program. In one embodiment, computer program comprises a computer program which identifies open reading frames. In a further embodiment, the computer program comprises a computer program which identifies linear or structural motifs in a polypeptide sequence. In another embodiment, the computer program comprises a molecular modeling program. The method may be performed by reading a single sequence or at least 2, 5, 10, 15, 20, 25, 30, or 50 of the cDNA codes of SEQ ID NOs. 24-73 or the polypeptide codes of SEQ ID NOS. 74-123 through the use of the computer program and identifying features within the cDNA codes or polypeptide codes with the computer program.

The cDNA codes of SEQ ID NOs. 24-73 or the polypeptide codes of SEQ ID NOS. 74-123 may be stored and manipulated in a variety of data processor programs in a variety of formats. For example, the cDNA codes of SEQ ID NOs. 24-73 or the polypeptide codes of SEQ ID NOS. 74-123 may be stored as text in a word processing file, such as Microsoft-WORD or WORDPERFECT or as an ASCII file in a variety of database programs familiar to those of skill in the art, such as DB2, SYBASE, or ORACLE. In addition, many computer programs and databases may be used as sequence comparers, identifiers, or sources of reference nucleotide or polypeptide sequences to be compared to the cDNA codes of SEQ ID NOs. 24-73 or the polypeptide codes of SEQ ID NOS. 74-123. The following list is intended not to limit the invention but to provide guidance to programs and databases which are useful with the cDNA codes of SEQ ID NOs. 24-73 or the polypeptide codes of SEQ ID NOS. 74-123. The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990)), FASTA (Pearson and Lipman, *Proc. Natl. Acad. Sci. USA*, 85: 2444 (1988)), FASTDB (Brutlag et al. Comp. App. Biosci. 6:237-245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMB-LiSwissprotein database, the MDL Available Chemicals Directory database, the MDL Drug Data Report data base, the Comprehensive Medicinal Chemistry database, Derwents's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

EXAMPLE 55

Methods of Making Nucleic Acids

The present invention also comprises methods of making the cDNA of SEQ ID Nos.24-73, genomic DNA obtainable therefrom, or fragment thereof. The methods comprise sequentially linking together nucleotides to produce the nucleic acids having the preceding sequences. A variety of methods of synthesizing nucleic acids are known to those skilled in the art.

In many of these methods, synthesis is conducted on a solid support. These included the 3' phosphoramidite methods in which the 3' terminal base of the desired. oligonucleotide is immobilized on an insoluble carrier. The nucleotide base to be added is blocked at the 5' hydroxyl and activated at the 3' hydroxyl so as to cause coupling with the immobilized nucleotide base. Deblocking of the new immobilized nucleotide compound and repetition of the cycle will produce the desired polynucleotide. Alternatively, polynucleotides may be prepared as described in U.S. Pat. No. 5,049,656. In some embodiments, several polynucleotides prepared as described above are ligated together to generate longer polynucleotides having a desired sequence.

EXAMPLE 56

Methods of Making Polypeptides

The present invention also comprises methods of making the polynucleotides encoded by the cDNA of SEQ ID Nos.24-73, genomic DNA obtainable therefrom, or fragments thereof and methods of making the polypeptides of SEQ ID Nos.74-123 or fragments thereof. The methods comprise sequentially linking together amino acids to produce the nucleic polypeptides having the preceding sequences. In some embodiments, the polypeptides made by these methods are 150 amino acids or less in length. In other embodiments, the polypeptides made by these methods are 120 amino acids or less in length.

A variety of methods of making polypeptides are known to those skilled in the art, including methods in which the carboxyl terminal amino acid is bound to polyvinyl benzene or another suitable resin. The amino acid to be added possesses blocking groups on its amino moiety and any side chain reactive groups so that only its carboxyl moiety can react. The carboxyl group is activated with carbodiimide or another activating agent and allowed to couple to the immobilized amino acid. After removal of the blocking group, the cycle is repeated to generate a polypeptide having the desired sequence. Alternatively, the methods described in U.S. Pat. No. 5,049,656 may be used.

EXAMPLE 57

Immunoaffinity Chromatography

Antibodies prepared as described above are coupled to a support. Preferably, the antibodies are monoclonal antibodies, but polyclonal antibodies may also be used. The support may be any of those typically employed in immunoaffinity chromatography, including Sepharose CL-4B (Pharmacia, Piscataway, N.J.), Sepharose CL-2B (Pharmacia, Piscataway, N.J.), Affi-gel 10 (Biorad, Richmond, Calif.), or glass beads.

The antibodies may be coupled to the support using any of the coupling reagents typically used in immunoaffmity chromatography, including cyanogen bromide. After coupling the antibody to the support, the support is contacted with a sample which contains a target polypeptide whose isolation, purification or enrichment is desired. The target polypeptide may be a polypeptide of SEQ ID NOs. 74-123, a fragment thereof, or a fusion protein comprising a polypeptide of SEQ ID NOs. 74-123 or a fragment thereof.

Preferably, the sample is placed in contact with the support for a sufficient amount of time and under appropriate conditions to allow at least 50% of the target polypeptide to specifically bind to the antibody coupled to the support.

Thereafter, the support is washed with an appropriate wash solution to remove polypeptides which have non-specifically adhered to the support. The wash solution may be any of those typically employed in immunoaffinity chromatography, including PBS, Tris-lithium chloride buffer (0.1M lysine base and 0.5M lithium chloride, pH 8.0), Tris-hydrochloride buffer (0.05M Tris-hydrochloride, pH 8.0), or Tris/Triton/NaCl buffer (50 mM Tris.cl, pH 8.0 or 9.0, 0.1% Triton X-100, and 0.5MNaCl).

After washing, the specifically bound target polypeptide is eluted from the support using the high pH or low pH elution solutions typically employed in immunoaffinity chromatography. In particular, the elution solutions may contain an eluant such as triethanolamine, diethylamine, calcium chloride, sodium thiocyanate, potasssium bromide, acetic acid, or glycine. In some embodiments, the elution solution may also contain a detergent such as Triton X-100 or octyl-β-D-glucoside.

As discussed above, the cDNAs of the present invention or fragments thereof can be used for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; for selecting and making oligomers for attachment to a "gene chip" or other support, including for examination for expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791-803 (1993)) to identify polynucleotides encoding the other protein with which binding occurs or to identify inhibitors of the binding interaction.

The proteins or polypeptides provided by the present invention can similarly be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning; A Laboratory Manual", 2d ed., Cole Spring Harbor Laboratory Press, Sambrook, J., E. F. Fritsch and T. Maniatis eds., 1989, and "Methods in Enzymology; Guide to Molecular Cloning Techniques", Academic Press, Berger, S. L. and A. R. Kimmel eds., 1987.

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All documents cited herein are incorporated herein by reference in their entirety.

TABLE I

| Id | FCS Location | SigPep Location | Mature Polypeptide Location | Stop Codon Location | PolyA Signal Location | PolyA Site Location |
|---|---|---|---|---|---|---|
| 24 | 153/1127 | 153/230 | 231/1127 | 1128 | 1415/1420 | 1434/1450 |
| 25 | 261/1166 | 261/314 | 315/1166 | 1167 | — | 1524/1556 |
| 26 | 67/813 | 67/111 | 112/813 | 814 | 1023/1028 | 1042/1058 |
| 27 | 187/438 | — | 187/438 | 439 | 612/617 | 632/648 |
| 28 | 92/1753 | 92/130 | 131/1753 | 1754 | 2070/2075 | 2090/2104 |
| 29 | 144/440 | 144/287 | 288/440 | 441 | 457/462 | 500/515 |
| 30 | 174/443 | 174/269 | 270/443 | 444 | 623/628 | 647/661 |
| 31 | 55/399 | 55/192 | 193/399 | 400 | 654/659 | 680/694 |
| 32 | 90/287 | 90/146 | 147/287 | 288 | 1078/1083 | 1096/1110 |
| 33 | 49/447 | 49/111 | 112/447 | 448 | 579/584 | 602/623 |
| 34 | 199/618 | 199/408 | 409/618 | 619 | 626/631 | 643/657 |
| 35 | 271/969 | 271/366 | 367/969 | 970 | 1092/1097 | 1123/1137 |
| 36 | 192/440 | 192/278 | 279/440 | 441 | 590/595 | 622/636 |
| 37 | 59/703 | 59/181 | 182/703 | 704 | 783/788 | 804/818 |
| 38 | 139/1389 | 139/198 | 199/1389 | 1390 | 1854/1859 | 1873/1888 |
| 39 | 21/1118 | 21/89 | 90/1118 | 1119 | 1858/1863 | 1879/1894 |
| 40 | 143/592 | 143/277 | 278/592 | 593 | 1877/1882 | 1899/1913 |
| 41 | 76/999 | 76/279 | 280/999 | 1000 | 1711/1716 | 1729/1744 |
| 42 | 123/464 | 123/269 | 270/464 | 465 | 908/913 | 931/946 |
| 43 | 85/1230 | 85/129 | 130/1230 | 1231 | 1589/1594 | 1607/1622 |
| 44 | 29/664 | 29/619 | 620/664 | 665 | 657/662 | 699/715 |
| 45 | 18/878 | 18/95 | 96/878 | 879 | 1500/1505 | 1533/1549 |
| 46 | 73/1008 | 73/147 | 148/1008 | 1009 | 1286/1291 | 1312/1328 |
| 47 | 165/842 | 165/251 | 252/842 | 843 | 1474/1479 | 1500/1515 |
| 48 | 31/1248 | 31/135 | 136/1248 | 1249 | 1580/1585 | 1607/1622 |
| 49 | 131/490 | 131/301 | 302/490 | 491 | 1411/1416 | 1434/1448 |
| 50 | 61/690 | 61/168 | 169/690 | 691 | 858/863 | 879/894 |
| 51 | 501/1253 | 501/1229 | 1230/1253 | 1254 | 1392/1397 | 1432/1447 |
| 52 | 25/402 | 25/96 | 97/402 | 403 | 1500/1505 | 1525/1540 |
| 53 | 280/678 | 280/411 | 412/678 | 679 | 1606/1611 | 1628/1643 |
| 54 | 64/726 | 64/147 | 148/726 | 727 | 1279/1284 | 1300/1314 |

TABLE I-continued

| Id | FCS Location | SigPep Location | Mature Polypeptide Location | Stop Codon Location | PolyA Signal Location | PolyA Site Location |
|---|---|---|---|---|---|---|
| 55 | 42/1097 | 42/110 | 111/1097 | 1098 | 2323/2328 | 2341/2356 |
| 56 | 245/1399 | 245/796 | 797/1399 | 1400 | 1669/1674 | 1687/1701 |
| 57 | 235/441 | 235/303 | 304/441 | 442 | — | 758/772 |
| 58 | 88/411 | 88/234 | 235/411 | 412 | 938/943 | 964/987 |
| 59 | 129/452 | 129/212 | 213/452 | 453 | 1290/1295 | 1309/1324 |
| 60 | 238/612 | 238/348 | 349/612 | 613 | 1885/1890 | 1905/1918 |
| 61 | 229/735 | 229/492 | 493/735 | 736 | 816/821 | 841/852 |
| 62 | 168/413 | 168/335 | 336/413 | 414 | 684/689 | 708/726 |
| 63 | 100/852 | 100/159 | 160/852 | 853 | 998/1003 | 1019/1039 |
| 64 | 238/1152 | 238/339 | 340/1152 | 1153 | 1298/1303 | 1324/1355 |
| 65 | 187/369 | 187/312 | 313/369 | 370 | 489/494 | 558/572 |
| 66 | 121/459 | 121/165 | 166/459 | 460 | 497/502 | 521/535 |
| 67 | 34/336 | 34/123 | 124/336 | 337 | 536/541 | 556/572 |
| 68 | 119/409 | 119/388 | 389/409 | 410 | 769/774 | 789/804 |
| 69 | 232/534 | 232/306 | 307/534 | 535 | 595/600 | 615/629 |
| 70 | 140/595 | 140/442 | 443/595 | 596 | 630/635 | 655/669 |
| 71 | 32/658 | 32/289 | 290/658 | 659 | 936/941 | 959/973 |
| 72 | 14/280 | 14/76 | 77/280 | 281 | — | 776/791 |
| 73 | 93/290 | 93/149 | 150/290 | 291 | 1078/1083 | 1096/1110 |

TABLE II

| Seq Id No | Full Length Polypeptide Location | Signal Peptide Location | Mature Polypeptide Location |
|---|---|---|---|
| 74 | −26 through 299 | −26 through −1 | 1 through 299 |
| 75 | −18 through 284 | −18 through −1 | 1 through 284 |
| 76 | −15 through 234 | −15 through −1 | 1 through 234 |
| 77 | 1 through 84 | — | 1 through 84 |
| 78 | −13 through 541 | −13 through −1 | 1 through 541 |
| 79 | −48 through 51 | −48 through −1 | 1 through 51 |
| 80 | −32 through 58 | −32 through −1 | 1 through 58 |
| 81 | −46 through 69 | −46 through −1 | 1 through 69 |
| 82 | −19 through 47 | −19 through −1 | 1 through 47 |
| 83 | −21 through 112 | −21 through −1 | 1 through 112 |
| 84 | −70 through 70 | −70 through −1 | 1 through 70 |
| 85 | −32 through 201 | −32 through −1 | 1 through 201 |
| 86 | −29 through 54 | −29 through −1 | 1 through 54 |
| 87 | −41 through 174 | −41 through −1 | 1 through 174 |
| 88 | −20 through 397 | −20 through −1 | 1 through 397 |
| 89 | −23 through 343 | −23 through −1 | 1 through 343 |
| 90 | −45 through 105 | −45 through −1 | 1 through 105 |
| 91 | −68 through 240 | −68 through −1 | 1 through 240 |
| 92 | −49 through 65 | −49 through −1 | 1 through 65 |
| 93 | −15 through 367 | −15 through −1 | 1 through 367 |
| 94 | −197 through 15 | −197 through −1 | 1 through 15 |
| 95 | −26 through 261 | −26 through −1 | 1 through 261 |
| 96 | −25 through 287 | −25 through −1 | 1 through 287 |
| 97 | −29 through 197 | −29 through −1 | 1 through 197 |
| 98 | −35 through 371 | −35 through −1 | 1 through 371 |
| 99 | −57 through 63 | −57 through −1 | 1 through 63 |
| 100 | −36 through 174 | −36 through −1 | 1 through 174 |
| 101 | −243 through 8 | −243 through −1 | 1 through 8 |
| 102 | −24 through 102 | −24 through −1 | 1 through 102 |
| 103 | −44 through 89 | −44 through −1 | 1 through 89 |
| 104 | −28 through 193 | −28 through −1 | 1 through 193 |
| 105 | −23 through 329 | −23 through −1 | 1 through 329 |
| 106 | −184 through 201 | −184 through −1 | 1 through 201 |
| 107 | −23 through 46 | −23 through −1 | 1 through 46 |
| 108 | −49 through 59 | −49 through −1 | 1 through 59 |
| 109 | −28 through 80 | −28 through −1 | 1 through 80 |
| 110 | −37 through 88 | −37 through −1 | 1 through 88 |
| 111 | −88 through 81 | −88 through −1 | 1 through 81 |
| 112 | −56 through 26 | −56 through −1 | 1 through 26 |
| 113 | −20 through 231 | −20 through −1 | 1 through 231 |
| 114 | −34 through 271 | −34 through −1 | 1 through 271 |
| 115 | −42 through 19 | −42 through −1 | 1 through 19 |
| 116 | −15 through 98 | −15 through −1 | 1 through 98 |
| 117 | −30 through 71 | −30 through −1 | 1 through 71 |
| 118 | −90 through 7 | −90 through −1 | 1 through 7 |
| 119 | −25 through 76 | −25 through −1 | 1 through 76 |
| 120 | −101 through 51 | −101 through −1 | 1 through 51 |
| 121 | −86 through 123 | −86 through −1 | 1 through 123 |
| 122 | −21 through 68 | −21 through −1 | 1 through 68 |
| 123 | −19 through 47 | −19 through −1 | 1 through 47 |

TABLE III

| Id | Positions of preferred fragments |
|---|---|
| 24 | 1-126, 164-259, 420-432, 1404-1450 |
| 25 | 32-44, 4199-1556 |
| 26 | 1-19, 1011-1058 |
| 27 | 1-16, 108-159, 595-648 |
| 28 | 1-119, 486-665, 1968-2009, 2055-2104 |
| 29 | 424-435, 500-515 |
| 30 | 1-122, 242-661 |
| 31 | 1-16, 649-694 |
| 32 | 1-663, 1070-110 |
| 33 | 1-129, 541-623 |
| 34 | 1-200, 614-657 |
| 35 | 1-419, 1094-1137 |
| 36 | 1-127, 323-331, 595-636 |
| 37 | 804-818 |
| 38 | 1-47, 438-611, 1005-1133, 1846-1888 |
| 39 | 1-430, 527-1894 |
| 40 | 1-119, 1743-1792, 1866-1913 |
| 41 | 1-70, 133-1235, 1729-1744 |
| 42 | 575-615, 896-946 |
| 43 | 513-526, 950-960, 1577-1622 |
| 44 | 1-2, 210-265, 674-715 |
| 45 | 1400-1441, 1508-1549 |
| 46 | 1-4, 1284, 1328 |

TABLE IVa

| Seq Id N° | Preferred fragments |
|---|---|
| 24 | 1-58: 343-1359: 1434-1450 |
| 25 | 455-1556 |
| 26 | 553-634: 1042-1058 |
| 27 | 608-648 |
| 28 | 452-481: 620-2104 |
| 29 | 424-515 |
| 30 | 497-661 |

TABLE IVa-continued

| Seq Id N° | Preferred fragments |
|---|---|
| 31 | 529-694 |
| 32 | 639-1110 |
| 33 | 505-623 |
| 34 | 536-657 |
| 35 | 444-1137 |
| 36 | 593-636 |
| 37 | 448-818 |
| 38 | 643-1346: 1809-1888 |
| 39 | 276-1894 |
| 40 | 332-1913 |
| 41 | 392-1744 |
| 42 | 578-946 |
| 43 | 1-240: 645-1224: 1341-1622 |
| 44 | 695-715 |
| 45 | 472-706: 924-1549 |
| 46 | 495-1328 |
| 47 | 440-1193: 1494-1515 |
| 48 | 532-1024: 1065-1622 |
| 49 | 495-582: 1412-1448 |
| 50 | 427-894 |
| 51 | 500-1321: 1424-1447 |
| 52 | 487-1540 |
| 53 | 441-1272: 1330-1643 |
| 54 | 915-1314 |
| 55 | 453-2356 |
| 56 | 519-1701 |
| 57 | 550-772 |
| 58 | 340-987 |
| 59 | 467-1324 |
| 60 | 442-1918 |
| 61 | 521-852 |
| 62 | 452-726 |
| 63 | 128-143: 481-1039 |
| 64 | 492-1355 |
| 65 | 527-572 |
| 66 | 521-535 |
| 67 | 526-572 |
| 68 | 512-804 |
| 69 | 552-629 |
| 70 | 655-669 |
| 71 | 423-973 |
| 72 | 529-791 |
| 73 | 642-1110 |

TABLE IVb

| Seq Id N° | Excluded fragments |
|---|---|
| 24 | 59-342: 1360-1433 |
| 25 | 1-454 |
| 26 | 1-552: 635-1041 |
| 27 | 1-607 |
| 28 | 1-451: 482-619 |
| 29 | 1-423 |
| 30 | 1-496 |
| 31 | 1-528 |
| 32 | 1-638 |
| 33 | 1-504 |
| 34 | 1-535 |
| 35 | 1-443 |
| 36 | 1-592 |
| 37 | 1-447 |
| 38 | 1-642: 1347-1808 |
| 39 | 1-275 |
| 40 | 1-331 |
| 41 | 1-391 |
| 42 | 1-577 |
| 43 | 241-644: 1225-1340 |
| 44 | 1-694 |
| 45 | 1-471: 707-923 |
| 46 | 1-494 |
| 47 | 1-439: 1194-1493 |
| 48 | 1-531: 1025-1064 |
| 49 | 1-494: 583-1411 |
| 50 | 1-426 |
| 51 | 1-499: 1322-1423 |
| 52 | 1-486 |
| 53 | 1-440: 1273-1329 |
| 54 | 1-914 |
| 55 | 1-452 |
| 56 | 1-518 |
| 57 | 1-549 |
| 58 | 1-339 |
| 59 | 1-466 |
| 60 | 1-441 |
| 61 | 1-520 |
| 62 | 1-451 |
| 63 | 1-127: 144-480 |
| 64 | 1-491 |
| 65 | 1-526 |
| 66 | 1-520 |
| 67 | 1-525 |
| 68 | 1-511 |
| 69 | 1-551 |
| 70 | 1-654 |
| 71 | 1-422 |
| 72 | 1-528 |
| 73 | 1-641 |

TABLE V

| Internal designation | Id | Type of sequence |
|---|---|---|
| 105-016-3-0-E3-FL | 24 | DNA |
| 105-031-3-0-D6-FL | 25 | DNA |
| 105-095-1-0-D10-FL | 26 | DNA |
| 105-118-4-0-E6-FL | 27 | DNA |
| 114-025-2-0-F11-FL | 28 | DNA |
| 116-005-4-0-G11-FL | 29 | DNA |
| 116-032-2-0-F9-FL | 30 | DNA |
| 116-047-3-0-B1-FL | 31 | DNA |
| 116-048-4-0-A6-FL | 32 | DNA |
| 116-049-1-0-F2-FL | 33 | DNA |
| 116-050-2-0-A11-FL | 34 | DNA |
| 116-054-3-0-E6-FL | 35 | DNA |
| 116-054-3-0-G12-FL | 36 | DNA |
| 116-073-4-0-C8-FL | 37 | DNA |
| 117-002-3-0-G3-FL | 38 | DNA |
| 117-005-2-0-E10-FL | 39 | DNA |
| 117-005-3-0-F2-FL | 40 | DNA |
| 117-005-4-0-E5-FL | 41 | DNA |
| 117-007-2-0-B5-FL | 42 | DNA |
| 117-007-2-0-C4-FL | 43 | DNA |
| 121-004-3-0-F6-FL | 44 | DNA |
| 122-005-2-0-F11-FL | 45 | DNA |
| 122-007-3-0-D10-FL | 46 | DNA |
| 108-004-5-0-B12-FL | 47 | DNA |
| 108-004-5-0-C10-FL | 48 | DNA |
| 108-004-5-0-G10-FL | 49 | DNA |
| 108-005-5-0-D4-FL | 50 | DNA |
| 108-005-5-0-F9-FL | 51 | DNA |
| 108-006-5-0-C7-FL | 52 | DNA |
| 108-006-5-0-E1-FL | 53 | DNA |
| 108-008-5-0-C5-FL | 54 | DNA |
| 108-008-5-0-G5-FL | 55 | DNA |
| 108-011-5-0-B12-FL | 56 | DNA |
| 108-011-5-0-C7-FL | 57 | DNA |
| 108-011-5-0-G8-FL | 58 | DNA |
| 108-011-5-0-H2-FL | 59 | DNA |
| 108-013-5-0-G5-FL | 60 | DNA |
| 108-013-5-0-H9-FL | 61 | DNA |
| 108-014-5-0-A10-FL | 62 | DNA |
| 108-014-5-0-C7-FL | 63 | DNA |
| 108-014-5-0-D12-FL | 64 | DNA |
| 108-014-5-0-H8-FL | 65 | DNA |
| 108-015-5-0-E2-FL | 66 | DNA |
| 108-016-5-0-C12-FL | 67 | DNA |
| 108-016-5-0-D4-FL | 68 | DNA |

TABLE V-continued

| Internal designation | Id | Type of sequence |
|---|---|---|
| 108-019-5-0-F10-FL | 69 | DNA |
| 108-019-5-0-F5-FL | 70 | DNA |
| 108-019-5-0-H3-FL | 71 | DNA |
| 108-020-5-0-D4-FL | 72 | DNA |
| 108-020-5-0-E3-FL | 73 | DNA |
| 105-016-3-0-E3-FL | 74 | PRT |
| 105-031-3-0-D6-FL | 75 | PRT |
| 105-095-1-0-D10-FL | 76 | PRT |
| 105-118-4-0-E6-FL | 77 | PRT |
| 114-025-2-0-F11-FL | 78 | PRT |
| 116-005-4-0-G11-FL | 79 | PRT |
| 116-032-2-0-F9-FL | 80 | PRT |
| 116-047-3-0-B1-FL | 81 | PRT |
| 116-048-4-0-A6-FL | 82 | PRT |
| 116-049-1-0-F2-FL | 83 | PRT |
| 116-050-2-0-A11-FL | 84 | PRT |
| 116-054-3-0-E6-FL | 85 | PRT |
| 116-054-3-0-G12-FL | 86 | PRT |
| 116-073-4-0-C8-FL | 87 | PRT |
| 117-002-3-0-G3-FL | 88 | PRT |
| 117-005-2-0-E10-FL | 89 | PRT |
| 117-005-3-0-F2-FL | 90 | PRT |
| 117-005-4-0-E5-FL | 91 | PRT |
| 117-007-2-0-B5-FL | 92 | PRT |
| 117-007-2-0-C4-FL | 93 | PRT |
| 121-004-3-0-F6-FL | 94 | PRT |
| 122-005-2-0-F11-FL | 95 | PRT |
| 122-007-3-0-D10-FL | 96 | PRT |
| 108-004-5-0-B12-FL | 97 | PRT |
| 108-004-5-0-C10-FL | 98 | PRT |
| 108-004-5-0-G10-FL | 99 | PRT |
| 108-005-5-0-D4-FL | 100 | PRT |
| 108-005-5-0-F9-FL | 101 | PRT |
| 108-006-5-0-C7-FL | 102 | PRT |
| 108-006-5-0-E1-FL | 103 | PRT |
| 108-008-5-0-C5-FL | 104 | PRT |
| 108-008-5-0-G5-FL | 105 | PRT |
| 108-011-5-0-B12-FL | 106 | PRT |
| 108-011-5-0-C7-FL | 107 | PRT |
| 108-011-5-0-G8-FL | 108 | PRT |
| 108-011-5-0-H2-FL | 109 | PRT |
| 108-013-5-0-G5-FL | 110 | PRT |
| 108-013-5-0-H9-FL | 111 | PRT |
| 108-014-5-0-A10-FL | 112 | PRT |
| 108-014-5-0-C7-FL | 113 | PRT |
| 108-014-5-0-D12-FL | 114 | PRT |
| 108-014-5-0-H8-FL | 115 | PRT |
| 108-015-5-0-E2-FL | 116 | PRT |
| 108-016-5-0-C12-FL | 117 | PRT |
| 108-016-5-0-D4-FL | 118 | PRT |
| 108-019-5-0-F10-FL | 119 | PRT |
| 108-019-5-0-F5-FL | 120 | PRT |
| 108-019-5-0-H3-FL | 121 | PRT |
| 108-020-5-0-D4-FL | 122 | PRT |
| 108-020-5-0-E3-FL | 123 | PRT |

TABLE VI

| Seq Id No | Tissue expression |
|---|---|
| 24 | prostate: 2 |
| 25 | fetal kidney: 1 prostate: 3 |
| 27 | prostate: 1 |
| 28 | liver: 1 |
| 29 | testis: 1 |
| 30 | testis: 3 |
| 31 | testis: 1 |
| 32 | testis: 1 |
| 33 | testis: 1 |
| 34 | liver: 1 testis: 3 |
| 35 | liver: 1 testis: 3 |
| 36 | testis: 1 |
| 37 | testis: 1 |
| 38 | liver: 2 |

TABLE VI-continued

| Seq Id No | Tissue expression |
|---|---|
| 39 | liver: 3 |
| 40 | liver: 1 |
| 41 | liver: 1 |
| 42 | brain: 2 liver: 1 placenta: 6 salivary gland: 1 |
| 44 | fetal brain: 6 |
| 45 | fetal brain: 6 placenta: 2 |
| 46 | fetal brain: 9 |
| 47 | prostate: 2 |
| 48 | prostate: 3 |
| 49 | prostate: 1 |
| 50 | prostate: 1 |
| 51 | prostate: 3 |
| 52 | prostate: 3 |
| 53 | prostate: 2 |
| 54 | prostate: 1 |
| 55 | prostate: 1 |
| 56 | liver: 15 testis: 3 |
| 57 | liver: 1 testis: 8 |
| 58 | brain: 1 |
| 59 | prostate: 1 |
| 60 | liver: 15 |
| 61 | prostate: 2 |
| 62 | testis: 1 |
| 63 | testis: 3 |
| 64 | liver: 2 |
| 65 | liver: 1 testis: 2 |
| 66 | liver: 5 testis: 20 |
| 67 | brain: 4 fetal brain: 10 fetal kidney: 1 fetal livery: 1 placenta: 1 prostate: 1 |
| 68 | brain: 3 fetal brain: 4 fetal kidney: 7 prostate: 1 salivary gland: 1 testis: 2 |
| 69 | liver: 1 testis: 1 |
| 70 | fetal livery: 1 prostate: 1 salivary gland: 3 stomach/intestine: 2 testis: 1 |
| 71 | testis: 1 |
| 72 | fetal brain: 4 |
| 73 | brain: 85 |

TABLE VII

| Seq Id No | Preferential expression |
|---|---|
| 24 | Prostate |
| 25 | Prostate |
| 27 | Prostate |
| 28 | None |
| 29 | None |
| 30 | Testis |
| 31 | None |
| 32 | None |
| 33 | None |
| 34 | Testis |
| 35 | Testis |
| 36 | None |
| 37 | None |
| 38 | Liver |
| 39 | Liver |
| 40 | None |
| 41 | None |
| 42 | Placenta |
| 44 | Fetal brain |
| 45 | None |
| 46 | Fetal brain |
| 47 | Prostate |
| 48 | Prostate |
| 49 | Prostate |
| 50 | Prostate |
| 51 | Prostate |
| 52 | Prostate |
| 53 | Prostate |
| 54 | Prostate |
| 55 | Prostate |
| 56 | Liver |

TABLE VII-continued

| Seq Id No | Preferential expression |
|---|---|
| 57 | Testis |
| 58 | None |
| 59 | Prostate |
| 60 | Liver |
| 61 | Prostate |
| 62 | None |
| 63 | Testis |
| 64 | Liver |
| 65 | None |
| 66 | Testis |
| 67 | None |
| 68 | Fetal kidney |
| 69 | None |
| 70 | Salivary gland, Stomach/Intestine |
| 71 | None |
| 72 | Fetal brain |
| 73 | Brain |

TABLE VIII

| Seq Id No | Public expression |
|---|---|
| 24 | frontal lobe(2) |
| 25 | B-cell, chronic lymphotic leukemia(2), "adenocarcinoma"(2), "germinal center B cell"(2), "liver"(1), "lung"(1), "tumor"(1) |
| 27 | 2 pooled tumors (clear cell type)(5), "adenocarcinoma"(1), "anaplastic oligodendroglioma"(4), "brain"(3), "breast"(4), "breast tumor"(1), "carcinoid"(5), "cerebellum"(1), "colon"(4), "colon tumor RER+"(2), "frontal lobe"(5), "germinal center B cell"(4), "glioblastoma (pooled)"(2), "moderately-differentiated adenocarcinoma"(1), "normal prostate"(3), "ovary"(2), "parathyroid tumor"(4), "pectoral muscle (after mastectomy) "(1), "pooled germ cell tumors"(5), "senescent fibroblast"(4), "tumor"(1), "tumor, 5 pooled (see description)"(1) |
| 28 | colon(1), "neuroepithelial cells"(1) |
| 29 | 2 pooled tumors (clear cell type)(2), "anaplastic oligodendroglioma"(2), "borderline ovarian carcinoma"(1), "carcinoid"(3), "colon"(1), "epithelium (cell line)"(1), "glioblastoma (pooled)"(1), "ovarian tumor"(1), "pooled germ cell tumors"(2) |
| 30 | NONE |
| 31 | 2 pooled tumors (clear cell type)(5), "breast"(1), "carcinoid"(1), "colon tumor, RER+"(1), "kidney tumor"(1), "pooled germ cell tumors"(1) |
| 32 | NONE |
| 33 | 2 pooled tumors (clear cell type)(2) |
| 34 | NONE |
| 35 | NONE |
| 36 | 2 pooled tumors (clear cell type)(4), "breast"(1), "prostate"(1) |
| 37 | pooled germ cell tumors(1) |
| 38 | NONE |
| 39 | liver(2) |
| 40 | B-cell, chronic lymphotic leukemia(2), "brain"(1), "carcinoid"(1), "colon"(1) |
| 41 | NONE |
| 42 | anaplastic oligodendroglioma(2), "cerebellum"(1), "colon"(1), "glioblastoma (pooled)"(5), "metastatic prostate bone lesion"(1), "normal epithelium"(1), "parathyroid tumor"(1), "pooled germ cell tumors"(1), "renal cell tumor"(1), "retina"(2), "squamous cell carcinoma"(1), "squamous cell carcinoma from base of tongue"(1), "three pooled meningiomas"(1) |
| 44 | anaplastic oligodendroglioma(1), "brain"(1), "frontal lobe"(6), "total brain"(2) |
| 45 | Lung(1), "muscle"(1), "parathyroid tumor"(1), "synovial membrane"(1) |
| 46 | neuroepithelial cells(1), "total brain"(1) |
| 47 | Bone(1), "bone marrow stroma"(1), "brain"(1), "testis"(1) |
| 48 | NONE |
| 49 | parathyroid tumor(1), "retina"(1), "total brain"(2) |
| 50 | NONE |
| 51 | ovarian tumor(3), "retina"(1), "senescent fibroblast"(1) |
| 52 | normal prostate(1) |
| 53 | NONE |
| 54 | foreskin(1) |
| 55 | NONE |
| 56 | NONE |
| 57 | NONE |
| 58 | NONE |
| 59 | adenocarcinoma(1), "pectoral muscle (after mastectomy)"(1) |
| 60 | juvenile granulosa tumor(1), "liver"(1), "senescent fibroblast"(1) |
| 61 | 2 pooled tumors (clear cell type)(2), "germinal center B cell"(6) |
| 62 | NONE |
| 63 | NONE |
| 64 | NONE |
| 65 | NONE |
| 66 | NONE |
| 67 | B-cell, chronic lymphotic leukemia(1), "adenocarcinoma"(1), "anaplastic oligodendroglioma"(3), "carcinoid"(3), "frontal lobe"(2), "glioblastoma (pooled)"(4), "normal epithelium"(1), "pooled germ cell tumors"(1) |

TABLE VIII-continued

| Seq Id No | Public expression |
|---|---|
| 68 | 2 pooled tumors (clear cell type)(5), "Lung"(1), "adenocarcinoma"(4), "adipose tissue, white"(1), "adrenal adenoma"(1), "anaplastic oligodendroglioma"(2), "breast tumor"(1), "carcinoid"(1), "colon"(4), "epithelium (cell line)"(1), "liver"(1), "melanocyte"(1), "ovarian tumor"(1), "parathyroid tumor"(6), "pectoral muscle (after mastectomy)"(4), "squamous cell carcinoma"(1), "synovial membrane"(3) |
| 69 | NONE |
| 70 | 2 pooled tumors (clear cell type)(1), "anaplastic oligodendroglioma"(2), "carcinoid"(3), "colon"(4), "epithelium (cell line)"(1), "glioblastoma (pooled)"(1), "normal prostate"(2), "ovarian tumor"(2), "pooled germ cell tumors"(3), "senescent fibroblast"(2), "testis"(1) |
| 71 | NONE |
| 72 | anaplastic oligodendroglioma(2), "astrocytoma"(1), "glioblastoma (pooled)"(1), "total brain"(1) |
| 73 | NONE |

TABLE IX

| Seq Id No | Positions | Motif designation | Database |
|---|---|---|---|
| 74 | none | none | none |
| 75 | none | none | none |
| 76 | none | none | none |
| 77 | 33-79 | PHD | Pfam |
| 78 | none | none | none |
| 79 | none | none | none |
| 80 | none | none | none |
| 81 | 28-94 | pfkB | Pfam |
| 82 | none | none | none |
| 83 | none | none | none |
| 84 | none | none | none |
| 85 | none | none | none |
| 86 | none | none | none |
| 87 | 88-213 | lys | Pfam |
| 87 | 183-202 | BL00128C Alpha-lactalbumin/lysozyme C signature | BLOCKSPLUS |
| 87 | 111-120 | PR00135B LYSOZYME/ALPHA-LACTALBUMIN SUPERFAMILY SIGNATURE | BLOCKSPLUS |
| 87 | 162-180 | Alpha-lactalbumin/lysozyme C signature | PROSITE |
| 88 | 246-266 | PSAP | Pfam |
| 89 | 92-207 | NusB | Pfam |
| 89 | 4-251 | Apolipoprotein | Pfam |
| 89 | 110-263 | Nop | Pfam |
| 90 | none | none | none |
| 91 | 2-134 | mito_carr 1/2 | Pfam |
| 91 | 156-303 | mito_carr 2/2 | Pfam |
| 91 | 5-29 | BL00215A Mitochondrial energy transfer proteins | BLOCKSPLUS |
| 91 | 223-247 | BL00215A Mitochondrial energy transfer proteins | BLOCKSPLUS |
| 91 | 102-125 | BL00215A Mitochondrial energy transfer proteins | BLOCKSPLUS |
| 91 | 169-182 | BL00215B Mitochondrial energy transfer proteins | BLOCKSPLUS |
| 92 | none | none | none |
| 93 | 37-104 | cystatin 1/2 | Pfam |
| 93 | 157-254 | cystatin 2/2 | Pfam |
| 94 | 105-154 | GST | Pfam |
| 95 | 27-131 | Cyt_reductase | Pfam |
| 95 | 158-272 | oxidored_fad | Pfam |
| 95 | 256-265 | PR00406F CYTOCHROME B5 REDUCTASE SIGNATURE | BLOCKSPLUS |
| 95 | 123-138 | PR00406C CYTOCHROME B5 REDUCTASE SIGNATURE | BLOCKSPLUS |
| 95 | 256-268 | BL00559L Eukaryotic molybdopterin oxidoreductases proteins | BLOCKSPLUS |
| 95 | 163-180 | PR00406D CYTOCHROME B5 REDUCTASE SIGNATURE | BLOCKSPLUS |
| 95 | 163-179 | PR00371D FLAVOPROTEIN PYRIDINE NUCLEOTIDE CYTOCHROME REDUCTASE SIGNATURE | BLOCKSPLUS |
| 95 | 110-120 | PR00371C FLAVOPROTEIN PYRIDINE NUCLEOTIDE CYTOCHROME REDUCTASE SIGNATURE | BLOCKSPLUS |
| 96 | 7-27 | PR00953B FLAGELLAR BIOSYNTHETIC PROTEIN FLIR SIGNATURE | BLOCKSPLUS |
| 97 | none | none | none |
| 98 | none | none | none |
| 99 | none | none | none |

TABLE IX-continued

| Seq Id No | Positions | Motif designation | Database |
|---|---|---|---|
| 100 | none | none | none |
| 101 | 7-214 | Hydrolase | Pfam |
| 102 | 48-53 | Cytochrome c family heme-binding site | PROSITE |
| 102 | 24-26 | Protein kinase C phosphorylation site | PROSITE |
| 103 | none | none | none |
| 104 | none | none | none |
| 105 | 302-339 | zf-C3HC4 | Pfam |
| 106 | none | none | none |
| 107 | 17-67 | rnaseA | Pfam |
| 108 | none | none | none |
| 109 | none | none | none |
| 110 | 17-40 | A2M_N | Pfam |
| 111 | 52-66 | PR00111B ALPHA/BETA HYDROLASE FOLD SIGNATURE | BLOCKSPLUS |
| 112 | none | none | none |
| 113 | 59-61 | Cell attachment sequence | PROSITE |
| 114 | 258-298 | zf-C3HC4 | Pfam |
| 114 | 257-301 | PHD | Pfam |
| 115 | none | none | none |
| 116 | none | none | none |
| 117 | none | none | none |
| 118 | none | none | none |
| 119 | none | none | none |
| 120 | none | none | none |
| 121 | none | none | none |
| 122 | none | none | none |
| 123 | none | none | none |

TABLE X

| Seq Id No | Antigenic epitopes |
|---|---|
| 74 | 58, 86-88, 148-149, 175-177, 238-239, 319 |
| 75 | 43-45, 58, 63-64, 72-74, 202, 204-205, 207, 237-238, 298 |
| 76 | 119, 121 |
| 77 | 21, 40-43 |
| 78 | 41, 43-44, 83, 103-104, 184-185, 187-188, 210-212, 366-367, 372-373, 396-397, 421, 475-477 |
| 79 | 84, 86-87 |
| 80 | 17, 37-38, 40-41, 43-44 |
| 81 | 97-98 |
| 82 | 34 |
| 83 | 20, 26-30, 83-86, 103, 111-112, 131 |
| 84 | 9-10, 96-97 |
| 85 | 220-222, 230-231 |
| 86 | 36, 44-47, 50-51, 67-68, 81-83 |
| 87 | 44-45, 105-106, 108-109, 147-149, 173, 202-203 |
| 88 | 129-130, 178, 311-312, 333-335, 368-369 |
| 89 | 34, 36-37, 319-320, 331-333 |
| 90 | 60 |
| 91 | 31-32, 157-158, 180, 215-216, 250 |
| 92 | 60-61 |
| 93 | 35, 37-38, 54-55, 57-58, 75-76, 160-161, 183-184, 215-216, 230, 291-292, 296, 302, 309 |
| 94 | 5, 9, 11, 99, 184 |
| 95 | 61-62, 87-88, 109-110, 147-148, 216-217, 229-231, 252, 273 |
| 96 | 83, 89, 249-250 |
| 97 | 34-35, 209-211 |
| 98 | 104-106, 199-200, 228-229, 245-246, 292, 326-327, 342-343 |
| 99 | 25-28, 105-106, 108-109 |
| 100 | 59-60, 97-98, 101-102, 106-107, 159-160, 193-194, 207-208 |
| 101 | 61 |
| 102 | 56-57, 61-63, 83-84 |
| 103 | 47-48, 77-80, 100, 107 |
| 104 | 92-93 |
| 105 | 3-5, 59, 112-113, 213-214 |
| 106 | 31-32, 66, 108-109, 148-149, 165-167, 170-172, 290-291, 339-340 |
| 107 | 32-34, 37-38, 57 |
| 108 | 6-7, 9, 11-12, 56-57 |
| 109 | 47-49, 91-92 |
| 110 | 38-39, 74, 92-93, 108-109, 116 |
| 111 | 17, 96 |
| 112 | 41-43 |
| 113 | 34-34, 84-85 |
| 114 | 83-84, 135-136, 264-265 |
| 115 | 19-23, 41 |
| 116 | 44-44, 109-109 |
| 117 | 4-5, 7-8, 55-56, 94-95 |
| 118 | 31-32, 38-40, 59-60 |
| 119 | 54-55, 59 |
| 120 | 137-137, 139-140 |
| 121 | 56, 86 |
| 122 | 4-5, 58-58, 67-68, 70-72, 74-77, 82-83 |
| 123 | 34 |

TABLE XI

| Seq Id No | Chromosomal location |
|---|---|
| 24 | none |
| 25 | 9 |
| 26 | 20 |
| 27 | 17 |
| 28 | 8 |
| 29 | 16 |
| 30 | 1 |
| 31 | none |
| 32 | none |
| 33 | none |
| 34 | none |
| 35 | none |
| 36 | none |
| 37 | 17 |
| 38 | 12q |
| 39 | 11 |

TABLE XI-continued

| Seq Id No | Chromosomal location |
|---|---|
| 40 | 18 |
| 41 | 14 |
| 42 | 6p23-25.1 |
| 43 | none |
| 44 | 20q12 |
| 45 | none |
| 46 | 3 |
| 47 | none |
| 48 | 1 |
| 49 | 20 |
| 50 | none |
| 51 | 9 |
| 52 | 11q24 |
| 53 | 17 |
| 54 | none |
| 55 | 1 |
| 56 | 3 |
| 57 | 14 |
| 58 | 16 |
| 59 | 11 |
| 60 | 10 |
| 61 | none |
| 62 | none |
| 63 | 19 |
| 64 | none |
| 65 | 6 |
| 66 | X |
| 67 | 6p12.3-21.2 |
| 68 | 5 |
| 69 | none |
| 70 | 16 |
| 71 | 9 |
| 72 | 20 |
| 73 | none |

FREE TEXT

Von Heijne matrix
Score
oligonucleotide used as a primer
matinspector prediction
name
complement

What is claimed is:

1. A purified and isolated polypeptide comprising SEQ ID NO: 74.

2. The polypeptide of claim 1, wherein said polypeptide comprises amino acids 1-299 of SEQ ID NO: 74.

3. The polypeptide of claim 1, wherein said polypeptide inhibits cell proliferation.

4. The polypeptide of claim 2, wherein said polypeptide inhibits cell proliferation.

5. A purified and isolated polypeptide having an amino acid sequence at least 90% identical to:
   a) the polypeptide comprising SEQ ID NO: 74; or
   b) the polypeptide comprising amino acids 1-299 of SEQ ID NO: 74.

6. The polypeptide of claim 5, wherein said polypeptide inhibits cell proliferation.

7. The polypeptide of claim 5, wherein said polypeptide is at least 90% identical to the polypeptide comprising SEQ ID NO: 74.

8. The polypeptide of claim 5, wherein said polypeptide is at least 90% identical to the polypeptide comprising amino acids 1-299 of SEQ ID NO: 74.

9. The polypeptide of claim 6, wherein said polypeptide is at least 90% identical to the polypeptide comprising SEQ ID NO: 74.

10. The polypeptide of claim 6, wherein said polypeptide is at least 90% identical to the polypeptide comprising amino acids 1-299 of SEQ ID NO: 74.

* * * * *

SEQUENCE LISTING

```
<160> NUMBER OF SEQ ID NOS: 123

<210> SEQ ID NO 1
<211> LENGTH: 1447
<212> TYPE: DNA
<213> ORGANISM: Homo sapiens
<220> FEATURE:
<221> NAME/KEY: CDS
<222> LOCATION: 501..1253
<220> FEATURE:
<221> NAME/KEY: sig_peptide
<222> LOCATION: 501..1229
<223> OTHER INFORMATION: Von Heijne matrix
      score 4.1
      seq LPSLAHLLPALDC/LE
<220> FEATURE:
<221> NAME/KEY: polyA_signal
<222> LOCATION: 1392..1397
<220> FEATURE:
<221> NAME/KEY: polyA_site
<222> LOCATION: 1432..1447
<220> FEATURE:
<221> NAME/KEY: misc_feature
<222> LOCATION: 243,252,278,285,387,1429
<223> OTHER INFORMATION: n=a, g, c or t

<400> SEQUENCE: 1
gtgagtcagg tgggtcctgg gcccaggaac cggcccggag ccgtggacgc cctacagctg      60 agaagggac ccaaggggtc ggccgcggcc aaggccccta ggaccgccgc cccagctcac     120
gctgccgacg gcagctatag acattctgcg tcaggtccgg gctcctggac tttgccttc      180 ccgagccctg gaggtgggga gaaaaggttc accaattttt aaaatccaaa tatatctcat     240
ggntacagtg gnaagaactg gccagagagt ctggaagntt tgggnttctg gtcctggctg     300
tgccactgac tcactgtgac cttgggatct tgtgctgtga agacatttcc caagtgcttc     360
atgttagcca gcaaatctga cccacanggc ctggaaagag gtgattgtta ggttgcgcag     420
aggtggtctt atccagctca gcttcccctg ggacccaccg tgggacctga ggcagaactg     480
```

-continued

```
gggtggactt ggcctcctcc atg gca cac cgg ctg cag ata cga ctg ctg acg        533
                     Met Ala His Arg Leu Gln Ile Arg Leu Leu Thr
                         -240                    -235 tgg gat gtg aag gac acg ctg ctc agg ctc cgc cac ccc tta ggg gag           581
Trp Asp Val Lys Asp Thr Leu Leu Arg Leu Arg His Pro Leu Gly Glu
        -230                -225                -220 gcc tat gcc acc aag gcc cgg gcc cat ggg ctg gag gtg gag ccc tca           629
Ala Tyr Ala Thr Lys Ala Arg Ala His Gly Leu Glu Val Glu Pro Ser
    -215                -210                -205 gcc ctg gaa caa ggc ttc agg cag gca tac agg gct cag agc cac agc           677
Ala Leu Glu Gln Gly Phe Arg Gln Ala Tyr Arg Ala Gln Ser His Ser
-200                -195                -190                -185 ttc ccc aac tac ggc ctg agc cac ggc cta acc tcc cgc cag tgg tgg           725
Phe Pro Asn Tyr Gly Leu Ser His Gly Leu Thr Ser Arg Gln Trp Trp
            -180                -175                -170 ctg gat gtg gtc ctg cag acc ttc cac ctg gcg ggt gtc cag gat gct           773
Leu Asp Val Val Leu Gln Thr Phe His Leu Ala Gly Val Gln Asp Ala
                -165                -160                -155 cag gct gta gcc ccc atc gct gaa cag ctt tat aaa gac ttc agc cac           821
Gln Ala Val Ala Pro Ile Ala Glu Gln Leu Tyr Lys Asp Phe Ser His
            -150                -145                -140 ccc tgc acc tgg cag gtg ttg gat ggg gct gag gac acc ctg agg gag           869
Pro Cys Thr Trp Gln Val Leu Asp Gly Ala Glu Asp Thr Leu Arg Glu
        -135                -130                -125 tgc cgc aca cgg ggt ctg aga ctg gca gtg atc tcc aac ttt gac cga           917
Cys Arg Thr Arg Gly Leu Arg Leu Ala Val Ile Ser Asn Phe Asp Arg
-120                -115                -110                -105 cgg cta gag ggc atc ctg gag ggc ctt ggc ctg cgt gaa cac ttc gac           965
Arg Leu Glu Gly Ile Leu Glu Gly Leu Gly Leu Arg Glu His Phe Asp
            -100                 -95                 -90 ttt gtg ctg acc tcc gag gct gct ggc tgg ccc aag ccg gac ccc cgc          1013
Phe Val Leu Thr Ser Glu Ala Ala Gly Trp Pro Lys Pro Asp Pro Arg
         -85                 -80                 -75 att ttc cag gag gcc ttg cgg ctt gct cat atg gaa cca gta gtg gca          1061
Ile Phe Gln Glu Ala Leu Arg Leu Ala His Met Glu Pro Val Val Ala
     -70                 -65                 -60 gcc cat gtt ggg gat aat tac ctc tgc gat tac cag ggg cct cgg gct          1109
Ala His Val Gly Asp Asn Tyr Leu Cys Asp Tyr Gln Gly Pro Arg Ala
 -55                 -50                 -45 gtg ggc atg cac agc ttc ctg gtg gtt ggc cca cag gca ctg gac ccc          1157
Val Gly Met His Ser Phe Leu Val Val Gly Pro Gln Ala Leu Asp Pro
-40                 -35                 -30                 -25 gtg gtc agg gat tct gta cct aaa gaa cac atc ctc ccc tct ctg gcc          1205
Val Val Arg Asp Ser Val Pro Lys Glu His Ile Leu Pro Ser Leu Ala
            -20                 -15                 -10 cat ctc ctg cct gcc ctt gac tgc cta gag ggc tca act cca ggg ctt          1253
His Leu Leu Pro Ala Leu Asp Cys Leu Glu Gly Ser Thr Pro Gly Leu
         -5                   1                   5 tgaggccagt gagggaagtg gctgggccct aggccatgga gaaaccctta aacaaaccct        1313
ggagacaggg agccccttct ttctccacag ctctggacct ttccccctct cctgcggcc        1373 tttgtcacct actgtgataa taaagcagtg agtgctgagc tctcacccntt ccccncccaa       1433 aaaaaaaaaa aaaa                                                          1447
```

<210> SEQ ID NO 2
<211> LENGTH: 251
<212> TYPE: PRT
<213> ORGANISM: Homo sapiens
<220> FEATURE:
<221> NAME/KEY: SIGNAL

<222> LOCATION: -243..-1

<400> SEQUENCE: 2

Met Ala His Arg Leu Gln Ile Arg Leu Leu Thr Trp Asp Val Lys Asp
         -240                -235                -230
Thr Leu Leu Arg Leu Arg His Pro Leu Gly Glu Ala Tyr Ala Thr Lys
         -225                -220                -215
Ala Arg Ala His Gly Leu Glu Val Glu Pro Ser Ala Leu Glu Gln Gly
    -210                -205                -200
Phe Arg Gln Ala Tyr Arg Ala Gln Ser His Ser Phe Pro Asn Tyr Gly
-195                -190                -185                -180
Leu Ser His Gly Leu Thr Ser Arg Gln Trp Trp Leu Asp Val Val Leu
             -175                -170                -165
Gln Thr Phe His Leu Ala Gly Val Gln Asp Ala Gln Ala Val Ala Pro
         -160                -155                -150
Ile Ala Glu Gln Leu Tyr Lys Asp Phe Ser His Pro Cys Thr Trp Gln
         -145                -140                -135
Val Leu Asp Gly Ala Glu Asp Thr Leu Arg Glu Cys Arg Thr Arg Gly
    -130                -125                -120
Leu Arg Leu Ala Val Ile Ser Asn Phe Asp Arg Arg Leu Glu Gly Ile
-115                -110                -105                -100
Leu Glu Gly Leu Gly Leu Arg Glu His Phe Asp Phe Val Leu Thr Ser
             -95                 -90                 -85
Glu Ala Ala Gly Trp Pro Lys Pro Asp Pro Arg Ile Phe Gln Glu Ala
         -80                 -75                  -70
Leu Arg Leu Ala His Met Glu Pro Val Val Ala Ala His Val Gly Asp
         -65                 -60                  -55
Asn Tyr Leu Cys Asp Tyr Gln Gly Pro Arg Ala Val Gly Met His Ser
    -50                 -45                  -40
Phe Leu Val Val Gly Pro Gln Ala Leu Asp Pro Val Val Arg Asp Ser
-35                 -30                  -25                  -20
Val Pro Lys Glu His Ile Leu Pro Ser Leu Ala His Leu Leu Pro Ala
             -15                 -10                  -5
Leu Asp Cys Leu Glu Gly Ser Thr Pro Gly Leu
         1                   5

<210> SEQ ID NO 3
<211> LENGTH: 1448
<212> TYPE: DNA
<213> ORGANISM: Homo sapiens
<220> FEATURE:
<221> NAME/KEY: CDS
<222> LOCATION: 131..490
<220> FEATURE:
<221> NAME/KEY: sig_peptide
<222> LOCATION: 131..301
<223> OTHER INFORMATION: Von Heijne matrix
      score 5.31
      seq AIALATVLFLIGA/FL
<220> FEATURE:
<221> NAME/KEY: polyA_signal
<222> LOCATION: 1411..1416
<220> FEATURE:
<221> NAME/KEY: polyA_site
<222> LOCATION: 1434..1448

<400> SEQUENCE: 3
ctgatcccgc ctggggccgg ctgagtggca cttaagcggg ccatgccatg caaccttggg      60
cgctgccaac cgtgggcgag ctctgggtgt gcgggcggcc tcgcgcggcg ctccgctgtg     120

-continued

| | |
|---|---|
| tcagcgtgtt atg atg ccg tcc cgt acc aac ctg gct act gga atc ccc<br>     Met Met Pro Ser Arg Thr Asn Leu Ala Thr Gly Ile Pro<br>         -55       -50       -45 | 169 |
| agt agt aaa gtg aaa tat tca agg ctc tcc agc aca gac gat ggc tac<br>Ser Ser Lys Val Lys Tyr Ser Arg Leu Ser Ser Thr Asp Asp Gly Tyr<br>    -40       -35       -30 | 217 |
| att gac ctt cag ttt aag aaa acc cct cct aag atc cct tat aag gcc<br>Ile Asp Leu Gln Phe Lys Lys Thr Pro Pro Lys Ile Pro Tyr Lys Ala<br>    -25       -20       -15 | 265 |
| atc gca ctt gcc act gtg ctg ttt ttg att ggc gcc ttt ctc att att<br>Ile Ala Leu Ala Thr Val Leu Phe Leu Ile Gly Ala Phe Leu Ile Ile<br>    -10       -5        1 | 313 |
| ata ggc tcc ctc ctg ctg tca ggc tac atc agc aaa ggg ggg gca gac<br>Ile Gly Ser Leu Leu Leu Ser Gly Tyr Ile Ser Lys Gly Gly Ala Asp<br>5       10       15       20 | 361 |
| cgg gcc gtt cca gtg ctg atc att ggc att ctg gtg ttc cta ccc gga<br>Arg Ala Val Pro Val Leu Ile Ile Gly Ile Leu Val Phe Leu Pro Gly<br>    25       30       35 | 409 |
| ttt tac cac ctg cgc atc gct tac tat gca tcc aaa ggc tac cgt ggt<br>Phe Tyr His Leu Arg Ile Ala Tyr Tyr Ala Ser Lys Gly Tyr Arg Gly<br>    40       45       50 | 457 |
| tac tcc tat gat gac att cca gac ttt gat gac tagcacccac cccatagctg<br>Tyr Ser Tyr Asp Asp Ile Pro Asp Phe Asp Asp<br>    55       60 | 510 |
| aggaggagtc acagtggaac tgtcccagct ttaagatatc tagcagaaac tatagctgag | 570 |
| gactaaggaa ttctgcagct tgcagatgtt taagaaaata atggccagat tttttgggtc | 630 |
| cttcccaaag atgttaagtg aacctacagt tagctaatta ggacaagctc tattttcat | 690 |
| ccctgggccc tgacaagttt ttccacagga atatgtatca tggaagaata gaggttattc | 750 |
| tgtaatggaa aagtgttgcc tgccaccacc ctctgtagag ctgagcattt cttttaaata | 810 |
| gtcttcattg ccaatttgtt cttgtagcaa atggaacaat gtggtatggc taatttctta | 870 |
| ttattaagta atttatttta aaaatatctg agtatattat cctgtacact tatccctacc | 930 |
| ttcatgttcc agtggaagac cttagtaaaa tcaaagatca gtgagttcat ctgtaatatt | 990 |
| tttttactt gctttcttac tgacagcaac caggaatttt tttatcctgc agagcaagtt | 1050 |
| ttcaaaatgt aaatacttcc tctgtttaac agtccttgga ccattctgat ccagttcacc | 1110 |
| agtaggttgg acagcatata atttgcatca ttttgtccct tgtaaatcaa gatgttctgc | 1170 |
| agattattcc tttaacggcc ggacttttgg ctgtttccta atgaaacatg tagtggttat | 1230 |
| tatttagagt ttatagccgt attgctagca ccttgtagta tgtcatcatt ctgctcatga | 1290 |
| ttccaaggat cagcctggat gcctagagga ctagatcacc ttagtttgat tctattttt | 1350 |
| agcttgcaaa aagtgactta tattccaaag aaattaaaat gttgaaatcc aaatcctaga | 1410 |
| aataaaatga gttaacttca acaaaaaaa aaaaaaaa | 1448 |

<210> SEQ ID NO 4
<211> LENGTH: 120
<212> TYPE: PRT
<213> ORGANISM: Homo sapiens
<220> FEATURE:
<221> NAME/KEY: SIGNAL
<222> LOCATION: -57...-1

<400> SEQUENCE: 4

Met Met Pro Ser Arg Thr Asn Leu Ala Thr Gly Ile Pro Ser Ser Lys
    -55       -50       -45

Val Lys Tyr Ser Arg Leu Ser Ser Thr Asp Asp Gly Tyr Ile Asp Leu

-continued

```
                    -40                 -35                 -30
Gln Phe Lys Lys Thr Pro Pro Lys Ile Pro Tyr Lys Ala Ile Ala Leu
-25                 -20                 -15                 -10

Ala Thr Val Leu Phe Leu Ile Gly Ala Phe Leu Ile Ile Ile Gly Ser
                -5                   1                   5

Leu Leu Leu Ser Gly Tyr Ile Ser Lys Gly Gly Ala Asp Arg Ala Val
             10                  15                  20

Pro Val Leu Ile Ile Gly Ile Leu Val Phe Leu Pro Gly Phe Tyr His
         25                  30                  35

Leu Arg Ile Ala Tyr Tyr Ala Ser Lys Gly Tyr Arg Gly Tyr Ser Tyr
40                  45                  50                  55

Asp Asp Ile Pro Asp Phe Asp Asp
                60

<210> SEQ ID NO 5
<211> LENGTH: 1515
<212> TYPE: DNA
<213> ORGANISM: Homo sapiens
<220> FEATURE:
<221> NAME/KEY: CDS
<222> LOCATION: 165..842
<220> FEATURE:
<221> NAME/KEY: sig_peptide
<222> LOCATION: 165..251
<223> OTHER INFORMATION: Von Heijne matrix
      score 7.01
      seq LASFAALVLVCRQ/RY
<220> FEATURE:
<221> NAME/KEY: polyA_signal
<222> LOCATION: 1474..1479
<220> FEATURE:
<221> NAME/KEY: polyA_site
<222> LOCATION: 1500..1515

<400> SEQUENCE: 5
agtcgcggga tgcgcccggg agccacagcc tgaggccctc aggtctctgc aggtgtcgtg      60
gaggaaccta gcacctgcca tcctcttccc caatttgcca cttccagcag ctttagccca     120
tgaggaggat gtgaccggga ctgagtcagg agccctctgg aagc atg gag act gtg     176
                                               Met Glu Thr Val gtg att gtt gcc ata ggt gtg ctg gcc acc atc ttt ctg gct tcg ttt      224
Val Ile Val Ala Ile Gly Val Leu Ala Thr Ile Phe Leu Ala Ser Phe
-25                 -20                 -15                 -10 gca gcc ttg gtg ctg gtt tgc agg cag cgc tac tgc cgg ccg cga gac      272
Ala Ala Leu Val Leu Val Cys Arg Gln Arg Tyr Cys Arg Pro Arg Asp
                -5                   1                   5 ctg ctg cag cgc tat gat tct aag ccc att gtg gac ctc att ggt gcc      320
Leu Leu Gln Arg Tyr Asp Ser Lys Pro Ile Val Asp Leu Ile Gly Ala
             10                  15                  20 atg gag acc cag tct gag ccc tct gag tta gaa ctg gac gat gtc gtt      368
Met Glu Thr Gln Ser Glu Pro Ser Glu Leu Glu Leu Asp Asp Val Val
         25                  30                  35 atc acc aac ccc cac att gag gcc att ctg gag aat gaa gac tgg atc      416
Ile Thr Asn Pro His Ile Glu Ala Ile Leu Glu Asn Glu Asp Trp Ile
40                  45                  50                  55 gaa gat gcc tcg ggt ctc atg tcc cac tgc att gcc atc ttg aag att      464
Glu Asp Ala Ser Gly Leu Met Ser His Cys Ile Ala Ile Leu Lys Ile
                 60                  65                  70 tgt cac act ctg aca gag aag ctt gtt gcc atg aca atg ggc tct ggg      512
Cys His Thr Leu Thr Glu Lys Leu Val Ala Met Thr Met Gly Ser Gly
             75                  80                  85 gcc aag atg aag act tca gcc agt gtc agc gac atc att gtg gtg gcc      560
```

-continued

```
Ala Lys Met Lys Thr Ser Ala Ser Val Ser Asp Ile Ile Val Ala
         90                  95                 100 aag cgg atc agc ccc agg gtg gat gat gtt gtg aag tcg atg tac cct    608
Lys Arg Ile Ser Pro Arg Val Asp Asp Val Val Lys Ser Met Tyr Pro
         105                 110                 115 ccg ttg gac ccc aaa ctc ctg gac gca cgg acg act gcc ctc ctg        656
Pro Leu Asp Pro Lys Leu Leu Asp Ala Arg Thr Thr Ala Leu Leu Leu
120                 125                 130                 135 tct gtc agt cac ctg gtg ctg gtg aca agg aat gcc tgc cat ctg acg    704
Ser Val Ser His Leu Val Leu Val Thr Arg Asn Ala Cys His Leu Thr
                140                 145                 150 gga ggc ctg gac tgg att gac cag tct ctg tcg gct gct gag gag cat    752
Gly Gly Leu Asp Trp Ile Asp Gln Ser Leu Ser Ala Ala Glu Glu His
                155                 160                 165 ttg gaa gtc ctt cga gaa gca gcc cta gct tct gag cca gat aaa ggc    800
Leu Glu Val Leu Arg Glu Ala Ala Leu Ala Ser Glu Pro Asp Lys Gly
         170                 175                 180 ctc cca ggc cct gaa ggc ttc ctg cag gag cag tct gca att            842
Leu Pro Gly Pro Glu Gly Phe Leu Gln Glu Gln Ser Ala Ile
185                 190                 195 tagtgcctac aggccagcag ctagccatga aggcccctgc cgccatccct ggatggctca   902
gcttagcctt ctactttttc ctatagagtt agttgttctc cacggctgga gagttcagct   962
gtgtgtgcat agtaaagcag gagatccccg tcagtttatg cctcttttgc agttgcaaac  1022
tgtggctggt gagtggcagt ctaatactac agttagggga gatgccattc actctctgca  1082
agaggagtat tgaaaactgg tggactgtca gctttattta gctcacctag tgttttcaag  1142
aaaattgagc caccgtctaa gaaatcaaga ggtttcacat taaaattaga atttctggcc  1202
tctctcgatc ggtcagaatg tgtggcaatt ctgatctgca ttttcagaag aggacaatca  1262
attgaaacta gtaggggtt tcttcttttg gcaagacttg tactctctca cctggcctgt   1322
ttcatttatt tgtattatct gcctggtccc tgaggcgtct gggtctctcc tctcccttgc  1382
aggtttgggt ttgaagctga ggaactacaa agttgatgat ttctttttta tctttatgcc  1442 tgcaattttta cctagctacc actaggtgga tagtaaattt atacttatgt ttcccccaaa  1502
aaaaaaaaaa aaa                                                     1515

<210> SEQ ID NO 6
<211> LENGTH: 226
<212> TYPE: PRT
<213> ORGANISM: Homo sapiens
<220> FEATURE:
<221> NAME/KEY: SIGNAL
<222> LOCATION: -29..-1

<400> SEQUENCE: 6

Met Glu Thr Val Val Ile Val Ala Ile Gly Val Leu Ala Thr Ile Phe
              -25                 -20                 -15

Leu Ala Ser Phe Ala Ala Leu Val Leu Val Cys Arg Gln Arg Tyr Cys
         -10                  -5                  1

Arg Pro Arg Asp Leu Leu Gln Arg Tyr Asp Ser Lys Pro Ile Val Asp
  5                  10                  15

Leu Ile Gly Ala Met Glu Thr Gln Ser Glu Pro Ser Glu Leu Glu Leu
20                  25                  30                  35

Asp Asp Val Val Ile Thr Asn Pro His Ile Glu Ala Ile Leu Glu Asn
                 40                  45                  50

Glu Asp Trp Ile Glu Asp Ala Ser Gly Leu Met Ser His Cys Ile Ala
         55                  60                  65
```

```
Ile Leu Lys Ile Cys His Thr Leu Thr Glu Lys Leu Val Ala Met Thr
            70                  75                  80

Met Gly Ser Gly Ala Lys Met Lys Thr Ser Ala Ser Val Ser Asp Ile
        85                  90                  95

Ile Val Val Ala Lys Arg Ile Ser Pro Arg Val Asp Asp Val Val Lys
100                 105                 110                 115

Ser Met Tyr Pro Pro Leu Asp Pro Lys Leu Leu Asp Ala Arg Thr Thr
                120                 125                 130

Ala Leu Leu Leu Ser Val Ser His Leu Val Leu Val Thr Arg Asn Ala
            135                 140                 145

Cys His Leu Thr Gly Gly Leu Asp Trp Ile Asp Gln Ser Leu Ser Ala
        150                 155                 160

Ala Glu Glu His Leu Glu Val Leu Arg Glu Ala Ala Leu Ala Ser Glu
    165                 170                 175

Pro Asp Lys Gly Leu Pro Gly Pro Glu Gly Phe Leu Gln Glu Gln Ser
180                 185                 190                 195

Ala Ile
```

<210> SEQ ID NO 7
<211> LENGTH: 1918
<212> TYPE: DNA
<213> ORGANISM: Homo sapiens
<220> FEATURE:
<221> NAME/KEY: CDS
<222> LOCATION: 238..612
<220> FEATURE:
<221> NAME/KEY: sig_peptide
<222> LOCATION: 238..348
<223> OTHER INFORMATION: Von Heijne matrix
      score 9.4
      seq LLCCVLSASQLSS/QD
<220> FEATURE:
<221> NAME/KEY: polyA_signal
<222> LOCATION: 1885..1890
<220> FEATURE:
<221> NAME/KEY: polyA_site
<222> LOCATION: 1905..1918
<220> FEATURE:
<221> NAME/KEY: misc_feature
<222> LOCATION: 945,1624
<223> OTHER INFORMATION: n=a, g, c or t

<400> SEQUENCE: 7

```
aaaaatctaa gcgacttcga tgccaaggaa gttgtgtaaa tgtgcacgcg ctacaccaca    60
cccagggtgg aaaccacagt tgcagagtca ttaaacaatc aattgtttgt ttaacatctg   120
tgataggcag cttttccttct tttcaacagt gataccctacg aaaatcaaaa taaatgcaag   180
ctgaggtttt tgctcactg aaagggctgt caaccccaga aggccgacac aaaaaaa       237 atg gta tgt gaa gat gca ccg tct ttt caa atg gcc tgg gag agt caa    285
Met Val Cys Glu Asp Ala Pro Ser Phe Gln Met Ala Trp Glu Ser Gln
        -35                 -30                 -25 atg gcc tgg gag agg ggg cct gcc ctt ctc tgc tgt gtc ctt tcg gct    333
Met Ala Trp Glu Arg Gly Pro Ala Leu Leu Cys Cys Val Leu Ser Ala
    -20                 -15                 -10 tcc cag ttg agc tcc caa gac cag gac cca ctg ggg cat ata aaa tct    381
Ser Gln Leu Ser Ser Gln Asp Gln Asp Pro Leu Gly His Ile Lys Ser
-5                   1                   5                  10 ctg ctg tat cct ttc ggc ttc cca gtt gag ctc cca aga cca gga ccc    429
Leu Leu Tyr Pro Phe Gly Phe Pro Val Glu Leu Pro Arg Pro Gly Pro
                15                  20                  25 act ggg gca tat aaa aaa gtc aaa aat caa aat caa aca aca agt tct    477
```

```
            Thr Gly Ala Tyr Lys Lys Val Lys Asn Gln Asn Gln Thr Thr Ser Ser
                    30                  35                  40 gag tta ctt agg aaa cag act tcg cat ttc aat cag aga ggc cac aga        525
Glu Leu Leu Arg Lys Gln Thr Ser His Phe Asn Gln Arg Gly His Arg
 45                  50                  55 gca agg tct aaa ctt ctg gct tct aga caa att cct gat aga aca ttt        573
Ala Arg Ser Lys Leu Leu Ala Ser Arg Gln Ile Pro Asp Arg Thr Phe
 60                  65                  70                  75 aaa tgt ggg aag tgg ctt ccc cag gtc cca tcc cct gtt tagggataga         622
Lys Cys Gly Lys Trp Leu Pro Gln Val Pro Ser Pro Val
                 80                  85 gttgatatca ttttatagt tgccatgtat gcctctgcct gaatttttt aattgacttt       682 tgagcttttg agattgcacg agggagaaca aggcctttgc tgttgtggat aggaaagact      742
taacctaaaa ttaaaccagc aagaaagcat tagtaaaaat ctaacaatat gaagggctct     802
tatgagtcat ttttttcaaa agatgaaaac tccagaaacg cacaggaacg aaatacctcc     862
cagaaacatg aagcaatcat cgaagactca ctggtaatat ttttaaaaag tatacagatc     922
aaagcaaaaa gaagccatgt gtnaacaaag agaaatgtgc aaatattttt taaggcagta     982
ttaagtgcaa gaggagtaac atgaaataaa cattctttca catggctact gggaatataa    1042
atttcgctcc agaaaggccg tagcagtttg acgataggtg gcaaaacctt aagattgtgt    1102 actgggccc agaattttta tttctaggaa tgtatcctga ggaaattatc cgagatcccc     1162
acaaactgca atgtttagga attgtcctta tagcattgca tacacaagaa aaacagagaa    1222
aagcctgatc cctgtcagtg aaaaggggt tcaatgaatt acggtgtgtc tgcatgaggc     1282
ttttatgaca ttaaaaattg ttgaacaacg gccaggcaca gtggctcatg cctgtaatcc    1342
taacactttg ggaggccaag gtgggaagat tgcctgagct caggagtttg agaccagcct    1402
gggcaacacg gtgaaacccc gtctctacta aaatacaaaa aattagccgg gcgtcgcagc    1462
atgcgcctgt agtcccagct gctcaggagg ctgaggcagg agaattgatt gaacccggga    1522
ggcagaggtt gcactgagct gagattaagc caccgcactc cagcctgggc gacagagcaa    1582
gattccgttc ccaagaaaaa aaattgttc aacaataagg gncaaaggga gagaatcata    1642
acatctgatt aaacagaaaa agcaagattt ttaaaactaa ctatataagg atggtcccag    1702
ctgtgtcaaa aggaagcttg tttgtaatac gtgtgcataa aaattaaata gaggtgaaca    1762
caattatttt aaggcagtta aattatctct gtattgtgaa ctaagacttt ctagaatttt    1822
acttattcat tctgtactta aatttttct aatgaacaca tatacttttg taatcagaaa    1882
atattaaatg catgtatttt tcaaaaaaaa aaaaaa                             1918
```

<210> SEQ ID NO 8
<211> LENGTH: 125
<212> TYPE: PRT
<213> ORGANISM: Homo sapiens
<220> FEATURE:
<221> NAME/KEY: SIGNAL
<222> LOCATION: -37..-1

<400> SEQUENCE: 8

```
Met Val Cys Glu Asp Ala Pro Ser Phe Gln Met Ala Trp Glu Ser Gln
        -35                 -30                 -25

Met Ala Trp Glu Arg Gly Pro Ala Leu Leu Cys Cys Val Leu Ser Ala
        -20                 -15                 -10

Ser Gln Leu Ser Ser Gln Asp Gln Asp Pro Leu Gly His Ile Lys Ser
 -5                   1                   5                  10
```

```
                Leu Leu Tyr Pro Phe Gly Phe Pro Val Glu Leu Pro Arg Pro Gly Pro
                            15                  20                  25

Thr Gly Ala Tyr Lys Lys Val Lys Asn Gln Asn Gln Thr Thr Ser Ser
                        30                  35                  40

Glu Leu Leu Arg Lys Gln Thr Ser His Phe Asn Gln Arg Gly His Arg
                    45                  50                  55

Ala Arg Ser Lys Leu Leu Ala Ser Arg Gln Ile Pro Asp Arg Thr Phe
                60                  65                  70                  75

Lys Cys Gly Lys Trp Leu Pro Gln Val Pro Ser Pro Val
                                80                  85

<210> SEQ ID NO 9
<211> LENGTH: 852
<212> TYPE: DNA
<213> ORGANISM: Homo sapiens
<220> FEATURE:
<221> NAME/KEY: CDS
<222> LOCATION: 229..735
<220> FEATURE:
<221> NAME/KEY: sig_peptide
<222> LOCATION: 229..492
<223> OTHER INFORMATION: Von Heijne matrix
      score 6.7
      seq VFALSSFLNKASA/VY
<220> FEATURE:
<221> NAME/KEY: polyA_signal
<222> LOCATION: 816..821
<220> FEATURE:
<221> NAME/KEY: polyA_site
<222> LOCATION: 841..852

<400> SEQUENCE: 9
aatgactggc agtggcatca gcgatggcgg ctgcgtcggg gtcggttctg cagcgctgta      60
tcgtgtcgcc ggcagggagg catagcgcct ctctgatctt cctgcatggc tcaggtgatt     120
ctggacaagg attaagaatg tggatcaagc aggtttttaa atcaagattt aacattccaa     180
cacataaaaa ttatttatcc aacagctcct cccagatcat atactcct atg aaa gga     237
                                                    Met Lys Gly gga atc tcc aat gta tgg ttt gac aga ttt aaa ata acc aat gac tgc      285
Gly Ile Ser Asn Val Trp Phe Asp Arg Phe Lys Ile Thr Asn Asp Cys
-85                 -80                 -75                 -70 cca gaa cac ctt gaa tca att gat gtc atg tgt caa gtg ctt act gat      333
Pro Glu His Leu Glu Ser Ile Asp Val Met Cys Gln Val Leu Thr Asp
                -65                 -60                 -55 ttg att gat gaa gaa gta aaa agt ggc atc aag aag aac agg ata tta      381
Leu Ile Asp Glu Glu Val Lys Ser Gly Ile Lys Lys Asn Arg Ile Leu
            -50                 -45                 -40 ata gga gga ttc tct atg gga gga tgc atg gca atg cat tta gca tat      429
Ile Gly Gly Phe Ser Met Gly Gly Cys Met Ala Met His Leu Ala Tyr
        -35                 -30                 -25 aga aat cat caa gat gtg gca gga gta ttt gct ctt tct agt ttt ctg      477
Arg Asn His Gln Asp Val Ala Gly Val Phe Ala Leu Ser Ser Phe Leu
    -20                 -15                 -10 aat aaa gca tct gct gtt tac cag gct ctt cag aag agt aat ggt gta      525
Asn Lys Ala Ser Ala Val Tyr Gln Ala Leu Gln Lys Ser Asn Gly Val
-5                   1                   5                  10 ctt cct gaa tta ttt cag tgt cat ggt act gca gat gag tta gtt ctt      573
Leu Pro Glu Leu Phe Gln Cys His Gly Thr Ala Asp Glu Leu Val Leu
                15                  20                  25 cat tct tgg gca gaa gag aca aac tca atg tta aaa tct cta gga gtg      621
His Ser Trp Ala Glu Glu Thr Asn Ser Met Leu Lys Ser Leu Gly Val
        30                  35                  40
```

-continued

```
acc acg aag ttt cat agt ttt cca aat gtt tac cat gag cta agc aaa      669
Thr Thr Lys Phe His Ser Phe Pro Asn Val Tyr His Glu Leu Ser Lys
    45              50                  55 act gag tta gac ata ttg aag tta tgg att ctt aca aag ctg cca gga      717
Thr Glu Leu Asp Ile Leu Lys Leu Trp Ile Leu Thr Lys Leu Pro Gly
60              65                  70                  75 gaa atg gaa aaa caa aaa tgaatgaatc aagagtgatt tgttaatgta             765
Glu Met Glu Lys Gln Lys
                80 agtgtaatgt ctttgtgaaa agtgattttt actgccaaat tataatgata attaaaatat    825 taagaaatag caaaaaaaaa aaaaaaa                                         852
```

```
<210> SEQ ID NO 10
<211> LENGTH: 169
<212> TYPE: PRT
<213> ORGANISM: Homo sapiens
<220> FEATURE:
<221> NAME/KEY: SIGNAL
<222> LOCATION: -88...-1

<400> SEQUENCE: 10
```

Met Lys Gly Gly Ile Ser Asn Val Trp Phe Asp Arg Phe Lys Ile Thr
            -85                 -80                 -75

Asn Asp Cys Pro Glu His Leu Glu Ser Ile Asp Val Met Cys Gln Val
        -70                 -65                 -60

Leu Thr Asp Leu Ile Asp Glu Glu Val Lys Ser Gly Ile Lys Lys Asn
    -55                 -50                 -45

Arg Ile Leu Ile Gly Gly Phe Ser Met Gly Gly Cys Met Ala Met His
-40                 -35                 -30                 -25

Leu Ala Tyr Arg Asn His Gln Asp Val Ala Gly Val Phe Ala Leu Ser
                -20                 -15                 -10

Ser Phe Leu Asn Lys Ala Ser Ala Val Tyr Gln Ala Leu Gln Lys Ser
            -5                   1                   5

Asn Gly Val Leu Pro Glu Leu Phe Gln Cys His Gly Thr Ala Asp Glu
        10                  15                  20

Leu Val Leu His Ser Trp Ala Glu Glu Thr Asn Ser Met Leu Lys Ser
25                  30                  35                  40

Leu Gly Val Thr Thr Lys Phe His Ser Phe Pro Asn Val Tyr His Glu
                45                  50                  55

Leu Ser Lys Thr Glu Leu Asp Ile Leu Lys Leu Trp Ile Leu Thr Lys
            60                  65                  70

Leu Pro Gly Glu Met Glu Lys Gln Lys
            75                  80

```
<210> SEQ ID NO 11
<211> LENGTH: 1602
<212> TYPE: DNA
<213> ORGANISM: Homo sapiens
<220> FEATURE:
<221> NAME/KEY: CDS
<222> LOCATION: 24..1004
<220> FEATURE:
<221> NAME/KEY: sig_peptide
<222> LOCATION: 24..170
<223> OTHER INFORMATION: Von Heijne matrix
      score 5.6
      seq ACLSLGFFSLLWL/QL
<220> FEATURE:
<221> NAME/KEY: polyA_site
<222> LOCATION: 1586..1602

<400> SEQUENCE: 11
```

```
atgcgccgcc gcctctccgc acg atg ttc ccc tcg cgg agg aaa gcg gcg cag      53
                         Met Phe Pro Ser Arg Arg Lys Ala Ala Gln
                                     -45                     -40 ctg ccc tgg gag gac ggc agg tcc ggg ttg ctc tcc ggc ggc ctc cct         101
Leu Pro Trp Glu Asp Gly Arg Ser Gly Leu Leu Ser Gly Gly Leu Pro
        -35                 -30                 -25 cgg aag tgt tcc gtc ttc cac ctg ttc gtg gcc tgc ctc tcg ctg ggc         149
Arg Lys Cys Ser Val Phe His Leu Phe Val Ala Cys Leu Ser Leu Gly
            -20                 -15                 -10 ttc ttc tcc cta ctc tgg ctg cag ctc agc tgc tct ggg gac gtg gcc         197
Phe Phe Ser Leu Leu Trp Leu Gln Leu Ser Cys Ser Gly Asp Val Ala
        -5                   1                   5 cgg gca gtc agg gga caa ggg cag gag acc tcg ggc cct ccc cgt gcc         245
Arg Ala Val Arg Gly Gln Gly Gln Glu Thr Ser Gly Pro Pro Arg Ala
10                  15                  20                  25 tgc ccc cca gag ccg ccc cct gag cac tgg gaa gaa gac gca tcc tgg         293
Cys Pro Pro Glu Pro Pro Pro Glu His Trp Glu Glu Asp Ala Ser Trp
            30                  35                  40 ggc ccc cac cgc ctg gca gtg ctg gtg ccc ttc cgc gaa cgc ttc gag         341
Gly Pro His Arg Leu Ala Val Leu Val Pro Phe Arg Glu Arg Phe Glu
            45                  50                  55 gag ctc ctg gtc ttc gtg ccc cac atg cgc cgc ttc ctg agc agg aag         389
Glu Leu Leu Val Phe Val Pro His Met Arg Arg Phe Leu Ser Arg Lys
            60                  65                  70 aag atc cgg cac cac atc tac gtg ctc aac cag gtg gac cac ttc agg         437
Lys Ile Arg His His Ile Tyr Val Leu Asn Gln Val Asp His Phe Arg
75                  80                  85 ttc aac cgg gca gcg ctc atc aac gtg ggc ttc ctg gag agc agc aac         485
Phe Asn Arg Ala Ala Leu Ile Asn Val Gly Phe Leu Glu Ser Ser Asn
90                  95                  100                 105 agc acg gac tac att gcc atg cac gac gtt gac ctg ctc cct ctc aac         533
Ser Thr Asp Tyr Ile Ala Met His Asp Val Asp Leu Leu Pro Leu Asn
                110                 115                 120 gag gag ctg gac tat ggc ttt cct gag gct ggg ccc ttc cac gtg gcc         581
Glu Glu Leu Asp Tyr Gly Phe Pro Glu Ala Gly Pro Phe His Val Ala
            125                 130                 135 tcc ccg gag ctc cac cct ctc tac cac tac aag acc tat gtc ggc ggc         629
Ser Pro Glu Leu His Pro Leu Tyr His Tyr Lys Thr Tyr Val Gly Gly
        140                 145                 150 atc ctg ctg ctc tcc aag cag cac tac cgg ctg tgc aat ggg atg tcc         677
Ile Leu Leu Leu Ser Lys Gln His Tyr Arg Leu Cys Asn Gly Met Ser
155                 160                 165 aac cgc ttc tgg ggc tgg ggc cgc gag gac gac gag ttc tac cgg cgc         725
Asn Arg Phe Trp Gly Trp Gly Arg Glu Asp Asp Glu Phe Tyr Arg Arg
170                 175                 180                 185 att aag gga gct ggg ctc cag ctt ttc cgc ccc tcg gga atc aca act         773
Ile Lys Gly Ala Gly Leu Gln Leu Phe Arg Pro Ser Gly Ile Thr Thr
                190                 195                 200 ggg tac aag aca ttt cgc cac ctg cat gac cca gcc tgg cgg aag agg         821
Gly Tyr Lys Thr Phe Arg His Leu His Asp Pro Ala Trp Arg Lys Arg
            205                 210                 215 gac cag aag cgc atc gca gct caa aaa cag gag cag ttc aag gtg gac         869
Asp Gln Lys Arg Ile Ala Ala Gln Lys Gln Glu Gln Phe Lys Val Asp
        220                 225                 230 agg gag gga ggc ctg aac act gtg aag tac cat gtg gct tcc cgc act         917
Arg Glu Gly Gly Leu Asn Thr Val Lys Tyr His Val Ala Ser Arg Thr
235                 240                 245 gcc ctg tct gtg ggc ggg gcc ccc tgc act gtc ctc aac atc atg ttg         965
Ala Leu Ser Val Gly Gly Ala Pro Cys Thr Val Leu Asn Ile Met Leu
```

-continued

```
                 250                 255                 260                 265
gac tgt gac aag acc gcc aca ccc tgg tgc aca ttc agc tgagctggat        1014
Asp Cys Asp Lys Thr Ala Thr Pro Trp Cys Thr Phe Ser
                270                 275 ggacagtgag gaagcctgta cctacaggcc atattgctca ggctcaggac aaggcctcag    1074
gtcgtgggcc cagctctgac aggatgtgga gtggccagga ccaagacagc aagctacgca    1134
attgcagcca cccggccgcc aaggcaggct gggctgggc caggacacgt ggggtgcctg     1194
ggacgctgct tgccatgcac agtgatcaga gagaggctgg ggtgtgtcct gtccgggacc    1254 cccccctgcct tcctgctcac cctactctga cctccttcac gtgcccaggc ctgtgggtag   1314
tggggagggc tgaacaggac aacctctcat cacccccact tttgttcctt cctgctgggc    1374
tgcctcgtgc agagacacag tgtaggggcc atgcagctgg cgtaggtggc agttgggcct    1434
ggtgagggtt aggacttcag aaaccagagc acaagcccca cagaggggga acagccagca    1494
ccgctctagc tggttgttgc catgccgaa tgtgggccta gtgttgccag atcttctgat      1554
ttttcgaaag aaactagaat gctggattct caaaaaaaaa aaaaaaaa                  1602
```

<210> SEQ ID NO 12
<211> LENGTH: 327
<212> TYPE: PRT
<213> ORGANISM: Homo sapiens
<220> FEATURE:
<221> NAME/KEY: SIGNAL
<222> LOCATION: -49..-1

<400> SEQUENCE: 12

```
Met Phe Pro Ser Arg Arg Lys Ala Ala Gln Leu Pro Trp Glu Asp Gly
              -45                 -40                 -35

Arg Ser Gly Leu Leu Ser Gly Gly Leu Pro Arg Lys Cys Ser Val Phe
          -30                 -25                 -20

His Leu Phe Val Ala Cys Leu Ser Leu Gly Phe Phe Ser Leu Leu Trp
      -15                 -10                  -5

Leu Gln Leu Ser Cys Ser Gly Asp Val Ala Arg Ala Val Arg Gly Gln
  1               5                  10                  15

Gly Gln Glu Thr Ser Gly Pro Pro Arg Ala Cys Pro Glu Pro Pro
             20                  25                  30

Pro Glu His Trp Glu Glu Asp Ala Ser Trp Gly Pro His Arg Leu Ala
             35                  40                  45

Val Leu Val Pro Phe Arg Glu Arg Phe Glu Glu Leu Leu Val Phe Val
         50                  55                  60

Pro His Met Arg Arg Phe Leu Ser Arg Lys Lys Ile Arg His His Ile
     65                  70                  75

Tyr Val Leu Asn Gln Val Asp His Phe Arg Phe Asn Arg Ala Ala Leu
 80                  85                  90                  95

Ile Asn Val Gly Phe Leu Glu Ser Ser Asn Ser Thr Asp Tyr Ile Ala
                100                 105                 110

Met His Asp Val Asp Leu Leu Pro Leu Asn Glu Glu Leu Asp Tyr Gly
            115                 120                 125

Phe Pro Glu Ala Gly Pro Phe His Val Ala Ser Pro Glu Leu His Pro
        130                 135                 140

Leu Tyr His Tyr Lys Thr Tyr Val Gly Gly Ile Leu Leu Leu Ser Lys
    145                 150                 155

Gln His Tyr Arg Leu Cys Asn Gly Met Ser Asn Arg Phe Trp Gly Trp
160                 165                 170                 175
```

```
Gly Arg Glu Asp Asp Glu Phe Tyr Arg Arg Ile Lys Gly Ala Gly Leu
            180                 185                 190

Gln Leu Phe Arg Pro Ser Gly Ile Thr Thr Gly Tyr Lys Thr Phe Arg
        195                 200                 205

His Leu His Asp Pro Ala Trp Arg Lys Arg Asp Gln Lys Arg Ile Ala
    210                 215                 220

Ala Gln Lys Gln Glu Gln Phe Lys Val Asp Arg Glu Gly Gly Leu Asn
225                 230                 235

Thr Val Lys Tyr His Val Ala Ser Arg Thr Ala Leu Ser Val Gly Gly
240                 245                 250                 255

Ala Pro Cys Thr Val Leu Asn Ile Met Leu Asp Cys Asp Lys Thr Ala
                260                 265                 270

Thr Pro Trp Cys Thr Phe Ser
            275

<210> SEQ ID NO 13
<211> LENGTH: 948
<212> TYPE: DNA
<213> ORGANISM: Homo sapiens
<220> FEATURE:
<221> NAME/KEY: CDS
<222> LOCATION: 80..784
<220> FEATURE:
<221> NAME/KEY: sig_peptide
<222> LOCATION: 80..139
<223> OTHER INFORMATION: Von Heijne matrix
      score 4
      seq LLKVVFVVFASLC/AW
<220> FEATURE:
<221> NAME/KEY: polyA_signal
<222> LOCATION: 910..915
<220> FEATURE:
<221> NAME/KEY: polyA_site
<222> LOCATION: 933..948

<400> SEQUENCE: 13
cttcctgacc cagggggctcc gctggctgcg gtcgcctggg agctgccgcc agggccagga      60
ggggagcggc acctggaag atg cgc cca ttg gct ggt ggc ctg ctc aag gtg      112
                    Met Arg Pro Leu Ala Gly Gly Leu Leu Lys Val
                    -20             -15                 -10 gtg ttc gtg gtc ttc gcc tcc ttg tgt gcc tgg tat tcg ggg tac ctg      160
Val Phe Val Val Phe Ala Ser Leu Cys Ala Trp Tyr Ser Gly Tyr Leu
            -5                  1               5 ctc gca gag ctc att cca gat gca ccc ctg tcc agt gct gcc tat agc      208
Leu Ala Glu Leu Ile Pro Asp Ala Pro Leu Ser Ser Ala Ala Tyr Ser
        10                  15                  20 atc cgc agc atc ggg gag agg cct gtc ctc aaa gct cca gtc ccc aaa      256
Ile Arg Ser Ile Gly Glu Arg Pro Val Leu Lys Ala Pro Val Pro Lys
    25                  30                  35 agg caa aaa tgt gac cac tgg act ccc tgc cca tct gac acc tat gcc      304
Arg Gln Lys Cys Asp His Trp Thr Pro Cys Pro Ser Asp Thr Tyr Ala
40                  45                  50                  55 tac agg tta ctc agc gga ggt ggc aga agc aag tac gcc aaa atc tgc      352
Tyr Arg Leu Leu Ser Gly Gly Gly Arg Ser Lys Tyr Ala Lys Ile Cys
                60                  65                  70 ttt gag gat aac cta ctt atg gga gaa cag ctg gga aat gtt gcc aga      400
Phe Glu Asp Asn Leu Leu Met Gly Glu Gln Leu Gly Asn Val Ala Arg
            75                  80                  85 gga ata aac att gcc att gtc aac tat gta act ggg aat gtg aca gca      448
Gly Ile Asn Ile Ala Ile Val Asn Tyr Val Thr Gly Asn Val Thr Ala
        90                  95                  100 aca cga tgt ttt gat atg tat gaa ggc gat aac tct gga ccg atg aca      496
```

```
                                              -continued

Thr Arg Cys Phe Asp Met Tyr Glu Gly Asp Asn Ser Gly Pro Met Thr
    105                 110                 115 aag ttt att cag agt gct gct cca aaa tcc ctg ctc ttc atg gtg acc    544
Lys Phe Ile Gln Ser Ala Ala Pro Lys Ser Leu Leu Phe Met Val Thr
120                 125                 130                 135 tat gac gac gga agc aca aga ctg aat aac gat gcc aag aat gcc ata    592
Tyr Asp Asp Gly Ser Thr Arg Leu Asn Asn Asp Ala Lys Asn Ala Ile
                140                 145                 150 gaa gca ctt gga agt aaa gaa atc agg aac atg aaa ttc agg tct agc    640
Glu Ala Leu Gly Ser Lys Glu Ile Arg Asn Met Lys Phe Arg Ser Ser
                155                 160                 165 tgg gta ttt att gca gca aaa ggc ttg gaa ctc cct tcc gaa att cag    688
Trp Val Phe Ile Ala Ala Lys Gly Leu Glu Leu Pro Ser Glu Ile Gln
            170                 175                 180 aga gaa aag atc aac cac tct gat gct aag aac aac aga tat tct ggc    736
Arg Glu Lys Ile Asn His Ser Asp Ala Lys Asn Asn Arg Tyr Ser Gly
        185                 190                 195 tgg cct gca gag atc cag ata gaa ggc tgc ata ccc aaa gaa cga agc    784
Trp Pro Ala Glu Ile Gln Ile Glu Gly Cys Ile Pro Lys Glu Arg Ser
200                 205                 210                 215 tgacactgca gggtcctgag taaatgtgtt ctgtataaac aaatgcagct ggaatcgctc    844
aagaatctta ttttctaaa tccaacagcc catatttgat gagtattttg ggtttgttgt    904
aaaccaatga acatttgcta gttgtaccaa aaaaaaaaaa aaaa                    948

<210> SEQ ID NO 14
<211> LENGTH: 235
<212> TYPE: PRT
<213> ORGANISM: Homo sapiens
<220> FEATURE:
<221> NAME/KEY: SIGNAL
<222> LOCATION: -20..-1

<400> SEQUENCE: 14

Met Arg Pro Leu Ala Gly Gly Leu Leu Lys Val Val Phe Val Val Phe
-20                 -15                 -10                 -5

Ala Ser Leu Cys Ala Trp Tyr Ser Gly Tyr Leu Leu Ala Glu Leu Ile
                1               5                   10

Pro Asp Ala Pro Leu Ser Ser Ala Ala Tyr Ser Ile Arg Ser Ile Gly
            15                  20                  25

Glu Arg Pro Val Leu Lys Ala Pro Val Pro Lys Arg Gln Lys Cys Asp
        30                  35                  40

His Trp Thr Pro Cys Pro Ser Asp Thr Tyr Ala Tyr Arg Leu Leu Ser
45                  50                  55                  60

Gly Gly Gly Arg Ser Lys Tyr Ala Lys Ile Cys Phe Glu Asp Asn Leu
                65                  70                  75

Leu Met Gly Glu Gln Leu Gly Asn Val Ala Arg Gly Ile Asn Ile Ala
            80                  85                  90

Ile Val Asn Tyr Val Thr Gly Asn Val Thr Ala Thr Arg Cys Phe Asp
        95                  100                 105

Met Tyr Glu Gly Asp Asn Ser Gly Pro Met Thr Lys Phe Ile Gln Ser
    110                 115                 120

Ala Ala Pro Lys Ser Leu Leu Phe Met Val Thr Tyr Asp Asp Gly Ser
125                 130                 135                 140

Thr Arg Leu Asn Asn Asp Ala Lys Asn Ala Ile Glu Ala Leu Gly Ser
                145                 150                 155

Lys Glu Ile Arg Asn Met Lys Phe Arg Ser Ser Trp Val Phe Ile Ala
            160                 165                 170
```

-continued

```
Ala Lys Gly Leu Glu Leu Pro Ser Glu Ile Gln Arg Glu Lys Ile Asn
        175                 180                 185

His Ser Asp Ala Lys Asn Asn Arg Tyr Ser Gly Trp Pro Ala Glu Ile
    190                 195                 200

Gln Ile Glu Gly Cys Ile Pro Lys Glu Arg Ser
205                 210                 215

<210> SEQ ID NO 15
<211> LENGTH: 25
<212> TYPE: DNA
<213> ORGANISM: Artificial Sequence
<220> FEATURE:
<223> OTHER INFORMATION: oligonucleotide used as a primer

<400> SEQUENCE: 15
gggaagatgg agatagtatt gcctg                                          25

<210> SEQ ID NO 16
<211> LENGTH: 26
<212> TYPE: DNA
<213> ORGANISM: Artificial Sequence
<220> FEATURE:
<223> OTHER INFORMATION: oligonucleotide used as a primer

<400> SEQUENCE: 16
ctgccatgta catgatagag agattc                                         26

<210> SEQ ID NO 17
<211> LENGTH: 546
<212> TYPE: DNA
<213> ORGANISM: Homo Sapiens
<220> FEATURE:
<221> NAME/KEY: promoter
<222> LOCATION: 1..517
<220> FEATURE:
<221> NAME/KEY: transcription start site
<222> LOCATION: 518
<220> FEATURE:
<221> NAME/KEY: protein_bind
<222> LOCATION: 17..25
<223> OTHER INFORMATION: matinspector prediction
      name CMYB_01
      score 0.983
      sequence tgtcagttg
<220> FEATURE:
<221> NAME/KEY: protein_bind
<222> LOCATION: complement(18..27)
<223> OTHER INFORMATION: matinspector prediction
      name MYOD_Q6
      score 0.961
      sequence cccaactgac
<220> FEATURE:
<221> NAME/KEY: protein_bind
<222> LOCATION: complement(75..85)
<223> OTHER INFORMATION: matinspector prediction
      name S8_01
      score 0.960
      sequence aatagaattag
<220> FEATURE:
<221> NAME/KEY: protein_bind
<222> LOCATION: 94..104
<223> OTHER INFORMATION: matinspector prediction
      name S8_01
      score 0.966
      sequence aactaaattag
<220> FEATURE:
<221> NAME/KEY: protein_bind
<222> LOCATION: complement(129..139)
<223> OTHER INFORMATION: matinspector prediction
      name DELTAEF1_01
      score 0.960
```

```
      sequence gcacacctcag
<220> FEATURE:
<221> NAME/KEY: protein_bind
<222> LOCATION: complement(155..165)
<223> OTHER INFORMATION: matinspector prediction
      name GATA_C
      score 0.964
      sequence agataaatcca
<220> FEATURE:
<221> NAME/KEY: protein_bind
<222> LOCATION: 170..178
<223> OTHER INFORMATION: matinspector prediction
      name CMYB_01
      score 0.958
      sequence cttcagttg
<220> FEATURE:
<221> NAME/KEY: protein_bind
<222> LOCATION: 176..189
<223> OTHER INFORMATION: matinspector prediction
      name GATA1_02
      score 0.959
      sequence ttgtagataggaca
<220> FEATURE:
<221> NAME/KEY: protein_bind
<222> LOCATION: 180..190
<223> OTHER INFORMATION: matinspector prediction
      name GATA_C
      score 0.953
      sequence agataggacat
<220> FEATURE:
<221> NAME/KEY: protein_bind
<222> LOCATION: 284..299
<223> OTHER INFORMATION: matinspector prediction
      name TAL1ALPHAE47_01
      score 0.973
      sequence cataacagatggtaag
<220> FEATURE:
<221> NAME/KEY: protein_bind
<222> LOCATION: 284..299
<223> OTHER INFORMATION: matinspector prediction
      name TAL1BETAE47_01
      score 0.983
      sequence cataacagatggtaag
<220> FEATURE:
<221> NAME/KEY: protein_bind
<222> LOCATION: 284..299
<223> OTHER INFORMATION: matinspector prediction
      name TAL1BETAITF2_01
      score 0.978
      sequence cataacagatggtaag
<220> FEATURE:
<221> NAME/KEY: protein_bind
<222> LOCATION: complement(287..296)
<223> OTHER INFORMATION: matinspector prediction
      name MYOD_Q6
      score 0.954
      sequence accatctgtt
<220> FEATURE:
<221> NAME/KEY: protein_bind
<222> LOCATION: complement(302..314)
<223> OTHER INFORMATION: matinspector prediction
      name GATA1_04
      score 0.953
      sequence tcaagataaagta
<220> FEATURE:
<221> NAME/KEY: protein_bind
<222> LOCATION: 393..405
<223> OTHER INFORMATION: matinspector prediction
      name IK1_01
      score 0.963
      sequence agttgggaattcc
<220> FEATURE:
<221> NAME/KEY: protein_bind
<222> LOCATION: 393..404
<223> OTHER INFORMATION: matinspector prediction
      name IK2_01
      score 0.985
      sequence agttgggaattc
<220> FEATURE:
```

```
<221> NAME/KEY: protein_bind
<222> LOCATION: 396..405
<223> OTHER INFORMATION: matinspector prediction
       name CREL_01
       score 0.962
       sequence tgggaattcc
<220> FEATURE:
<221> NAME/KEY: protein_bind
<222> LOCATION: 423..436
<223> OTHER INFORMATION: matinspector prediction
       name GATA1_02
       score 0.950
       sequence tcagtgatatggca
<220> FEATURE:
<221> NAME/KEY: protein_bind
<222> LOCATION: complement(478..489)
<223> OTHER INFORMATION: matinspector prediction
       name SRY_02
       score 0.951
       sequence taaaacaaaaca
<220> FEATURE:
<221> NAME/KEY: protein_bind
<222> LOCATION: 486..493
<223> OTHER INFORMATION: matinspector prediction
       name E2F_02
       score 0.957
       sequence tttagcgc
<220> FEATURE:
<221> NAME/KEY: protein_bind
<222> LOCATION: complement(514..521)
<223> OTHER INFORMATION: matinspector prediction
       name MZF1_01
       score 0.975
       sequence tgagggga

<400> SEQUENCE: 17
tgagtgcagt gttacatgtc agttgggtta agtttgttaa tgtcattcaa atcttctatg      60
tcttgatttg cctgctaatt ctattatttc tggaactaaa ttagtttgat ggttctatta     120
gttattgact gaggtgtgct aatctcccat tatgtggatt tatctatttc ttcagttgta     180
gataggacat tgatagatac ataagtacca ggacaaaagc agggagatct tttttccaaa     240
atcaggagaa aaaaatgaca tctggaaaac ctatagggaa aggcataaca gatggtaagg     300
atactttatc ttgagtagga gagccttcct gtggcaacgt ggagaaggga agaggtcgta     360
gaattgagga gtcagctcag ttagaagcag ggagttggga attccgttca tgtgatttag     420
catcagtgat atggcaaatg tgggactaag ggtagtgatc agagggttaa aattgtgtgt     480
tttgttttag cgctgctggg gcatcgcctt gggtcccctc aaacagattc ccatgaatct     540
cttcat                                                                546

<210> SEQ ID NO 18
<211> LENGTH: 23
<212> TYPE: DNA
<213> ORGANISM: Artificial Sequence
<220> FEATURE:
<223> OTHER INFORMATION: oligonucleotide used as a primer

<400> SEQUENCE: 18
gtaccaggga ctgtgaccat tgc                                              23

<210> SEQ ID NO 19
<211> LENGTH: 24
<212> TYPE: DNA
<213> ORGANISM: Artificial Sequence
<220> FEATURE:
<223> OTHER INFORMATION: oligonucleotide used as a primer

<400> SEQUENCE: 19
```
ctgtgaccat tgctcccaag agag                                                      24

<210> SEQ ID NO 20
<211> LENGTH: 861
<212> TYPE: DNA
<213> ORGANISM: Homo Sapiens
<220> FEATURE:
<221> NAME/KEY: promoter
<222> LOCATION: 1..806
<220> FEATURE:
<221> NAME/KEY: transcription start site
<222> LOCATION: 807
<220> FEATURE:
<221> NAME/KEY: protein_bind
<222> LOCATION: complement(60..70)
<223> OTHER INFORMATION: matinspector prediction
      name NFY_Q6
      score 0.956
      sequence ggaccaatcat
<220> FEATURE:
<221> NAME/KEY: protein_bind
<222> LOCATION: 70..77
<223> OTHER INFORMATION: matinspector prediction
      name MZF1_01
      score 0.962
      sequence cctgggga
<220> FEATURE:
<221> NAME/KEY: protein_bind
<222> LOCATION: 124..132
<223> OTHER INFORMATION: matinspector prediction
      name CMYB_01
      score 0.994
      sequence tgaccgttg
<220> FEATURE:
<221> NAME/KEY: protein_bind
<222> LOCATION: complement(126..134)
<223> OTHER INFORMATION: matinspector prediction
      name VMYB_02
      score 0.985
      sequence tccaacggt
<220> FEATURE:
<221> NAME/KEY: protein_bind
<222> LOCATION: 135..143
<223> OTHER INFORMATION: matinspector prediction
      name STAT_01
      score 0.968
      sequence ttcctggaa
<220> FEATURE:
<221> NAME/KEY: protein_bind
<222> LOCATION: complement(135..143)
<223> OTHER INFORMATION: matinspector prediction
      name STAT_01
      score 0.951
      sequence ttccaggaa
<220> FEATURE:
<221> NAME/KEY: protein_bind
<222> LOCATION: complement(252..259)
<223> OTHER INFORMATION: matinspector prediction
      name MZF1_01
      score 0.956
      sequence ttggggga
<220> FEATURE:
<221> NAME/KEY: protein_bind
<222> LOCATION: 357..368
<223> OTHER INFORMATION: matinspector prediction
      name IK2_01
      score 0.965
      sequence gaatgggatttc
<220> FEATURE:
<221> NAME/KEY: protein_bind
<222> LOCATION: 384..391
<223> OTHER INFORMATION: matinspector prediction
      name MZF1_01
      score 0.986
      sequence agagggga
<220> FEATURE:
<221> NAME/KEY: protein_bind
<222> LOCATION: complement(410..421)

```
<223> OTHER INFORMATION: matinspector prediction
        name SRY_02
        score 0.955
        sequence gaaaacaaaaca
<220> FEATURE:
<221> NAME/KEY: protein_bind
<222> LOCATION: 592..599
<223> OTHER INFORMATION: matinspector prediction
        name MZF1_01
        score 0.960
        sequence gaagggga
<220> FEATURE:
<221> NAME/KEY: protein_bind
<222> LOCATION: 618..627
<223> OTHER INFORMATION: matinspector prediction
        name MYOD_Q6
        score 0.981
        sequence agcatctgcc
<220> FEATURE:
<221> NAME/KEY: protein_bind
<222> LOCATION: 632..642
<223> OTHER INFORMATION: matinspector prediction
        name DELTAEF1_01
        score 0.958
        sequence tcccaccttcc
<220> FEATURE:
<221> NAME/KEY: protein_bind
<222> LOCATION: complement(813..823)
<223> OTHER INFORMATION: matinspector prediction
        name S8_01
        score 0.992
        sequence gaggcaattat
<220> FEATURE:
<221> NAME/KEY: protein_bind
<222> LOCATION: complement(824..831)
<223> OTHER INFORMATION: matinspector prediction
        name MZF1_01
        score 0.986
        sequence agagggga
<220> FEATURE:
<221> NAME/KEY: misc_feature
<222> LOCATION: 335,376
<223> OTHER INFORMATION: n=a, g, c or t

<400> SEQUENCE: 20 tactatagggg cacgcgtggt cgacggccgg gctgttctgg agcagagggc atgtcagtaa      60
tgattggtcc ctggggaagg tctggctggc tccagcacag tgaggcattt aggtatctct     120
cggtgaccgt tggattcctg gaagcagtag ctgttctgtt tggatctggt agggacaggg     180
ctcagagggc taggcacgag ggaaggtcag aggagaaggs aggsarggcc cagtgagarg     240
ggagcatgcc ttcccccaac cctggcttsc ycttggymam agggcgktty tgggmacttr     300
aaytcagggc ccaascagaa scacaggccc aktcntggct smaagcacaa tagcctgaat     360
gggatttcag gttagncagg gtgagagggg aggctctctg gcttagtttt gttttgtttt     420
ccaaatcaag gtaacttgct cccttctgct acgggccttg gtcttggctt gtcctcaccc     480
agtcggaact ccctaccact ttcaggagag tggttttagg cccgtggggc tgttctgttc     540
caagcagtgt gagaacatgg ctggtagagg ctctagctgt gtgcgggcc tgaagggggag     600 tgggttctcg cccaaagagc atctgccat tcccaccttcc ccttctccc accagaagct      660 tgcctgagct gtttggacaa aaatccaaac cccacttggc tactctggcc tggcttcagc     720
ttggaaccca atacctaggc ttacaggcca tcctgagcca ggggcctctg gaaattctct     780
tcctgatggt cctttaggtt tgggcacaaa atataattgc ctctccctc tcccattttc      840 tctcttggga gcaatggtca c                                                861

<210> SEQ ID NO 21
<211> LENGTH: 20
```

```
<212> TYPE: DNA
<213> ORGANISM: Artificial Sequence
<220> FEATURE:
<223> OTHER INFORMATION: oligonucleotide used as a primer

<400> SEQUENCE: 21
ctgggatgga aggcacggta                                                 20

<210> SEQ ID NO 22
<211> LENGTH: 20
<212> TYPE: DNA
<213> ORGANISM: Artificial Sequence
<220> FEATURE:
<223> OTHER INFORMATION: oligonucleotide used as a primer

<400> SEQUENCE: 22
gagaccacac agctagacaa                                                 20

<210> SEQ ID NO 23
<211> LENGTH: 555
<212> TYPE: DNA
<213> ORGANISM: Homo Sapiens
<220> FEATURE:
<221> NAME/KEY: promoter
<222> LOCATION: 1..500
<220> FEATURE:
<221> NAME/KEY: transcription start site
<222> LOCATION: 501
<220> FEATURE:
<221> NAME/KEY: protein_bind
<222> LOCATION: 191..206
<223> OTHER INFORMATION: matinspector prediction
      name ARNT_01
      score 0.964
      sequence ggactcacgtgctgct
<220> FEATURE:
<221> NAME/KEY: protein_bind
<222> LOCATION: 193..204
<223> OTHER INFORMATION: matinspector prediction
      name NMYC_01
      score 0.965
      sequence actcacgtgctg
<220> FEATURE:
<221> NAME/KEY: protein_bind
<222> LOCATION: 193..204
<223> OTHER INFORMATION: matinspector prediction
      name USF_01
      score 0.985
      sequence actcacgtgctg
<220> FEATURE:
<221> NAME/KEY: protein_bind
<222> LOCATION: complement(193..204)
<223> OTHER INFORMATION: matinspector prediction
      name USF_01
      score 0.985
      sequence cagcacgtgagt
<220> FEATURE:
<221> NAME/KEY: protein_bind
<222> LOCATION: complement(193..204)
<223> OTHER INFORMATION: matinspector prediction
      name NMYC_01
      score 0.956
      sequence cagcacgtgagt
<220> FEATURE:
<221> NAME/KEY: protein_bind
<222> LOCATION: complement(193..204)
<223> OTHER INFORMATION: matinspector prediction
      name MYCMAX_02
      score 0.972
      sequence cagcacgtgagt
<220> FEATURE:
<221> NAME/KEY: protein_bind
<222> LOCATION: 195..202
<223> OTHER INFORMATION: matinspector prediction
      name USF_C
```

```
          score 0.997
          sequence tcacgtgc
<220> FEATURE:
<221> NAME/KEY: protein_bind
<222> LOCATION: complement(195..202)
<223> OTHER INFORMATION: matinspector prediction
          name USF_C
          score 0.991
          sequence gcacgtga
<220> FEATURE:
<221> NAME/KEY: protein_bind
<222> LOCATION: complement(210..217)
<223> OTHER INFORMATION: matinspector prediction
          name MZF1_01
          score 0.968
          sequence catgggga
<220> FEATURE:
<221> NAME/KEY: protein_bind
<222> LOCATION: 397..410
<223> OTHER INFORMATION: matinspector prediction
          name ELK1_02
          score 0.963
          sequence ctctccggaagcct
<220> FEATURE:
<221> NAME/KEY: protein_bind
<222> LOCATION: 400..409
<223> OTHER INFORMATION: matinspector prediction
          name CETS1P54_01
          score 0.974
          sequence tccggaagcc
<220> FEATURE:
<221> NAME/KEY: protein_bind
<222> LOCATION: complement(460..470)
<223> OTHER INFORMATION: matinspector prediction
          name AP1_Q4
          score 0.963
          sequence agtgactgaac
<220> FEATURE:
<221> NAME/KEY: protein_bind
<222> LOCATION: complement(460..470)
<223> OTHER INFORMATION: matinspector prediction
          name AP1FJ_Q2
          score 0.961
          sequence agtgactgaac
<220> FEATURE:
<221> NAME/KEY: protein_bind
<222> LOCATION: 547..555
<223> OTHER INFORMATION: matinspector prediction
          name PADS_C
          score 1.000
          sequence tgtggtctc

<400> SEQUENCE: 23
ctatagggca cgcktggtcg acggcccggg ctggtctggt ctgtkgtgga gtcgggttga      60
aggacagcat ttgtkacatc tggtctactg caccttccct ctgccgtgca cttggccttt    120
kawaagctca gcaccggtgc ccatcacagg gccggcagca cacacatccc attactcaga    180
aggaactgac ggactcacgt gctgctccgt ccccatgagc tcagtggacc tgtctatgta    240
gagcagtcag acagtgcctg ggatagagtg agagttcagc cagtaaatcc aagtgattgt    300
cattcctgtc tgcattagta actcccaacc tagatgtgaa aacttagttc tttctcatag    360
gttgctctgc ccatggtccc actgcagacc caggcactct ccggaagcct ggaaatcacc    420
cgtgtcttct gcctgctccc gctcacatcc cacacttgtg ttcagtcact gagttacaga    480
ttttgcctcc tcaatttctc ttgtcttagt cccatcctct gttccctgg ccagtttgtc     540 tagctgtgtg gtctc                                                     555

<210> SEQ ID NO 24
<211> LENGTH: 1450
<212> TYPE: DNA
<213> ORGANISM: Homo Sapiens
```

```
<220> FEATURE:
<221> NAME/KEY: CDS
<222> LOCATION: 153..1127
<220> FEATURE:
<221> NAME/KEY: sig_peptide
<222> LOCATION: 153..230
<223> OTHER INFORMATION: Von Heijne matrix
      score 8.40
      seq RLLRLLLSGLVLG/AA
<220> FEATURE:
<221> NAME/KEY: polyA_signal
<222> LOCATION: 1415..1420
<220> FEATURE:
<221> NAME/KEY: polyA_site
<222> LOCATION: 1434..1450
<220> FEATURE:
<221> NAME/KEY: misc_feature
<222> LOCATION: 88
<223> OTHER INFORMATION: n=a, g, c or t

<400> SEQUENCE: 24
ctttcctctt cctcctcctc ctccttggca tccgcctctt cttcctcctg cgtcctcccc      60
cgctgcctcc gctgctcccg acgcggancc cggagcccgc gccgagcccc tggcctcgcg     120
gtgccatgct gccccggcgg cggcgctgaa gg atg gcg acg ccg ctg cct ccg      173
                                    Met Ala Thr Pro Leu Pro Pro
                                        -25                 -20 ccc tcc ccg cgg cac ctg cgg ctg ctg cgg ctg ctc tcc ggc ctc          221
Pro Ser Pro Arg His Leu Arg Leu Leu Arg Leu Leu Leu Ser Gly Leu
        -15                 -10                 -5 gtc ctc ggc gcc gcc ctg cgt gga gcc gcc gcc ggc cac ccg gat gta      269
Val Leu Gly Ala Ala Leu Arg Gly Ala Ala Ala Gly His Pro Asp Val
            1               5                  10 gcc gcc tgt ccc ggg agc ctg gac tgt gcc ctg aag agg cgg gca agg      317
Ala Ala Cys Pro Gly Ser Leu Asp Cys Ala Leu Lys Arg Arg Ala Arg
        15                  20                  25 tgt cct cct ggt gca cat gcc tgt ggg ccc tgc ctt cag ccc ttc cag      365
Cys Pro Pro Gly Ala His Ala Cys Gly Pro Cys Leu Gln Pro Phe Gln
30                  35                  40                  45 gag gac cag caa ggg ctc tgt gtg ccc agg atg cgc cgg cct cca ggc      413
Glu Asp Gln Gln Gly Leu Cys Val Pro Arg Met Arg Arg Pro Pro Gly
                50                  55                  60 ggg ggc cgg ccc cag ccc aga ctg gaa gat gag att gac ttc ctg gcc      461
Gly Gly Arg Pro Gln Pro Arg Leu Glu Asp Glu Ile Asp Phe Leu Ala
            65                  70                  75 cag gag ctt gcc cgg aag gag tct gga cac tca act ccg ccc cta ccc      509
Gln Glu Leu Ala Arg Lys Glu Ser Gly His Ser Thr Pro Pro Leu Pro
        80                  85                  90 aag gac cga cag cgg ctc ccg gag cct gcc acc ctg ggc ttc tcg gca      557
Lys Asp Arg Gln Arg Leu Pro Glu Pro Ala Thr Leu Gly Phe Ser Ala
    95                  100                 105 cgg ggg cag ggg ctg gag ctg ggc ctc ccc tcc act cca gga acc ccc      605
Arg Gly Gln Gly Leu Glu Leu Gly Leu Pro Ser Thr Pro Gly Thr Pro
110                 115                 120                 125 acg ccc acg ccc cac acc tcc ctg ggc tcc cct gtg tca tcc gac ccg      653
Thr Pro Thr Pro His Thr Ser Leu Gly Ser Pro Val Ser Ser Asp Pro
                130                 135                 140 gtg cac atg tcg ccc ctg gag ccc cgg gga ggg caa ggc gac ggc ctc      701
Val His Met Ser Pro Leu Glu Pro Arg Gly Gly Gln Gly Asp Gly Leu
            145                 150                 155 gcc ctt gtg ctg atc ctg gcg ttc tgt gtg gcc ggt gca gcc gcc ctc      749
Ala Leu Val Leu Ile Leu Ala Phe Cys Val Ala Gly Ala Ala Ala Leu
        160                 165                 170 tcc gta gcc tcc ctc tgc tgg tgc agg ctg cag cgt gag atc cgc ctg      797
```

-continued

```
          Ser Val Ala Ser Leu Cys Trp Cys Arg Leu Gln Arg Glu Ile Arg Leu
              175                 180                 185 act cag aag gcc gac tac gcc act gcg aag gcc cct ggc tca cct gca       845
Thr Gln Lys Ala Asp Tyr Ala Thr Ala Lys Ala Pro Gly Ser Pro Ala
190                 195                 200                 205 gct ccc cgg atc tcg cct ggg gac cag cgg ctg gca cag agc gcg gag       893
Ala Pro Arg Ile Ser Pro Gly Asp Gln Arg Leu Ala Gln Ser Ala Glu
            210                 215                 220 atg tac cac tac cag cac caa cgg caa cag atg ctg tgc ctg gag cgg       941
Met Tyr His Tyr Gln His Gln Arg Gln Gln Met Leu Cys Leu Glu Arg
                225                 230                 235 cat aaa gag cca ccc aag gag ctg gac acg gcc tcc tcg gat gag gag       989
His Lys Glu Pro Pro Lys Glu Leu Asp Thr Ala Ser Ser Asp Glu Glu
            240                 245                 250 aat gag gac gga gac ttc acg gtg tac gag tgc ccg ggc ctg gcc ccg      1037
Asn Glu Asp Gly Asp Phe Thr Val Tyr Glu Cys Pro Gly Leu Ala Pro
                255                 260                 265 acc ggg gaa atg gag gtg cgc aac cct ctg ttc gac cac gcc gca ctg      1085
Thr Gly Glu Met Glu Val Arg Asn Pro Leu Phe Asp His Ala Ala Leu
270                 275                 280                 285 tcc gcg ccc ctg ccg gcc ccc agc tca ccg cct gca ctg cca              1127
Ser Ala Pro Leu Pro Ala Pro Ser Ser Pro Pro Ala Leu Pro
                290                 295 tgacctggag gcagacagac gcccacctgc tccccgacct cgaggccccc ggggaggggc     1187
agggcctgga gcttcccact aaaaacatgt tttgatgctg tgtgcttttg gctgggcctt    1247
gggctccagg ccctgggacc ccttgccagg gagaccccg aacctttgtg ccaggacacc     1307
tcctggtccc ctgcacctct cctgtttggt ttagaccccc aaactggagg gggcatggag    1367
aaccgtagag cgcaggaacg ggtgggtaat tctagagaca aaagccaatt aaagtccatt    1427
tcagacaaaa aaaaaaaaaa aaa                                            1450

<210> SEQ ID NO 25
<211> LENGTH: 1556
<212> TYPE: DNA
<213> ORGANISM: Homo Sapiens
<220> FEATURE:
<221> NAME/KEY: CDS
<222> LOCATION: 261..1166
<220> FEATURE:
<221> NAME/KEY: sig_peptide
<222> LOCATION: 261..314
<223> OTHER INFORMATION: Von Heijne matrix
      score 8.80
      seq RLVLIILCSVVFS/AV
<220> FEATURE:
<221> NAME/KEY: polyA_site
<222> LOCATION: 1524..1556

<400> SEQUENCE: 25
cagcccagtc ggcccggccc gggggccatg gagctccgag cggcgatcgc gagcctcctg     60
cgaaccccag cctgcacgcc cggttagcat tcggccggga gatgcggcag tggaatctgg    120
aagggcggtg aaaaacctac gtcctgccct cgcccggcct ctccattcgt ccccccgggta   180 gagaggtgcc cggctcccac cccttcccag ccccagccct ggagacagca gcccctagac    240
tactgaggga cagcgacagc atg aag gct ccg ggt cgg ctc gtg ctc atc atc    293
                        Met Lys Ala Pro Gly Arg Leu Val Leu Ile Ile
                                        -15                 -10 ctg tgc tcc gtg gtc ttc tct gcc gtc tac atc ctc ctg tgc tgc tgg      341
Leu Cys Ser Val Val Phe Ser Ala Val Tyr Ile Leu Leu Cys Cys Trp
        -5                  1               5
```

|     |     |     |     |     |     |     |     |     |     |     |     |     |     |     |
| --- | --- | --- | --- | --- | --- | --- | --- | --- | --- | --- | --- | --- | --- | --- |
| gcc | ggc | ctg | ccc | ctc | tgc | ctg | gcc | acc | tgc | ctg | gac | cac | cac | ttc | ccc | 389 |
| Ala | Gly | Leu | Pro | Leu | Cys | Leu | Ala | Thr | Cys | Leu | Asp | His | His | Phe | Pro |
| 10 |     |     |     | 15  |     |     |     | 20  |     |     |     |     | 25  |     |     | aca ggc tcc agg ccc act gtg ccg gga ccc ctg cac ttc agt gga tat   437
Thr Gly Ser Arg Pro Thr Val Pro Gly Pro Leu His Phe Ser Gly Tyr
            30                  35                      40 agc agt gtg cca gat ggg aag ccg ctg gtc cgc gag ccc tgc cgc agc   485
Ser Ser Val Pro Asp Gly Lys Pro Leu Val Arg Glu Pro Cys Arg Ser
            45                  50                  55 tgt gcc gtg gtg tcc agc tcc ggc caa atg ctg ggc tca ggc ctg ggt   533
Cys Ala Val Val Ser Ser Ser Gly Gln Met Leu Gly Ser Gly Leu Gly
            60                  65                  70 gct gag atc gac agt gcc gag tgc gtg ttc cgc atg aac cag gcg ccc   581
Ala Glu Ile Asp Ser Ala Glu Cys Val Phe Arg Met Asn Gln Ala Pro
75                      80                  85 acc gtg ggc ttt gag gcg gat gtg ggc cag cgc agc acc ctg cgt gtc   629
Thr Val Gly Phe Glu Ala Asp Val Gly Gln Arg Ser Thr Leu Arg Val
90                  95                      100                 105 gtc tca cac aca agc gtg ccg ctg ctg ctg cgc aac tat tca cac tac   677
Val Ser His Thr Ser Val Pro Leu Leu Leu Arg Asn Tyr Ser His Tyr
                    110                 115                 120 ttc cag aag gcc cga gac acg ctc tac atg gtg tgg ggc cag ggc agg   725
Phe Gln Lys Ala Arg Asp Thr Leu Tyr Met Val Trp Gly Gln Gly Arg
                125                 130                 135 cac atg gac cgg gtg ctc ggc ggc cgc acc tac cgc acg ctg ctg cag   773
His Met Asp Arg Val Leu Gly Gly Arg Thr Tyr Arg Thr Leu Leu Gln
            140                 145                 150 ctc acc agg atg tac ccc ggc ctg cag gtg tac acc ttc acg gag cgc   821
Leu Thr Arg Met Tyr Pro Gly Leu Gln Val Tyr Thr Phe Thr Glu Arg
            155                 160                 165 atg atg gcc tac tgc gac cag atc ttc cag gac gag acg ggc aag aac   869
Met Met Ala Tyr Cys Asp Gln Ile Phe Gln Asp Glu Thr Gly Lys Asn
170                 175                 180                 185 cgg agg cag tcg ggc tcc ttc ctc agc acc ggc tgg ttc acc atg atc   917
Arg Arg Gln Ser Gly Ser Phe Leu Ser Thr Gly Trp Phe Thr Met Ile
                190                 195                 200 ctc gcg ctg gag ctg tgt gag gag atc gtg gtc tat ggg atg gtc agc   965
Leu Ala Leu Glu Leu Cys Glu Glu Ile Val Val Tyr Gly Met Val Ser
            205                 210                 215 gac agc tac tgc agg gag aag agc cac ccc tca gtg cct tac cac tac   1013
Asp Ser Tyr Cys Arg Glu Lys Ser His Pro Ser Val Pro Tyr His Tyr
            220                 225                 230 ttt gag aag ggc cgg cta gat gag tgt cag atg tac ctg gca cac gag   1061
Phe Glu Lys Gly Arg Leu Asp Glu Cys Gln Met Tyr Leu Ala His Glu
235                 240                 245 cag gcg ccc cga agc gcc cac cgc ttc atc act gag aag gcg gtc ttc   1109
Gln Ala Pro Arg Ser Ala His Arg Phe Ile Thr Glu Lys Ala Val Phe
250                 255                 260                 265 tcc cgc tgg gcc aag aag agg ccc atc gtg ttc gcc cat ccg tcc tgg   1157
Ser Arg Trp Ala Lys Lys Arg Pro Ile Val Phe Ala His Pro Ser Trp
                270                 275                 280 agg act gag tagcttccgt cgtcctgcca gccgccatgc cgttgcgagg          1206
Arg Thr Glu cctccgggat gtcccatccc aagccatcac actccactcc ctgagtaatt catggcattt   1266
gggggctcac cacctccagg tctgtcaagt ggcctttgtc cctggggctg atggccccca   1326
actcaccagc atcatgacct tgtgccagtc ctggtcctcc ctcccagcc gcccctacca   1386 cctttggtg ccacacttct caggctggcc gccctggttg gggcagccga gagcctgggg   1446

```
ttcattggtg aaggggcctt ggagttgtga ctgccggggc cgtatcagga acgtacgggt    1506
aaacgtgtgt tttctggaaa aaaaaaaaaa aacaaaaaaa aaaaaaaaaa              1556

<210> SEQ ID NO 26
<211> LENGTH: 1058
<212> TYPE: DNA
<213> ORGANISM: Homo Sapiens
<220> FEATURE:
<221> NAME/KEY: CDS
<222> LOCATION: 67..813
<220> FEATURE:
<221> NAME/KEY: sig_peptide
<222> LOCATION: 67..111
<223> OTHER INFORMATION: Von Heijne matrix
      score 5.20
      seq QLWKLVLLCGVLT/GT
<220> FEATURE:
<221> NAME/KEY: polyA_signal
<222> LOCATION: 1023..1028
<220> FEATURE:
<221> NAME/KEY: polyA_site
<222> LOCATION: 1042..1058

<400> SEQUENCE: 26
agcagactgt gcagtggggc aaggatttca tgagcatcct cctctaaacg cgtgacaaga    60 caaaag atg ctt cag ctt tgg aaa ctt gtt ctc ctg tgc ggc gtg ctc      108
       Met Leu Gln Leu Trp Lys Leu Val Leu Leu Cys Gly Val Leu
       -15                 -10                 -5 act ggg acc tca gag tct ctt ctt gac aat ctt ggc aat gac cta agc     156
Thr Gly Thr Ser Glu Ser Leu Leu Asp Asn Leu Gly Asn Asp Leu Ser
 1               5                  10                  15 aat gtc gtg gat aag ctg gaa cct gtt ctt cac gag gga ctt gag aca     204
Asn Val Val Asp Lys Leu Glu Pro Val Leu His Glu Gly Leu Glu Thr
             20                  25                  30 gtt gac aat act ctt aaa ggc atc ctt gag aaa ctg aag gtc gac cta     252
Val Asp Asn Thr Leu Lys Gly Ile Leu Glu Lys Leu Lys Val Asp Leu
         35                  40                  45 gga gtg ctt cag aaa tcc agt gct tgg caa ctg gcc aag cag aag gcc     300
Gly Val Leu Gln Lys Ser Ser Ala Trp Gln Leu Ala Lys Gln Lys Ala
     50                  55                  60 cag gaa gct gag aaa ttg ctg aac aat gtc att tct aag ctg ctt cca     348
Gln Glu Ala Glu Lys Leu Leu Asn Asn Val Ile Ser Lys Leu Leu Pro
 65                  70                  75 act aac acg gac att ttt ggg ttg aaa atc agc aac tcc ctc atc ctg     396
Thr Asn Thr Asp Ile Phe Gly Leu Lys Ile Ser Asn Ser Leu Ile Leu
 80                  85                  90                  95 gat gtc aaa gct gaa ccg atc gat gat ggc aaa ggc ctt aac ctg agc     444
Asp Val Lys Ala Glu Pro Ile Asp Asp Gly Lys Gly Leu Asn Leu Ser
            100                 105                 110 ttc cct gtc acc gcg aat gtc act gtg gcc ggg ccc atc att ggc cag     492
Phe Pro Val Thr Ala Asn Val Thr Val Ala Gly Pro Ile Ile Gly Gln
        115                 120                 125 att atc aac ctg aaa gcc tcc ttg gac ctc ctg acc gca gtc aca att     540
Ile Ile Asn Leu Lys Ala Ser Leu Asp Leu Leu Thr Ala Val Thr Ile
    130                 135                 140 gaa act gat ccc cag aca cac cag cct gtt gcc gtc ctg gga gaa tgc     588
Glu Thr Asp Pro Gln Thr His Gln Pro Val Ala Val Leu Gly Glu Cys
145                 150                 155 gcc agt gac cca acc agc atc tca ctt tcc ttg ctg gac aaa cac agc     636
Ala Ser Asp Pro Thr Ser Ile Ser Leu Ser Leu Leu Asp Lys His Ser
160                 165                 170                 175 caa atc atc aac aag ttc gtg aat agc gtg atc aac acg ctg aaa agc     684
Gln Ile Ile Asn Lys Phe Val Asn Ser Val Ile Asn Thr Leu Lys Ser
```

```
                180              185              190
act gta tcc tcc ctg ctg cag aag gag ata tgt cca ctg atc cgc atc         732
Thr Val Ser Ser Leu Leu Gln Lys Glu Ile Cys Pro Leu Ile Arg Ile
            195              200              205 ttc atc cac tcc ctg gat gtg aat gtc att cag cag gtc gtc gat aat         780
Phe Ile His Ser Leu Asp Val Asn Val Ile Gln Gln Val Val Asp Asn
            210              215              220 cct cag cac aaa acc cag ctg caa acc ctc atc tgaagaggac gaatgaggag       833
Pro Gln His Lys Thr Gln Leu Gln Thr Leu Ile
            225              230 gaccactgtg gtgcatgctg attggttccc agtggcttgc cccaccccct tatagcatct       893
ccctccagga agctgctgcc accacctaac cagcgtgaaa gcctgagtcc caccagaagg       953
accttcccag ataccccttc tcctcacagt cagaacagca gcctctacac atgttgtcct      1013
gcccctggca ataaaggccc atttctgcaa aaaaaaaaa aaaaa                      1058

<210> SEQ ID NO 27
<211> LENGTH: 648
<212> TYPE: DNA
<213> ORGANISM: Homo Sapiens
<220> FEATURE:
<221> NAME/KEY: CDS
<222> LOCATION: 187..438
<220> FEATURE:
<221> NAME/KEY: polyA_signal
<222> LOCATION: 612..617
<220> FEATURE:
<221> NAME/KEY: polyA_site
<222> LOCATION: 632..648

<400> SEQUENCE: 27
agtgcgcact ggcgtgcgag actcggcggg cgctgttgag ggagtcgggc cgcgactgtg        60
gtcgttttta taccttcccg cgcggacgcc ggcgctgcca acggaagggc ggagacggag       120
tttcgtcatg ttggccaggc ccatttgaga tctttgaaga tatcctcaac gtgaggctct       180 gctgcc atg aag gtg aag att aag tgc tgg aac ggc gtg gcc act tgg         228
        Met Lys Val Lys Ile Lys Cys Trp Asn Gly Val Ala Thr Trp
          1               5                  10 ctc tgg gtg gcc aac gat gag aac tgt ggc atc tgc agg atg gca ttt         276
Leu Trp Val Ala Asn Asp Glu Asn Cys Gly Ile Cys Arg Met Ala Phe
15              20              25                  30 aac gga tgc tgc cct gac tgc aag gtg ccc ggc gac gac tgc ccg ctg         324
Asn Gly Cys Cys Pro Asp Cys Lys Val Pro Gly Asp Asp Cys Pro Leu
                35              40              45 gtg tgg ggc cag tgc tcc cac tgc ttc cac atg cat tgc atc ctc aag         372
Val Trp Gly Gln Cys Ser His Cys Phe His Met His Cys Ile Leu Lys
            50              55              60 tgg ctg cac gca cag cag gtg cag cag cac tgc ccc atg tgc cgc cag         420
Trp Leu His Ala Gln Gln Val Gln Gln His Cys Pro Met Cys Arg Gln
65              70              75 gaa tgg aag ttc aag gag tgaggcccga cctggctctc gctggagggg               468
Glu Trp Lys Phe Lys Glu
            80 catcctgaga ctccttcctc atgctggcgc cgatggctgc tggggacagc gcccctgagc       528 tgcaacaagg tggaaacaag ggctggagct gcgtttgttt tgccatcact atgttgacac       588 ttttatccaa taagtgaaaa ctcattaaac tactcaaatc tcgaaaaaaa aaaaaaaaaa       648

<210> SEQ ID NO 28
<211> LENGTH: 2104
<212> TYPE: DNA
```

```
<213> ORGANISM: Homo Sapiens
<220> FEATURE:
<221> NAME/KEY: CDS
<222> LOCATION: 92..1753
<220> FEATURE:
<221> NAME/KEY: sig_peptide
<222> LOCATION: 92..130
<223> OTHER INFORMATION: Von Heijne matrix
      score 3.90
      seq MLYLQGWSMPAVA/EV
<220> FEATURE:
<221> NAME/KEY: polyA_signal
<222> LOCATION: 2070..2075
<220> FEATURE:
<221> NAME/KEY: polyA_site
<222> LOCATION: 2090..2104
<220> FEATURE:
<221> NAME/KEY: misc_feature
<222> LOCATION: 905
<223> OTHER INFORMATION: n=a, g, c or t
<220> FEATURE:
<221> NAME/KEY: unsure
<222> LOCATION: 259
<223> OTHER INFORMATION: Xaa = Asp,His,Asn,Tyr

<400> SEQUENCE: 28
atagacttta tcatacttcg tagcatccag tatgttttct ttgctaagat tattgatttt      60
gtattgaagg gtcccatgtc catcgttttc a atg ctt tat ctc cag ggt tgg        112
                                   Met Leu Tyr Leu Gln Gly Trp
                                                       -10 agc atg cct gct gtg gca gag gta aaa ctt cga gat gat caa tat aca       160
Ser Met Pro Ala Val Ala Glu Val Lys Leu Arg Asp Asp Gln Tyr Thr
     -5                 1               5                      10 ctg gaa cac atg cat gct ttt gga atg tat aat tac ctg cac tgt gat       208
Leu Glu His Met His Ala Phe Gly Met Tyr Asn Tyr Leu His Cys Asp
                15                  20                  25 tca tgg tat caa gac agt gtc tac tat att gat acc ctt gga aga att       256
Ser Trp Tyr Gln Asp Ser Val Tyr Tyr Ile Asp Thr Leu Gly Arg Ile
            30                  35                  40 atg aat tta aca gta atg ctg gac act gcc tta gga aaa cca cga gag       304
Met Asn Leu Thr Val Met Leu Asp Thr Ala Leu Gly Lys Pro Arg Glu
        45                  50                  55 gtg ttt cga ctt cct aca gat ttg aca gca tgt gac aac cgt ctt tgt       352
Val Phe Arg Leu Pro Thr Asp Leu Thr Ala Cys Asp Asn Arg Leu Cys
    60                  65                  70 gca tct atc cat ttc tca tct tct acc tgg gtt acc ttg tca gat gga       400
Ala Ser Ile His Phe Ser Ser Ser Thr Trp Val Thr Leu Ser Asp Gly
75                  80                  85                  90 act gga aga ttg tat gtc att gga aca ggt gaa cgt gga aat agc gct       448
Thr Gly Arg Leu Tyr Val Ile Gly Thr Gly Glu Arg Gly Asn Ser Ala
                95                 100                 105 tct gaa aaa tgg gag att atg ttt aat gaa gaa ctt ggg gat cct ttt       496
Ser Glu Lys Trp Glu Ile Met Phe Asn Glu Glu Leu Gly Asp Pro Phe
            110                 115                 120 att ata att cac agt atc tca ctg cta aat gct gaa gaa cat tct ata       544
Ile Ile Ile His Ser Ile Ser Leu Leu Asn Ala Glu Glu His Ser Ile
        125                 130                 135 gct acc cta ctt ctt cga ata gag aaa gag gaa ttg gat atg aaa gga       592
Ala Thr Leu Leu Leu Arg Ile Glu Lys Glu Glu Leu Asp Met Lys Gly
    140                 145                 150 agt ggt ttc tat gtt tct ctg gag tgg gtc act atc agt aag aaa aat       640
Ser Gly Phe Tyr Val Ser Leu Glu Trp Val Thr Ile Ser Lys Lys Asn
155                 160                 165                 170 caa gat aat aaa aaa tat gaa att att aag cgt gat att ctc cgt gga       688
Gln Asp Asn Lys Lys Tyr Glu Ile Ile Lys Arg Asp Ile Leu Arg Gly
```

-continued

```
                     175                 180                 185
aag tca gtg cca cat tat gct gct att aag cct gat gga aat ggt cta       736
Lys Ser Val Pro His Tyr Ala Ala Ile Lys Pro Asp Gly Asn Gly Leu
            190                 195                 200 atg att gta tcc tac aag tct tta aca ttt gtt cag gct ggt caa gat       784
Met Ile Val Ser Tyr Lys Ser Leu Thr Phe Val Gln Ala Gly Gln Asp
            205                 210                 215 ctt gaa gaa aat atg gat gaa gac ata tca gag aaa atc aaa gaa cct       832
Leu Glu Glu Asn Met Asp Glu Asp Ile Ser Glu Lys Ile Lys Glu Pro
    220                 225                 230 ctg tat tac tgg caa cag act gaa gat gat ttg aca gta acc ata cgg       880
Leu Tyr Tyr Trp Gln Gln Thr Glu Asp Asp Leu Thr Val Thr Ile Arg
235                 240                 245                 250 ctt cca gaa gac agt act aag gag nac att caa ata cag ttt ttg cct       928
Leu Pro Glu Asp Ser Thr Lys Glu Xaa Ile Gln Ile Gln Phe Leu Pro
                255                 260                 265 gat cac atc aac att gta ctg aag gat cac cag ttt tta gaa gga aaa       976
Asp His Ile Asn Ile Val Leu Lys Asp His Gln Phe Leu Glu Gly Lys
            270                 275                 280 ctc tat tca tct att gat cat gaa agc agt aca tgg ata att aaa gag      1024
Leu Tyr Ser Ser Ile Asp His Glu Ser Ser Thr Trp Ile Ile Lys Glu
            285                 290                 295 agt aat agc ttg gag att tcc ttg att aag aag aat gaa gga ctg acc      1072
Ser Asn Ser Leu Glu Ile Ser Leu Ile Lys Lys Asn Glu Gly Leu Thr
    300                 305                 310 tgg cca gag cta gta att gga gat aaa caa ggg gaa ctt ata aga gat      1120
Trp Pro Glu Leu Val Ile Gly Asp Lys Gln Gly Glu Leu Ile Arg Asp
315                 320                 325                 330 tca gcc cag tgt gct gca ata gct gaa cgt ttg atg cat ttg acc tct      1168
Ser Ala Gln Cys Ala Ala Ile Ala Glu Arg Leu Met His Leu Thr Ser
                335                 340                 345 gaa gaa ctg aat cca aat cca gat aaa gaa aaa cca cct tgc aat gct      1216
Glu Glu Leu Asn Pro Asn Pro Asp Lys Glu Lys Pro Pro Cys Asn Ala
            350                 355                 360 caa gag tta gaa gaa tgt gat att ttc ttt gaa gag agc tcc agt tta      1264
Gln Glu Leu Glu Glu Cys Asp Ile Phe Phe Glu Glu Ser Ser Ser Leu
            365                 370                 375 tgc aga ttt gat ggc aat aca tta aaa act act cat gtg gtg aat ctt      1312
Cys Arg Phe Asp Gly Asn Thr Leu Lys Thr Thr His Val Val Asn Leu
    380                 385                 390 gga agc aac cag tac ctt ttc tct gtc ata gtg gat cct aaa gaa atg      1360
Gly Ser Asn Gln Tyr Leu Phe Ser Val Ile Val Asp Pro Lys Glu Met
395                 400                 405                 410 ccc tgc ttc tgt ttg cgc cat gat gtt gat gcc cta ctc tgg caa cca      1408
Pro Cys Phe Cys Leu Arg His Asp Val Asp Ala Leu Leu Trp Gln Pro
                415                 420                 425 cac tcc agc aaa caa gat gat atg tgg gag cac atc gca act ttc aat      1456
His Ser Ser Lys Gln Asp Asp Met Trp Glu His Ile Ala Thr Phe Asn
            430                 435                 440 gct tta ggc tat gtc caa gca tca aag aga gac aaa aaa ttt ttt gcc      1504
Ala Leu Gly Tyr Val Gln Ala Ser Lys Arg Asp Lys Lys Phe Phe Ala
            445                 450                 455 tgt gct cca aat tac tcg tat gca gcc ctt tgt gag tgc ctt cgt cga      1552
Cys Ala Pro Asn Tyr Ser Tyr Ala Ala Leu Cys Glu Cys Leu Arg Arg
    460                 465                 470 gta ttc atc tat cgt cag cct gct ccc atg tcc act gta ctt tac aac      1600
Val Phe Ile Tyr Arg Gln Pro Ala Pro Met Ser Thr Val Leu Tyr Asn
475                 480                 485                 490 aga aag gaa ggc agg caa gta gga cag gtt gct aag cag caa gta gca      1648
```

-continued

| | | | | | | | | | | | | |
|---|---|---|---|---|---|---|---|---|---|---|---|---|
|Arg|Lys|Glu|Gly|Arg|Gln|Val|Gly|Gln|Val|Ala|Lys|Gln|Gln|Val|Ala|
| | | |495| | | |500| | | |505| | | | |

```
agc cta gaa acc aat gat cct att tta gga ttt cag gca aca aat gag   1696
Ser Leu Glu Thr Asn Asp Pro Ile Leu Gly Phe Gln Ala Thr Asn Glu
        510                 515                 520 aga tta ttt gtt ctt act acc aaa aac ctc ttt tta ata aaa gta aat   1744
Arg Leu Phe Val Leu Thr Thr Lys Asn Leu Phe Leu Ile Lys Val Asn
        525                 530                 535 aca gag aat taattattct aacatattgg cctctttgta ctggaaaagt           1793
Thr Glu Asn
    540 attcagtggt acctggaggt ctggacagtt atactgtaac ctcttaagtt ttaatgtgct  1853 aaatatatct tgtatgattt tttatttttt aataacattg gaaatatatt caagagatta  1913 tgattctgta aagctgtgga atgaagctgc agatttagag aacattggct tctgaaaaaa  1973 aaaaagagtg aagatagtac tagcaagtat acttattttt taaaacaggc tagaatctca  2033 tgttttatat gaaagatgta caattcagtg tttaaaaata aaaatattta ttgtgtaaaa  2093 aaaaaaaaaa a                                                      2104

<210> SEQ ID NO 29
<211> LENGTH: 515
<212> TYPE: DNA
<213> ORGANISM: Homo Sapiens
<220> FEATURE:
<221> NAME/KEY: CDS
<222> LOCATION: 144..440
<220> FEATURE:
<221> NAME/KEY: sig_peptide
<222> LOCATION: 144..287
<223> OTHER INFORMATION: Von Heijne matrix
      score 4.10
      seq VFMLIVSVLALIP/ET
<220> FEATURE:
<221> NAME/KEY: polyA_signal
<222> LOCATION: 457..462
<220> FEATURE:
<221> NAME/KEY: polyA_site
<222> LOCATION: 500..515
<220> FEATURE:
<221> NAME/KEY: misc_feature
<222> LOCATION: 60
<223> OTHER INFORMATION: n=a, g, c or t

<400> SEQUENCE: 29
agagagcggg aagccgagct gggcgagaag taggggaggg cggtgctccg cgcggtggcn   60
gttgctatcg cttcgcagaa cctactcagg cagccagctg agaagagttg agggaaagtg   120
ctgctgctgg gtctgcagac gcg atg gat aac gtg cag ccg aaa ata aaa cat  173
                            Met Asp Asn Val Gln Pro Lys Ile Lys His
                                -45                 -40 cgc ccc ttc tgc ttc agt gtg aaa ggc cac gtg aag atg ctg cgg ctg   221
Arg Pro Phe Cys Phe Ser Val Lys Gly His Val Lys Met Leu Arg Leu
        -35                 -30                 -25 gat att atc aac tca ctg gta aca aca gta ttc atg ctc atc gta tct   269
Asp Ile Ile Asn Ser Leu Val Thr Thr Val Phe Met Leu Ile Val Ser
        -20                 -15                 -10 gtg ttg gca ctg ata cca gaa acc aca aca ttg aca gtt ggt gga ggg   317
Val Leu Ala Leu Ile Pro Glu Thr Thr Thr Leu Thr Val Gly Gly Gly
        -5                  1                   5                   10 gtg ttt gca ctt gtg aca gca gta tgc tgt ctt gcc gac ggg gcc ctt   365
Val Phe Ala Leu Val Thr Ala Val Cys Cys Leu Ala Asp Gly Ala Leu
                15                  20                  25 att tac cgg aag ctt ctg ttc aat ccc agc ggt cct tac cag aaa aag   413
```

```
                Ile Tyr Arg Lys Leu Leu Phe Asn Pro Ser Gly Pro Tyr Gln Lys Lys
                                30                  35                  40 cct gtg cat gaa aaa aaa gaa gtt ttg taattttata ttacttttta                     460
Pro Val His Glu Lys Lys Glu Val Leu
        45                  50 gtttgatact aagtattaaa catatttctg tattcttcca aaaaaaaaaa aaaat                  515

<210> SEQ ID NO 30
<211> LENGTH: 661
<212> TYPE: DNA
<213> ORGANISM: Homo Sapiens
<220> FEATURE:
<221> NAME/KEY: CDS
<222> LOCATION: 174..443
<220> FEATURE:
<221> NAME/KEY: sig_peptide
<222> LOCATION: 174..269
<223> OTHER INFORMATION: Von Heijne matrix
      score 4.10
      seq SSLAFCQVGFLTA/QP
<220> FEATURE:
<221> NAME/KEY: polyA_signal
<222> LOCATION: 623..628
<220> FEATURE:
<221> NAME/KEY: polyA_site
<222> LOCATION: 647..661

<400> SEQUENCE: 30
aaaaaggaac tttcagtgat aatgaacaaa actcaggagc tatgtggatg acaggagcac             60
ctagatgacc gactttaccc acttcaaatg ctaccttgac cctagcactc tctccaccct            120
gcatcctcac ctcagaccat cagttggtta ggccaacagc tcaccatcaa ttc atg              176
                                                               Met ccc tgc cta gac caa cag ctc act gtt cat gcc cta ccc tgc cct gcc             224
Pro Cys Leu Asp Gln Gln Leu Thr Val His Ala Leu Pro Cys Pro Ala
    -30                 -25                 -20 cag ccc tcc tct ctg gcc ttc tgc caa gtg ggg ttc tta aca gca cag             272
Gln Pro Ser Ser Leu Ala Phe Cys Gln Val Gly Phe Leu Thr Ala Gln
-15                 -10                  -5                   1 cct tca cct ccg aga agg cgc aat ggg aaa gac aga tac acg ttg gtt             320
Pro Ser Pro Pro Arg Arg Arg Asn Gly Lys Asp Arg Tyr Thr Leu Val
            5                   10                  15 ctg caa cac cag gaa tgc cag gat gat tta gcc acc tcc tca ctt gtc             368
Leu Gln His Gln Glu Cys Gln Asp Asp Leu Ala Thr Ser Ser Leu Val
        20                  25                  30 tac ctt tcc ctc ccc tgc ttc aaa gac ttg ggt cga tcg aag cac caa             416
Tyr Leu Ser Leu Pro Cys Phe Lys Asp Leu Gly Arg Ser Lys His Gln
    35                  40                  45 agc atc act gtt gct gac act aac aag tagtgccaag ggattgcctt                   463
Ser Ile Thr Val Ala Asp Thr Asn Lys
50                  55 taaggaagat caggagcgga acatctggtg gcaaagaaaa tctttctaat agccccattc           523
tagtgaccac cttcaaccctc ctcatagcag gagagtttgg gagtagggga cttaggatgt          583
tttgttcttt taatcaattc agaaatatatg tatgtttgaa ataaaaataa aaatacttga          643
gccaaaaaaa aaaaaaaa                                                         661

<210> SEQ ID NO 31
<211> LENGTH: 694
<212> TYPE: DNA
<213> ORGANISM: Homo Sapiens
<220> FEATURE:
<221> NAME/KEY: CDS
<222> LOCATION: 55..399
```

```
<220> FEATURE:
<221> NAME/KEY: sig_peptide
<222> LOCATION: 55..192
<223> OTHER INFORMATION: Von Heijne matrix
      score 4.70
      seq ILTGLTVGSAADA/GE
<220> FEATURE:
<221> NAME/KEY: polyA_signal
<222> LOCATION: 654..659
<220> FEATURE:
<221> NAME/KEY: polyA_site
<222> LOCATION: 680..694

<400> SEQUENCE: 31
aatgcttgag gaaaactggg aacagtatat tgttctgaaa acctaaaaag ttta atg          57
                                                              Met aaa acc ttg ttc aat cca gcc cct gcc att gct gac ctg gat ccc cag         105
Lys Thr Leu Phe Asn Pro Ala Pro Ala Ile Ala Asp Leu Asp Pro Gln
-45                 -40                 -35                 -30 ttc tac acc ctc tca gat gtg ttc tgc tgc aat gaa agt gag gct gag         153
Phe Tyr Thr Leu Ser Asp Val Phe Cys Cys Asn Glu Ser Glu Ala Glu
                -25                 -20                 -15 att tta act ggc ctc acg gtg ggc agc gct gca gat gct ggg gag gct         201
Ile Leu Thr Gly Leu Thr Val Gly Ser Ala Ala Asp Ala Gly Glu Ala
        -10                  -5                   1 gca tta gtg ctc ttg aaa agg ggc tgc cag gtg gta atc att acc tta         249
Ala Leu Val Leu Leu Lys Arg Gly Cys Gln Val Val Ile Ile Thr Leu
  5                  10                  15 ggg gct gaa gga tgt gtg gtg ctg tca cag aca gaa cct gag cca aag         297
Gly Ala Glu Gly Cys Val Val Leu Ser Gln Thr Glu Pro Glu Pro Lys
 20                  25                  30                  35 cac att ccc aca gag aaa gtc aag gct gtg gat acc acg tgt aga cct         345
His Ile Pro Thr Glu Lys Val Lys Ala Val Asp Thr Thr Cys Arg Pro
                 40                  45                  50 ggc tca aga ccc aag agt gaa gca gca agt gtg aag aag cag aaa cat         393
Gly Ser Arg Pro Lys Ser Glu Ala Ala Ser Val Lys Lys Gln Lys His
                 55                  60                  65 tat aaa taacccagag aatccttta taacagcaac tgcctactga ttttgtggcc           449
Tyr Lys taacagctcg agcaaaaatg aatataaata caacattgtg caatgactaa ttactcaaaa       509
ttttgtgcat cagcagaagt ggaacctgtg gttggtgcta atattatgaa atgcctttgc       569
tgtttaataa tctggtagct ctgtattatt tagcatgcat ttttcttgga gaacaatgat       629
tttatttcaa gtacctctca ctgaaataaa aaagcagctg ttagaagacg aaaaaaaaaa       689
aaaaa                                                                   694

<210> SEQ ID NO 32
<211> LENGTH: 1110
<212> TYPE: DNA
<213> ORGANISM: Homo Sapiens
<220> FEATURE:
<221> NAME/KEY: CDS
<222> LOCATION: 90..287
<220> FEATURE:
<221> NAME/KEY: sig_peptide
<222> LOCATION: 90..146
<223> OTHER INFORMATION: Von Heijne matrix
      score 9.30
      seq VFVFLFLWDPVLA/GI
<220> FEATURE:
<221> NAME/KEY: polyA_signal
<222> LOCATION: 1078..1083
<220> FEATURE:
<221> NAME/KEY: polyA_site
<222> LOCATION: 1096..1110
```

<400> SEQUENCE: 32

```
atcatcttac atcagcacaa gaagaagagt gagcatagca caccgatgtc agaccctgcc      60
actagcctcc ttaacagaag ttcccagcc atg aag cct ctc ctt gtt gtg ttt      113
                                Met Lys Pro Leu Leu Val Val Phe
                                    -15 gtc ttt ctt ttc ctt tgg gat cca gtg ctg gca ggt ata aat tca tta      161
Val Phe Leu Phe Leu Trp Asp Pro Val Leu Ala Gly Ile Asn Ser Leu
    -10              -5                  1               5 tca tca gaa atg cac aag aaa tgc tat aaa aat ggc atc tgc aga ctt      209
Ser Ser Glu Met His Lys Lys Cys Tyr Lys Asn Gly Ile Cys Arg Leu
             10              15              20 gaa tgc tat gag agt gaa atg tta gtt gcc tac tgt atg ttt cag ctg      257
Glu Cys Tyr Glu Ser Glu Met Leu Val Ala Tyr Cys Met Phe Gln Leu
         25              30              35 gag tgc tgt gtc aaa gga aat cct gca ccc tgacataaga aaccaatgaa        307
Glu Cys Cys Val Lys Gly Asn Pro Ala Pro
         40              45 tggccactat cctgtaggcc cttgattctg ccatctttca caaaaccagg gaatttagat    367
caaactgtga caccatgatg tgtccatgac tactggtttt tagcattttt ataggccagc    427
agactcttgt ggtcttaaat ttaaagagct gagctgtagc cttctttaaa agagctcggt    487
ttttcacaaa aacaatgtag aagatatttt ctcacctcaa cgtgatgtcc agtgtgctca    547
tcagcacctg tttctccctc taatcataga ggatattctt attatttaga aaggcttcaa    607
gggaaacaac ttttggcacc taagtcgtgt cctaccttcg cttcagcttc gcatttccca    667
tttctgtgaa attcccaact ttagagaagc agatttgcca tggccttctg acaaccttgt    727
acatctctca cataaaccgc ataggcaggg cttaactaca ggctggcccg agtctggact    787
gagtctgacc ctgaagttcc tttggaacag gagaggccat cttgtgatgg ctggaacaa     847 ggtaatttct catccacctc cctagtttca gttgagcaat ggaacttccc acctgagccc    907
ctagggttca gctacaggct ataagactgc cgtcctgtgg tttagtgttg gttccttagc    967
agcagagtga tgccacctct gctgcccgtc atctgactcc tctggatggg tgttatcctg   1027
tggcttaaga gctaacacca tgctgatctt gctttgctat atgtgtaact aataaactgc   1087
ctaaatgcaa aaaaaaaaa aaa                                            1110
```

<210> SEQ ID NO 33
<211> LENGTH: 623
<212> TYPE: DNA
<213> ORGANISM: Homo Sapiens
<220> FEATURE:
<221> NAME/KEY: CDS
<222> LOCATION: 49..447
<220> FEATURE:
<221> NAME/KEY: sig_peptide
<222> LOCATION: 49..111
<223> OTHER INFORMATION: Von Heijne matrix
      score 5.00
      seq LIVIFFYCWLSSS/HE
<220> FEATURE:
<221> NAME/KEY: polyA_signal
<222> LOCATION: 579..584
<220> FEATURE:
<221> NAME/KEY: polyA_site
<222> LOCATION: 602..623

<400> SEQUENCE: 33

```
attagaattt tctttctcaa attaaaggtt tgagaaattc gtgatgag atg tcc tgt       57
                                                    Met Ser Cys
                                                        -20
```

```
tcc cta aag ttt act ttg att gta att ttt ttt tac tgt tgg ctt tca      105
Ser Leu Lys Phe Thr Leu Ile Val Ile Phe Phe Tyr Cys Trp Leu Ser
        -15             -10                     -5 tcc agc cat gag gag tta gaa ggt ggt aca tcg aag tct ttt gac ctc      153
Ser Ser His Glu Glu Leu Glu Gly Gly Thr Ser Lys Ser Phe Asp Leu
         1               5                      10 cat aca gtg att atg ctt gtc atc gct ggt ggt atc ctg gcg gcc ttg      201
His Thr Val Ile Met Leu Val Ile Ala Gly Gly Ile Leu Ala Ala Leu
 15              20                  25                      30 ctc ctg ctg ata gtt gtc gtg ctc tgt ctt tac ttc aaa ata cac aac      249
Leu Leu Leu Ile Val Val Val Leu Cys Leu Tyr Phe Lys Ile His Asn
                 35                  40                      45 gcg cta aaa gct gca aag gaa cct gaa gct gtg gct gta aaa aat cac      297
Ala Leu Lys Ala Ala Lys Glu Pro Glu Ala Val Ala Val Lys Asn His
         50                  55                      60 aac cca gac aag gtg tgg tgg gcc aag aac agc cag gcc aaa acc att      345
Asn Pro Asp Lys Val Trp Trp Ala Lys Asn Ser Gln Ala Lys Thr Ile
         65                  70                      75 gcc acg gag tct tgt cct gcc ctg cag tgc tgt gaa gga tat aga atg      393
Ala Thr Glu Ser Cys Pro Ala Leu Gln Cys Cys Glu Gly Tyr Arg Met
 80              85                  90 tgt gcc agt ttt gat tcc ctg cca cct tgc tgt tgc gac ata aat gag      441
Cys Ala Ser Phe Asp Ser Leu Pro Pro Cys Cys Cys Asp Ile Asn Glu
 95              100                 105                     110 ggc ctc tgagttagga aaggtgggca caaaaatctt catgagcaat acttcttagt       497
Gly Leu agattgtttt gttattcaaa tcaagttcta gtgttttat gtgagattat ataatttaca     557
gtgttgtttt atatactttt gaataaatgt acactattaa aataaaaaaa aaaaaaaat     617 gccaaa                                                               623

<210> SEQ ID NO 34
<211> LENGTH: 657
<212> TYPE: DNA
<213> ORGANISM: Homo Sapiens
<220> FEATURE:
<221> NAME/KEY: CDS
<222> LOCATION: 199..618
<220> FEATURE:
<221> NAME/KEY: sig_peptide
<222> LOCATION: 199..408
<223> OTHER INFORMATION: Von Heijne matrix
      score 3.90
      seq FKVLTQPLSLLWG/CD
<220> FEATURE:
<221> NAME/KEY: polyA_signal
<222> LOCATION: 626..631
<220> FEATURE:
<221> NAME/KEY: polyA_site
<222> LOCATION: 643..657

<400> SEQUENCE: 34
aactggatag agtactgccc ccttcagccc atggagaaag gcaaatgcct ccttcagagt      60
ctacctaatg ctttctcaga taaataagca tgaagaaaag tcaaagtcca ttctagctct     120
aaaataagga atgaaatgtt ttcctgatat gatttttgt tttcatctga taataatttt      180
atatatcaca gaaacagc atg gtt ctt act aaa cct ctt caa aga aat ggc       231
                    Met Val Leu Thr Lys Pro Leu Gln Arg Asn Gly
                        -70             -65                 -60 agc atg atg agc ttt gaa aat gtg aaa gaa aag agc aga gaa gga ggg       279
Ser Met Met Ser Phe Glu Asn Val Lys Glu Lys Ser Arg Glu Gly Gly
        -55                 -50                 -45
```

```
ccc cat gca cac aca ccc gaa gaa gaa ttg tgt ttc gtg gta aca cac       327
Pro His Ala His Thr Pro Glu Glu Glu Leu Cys Phe Val Val Thr His
            -40                 -35                 -30 tac cct cag gtt cag acc aca ctc aac ctg ttt ttc cat ata ttc aag       375
Tyr Pro Gln Val Gln Thr Thr Leu Asn Leu Phe Phe His Ile Phe Lys
        -25                 -20                 -15 gtt ctt act caa cca ctt tcc ctt ctg tgg ggt tgt gat cag aag cct       423
Val Leu Thr Gln Pro Leu Ser Leu Leu Trp Gly Cys Asp Gln Lys Pro
    -10                  -5                   1                   5 cgt act gtt cct acc ctt gga aac ggc gca tgg gat acc tgc caa caa       471
Arg Thr Val Pro Thr Leu Gly Asn Gly Ala Trp Asp Thr Cys Gln Gln
                 10                  15                  20 cac ata cgc act tca tca tgg aca gca aac aca ctc gtc att caa aac       519
His Ile Arg Thr Ser Ser Trp Thr Ala Asn Thr Leu Val Ile Gln Asn
             25                  30                  35 cag cat tca cgg gaa agc act gtt tct gtt tgc ctt ttt atg tta atc       567
Gln His Ser Arg Glu Ser Thr Val Ser Val Cys Leu Phe Met Leu Ile
         40                  45                  50 cgc atg caa cat att ttg aaa aca gat aca ctt caa cag ttc aga ata       615
Arg Met Gln His Ile Leu Lys Thr Asp Thr Leu Gln Gln Phe Arg Ile
     55                  60                  65 tgc tagtactaat aaaaccaaca tgttaaaaaa aaaaaaaaa                        657
Cys
70

<210> SEQ ID NO 35
<211> LENGTH: 1137
<212> TYPE: DNA
<213> ORGANISM: Homo Sapiens
<220> FEATURE:
<221> NAME/KEY: CDS
<222> LOCATION: 271..969
<220> FEATURE:
<221> NAME/KEY: sig_peptide
<222> LOCATION: 271..366
<223> OTHER INFORMATION: Von Heijne matrix
      score 5.60
      seq WMGLACFRSLAAS/SP
<220> FEATURE:
<221> NAME/KEY: polyA_signal
<222> LOCATION: 1092..1097
<220> FEATURE:
<221> NAME/KEY: polyA_site
<222> LOCATION: 1123..1137

<400> SEQUENCE: 35 aaaaacctttt caagtgcccc ctcctttcct taaagtcttt tataggggtc cccttcttgg       60
ccatctccat cctgtgagtc aggactgaaa gggcacagac aggtcactgc cagcattgtt      120
ggggcaagcc tgcaagcacg catcactggg gatctgacat gacaatggcc gcctgccccc      180
tctgagggct acaggactta ccccagtggg aagcagctaa gcaggtctga ccagccgacc      240
tggacctggc caagggtcct gtcatccctc atg gcc acc ccg cca ttc cgg ctg       294
                                    Met Ala Thr Pro Pro Phe Arg Leu
                                        -30                 -25 ata agg aag atg ttt tcc ttc aag gtg agc aga tgg atg ggc ctt gcc       342
Ile Arg Lys Met Phe Ser Phe Lys Val Ser Arg Trp Met Gly Leu Ala
             -20                 -15                 -10 tgc ttc cgg tcc ctg gcg gca tcc tct ccc agt att cgc cag aag aaa       390
Cys Phe Arg Ser Leu Ala Ala Ser Ser Pro Ser Ile Arg Gln Lys Lys
         -5                   1                   5 cta atg cac aag ctg cag gag gaa aag gct ttt cgc gaa gag atg aaa       438
Leu Met His Lys Leu Gln Glu Glu Lys Ala Phe Arg Glu Glu Met Lys
     10                  15                  20
```

```
att ttt cgt gaa aaa ata gag gac ttc agg gaa gag atg tgg act ttc          486
Ile Phe Arg Glu Lys Ile Glu Asp Phe Arg Glu Glu Met Trp Thr Phe
 25                  30                  35                  40 cga ggc aag atc cat gct ttc cgg ggc cag atc ctg ggt ttt tgg gaa          534
Arg Gly Lys Ile His Ala Phe Arg Gly Gln Ile Leu Gly Phe Trp Glu
                 45                  50                  55 gag gag aga cct ttc tgg gaa gag gag aaa acc ttc tgg aaa gag gaa          582
Glu Glu Arg Pro Phe Trp Glu Glu Glu Lys Thr Phe Trp Lys Glu Glu
             60                  65                  70 aaa tcc ttc tgg gaa atg gaa aag tct ttc agg gag gaa gag aaa act          630
Lys Ser Phe Trp Glu Met Glu Lys Ser Phe Arg Glu Glu Glu Lys Thr
         75                  80                  85 ttc tgg aaa aag tac cgc act ttc tgg aag gag gat aag gcc ttc tgg          678
Phe Trp Lys Lys Tyr Arg Thr Phe Trp Lys Glu Asp Lys Ala Phe Trp
     90                  95                 100 aaa gag gac aat gcc tta tgg gaa aga gac cgg aac ctt ctt cag gag          726
Lys Glu Asp Asn Ala Leu Trp Glu Arg Asp Arg Asn Leu Leu Gln Glu
105                 110                 115                 120 gac aag gcc ctg tgg gag gaa gaa aag gcc ctg tgg gta gag gaa aga          774
Asp Lys Ala Leu Trp Glu Glu Lys Ala Leu Trp Val Glu Glu Arg
                125                 130                 135 gcc ctc ctt gag ggg gag aaa gcc ctg tgg gaa gat aaa acg tcc ctc          822
Ala Leu Leu Glu Gly Glu Lys Ala Leu Trp Glu Asp Lys Thr Ser Leu
            140                 145                 150 tgg gag gaa gag aat gcc ctc tgg gag gaa gag agg gcc ttc tgg atg          870
Trp Glu Glu Glu Asn Ala Leu Trp Glu Glu Glu Arg Ala Phe Trp Met
        155                 160                 165 gag aac aat ggc cac att gcc gga gag cag atg ctc gaa gat ggg ccc          918
Glu Asn Asn Gly His Ile Ala Gly Glu Gln Met Leu Glu Asp Gly Pro
    170                 175                 180 cac aac gcc aac aga ggg cag cgc ttg ctg gcc ttc tcc cga ggc agg          966
His Asn Ala Asn Arg Gly Gln Arg Leu Leu Ala Phe Ser Arg Gly Arg
185                 190                 195                 200 gcg tagccagcat gcaggtgcag ggccctgtgg tccagactcc cctgggttgg             1019
Ala gattcaagtc cagggtgagc ccatgtgctg gagaaaatac acactcattg gtctccttgc       1079
tttgaaagat ccaataaagt cctgaggcaa ggtttggaaa accaaaaaaa aaaaaaaa         1137

<210> SEQ ID NO 36
<211> LENGTH: 636
<212> TYPE: DNA
<213> ORGANISM: Homo Sapiens
<220> FEATURE:
<221> NAME/KEY: CDS
<222> LOCATION: 192..440
<220> FEATURE:
<221> NAME/KEY: sig_peptide
<222> LOCATION: 192..278
<223> OTHER INFORMATION: Von Heijne matrix
      score 5.20
      seq VVFMTVAAGGASS/FA
<220> FEATURE:
<221> NAME/KEY: polyA_signal
<222> LOCATION: 590..595
<220> FEATURE:
<221> NAME/KEY: polyA_site
<222> LOCATION: 622..636

<400> SEQUENCE: 36
aaaagcgagt caggtccctc gcgctcccgc cccacgcgcg tgaccagagc gcgctggccc         60
ggcccacccg gggcggttgt ggtcgctata tataaggtgg ggaggccgcc ggcccgttcg        120
gttccgggcg ttaccatcgt ccgtgcgcac cgcccggcgt ccagatttgg caattcttcg       180
```

```
ctgaagtcat c atg agc ttt ttc caa ctc ctg atg aaa agg aag gaa ctc       230
            Met Ser Phe Phe Gln Leu Leu Met Lys Arg Lys Glu Leu
                    -25                 -20 att ccc ttg gtg gtg ttc atg act gtg gcg gcg ggt gga gcc tca tct       278
Ile Pro Leu Val Val Phe Met Thr Val Ala Ala Gly Gly Ala Ser Ser
    -15                 -10                 -5 ttc gct gtg tat tct ctt tgg aaa acc gat gtg atc ctt gat cga aaa       326
Phe Ala Val Tyr Ser Leu Trp Lys Thr Asp Val Ile Leu Asp Arg Lys
1               5                   10                  15 aaa aat cca gaa cct tgg gaa act gtg gac cct act gta cct caa aag       374
Lys Asn Pro Glu Pro Trp Glu Thr Val Asp Pro Thr Val Pro Gln Lys
            20                  25                  30 ctt ata aca atc aac caa caa tgg aaa ccc att gaa gag ttg caa aat       422
Leu Ile Thr Ile Asn Gln Gln Trp Lys Pro Ile Glu Glu Leu Gln Asn
                35                  40                  45 gtc caa agg gtg acc aaa tgacgagccc tcgcctcttt cttctgaaga             470
Val Gln Arg Val Thr Lys
                50 gtactctata aatctagtgg aaacatttct gcacaaacta gattctggac accagtgtgc    530 ggaaatgctt ctgctacatt tttagggttt gtctacattt tttgggctct ggataaggaa    590 ttaaaggagt gcagcaataa ctgcactgtc caaaaaaaaa aaaaaa                   636

<210> SEQ ID NO 37
<211> LENGTH: 818
<212> TYPE: DNA
<213> ORGANISM: Homo Sapiens
<220> FEATURE:
<221> NAME/KEY: CDS
<222> LOCATION: 59..703
<220> FEATURE:
<221> NAME/KEY: sig_peptide
<222> LOCATION: 59..181
<223> OTHER INFORMATION: Von Heijne matrix
      score 6.80
      seq LVSCLSSQSSALS/QS
<220> FEATURE:
<221> NAME/KEY: polyA_signal
<222> LOCATION: 783..788
<220> FEATURE:
<221> NAME/KEY: polyA_site
<222> LOCATION: 804..818

<400> SEQUENCE: 37
gacatcttga gctgaagcag ggttttgagc cactgctgct gctgctgcca ttgtcacc       58 atg gtc tca gct ctg cgg gga gca ccc ctg atc agg gtg cac tca agc      106
Met Val Ser Ala Leu Arg Gly Ala Pro Leu Ile Arg Val His Ser Ser
    -40                 -35                 -30 cct gtt tct tct cct tct gtg agt gga cca cgg agg ctg gtg agc tgc      154
Pro Val Ser Ser Pro Ser Val Ser Gly Pro Arg Arg Leu Val Ser Cys
-25                 -20                 -15                 -10 ctg tca tcc caa agc tca gct ctg agc cag agt ggt ggt ggc tcc acc      202
Leu Ser Ser Gln Ser Ser Ala Leu Ser Gln Ser Gly Gly Gly Ser Thr
                -5                  1                   5 tct gcc gcc ggc ata gaa gcc agg agc agg gct ctc aga agg cgg tgg      250
Ser Ala Ala Gly Ile Glu Ala Arg Ser Arg Ala Leu Arg Arg Arg Trp
        10                  15                  20 tgc cca gct ggg atc atg ttg ttg gcc ctg gtc tgt ctg ctc agc tgc      298
Cys Pro Ala Gly Ile Met Leu Leu Ala Leu Val Cys Leu Leu Ser Cys
    25                  30                  35 ctg cta ccc tcc agt gag gcc aag ctc tac ggt cgt tgt gaa ctg gcc      346
Leu Leu Pro Ser Ser Glu Ala Lys Leu Tyr Gly Arg Cys Glu Leu Ala
40                  45                  50                  55
```

```
aga gtg cta cat gac ttc ggg ctg gac gga tac cgg gga tac agc ctg      394
Arg Val Leu His Asp Phe Gly Leu Asp Gly Tyr Arg Gly Tyr Ser Leu
             60                  65                  70 gct gac tgg gtc tgc ctt gct tat ttc aca agc ggt ttc aac gca gct      442
Ala Asp Trp Val Cys Leu Ala Tyr Phe Thr Ser Gly Phe Asn Ala Ala
         75                  80                  85 gct ttg gac tac gag gct gat ggg agc acc aac aac ggg atc ttc cag      490
Ala Leu Asp Tyr Glu Ala Asp Gly Ser Thr Asn Asn Gly Ile Phe Gln
             90                  95                 100 atc aac agc cgg agg tgg tgc agc aac ctc acc ccg aac gtc ccc aac      538
Ile Asn Ser Arg Arg Trp Cys Ser Asn Leu Thr Pro Asn Val Pro Asn
    105                 110                 115 gtg tgc cgg atg tac tgc tca gat ttg ttg aat cct aat ctc aag gat      586
Val Cys Arg Met Tyr Cys Ser Asp Leu Leu Asn Pro Asn Leu Lys Asp
120                 125                 130                 135 acc gtt atc tgt gcc atg aag ata acc caa gag cct cag ggt ctg ggt      634
Thr Val Ile Cys Ala Met Lys Ile Thr Gln Glu Pro Gln Gly Leu Gly
                140                 145                 150 tac tgg gag gcc tgg agg cat cac tgc cag gga aaa gac ctc act gaa      682
Tyr Trp Glu Ala Trp Arg His His Cys Gln Gly Lys Asp Leu Thr Glu
            155                 160                 165 tgg gtg gat ggc tgt gac ttc taggatggac ggaaccatgc acagcaggct         733
Trp Val Asp Gly Cys Asp Phe
            170 gggaaatgtg gtttggttcc tgacctaggc ttgggaagac aagccagcga ataaaggatg    793 gttgaacgtg aaaaaaaaaa aaaaa                                          818

<210> SEQ ID NO 38
<211> LENGTH: 1888
<212> TYPE: DNA
<213> ORGANISM: Homo Sapiens
<220> FEATURE:
<221> NAME/KEY: CDS
<222> LOCATION: 139..1389
<220> FEATURE:
<221> NAME/KEY: sig_peptide
<222> LOCATION: 139..198
<223> OTHER INFORMATION: Von Heijne matrix
      score 5.00
      seq HLLAGFCVWVVLG/WV
<220> FEATURE:
<221> NAME/KEY: polyA_signal
<222> LOCATION: 1854..1859
<220> FEATURE:
<221> NAME/KEY: polyA_site
<222> LOCATION: 1873..1888

<400> SEQUENCE: 38
cccccccagc tggaaccaag aaggttgtgt ccccttcct ctgggtgtcc ttgtctcctg      60
ctatcagggc acagtcctca ggatgtttcg gggagaatag agccagaac ctgagcccct     120 aagccattcc cctcacca atg atg ggg tcc cca gtg agt cat ctg ctg gcc      171
                     Met Met Gly Ser Pro Val Ser His Leu Leu Ala
                     -20                 -15                 -10 ggc ttc tgt gtg tgg gtc gtc ttg ggc tgg gta ggg ggc tca gtc ccc      219
Gly Phe Cys Val Trp Val Val Leu Gly Trp Val Gly Gly Ser Val Pro
         -5                   1                   5 aac ctg ggc cct gct gag cag gag cag aac cat tac ctg gcc cag ctg      267
Asn Leu Gly Pro Ala Glu Gln Glu Gln Asn His Tyr Leu Ala Gln Leu
             10                  15                  20 ttt ggc ctg tac ggc gag aat ggg acg ctg act gca ggg ggc ttg gcg      315
Phe Gly Leu Tyr Gly Glu Asn Gly Thr Leu Thr Ala Gly Gly Leu Ala
    25                  30                  35
```

```
cgg ctt ctc cac agc ctg ggg cta ggc cga gtt cag ggg ctt cgc ctg    363
Arg Leu Leu His Ser Leu Gly Leu Gly Arg Val Gln Gly Leu Arg Leu
 40                  45                  50                  55 gga cag cat ggg cct ctg act gga cgg gct gca tcc cca gct gca gac    411
Gly Gln His Gly Pro Leu Thr Gly Arg Ala Ala Ser Pro Ala Ala Asp
                 60                  65                  70 aat tcc aca cac agg cca cag aac cct gag ctg agt gtg gat gtc tgg    459
Asn Ser Thr His Arg Pro Gln Asn Pro Glu Leu Ser Val Asp Val Trp
             75                  80                  85 gca ggg atg cct ctg ggt ccc tca ggg tgg ggt gac ctg gaa gag tca    507
Ala Gly Met Pro Leu Gly Pro Ser Gly Trp Gly Asp Leu Glu Glu Ser
         90                  95                 100 aag gcc cct cac cta ccc cgt ggg cca gcc ccc tcg ggc ctg gac ctc    555
Lys Ala Pro His Leu Pro Arg Gly Pro Ala Pro Ser Gly Leu Asp Leu
     105                 110                 115 ctt cac agg ctt ctg ttg ctg gac cac tca ttg gct gac cac ctg aat    603
Leu His Arg Leu Leu Leu Leu Asp His Ser Leu Ala Asp His Leu Asn
 120                 125                 130                 135 gag gat tgt ctg aac ggc tcc cag ctg ctg gtc aat ttt ggc ttg agc    651
Glu Asp Cys Leu Asn Gly Ser Gln Leu Leu Val Asn Phe Gly Leu Ser
                 140                 145                 150 ccc gct gct cct ctg acc cct cgt cag ttt gct ctg ctg tgc cca gcc    699
Pro Ala Ala Pro Leu Thr Pro Arg Gln Phe Ala Leu Leu Cys Pro Ala
             155                 160                 165 ctg ctt tat cag atc gac agc cgc gtc tgc atc ggc gct ccg gcc cct    747
Leu Leu Tyr Gln Ile Asp Ser Arg Val Cys Ile Gly Ala Pro Ala Pro
         170                 175                 180 gca ccc cca ggg gat cta cta tct gcc ctg ctt cag agt gcc ctg gca    795
Ala Pro Pro Gly Asp Leu Leu Ser Ala Leu Leu Gln Ser Ala Leu Ala
     185                 190                 195 gtc ctg ttg ctc agc ctc cct tct ccc cta tcc ctg ctg ctg cgg        843
Val Leu Leu Leu Ser Leu Pro Ser Pro Leu Ser Leu Leu Leu Arg
 200                 205                 210                 215 ctc ctg gga cct cgt cta cta cgg ccc ttg ctg ggc ttc ctg ggg gcc    891
Leu Leu Gly Pro Arg Leu Leu Arg Pro Leu Leu Gly Phe Leu Gly Ala
                 220                 225                 230 ctg gcg gtg ggc act ctt tgt ggg gat gca ctg cta cat ctg cta ccg    939
Leu Ala Val Gly Thr Leu Cys Gly Asp Ala Leu Leu His Leu Leu Pro
             235                 240                 245 cat gca caa gaa ggg cgg cac gca gga cct ggc gga cta cca gag aag    987
His Ala Gln Glu Gly Arg His Ala Gly Pro Gly Gly Leu Pro Glu Lys
         250                 255                 260 gac ctg ggc ccg ggg ctg tca gtg ctc gga ggc ctc ttc ctg ctc ttt   1035
Asp Leu Gly Pro Gly Leu Ser Val Leu Gly Gly Leu Phe Leu Leu Phe
     265                 270                 275 gtg ctg gag aac atg ctg ggg ctt ttg cgg cac cga ggg ctc agg cca   1083
Val Leu Glu Asn Met Leu Gly Leu Leu Arg His Arg Gly Leu Arg Pro
 280                 285                 290                 295 aga tgc tgc agg cga aaa cga agg aat ctc gaa aca cgc aac ttg gat   1131
Arg Cys Cys Arg Arg Lys Arg Arg Asn Leu Glu Thr Arg Asn Leu Asp
                 300                 305                 310 ccg gag aat ggc agt ggg atg gcc ctt cag ccc cta cag gca gct cca   1179
Pro Glu Asn Gly Ser Gly Met Ala Leu Gln Pro Leu Gln Ala Ala Pro
             315                 320                 325 gag cca ggg gct cag ggc cag agg gag aag aac agc cag cac cca cca   1227
Glu Pro Gly Ala Gln Gly Gln Arg Glu Lys Asn Ser Gln His Pro Pro
         330                 335                 340 gct ctg gcc cct cct ggg cac caa ggc cac agt cat ggg cac cag ggt   1275
Ala Leu Ala Pro Pro Gly His Gln Gly His Ser His Gly His Gln Gly
```

```
       345                 350                 355
ggc act gat atc acg tgg atg gtc ctc ctg gga gat ggt cta cac aac        1323
Gly Thr Asp Ile Thr Trp Met Val Leu Leu Gly Asp Gly Leu His Asn
360                 365                 370                 375 ctc act gat ggg ctg gcc ata ggt gct gcc ttc tct gat ggc ttc tcc        1371
Leu Thr Asp Gly Leu Ala Ile Gly Ala Ala Phe Ser Asp Gly Phe Ser
                380                 385                 390 gcg gcc tca gta cca cct tagcggtctt ctgccatgag ctgccccacg              1419
Ala Ala Ser Val Pro Pro
                395 aactgggtga ctttgccatg ctgctccagt cagggctgtc ctttcggcgg ctgctgctgc     1479 tgagcctcgt gtctggagcc ctgggattgg ggggtgcagt cctgggggtg gggctcagcc     1539 tgggcccctgt cccctcact ccctgggtgt ttggggtcac tgctgggtc ttcctctatg      1599 tggcccttgt ggacatgcta ccagccctgc ttcgtcctcc ggagcccctg cctacgcccc     1659 atgtgctcct gcaggggctg gggctgctgc tgggggcgg cctcatgctt gccataaccc      1719 tgctggagga gcggctactg cccgtgacca ctgagggctg atggggccag tggaaagggg     1779 tcgggttgcc cttccttccc cccaaccaca ggaatggagg cgggacacag gccagtagg      1839 agcaatagga ttttaataaa cagaacccat cccaaaaaaa aaaaaaaaa                 1888

<210> SEQ ID NO 39
<211> LENGTH: 1894
<212> TYPE: DNA
<213> ORGANISM: Homo Sapiens
<220> FEATURE:
<221> NAME/KEY: CDS
<222> LOCATION: 21..1118
<220> FEATURE:
<221> NAME/KEY: sig_peptide
<222> LOCATION: 21..89
<223> OTHER INFORMATION: Von Heijne matrix
      score 10.80
      seq ALALLSAFSATQA/RK
<220> FEATURE:
<221> NAME/KEY: polyA_signal
<222> LOCATION: 1858..1863
<220> FEATURE:
<221> NAME/KEY: polyA_site
<222> LOCATION: 1879..1894
<220> FEATURE:
<221> NAME/KEY: misc_feature
<222> LOCATION: 1695
<223> OTHER INFORMATION: n=a, g, c or t

<400> SEQUENCE: 39
agacgtgagc agagcagata atg gca agc atg gct gcc gtg ctc acc tgg gct      53
                     Met Ala Ser Met Ala Ala Val Leu Thr Trp Ala
                     -20                 -15 ctg gct ctt ctt tca gcg ttt tcg gcc acc cag gca cgg aaa ggc ttc       101
Leu Ala Leu Leu Ser Ala Phe Ser Ala Thr Gln Ala Arg Lys Gly Phe
        -10                 -5                  1 tgg gac tac ttc agc cag acc agc ggg gac aaa ggc agg gtg gag cag       149
Trp Asp Tyr Phe Ser Gln Thr Ser Gly Asp Lys Gly Arg Val Glu Gln
5                   10                  15                  20 atc cat cag cag aag atg gct cgc gag ccc gcg acc ctg aaa gac agc       197
Ile His Gln Gln Lys Met Ala Arg Glu Pro Ala Thr Leu Lys Asp Ser
                25                  30                  35 ctt gag caa gac ctc aac aat atg aac aag ttc ctg gaa aag ctg agg       245
Leu Glu Gln Asp Leu Asn Asn Met Asn Lys Phe Leu Glu Lys Leu Arg
            40                  45                  50 cct ctg agt ggg agc gag gct cct cgg ctc cca cag gac ccg gtg ggc       293
Pro Leu Ser Gly Ser Glu Ala Pro Arg Leu Pro Gln Asp Pro Val Gly
```

```
                55                  60                  65
atg cgg cgg cag ctg cag gag gag ttg gag gag gtg aag gct cgc ctc      341
Met Arg Arg Gln Leu Gln Glu Glu Leu Glu Glu Val Lys Ala Arg Leu
    70                  75                  80 cag ccc tac atg gca gag gcg cac gag ctg gtg ggc tgg aat ttg gag      389
Gln Pro Tyr Met Ala Glu Ala His Glu Leu Val Gly Trp Asn Leu Glu
85                  90                  95                 100 ggc ttg cgg cag caa ctg aag ccc tac acg atg gat ctg atg gag cag      437
Gly Leu Arg Gln Gln Leu Lys Pro Tyr Thr Met Asp Leu Met Glu Gln
                105                 110                 115 gtg gcc ctg cgc gtg cag gag ctg cag gag cag ttg cgc gtg gtg ggg      485
Val Ala Leu Arg Val Gln Glu Leu Gln Glu Gln Leu Arg Val Val Gly
            120                 125                 130 gaa gac acc aag gcc cag ttg ctg ggg ggc gtg gac gag gct tgg gct      533
Glu Asp Thr Lys Ala Gln Leu Leu Gly Gly Val Asp Glu Ala Trp Ala
        135                 140                 145 ttg ctg cag gga ctg cag agc cgc gtg gtg cac cac acc ggc cgc ttc      581
Leu Leu Gln Gly Leu Gln Ser Arg Val Val His His Thr Gly Arg Phe
    150                 155                 160 aaa gag ctc ttc cac cca tac gcc gag agc ctg gtg agc ggc atc ggg      629
Lys Glu Leu Phe His Pro Tyr Ala Glu Ser Leu Val Ser Gly Ile Gly
165                 170                 175                 180 cgc cac gtg cag gag ctg cac cgc agt gtg gct ccg cac gcc ccc gcc      677
Arg His Val Gln Glu Leu His Arg Ser Val Ala Pro His Ala Pro Ala
                185                 190                 195 agc ccc gcg cgc ctc agt cgc tgc gtg cag gtg ctc tcc cgg aag ctc      725
Ser Pro Ala Arg Leu Ser Arg Cys Val Gln Val Leu Ser Arg Lys Leu
            200                 205                 210 acg ctc aag gcc aag gcc ctg cac gca cgc atc cag cag aac ctg gac      773
Thr Leu Lys Ala Lys Ala Leu His Ala Arg Ile Gln Gln Asn Leu Asp
        215                 220                 225 cag ctg cgc gaa gag ctc agc aga gcc ttt gca ggc act ggg act gag      821
Gln Leu Arg Glu Glu Leu Ser Arg Ala Phe Ala Gly Thr Gly Thr Glu
    230                 235                 240 gaa ggg gcc ggc ccg gac ccc cag atg ctc tcc gag gag gtg cgc cag      869
Glu Gly Ala Gly Pro Asp Pro Gln Met Leu Ser Glu Glu Val Arg Gln
245                 250                 255                 260 cga ctt cag gct ttc cgc cag gac acc tac ctg cag ata gct gcc ttc      917
Arg Leu Gln Ala Phe Arg Gln Asp Thr Tyr Leu Gln Ile Ala Ala Phe
                265                 270                 275 act cgc gcc atc gac cag gag act gag gag gtc cag cag cag ctg gcg      965
Thr Arg Ala Ile Asp Gln Glu Thr Glu Glu Val Gln Gln Gln Leu Ala
            280                 285                 290 cca cct cca cca ggc cac agt gcc ttc gcc cca gag ttt caa caa aca     1013
Pro Pro Pro Pro Gly His Ser Ala Phe Ala Pro Glu Phe Gln Gln Thr
        295                 300                 305 gac agt ggc aag gtt ctg agc aag ctg cag gcc cgt ctg gat gac ctg     1061
Asp Ser Gly Lys Val Leu Ser Lys Leu Gln Ala Arg Leu Asp Asp Leu
    310                 315                 320 tgg gaa gac atc act cac agc ctt cat gac cag ggc cac agc cat ctg     1109
Trp Glu Asp Ile Thr His Ser Leu His Asp Gln Gly His Ser His Leu
325                 330                 335                 340 ggg gac ccc tgaggatcta cctgcccagg cccattccca gctccttgtc            1158
Gly Asp Pro tggggagcct tggctctgag cctctagcat ggttcagtcc ttgaaagtgg cctgttgggt   1218
ggagggtgga aggtcctgtg caggacaggg aggccaccaa aggggctgct gtctcctgca   1278
tatccagcct cctgcgactc cccaatctgg atgcattaca ttcaccaggc tttgcaaacc   1338
```

```
cagcctccca gtgctcattt gggaatgctc atgagttact ccattcaagg gtgagggagt      1398
agggagggag aggcaccatg catgtgggtg attatctgca agcctgtttg ccgtgatgct      1458
ggaagcctgt gccactacat cctggagttt ggctctagtc acttctggct gcctggtggc      1518
cactgctaca gctggtccac agagaggagc acttgtctcc ccagggctgc catggcagct      1578
atcaggggaa tagaagggag aaagagaata tcatggggag aacatgtgat ggtgtgtgaa      1638
tatccctgct ggctctgatg ctggtgggta cgaaaggtgt gggctgtgat aggagangGc      1698
agagcccatg tttcctgaca tagctctaca cctaaataag ggactgaacc ctcccaactg      1758
tgggagctcc ttaaaccctc tggggagcat actgtgtgct ctccccatct ccagcccctc      1818
cctctgggtt cccaagttga agcctagact tctggctcaa atgaaataga tgtttatgat      1878
aaaaaaaaaa aaaaa                                                       1894

<210> SEQ ID NO 40
<211> LENGTH: 1913
<212> TYPE: DNA
<213> ORGANISM: Homo Sapiens
<220> FEATURE:
<221> NAME/KEY: CDS
<222> LOCATION: 143..592
<220> FEATURE:
<221> NAME/KEY: sig_peptide
<222> LOCATION: 143..277
<223> OTHER INFORMATION: Von Heijne matrix
      score 5.90
      seq VLVDLAILGQAYA/FA
<220> FEATURE:
<221> NAME/KEY: polyA_signal
<222> LOCATION: 1877..1882
<220> FEATURE:
<221> NAME/KEY: polyA_site
<222> LOCATION: 1899..1913

<400> SEQUENCE: 40 attttttgt gcctaagatg cccagtgcgt tgctgggttt ttctgctgtc ctcgggctct        60
ggacatgagg ccagaccttg tgaccttgtt ggcagtgggc agtggcttga tgtgaggtcc      120
cagagacggc aggttcatca ag atg gtg ctc atg tgg acc agt ggt gac gcc      172
                         Met Val Leu Met Trp Thr Ser Gly Asp Ala
                         -45                 -40 ttc aag acg gcc tac ttc ctg ctg aag ggt gcc cct ctg cag ttc tcc      220
Phe Lys Thr Ala Tyr Phe Leu Leu Lys Gly Ala Pro Leu Gln Phe Ser
-35                 -30                 -25                 -20 gtg tgc ggc ctg ctg cag gtg ctg gtg gac ctg gcc atc ctg ggg cag      268
Val Cys Gly Leu Leu Gln Val Leu Val Asp Leu Ala Ile Leu Gly Gln
                -15                 -10                  -5 gcc tac gcc ttc gcc cca ccc cca gaa gcc ggc gcc cca cgc cgt gca      316
Ala Tyr Ala Phe Ala Pro Pro Pro Glu Ala Gly Ala Pro Arg Arg Ala
             1                5                  10 ccc cac tgg cac caa ggc cct ctg aca gtg ggg agg acg agg atg tgg      364
Pro His Trp His Gln Gly Pro Leu Thr Val Gly Arg Thr Arg Met Trp
        15                  20                  25 gac cgc cag ccg cgg gca ctg gtg ggc cct gac ctc ccc gcg ggg agg      412
Asp Arg Gln Pro Arg Ala Leu Val Gly Pro Asp Leu Pro Ala Gly Arg
 30                  35                  40                  45 gtg ggt gcc gtg gcc cct gca ggt gtg gca gag atg ggg cac ggg cat      460
Val Gly Ala Val Ala Pro Ala Gly Val Ala Glu Met Gly His Gly His
                 50                  55                  60 tgg ggt ctc cat cag cct ctg tgg ggt gtc tca ggg tgg gca gtg ggg      508
Trp Gly Leu His Gln Pro Leu Trp Gly Val Ser Gly Trp Ala Val Gly
            65                  70                  75
```

| | | | | | | | | | | | | | | |
|---|---|---|---|---|---|---|---|---|---|---|---|---|---|---|
| gtg | ggg | ctg | gga | cgc | tgt | ttg | tgc | tca | gcg | ggg | aca | gcc | agg | gtt gat | 556 |
| Val | Gly | Leu | Gly | Arg | Cys | Leu | Cys | Ser | Ala | Gly | Thr | Ala | Arg | Val Asp | |
| | 80 | | | | | 85 | | | | | 90 | | | | |

| | | | | | | | | | | |
|---|---|---|---|---|---|---|---|---|---|---|
| ctg | gcc | ccg | agg | gtt | ttg | gat | gtt | ttt | agg atg | aca taaaaagcaa | 602 |
| Leu | Ala | Pro | Arg | Val | Leu | Asp | Val | Phe | Arg Met | Thr | |
| | 95 | | | | 100 | | | | | 105 | |

```
gtgttttccc catttcctct tatgaaacac cgtctgagcc caaggtacac attgggcggc   662
ctgcaggaac ctgctccagg tggacacacg ggccagcagc cgcgaacctt gaagctgggg   722
tgaccgcagg agaccctgta aggcctgtga gcggagccct cgaccccgtg cacccctggc   782
cagacaccct gcttggactg gggtggcctc tgctacccag gggtctggca cggggggaggg   842
ctggggcttt ctctgcctgg tacacacgga aaggcggctg tgcggacgca gggtcaccgt   902
gctccgggtt ttctgacagt cggtgtttcc tgggcctttg gagtggctgc gaggcctgaa   962
cgccttgtgg atccgctgtg tccagcccgg ctgagcatcg ccagggctag ctcatgctgc  1022
tcttgtcagc ctctggttct cctcgagtcc ttggggacgt ggcagatgcc agcgaccatc  1082
agacaacgtg gaggccctca tgggcaatgg ctgaggggc cgggctgagg ctgtgcacat   1142
gcagtctgca cgccactctt gggctctgct ggcggagatc ccttccttc tgggtgcaga   1202
ctgcacctcc ggatgcagtt ttgatgtcca tcttccagga gagagacggt ctcgggtcca   1262
gggagtggag ggggctgccc ctgccgtgca ggtcctggcc gatggcgcct accctgctg    1322
ccctgggctt ttggcctgaa gcaaattcct gagtggggg tactggggcc tgccgcatcc   1382
tgtcctgtcc actgcccacc ccgtgtgct ggctccctca cttctggctg cagtgggagc    1442
cgccagtctg acccttgtca ccgcacgctc tgcccccacc ccgttgcaag aggtcacacc   1502
atgtcagcag ccttgcactg accgcagccg gcccccaggc ctcagagttc tggatgcttc   1562
cgtgcggctc caacaggcat cgtcttccct tccgcaggtg gaggggccgc ttcccgcagg   1622
catctgagct ctgtgccggg gccgtggcca tgggaagatg ttccacgctg cctcctcctc   1682
gagttttcct cggaaacact cttgaatgtc tgagtgaggg tcctgcttag ctctttggcc   1742
tgtgagatgc tttgaaaatt tttatttttt taagatgaag caagatgtct gtagcggtaa   1802
ttgcctcaca ttaaactgtc gccgactgca ggcgcagtga ctgctgaatg taccctgtgt   1862
ggcgacttgg aatcaataaa ccatttgtgg atcctaaaaa aaaaaaaaaa a           1913
```

```
<210> SEQ ID NO 41
<211> LENGTH: 1744
<212> TYPE: DNA
<213> ORGANISM: Homo Sapiens
<220> FEATURE:
<221> NAME/KEY: CDS
<222> LOCATION: 76..999
<220> FEATURE:
<221> NAME/KEY: sig_peptide
<222> LOCATION: 76..279
<223> OTHER INFORMATION: Von Heijne matrix
      score 5.10
      seq LSLPVCTVSLVSS/VS
<220> FEATURE:
<221> NAME/KEY: polyA_signal
<222> LOCATION: 1711..1716
<220> FEATURE:
<221> NAME/KEY: polyA_site
<222> LOCATION: 1729..1744
<220> FEATURE:
<221> NAME/KEY: misc_feature
<222> LOCATION: 336
<223> OTHER INFORMATION: n=a, g, c or t

<400> SEQUENCE: 41
```

```
aagttgaggc caccctggtg gcaccaaagc cctctcaggc aggcagaccc agggcctccc    60
cgccacacct tgttc atg gat ttt gtc gct gga gcc atc gga ggc gtc tgc   111
              Met Asp Phe Val Ala Gly Ala Ile Gly Gly Val Cys
                      -65                 -60 ggt gtt gct gtg ggc tac ccc ctg gac acg gtg aag gtc agg atc cag   159
Gly Val Ala Val Gly Tyr Pro Leu Asp Thr Val Lys Val Arg Ile Gln
            -55                 -50                 -45 acg gag cca aag tac aca ggc atc tgg cac tgc gtc cgg gat acg tat   207
Thr Glu Pro Lys Tyr Thr Gly Ile Trp His Cys Val Arg Asp Thr Tyr
-40                 -35                 -30                 -25 cac cga gag cgc gtg tgg ggc ttc tac cgg ggc ctc tcg ctg ccc gtg   255
His Arg Glu Arg Val Trp Gly Phe Tyr Arg Gly Leu Ser Leu Pro Val
                -20                 -15                 -10 tgc acg gtg tcc ctg gta tct tcc gtg tct ttt ggc acc tac cgc cac   303
Cys Thr Val Ser Leu Val Ser Ser Val Ser Phe Gly Thr Tyr Arg His
                 -5                  1                  5 tgc ctg gcg cac atc tgc cgg ctc cgg tac ggn aac cct gac gcc aag   351
Cys Leu Ala His Ile Cys Arg Leu Arg Tyr Gly Asn Pro Asp Ala Lys
 10                  15                  20 ccc acc aag gcc gac atc acg ctc tcg gga tgc gcc tcc ggc ctc gtc   399
Pro Thr Lys Ala Asp Ile Thr Leu Ser Gly Cys Ala Ser Gly Leu Val
 25                  30                  35                  40 cgc gtg ttc ctg acg tcg ccc act gag gtg gcc aaa gtc cgc ttg cag   447
Arg Val Phe Leu Thr Ser Pro Thr Glu Val Ala Lys Val Arg Leu Gln
                 45                  50                  55 acg cag aca cag gcg cag aag cag cag cgg ctg ctt tcg gcc tcg ggg   495
Thr Gln Thr Gln Ala Gln Lys Gln Gln Arg Leu Leu Ser Ala Ser Gly
                 60                  65                  70 ccg ttg gct gtg ccc ccc atg tgt cct gtg ccc cca gcc tgc cca gag   543
Pro Leu Ala Val Pro Pro Met Cys Pro Val Pro Pro Ala Cys Pro Glu
             75                  80                  85 ccc aag tac cgc ggg cca ctg cac tgc ctg gcc acg gta gcc cgt gag   591
Pro Lys Tyr Arg Gly Pro Leu His Cys Leu Ala Thr Val Ala Arg Glu
             90                  95                 100 gag ggg ctg tgc ggc ctc tac aag ggc agc tcg gcc ctg gtc tta cgg   639
Glu Gly Leu Cys Gly Leu Tyr Lys Gly Ser Ser Ala Leu Val Leu Arg
105                 110                 115                 120 gac ggc cac tcc ttt gcc acc tac ttc ctt tcc tac gcg gtc ctc tgc   687
Asp Gly His Ser Phe Ala Thr Tyr Phe Leu Ser Tyr Ala Val Leu Cys
                125                 130                 135 gag tgg ctc agc ccc gct ggc cac agc cgg cca gat gtc ccg ggc gtg   735
Glu Trp Leu Ser Pro Ala Gly His Ser Arg Pro Asp Val Pro Gly Val
            140                 145                 150 ctg gtg gcc ggg ggc tgt gca gga gtc ctg gcc tgg gct gtg gcc acc   783
Leu Val Ala Gly Gly Cys Ala Gly Val Leu Ala Trp Ala Val Ala Thr
            155                 160                 165 ccc atg gac gtg atc aag tcg aga ctg cag gca gac ggg cag ggc cag   831
Pro Met Asp Val Ile Lys Ser Arg Leu Gln Ala Asp Gly Gln Gly Gln
170                 175                 180 agg cgc tac cgg ggt ctc ctg cac tgt atg gtg acc agc gtt cga gag   879
Arg Arg Tyr Arg Gly Leu Leu His Cys Met Val Thr Ser Val Arg Glu
185                 190                 195                 200 gag gga ccc cgg gtc ctt ttc aag ggg ctg gta ctc aat tgc tgc cgc   927
Glu Gly Pro Arg Val Leu Phe Lys Gly Leu Val Leu Asn Cys Cys Arg
                205                 210                 215 gcc ttc cct gtc aac atg gtg gtc ttc gtc gcc tat gag gca gtg ctg   975
Ala Phe Pro Val Asn Met Val Val Phe Val Ala Tyr Glu Ala Val Leu
                220                 225                 230 agg ctc gcc cgg ggt ctg ctc aca tagccggtcc ccacgcccag cggcccaccc  1029
Arg Leu Ala Arg Gly Leu Leu Thr
```

```
Arg Leu Ala Arg Gly Leu Leu Thr
        235                 240 accagcagct gctggaggtc gtagtggctg gaggaggcaa ggggtagtgt ggctgggttc    1089
gggaccccac agggccattg cccaggagaa tgaggagcct ccctgcagtg ttgtcggccg    1149
aggcctaagc tcgccctgcc cagctactga cctcaggtcg aggggcccgc cagccatcag    1209
ccagggttgg cctagggtgg caggagccag gggagagtgg gcctctttga tgagagcgtt    1269
gagttgcatg gagtcggttg ttcatcccag cctccccatg gccctcgcct ccatgtctt     1329 tgaagcaccc ctccagggag tcaggtgtgt gctcagccac cctctgcccc attcctagac    1389
cctcaccccc accactgttc ctgtgtcttc atgagctgtc ccttacaggc aggggcttcc    1449
cacaggctgg gggcctcggg gcggggagca tgagctgggc tggcaccacg actgagggct    1509
cccggcccgg cttcttcccc acagcaggct gctcagaggg ggtgctgccg ggactgccat    1569
gcccacctga gggggcctg gggtggccgt cctcggccgg ttagggaatt tggggtgagg    1629
ttcctcagga gccctcactc tgcctgtgga cgctgcacct gccacttaaa gaccccaaag    1689
actctgttgg gaactgttgt cataaaatg tttctgagga aaaaaaaaaa aaaaa          1744

<210> SEQ ID NO 42
<211> LENGTH: 946
<212> TYPE: DNA
<213> ORGANISM: Homo Sapiens
<220> FEATURE:
<221> NAME/KEY: CDS
<222> LOCATION: 123..464
<220> FEATURE:
<221> NAME/KEY: sig_peptide
<222> LOCATION: 123..269
<223> OTHER INFORMATION: Von Heijne matrix
      score 4.90
      seq PSLAAGLLFGSLA/GL
<220> FEATURE:
<221> NAME/KEY: polyA_signal
<222> LOCATION: 908..913
<220> FEATURE:
<221> NAME/KEY: polyA_site
<222> LOCATION: 931..946

<400> SEQUENCE: 42
aaatcgcgtt tccggagaga cctggctgct gtgtcccgcg gcttgcgctc cgtagtggac    60
tccgcgggcc ttcggcagat gcaggcctgg ggtagtctcc tttctggact gagaagagaa   120 ga atg gag aag ccc ctc ttc cca tta gtg cct ttg cat tgg ttt ggc      167
   Met Glu Lys Pro Leu Phe Pro Leu Val Pro Leu His Trp Phe Gly
        -45                 -40                 -35 ttt ggc tac aca gca ctg gtt gtt tct ggt ggg atc gtt ggc tat gta     215
Phe Gly Tyr Thr Ala Leu Val Val Ser Gly Gly Ile Val Gly Tyr Val
            -30                 -25                 -20 aaa aca ggc agc gtg ccg tcc ctg gct gca ggg ctg ctc ttc ggc agt     263
Lys Thr Gly Ser Val Pro Ser Leu Ala Ala Gly Leu Leu Phe Gly Ser
        -15                 -10                 -5 cta gcc ggc ctg ggt gct tac cag ctg tat cag gat cca agg aac gtt     311
Leu Ala Gly Leu Gly Ala Tyr Gln Leu Tyr Gln Asp Pro Arg Asn Val
 1                   5                  10 tgg ggt ttc cta gcc gct aca tct gtt act ttt gtt ggt gtt atg gga     359
Trp Gly Phe Leu Ala Ala Thr Ser Val Thr Phe Val Gly Val Met Gly
15                  20                  25                  30 atg aga tcc tac tac tat gga aaa ttc atg cct gta ggt tta att gca     407
Met Arg Ser Tyr Tyr Tyr Gly Lys Phe Met Pro Val Gly Leu Ile Ala
                35                  40                  45 ggt gcc agt ttg ctg atg gcc gcc aaa gtt gga gtt cgt atg ttg atg     455
```

```
Gly Ala Ser Leu Leu Met Ala Ala Lys Val Gly Val Arg Met Leu Met
            50                  55                  60 aca tct gat tagcagaagt catgttccag cttggactca tgaaggatta           504
Thr Ser Asp
        65 aaaatctgca tcttccacta ttttcaatgt attaagagaa ataagtgcag cattttgca  564 tctgacattt tacctaaaaa aaaaaagaca ccaaatttgg cggaggggtg aaaatcagt  624 tgttaccatt ataaccctac agaggtggtg agcatgtaac atgagcttat tgagaccatc 684 atagagatcg attcttgtat attgatttta tctctttctg tatctatagg taaatctcaa 744 gggtaaaatg ttaggtgttg acattgagaa ccctgaaacc ccattccctg ctcagaggaa 804 cagtgtgaaa aaaatctct tgagagattt agaatatctt ttcttttgct catcttagac  864 cacagactga ctttgaaatt atgttaagtg aaatatcaat gaaaataaag tttactataa 924 ataattaaaa aaaaaaaaa aa                                           946

<210> SEQ ID NO 43
<211> LENGTH: 1622
<212> TYPE: DNA
<213> ORGANISM: Homo Sapiens
<220> FEATURE:
<221> NAME/KEY: CDS
<222> LOCATION: 85..1230
<220> FEATURE:
<221> NAME/KEY: sig_peptide
<222> LOCATION: 85..129
<223> OTHER INFORMATION: Von Heijne matrix
      score 10.10
      seq LLLPLALCILVLC/CG
<220> FEATURE:
<221> NAME/KEY: polyA_signal
<222> LOCATION: 1589..1594
<220> FEATURE:
<221> NAME/KEY: polyA_site
<222> LOCATION: 1607..1622

<400> SEQUENCE: 43
aaagtctgcc ttaaagagcc ttacaagcca gccagtccct gcagctccac aaactgaccc   60
atcctgggcc ttgttctcca caga atg ggt ctg ctc ctt ccc ctg gca ctc     111
                           Met Gly Leu Leu Leu Pro Leu Ala Leu
                           -15                 -10 tgc atc cta gtc ctg tgc tgc gga gca atg tct cca ccc cag ctg gcc   159
Cys Ile Leu Val Leu Cys Cys Gly Ala Met Ser Pro Pro Gln Leu Ala
     -5                   1               5                  10 ctc aac ccc tcg gct ctg ctc tcc cgg ggc tgc aat gac tca gat gtg   207
Leu Asn Pro Ser Ala Leu Leu Ser Arg Gly Cys Asn Asp Ser Asp Val
                 15                  20                  25 ctg gca gtt gca ggc ttt gcc ctg cgg gat att aac aaa gac aga aag   255
Leu Ala Val Ala Gly Phe Ala Leu Arg Asp Ile Asn Lys Asp Arg Lys
             30                  35                  40 gat ggc tat gtg ctg aga ctc aac cga gtg aac gac gcc cag gaa tac   303
Asp Gly Tyr Val Leu Arg Leu Asn Arg Val Asn Asp Ala Gln Glu Tyr
         45                  50                  55 aga cgg ggt ggc ctg gga tct ctg ttc tat ctt aca ctg gat gtg cta   351
Arg Arg Gly Gly Leu Gly Ser Leu Phe Tyr Leu Thr Leu Asp Val Leu
     60                  65                  70 gag act gac tgc cat gtg ctc aga aag aag gca tgg caa gac tgt gga   399
Glu Thr Asp Cys His Val Leu Arg Lys Lys Ala Trp Gln Asp Cys Gly
 75                  80                  85                  90 atg agg ata ttt ttt gaa tca gtt tat ggt caa tgc aaa gca ata ttt   447
Met Arg Ile Phe Phe Glu Ser Val Tyr Gly Gln Cys Lys Ala Ile Phe
                 95                  100                 105
```

```
tat atg aac aac cca agt aga gtt ctc tat tta gct gct tat aac tgt    495
Tyr Met Asn Asn Pro Ser Arg Val Leu Tyr Leu Ala Ala Tyr Asn Cys
        110                 115                 120 act ctt cgc cca gtt tca aaa aaa aag att tac atg acg tgc cct gac    543
Thr Leu Arg Pro Val Ser Lys Lys Lys Ile Tyr Met Thr Cys Pro Asp
                125                 130                 135 tgc cca agc tcc ata ccc act gac tct tcc aat cac caa gtg ctg gag    591
Cys Pro Ser Ser Ile Pro Thr Asp Ser Ser Asn His Gln Val Leu Glu
        140                 145                 150 gct gcc acc gag tct ctt gcg aaa tac aac aat gag aac aca tcc aag    639
Ala Ala Thr Glu Ser Leu Ala Lys Tyr Asn Asn Glu Asn Thr Ser Lys
155                 160                 165                 170 cag tat tct ctc ttc aaa gtc acc agg gct tct agc cag tgg gtg gtc    687
Gln Tyr Ser Leu Phe Lys Val Thr Arg Ala Ser Ser Gln Trp Val Val
                175                 180                 185 ggc cct tct tac ttt gtg gaa tac tta att aaa gaa tca cca tgt act    735
Gly Pro Ser Tyr Phe Val Glu Tyr Leu Ile Lys Glu Ser Pro Cys Thr
        190                 195                 200 aaa tcc cag gcc agc agc tgt tca ctt cag tcc tcc gac tct gtg cct    783
Lys Ser Gln Ala Ser Ser Cys Ser Leu Gln Ser Ser Asp Ser Val Pro
                205                 210                 215 gtt ggt ctt tgc aaa ggt tct ctg act cga aca cac tgg gaa aag ttt    831
Val Gly Leu Cys Lys Gly Ser Leu Thr Arg Thr His Trp Glu Lys Phe
        220                 225                 230 gtc tct gtg act tgt gac ttc ttt gaa tca cag gct cca gcc act gga    879
Val Ser Val Thr Cys Asp Phe Phe Glu Ser Gln Ala Pro Ala Thr Gly
235                 240                 245                 250 agt gaa aac tct gct gtt aac cag aaa cct aca aac ctt ccc aag gtg    927
Ser Glu Asn Ser Ala Val Asn Gln Lys Pro Thr Asn Leu Pro Lys Val
                255                 260                 265 gaa gaa tcc cag cag aaa aac acc ccc aca gac tcc ccc tcc aaa        975
Glu Glu Ser Gln Gln Lys Asn Thr Pro Thr Asp Ser Pro Ser Lys
        270                 275                 280 gct ggg cca aga gga tct gtc caa tat ctt cct gac ttg gat gat aaa    1023
Ala Gly Pro Arg Gly Ser Val Gln Tyr Leu Pro Asp Leu Asp Asp Lys
                285                 290                 295 aat tcc cag gaa aag ggc cct cag gag gcc ttt cct gtg cat ctg gac    1071
Asn Ser Gln Glu Lys Gly Pro Gln Glu Ala Phe Pro Val His Leu Asp
300                 305                 310 cta acc acg aat ccc cag gga gaa acc ctg gat att tcc ttc ctc ttc    1119
Leu Thr Thr Asn Pro Gln Gly Glu Thr Leu Asp Ile Ser Phe Leu Phe
315                 320                 325                 330 ctg gag cct atg gag gag aag ctg gtg gtc ctg cct ttc ccc aaa gaa    1167
Leu Glu Pro Met Glu Glu Lys Leu Val Val Leu Pro Phe Pro Lys Glu
                335                 340                 345 aaa gca cgc act gct gag tgc cca ggg cca gcc cag aat gcc agc cct    1215
Lys Ala Arg Thr Ala Glu Cys Pro Gly Pro Ala Gln Asn Ala Ser Pro
                350                 355                 360 ctt gtc ctt ccg cca tgagaatcac acagagtctt ctgtaggggt atggtgcgcc    1270
Leu Val Leu Pro Pro
                365 gcatgacatg ggaggcgatg gggacgatgg acagagacag agcgtgcaca cgtagagtgg    1330 ctagtgaagg acgcctttt gactcttctt ggtctcagca tgttgactgg gattggaaat    1390 aatgagactg agccctcggc ttgggctgca ctctaccctg tacactgcct tgtaccctga    1450 gctgcatcac ctcctaaact gagcagtctc ataccatgga gagatgcctc tcttatgtct    1510 tcagccactc acttataaag atacttatct tttcagcagt atatatgtgc tgaaatctca    1570
```

```
gcatgaaagc attgcatgag taaagatact ttccctaaaa aaaaaaaaaa aa            1622
```

```
<210> SEQ ID NO 44
<211> LENGTH: 715
<212> TYPE: DNA
<213> ORGANISM: Homo Sapiens
<220> FEATURE:
<221> NAME/KEY: CDS
<222> LOCATION: 29..664
<220> FEATURE:
<221> NAME/KEY: sig_peptide
<222> LOCATION: 29..619
<223> OTHER INFORMATION: Von Heijne matrix
      score 4.80
      seq SFFGASFLMGSLG/GM
<220> FEATURE:
<221> NAME/KEY: polyA_signal
<222> LOCATION: 657..662
<220> FEATURE:
<221> NAME/KEY: polyA_site
<222> LOCATION: 699..715
<220> FEATURE:
<221> NAME/KEY: misc_feature
<222> LOCATION: 295,357
<223> OTHER INFORMATION: n=a, g, c or t
<220> FEATURE:
<221> NAME/KEY: unsure
<222> LOCATION: -88
<223> OTHER INFORMATION: Xaa = Ala,Asp,Gly,Val
<220> FEATURE:
<221> NAME/KEY: unsure
<222> LOCATION: -109
<223> OTHER INFORMATION: Xaa = Asp,Glu

<400> SEQUENCE: 44
cttttcctgc ctctgattcc gggctgtc atg gcg acc ccc aac aat ctg acc         52
                               Met Ala Thr Pro Asn Asn Leu Thr
                                   -195             -190 ccc acc aac tgc agc tgg tgg ccc atc tcc gcg ctg gag agc gat gcg     100
Pro Thr Asn Cys Ser Trp Trp Pro Ile Ser Ala Leu Glu Ser Asp Ala
            -185             -180             -175 gcc aag cca gcg gag gcc ccc gac gct ccc gag gcg gcc agc ccc gcc     148
Ala Lys Pro Ala Glu Ala Pro Asp Ala Pro Glu Ala Ala Ser Pro Ala
        -170             -165             -160 cat tgg ccc agg gag agc ctg gtt ctg tac cac tgg acc cag tcc ttc     196
His Trp Pro Arg Glu Ser Leu Val Leu Tyr His Trp Thr Gln Ser Phe
    -155             -150             -145 agc tcg cag aag gcc aag atc ttg gag cat gat gat gtg agc tac ctg     244
Ser Ser Gln Lys Ala Lys Ile Leu Glu His Asp Asp Val Ser Tyr Leu
-140             -135             -130 aag aag atc ctc ggg gaa ctg gcc atg gtg ctg gac cag att gag gcg     292
Lys Lys Ile Leu Gly Glu Leu Ala Met Val Leu Asp Gln Ile Glu Ala
-125             -120             -115             -110 gan ctg gag aag agg aag ctg gag aac gag ggg cag aaa tgc gag ctg     340
Xaa Leu Glu Lys Arg Lys Leu Glu Asn Glu Gly Gln Lys Cys Glu Leu
            -105             -100              -95 tgg ctc tgt ggc tgt gnc ttc acc ctc gct gat gtc ctc ctg gga gcc     388
Trp Leu Cys Gly Cys Xaa Phe Thr Leu Ala Asp Val Leu Leu Gly Ala
         -90              -85              -80 acc ctg cac cgc ctc aag ttc ctg gga ctg tcc aag aaa tac tgg gaa     436
Thr Leu His Arg Leu Lys Phe Leu Gly Leu Ser Lys Lys Tyr Trp Glu
     -75              -70              -65 gat ggc agc cgg ccc aac ctg cag tcc ttc ttt gag agg gtc cag aga     484
Asp Gly Ser Arg Pro Asn Leu Gln Ser Phe Phe Glu Arg Val Gln Arg
 -60              -55              -50 cgc ttt gcc ttc cgg aaa gtc ctg ggt gac atc cac acc acc ctg ctg     532
Arg Phe Ala Phe Arg Lys Val Leu Gly Asp Ile His Thr Thr Leu Leu
```

```
        -45                 -40                 -35                 -30
tcg gcc gtc atc ccc aat gct ttc cgg ctg gtc aag agg aaa ccc cca             580
Ser Ala Val Ile Pro Asn Ala Phe Arg Leu Val Lys Arg Lys Pro Pro
                -25                 -20                 -15 tcc ttc ttc ggg gcg tcc ttc ctc atg ggc tcc ctg ggt ggg atg ggc             628
Ser Phe Phe Gly Ala Ser Phe Leu Met Gly Ser Leu Gly Gly Met Gly
        -10                  -5                          1 tac ttt gcc tac tgg tac ctc aag aaa aaa tac atc tagggccagg                  674
Tyr Phe Ala Tyr Trp Tyr Leu Lys Lys Lys Tyr Ile
  5                  10                  15 cctggggctt ggtgtctgac tgccaaaaaa aaaaaaaaaa a                               715

<210> SEQ ID NO 45
<211> LENGTH: 1549
<212> TYPE: DNA
<213> ORGANISM: Homo Sapiens
<220> FEATURE:
<221> NAME/KEY: CDS
<222> LOCATION: 18..878
<220> FEATURE:
<221> NAME/KEY: sig_peptide
<222> LOCATION: 18..95
<223> OTHER INFORMATION: Von Heijne matrix
      score 6.30
      seq GVGLVTLLGLAVG/SY
<220> FEATURE:
<221> NAME/KEY: polyA_signal
<222> LOCATION: 1500..1505
<220> FEATURE:
<221> NAME/KEY: polyA_site
<222> LOCATION: 1533..1549
<220> FEATURE:
<221> NAME/KEY: misc_feature
<222> LOCATION: 944
<223> OTHER INFORMATION: n=a, g, c or t

<400> SEQUENCE: 45
ggaaaaggcg ctccgtc atg ggg atc cag acg agc ccc gtc ctg ctg gcc             50
                   Met Gly Ile Gln Thr Ser Pro Val Leu Leu Ala
                       -25                 -20 tcc ctg ggg gtg ggg ctg gtc act ctg ctc ggc ctg gct gtg ggc tcc             98
Ser Leu Gly Val Gly Leu Val Thr Leu Leu Gly Leu Ala Val Gly Ser
-15                 -10                  -5                   1 tac ttg gtt cgg agg tcc cgc cgg cct cag gtc act ctc ctg gac ccc             146
Tyr Leu Val Arg Arg Ser Arg Arg Pro Gln Val Thr Leu Leu Asp Pro
          5                  10                  15 aat gaa aag tac ctg cta cga ctg cta gac aag acg ctc tct gca cgg             194
Asn Glu Lys Tyr Leu Leu Arg Leu Leu Asp Lys Thr Leu Ser Ala Arg
         20                  25                  30 tcc cca ggc aaa cat atc tac ctc tcc acc cga att gat ggc agc ctg             242
Ser Pro Gly Lys His Ile Tyr Leu Ser Thr Arg Ile Asp Gly Ser Leu
     35                  40                  45 gtc atc agg cca tac act cct gtc acc agt gat gag gat caa ggc tat             290
Val Ile Arg Pro Tyr Thr Pro Val Thr Ser Asp Glu Asp Gln Gly Tyr
 50                  55                  60                  65 gtg gat ctt gtc atc aag gtc tac ctg aag ggt gtg cac ccc aaa ttt             338
Val Asp Leu Val Ile Lys Val Tyr Leu Lys Gly Val His Pro Lys Phe
                 70                  75                  80 cct gag gga ggg aag atg tct cag tac ctg gat agc ctg aag gtt ggg             386
Pro Glu Gly Gly Lys Met Ser Gln Tyr Leu Asp Ser Leu Lys Val Gly
             85                  90                  95 gat gtg gtg gag ttt cgg ggg cca agc ggg ttg ctc act tac act gga             434
Asp Val Val Glu Phe Arg Gly Pro Ser Gly Leu Leu Thr Tyr Thr Gly
         100                 105                 110
```

```
aaa ggg cat ttt aac att cag ccc aac aag aaa tct cca cca gaa ccc      482
Lys Gly His Phe Asn Ile Gln Pro Asn Lys Lys Ser Pro Pro Glu Pro
    115                 120                 125 cga gtg gcg aag aaa ctg gga atg att gcc ggc ggg aca gga atc acc      530
Arg Val Ala Lys Lys Leu Gly Met Ile Ala Gly Gly Thr Gly Ile Thr
130                 135                 140                 145 cca atg cta cag ctg atc cgg gcc atc ctg aaa gtc cct gaa gat cca      578
Pro Met Leu Gln Leu Ile Arg Ala Ile Leu Lys Val Pro Glu Asp Pro
                150                 155                 160 acc cag tgc ttt ctg ctt ttt gcc aac cag aca gaa aag gat atc atc      626
Thr Gln Cys Phe Leu Leu Phe Ala Asn Gln Thr Glu Lys Asp Ile Ile
            165                 170                 175 ttg cgg gag gac tta gag gaa ctg cag gcc cgc tat ccc aat cgc ttt      674
Leu Arg Glu Asp Leu Glu Glu Leu Gln Ala Arg Tyr Pro Asn Arg Phe
    180                 185                 190 aag ctc tgg ttc act ctg gat cat ccc cca aaa gat tgg gcc tac agc      722
Lys Leu Trp Phe Thr Leu Asp His Pro Pro Lys Asp Trp Ala Tyr Ser
195                 200                 205 aag ggc ttt gtg act gcc gac atg atc cgg gaa cac ctg ccc gct cca      770
Lys Gly Phe Val Thr Ala Asp Met Ile Arg Glu His Leu Pro Ala Pro
210                 215                 220                 225 ggg gat gat gtg ctg gta ctg ctt tgt ggg cca ccc cca atg gtg cag      818
Gly Asp Asp Val Leu Val Leu Leu Cys Gly Pro Pro Pro Met Val Gln
                230                 235                 240 ctg gcc tgc cat ccc aac ttg gac aaa ctg ggc tac tca caa aag atg      866
Leu Ala Cys His Pro Asn Leu Asp Lys Leu Gly Tyr Ser Gln Lys Met
            245                 250                 255 cga ttc acc tac tgagcatcct ccagcttccc tggtgctgtt cgctgcagtt         918
Arg Phe Thr Tyr
    260 gttccccatc agtactcaag cactanaagc cttagattcc tttcctcaga gtttcaggtt    978 ttttcagtta catctagagc tgaaatctgg atagtacctg caggaacaat attcctgtag    1038 ccatggaaga gggccaaggc tcagtcactc cttggatggc ctcctaaatc tccccgtggc    1098 aacaggtcca ggagaggccc atggagcagt ctcttccatg gagtaagaag gaagggagca    1158 tgtacgcttg gtccaagatt ggctagttcc ttgatagcat cttactctca ccttctttgt    1218 gtctgtgatg aaaggaacag tctgtgcaat gggttttact taaacttcac tgttcaacct    1278 atgagcaaat ctgtatgtgt gagtataagt tgagcatagc atacttccag aggtggtctt    1338 atggagatgg caagaaagga ggaaatgatt tcttcagatc tcaaaggagt ctgaaatatc    1398 atatttctgt gtgtgtctct ctcagcccct gcccaggcta gagggaaaca gctactgata    1458 atcgaaaact gctgtttgtg gcaggaaccc ctggctgtgc aaataaatgg ggctgaggcc    1518 cctgtgtgat attcaaaaaa aaaaaaaaaa a                                   1549

<210> SEQ ID NO 46
<211> LENGTH: 1328
<212> TYPE: DNA
<213> ORGANISM: Homo Sapiens
<220> FEATURE:
<221> NAME/KEY: CDS
<222> LOCATION: 73..1008
<220> FEATURE:
<221> NAME/KEY: sig_peptide
<222> LOCATION: 73..147
<223> OTHER INFORMATION: Von Heijne matrix
      score 14.10
      seq LTLLLLLTLLAFA/GY
<220> FEATURE:
<221> NAME/KEY: polyA_signal
<222> LOCATION: 1286..1291
```

```
<220> FEATURE:
<221> NAME/KEY: polyA_site
<222> LOCATION: 1312..1328

<400> SEQUENCE: 46
actgcgcgga tcggcgtccg cagcgggcgg ctgctgagct gccttgaggt gcagtgttgg      60
ggatccagag cc atg tcg gac ctg cta cta ctg ggc ctg att ggg ggc ctg     111
              Met Ser Asp Leu Leu Leu Leu Gly Leu Ile Gly Gly Leu
                  -25             -20                 -15 act ctc tta ctg ctg ctg acg ctg cta gcc ttt gcc ggg tac tca ggg       159
Thr Leu Leu Leu Leu Leu Thr Leu Leu Ala Phe Ala Gly Tyr Ser Gly
        -10                 -5                   1 cta ctg gct ggg gtg gaa gtg agt gct ggg tca ccc ccc atc cgc aac       207
Leu Leu Ala Gly Val Glu Val Ser Ala Gly Ser Pro Pro Ile Arg Asn
 5            10                  15                  20 gtc act gtg gcc tac aag ttc cac atg ggg ctc tat ggt gag act ggg       255
Val Thr Val Ala Tyr Lys Phe His Met Gly Leu Tyr Gly Glu Thr Gly
                25                  30                  35 cgg ctt ttc act gag agc tgc atc tct ccc aag ctc cgc tcc atc gct       303
Arg Leu Phe Thr Glu Ser Cys Ile Ser Pro Lys Leu Arg Ser Ile Ala
            40                  45                  50 gtc tac tat gac aac ccc cac atg gtg ccc cct gat aag tgc cga tgt       351
Val Tyr Tyr Asp Asn Pro His Met Val Pro Pro Asp Lys Cys Arg Cys
        55                  60                  65 gcc gtg ggc agc atc ctg agt gaa ggt gag gaa tcg ccc tcc cct gag       399
Ala Val Gly Ser Ile Leu Ser Glu Gly Glu Glu Ser Pro Ser Pro Glu
 70                  75                  80 ctc atc gac ctc tac cag aaa ttt ggc ttc aag gtg ttc tcc ttc ccg       447
Leu Ile Asp Leu Tyr Gln Lys Phe Gly Phe Lys Val Phe Ser Phe Pro
85                  90                  95                 100 gca ccc agc cat gtg gtg aca gcc acc ttc ccc tac acc acc att ctg       495
Ala Pro Ser His Val Val Thr Ala Thr Phe Pro Tyr Thr Thr Ile Leu
                105                 110                 115 tcc atc tgg ctg gct acc cgc cgt gtc cat cct gcc ttg gac acc tac       543
Ser Ile Trp Leu Ala Thr Arg Arg Val His Pro Ala Leu Asp Thr Tyr
            120                 125                 130 atc aag gag cgg aag ctg tgt gcc tat cct cgg ctg gag atc tac cag       591
Ile Lys Glu Arg Lys Leu Cys Ala Tyr Pro Arg Leu Glu Ile Tyr Gln
        135                 140                 145 gaa gac cag atc cat ttc atg tgc cca ctg gca cgg cag gga gac ttc       639
Glu Asp Gln Ile His Phe Met Cys Pro Leu Ala Arg Gln Gly Asp Phe
    150                 155                 160 tat gtg cct gag atg aag gag aca gag tgg aaa tgg cgg ggg ctt gtg      687
Tyr Val Pro Glu Met Lys Glu Thr Glu Trp Lys Trp Arg Gly Leu Val
165                 170                 175                 180 gag gcc att gac acc cag gtg gat ggc aca gga gct gac aca atg agt       735
Glu Ala Ile Asp Thr Gln Val Asp Gly Thr Gly Ala Asp Thr Met Ser
                185                 190                 195 gac acg agt tct gta agc ttg gaa gtg agc cct ggc agc cgg gag act       783
Asp Thr Ser Ser Val Ser Leu Glu Val Ser Pro Gly Ser Arg Glu Thr
            200                 205                 210 tca gct gcc aca ctg tca cct ggg gcg agc agc cgt ggc tgg gat gac       831
Ser Ala Ala Thr Leu Ser Pro Gly Ala Ser Ser Arg Gly Trp Asp Asp
        215                 220                 225 ggt gac acc cgc agc gag cac agc tac agc gag tca ggt gcc agc ggc       879
Gly Asp Thr Arg Ser Glu His Ser Tyr Ser Glu Ser Gly Ala Ser Gly
    230                 235                 240 tcc tct ttt gag gag ctg gac ttg gag ggc gag ggg ccc tta ggg gag       927
Ser Ser Phe Glu Glu Leu Asp Leu Glu Gly Glu Gly Pro Leu Gly Glu
245                 250                 255                 260
```

```
tca cgg ctg gac cct ggg act gag ccc ctg ggg act acc aag tgg ctc        975
Ser Arg Leu Asp Pro Gly Thr Glu Pro Leu Gly Thr Thr Lys Trp Leu
            265                 270                 275 tgg gag ccc act gcc cct gag aag ggc aag gag taacccatgg cctgcaccct     1028
Trp Glu Pro Thr Ala Pro Glu Lys Gly Lys Glu
        280                 285 cctgcagtgc agttgctgag gaactgagca gactctccag cagactctcc agccctcttc     1088
ctccttcctc tgggggagga ggggttcctg agggacctga cttccctgc tccaggcctc      1148 ttgctaagcc ttctcctcac tgcccttag gctcccaggg ccagaggagc cagggactat      1208
tttctgcacc agccccagg gctgccaccc ctgttgtgtc ttttttcag actcacagtg       1268 gagcttccag gacccagaat aaagccaatg atttacttgt tcaaaaaaa aaaaaaaaa       1328

<210> SEQ ID NO 47
<211> LENGTH: 1515
<212> TYPE: DNA
<213> ORGANISM: Homo Sapiens
<220> FEATURE:
<221> NAME/KEY: CDS
<222> LOCATION: 165..842
<220> FEATURE:
<221> NAME/KEY: sig_peptide
<222> LOCATION: 165..251
<223> OTHER INFORMATION: Von Heijne matrix
      score 7.00
      seq LASFAALVLVCRQ/RY
<220> FEATURE:
<221> NAME/KEY: polyA_signal
<222> LOCATION: 1474..1479
<220> FEATURE:
<221> NAME/KEY: polyA_site
<222> LOCATION: 1500..1515

<400> SEQUENCE: 47
agtcgcggga tgcgcccggg agccacagcc tgaggccctc aggtctctgc aggtgtcgtg       60
gaggaaccta gcacctgcca tcctcttccc caatttgcca cttccagcag ctttagccca      120
tgaggaggat gtgaccggga ctgagtcagg agccctctgg aagc atg gag act gtg       176
                                                   Met Glu Thr Val gtg att gtt gcc ata ggt gtg ctg gcc acc atc ttt ctg gct tcg ttt        224
Val Ile Val Ala Ile Gly Val Leu Ala Thr Ile Phe Leu Ala Ser Phe
-25                 -20                 -15                 -10 gca gcc ttg gtg ctg gtt tgc agg cag cgc tac tgc cgg ccg cga gac        272
Ala Ala Leu Val Leu Val Cys Arg Gln Arg Tyr Cys Arg Pro Arg Asp
            -5                  1                   5 ctg ctg cag cgc tat gat tct aag ccc att gtg gac ctc att ggt gcc        320
Leu Leu Gln Arg Tyr Asp Ser Lys Pro Ile Val Asp Leu Ile Gly Ala
            10                  15                  20 atg gag acc cag tct gag ccc tct gag tta gaa ctg gac gat gtc gtt        368
Met Glu Thr Gln Ser Glu Pro Ser Glu Leu Glu Leu Asp Asp Val Val
            25                  30                  35 atc acc aac ccc cac att gag gcc att ctg gag aat gaa gac tgg atc        416
Ile Thr Asn Pro His Ile Glu Ala Ile Leu Glu Asn Glu Asp Trp Ile
40                  45                  50                  55 gaa gat gcc tcg ggt ctc atg tcc cac tgc att gcc atc ttg aag att        464
Glu Asp Ala Ser Gly Leu Met Ser His Cys Ile Ala Ile Leu Lys Ile
                60                  65                  70 tgt cac act ctg aca gag aag ctt gtt gcc atg aca atg ggc tct ggg        512
Cys His Thr Leu Thr Glu Lys Leu Val Ala Met Thr Met Gly Ser Gly
            75                  80                  85 gcc aag atg aag act tca gcc agt gtc agc gac atc att gtg gtg gcc        560
Ala Lys Met Lys Thr Ser Ala Ser Val Ser Asp Ile Ile Val Val Ala
```

```
                    90                  95                 100
aag cgg atc agc ccc agg gtg gat gat gtt gtg aag tcg atg tac cct      608
Lys Arg Ile Ser Pro Arg Val Asp Asp Val Val Lys Ser Met Tyr Pro
    105                 110                115 ccg ttg gac ccc aaa ctc ctg gac gca cgg acg act gcc ctg ctc ctg      656
Pro Leu Asp Pro Lys Leu Leu Asp Ala Arg Thr Thr Ala Leu Leu Leu
120                 125                 130                 135 tct gtc agt cac ctg gtg ctg gtg aca agg aat gcc tgc cat ctg acg      704
Ser Val Ser His Leu Val Leu Val Thr Arg Asn Ala Cys His Leu Thr
                140                 145                 150 gga ggc ctg gac tgg att gac cag tct ctg tcg gct gct gag gag cat      752
Gly Gly Leu Asp Trp Ile Asp Gln Ser Leu Ser Ala Ala Glu Glu His
            155                 160                 165 ttg gaa gtc ctt cga gaa gca gcc cta gct tct gag cca gat aaa ggc      800
Leu Glu Val Leu Arg Glu Ala Ala Leu Ala Ser Glu Pro Asp Lys Gly
        170                 175                 180 ctc cca ggc cct gaa ggc ttc ctg cag gag cag tct gca att                842
Leu Pro Gly Pro Glu Gly Phe Leu Gln Glu Gln Ser Ala Ile
    185                 190                 195 tagtgcctac aggccagcag ctagccatga aggcccctgc cgccatccct ggatggctca     902
gcttagcctt ctactttttc ctatagagtt agttgttctc cacggctgga gagttcagct     962
gtgtgtgcat agtaaagcag agatccccg tcagtttatg cctcttttgc agttgcaaac     1022
tgtggctggt gagtggcagt ctaatactac agttagggga gatgccattc actctctgca    1082
agaggagtat tgaaaactgg tggactgtca gctttattta gctcacctag tgttttcaag    1142
aaaattgagc caccgtctaa gaaatcaaga ggtttcacat taaaattaga atttctggcc    1202
tctctcgatc ggtcagaatg tgtggcaatt ctgatctgca ttttcagaag aggacaatca    1262
attgaaacta gtaggggtt tcttcttttg gcaagacttg tactctctca cctggcctgt     1322
ttcatttatt tgtattatct gcctggtccc tgaggcgtct gggtctctcc tctcccttgc    1382
aggtttgggt ttgaagctga ggaactacaa agttgatgat ttcttttta tctttatgcc     1442 tgcaatttta cctagctacc actaggtgga tagtaaattt atacttatgt ttcccccaaa    1502
aaaaaaaaaa aaa                                                       1515

<210> SEQ ID NO 48
<211> LENGTH: 1622
<212> TYPE: DNA
<213> ORGANISM: Homo Sapiens
<220> FEATURE:
<221> NAME/KEY: CDS
<222> LOCATION: 31..1248
<220> FEATURE:
<221> NAME/KEY: sig_peptide
<222> LOCATION: 31..135
<223> OTHER INFORMATION: Von Heijne matrix
      score 6.30
      seq TLLLFAAPFGLLG/EK
<220> FEATURE:
<221> NAME/KEY: polyA_signal
<222> LOCATION: 1580..1585
<220> FEATURE:
<221> NAME/KEY: polyA_site
<222> LOCATION: 1607..1622

<400> SEQUENCE: 48
aacctcttcc gtcggctgaa ttgcggccgt atg cgc ggc tct gtg gag tgc acc     54
                                 Met Arg Gly Ser Val Glu Cys Thr
                                 -35                 -30 tgg ggt tgg ggg cac tgt gcc ccc agc ccc ctg ctc ctt tgg act cta     102
Trp Gly Trp Gly His Cys Ala Pro Ser Pro Leu Leu Leu Trp Thr Leu
```

|  |  |  |  |  |  |  |  |  |  |  |  |  |  |
|---|---|---|---|---|---|---|---|---|---|---|---|---|---|
| | -25 | | | -20 | | | | -15 | | | | | |
| ctt | ctg | ttt | gca | gcc | cca | ttt | ggc | ctg | ctg | ggg | gag | aag | acc cgc cag | 150 |
| Leu | Leu | Phe | Ala | Ala | Pro | Phe | Gly | Leu | Leu | Gly | Glu | Lys | Thr Arg Gln | |
| | -10 | | | | -5 | | | | | 1 | | | 5 | |
| gtg | tct | ctg | gag | gtc | atc | cct | aac | tgg | ctg | ggc | ccc | ctg | cag aac ctg | 198 |
| Val | Ser | Leu | Glu | Val | Ile | Pro | Asn | Trp | Leu | Gly | Pro | Leu | Gln Asn Leu | |
| | | | | 10 | | | | | 15 | | | | 20 | |
| ctt | cat | ata | cgg | gca | gtg | ggc | acc | aat | tcc | aca | ctg | cac | tat gtg tgg | 246 |
| Leu | His | Ile | Arg | Ala | Val | Gly | Thr | Asn | Ser | Thr | Leu | His | Tyr Val Trp | |
| | | | 25 | | | | | 30 | | | | | 35 | |
| agc | agc | ctg | ggg | cct | ctg | gca | gtg | gta | atg | gtg | gcc | acc | aac acc ccc | 294 |
| Ser | Ser | Leu | Gly | Pro | Leu | Ala | Val | Val | Met | Val | Ala | Thr | Asn Thr Pro | |
| | | | 40 | | | | | 45 | | | | | 50 | |
| cac | agc | acc | ctg | agc | gtc | aac | tgg | agc | ctc | ctg | cta | tcc | cct gag ccc | 342 |
| His | Ser | Thr | Leu | Ser | Val | Asn | Trp | Ser | Leu | Leu | Leu | Ser | Pro Glu Pro | |
| | | | 55 | | | | | 60 | | | | | 65 | |
| gat | ggg | ggc | ctg | atg | gtg | ctc | cct | aag | gac | agc | att | cag | ttt tct tct | 390 |
| Asp | Gly | Gly | Leu | Met | Val | Leu | Pro | Lys | Asp | Ser | Ile | Gln | Phe Ser Ser | |
| 70 | | | | | 75 | | | | | 80 | | | | 85 |
| gcc | ctt | gtt | ttt | acc | agg | ctg | ctt | gag | ttt | gac | agc | acc | aac gtg tcc | 438 |
| Ala | Leu | Val | Phe | Thr | Arg | Leu | Leu | Glu | Phe | Asp | Ser | Thr | Asn Val Ser | |
| | | | | 90 | | | | | 95 | | | | 100 | |
| gat | acg | gca | gca | aag | cct | ttg | gga | aga | cca | tat | cct | cca | tac tcc ttg | 486 |
| Asp | Thr | Ala | Ala | Lys | Pro | Leu | Gly | Arg | Pro | Tyr | Pro | Pro | Tyr Ser Leu | |
| | | | 105 | | | | | 110 | | | | | 115 | |
| gcc | gat | ttc | tct | tgg | aac | aac | atc | act | gat | tca | ttg | gat | cct gcc acc | 534 |
| Ala | Asp | Phe | Ser | Trp | Asn | Asn | Ile | Thr | Asp | Ser | Leu | Asp | Pro Ala Thr | |
| | | | 120 | | | | | 125 | | | | | 130 | |
| ctg | agt | gcc | aca | ttt | caa | ggc | cac | ccc | atg | aac | gac | cct | acc agg act | 582 |
| Leu | Ser | Ala | Thr | Phe | Gln | Gly | His | Pro | Met | Asn | Asp | Pro | Thr Arg Thr | |
| | 135 | | | | | 140 | | | | | 145 | | | |
| ttt | gcc | aat | ggc | agc | ctg | gcc | ttc | agg | gtc | cag | gcc | ttt | tcc agg tcc | 630 |
| Phe | Ala | Asn | Gly | Ser | Leu | Ala | Phe | Arg | Val | Gln | Ala | Phe | Ser Arg Ser | |
| 150 | | | | | 155 | | | | | 160 | | | | 165 |
| agc | cga | cca | gcc | caa | ccc | cct | cgc | ctc | ctg | cac | aca | gca | gac acc tgt | 678 |
| Ser | Arg | Pro | Ala | Gln | Pro | Pro | Arg | Leu | Leu | His | Thr | Ala | Asp Thr Cys | |
| | | | 170 | | | | | 175 | | | | | 180 | |
| cag | cta | gag | gtg | gcc | ctg | att | gga | gcc | tct | ccc | cgg | gga | aac cgt tcc | 726 |
| Gln | Leu | Glu | Val | Ala | Leu | Ile | Gly | Ala | Ser | Pro | Arg | Gly | Asn Arg Ser | |
| | | | 185 | | | | | 190 | | | | | 195 | |
| ctg | ttt | ggg | ctg | gag | gta | gcc | aca | ttg | ggc | cag | ggc | cct | gac tgc ccc | 774 |
| Leu | Phe | Gly | Leu | Glu | Val | Ala | Thr | Leu | Gly | Gln | Gly | Pro | Asp Cys Pro | |
| | | | 200 | | | | | 205 | | | | | 210 | |
| tca | atg | cag | gag | cag | cac | tcc | atc | gac | gat | gaa | tat | gca | ccg gcc gtc | 822 |
| Ser | Met | Gln | Glu | Gln | His | Ser | Ile | Asp | Asp | Glu | Tyr | Ala | Pro Ala Val | |
| | | | 215 | | | | | 220 | | | | | 225 | |
| ttc | cag | ttg | gac | cag | cta | ctg | tgg | ggc | tcc | ctc | cca | tca | ggc ttt gca | 870 |
| Phe | Gln | Leu | Asp | Gln | Leu | Leu | Trp | Gly | Ser | Leu | Pro | Ser | Gly Phe Ala | |
| 230 | | | | | 235 | | | | | 240 | | | | 245 |
| cag | tgg | cga | cca | gtg | gct | tac | tcc | cag | aag | ccg | ggg | ggc | cga gaa tca | 918 |
| Gln | Trp | Arg | Pro | Val | Ala | Tyr | Ser | Gln | Lys | Pro | Gly | Gly | Arg Glu Ser | |
| | | | 250 | | | | | 255 | | | | | 260 | |
| gcc | ctg | ccc | tgc | caa | gct | tcc | cct | ctt | cat | cct | gcc | tta | gca tac tct | 966 |
| Ala | Leu | Pro | Cys | Gln | Ala | Ser | Pro | Leu | His | Pro | Ala | Leu | Ala Tyr Ser | |
| | | | 265 | | | | | 270 | | | | | 275 | |
| ctt | ccc | cag | tca | ccc | att | gtc | cga | gcc | ttc | ttt | ggg | tcc | cag aat aac | 1014 |
| Leu | Pro | Gln | Ser | Pro | Ile | Val | Arg | Ala | Phe | Phe | Gly | Ser | Gln Asn Asn | |
| | | | 280 | | | | | 285 | | | | | 290 | |
| ttc | tgt | gcc | ttc | aat | ctg | acg | ttc | ggg | gct | tcc | aca | ggc | cct ggc tat | 1062 |

```
        Phe Cys Ala Phe Asn Leu Thr Phe Gly Ala Ser Thr Gly Pro Gly Tyr
            295                 300                 305 tgg gac caa cac tac ctc agc tgg tcg atg ctc ctg ggt gtg ggc ttc      1110
Trp Asp Gln His Tyr Leu Ser Trp Ser Met Leu Leu Gly Val Gly Phe
310                 315                 320                 325 cct cca gtg gac ggc ttg tcc cca cta gtc ctg ggc atc atg gca gtg      1158
Pro Pro Val Asp Gly Leu Ser Pro Leu Val Leu Gly Ile Met Ala Val
                330                 335                 340 gcc ctg ggt gcc cca ggg ctc atg ctg cta ggg ggc ttg gtt ctg          1206
Ala Leu Gly Ala Pro Gly Leu Met Leu Leu Gly Gly Leu Val Leu
                345                 350                 355 ctg ctg cac cac aag aag tac tca gag tac cag tcc ata aat              1248
Leu Leu His His Lys Lys Tyr Ser Glu Tyr Gln Ser Ile Asn
                360                 365                 370 taaggcccgc tctctggagg gaaggacatt actgaacctg tcttgctgtg cctcgaaact    1308
ctggaggttg gagcatcaag ttccagcccc cttcactccc ccatcttgct tttctgtgga    1368
acctcagagg ccagcctcga cttcctggag accccaggt ggggcttcct tcatactttg    1428
ttgggggact tggaggcgg gcaggggaca gggctattga taaggtcccc ttggtgttgc     1488
cttcttgcat ctccacacat ttcccttgga tgggacttgc aggcctaaat gagaggcatt    1548
ctgactggtt ggctgccctg gaaggcaaga aaatagattt atttttttt cacagggcaa     1608 aaaaaaaaaa aaaa                                                      1622

<210> SEQ ID NO 49
<211> LENGTH: 1448
<212> TYPE: DNA
<213> ORGANISM: Homo Sapiens
<220> FEATURE:
<221> NAME/KEY: CDS
<222> LOCATION: 131..490
<220> FEATURE:
<221> NAME/KEY: sig_peptide
<222> LOCATION: 131..301
<223> OTHER INFORMATION: Von Heijne matrix
      score 5.30
      seq AIALATVLFLIGA/FL
<220> FEATURE:
<221> NAME/KEY: polyA_signal
<222> LOCATION: 1411..1416
<220> FEATURE:
<221> NAME/KEY: polyA_site
<222> LOCATION: 1434..1448

<400> SEQUENCE: 49
ctgatcccgc ctggggccgg ctgagtggca cttaagcggg ccatgccatg caaccttggg     60
cgctgccaac cgtgggcgag ctctgggtgt gcgggcggcc tcgcgcgcg ctccgctgtg    120 tcagcgtgtt atg atg ccg tcc cgt acc aac ctg gct act gga atc ccc      169
            Met Met Pro Ser Arg Thr Asn Leu Ala Thr Gly Ile Pro
                -55                 -50                 -45 agt agt aaa gtg aaa tat tca agg ctc tcc agc aca gac gat ggc tac     217
Ser Ser Lys Val Lys Tyr Ser Arg Leu Ser Ser Thr Asp Asp Gly Tyr
                -40                 -35                 -30 att gac ctt cag ttt aag aaa acc cct cct aag atc cct tat aag gcc     265
Ile Asp Leu Gln Phe Lys Lys Thr Pro Pro Lys Ile Pro Tyr Lys Ala
            -25                 -20                 -15 atc gca ctt gcc act gtg ctg ttt ttg att ggc gcc ttt ctc att att     313
Ile Ala Leu Ala Thr Val Leu Phe Leu Ile Gly Ala Phe Leu Ile Ile
            -10                 -5                  1 ata ggc tcc ctc ctg ctg tca ggc tac atc agc aaa ggg ggg gca gac     361
Ile Gly Ser Leu Leu Leu Ser Gly Tyr Ile Ser Lys Gly Gly Ala Asp
5                   10                  15                  20
```

```
cgg gcc gtt cca gtg ctg atc att ggc att ctg gtg ttc cta ccc gga      409
Arg Ala Val Pro Val Leu Ile Ile Gly Ile Leu Val Phe Leu Pro Gly
             25                  30                  35 ttt tac cac ctg cgc atc gct tac tat gca tcc aaa ggc tac cgt ggt      457
Phe Tyr His Leu Arg Ile Ala Tyr Tyr Ala Ser Lys Gly Tyr Arg Gly
         40                  45                  50 tac tcc tat gat gac att cca gac ttt gat gac tagcacccac cccatagctg    510
Tyr Ser Tyr Asp Asp Ile Pro Asp Phe Asp Asp
     55                  60 aggaggagtc acagtggaac tgtcccagct ttaagatatc tagcagaaac tatagctgag    570
gactaaggaa ttctgcagct tgcagatgtt taagaaaata atggccagat tttttgggtc    630
cttcccaaag atgttaagtg aacctacagt tagctaatta ggacaagctc tattttcat    690 ccctgggccc tgacaagttt ttccacagga atatgtatca tggaagaata gaggttattc    750
tgtaatggaa aagtgttgcc tgccaccacc ctctgtagag ctgagcattt cttttaaata    810
gtcttcattg ccaatttgtt cttgtagcaa atggaacaat gtggtatggc taatttctta    870
ttattaagta atttatttta aaaatatctg agtatattat cctgtacact tatccctacc    930
ttcatgttcc agtggaagac cttagtaaaa tcaaagatca gtgagttcat ctgtaatatt    990 tttttactt gctttcttac tgacagcaac caggaatttt tttatcctgc agagcaagtt   1050
ttcaaaatgt aaatacttcc tctgtttaac agtccttgga ccattctgat ccagttcacc   1110
agtaggttgg acagcatata atttgcatca ttttgtccct tgtaaatcaa gatgttctgc   1170
agattattcc tttaacggcc ggacttttgg ctgtttccta atgaaacatg tagtggttat   1230
tatttagagt ttatagccgt attgctagca ccttgtagta tgtcatcatt ctgctcatga   1290
ttccaaggat cagcctggat gcctagagga ctagatcacc ttagtttgat tctatttttt   1350
agcttgcaaa aagtgactta tattccaaag aaattaaaat gttgaaatcc aaatcctaga   1410
aataaaatga gttaacttca aacaaaaaaa aaaaaaaa                             1448

<210> SEQ ID NO 50
<211> LENGTH: 894
<212> TYPE: DNA
<213> ORGANISM: Homo Sapiens
<220> FEATURE:
<221> NAME/KEY: CDS
<222> LOCATION: 61..690
<220> FEATURE:
<221> NAME/KEY: sig_peptide
<222> LOCATION: 61..168
<223> OTHER INFORMATION: Von Heijne matrix
      score 4.60
      seq GTVVLVAGTLCFA/WW
<220> FEATURE:
<221> NAME/KEY: polyA_signal
<222> LOCATION: 858..863
<220> FEATURE:
<221> NAME/KEY: polyA_site
<222> LOCATION: 879..894

<400> SEQUENCE: 50
acaccttcac ctgcgcccag ctccctgcgc gcctggacag cgcctgctgc ccgcctcccg      60 atg gcc ctg ccc cag atg tgt gac ggg agc cac ttg gcc tcc acc ctc      108
Met Ala Leu Pro Gln Met Cys Asp Gly Ser His Leu Ala Ser Thr Leu
    -35                 -30                 -25 cgc tat tgc atg aca gtc agc ggc aca gtg gtt ctg gtg gcc ggg acg      156
Arg Tyr Cys Met Thr Val Ser Gly Thr Val Val Leu Val Ala Gly Thr
-20                 -15                 -10                  -5 ctc tgc ttc gct tgg tgg agc gaa ggg gat gca acc gcc cag cct ggc      204
```

```
Leu Cys Phe Ala Trp Trp Ser Glu Gly Asp Ala Thr Ala Gln Pro Gly
         1               5                    10 cag ctg gcc cca ccc acg gag tat ccg gtg cct gag ggc ccc agc ccc      252
Gln Leu Ala Pro Pro Thr Glu Tyr Pro Val Pro Glu Gly Pro Ser Pro
         15                  20                  25 ctg ctc agg tcc gtc agc ttc gtc tgc tgc ggt gca ggt ggc ctg ctg      300
Leu Leu Arg Ser Val Ser Phe Val Cys Cys Gly Ala Gly Gly Leu Leu
     30                  35                  40 ctg ctc att ggc ctg ctg tgg tcc gtc aag gcc agc atc cca ggg cca      348
Leu Leu Ile Gly Leu Leu Trp Ser Val Lys Ala Ser Ile Pro Gly Pro
 45              50                  55                  60 cct cga tgg gac ccc tat cac ctc tcc aga gac ctg tac tac ctc act      396
Pro Arg Trp Asp Pro Tyr His Leu Ser Arg Asp Leu Tyr Tyr Leu Thr
                 65                  70                  75 gtg gag tcc tca gag aag gag agc tgc agg acc ccc aaa gtg gtt gac      444
Val Glu Ser Ser Glu Lys Glu Ser Cys Arg Thr Pro Lys Val Val Asp
             80                  85                  90 atc ccc act tac gag gaa gcc gtg agc ttc cca gtg gcc gag ggg ccc      492
Ile Pro Thr Tyr Glu Glu Ala Val Ser Phe Pro Val Ala Glu Gly Pro
         95                  100                 105 cca aca cca cct gca tac cct acg gag gaa gcc ctg gag cca agt gga      540
Pro Thr Pro Pro Ala Tyr Pro Thr Glu Glu Ala Leu Glu Pro Ser Gly
     110                 115                 120 tcg agg gat gcc ctg ctc agc acc cag ccc gcc tgg cct cca ccc agc      588
Ser Arg Asp Ala Leu Leu Ser Thr Gln Pro Ala Trp Pro Pro Pro Ser
125                 130                 135                 140 tat gag agc atc agc ctt gct ctt gat gcc gtt tct gca gag acg aca      636
Tyr Glu Ser Ile Ser Leu Ala Leu Asp Ala Val Ser Ala Glu Thr Thr
                 145                 150                 155 ccg agt gcc aca cgc tcc tgc tca ggc ctg gtt cag act gca cgg gga      684
Pro Ser Ala Thr Arg Ser Cys Ser Gly Leu Val Gln Thr Ala Arg Gly
             160                 165                 170 gga agt taaaggctcc tagcaggtcc tgaatccaga gacaaaatg ctgtgccttc        740
Gly Ser tccagagtct tatgcagtgc ctgggacaca gtaggcactc agcaaacgtt cgttgttgaa   800
ggctgttcta tttatctatt gctgtataac aaaccacccc agaatttagt ggcttaaaat   860
aaatcccatt ttattacgaa aaaaaaaaaa aaaa                               894
```

```
<210> SEQ ID NO 51
<211> LENGTH: 1447
<212> TYPE: DNA
<213> ORGANISM: Homo Sapiens
<220> FEATURE:
<221> NAME/KEY: CDS
<222> LOCATION: 501..1253
<220> FEATURE:
<221> NAME/KEY: sig_peptide
<222> LOCATION: 501..1229
<223> OTHER INFORMATION: Von Heijne matrix
      score 4.10
      seq LPSLAHLLPALDC/LE
<220> FEATURE:
<221> NAME/KEY: polyA_signal
<222> LOCATION: 1392..1397
<220> FEATURE:
<221> NAME/KEY: polyA_site
<222> LOCATION: 1432..1447
<220> FEATURE:
<221> NAME/KEY: misc_feature
<222> LOCATION: 243,252,278,285,387,1429
<223> OTHER INFORMATION: n=a, g, c or t

<400> SEQUENCE: 51
```

```
gtgagtcagg tgggtcctgg gcccaggaac cggcccggag ccgtggacgc cctacagctg      60
agaaggggac ccaaggggtc ggccgcggcc aaggcccta ggaccgccgc cccagctcac      120
gctgccgacg gcagctatag acattctgcg tcaggtccgg gctcctggac tttgcctttc      180
ccgagccctg gaggtgggga gaaaaggttc accaattttt aaaatccaaa tatatctcat      240
ggntacagtg gnaagaactg gccagagagt ctggaagntt tgggnttctg gtcctggctg      300
tgccactgac tcactgtgac cttgggatct tgtgctgtga agacatttcc caagtgcttc      360
atgttagcca gcaaatctga cccacanggc ctggaaagag gtgattgtta ggttgcgcag      420
aggtggtctt atccagctca gcttcccctg ggacccaccg tgggacctga gcagaactg       480 gggtggactt ggcctcctcc atg gca cac cgg ctg cag ata cga ctg ctg acg      533
                        Met Ala His Arg Leu Gln Ile Arg Leu Leu Thr
                                -240                    -235
```

```
tgg gat gtg aag gac acg ctg ctc agg ctc cgc cac ccc tta ggg gag       581
Trp Asp Val Lys Asp Thr Leu Leu Arg Leu Arg His Pro Leu Gly Glu
        -230                -225                -220 gcc tat gcc acc aag gcc cgg gcc cat ggg ctg gag gtg gag ccc tca       629
Ala Tyr Ala Thr Lys Ala Arg Ala His Gly Leu Glu Val Glu Pro Ser
    -215                -210                -205 gcc ctg gaa caa ggc ttc agg cag gca tac agg gct cag agc cac agc       677
Ala Leu Glu Gln Gly Phe Arg Gln Ala Tyr Arg Ala Gln Ser His Ser
-200                -195                -190                -185 ttc ccc aac tac ggc ctg agc cac ggc cta acc tcc cgc cag tgg tgg       725
Phe Pro Asn Tyr Gly Leu Ser His Gly Leu Thr Ser Arg Gln Trp Trp
                -180                -175                -170 ctg gat gtg gtc ctg cag acc ttc cac ctg gcg ggt gtc cag gat gct       773
Leu Asp Val Val Leu Gln Thr Phe His Leu Ala Gly Val Gln Asp Ala
        -165                -160                -155 cag gct gta gcc ccc atc gct gaa cag ctt tat aaa gac ttc agc cac       821
Gln Ala Val Ala Pro Ile Ala Glu Gln Leu Tyr Lys Asp Phe Ser His
    -150                -145                -140 ccc tgc acc tgg cag gtg ttg gat ggg gct gag gac acc ctg agg gag       869
Pro Cys Thr Trp Gln Val Leu Asp Gly Ala Glu Asp Thr Leu Arg Glu
-135                -130                -125 tgc cgc aca cgg ggt ctg aga ctg gca gtg atc tcc aac ttt gac cga       917
Cys Arg Thr Arg Gly Leu Arg Leu Ala Val Ile Ser Asn Phe Asp Arg
-120                -115                -110                -105 cgg cta gag ggc atc ctg gag ggc ctt ggc ctg cgt gaa cac ttc gac       965
Arg Leu Glu Gly Ile Leu Glu Gly Leu Gly Leu Arg Glu His Phe Asp
            -100                -95                 -90 ttt gtg ctg acc tcc gag gct gct ggc tgg ccc aag ccg gac ccc cgc      1013
Phe Val Leu Thr Ser Glu Ala Ala Gly Trp Pro Lys Pro Asp Pro Arg
        -85                 -80                 -75 att ttc cag gag gcc ttg cgg ctt gct cat atg gaa cca gta gtg gca      1061
Ile Phe Gln Glu Ala Leu Arg Leu Ala His Met Glu Pro Val Val Ala
    -70                 -65                 -60 gcc cat gtt ggg gat aat tac ctc tgc gat tac cag ggg cct cgg gct      1109
Ala His Val Gly Asp Asn Tyr Leu Cys Asp Tyr Gln Gly Pro Arg Ala
-55                 -50                 -45 gtg ggc atg cac agc ttc ctg gtg gtt ggc cca cag gca ctg gac ccc      1157
Val Gly Met His Ser Phe Leu Val Val Gly Pro Gln Ala Leu Asp Pro
-40                 -35                 -30                 -25 gtg gtc agg gat tct gta cct aaa gaa cac atc ctc ccc tct ctg gcc      1205
Val Val Arg Asp Ser Val Pro Lys Glu His Ile Leu Pro Ser Leu Ala
            -20                 -15                 -10 cat ctc ctg cct gcc ctt gac tgc cta gag ggc tca act cca ggg ctt      1253
His Leu Leu Pro Ala Leu Asp Cys Leu Glu Gly Ser Thr Pro Gly Leu
        -5                   1                   5
```

```
tgaggccagt gagggaagtg gctgggccct aggccatgga gaaaacctta aacaaaccct     1313
ggagacaggg agcccttct ttctccacag ctctggacct ttccccctct ccctgcggcc     1373
tttgtcacct actgtgataa taaagcagtg agtgctgagc tctcacccett cccccnccaa   1433 aaaaaaaaaa aaaa                                                      1447
```

<210> SEQ ID NO 52
<211> LENGTH: 1540
<212> TYPE: DNA
<213> ORGANISM: Homo Sapiens
<220> FEATURE:
<221> NAME/KEY: CDS
<222> LOCATION: 25..402
<220> FEATURE:
<221> NAME/KEY: sig_peptide
<222> LOCATION: 25..96
<223> OTHER INFORMATION: Von Heijne matrix
      score 7.00
      seq LLCCFRALSGSLS/MR
<220> FEATURE:
<221> NAME/KEY: polyA_signal
<222> LOCATION: 1500..1505
<220> FEATURE:
<221> NAME/KEY: polyA_site
<222> LOCATION: 1525..1540
<220> FEATURE:
<221> NAME/KEY: misc_feature
<222> LOCATION: 625,1411,1432,1440,1450,1506
<223> OTHER INFORMATION: n=a, g, c or t

<400> SEQUENCE: 52

```
agcctggccc tccctctttc caaa atg gac aag tcc ctc ttg ctg gaa ctc           51
                         Met Asp Lys Ser Leu Leu Leu Glu Leu
                                         -20 ccc atc ctg ctc tgc tgc ttt agg gca tta tct gga tca ctt tca atg          99
Pro Ile Leu Leu Cys Cys Phe Arg Ala Leu Ser Gly Ser Leu Ser Met
-15              -10                  -5                    1 aga aat gat gca gtc aat gaa ata gtt gct gtg aaa aac aat ttt cct         147
Arg Asn Asp Ala Val Asn Glu Ile Val Ala Val Lys Asn Asn Phe Pro
              5                  10                  15 gtg ata gaa att att cag tgt agg atg tgc cac ctc cag ttc cca gga         195
Val Ile Glu Ile Ile Gln Cys Arg Met Cys His Leu Gln Phe Pro Gly
          20                  25                  30 gaa aag tgc tcc aga gga aga gga ata tgc aca gca aca aca gaa gag         243
Glu Lys Cys Ser Arg Gly Arg Gly Ile Cys Thr Ala Thr Thr Glu Glu
     35                  40                  45 gcc tgc atg gtt gga agg atg ttc aaa agg gat ggt aat ccc tgg tta         291
Ala Cys Met Val Gly Arg Met Phe Lys Arg Asp Gly Asn Pro Trp Leu
50                  55                  60                  65 acc ttc atg ggc tgc cta aag aac tgt gct gat gtg aaa ggc ata agg         339
Thr Phe Met Gly Cys Leu Lys Asn Cys Ala Asp Val Lys Gly Ile Arg
                 70                  75                  80 tgg agt gtc tat ttg gtg aac ttc agg tgc tgc agg agc cat gac ctg         387
Trp Ser Val Tyr Leu Val Asn Phe Arg Cys Cys Arg Ser His Asp Leu
             85                  90                  95 tgc aat gaa gac ctt tagaagttaa tggttcttct gtgactccaa tttctgggtg         442
Cys Asn Glu Asp Leu
            100 aggttgttgc ctcagcctct tcacaatgac tttctaaaaa aaatcacaca cacacacaca      502 cacactacag aagaggattg caaacacatg gctccatctt ctgcacacga aggaaagtc      562 cctctccttt tctacagtct ctgtcacgcc ccttaaaata agtaaataaa taaccttgag      622 agnaaagaac aagatcaata tatcctgcag gttgctacaa acccttgtgc tttcactgta     682
```

-continued

```
tagccagttc attcagaaaa ggaggaaagg gtagtttaat ttcaaaaaag aatcccttcc        742
tctttcctct gctgctttcc ttccttctgt ggcagggtat tttaatatat ttttcaaatt        802
tttttccttt ctgtgttatc cttcttatcc cactccaaag aaagcacata actgtggcct        862
gaagggatgg ggagtagcaa cataaaaaga agtggctcaa gtcttcttgg agtttgttca        922
tgaatgctga tcccagggtg aggagaagat tgggacatag aaaggaaact gcatcagaaa        982
catgaacaga gaaagattgt ctaccttcta gaatcagatc tgtttggggc tgggggttgg       1042
agaataaaag caggagaagt ctatgggatt ctagaaatag tacctgcatc cagcttccct       1102
gccaaactca aaggagaca tcaacctcta gacagggaac agcttcagga tacttccagg        1162
agacagagcc accagcagca aaacaaatat tcccatgcct ggagcatggc atagaggaag       1222
ctgagaaatg tggggtctga ggaagccatt tgagtctggc cactagacat ctcatcagcc       1282
acttgtgtga agagatgccc catgacccca gatgcctctc ccaccccttac ctccatctca       1342 cacacttgag cttgccactc tgtataattc taacatcctg gagaaaaatg gcagtttgac        1402
cgaacctgnt tcacaagggt agaggctgan ttctaacnga aacttgtnag aatgaagcct       1462
ggaaagagtg atgaattata ttatattata taaaaataat aatnaaaaat ataagaaag        1522 ctaaaaaaaa aaaaaaaa                                                     1540

<210> SEQ ID NO 53
<211> LENGTH: 1643
<212> TYPE: DNA
<213> ORGANISM: Homo Sapiens
<220> FEATURE:
<221> NAME/KEY: CDS
<222> LOCATION: 280..678
<220> FEATURE:
<221> NAME/KEY: sig_peptide
<222> LOCATION: 280..411
<223> OTHER INFORMATION: Von Heijne matrix
      score 3.90
      seq LSDSLWSPHCSWS/ER
<220> FEATURE:
<221> NAME/KEY: polyA_signal
<222> LOCATION: 1606..1611
<220> FEATURE:
<221> NAME/KEY: polyA_site
<222> LOCATION: 1628..1643

<400> SEQUENCE: 53
cctaagtttt ctcaaaaatg tcttttaca gttagtttaa gtcaggatct aaacaaagtt          60
catacattac atttgcttga tgtctctcaa ctgtcttata acctataaca attgctccca        120
atccattttt catgccatta ctttatttaa aaacctgggc caacccagtt ctcaaaaggt        180
attggacatc tcagaaaag atgactgctc tatgttgaac caaacaactg attcttacag         240
gtttcttcct cacttgtcct ctggctgtgg cagccagat atg gac agg aga gct          294
                                             Met Asp Arg Arg Ala
                                                            -40 aca tcc ttc cct cca ctc cct gcc aaa gaa agg aga gct ggg ata agc        342
Thr Ser Phe Pro Pro Leu Pro Ala Lys Glu Arg Arg Ala Gly Ile Ser
          -35                 -30                 -25 agt gcc ctc ccc tgc cca ccc act atg tca ctt tct gac tcc ctt tgg        390
Ser Ala Leu Pro Cys Pro Pro Thr Met Ser Leu Ser Asp Ser Leu Trp
      -20                 -15                 -10 tcc cct cat tgc tct tgg agt gag aga cct cat tcc ttc tct cac tgg        438
Ser Pro His Cys Ser Trp Ser Glu Arg Pro His Ser Phe Ser His Trp
  -5                   1                 5 agg cag cca aga atg gga tcc tct ggt ggg tct ttg gat tat gta agt        486
```

```
                                                                -continued

Arg Gln Pro Arg Met Gly Ser Ser Gly Gly Ser Leu Asp Tyr Val Ser
 10              15                  20                  25 ttc aaa cac tgg ata cac agc tcc aga tct aaa ggc aag att gct gct      534
Phe Lys His Trp Ile His Ser Ser Arg Ser Lys Gly Lys Ile Ala Ala
                 30                  35                  40 cta gag gca gga ctg ttc att tcc tgc ctt ggg gat gca ccc aga ggc      582
Leu Glu Ala Gly Leu Phe Ile Ser Cys Leu Gly Asp Ala Pro Arg Gly
             45                  50                  55 ctg aat gct tcc caa gga aac caa aga aag aac atg gtc tgt ttc aga      630
Leu Asn Ala Ser Gln Gly Asn Gln Arg Lys Asn Met Val Cys Phe Arg
             60                  65                  70 ggt gga gtg gcc agt cta gct ctg cca tct ctc act cct tcc tgc ctt      678
Gly Gly Val Ala Ser Leu Ala Leu Pro Ser Leu Thr Pro Ser Cys Leu
 75                  80                  85 tagggtacca ctgaggtgga aagcctgaac tgctgtctct gctctggctt gtgctcaagc      738
tgtgtgtcct tggactggcc atctcctctc tgcaaccctc ggtcttctca tttgtaaaat      798
ggaagtgatc ctctctgccc atacttcctt acagggctgc ttggagacaa tcaatcaaga      858
tgagggaaat tgagattcta caaagagtgt gatgcctaca taacaaagta ttgttttttct     918 cacagttggt ggtatttgag gagaaggtga agattttggt tggaagaggg accagcagac      978
aaacttgttc tcttgtgtat aaaaagccat aacacgcccc acatccctca agctaggaag     1038
aaacctgggc tggatggtga cccactggag aagctgtgac atcctagcat ggggaagagt     1098
accaggatgc ccactcctct tccccaggaa ccaccaagga gcctggagcc tggctttatc     1158
tcagccctga gtccccctct cccggtgcgc acacccctaa cttttttttt tttagatgga     1218
atcttgctct gtcgcccagg ctggagtgca acggcagctc actgtaacct ccacctccca     1278
ggttcaagcg attctcctgc ctcagcctcc cgagtagctg ggattacagg cgcgtgactc     1338
catgcctggc taattttttgt attttttagta gaggtagggt ttcaccatgt tgaccagggt     1398
ggtctggaac tcctgatctc aggtgatctg cctgcctcca cctcccaaag tgctggaatt     1458
acaggtgtga gctaccgcgc ccggccaatc tggggctcct agctttggtg caccaactac     1518
tcaaatcccc aacttctctc aagaggaat ttcaagaaac actgaccaat ctggttacag      1578
aagctgaagg ggccccaacc aggctgcaat aaacctgctt tacccttcca aaaaaaaaaa     1638
aaaaa                                                                 1643

<210> SEQ ID NO 54
<211> LENGTH: 1314
<212> TYPE: DNA
<213> ORGANISM: Homo Sapiens
<220> FEATURE:
<221> NAME/KEY: CDS
<222> LOCATION: 64..726
<220> FEATURE:
<221> NAME/KEY: sig_peptide
<222> LOCATION: 64..147
<223> OTHER INFORMATION: Von Heijne matrix
     score 3.70
     seq VVFTLGMFSAGLS/DL
<220> FEATURE:
<221> NAME/KEY: polyA_signal
<222> LOCATION: 1279..1284
<220> FEATURE:
<221> NAME/KEY: polyA_site
<222> LOCATION: 1300..1314

<400> SEQUENCE: 54
agtaggtccc ggcaaccgca ggctcgcggc gggcgctggg cgcgggatcc gactctagtc       60 gta atg gag gcg ggc ggc ttt ctg gac tcg ctc att tac gga gca tgc        108
```

|  |  |  |  |  |  |  |  |  |  |  |  |  |  |  |  |
|---|---|---|---|---|---|---|---|---|---|---|---|---|---|---|---|
| | Met | Glu | Ala | Gly | Gly | Phe | Leu | Asp | Ser | Leu | Ile | Tyr | Gly | Ala | Cys |
| | | | | -25 | | | | -20 | | | | -15 | | | |

```
gtg gtc ttc acc ctt ggc atg ttc tcc gcc ggc ctc tcg gac ctc agg       156
Val Val Phe Thr Leu Gly Met Phe Ser Ala Gly Leu Ser Asp Leu Arg
            -10                  -5                   1 cac atg cga atg acc cgg agt gtg gac aac gtc cag ttc ctg ccc ttt       204
His Met Arg Met Thr Arg Ser Val Asp Asn Val Gln Phe Leu Pro Phe
  5                  10                  15 ctc acc acg gaa gtc aac aac ctg ggc tgg ctg agt tat ggg gct ttg       252
Leu Thr Thr Glu Val Asn Asn Leu Gly Trp Leu Ser Tyr Gly Ala Leu
 20                  25                  30                  35 aag gga gac ggg atc ctc atc gtc gtc aac aca gtg ggt gct gcg ctt       300
Lys Gly Asp Gly Ile Leu Ile Val Val Asn Thr Val Gly Ala Ala Leu
                 40                  45                  50 cag acc ctg tat atc ttg gca tat ctg cat tac tgc cct cgg aag cgt       348
Gln Thr Leu Tyr Ile Leu Ala Tyr Leu His Tyr Cys Pro Arg Lys Arg
             55                  60                  65 gtt gtg ctc cta cag act gca acc ctg cta ggg gtc ctt ctc ctg ggt       396
Val Val Leu Leu Gln Thr Ala Thr Leu Leu Gly Val Leu Leu Leu Gly
         70                  75                  80 tat ggc tac ttt tgg ctc ctg gta ccc aac cct gag gcc cgg ctt cag       444
Tyr Gly Tyr Phe Trp Leu Leu Val Pro Asn Pro Glu Ala Arg Leu Gln
 85                  90                  95 cag ttg ggc ctc ttc tgc agt gtc ttc acc atc agc atg tac ctc tca       492
Gln Leu Gly Leu Phe Cys Ser Val Phe Thr Ile Ser Met Tyr Leu Ser
100                 105                 110                 115 cca ctg gct gac ttg gct aag gtg att caa act aaa tca acc caa tgt       540
Pro Leu Ala Asp Leu Ala Lys Val Ile Gln Thr Lys Ser Thr Gln Cys
                120                 125                 130 ctc tcc tac cca ctc acc att gct acc ctt ctc acc tct gcc tcc tgg       588
Leu Ser Tyr Pro Leu Thr Ile Ala Thr Leu Leu Thr Ser Ala Ser Trp
            135                 140                 145 tgc ctc tat ggg ttt cga ctc aga gat ccc tat atc atg gtg tcc aac       636
Cys Leu Tyr Gly Phe Arg Leu Arg Asp Pro Tyr Ile Met Val Ser Asn
        150                 155                 160 ttt cca gga atc gtc acc agc ttt atc cgc ttc tgg ctt ttc tgg aag       684
Phe Pro Gly Ile Val Thr Ser Phe Ile Arg Phe Trp Leu Phe Trp Lys
165                 170                 175 tac ccc cag gag caa gac agg aac tac tgg ctc ctg caa acc                726
Tyr Pro Gln Glu Gln Asp Arg Asn Tyr Trp Leu Leu Gln Thr
180                 185                 190 tgaggctgct catctgacca ctgggcacct tagtgccaac ctgaaccaaa gagacctcct      786
tgtttcagct gggcctgctg tccagcttcc caggtgcagt gggttgtggg aacaagagat      846
gactttgagg ataaaaggac caaagaaaaa gctttactta gatgattgat tgggggcctag    906 gagatgaaat cacttttttat tttttagaga ttttttttttt ttaatttttgg aggttggggt  966 gcaatcttta gaatatgcct taaaaggccg ggcgcggtgg ctcacgcctg taatcccagc    1026
actttgggag gccaaggtgg gcggatcgcc tgaggtcagg agttcaagac caacctgact    1086
aacatggtga acccccatct ctactaaaaa tacaaaatta gccaggcatg atggcacatg    1146
cctgtaatcc cagatacttg ggaggctgag gcaggagaat tgcttgaacc caggaggtgg    1206
aggttgcagt gagctgagat cgtgccattg tgatataat atgccttata tgctgatatg     1266
aatatgcctt aaaataaagt gttccccacc cctaaaaaaa aaaaaaaa                 1314
```

<210> SEQ ID NO 55
<211> LENGTH: 2356
<212> TYPE: DNA

```
<213> ORGANISM: Homo Sapiens
<220> FEATURE:
<221> NAME/KEY: CDS
<222> LOCATION: 42..1097
<220> FEATURE:
<221> NAME/KEY: sig_peptide
<222> LOCATION: 42..110
<220> OTHER INFORMATION: Von Heijne matrix
       score 4.40
       seq QFILLGTTSVVTA/AL
<220> FEATURE:
<221> NAME/KEY: polyA_signal
<222> LOCATION: 2323..2328
<220> FEATURE:
<221> NAME/KEY: polyA_site
<222> LOCATION: 2341..2356

<400> SEQUENCE: 55
```

| | | |
|---|---|---|
| atccttggcg ccacagtcgg ccaccggggc tcgccgccgt c atg gag agc gga ggg | | 56 |
| Met Glu Ser Gly Gly | | |
| -20 | | |
| cgg ccc tcg ctg tgc cag ttc atc ctc ctg ggc acc acc tct gtg gtc | | 104 |
| Arg Pro Ser Leu Cys Gln Phe Ile Leu Leu Gly Thr Thr Ser Val Val | | |
| -15 -10 -5 | | |
| acc gcc gcc ctg tac tcc gtg tac cgg cag aag gcc cgg gtc tcc caa | | 152 |
| Thr Ala Ala Leu Tyr Ser Val Tyr Arg Gln Lys Ala Arg Val Ser Gln | | |
| 1 5 10 | | |
| gag ctc aag gga gct aaa aaa gtt cat ttg ggt gaa gat tta aag agt | | 200 |
| Glu Leu Lys Gly Ala Lys Lys Val His Leu Gly Glu Asp Leu Lys Ser | | |
| 15 20 25 30 | | |
| att ctt tca gaa gct cca gga aaa tgc gtg cct tat gct gtt ata gaa | | 248 |
| Ile Leu Ser Glu Ala Pro Gly Lys Cys Val Pro Tyr Ala Val Ile Glu | | |
| 35 40 45 | | |
| gga gct gtg cgg tct gtt aaa gaa acg ctt aac agc cag ttt gtg gaa | | 296 |
| Gly Ala Val Arg Ser Val Lys Glu Thr Leu Asn Ser Gln Phe Val Glu | | |
| 50 55 60 | | |
| aac tgc aag ggg gta att cag cgg ctg aca ctt cag gag cac aag atg | | 344 |
| Asn Cys Lys Gly Val Ile Gln Arg Leu Thr Leu Gln Glu His Lys Met | | |
| 65 70 75 | | |
| gtg tgg aat cga acc acc cac ctt tgg aat gat tgc tca aag atc att | | 392 |
| Val Trp Asn Arg Thr Thr His Leu Trp Asn Asp Cys Ser Lys Ile Ile | | |
| 80 85 90 | | |
| cat cag agg acc aac aca gtg ccc ttt gac ctg gtg ccc cac gag gat | | 440 |
| His Gln Arg Thr Asn Thr Val Pro Phe Asp Leu Val Pro His Glu Asp | | |
| 95 100 105 110 | | |
| ggc gtg gat gtg gct gtg cga gtg ctg aag ccc ctg gac tca gtg gat | | 488 |
| Gly Val Asp Val Ala Val Arg Val Leu Lys Pro Leu Asp Ser Val Asp | | |
| 115 120 125 | | |
| ctg ggt cta gag act gtg tat gag aag ttc cac ccc tcg att cag tcc | | 536 |
| Leu Gly Leu Glu Thr Val Tyr Glu Lys Phe His Pro Ser Ile Gln Ser | | |
| 130 135 140 | | |
| ttc acc gat gtc atc ggc cac tac atc agc ggt gag cgg ccc aaa ggc | | 584 |
| Phe Thr Asp Val Ile Gly His Tyr Ile Ser Gly Glu Arg Pro Lys Gly | | |
| 145 150 155 | | |
| atc caa gag acc gag gag atg ctg aag gtg ggg gcc acc ctc aca ggg | | 632 |
| Ile Gln Glu Thr Glu Glu Met Leu Lys Val Gly Ala Thr Leu Thr Gly | | |
| 160 165 170 | | |
| gtt ggc gaa ctg gtc ctg gac aac aac tct gtc cgc ctg cag ccg ccc | | 680 |
| Val Gly Glu Leu Val Leu Asp Asn Asn Ser Val Arg Leu Gln Pro Pro | | |
| 175 180 185 190 | | |
| aaa caa ggc atg cag tac tat cta agc agc cag gac ttc gac agc ctg | | 728 |
| Lys Gln Gly Met Gln Tyr Tyr Leu Ser Ser Gln Asp Phe Asp Ser Leu | | |
| 195 200 205 | | |

```
ctg cag agg cag gag tcg agc gtc agg ctc tgg aag gtg ctg gcg ctg        776
Leu Gln Arg Gln Glu Ser Ser Val Arg Leu Trp Lys Val Leu Ala Leu
        210                 215                 220 gtt ttt ggc ttt gcc aca tgt gcc acc ctc ttc ttc att ctc cgg aag        824
Val Phe Gly Phe Ala Thr Cys Ala Thr Leu Phe Phe Ile Leu Arg Lys
            225                 230                 235 cag tat ctg cag cgg cag gag cgc ctg cgc ctc aag cag atg cag gag        872
Gln Tyr Leu Gln Arg Gln Glu Arg Leu Arg Leu Lys Gln Met Gln Glu
    240                 245                 250 gag ttc cag gag cat gag gcc cag ctg ctg agc cga gcc aag cct gag        920
Glu Phe Gln Glu His Glu Ala Gln Leu Leu Ser Arg Ala Lys Pro Glu
255                 260                 265                 270 gac agg gag agt ctg aag agc gcc tgt gta gtg tgt ctg agc agc ttc        968
Asp Arg Glu Ser Leu Lys Ser Ala Cys Val Val Cys Leu Ser Ser Phe
                275                 280                 285 aag tcc tgc gtc ttt ctg gag tgt ggg cac gtt tgt tcc tgc acc gag       1016
Lys Ser Cys Val Phe Leu Glu Cys Gly His Val Cys Ser Cys Thr Glu
            290                 295                 300 tgc tac cgc gcc ttg cca gag ccc aag aag tgc cct atc tgc aga cag       1064
Cys Tyr Arg Ala Leu Pro Glu Pro Lys Lys Cys Pro Ile Cys Arg Gln
    305                 310                 315 gcg atc acc cgg gtg ata ccc ctg tac aac agc taatagtttg gaagccgcac     1117
Ala Ile Thr Arg Val Ile Pro Leu Tyr Asn Ser
320                 325 agcttgacct ggaagcaccc ctgcccctt ttcagggatt tttatctcga ggcctttgga     1177
ggagcagtgg tgggggtagc tgtcacctcc aggtatgatt gagggaggaa ttgggtagaa     1237
actctccaga cccatgcctc caatggcagg atgctgcctt tcccacctga gagggaccc      1297 tgtccatgtg cagcctcatc agagcctcac cctgggagga tgccgtggcg tctcctccca     1357
ggagccagat cagtgcgagt gtgactgaaa atgcctcatc acttaagcac caaagccagt     1417
gatcagcagc tcttctgttc ctgtgtcttc tgttttttc tggtgaatcg ttgcttgctg      1477
tggacttggt ggaggactca gaggggagga aaggctgggc cccgagtaca acggatgcct     1537
tgggtgctgc ctccgaagag actctgccgc agcttttctt cttttcctc atgccccggg      1597 aaacagtctt tcttcagaat tgtcaggctg ggcaggtcaa cttgtgttcc tttcccctca     1657
cctgcttgcc tccttaacgc ctgcacgtgt gtgtagagga caaaagaaag tgaagtcagc     1717
acatccgctt ctgcccagat ggtcggggcc ccgggcaaca gattgaagag agatcatgtg     1777
aagggcagtt ggtcaggcag gcctcctggt ttcgccactg gccctgattt gaactcctgc     1837
cacttgggag agctcgggt ggtccctggt tttccctcct ggagaatgag gcgcagaggc      1897
ctcgcctcct gaaggacgca gtgtggatgc cactggccta gtgtcctggc ctcacagctt     1957
ccttgcaagg ctgtcacaag gaaaagcagc cggctgcac cctgagcata tgccctcttg      2017
gggctccctc atccagcccg tcgcagcttt gacatcttgg tgtactcatg tcgcttctcc     2077
ttgtgttacc ccctcccagt attaccattt gcccctcacc tgcccttggt gagcttttta     2137
gtgcaagaca gatggggctg tttccccca ctctgagta gttggaggtc acatacacag       2197 ctctttttt attgccctt tctgcctctg aatgttcatc tctcgtcctc ctttgtgcag       2257
gcgaggaagg ggtgccctca ggggccgaca ctagtatgat gcagtgtcca gtgtgaacag     2317
cagaaattaa acatgttgca accaaaaaaa aaaaaaaaa                            2356
```

<210> SEQ ID NO 56
<211> LENGTH: 1701
<212> TYPE: DNA
<213> ORGANISM: Homo Sapiens

```
<220> FEATURE:
<221> NAME/KEY: CDS
<222> LOCATION: 245..1399
<220> FEATURE:
<221> NAME/KEY: sig_peptide
<222> LOCATION: 245..796
<223> OTHER INFORMATION: Von Heijne matrix
     score 5.10
     seq GWLPLLLLSLLVA/TW
<220> FEATURE:
<221> NAME/KEY: polyA_signal
<222> LOCATION: 1669..1674
<220> FEATURE:
<221> NAME/KEY: polyA_site
<222> LOCATION: 1687..1701

<400> SEQUENCE: 56
```

| | | |
|---|---|---:|
| atcccgcgca gtggcccggc gatgtcgctc gtgctgctaa gcctggccgc gctgtgcagg | | 60 |
| agcgccgtac cccgagagcc gaccgttcaa tgtggctctg aaactgggcc atctccagag | | 120 |
| tggatgctac aacatgatct aatcccggga gacttgaggg acctccgagt agaacctgtt | | 180 |
| acaactagtg ttgcaacagg ggactattca attttgatga atgtaagctg ggtactccgg | | 240 |

| | | |
|---|---|---:|
| gcag atg tgg aca ttt tcc tac atc ggc ttc cct gta gag ctg aac aca | | 289 |
|      Met Trp Thr Phe Ser Tyr Ile Gly Phe Pro Val Glu Leu Asn Thr | | |
|          -180                -175                -170            | | |
| gtc tat ttc att ggg gcc cat aaa att cct aat gca aat atg aat gaa | | 337 |
| Val Tyr Phe Ile Gly Ala His Lys Ile Pro Asn Ala Asn Met Asn Glu | | |
|         -165                -160                -155             | | |
| gat ggc cct tcc atg tct gtg aat ttc acc tca cca ggc tgc cta gac | | 385 |
| Asp Gly Pro Ser Met Ser Val Asn Phe Thr Ser Pro Gly Cys Leu Asp | | |
|     -150                -145                -140                 | | |
| cac ata atg aaa tat aaa aaa aag tgt gtc aag gcc gga agc ctg tgg | | 433 |
| His Ile Met Lys Tyr Lys Lys Lys Cys Val Lys Ala Gly Ser Leu Trp | | |
|     -135                -130                -125                 | | |
| gat ccg aac atc act gct tgt aag aag aat gag gag aca gta gaa gtg | | 481 |
| Asp Pro Asn Ile Thr Ala Cys Lys Lys Asn Glu Glu Thr Val Glu Val | | |
|     -120                -115                -110                 | | |
| aac ttc aca acc act ccc ctg gga aac aga tac atg gct ctt atc caa | | 529 |
| Asn Phe Thr Thr Thr Pro Leu Gly Asn Arg Tyr Met Ala Leu Ile Gln | | |
| -105                -100                -95                 -90  | | |
| cac agc act atc atc ggg ttt tct cag gtg ttt gag cca cac cag aag | | 577 |
| His Ser Thr Ile Ile Gly Phe Ser Gln Val Phe Glu Pro His Gln Lys | | |
|         -85                 -80                 -75              | | |
| aaa caa acg cga gct tca gtg gtg att cca gtg act ggg gat agt gaa | | 625 |
| Lys Gln Thr Arg Ala Ser Val Val Ile Pro Val Thr Gly Asp Ser Glu | | |
|     -70                 -65                 -60                  | | |
| ggt gct acg gtg cag ctg act cca tat ttt cct act tgt ggc agc gac | | 673 |
| Gly Ala Thr Val Gln Leu Thr Pro Tyr Phe Pro Thr Cys Gly Ser Asp | | |
|     -55                 -50                 -45                  | | |
| tgc atc cga cat aaa gga aca gtt gtg ctc tgc cca caa aca ggc gtc | | 721 |
| Cys Ile Arg His Lys Gly Thr Val Val Leu Cys Pro Gln Thr Gly Val | | |
|     -40                 -35                 -30                  | | |
| cct ttc cct ctg gat aac aac aaa agc aag ccg gga ggc tgg ctg cct | | 769 |
| Pro Phe Pro Leu Asp Asn Asn Lys Ser Lys Pro Gly Gly Trp Leu Pro | | |
| -25                 -20                 -15                 -10  | | |
| ctc ctc ctg ctg tct ctg ctg gtg gcc aca tgg gtg ctg gtg gca ggg | | 817 |
| Leu Leu Leu Leu Ser Leu Leu Val Ala Thr Trp Val Leu Val Ala Gly | | |
|             -5                   1                  5            | | |
| atc tat cta atg tgg agg cac gaa agg atc aag aag act tcc ttt tct | | 865 |
| Ile Tyr Leu Met Trp Arg His Glu Arg Ile Lys Lys Thr Ser Phe Ser | | |
|         10                  15                  20               | | |
| acc acc aca cta ctg ccc ccc att aag gtt ctt gtg gtt tac cca tct | | 913 |

|     |     |     |     |     |     |     |     |     |     |     |     |     |     |     |     |     |
|---|---|---|---|---|---|---|---|---|---|---|---|---|---|---|---|---|
| Thr | Thr | Thr | Leu | Leu | Pro | Pro | Ile | Lys | Val | Leu | Val | Tyr | Pro | Ser | | |
| | 25 | | | | 30 | | | | | 35 | | | | | | |

```
gaa ata tgt ttc cat cac aca att tgt tac ttc act gaa ttt ctt caa       961
Glu Ile Cys Phe His His Thr Ile Cys Tyr Phe Thr Glu Phe Leu Gln
 40              45                  50                  55 aac cat tgc aga agt gag gtc atc ctt gaa aag tgg cag aaa aag aaa      1009
Asn His Cys Arg Ser Glu Val Ile Leu Glu Lys Trp Gln Lys Lys Lys
                 60                  65                  70 ata gca gag atg ggt cca gtg cag tgg ctt gcc act caa aag aag gca      1057
Ile Ala Glu Met Gly Pro Val Gln Trp Leu Ala Thr Gln Lys Lys Ala
             75                  80                  85 gca gac aaa gtc gtc ttc ctt ctt tcc aat gac gtc aac agt gtg tgc      1105
Ala Asp Lys Val Val Phe Leu Leu Ser Asn Asp Val Asn Ser Val Cys
         90                  95                 100 gat ggt acc tgt ggc aag agc gag ggc agt ccc agt gag aac tct caa      1153
Asp Gly Thr Cys Gly Lys Ser Glu Gly Ser Pro Ser Glu Asn Ser Gln
    105                 110                 115 gac ctc ttc ccc ctt gcc ttt aac ctt ttc tgc agt gat cta aga agc      1201
Asp Leu Phe Pro Leu Ala Phe Asn Leu Phe Cys Ser Asp Leu Arg Ser
120                 125                 130                 135 cag att cat ctg cac aaa tac gtg gtg gtc tac ttt aga gag att gat      1249
Gln Ile His Leu His Lys Tyr Val Val Val Tyr Phe Arg Glu Ile Asp
                140                 145                 150 aca aaa gac gat tac aat gct ctc agt gtc tgc ccc aag tac cac ctc      1297
Thr Lys Asp Asp Tyr Asn Ala Leu Ser Val Cys Pro Lys Tyr His Leu
            155                 160                 165 atg aag gat gcc act gct ttc tgt gca gaa ctt ctc cat gtc aag cag      1345
Met Lys Asp Ala Thr Ala Phe Cys Ala Glu Leu Leu His Val Lys Gln
        170                 175                 180 cag gtg tca gca gga aaa aga tca caa gcc tgc cac gat ggc tgc tgc      1393
Gln Val Ser Ala Gly Lys Arg Ser Gln Ala Cys His Asp Gly Cys Cys
    185                 190                 195 tcc ttg tagcccaccc atgagaagca agagaccta aaggcttcct atcccaccaa        1449
Ser Leu
200 ttacagggaa aaacgtgtg atgatcctga agcttactat gcagcctaca acagcctta     1509 gtaattaaaa cattttatac caataaaatt ttcaaatatt gctaactaat gtagcattaa   1569 ctaacgattg gaaactacat ttcaacttc aaagctgttt tatacataga aatcaattac    1629 agttttaatt gaaaactata accatttga taatgcaaca ataaagcatc ttcagccaaa    1689 aaaaaaaaaa aa                                                       1701

<210> SEQ ID NO 57
<211> LENGTH: 772
<212> TYPE: DNA
<213> ORGANISM: Homo Sapiens
<220> FEATURE:
<221> NAME/KEY: CDS
<222> LOCATION: 235..441
<220> FEATURE:
<221> NAME/KEY: sig_peptide
<222> LOCATION: 235..303
<223> OTHER INFORMATION: Von Heijne matrix
      score 5.30
      seq LLLDVTVFIPALP/FS
<220> FEATURE:
<221> NAME/KEY: polyA_site
<222> LOCATION: 758..772
<220> FEATURE:
<221> NAME/KEY: misc_feature
<222> LOCATION: 573
<223> OTHER INFORMATION: n=a, g, c or t
```

```
<400> SEQUENCE: 57
aatacctggc aatctgttta agatcattga caggcctgag agttttccat acggcctgca      60
ccctaacctc tgggaagaaa atatccacaa tgaaatttct acaagattag aggaaggaga     120
gaggcaacgg ggattccatt tctactagga gtatcaacct ctgagaggga tatatccatc     180
tctgtggatg tcatctgctc tgcagaaaac cctttcttgg aactaccagg aaac atg      237
                                                              Met aat ctg atg tgg acc ctc ctc ctt ttc ctc ctt ttg gac gta act gtc      285
Asn Leu Met Trp Thr Leu Leu Leu Phe Leu Leu Leu Asp Val Thr Val
        -20             -15                 -10 ttc att cca gcc ctg ccc ttc tca aca cga cat ata gac aac ccc agg      333
Phe Ile Pro Ala Leu Pro Phe Ser Thr Arg His Ile Asp Asn Pro Arg
 -5                  1               5                      10 tcg tgg gtc cct aga gga cac cac cga tac tgt gat gtg atg atg agg      381
Ser Trp Val Pro Arg Gly His His Arg Tyr Cys Asp Val Met Met Arg
                15              20              25 cgc cgt tgg ctg atc tat agg ggt aaa tgc gag cag atc cac aca ttc      429
Arg Arg Trp Leu Ile Tyr Arg Gly Lys Cys Glu Gln Ile His Thr Phe
            30              35              40 att cat aga atc tgaccaccat agcagatttc tgcagaactc caccactgcc          481
Ile His Arg Ile
        45 ctgtaccaac agcccctcca tgtgcagctg ccacaacagt actcatgatg tcaatgtcac     541 tgactgcttt gccagcacag ggacccgacc tnttcactgc cactaccaaa aataaggagt     601 ccaccaggcc catgcgagtg ggctgcaaga aggggggcatc tgttcacctg gatggctagg   661 ttcctcctga caacggcacc tgaatgactt gcaccctacg ccttcaaatc tgtgcagcac    721 tgtcaaggtc ttctttgtaa atgcttcgtc ctttgcaaaa aaaaaaaaaa a             772

<210> SEQ ID NO 58
<211> LENGTH: 987
<212> TYPE: DNA
<213> ORGANISM: Homo Sapiens
<220> FEATURE:
<221> NAME/KEY: CDS
<222> LOCATION: 88..411
<220> FEATURE:
<221> NAME/KEY: sig_peptide
<222> LOCATION: 88..234
<223> OTHER INFORMATION: Von Heijne matrix
      score 4.70
      seq LLLVSTWSADLMS/YR
<220> FEATURE:
<221> NAME/KEY: polyA_signal
<222> LOCATION: 938..943
<220> FEATURE:
<221> NAME/KEY: polyA_site
<222> LOCATION: 964..987
<220> FEATURE:
<221> NAME/KEY: misc_feature
<222> LOCATION: 828,832
<223> OTHER INFORMATION: n=a, g, c or t

<400> SEQUENCE: 58
tttttctttt gacatgttca gatgttggca aggctgaaaa ctgcagggga tctggttgtg      60
ataatccagg cctgaatata tacaaat atg aac aag acc cac aag gac tgc tca    114
                            Met Asn Lys Thr His Lys Asp Cys Ser
                                                         -45 tca ccc cag tat tcc att tac aac atc ctg aat gaa ctc ccg acc agg      162
Ser Pro Gln Tyr Ser Ile Tyr Asn Ile Leu Asn Glu Leu Pro Thr Arg
-40                 -35             -30                 -25 cct ata att ctc tct tgc agc caa ata tcc tgc tta ctc ctg gta tct     210
```

```
Pro Ile Ile Leu Ser Cys Ser Gln Ile Ser Cys Leu Leu Val Ser
            -20             -15             -10 acc tgg tca gca gac ctc atg agt tat cgc cca gtc aca aaa cca tcc      258
Thr Trp Ser Ala Asp Leu Met Ser Tyr Arg Pro Val Thr Lys Pro Ser
        -5                   1                   5 caa aga tgc acc agt cca gca caa agt atg act gtc aat ctc aca aaa      306
Gln Arg Cys Thr Ser Pro Ala Gln Ser Met Thr Val Asn Leu Thr Lys
        10                  15                  20 gat gta ggg ttc tac gag gat act cag agt ata aga att acg cta agt      354
Asp Val Gly Phe Tyr Glu Asp Thr Gln Ser Ile Arg Ile Thr Leu Ser
25                  30                  35                  40 gaa ata agc caa gcc cag aaa gac aca tac ttt att att tca tgt atc      402
Glu Ile Ser Gln Ala Gln Lys Asp Thr Tyr Phe Ile Ile Ser Cys Ile
                45                  50                  55 tgt gga atc taaaagagtc aaattcatgg cagcagggag agggctgaag              451
Cys Gly Ile aaggggggaga tgttgatcaa agtttctatg tatacaaaga ccaaaccatc acattatgcc   511
tcataaatat atacaattat tatttgctaa ttacaagtaa agcaatacaa gaagaaaaaa    571
aggaatcata agtaaatcca tgacaagtga aaacgcaatg gagagaaggg aatcaatgat    631
tgaagaagag aaaggacagt ggatttacaa ctgcttcgaa agagtgattt gactggcaaa    691
ggactgggga gaggtccttt gggaaatgga caaaaccctc gaatggttag gaaagacaat    751
ctctttataa atgcggggca taagctgagc acaaggtgaa gtttggcatg tactgccgtg    811
ggatgttgta aaaattnatg ntcaaaagca aagcaattct tggttcatct gtgttcactg    871
tgagactagc ctattattgg ggttaaactt ataaacaaac ttctgttcat catttttttt    931
ctccaaaata aagtgatcaa attgtcccac agaaaaaaaa aaaaaaaaaa aaaaaa        987

<210> SEQ ID NO 59
<211> LENGTH: 1324
<212> TYPE: DNA
<213> ORGANISM: Homo Sapiens
<220> FEATURE:
<221> NAME/KEY: CDS
<222> LOCATION: 129..452
<220> FEATURE:
<221> NAME/KEY: sig_peptide
<222> LOCATION: 129..212
<223> OTHER INFORMATION: Von Heijne matrix
      score 5.20
      seq LDIVISFVGAVSS/ST
<220> FEATURE:
<221> NAME/KEY: polyA_signal
<222> LOCATION: 1290..1295
<220> FEATURE:
<221> NAME/KEY: polyA_site
<222> LOCATION: 1309..1324
<220> FEATURE:
<221> NAME/KEY: misc_feature
<222> LOCATION: 888,1080
<223> OTHER INFORMATION: n=a, g, c or t

<400> SEQUENCE: 59
gatttttttc acaagcaata gtttagtagt tcaactttca ttaattattt ctagtaatta     60
ctttcagtat tgaaaatact tactgttaat attcatgtaa gtaacaaaca tttaaataag   120 aaaaataaa atg tat ttt cat ttt cta ggt gcc gga gca att ctt att cct   170
              Met Tyr Phe His Phe Leu Gly Ala Gly Ala Ile Leu Ile Pro
                      -25                 -20                 -15 cgt tta gac att gtg att tcc ttc gtt gga gct gtg agc agc agc aca      218
Arg Leu Asp Ile Val Ile Ser Phe Val Gly Ala Val Ser Ser Ser Thr
            -10                  -5                   1
```

```
ttg gcc cta atc ctg cca cct ttg gtt gaa att ctt aca ttt tcg aag      266
Leu Ala Leu Ile Leu Pro Pro Leu Val Glu Ile Leu Thr Phe Ser Lys
         5                  10                  15 gaa cat tat aat ata tgg atg gtc ctg aaa aat att tct ata gca ttc      314
Glu His Tyr Asn Ile Trp Met Val Leu Lys Asn Ile Ser Ile Ala Phe
 20                  25                  30 act gga gtt gtt ggc ttc tta tta ggt aca tat ata act gtt gaa gaa      362
Thr Gly Val Val Gly Phe Leu Leu Gly Thr Tyr Ile Thr Val Glu Glu
35                  40                  45                  50 att att tat cct act ccc aaa gtt gta gct ggc act cca cag agt cct      410
Ile Ile Tyr Pro Thr Pro Lys Val Val Ala Gly Thr Pro Gln Ser Pro
                 55                  60                  65 ttt cta aat ttg aat tca aca tgc tta aca tct ggt ttg aaa              452
Phe Leu Asn Leu Asn Ser Thr Cys Leu Thr Ser Gly Leu Lys
             70                  75                  80 tagtaaaagc agaatcatga gtcttctatt tttgtcccat ttctgaaaat tatcaagata    512
actagtaaaa tacattgcta tatacataaa aatggtaaca aactctgttt tctttggcac    572
gatattaata ttttggaagt aatcataact ctttaccagt agtggtaaac ctatgaaaaa    632
tccttgcttt taagtgttag caatagttca aaaaattaag ttctgaaaat tgaaaaaatt    692
aaaatgtaaa aaaattaaag aataaaaata cttctattat tcttttatct cagtaagaaa    752
taccttaacc aagatatctc tcttttatgc tactcttttg ccactcactt gagaacagaa    812
taggatttca acaataagag aataaaataa gaacatgtat aacaaaaagc tctctccaga    872
tcatccctgt gaatgnccaa agtaaacttt atgtacagtg taaaaaaaaa aaaatctcag    932
ttatgttttt attagccaaa ttctaatgat tggctcctgg aagtatagaa aactcccatt    992
aacataatat aagcatcaga aaattgcaaa cactagaatt aatttacac tctaatggta    1052 gttgatcttc atagtcaaga ggcactgntc aagatcatga cttagtgttt caatgaaatt    1112
tgacaaggga ctttaaaact tatccagtgc aactcccttg tttttcgtca gaggaaaagg    1172
aggcctagaa aggttaagta acttggtcga gaccactcag ccttgagatc aagaaaacct    1232
aatcttctga ctcccaggcc aggatgtttt atttctcaca tcatgtccaa gaaaagaat    1292 aaattatgtt cagctcaaaa aaaaaaaaaa aa                                  1324
```

<210> SEQ ID NO 60
<211> LENGTH: 1918
<212> TYPE: DNA
<213> ORGANISM: Homo Sapiens
<220> FEATURE:
<221> NAME/KEY: CDS
<222> LOCATION: 238..612
<220> FEATURE:
<221> NAME/KEY: sig_peptide
<222> LOCATION: 238..348
<223> OTHER INFORMATION: Von Heijne matrix
    score 9.40
    seq LLCCVLSASQLSS/QD
<220> FEATURE:
<221> NAME/KEY: polyA_signal
<222> LOCATION: 1885..1890
<220> FEATURE:
<221> NAME/KEY: polyA_site
<222> LOCATION: 1905..1918
<220> FEATURE:
<221> NAME/KEY: misc_feature
<222> LOCATION: 945,1624
<223> OTHER INFORMATION: n=a, g, c or t

<400> SEQUENCE: 60
aaaaatctaa gcgacttcga tgccaaggaa gttgtgtaaa tgtgcacgcg ctacaccaca     60

```
cccagggtgg aaaccacagt tgcagagtca ttaaacaatc aattgtttgt ttaacatctg      120
tgataggcag ctttccttct tttcaacagt gatacctacg aaaatcaaaa taaatgcaag      180
ctgaggtttt gtgctcactg aaagggctgt caaccccaga aggccgacac aaaaaaa        237 atg gta tgt gaa gat gca ccg tct ttt caa atg gcc tgg gag agt caa        285
Met Val Cys Glu Asp Ala Pro Ser Phe Gln Met Ala Trp Glu Ser Gln
        -35                 -30                 -25 atg gcc tgg gag agg ggg cct gcc ctt ctc tgc tgt gtc ctt tcg gct        333
Met Ala Trp Glu Arg Gly Pro Ala Leu Leu Cys Cys Val Leu Ser Ala
        -20                 -15                 -10 tcc cag ttg agc tcc caa gac cag gac cca ctg ggg cat ata aaa tct        381
Ser Gln Leu Ser Ser Gln Asp Gln Asp Pro Leu Gly His Ile Lys Ser
 -5              1                   5                   10 ctg ctg tat cct ttc ggc ttc cca gtt gag ctc cca aga cca gga ccc        429
Leu Leu Tyr Pro Phe Gly Phe Pro Val Glu Leu Pro Arg Pro Gly Pro
                15                  20                  25 act ggg gca tat aaa aaa gtc aaa aat caa aat caa aca aca agt tct        477
Thr Gly Ala Tyr Lys Lys Val Lys Asn Gln Asn Gln Thr Thr Ser Ser
            30                  35                  40 gag tta ctt agg aaa cag act tcg cat ttc aat cag aga ggc cac aga        525
Glu Leu Leu Arg Lys Gln Thr Ser His Phe Asn Gln Arg Gly His Arg
        45                  50                  55 gca agg tct aaa ctt ctg gct tct aga caa att cct gat aga aca ttt        573
Ala Arg Ser Lys Leu Leu Ala Ser Arg Gln Ile Pro Asp Arg Thr Phe
 60             65                  70                  75 aaa tgt ggg aag tgg ctt ccc cag gtc cca tcc cct gtt tagggataga        622
Lys Cys Gly Lys Trp Leu Pro Gln Val Pro Ser Pro Val
                80                  85 gttgatatca ttttatagt tgccatgtat gcctctgcct gaattttttt aattgacttt       682
tgagcttttg agattgcacg agggagaaca aggcctttgc tgttgtggat aggaaagact      742
taacctaaaa ttaaaccagc aagaaagcat tagtaaaaat ctaacaatat gaagggctct      802
tatgagtcat ttttttcaaa agatgaaaac tccagaaacg cacaggaacg aaatacctcc      862
cagaaacatg aagcaatcat cgaagactca ctggtaatat tttttaaaag tatacagatc      922
aaagcaaaaa gaagccatgt gtnaacaaag agaaatgtgc aaatatttt taaggcagta      982 ttaagtgcaa gaggagtaac atgaaataaa cattctttca catggctact gggaatataa     1042
atttcgctcc agaaaggccg tagcagtttg acgataggtg gcaaaacctt aagattgtgt     1102 actgggccc agaattttta tttctaggaa tgtatcctga ggaaattatc cgagatcccc     1162
acaaactgca atgtttagga attgtcctta tagcattgca tacacaagaa aaacagagaa     1222
aagcctgatc cctgtcagtg aaaaggggt tcaatgaatt acggtgtgtc tgcatgaggc     1282
ttttatgaca ttaaaaattg ttgaacaacg gccaggcaca gtggctcatg cctgtaatcc     1342
taacactttg ggaggccaag gtgggaagat tgcctgagct caggagtttg agaccagcct     1402
gggcaacacg gtgaaacccc gtctctacta aaatacaaaa aattagccgg gcgtcgcagc     1462
atgcgcctgt agtcccagct gctcaggagg ctgaggcagg agaattgatt gaacccggga     1522
ggcagaggtt gcactgagct gagattaagc caccgcactc cagcctgggc gacagagcaa     1582
gattccgttc caagaaaaa aaaattgttc aacaataagg gncaaaggga gagaatcata     1642
acatctgatt aaacagaaaa agcaagattt ttaaaactaa ctatataagg atggtcccag     1702
ctgtgtcaaa aggaagcttg tttgtaatac gtgtgcataa aaattaaata gaggtgaaca     1762
caattatttt aaggcagtta aattatctct gtattgtgaa ctaagacttt ctagaatttt     1822
acttattcat tctgtactta aatttttct aatgaacaca tatactttg taatcagaaa     1882
```

```
atattaaatg catgtatttt tcaaaaaaaa aaaaaa                              1918

<210> SEQ ID NO 61
<211> LENGTH: 852
<212> TYPE: DNA
<213> ORGANISM: Homo Sapiens
<220> FEATURE:
<221> NAME/KEY: CDS
<222> LOCATION: 229..735
<220> FEATURE:
<221> NAME/KEY: sig_peptide
<222> LOCATION: 229..492
<223> OTHER INFORMATION: Von Heijne matrix
      score 6.70
      seq VFALSSFLNKASA/VY
<220> FEATURE:
<221> NAME/KEY: polyA_signal
<222> LOCATION: 816..821
<220> FEATURE:
<221> NAME/KEY: polyA_site
<222> LOCATION: 841..852

<400> SEQUENCE: 61
aatgactggc agtggcatca gcgatggcgg ctgcgtcggg gtcggttctg cagcgctgta    60
tcgtgtcgcc ggcagggagg catagcgcct ctctgatctt cctgcatggc tcaggtgatt   120
ctggacaagg attaagaatg tggatcaagc aggttttttaa atcaagattt aacattccaa   180
cacataaaaa ttatttatcc aacagctcct cccagatcat atactcct atg aaa gga    237
                                                    Met Lys Gly gga atc tcc aat gta tgg ttt gac aga ttt aaa ata acc aat gac tgc    285
Gly Ile Ser Asn Val Trp Phe Asp Arg Phe Lys Ile Thr Asn Asp Cys
-85                 -80                 -75                 -70 cca gaa cac ctt gaa tca att gat gtc atg tgt caa gtg ctt act gat    333
Pro Glu His Leu Glu Ser Ile Asp Val Met Cys Gln Val Leu Thr Asp
                -65                 -60                 -55 ttg att gat gaa gaa gta aaa agt ggc atc aag aag aac agg ata tta    381
Leu Ile Asp Glu Glu Val Lys Ser Gly Ile Lys Lys Asn Arg Ile Leu
            -50                 -45                 -40 ata gga gga ttc tct atg gga gga tgc atg gca atg cat tta gca tat    429
Ile Gly Gly Phe Ser Met Gly Gly Cys Met Ala Met His Leu Ala Tyr
        -35                 -30                 -25 aga aat cat caa gat gtg gca gga gta ttt gct ctt tct agt ttt ctg    477
Arg Asn His Gln Asp Val Ala Gly Val Phe Ala Leu Ser Ser Phe Leu
    -20                 -15                 -10 aat aaa gca tct gct gtt tac cag gct ctt cag aag agt aat ggt gta    525
Asn Lys Ala Ser Ala Val Tyr Gln Ala Leu Gln Lys Ser Asn Gly Val
-5                   1               5                  10 ctt cct gaa tta ttt cag tgt cat ggt act gca gat gag tta gtt ctt    573
Leu Pro Glu Leu Phe Gln Cys His Gly Thr Ala Asp Glu Leu Val Leu
         15                  20                  25 cat tct tgg gca gaa gag aca aac tca atg tta aaa tct cta gga gtg    621
His Ser Trp Ala Glu Glu Thr Asn Ser Met Leu Lys Ser Leu Gly Val
             30                  35                  40 acc acg aag ttt cat agt ttt cca aat gtt tac cat gag cta agc aaa    669
Thr Thr Lys Phe His Ser Phe Pro Asn Val Tyr His Glu Leu Ser Lys
         45                  50                  55 act gag tta gac ata ttg aag tta tgg att ctt aca aag ctg cca gga    717
Thr Glu Leu Asp Ile Leu Lys Leu Trp Ile Leu Thr Lys Leu Pro Gly
60                  65                  70                  75 gaa atg gaa aaa caa aaa tgaatgaatc aagagtgatt tgttaatgta            765
Glu Met Glu Lys Gln Lys
                80
```

```
agtgtaatgt ctttgtgaaa agtgattttt actgccaaat tataatgata attaaaatat    825
taagaaatag caaaaaaaaa aaaaaaa                                        852

<210> SEQ ID NO 62
<211> LENGTH: 726
<212> TYPE: DNA
<213> ORGANISM: Homo Sapiens
<220> FEATURE:
<221> NAME/KEY: CDS
<222> LOCATION: 168..413
<220> FEATURE:
<221> NAME/KEY: sig_peptide
<222> LOCATION: 168..335
<223> OTHER INFORMATION: Von Heijne matrix
      score 3.80
      seq QMIMLVCFNLSRG/CL
<220> FEATURE:
<221> NAME/KEY: polyA_signal
<222> LOCATION: 684..689
<220> FEATURE:
<221> NAME/KEY: polyA_site
<222> LOCATION: 708..726
<220> FEATURE:
<221> NAME/KEY: misc_feature
<222> LOCATION: 723
<223> OTHER INFORMATION: n=a, g, c or t

<400> SEQUENCE: 62
cagcaaaatg gcagggaagg cagctctaag ctcccatcct tccataggaa tgttgaataa     60
acaaccagac actgtcagaa ccaactttgt gagaaccggg aaaataatca aggtgtacg    120 gcaactaaaa gaatgctgga tcaacacaaa ggaaacttaa aaatgat atg aaa gct    176
                                                    Met Lys Ala
                                                        -55 gtg tgg cat ttt tgc ttg tcc cac aag tcc agc ttg gtg ata gtc ttg    224
Val Trp His Phe Cys Leu Ser His Lys Ser Ser Leu Val Ile Val Leu
        -50                 -45                 -40 aag acg gca ggc tgg att ccc cag gct ggg acc ctt atc cct ggt tcc    272
Lys Thr Ala Gly Trp Ile Pro Gln Ala Gly Thr Leu Ile Pro Gly Ser
    -35                 -30                 -25 aga gag gag agc aga tct gat tca caa atg att atg ctt gtc tgt ttt    320
Arg Glu Glu Ser Arg Ser Asp Ser Gln Met Ile Met Leu Val Cys Phe
-20                 -15                 -10 aat ctt tcc aga ggc tgt ctg aag aag gta ttc atc atc tct gtt tta    368
Asn Leu Ser Arg Gly Cys Leu Lys Lys Val Phe Ile Ile Ser Val Leu
 -5              1                   5                  10 cct gac cca gaa acc att ctg cta gga aaa aca gtg ggc att gct        413
Pro Asp Pro Glu Thr Ile Leu Leu Gly Lys Thr Val Gly Ile Ala
             15                  20                  25 tgaaaacagt gttctgtggt tgaaaaaccc acagtcacct tgggctggtg ggaatgtaaa    473
atggcgcctc ttctggatca tcgtttggca gtttctcaaa aggtcaaacg tagaatcact    533
atttgatcca acaattctac tcctaggtat atccccaaaa gaattgaaaa caaggatgca    593
aacatatgcg tgtacactaa tgtttataga aaaatattc acaataatca aaggcagaa     653 acaacccaag tgtccaataa cagaagaatg aataaacagt gtgatataaa cataaaaaaa    713 aaaaaaaan aaa                                                       726

<210> SEQ ID NO 63
<211> LENGTH: 1039
<212> TYPE: DNA
<213> ORGANISM: Homo Sapiens
<220> FEATURE:
<221> NAME/KEY: CDS
<222> LOCATION: 100..852
```

```
<220> FEATURE:
<221> NAME/KEY: sig_peptide
<222> LOCATION: 100..159
<223> OTHER INFORMATION: Von Heijne matrix
      score 6.10
      seq FLILFLFLMECQL/HL
<220> FEATURE:
<221> NAME/KEY: polyA_signal
<222> LOCATION: 998..1003
<220> FEATURE:
<221> NAME/KEY: polyA_site
<222> LOCATION: 1019..1039

<400> SEQUENCE: 63
agaacttctt gattcctcag ataaatagag gacagatgct ggactgtagc taagtatttc      60
ctttcatcta cgggataaaa tactgataat tgagagtg atg gac aag gtt cag         114
                                          Met Asp Lys Val Gln
                                                      -20 agt ggt ttc ctc att ttg ttt ttg ttt tta atg gaa tgc caa ctt cat       162
Ser Gly Phe Leu Ile Leu Phe Leu Phe Leu Met Glu Cys Gln Leu His
-15                 -10                  -5                   1 tta tgc ttg ccg tat gca gat gga ctc cat ccc act gga aac ata aca       210
Leu Cys Leu Pro Tyr Ala Asp Gly Leu His Pro Thr Gly Asn Ile Thr
              5                  10                  15 ggc tta cca ggt agc ttc aac cac tgg ttt tat gtg act cag gga gaa       258
Gly Leu Pro Gly Ser Phe Asn His Trp Phe Tyr Val Thr Gln Gly Glu
         20                  25                  30 ttg aaa agc tgt ttc agg gga gat aaa aag aag gta att aca ttt cac       306
Leu Lys Ser Cys Phe Arg Gly Asp Lys Lys Lys Val Ile Thr Phe His
     35                  40                  45 cgc aaa aag ttt tct ttt caa ggc agt aaa cgg tca caa cca ccc aga       354
Arg Lys Lys Phe Ser Phe Gln Gly Ser Lys Arg Ser Gln Pro Pro Arg
50                  55                  60                  65 aac atc acc aaa gag ccc aaa gtg ttc ttt cat aaa acc cag ttg cct       402
Asn Ile Thr Lys Glu Pro Lys Val Phe Phe His Lys Thr Gln Leu Pro
             70                  75                  80 ggg att caa ggg gct gcc tcg aga tcc acg gct gca tcc cct acg aac       450
Gly Ile Gln Gly Ala Ala Ser Arg Ser Thr Ala Ala Ser Pro Thr Asn
         85                  90                  95 ccc atg aaa ttc ctg agg aat aaa gca ata att cgg cat aga cct gct       498
Pro Met Lys Phe Leu Arg Asn Lys Ala Ile Ile Arg His Arg Pro Ala
    100                 105                 110 ctt gtt aaa gta att tta att tcg agc gta gcc ttc agc att gcc ctg       546
Leu Val Lys Val Ile Leu Ile Ser Ser Val Ala Phe Ser Ile Ala Leu
        115                 120                 125 ata tgt ggg atg gca atc tcc tat atg ata tat cga ctg gca cag gct       594
Ile Cys Gly Met Ala Ile Ser Tyr Met Ile Tyr Arg Leu Ala Gln Ala
130                 135                 140                 145 gag gaa aga caa cag ctc gag tca ctt tat aag aac ctc agg ata ccg       642
Glu Glu Arg Gln Gln Leu Glu Ser Leu Tyr Lys Asn Leu Arg Ile Pro
                150                 155                 160 tta tta gga gat gaa gaa gag ggc tca gag gac gag ggt gag tcc acg       690
Leu Leu Gly Asp Glu Glu Glu Gly Ser Glu Asp Glu Gly Glu Ser Thr
            165                 170                 175 cac cta ctt cca aag aac gaa aat gag ctg gaa aag ttc atc cac tca       738
His Leu Leu Pro Lys Asn Glu Asn Glu Leu Glu Lys Phe Ile His Ser
        180                 185                 190 gtt att ata tca aaa aga agc aaa aat att aag aag aaa ctg aag gaa       786
Val Ile Ile Ser Lys Arg Ser Lys Asn Ile Lys Lys Lys Leu Lys Glu
    195                 200                 205 gag caa aac tca gta aca gaa aac aaa aca aag aat gcg tca cat aat       834
Glu Gln Asn Ser Val Thr Glu Asn Lys Thr Lys Asn Ala Ser His Asn
```

```
                  210                 215                 220                  225 gga aaa atg gaa gac ttg tgaacgcaga cgacagaggt gccggctgag                  882
Gly Lys Met Glu Asp Leu
                230 gcagaggaga aactatgggg gtgctgggag actgagcctg tgggcgtggc ttgctcccag         942 agaaccttat ggaagaggac atcaaagaaa gaaatgccag acctgtatcc cagaaaataa        1002 agccacatga tatagcaaaa aaaaaaaaaa aaaaaaa                                  1039

<210> SEQ ID NO 64
<211> LENGTH: 1355
<212> TYPE: DNA
<213> ORGANISM: Homo Sapiens
<220> FEATURE:
<221> NAME/KEY: CDS
<222> LOCATION: 238..1152
<220> FEATURE:
<221> NAME/KEY: sig_peptide
<222> LOCATION: 238..339
<223> OTHER INFORMATION: Von Heijne matrix
      score 8.50
      seq SIFLLLSFPDSNG/KA
<220> FEATURE:
<221> NAME/KEY: polyA_signal
<222> LOCATION: 1298..1303
<220> FEATURE:
<221> NAME/KEY: polyA_site
<222> LOCATION: 1324..1355

<400> SEQUENCE: 64
aattttcttg aaatcacatg gtaccaatca caagtcttgt tattttgttt cattatgaga         60
aagataatct actaaatatt aaaatactgg aaggagcaag atagctttga tccagggaga        120
ccttttccat ttatgtgctt tagtaatctg ccgccaacaa gctatcttct ttatgttctt        180
ctacaactga tgttgttttg ttttctcatg tttgtctctt aatagacaaa tggaggc           237 atg agc ttc ctt aga att acc cct tcg acg cat agt tct gtt tca tct         285
Met Ser Phe Leu Arg Ile Thr Pro Ser Thr His Ser Ser Val Ser Ser
                -30                 -25                 -20 gga ctt ttg agg ctt agt atc ttt cta cta ctt agc ttt cct gac tca         333
Gly Leu Leu Arg Leu Ser Ile Phe Leu Leu Leu Ser Phe Pro Asp Ser
            -15                 -10                  -5 aac gga aaa gcc att tgg aca gct cac ctg aat ata aca ttt cag gtt         381
Asn Gly Lys Ala Ile Trp Thr Ala His Leu Asn Ile Thr Phe Gln Val
         1               5                  10 gga aat gag atc aca tcg gaa tta gga gag agt gga gtg ttc ggg aat         429
Gly Asn Glu Ile Thr Ser Glu Leu Gly Glu Ser Gly Val Phe Gly Asn
 15              20                 25                  30 cat tct cct ctg gaa agg gtg tct ggt gtg gtg gca ctt cct gaa gaa         477
His Ser Pro Leu Glu Arg Val Ser Gly Val Val Ala Leu Pro Glu Glu
                 35                 40                  45 tgg aat cag aat gcc tgt cat cct ttg acc aat ttc agc agg ccc aaa         525
Trp Asn Gln Asn Ala Cys His Pro Leu Thr Asn Phe Ser Arg Pro Lys
             50                 55                  60 cag gca gac tca tgg ctg gcc ctc atc gaa cgt gga ggc tgt act ttt         573
Gln Ala Asp Ser Trp Leu Ala Leu Ile Glu Arg Gly Gly Cys Thr Phe
         65                 70                  75 aca cat aaa atc aac gtg gca gca gag aag gga gca aat ggg gtg atc         621
Thr His Lys Ile Asn Val Ala Ala Glu Lys Gly Ala Asn Gly Val Ile
     80                 85                  90 atc tac aac tat caa ggt acg ggc agt aaa gta ttt ccc atg tct cac         669
Ile Tyr Asn Tyr Gln Gly Thr Gly Ser Lys Val Phe Pro Met Ser His
 95                100                 105                 110
```

```
cag ggg acg gaa aat ata gtc gcg gtg atg ata agc aac ctg aaa ggc        717
Gln Gly Thr Glu Asn Ile Val Ala Val Met Ile Ser Asn Leu Lys Gly
                115                 120                 125 atg gaa att ttg cac tcg att cag aaa gga gtc tat gtg aca gtc atc        765
Met Glu Ile Leu His Ser Ile Gln Lys Gly Val Tyr Val Thr Val Ile
            130                 135                 140 att gaa gtg ggg aga atg cac atg cag tgg gtg agc cat tac atc atg        813
Ile Glu Val Gly Arg Met His Met Gln Trp Val Ser His Tyr Ile Met
        145                 150                 155 tat cta ttt acc ttc ctg gct gcc aca att gcc tac ttt tac tta gat        861
Tyr Leu Phe Thr Phe Leu Ala Ala Thr Ile Ala Tyr Phe Tyr Leu Asp
    160                 165                 170 tgc gtc tgg aga ctt aca cct aga gtg ccc aat tct ttc acc agg agg        909
Cys Val Trp Arg Leu Thr Pro Arg Val Pro Asn Ser Phe Thr Arg Arg
175                 180                 185                 190 cga agt caa ata aag aca gat gtg aag aaa gct att gac cag ctt caa        957
Arg Ser Gln Ile Lys Thr Asp Val Lys Lys Ala Ile Asp Gln Leu Gln
                195                 200                 205 ctg cga gtt ctc aaa gaa ggg gat gag gaa tta gac cta aat gaa gac       1005
Leu Arg Val Leu Lys Glu Gly Asp Glu Glu Leu Asp Leu Asn Glu Asp
            210                 215                 220 aac tgt gtt gtt tgc ttt gac aca tac aaa ccc caa gat gta gta cgc       1053
Asn Cys Val Val Cys Phe Asp Thr Tyr Lys Pro Gln Asp Val Val Arg
        225                 230                 235 att tta act tgc aaa cat ttt ttc cat aag gca tgc att gac ccc tgg       1101
Ile Leu Thr Cys Lys His Phe Phe His Lys Ala Cys Ile Asp Pro Trp
    240                 245                 250 ctt tta gcc cat agg aca tgt ccc atg tgc aag tgt gac atc ctg aaa       1149
Leu Leu Ala His Arg Thr Cys Pro Met Cys Lys Cys Asp Ile Leu Lys
255                 260                 265                 270 act taagaaatct ggagaatttt ctgaagatgt aaccagatct ttccaaatac            1202
Thr aaagattaga taaattgtct tattgtactt tatgtagaga gaaatttca gcttctctac      1262 ccaagtatga acaagggtga aatttgtgtt ttaaaaataa aactccttat catgcccagc     1322
taaaaaaaaa aaaaaaaaaa aaaaaaaaaa aaa                                  1355

<210> SEQ ID NO 65
<211> LENGTH: 572
<212> TYPE: DNA
<213> ORGANISM: Homo Sapiens
<220> FEATURE:
<221> NAME/KEY: CDS
<222> LOCATION: 187..369
<220> FEATURE:
<221> NAME/KEY: sig_peptide
<222> LOCATION: 187..312
<223> OTHER INFORMATION: Von Heijne matrix
      score 7.10
      seq LLPCSSVLTCGQA/SQ
<220> FEATURE:
<221> NAME/KEY: polyA_signal
<222> LOCATION: 489..494
<220> FEATURE:
<221> NAME/KEY: polyA_site
<222> LOCATION: 558..572
<220> FEATURE:
<221> NAME/KEY: misc_feature
<222> LOCATION: 94,527,537..538
<223> OTHER INFORMATION: n=a, g, c or t

<400> SEQUENCE: 65
cttcttcagt cagtggctgg ataatctaat tataatgtta taatccatca tttctctttt      60
tgaacagtca atttagttta acatttgctt aacnagccat tatgtatgcc aggtaatgtg     120
```

-continued

```
ctagatgctg gtggttcaaa gaaaggaacg atgtggacct gacctcaaag aaatccattg      180 gagaat atg aca gat tta gat tta atg atc aac ttt act ttt cct ata         228
       Met Thr Asp Leu Asp Leu Met Ile Asn Phe Thr Phe Pro Ile
           -40             -35                 -30 cag tgg gtc aac caa aac cgc atg gcg tac tac tct ctg aag cct cta         276
Gln Trp Val Asn Gln Asn Arg Met Ala Tyr Tyr Ser Leu Lys Pro Leu
        -25             -20                 -15 cta ccc tgc tcc tcc gtg ttg aca tgt ggt cag gca agc cag gac tta         324
Leu Pro Cys Ser Ser Val Leu Thr Cys Gly Gln Ala Ser Gln Asp Leu
        -10              -5                  1 ctc aca tca gct aca tca gtt act ggg atg gag aaa att gaa gcc             369
Leu Thr Ser Ala Thr Ser Val Thr Gly Met Glu Lys Ile Glu Ala
5                10                  15 tagaaagatc aagaaacttt ctccaggcca taaataggag aatcaggatt caaatcagat      429 agacccccagg gcttgttctc ttcaacacca cattaccccta cattattatt caattattaa     489 ataaaaccctt gcattagtgg catttccaaa tgcataanca aaaaaatnna aaaaaagta      549 acactggcaa aaaaaaaaaa aaa                                             572
```

<210> SEQ ID NO 66
<211> LENGTH: 535
<212> TYPE: DNA
<213> ORGANISM: Homo Sapiens
<220> FEATURE:
<221> NAME/KEY: CDS
<222> LOCATION: 121..459
<220> FEATURE:
<221> NAME/KEY: sig_peptide
<222> LOCATION: 121..165
<223> OTHER INFORMATION: Von Heijne matrix
      score 4.20
      seq FYLLLASSILCAL/IV
<220> FEATURE:
<221> NAME/KEY: polyA_signal
<222> LOCATION: 497..502
<220> FEATURE:
<221> NAME/KEY: polyA_site
<222> LOCATION: 521..535
<220> FEATURE:
<221> NAME/KEY: misc_feature
<222> LOCATION: 486,489
<223> OTHER INFORMATION: n=a, g, c or t

<400> SEQUENCE: 66

```
agttacacca ggcatcctgg cccaaagttt cccaaatcca ggcggctaga ggcccactgc       60
ttcccaacta ccagctgagg gggtccgtcc cgagaaggga gaagaggccg aagaggaaac     120 atg aac ttc tat tta ctc cta gcg agc agc att ctg tgt gcc ttg att       168
Met Asn Phe Tyr Leu Leu Leu Ala Ser Ser Ile Leu Cys Ala Leu Ile
-15              -10                 -5                  1 gtc ttc tgg aaa tat cgc cgc ttt cag aga aac act ggc gaa atg tca       216
Val Phe Trp Lys Tyr Arg Arg Phe Gln Arg Asn Thr Gly Glu Met Ser
        5                   10                  15 tca aat tca act gct ctt gca cta gtg aga ccc tct tct tct ggg tta       264
Ser Asn Ser Thr Ala Leu Ala Leu Val Arg Pro Ser Ser Ser Gly Leu
        20                  25                  30 att aac agc aat aca gac aac aat ctt gca gtc tac gac ctc tct cgg       312
Ile Asn Ser Asn Thr Asp Asn Asn Leu Ala Val Tyr Asp Leu Ser Arg
        35                  40                  45 gat att tta aat aat ttc cca cac tca ata gcc agg cag aag cga ata       360
Asp Ile Leu Asn Asn Phe Pro His Ser Ile Ala Arg Gln Lys Arg Ile
50                  55                  60                  65 ttg gta aac ctc agt atg gtg gaa aac aag ctg gtt gaa ctg gaa cat       408
```

```
                Leu Val Asn Leu Ser Met Val Glu Asn Lys Leu Val Glu Leu Glu His
                                70                  75                  80 act cta ctt agc aag ggt ttc aga ggt gca tca cct cac cgg aaa tcc              456
Thr Leu Leu Ser Lys Gly Phe Arg Gly Ala Ser Pro His Arg Lys Ser
            85                  90                  95 acc taaaagcgta caggatgtaa tgccagnggn ggaaatcatt aaagacactt                   509
Thr tgagtagatt caaaaaaaaa aaaaaa                                                 535

<210> SEQ ID NO 67
<211> LENGTH: 572
<212> TYPE: DNA
<213> ORGANISM: Homo Sapiens
<220> FEATURE:
<221> NAME/KEY: CDS
<222> LOCATION: 34..336
<220> FEATURE:
<221> NAME/KEY: sig_peptide
<222> LOCATION: 34..123
<223> OTHER INFORMATION: Von Heijne matrix
      score 7.80
      seq SVTLAQLLQLVQQ/GQ
<220> FEATURE:
<221> NAME/KEY: polyA_signal
<222> LOCATION: 536..541
<220> FEATURE:
<221> NAME/KEY: polyA_site
<222> LOCATION: 556..572
<220> FEATURE:
<221> NAME/KEY: misc_feature
<222> LOCATION: 545
<223> OTHER INFORMATION: n=a, g, c or t

<400> SEQUENCE: 67
gcattacacg ccggtcagga ttcgcgaccc gac atg gag cgt ccc cgc agt ccc              54
                                    Met Glu Arg Pro Arg Ser Pro
                                        -30                 -25 caa tgc tcg gcc ccg gcc tct gcc tca gct tcg gtt acc ctg gcg cag             102
Gln Cys Ser Ala Pro Ala Ser Ala Ser Ala Ser Val Thr Leu Ala Gln
        -20                 -15                 -10 ctc ctg cag ctg gtc cag cag ggc cag gaa ctc ccg ggc ctg gag aaa             150
Leu Leu Gln Leu Val Gln Gln Gly Gln Glu Leu Pro Gly Leu Glu Lys
        -5                   1               5 cgc cac atc gcg gcg atc cac ggc gaa ccc aca gcg tcc cgg ctg ccg             198
Arg His Ile Ala Ala Ile His Gly Glu Pro Thr Ala Ser Arg Leu Pro
10                  15                  20                  25 cgg agg ccc aag ccc tgg gag gcc gcg gct ttg gct gag tcc ctt ccc             246
Arg Arg Pro Lys Pro Trp Glu Ala Ala Ala Leu Ala Glu Ser Leu Pro
                30                  35                  40 cct ccg acc ctc agg ata gga acg gcc ccg gcg gag cct ggc ttg gtt             294
Pro Pro Thr Leu Arg Ile Gly Thr Ala Pro Ala Glu Pro Gly Leu Val
            45                  50                  55 gag gca gcg act gcg cct tct tca tgg cat aca gtg ggc ccc                     336
Glu Ala Ala Thr Ala Pro Ser Ser Trp His Thr Val Gly Pro
        60                  65                  70 tgaggttcca ggtcctttgc ggcggcgatc tggagggcgt ggctacagga cccgggatgc           396
cattcagtta ctcatctttt atgctttcgt cctgacctgt ctcaactaga cttgctcctg           456
caaccaccat gggggttttg catttacatt tgtggaccat gttacagtta agaaaaatcc           516
tgtttcagtc cttatatgta ataaaatgnt ttatgatgca aaaaaaaaaa aaaaaa               572

<210> SEQ ID NO 68
<211> LENGTH: 804
<212> TYPE: DNA
```

```
<213> ORGANISM: Homo Sapiens
<220> FEATURE:
<221> NAME/KEY: CDS
<222> LOCATION: 119..409
<220> FEATURE:
<221> NAME/KEY: sig_peptide
<222> LOCATION: 119..388
<223> OTHER INFORMATION: Von Heijne matrix
      score 4.30
      seq TCLTACWTALCCC/CL
<220> FEATURE:
<221> NAME/KEY: polyA_signal
<222> LOCATION: 769..774
<220> FEATURE:
<221> NAME/KEY: polyA_site
<222> LOCATION: 789..804
<220> FEATURE:
<221> NAME/KEY: misc_feature
<222> LOCATION: 274
<223> OTHER INFORMATION: n=a, g, c or t
<220> FEATURE:
<221> NAME/KEY: unsure
<222> LOCATION: -39
<223> OTHER INFORMATION: Xaa = His,Gln

<400> SEQUENCE: 68
acttgctctg agacaggtgc ggcaagtcta ctgcgggctg gtccgggctc ctcaggttca      60
gacccgaccg ttatccagtc ggttcgtgga gaggagaggt gcactttaca ggtcccca      118 atg aac caa gag aac cct cca cca tat cca ggc cct ggt cca acg gcc      166
Met Asn Gln Glu Asn Pro Pro Pro Tyr Pro Gly Pro Gly Pro Thr Ala
-90             -85                 -80                 -75 cca tac cca cct tat cca cca caa cca atg ggt cca gga cct atg ggg      214
Pro Tyr Pro Pro Tyr Pro Pro Gln Pro Met Gly Pro Gly Pro Met Gly
            -70                 -65                 -60 gga ccc tac cca cct cct caa ggg tac ccc tac caa gga tac cta cag      262
Gly Pro Tyr Pro Pro Pro Gln Gly Tyr Pro Tyr Gln Gly Tyr Leu Gln
        -55                 -50                 -45 tac ggc tgg can ggt gga cct cag gag cct cct aaa acc aca gtg tat      310
Tyr Gly Trp Xaa Gly Gly Pro Gln Glu Pro Pro Lys Thr Thr Val Tyr
    -40                 -35                 -30 gtg gta gaa gac caa aga aga gat gag cta gga cca tcc acc tgc ctc      358
Val Val Glu Asp Gln Arg Arg Asp Glu Leu Gly Pro Ser Thr Cys Leu
-25                 -20                 -15 aca gcc tgc tgg acg gct ctc tgt tgc tgc tgt ctc tgg gac atg ctc      406
Thr Ala Cys Trp Thr Ala Leu Cys Cys Cys Cys Leu Trp Asp Met Leu
-10             -5                  1                   5 acc tgaccagacc agcccagccg tcctgtcctg ccagctctgc tgccacctct            459
Thr gacaggtgtg cctgccccca tctcttctga ttgctgttaa caaatgacta gctttgcaca      519
gacacctcta ccttcagcac tatgggattc tagattaatg ggggttgcta ctgtttaatt      579
cagtgacttg atcttttttaa tgtccaaaat ccatttctta ttgatcttta aagatgtgct     639 aaaatgacttt tttggccaaa ggcttagttg tgaaaaatat aatttttaaa ttatacattc     699
aaggtagtgg ccaaatgtaa cacatcaatc atggaatgat ttctctgcta acagccgcct     759
gtatgtttca ataaatttgt ccaaagctca aaaaaaaaa aaaaa                      804

<210> SEQ ID NO 69
<211> LENGTH: 629
<212> TYPE: DNA
<213> ORGANISM: Homo Sapiens
<220> FEATURE:
<221> NAME/KEY: CDS
<222> LOCATION: 232..534
<220> FEATURE:
```

<221> NAME/KEY: sig_peptide
<222> LOCATION: 232..306
<223> OTHER INFORMATION: Von Heijne matrix
      score 3.70
      seq AKTCLVLCSRVLS/VI
<220> FEATURE:
<221> NAME/KEY: polyA_signal
<222> LOCATION: 595..600
<220> FEATURE:
<221> NAME/KEY: polyA_site
<222> LOCATION: 615..629

<400> SEQUENCE: 69

```
tatcactgtt acgaaccaag gatttacaga tcactggcaa aaattctgag aactttcaca      60
ccagtatact gtccaagccc attaagtggc atcacacctc tcttttatgt agctcagaca     120
agacagtcta atatcttcaa atactactg caatatggaa tcttagaaag agaaaaaaac     180
cctatcaaca ttgtcttaac aatagtactc taccctttcga gagtaagagt a atg gtt    237
                                                          Met Val
                                                           -25 gat cgt gaa ttg gct gac atc cat gaa gat gcc aaa aca tgt ttg gta      285
Asp Arg Glu Leu Ala Asp Ile His Glu Asp Ala Lys Thr Cys Leu Val
        -20              -15              -10 cta tgt tcc aga gtg ctt tct gtc att tca gtc aag gaa ata aag aca      333
Leu Cys Ser Arg Val Leu Ser Val Ile Ser Val Lys Glu Ile Lys Thr
    -5                1                5 cag ctg agt tta gga aga cat cca att att tca aat tgg ttt gat tac      381
Gln Leu Ser Leu Gly Arg His Pro Ile Ile Ser Asn Trp Phe Asp Tyr
 10              15              20              25 att cct tca aca aga tac aaa gat cca tgt gaa cta tta cat ctt tgc      429
Ile Pro Ser Thr Arg Tyr Lys Asp Pro Cys Glu Leu Leu His Leu Cys
             30              35              40 aga cta acc atc agg aat caa cta tta acc aac aat atg ctc cca gat      477
Arg Leu Thr Ile Arg Asn Gln Leu Leu Thr Asn Asn Met Leu Pro Asp
         45              50              55 gga ata ttt tca ctt cta att cct gct cgt cta caa aac tat ctg aat      525
Gly Ile Phe Ser Leu Leu Ile Pro Ala Arg Leu Gln Asn Tyr Leu Asn
     60              65              70 tta gaa atc taacatacgt cagtgtccta agttccttaa caatgcttac             574
Leu Glu Ile
 75 caatgtatgg cttagaagtt aataaaaatt cacttcatgc aaaaaaaaaa aaaaa         629
```

<210> SEQ ID NO 70
<211> LENGTH: 669
<212> TYPE: DNA
<213> ORGANISM: Homo Sapiens
<220> FEATURE:
<221> NAME/KEY: CDS
<222> LOCATION: 140..595
<220> FEATURE:
<221> NAME/KEY: sig_peptide
<222> LOCATION: 140..442
<223> OTHER INFORMATION: Von Heijne matrix
      score 4.10
      seq VFMLIVSVLALIP/ET
<220> FEATURE:
<221> NAME/KEY: polyA_signal
<222> LOCATION: 630..635
<220> FEATURE:
<221> NAME/KEY: polyA_site
<222> LOCATION: 655..669

<400> SEQUENCE: 70

```
gagcgggaag ccgagctggg cgagaagtag gggagggcgg tgctccgccg cggtggcggt      60
```

-continued

```
tgctatcgct tcgcagaacc tactcaggca gccagctgag aagagttgag ggattgctgc      120
tgctgggtct gcagacgcg atg gat aac gtg cag ccg aaa ata aaa cat cgc      172
               Met Asp Asn Val Gln Pro Lys Ile Lys His Arg
                   -100                -95 ccc ttc tgc ttc agt gtg aaa ggc cac gtg aag atg ctg cgg ctg gca      220
Pro Phe Cys Phe Ser Val Lys Gly His Val Lys Met Leu Arg Leu Ala
-90             -85                  -80                  -75 cta act gtg aca tct atg acc ttt ttt atc atc gca caa gcc cct gaa      268
Leu Thr Val Thr Ser Met Thr Phe Phe Ile Ile Ala Gln Ala Pro Glu
                -70                  -65                  -60 cca tat att gtt atc act gga ttt gaa gtc acc gtt atc tta ttt ttc      316
Pro Tyr Ile Val Ile Thr Gly Phe Glu Val Thr Val Ile Leu Phe Phe
            -55                  -50                  -45 ata ctt tta tat gta ctc aga ctt gat cga tta atg aag tgg tta ttt      364
Ile Leu Leu Tyr Val Leu Arg Leu Asp Arg Leu Met Lys Trp Leu Phe
        -40                  -35                  -30 tgg cct ttg ctt gat att atc aac tca ctg gta aca aca gta ttc atg      412
Trp Pro Leu Leu Asp Ile Ile Asn Ser Leu Val Thr Thr Val Phe Met
    -25                  -20                  -15 ctc atc gta tct gtg ttg gca ctg ata cca gaa acc aca aca ttg aca      460
Leu Ile Val Ser Val Leu Ala Leu Ile Pro Glu Thr Thr Thr Leu Thr
-10                  -5                   1                   5 gtt ggt gga ggg gtg ttt gca ctt gtg aca gca gta tgc tgt ctt gcc      508
Val Gly Gly Gly Val Phe Ala Leu Val Thr Ala Val Cys Cys Leu Ala
                10                  15                  20 gac ggg gcc ctt att tac cgg aag ctt ctg ttc aat ccc agc ggt cct      556
Asp Gly Ala Leu Ile Tyr Arg Lys Leu Leu Phe Asn Pro Ser Gly Pro
            25                  30                  35 tac cag aaa aag cct gtg cat gaa aaa aaa gaa gtt ttg taatttata       605
Tyr Gln Lys Lys Pro Val His Glu Lys Lys Glu Val Leu
        40                  45                  50 ttacttttta gtttgatact aagtattaaa catatttctg tattcttcca aaaaaaaaa     665 aaaa                                                                 669

<210> SEQ ID NO 71
<211> LENGTH: 973
<212> TYPE: DNA
<213> ORGANISM: Homo Sapiens
<220> FEATURE:
<221> NAME/KEY: CDS
<222> LOCATION: 32..658
<220> FEATURE:
<221> NAME/KEY: sig_peptide
<222> LOCATION: 32..289
<223> OTHER INFORMATION: Von Heijne matrix
      score 4.00
      seq KLWKLLFLMKSQG/WI
<220> FEATURE:
<221> NAME/KEY: polyA_signal
<222> LOCATION: 936..941
<220> FEATURE:
<221> NAME/KEY: polyA_site
<222> LOCATION: 959..973
<220> FEATURE:
<221> NAME/KEY: misc_feature
<222> LOCATION: 934
<223> OTHER INFORMATION: n=a, g, c or t

<400> SEQUENCE: 71
agggagaggg atggctagtg aggtttagat c atg ttg agc cct acc ttt gtt      52
                                 Met Leu Ser Pro Thr Phe Val
                                     -85                 -80 ttg tgg gat gtt gga tat ccc tta tac acc tat gga tcc atc tgc att     100
Leu Trp Asp Val Gly Tyr Pro Leu Tyr Thr Tyr Gly Ser Ile Cys Ile
```

-continued

```
                   -75                 -70                 -65
att gca tta att att tgg caa gtg aaa aag agc tgc caa aaa tta agc      148
Ile Ala Leu Ile Ile Trp Gln Val Lys Lys Ser Cys Gln Lys Leu Ser
            -60                 -55                 -50 ttg gta cct aac agg agc tgt tgc cgg tgt cac cga aga gtc caa caa      196
Leu Val Pro Asn Arg Ser Cys Cys Arg Cys His Arg Arg Val Gln Gln
        -45                 -40                 -35 aag tct gga gat aga aca tca aga gct agg aga act tca cag gaa gaa      244
Lys Ser Gly Asp Arg Thr Ser Arg Ala Arg Arg Thr Ser Gln Glu Glu
    -30                 -25                 -20 gcc gag aag ttg tgg aag ctg ctg ttt ctc atg aaa agc cag ggc tgg      292
Ala Glu Lys Leu Trp Lys Leu Leu Phe Leu Met Lys Ser Gln Gly Trp
-15                 -10                  -5                   1 att cct cag gaa gga agt gtg cgg cga atc ctg tgt gca gac ccc tgc      340
Ile Pro Gln Glu Gly Ser Val Arg Arg Ile Leu Cys Ala Asp Pro Cys
              5                  10                  15 tgc caa atc tgc aat gtt atg gct ctg gag att aag caa ttg ctg gca      388
Cys Gln Ile Cys Asn Val Met Ala Leu Glu Ile Lys Gln Leu Leu Ala
             20                  25                  30 gaa gct cca gaa gtt ggc ttg gat aac aag atg aag ctg ttt ctg cac      436
Glu Ala Pro Glu Val Gly Leu Asp Asn Lys Met Lys Leu Phe Leu His
         35                  40                  45 tgg att aac cct gaa atg aaa gat cga agg cat gag gaa tcc att ctc      484
Trp Ile Asn Pro Glu Met Lys Asp Arg Arg His Glu Glu Ser Ile Leu
 50                  55                  60                  65 ctt tct aag gct gag aca gtg acc caa gac agg aca aaa aac att gag      532
Leu Ser Lys Ala Glu Thr Val Thr Gln Asp Arg Thr Lys Asn Ile Glu
                 70                  75                  80 aag agt cca act gtc acc aaa gat cat gtg tgg gga gct aca aca cag      580
Lys Ser Pro Thr Val Thr Lys Asp His Val Trp Gly Ala Thr Thr Gln
             85                  90                  95 aag aca aca gag gac cct gag gct cag cct cct tct act gag gag gaa      628
Lys Thr Thr Glu Asp Pro Glu Ala Gln Pro Pro Ser Thr Glu Glu Glu
        100                 105                 110 ggc ctg atc ttc tgt gat gcc ccc agt gcc taaataatct gctctagcaa       678
Gly Leu Ile Phe Cys Asp Ala Pro Ser Ala
    115                 120 cactcccttc agtccagcca atcctgggtc ctgtgccact cctacaaatg ctccaaactc   738
tgtcctcaaa tgacttgtgc cactcaacca ggaaatctat cccaggtcta actcacctca   798
gcagaaggca ctgttttatg caagaatacc catcacaaga aaaggagtt cataggttcc    858 tgaacctctg caatccctg aaaaaggctt tcattgccat ttccattaac atgcaggtga    918
agcagggcat tctccnaaat atactttgta ccttttaagct aaaaaaaaaa aaaaa       973
```

<210> SEQ ID NO 72
<211> LENGTH: 791
<212> TYPE: DNA
<213> ORGANISM: Homo Sapiens
<220> FEATURE:
<221> NAME/KEY: CDS
<222> LOCATION: 14..280
<220> FEATURE:
<221> NAME/KEY: sig_peptide
<222> LOCATION: 14..76
<223> OTHER INFORMATION: Von Heijne matrix
      score 9.50
      seq ALVVLCAFQLVAA/LE
<220> FEATURE:
<221> NAME/KEY: polyA_site
<222> LOCATION: 776..791
<220> FEATURE:
<221> NAME/KEY: misc_feature
<222> LOCATION: 607
<223> OTHER INFORMATION: n=a, g, c or t

<400> SEQUENCE: 72

```
ataggcgcgc acc atg ggc tcc tgc tcc ggc cgc tgc gcg ctc gtc gtc          49
            Met Gly Ser Cys Ser Gly Arg Cys Ala Leu Val Val
            -20             -15                 -10 ctc tgc gct ttt cag ctg gtc gcc gcc ctg gag agg cag gtt ttt gac         97
Leu Cys Ala Phe Gln Leu Val Ala Ala Leu Glu Arg Gln Val Phe Asp
        -5                   1                   5 ttc ctg ggc tac cag tgg gcg ccc atc ctg gcc aac ttt gtc cac atc        145
Phe Leu Gly Tyr Gln Trp Ala Pro Ile Leu Ala Asn Phe Val His Ile
            10                  15                  20 atc atc gtc atc ctg gga ctc ttc ggc acc atc cag tac cgg ctg cgc        193
Ile Ile Val Ile Leu Gly Leu Phe Gly Thr Ile Gln Tyr Arg Leu Arg
        25                  30                  35 tat gtc atg tgt aca cgc tgt ggg cag ccg tct ggg tca cct gga acg        241
Tyr Val Met Cys Thr Arg Cys Gly Gln Pro Ser Gly Ser Pro Gly Thr
40                  45                  50                  55 tct tca tca tct gct tct acc tgg aag tcg gtg gcc tct taaaggacag        290
Ser Ser Ser Ser Ala Ser Thr Trp Lys Ser Val Ala Ser
                    60                  65 cgagctactg accttcagcc tctcccggca tcgctcctgg tggcgtgagc gctggccagg      350
ctgtctgcat gaggaggtgc cagcagtggg cctcggggcc cccatggcc aggccctggt      410 gtcaggtgct ggctgtgcca tggagcccag ctatgtggag ccctacaca gttgcctgca      470 gatcctgatc gcgcttctgg gctttgtctg tggctgccag gtggtcagcg tgtttacgga      530
ggaagaggac agctgcctgc gtaagtgagg aaacagctga tcctgctcct gtggcctcca      590
gcctcagcga ccgaccnagt gacaatgaca ggagctccca ggccttggga cgcgcccca      650 cccagcaccc cccaggcggc cggcagcacc tgccctgggt tctaagtact ggacaccagc      710
cagggcggca gggcagtgcc acggctggct gcagcgtcaa gagagtttgt aatttccttt      770
ctcttaaaaa aaaaaaaaa a                                                 791
```

<210> SEQ ID NO 73
<211> LENGTH: 1110
<212> TYPE: DNA
<213> ORGANISM: Homo Sapiens
<220> FEATURE:
<221> NAME/KEY: CDS
<222> LOCATION: 93..290
<220> FEATURE:
<221> NAME/KEY: sig_peptide
<222> LOCATION: 93..149
<223> OTHER INFORMATION: Von Heijne matrix
    score 9.30
    seq VFVFLFLWDPVLA/GI
<220> FEATURE:
<221> NAME/KEY: polyA_signal
<222> LOCATION: 1078..1083
<220> FEATURE:
<221> NAME/KEY: polyA_site
<222> LOCATION: 1096..1110

<400> SEQUENCE: 73

```
agtataggac tgtgtgctca acctcttctc tctgttccct gacagccgat gtcagaccct       60
gccactagcc tccttaacag aagttcccag cc atg aag cct ctc ctt gtt gtg       113
                                     Met Lys Pro Leu Leu Val Val
                                                     -15 ttt gtc ttt ctt ttc ctt tgg gat cca gtg ctg gca ggt ata aat tca       161
Phe Val Phe Leu Phe Leu Trp Asp Pro Val Leu Ala Gly Ile Asn Ser
            -10                 -5                  1
```

```
tta tca tca gaa atg cac aag aaa tgc tat aaa aat ggc atc tgc aga       209
Leu Ser Ser Glu Met His Lys Lys Cys Tyr Lys Asn Gly Ile Cys Arg
 5                  10                  15                  20 ctt gaa tgc tat gag agt gaa atg tta gtt gcc tac tgt atg ttt cag       257
Leu Glu Cys Tyr Glu Ser Glu Met Leu Val Ala Tyr Cys Met Phe Gln
                    25                  30                  35 ctg gag tgc tgt gtc aaa gga aat cct gca ccc tgacataaga aaccaatgaa     310
Leu Glu Cys Cys Val Lys Gly Asn Pro Ala Pro
                40                  45 tggccactat cctgtaggcc cttgattctg ccatctttca caaaaccagg gaatttagat     370
caaactgtga caccatgatg tgtccatgac tactggtttt tagcattttt ataggccagc     430
agactcttgt ggtcttaaat ttaaagagct gagctgtagc cttctttaaa agagctcggt     490
ttttcacaaa acaatgtag aagatatttt ctcacctcaa cgtgatgtcc agtgtgctca      550
tcagcacctg tttctccctc taatcataga ggatattctt attatttaga aaggcttcaa     610
gggaaacaac ttttgacacc taagtcgtgt cctaccttcg cttcagcttc gcatttccca     670
tttctgtgaa attcccaaca gagaagcaga tttgccatgg ccttctgaca accttgtaca     730
tctctcacat aaaccgcata ggcagggctt gactacaggc tggcccgagt ctgcactgag     790
tctgaccctg aagttccttt ggaacaggag aggccatctt gtgatgggct ggaacaaggt     850
aatttctcat ccacctccct agtttcagtt gagcaatgga acttcccacc tgagccccta    910
gggttcagct acaggctata agactgccgt cctgtggttt agtgttggtt ccttagcagc     970
agagtgatgc cacctctgct gcccgtcatc tgactcctct ggatgggtgt tatcctgtgg    1030
cttaagagct aacaccatgc tgatcttgct ttgctatatg tgtaactaat aaactgccta    1090
aatccaaaaa aaaaaaaaaa                                                1110

<210> SEQ ID NO 74
<211> LENGTH: 325
<212> TYPE: PRT
<213> ORGANISM: Homo Sapiens
<220> FEATURE:
<221> NAME/KEY: SIGNAL
<222> LOCATION: -26..-1

<400> SEQUENCE: 74

Met Ala Thr Pro Leu Pro Pro Ser Pro Arg His Leu Arg Leu Leu
    -25                 -20                 -15

Arg Leu Leu Leu Ser Gly Leu Val Leu Gly Ala Ala Leu Arg Gly Ala
-10                  -5                   1                5

Ala Ala Gly His Pro Asp Val Ala Ala Cys Pro Gly Ser Leu Asp Cys
                10                  15                  20

Ala Leu Lys Arg Arg Ala Arg Cys Pro Pro Gly Ala His Ala Cys Gly
                25                  30                  35

Pro Cys Leu Gln Pro Phe Gln Glu Asp Gln Gly Leu Cys Val Pro
    40                  45                  50

Arg Met Arg Arg Pro Pro Gly Gly Gly Arg Pro Gln Pro Arg Leu Glu
55                  60                  65                  70

Asp Glu Ile Asp Phe Leu Ala Gln Glu Leu Ala Arg Lys Glu Ser Gly
                75                  80                  85

His Ser Thr Pro Pro Leu Pro Lys Asp Arg Gln Arg Leu Pro Glu Pro
                90                  95                  100

Ala Thr Leu Gly Phe Ser Ala Arg Gly Gln Gly Leu Glu Leu Gly Leu
                105                 110                 115
```

```
Pro Ser Thr Pro Gly Thr Pro Thr Pro His Thr Ser Leu Gly
    120                 125             130

Ser Pro Val Ser Ser Asp Pro Val His Met Ser Pro Leu Glu Pro Arg
135                 140                 145                 150

Gly Gly Gln Gly Asp Gly Leu Ala Leu Val Leu Ile Leu Ala Phe Cys
                155                 160                 165

Val Ala Gly Ala Ala Ala Leu Ser Val Ala Ser Leu Cys Trp Cys Arg
        170                 175                 180

Leu Gln Arg Glu Ile Arg Leu Thr Gln Lys Ala Asp Tyr Ala Thr Ala
            185                 190                 195

Lys Ala Pro Gly Ser Pro Ala Ala Pro Arg Ile Ser Pro Gly Asp Gln
200                 205                 210

Arg Leu Ala Gln Ser Ala Glu Met Tyr His Tyr Gln His Gln Arg Gln
215                 220                 225                 230

Gln Met Leu Cys Leu Glu Arg His Lys Glu Pro Pro Lys Glu Leu Asp
                235                 240                 245

Thr Ala Ser Ser Asp Glu Glu Asn Glu Asp Gly Asp Phe Thr Val Tyr
                250                 255                 260

Glu Cys Pro Gly Leu Ala Pro Thr Gly Glu Met Glu Val Arg Asn Pro
            265                 270                 275

Leu Phe Asp His Ala Ala Leu Ser Ala Pro Leu Pro Ala Pro Ser Ser
    280                 285                 290

Pro Pro Ala Leu Pro
295

<210> SEQ ID NO 75
<211> LENGTH: 302
<212> TYPE: PRT
<213> ORGANISM: Homo Sapiens
<220> FEATURE:
<221> NAME/KEY: SIGNAL
<222> LOCATION: -18..-1

<400> SEQUENCE: 75

Met Lys Ala Pro Gly Arg Leu Val Leu Ile Ile Leu Cys Ser Val Val
            -15                 -10                 -5

Phe Ser Ala Val Tyr Ile Leu Leu Cys Cys Trp Ala Gly Leu Pro Leu
    1               5                   10

Cys Leu Ala Thr Cys Leu Asp His His Phe Pro Thr Gly Ser Arg Pro
15                  20                  25                  30

Thr Val Pro Gly Pro Leu His Phe Ser Gly Tyr Ser Val Pro Asp
                35                  40                  45

Gly Lys Pro Leu Val Arg Glu Pro Cys Arg Ser Cys Ala Val Val Ser
            50                  55                  60

Ser Ser Gly Gln Met Leu Gly Ser Gly Leu Gly Ala Glu Ile Asp Ser
            65                  70                  75

Ala Glu Cys Val Phe Arg Met Asn Gln Ala Pro Thr Val Gly Phe Glu
            80                  85                  90

Ala Asp Val Gly Gln Arg Ser Thr Leu Arg Val Val Ser His Thr Ser
95                  100                 105                 110

Val Pro Leu Leu Leu Arg Asn Tyr Ser His Tyr Phe Gln Lys Ala Arg
                115                 120                 125

Asp Thr Leu Tyr Met Val Trp Gly Gln Gly Arg His Met Asp Arg Val
            130                 135                 140

Leu Gly Gly Arg Thr Tyr Arg Thr Leu Leu Gln Leu Thr Arg Met Tyr
            145                 150                 155
```

```
Pro Gly Leu Gln Val Tyr Thr Phe Thr Glu Arg Met Met Ala Tyr Cys
    160                 165                 170

Asp Gln Ile Phe Gln Asp Glu Thr Gly Lys Asn Arg Arg Gln Ser Gly
175                 180                 185                 190

Ser Phe Leu Ser Thr Gly Trp Phe Thr Met Ile Leu Ala Leu Glu Leu
                195                 200                 205

Cys Glu Glu Ile Val Val Tyr Gly Met Val Ser Asp Ser Tyr Cys Arg
            210                 215                 220

Glu Lys Ser His Pro Ser Val Pro Tyr His Tyr Phe Glu Lys Gly Arg
        225                 230                 235

Leu Asp Glu Cys Gln Met Tyr Leu Ala His Glu Gln Ala Pro Arg Ser
    240                 245                 250

Ala His Arg Phe Ile Thr Glu Lys Ala Val Phe Ser Arg Trp Ala Lys
255                 260                 265                 270

Lys Arg Pro Ile Val Phe Ala His Pro Ser Trp Arg Thr Glu
                275                 280

<210> SEQ ID NO 76
<211> LENGTH: 249
<212> TYPE: PRT
<213> ORGANISM: Homo Sapiens
<220> FEATURE:
<221> NAME/KEY: SIGNAL
<222> LOCATION: -15..-1

<400> SEQUENCE: 76

Met Leu Gln Leu Trp Lys Leu Val Leu Leu Cys Gly Val Leu Thr Gly
-15                 -10                 -5                   1

Thr Ser Glu Ser Leu Leu Asp Asn Leu Gly Asn Asp Leu Ser Asn Val
                5                   10                  15

Val Asp Lys Leu Glu Pro Val Leu His Glu Gly Leu Glu Thr Val Asp
            20                  25                  30

Asn Thr Leu Lys Gly Ile Leu Glu Lys Leu Lys Val Asp Leu Gly Val
    35                  40                  45

Leu Gln Lys Ser Ser Ala Trp Gln Leu Ala Lys Gln Lys Ala Gln Glu
50                  55                  60                  65

Ala Glu Lys Leu Leu Asn Asn Val Ile Ser Lys Leu Leu Pro Thr Asn
                70                  75                  80

Thr Asp Ile Phe Gly Leu Lys Ile Ser Asn Ser Leu Ile Leu Asp Val
            85                  90                  95

Lys Ala Glu Pro Ile Asp Asp Gly Lys Gly Leu Asn Leu Ser Phe Pro
        100                 105                 110

Val Thr Ala Asn Val Thr Val Ala Gly Pro Ile Ile Gly Gln Ile Ile
    115                 120                 125

Asn Leu Lys Ala Ser Leu Asp Leu Leu Thr Ala Val Thr Ile Glu Thr
130                 135                 140                 145

Asp Pro Gln Thr His Gln Pro Val Ala Val Leu Gly Glu Cys Ala Ser
                150                 155                 160

Asp Pro Thr Ser Ile Ser Leu Ser Leu Leu Asp Lys His Ser Gln Ile
            165                 170                 175

Ile Asn Lys Phe Val Asn Ser Val Ile Asn Thr Leu Lys Ser Thr Val
        180                 185                 190

Ser Ser Leu Leu Gln Lys Glu Ile Cys Pro Leu Ile Arg Ile Phe Ile
    195                 200                 205

His Ser Leu Asp Val Asn Val Ile Gln Gln Val Val Asp Asn Pro Gln
```

```
210             215             220             225

His Lys Thr Gln Leu Gln Thr Leu Ile
            230

<210> SEQ ID NO 77
<211> LENGTH: 84
<212> TYPE: PRT
<213> ORGANISM: Homo Sapiens

<400> SEQUENCE: 77

Met Lys Val Lys Ile Lys Cys Trp Asn Gly Val Ala Thr Trp Leu Trp
1               5                   10                  15

Val Ala Asn Asp Glu Asn Cys Gly Ile Cys Arg Met Ala Phe Asn Gly
            20                  25                  30

Cys Cys Pro Asp Cys Lys Val Pro Gly Asp Cys Pro Leu Val Trp
        35                  40                  45

Gly Gln Cys Ser His Cys Phe His Met His Cys Ile Leu Lys Trp Leu
    50                  55                  60

His Ala Gln Gln Val Gln Gln His Cys Pro Met Cys Arg Gln Glu Trp
65                  70                  75                  80

Lys Phe Lys Glu

<210> SEQ ID NO 78
<211> LENGTH: 554
<212> TYPE: PRT
<213> ORGANISM: Homo Sapiens
<220> FEATURE:
<221> NAME/KEY: SIGNAL
<222> LOCATION: -13..-1
<220> FEATURE:
<221> NAME/KEY: UNSURE
<222> LOCATION: 259
<223> OTHER INFORMATION: Xaa = Asp,His,Asn,Tyr

<400> SEQUENCE: 78

Met Leu Tyr Leu Gln Gly Trp Ser Met Pro Ala Val Ala Glu Val Lys
            -10                 -5                  1

Leu Arg Asp Asp Gln Tyr Thr Leu Glu His Met His Ala Phe Gly Met
    5                   10                  15

Tyr Asn Tyr Leu His Cys Asp Ser Trp Tyr Gln Asp Ser Val Tyr Tyr
20                  25                  30                  35

Ile Asp Thr Leu Gly Arg Ile Met Asn Leu Thr Val Met Leu Asp Thr
            40                  45                  50

Ala Leu Gly Lys Pro Arg Glu Val Phe Arg Leu Pro Thr Asp Leu Thr
        55                  60                  65

Ala Cys Asp Asn Arg Leu Cys Ala Ser Ile His Phe Ser Ser Ser Thr
    70                  75                  80

Trp Val Thr Leu Ser Asp Gly Thr Gly Arg Leu Tyr Val Ile Gly Thr
85                  90                  95

Gly Glu Arg Gly Asn Ser Ala Ser Glu Lys Trp Glu Ile Met Phe Asn
100                 105                 110                 115

Glu Glu Leu Gly Asp Pro Phe Ile Ile His Ser Ile Ser Leu Leu
            120                 125                 130

Asn Ala Glu Glu His Ser Ile Ala Thr Leu Leu Leu Arg Ile Glu Lys
        135                 140                 145

Glu Glu Leu Asp Met Lys Gly Ser Gly Phe Tyr Val Ser Leu Glu Trp
    150                 155                 160

Val Thr Ile Ser Lys Lys Asn Gln Asp Asn Lys Lys Tyr Glu Ile Ile
```

```
                165                 170                 175
Lys Arg Asp Ile Leu Arg Gly Lys Ser Val Pro His Tyr Ala Ala Ile
180                 185                 190                 195

Lys Pro Asp Gly Asn Gly Leu Met Ile Val Ser Tyr Lys Ser Leu Thr
                200                 205                 210

Phe Val Gln Ala Gly Gln Asp Leu Glu Glu Asn Met Asp Glu Asp Ile
                215                 220                 225

Ser Glu Lys Ile Lys Glu Pro Leu Tyr Tyr Trp Gln Gln Thr Glu Asp
                230                 235                 240

Asp Leu Thr Val Thr Ile Arg Leu Pro Glu Asp Ser Thr Lys Glu Xaa
245                 250                 255

Ile Gln Ile Gln Phe Leu Pro Asp His Ile Asn Ile Val Leu Lys Asp
260                 265                 270                 275

His Gln Phe Leu Glu Gly Lys Leu Tyr Ser Ser Ile Asp His Glu Ser
                280                 285                 290

Ser Thr Trp Ile Ile Lys Glu Ser Asn Ser Leu Glu Ile Ser Leu Ile
                295                 300                 305

Lys Lys Asn Glu Gly Leu Thr Trp Pro Glu Leu Val Ile Gly Asp Lys
                310                 315                 320

Gln Gly Glu Leu Ile Arg Asp Ser Ala Gln Cys Ala Ala Ile Ala Glu
                325                 330                 335

Arg Leu Met His Leu Thr Ser Glu Glu Leu Asn Pro Asn Pro Asp Lys
340                 345                 350                 355

Glu Lys Pro Pro Cys Asn Ala Gln Glu Leu Glu Glu Cys Asp Ile Phe
                360                 365                 370

Phe Glu Glu Ser Ser Ser Leu Cys Arg Phe Asp Gly Asn Thr Leu Lys
                375                 380                 385

Thr Thr His Val Val Asn Leu Gly Ser Asn Gln Tyr Leu Phe Ser Val
                390                 395                 400

Ile Val Asp Pro Lys Glu Met Pro Cys Phe Cys Leu Arg His Asp Val
                405                 410                 415

Asp Ala Leu Leu Trp Gln Pro His Ser Ser Lys Gln Asp Asp Met Trp
420                 425                 430                 435

Glu His Ile Ala Thr Phe Asn Ala Leu Gly Tyr Val Gln Ala Ser Lys
                440                 445                 450

Arg Asp Lys Lys Phe Phe Ala Cys Ala Pro Asn Tyr Ser Tyr Ala Ala
                455                 460                 465

Leu Cys Glu Cys Leu Arg Arg Val Phe Ile Tyr Arg Gln Pro Ala Pro
                470                 475                 480

Met Ser Thr Val Leu Tyr Asn Arg Lys Glu Gly Arg Gln Val Gly Gln
                485                 490                 495

Val Ala Lys Gln Gln Val Ala Ser Leu Glu Thr Asn Asp Pro Ile Leu
500                 505                 510                 515

Gly Phe Gln Ala Thr Asn Glu Arg Leu Phe Val Leu Thr Thr Lys Asn
                520                 525                 530

Leu Phe Leu Ile Lys Val Asn Thr Glu Asn
                535                 540

<210> SEQ ID NO 79
<211> LENGTH: 99
<212> TYPE: PRT
<213> ORGANISM: Homo Sapiens
<220> FEATURE:
<221> NAME/KEY: SIGNAL
<222> LOCATION: -48..-1
```

```
<400> SEQUENCE: 79

Met Asp Asn Val Gln Pro Lys Ile Lys His Arg Pro Phe Cys Phe Ser
            -45                 -40                 -35

Val Lys Gly His Val Lys Met Leu Arg Leu Asp Ile Ile Asn Ser Leu
            -30                 -25                 -20

Val Thr Thr Val Phe Met Leu Ile Val Ser Val Leu Ala Leu Ile Pro
            -15                 -10                 -5

Glu Thr Thr Thr Leu Thr Val Gly Gly Val Phe Ala Leu Val Thr
1                5                   10                  15

Ala Val Cys Cys Leu Ala Asp Gly Ala Leu Ile Tyr Arg Lys Leu Leu
            20                  25                  30

Phe Asn Pro Ser Gly Pro Tyr Gln Lys Lys Pro Val His Glu Lys Lys
            35                  40                  45

Glu Val Leu
        50

<210> SEQ ID NO 80
<211> LENGTH: 90
<212> TYPE: PRT
<213> ORGANISM: Homo Sapiens
<220> FEATURE:
<221> NAME/KEY: SIGNAL
<222> LOCATION: -32...-1

<400> SEQUENCE: 80

Met Pro Cys Leu Asp Gln Gln Leu Thr Val His Ala Leu Pro Cys Pro
            -30                 -25                 -20

Ala Gln Pro Ser Ser Leu Ala Phe Cys Gln Val Gly Phe Leu Thr Ala
            -15                 -10                 -5

Gln Pro Ser Pro Pro Arg Arg Arg Asn Gly Lys Asp Arg Tyr Thr Leu
1               5                   10                  15

Val Leu Gln His Gln Glu Cys Gln Asp Asp Leu Ala Thr Ser Ser Leu
            20                  25                  30

Val Tyr Leu Ser Leu Pro Cys Phe Lys Asp Leu Gly Arg Ser Lys His
            35                  40                  45

Gln Ser Ile Thr Val Ala Asp Thr Asn Lys
        50                  55

<210> SEQ ID NO 81
<211> LENGTH: 115
<212> TYPE: PRT
<213> ORGANISM: Homo Sapiens
<220> FEATURE:
<221> NAME/KEY: SIGNAL
<222> LOCATION: -46...-1

<400> SEQUENCE: 81

Met Lys Thr Leu Phe Asn Pro Ala Pro Ala Ile Ala Asp Leu Asp Pro
            -45                 -40                 -35

Gln Phe Tyr Thr Leu Ser Asp Val Phe Cys Cys Asn Glu Ser Glu Ala
-30                 -25                 -20                 -15

Glu Ile Leu Thr Gly Leu Thr Val Gly Ser Ala Ala Asp Ala Gly Glu
                -10                 -5                  1

Ala Ala Leu Val Leu Leu Lys Arg Gly Cys Gln Val Val Ile Ile Thr
            5                   10                  15

Leu Gly Ala Glu Gly Cys Val Val Leu Ser Gln Thr Glu Pro Glu Pro
            20                  25                  30
```

-continued

```
Lys His Ile Pro Thr Glu Lys Val Lys Ala Val Asp Thr Thr Cys Arg
 35              40                  45                  50

Pro Gly Ser Arg Pro Lys Ser Glu Ala Ala Ser Val Lys Lys Gln Lys
                 55                  60                  65

His Tyr Lys

<210> SEQ ID NO 82
<211> LENGTH: 66
<212> TYPE: PRT
<213> ORGANISM: Homo Sapiens
<220> FEATURE:
<221> NAME/KEY: SIGNAL
<222> LOCATION: -19..-1

<400> SEQUENCE: 82

Met Lys Pro Leu Leu Val Val Phe Val Phe Leu Phe Leu Trp Asp Pro
                -15                 -10                  -5

Val Leu Ala Gly Ile Asn Ser Leu Ser Ser Glu Met His Lys Lys Cys
                 1               5                  10

Tyr Lys Asn Gly Ile Cys Arg Leu Glu Cys Tyr Glu Ser Glu Met Leu
         15                  20                  25

Val Ala Tyr Cys Met Phe Gln Leu Glu Cys Cys Val Lys Gly Asn Pro
 30              35                  40                  45

Ala Pro

<210> SEQ ID NO 83
<211> LENGTH: 133
<212> TYPE: PRT
<213> ORGANISM: Homo Sapiens
<220> FEATURE:
<221> NAME/KEY: SIGNAL
<222> LOCATION: -21..-1

<400> SEQUENCE: 83

Met Ser Cys Ser Leu Lys Phe Thr Leu Ile Val Ile Phe Phe Tyr Cys
        -20                 -15                 -10

Trp Leu Ser Ser Ser His Glu Glu Leu Glu Gly Gly Thr Ser Lys Ser
 -5                  1               5                  10

Phe Asp Leu His Thr Val Ile Met Leu Val Ile Ala Gly Gly Ile Leu
             15                  20                  25

Ala Ala Leu Leu Leu Leu Ile Val Val Leu Cys Leu Tyr Phe Lys
         30                  35                  40

Ile His Asn Ala Leu Lys Ala Lys Glu Pro Glu Ala Val Ala Val
     45                  50                  55

Lys Asn His Asn Pro Asp Lys Val Trp Trp Ala Lys Asn Ser Gln Ala
 60                  65                  70                  75

Lys Thr Ile Ala Thr Glu Ser Cys Pro Ala Leu Gln Cys Cys Glu Gly
             80                  85                  90

Tyr Arg Met Cys Ala Ser Phe Asp Ser Leu Pro Pro Cys Cys Cys Asp
             95                 100                 105

Ile Asn Glu Gly Leu
        110

<210> SEQ ID NO 84
<211> LENGTH: 140
<212> TYPE: PRT
<213> ORGANISM: Homo Sapiens
<220> FEATURE:
<221> NAME/KEY: SIGNAL
<222> LOCATION: -70..-1
```

```
<400> SEQUENCE: 84

Met Val Leu Thr Lys Pro Leu Gln Arg Asn Gly Ser Met Met Ser Phe
-70             -65                 -60                 -55

Glu Asn Val Lys Glu Lys Ser Arg Glu Gly Gly Pro His Ala His Thr
            -50                 -45                 -40

Pro Glu Glu Glu Leu Cys Phe Val Val Thr His Tyr Pro Gln Val Gln
            -35                 -30                 -25

Thr Thr Leu Asn Leu Phe Phe His Ile Phe Lys Val Leu Thr Gln Pro
            -20                 -15                 -10

Leu Ser Leu Leu Trp Gly Cys Asp Gln Lys Pro Arg Thr Val Pro Thr
-5               1                  5                       10

Leu Gly Asn Gly Ala Trp Asp Thr Cys Gln Gln His Ile Arg Thr Ser
                15                  20                  25

Ser Trp Thr Ala Asn Thr Leu Val Ile Gln Asn Gln His Ser Arg Glu
                30                  35                  40

Ser Thr Val Ser Val Cys Leu Phe Met Leu Ile Arg Met Gln His Ile
                45                  50                  55

Leu Lys Thr Asp Thr Leu Gln Gln Phe Arg Ile Cys
60                  65                  70

<210> SEQ ID NO 85
<211> LENGTH: 233
<212> TYPE: PRT
<213> ORGANISM: Homo Sapiens
<220> FEATURE:
<221> NAME/KEY: SIGNAL
<222> LOCATION: -32..-1

<400> SEQUENCE: 85

Met Ala Thr Pro Pro Phe Arg Leu Ile Arg Lys Met Phe Ser Phe Lys
        -30                 -25                 -20

Val Ser Arg Trp Met Gly Leu Ala Cys Phe Arg Ser Leu Ala Ala Ser
    -15                 -10                 -5

Ser Pro Ser Ile Arg Gln Lys Lys Leu Met His Lys Leu Gln Glu Glu
1               5                   10                  15

Lys Ala Phe Arg Glu Glu Met Lys Ile Phe Arg Glu Lys Ile Glu Asp
                20                  25                  30

Phe Arg Glu Glu Met Trp Thr Phe Arg Gly Lys Ile His Ala Phe Arg
                35                  40                  45

Gly Gln Ile Leu Gly Phe Trp Glu Glu Arg Pro Phe Trp Glu Glu
                50                  55                  60

Glu Lys Thr Phe Trp Lys Glu Lys Ser Phe Trp Glu Met Glu Lys
65                  70                  75                  80

Ser Phe Arg Glu Glu Lys Thr Phe Trp Lys Lys Tyr Arg Thr Phe
                85                  90                  95

Trp Lys Glu Asp Lys Ala Phe Trp Lys Glu Asp Asn Ala Leu Trp Glu
                100                 105                 110

Arg Asp Arg Asn Leu Leu Gln Glu Asp Lys Ala Leu Trp Glu Glu Glu
                115                 120                 125

Lys Ala Leu Trp Val Glu Glu Arg Ala Leu Leu Glu Gly Glu Lys Ala
                130                 135                 140

Leu Trp Glu Asp Lys Thr Ser Leu Trp Glu Glu Asn Ala Leu Trp
145                 150                 155                 160

Glu Glu Glu Arg Ala Phe Trp Met Glu Asn Asn Gly His Ile Ala Gly
                165                 170                 175
```

```
Glu Gln Met Leu Glu Asp Gly Pro His Asn Ala Asn Arg Gly Gln Arg
            180                 185                 190

Leu Leu Ala Phe Ser Arg Gly Arg Ala
            195                 200

<210> SEQ ID NO 86
<211> LENGTH: 83
<212> TYPE: PRT
<213> ORGANISM: Homo Sapiens
<220> FEATURE:
<221> NAME/KEY: SIGNAL
<222> LOCATION: -29..-1

<400> SEQUENCE: 86

Met Ser Phe Phe Gln Leu Leu Met Lys Arg Lys Glu Leu Ile Pro Leu
                -25                 -20                 -15

Val Val Phe Met Thr Val Ala Ala Gly Gly Ala Ser Ser Phe Ala Val
            -10                  -5                   1

Tyr Ser Leu Trp Lys Thr Asp Val Ile Leu Asp Arg Lys Lys Asn Pro
      5                  10                  15

Glu Pro Trp Glu Thr Val Asp Pro Thr Val Pro Gln Lys Leu Ile Thr
 20                  25                  30                  35

Ile Asn Gln Gln Trp Lys Pro Ile Glu Glu Leu Gln Asn Val Gln Arg
                 40                  45                  50

Val Thr Lys

<210> SEQ ID NO 87
<211> LENGTH: 215
<212> TYPE: PRT
<213> ORGANISM: Homo Sapiens
<220> FEATURE:
<221> NAME/KEY: SIGNAL
<222> LOCATION: -41..-1

<400> SEQUENCE: 87

Met Val Ser Ala Leu Arg Gly Ala Pro Leu Ile Arg Val His Ser Ser
    -40                 -35                 -30

Pro Val Ser Ser Pro Ser Val Ser Gly Pro Arg Arg Leu Val Ser Cys
-25                 -20                 -15                 -10

Leu Ser Ser Gln Ser Ser Ala Leu Ser Gln Ser Gly Gly Gly Ser Thr
                 -5                   1                   5

Ser Ala Ala Gly Ile Glu Ala Arg Ser Arg Ala Leu Arg Arg Arg Trp
             10                  15                  20

Cys Pro Ala Gly Ile Met Leu Leu Ala Leu Val Cys Leu Leu Ser Cys
 25                  30                  35

Leu Leu Pro Ser Ser Glu Ala Lys Leu Tyr Gly Arg Cys Glu Leu Ala
 40                  45                  50                  55

Arg Val Leu His Asp Phe Gly Leu Asp Gly Tyr Arg Gly Tyr Ser Leu
                 60                  65                  70

Ala Asp Trp Val Cys Leu Ala Tyr Phe Thr Ser Gly Phe Asn Ala Ala
             75                  80                  85

Ala Leu Asp Tyr Glu Ala Asp Gly Ser Thr Asn Asn Gly Ile Phe Gln
             90                  95                 100

Ile Asn Ser Arg Arg Trp Cys Ser Asn Leu Thr Pro Asn Val Pro Asn
            105                 110                 115

Val Cys Arg Met Tyr Cys Ser Asp Leu Leu Asn Pro Asn Leu Lys Asp
120                 125                 130                 135
```

```
Thr Val Ile Cys Ala Met Lys Ile Thr Gln Glu Pro Gln Gly Leu Gly
            140                 145                 150
Tyr Trp Glu Ala Trp Arg His His Cys Gln Gly Lys Asp Leu Thr Glu
            155                 160                 165
Trp Val Asp Gly Cys Asp Phe
            170

<210> SEQ ID NO 88
<211> LENGTH: 417
<212> TYPE: PRT
<213> ORGANISM: Homo Sapiens
<220> FEATURE:
<221> NAME/KEY: SIGNAL
<222> LOCATION: -20..-1

<400> SEQUENCE: 88

Met Met Gly Ser Pro Val Ser His Leu Leu Ala Gly Phe Cys Val Trp
-20                 -15                 -10                  -5
Val Val Leu Gly Trp Val Gly Gly Ser Val Pro Asn Leu Gly Pro Ala
                  1               5                  10
Glu Gln Glu Gln Asn His Tyr Leu Ala Gln Leu Phe Gly Leu Tyr Gly
            15                  20                  25
Glu Asn Gly Thr Leu Thr Ala Gly Gly Leu Ala Arg Leu Leu His Ser
        30                  35                  40
Leu Gly Leu Gly Arg Val Gln Gly Leu Arg Leu Gly Gln His Gly Pro
45                  50                  55                  60
Leu Thr Gly Arg Ala Ala Ser Pro Ala Ala Asp Asn Ser Thr His Arg
                65                  70                  75
Pro Gln Asn Pro Glu Leu Ser Val Asp Val Trp Ala Gly Met Pro Leu
            80                  85                  90
Gly Pro Ser Gly Trp Gly Asp Leu Glu Glu Ser Lys Ala Pro His Leu
        95                  100                 105
Pro Arg Gly Pro Ala Pro Ser Gly Leu Asp Leu Leu His Arg Leu Leu
    110                 115                 120
Leu Leu Asp His Ser Leu Ala Asp His Leu Asn Glu Asp Cys Leu Asn
125                 130                 135                 140
Gly Ser Gln Leu Leu Val Asn Phe Gly Leu Ser Pro Ala Ala Pro Leu
                145                 150                 155
Thr Pro Arg Gln Phe Ala Leu Leu Cys Pro Ala Leu Leu Tyr Gln Ile
            160                 165                 170
Asp Ser Arg Val Cys Ile Gly Ala Pro Ala Pro Ala Pro Gly Asp
            175                 180                 185
Leu Leu Ser Ala Leu Leu Gln Ser Ala Leu Ala Val Leu Leu Leu Ser
    190                 195                 200
Leu Pro Ser Pro Leu Ser Leu Leu Leu Arg Leu Leu Gly Pro Arg
205                 210                 215                 220
Leu Leu Arg Pro Leu Leu Gly Phe Leu Gly Ala Leu Ala Val Gly Thr
                225                 230                 235
Leu Cys Gly Asp Ala Leu Leu His Leu Leu Pro His Ala Gln Glu Gly
            240                 245                 250
Arg His Ala Gly Pro Gly Gly Leu Pro Glu Lys Asp Leu Gly Pro Gly
            255                 260                 265
Leu Ser Val Leu Gly Gly Leu Phe Leu Phe Val Leu Glu Asn Met
    270                 275                 280
Leu Gly Leu Leu Arg His Arg Gly Leu Arg Pro Arg Cys Cys Arg Arg
285                 290                 295                 300
```

```
Lys Arg Arg Asn Leu Glu Thr Arg Asn Leu Asp Pro Glu Asn Gly Ser
                305                 310                 315
Gly Met Ala Leu Gln Pro Leu Gln Ala Ala Pro Glu Pro Gly Ala Gln
                320                 325                 330
Gly Gln Arg Glu Lys Asn Ser Gln His Pro Pro Ala Leu Ala Pro Pro
                335                 340                 345
Gly His Gln Gly His Ser His Gly His Gln Gly Gly Thr Asp Ile Thr
                350                 355                 360
Trp Met Val Leu Leu Gly Asp Gly Leu His Asn Leu Thr Asp Gly Leu
365                 370                 375                 380
Ala Ile Gly Ala Ala Phe Ser Asp Gly Phe Ser Ala Ala Ser Val Pro
                385                 390                 395
Pro

<210> SEQ ID NO 89
<211> LENGTH: 366
<212> TYPE: PRT
<213> ORGANISM: Homo Sapiens
<220> FEATURE:
<221> NAME/KEY: SIGNAL
<222> LOCATION: -23..-1

<400> SEQUENCE: 89

Met Ala Ser Met Ala Ala Val Leu Thr Trp Ala Leu Ala Leu Leu Ser
                -20                 -15                 -10
Ala Phe Ser Ala Thr Gln Ala Arg Lys Gly Phe Trp Asp Tyr Phe Ser
            -5                   1               5
Gln Thr Ser Gly Asp Lys Gly Arg Val Glu Gln Ile His Gln Lys
10                  15                  20                  25
Met Ala Arg Glu Pro Ala Thr Leu Lys Asp Ser Leu Glu Gln Asp Leu
                30                  35                  40
Asn Asn Met Asn Lys Phe Leu Glu Lys Leu Arg Pro Leu Ser Gly Ser
                45                  50                  55
Glu Ala Pro Arg Leu Pro Gln Asp Pro Val Gly Met Arg Arg Gln Leu
                60                  65                  70
Gln Glu Glu Leu Glu Glu Val Lys Ala Arg Leu Gln Pro Tyr Met Ala
75                  80                  85
Glu Ala His Glu Leu Val Gly Trp Asn Leu Glu Gly Leu Arg Gln Gln
90                  95                  100                 105
Leu Lys Pro Tyr Thr Met Asp Leu Met Glu Gln Val Ala Leu Arg Val
                110                 115                 120
Gln Glu Leu Gln Glu Gln Leu Arg Val Val Gly Glu Asp Thr Lys Ala
                125                 130                 135
Gln Leu Leu Gly Gly Val Asp Glu Ala Trp Ala Leu Leu Gln Gly Leu
                140                 145                 150
Gln Ser Arg Val Val His Thr Gly Arg Phe Lys Glu Leu Phe His
                155                 160                 165
Pro Tyr Ala Glu Ser Leu Val Ser Gly Ile Gly Arg His Val Gln Glu
170                 175                 180                 185
Leu His Arg Ser Val Ala Pro His Ala Pro Ala Ser Pro Ala Arg Leu
                190                 195                 200
Ser Arg Cys Val Gln Val Leu Ser Arg Lys Leu Thr Leu Lys Ala Lys
                205                 210                 215
Ala Leu His Ala Arg Ile Gln Gln Asn Leu Asp Gln Leu Arg Glu Glu
                220                 225                 230
```

```
Leu Ser Arg Ala Phe Ala Gly Thr Gly Thr Glu Glu Gly Ala Gly Pro
    235                 240                 245

Asp Pro Gln Met Leu Ser Glu Val Arg Gln Arg Leu Gln Ala Phe
250                 255                 260                 265

Arg Gln Asp Thr Tyr Leu Gln Ile Ala Ala Phe Thr Arg Ala Ile Asp
                270                 275                 280

Gln Glu Thr Glu Glu Val Gln Gln Leu Ala Pro Pro Pro Gly
            285                 290                 295

His Ser Ala Phe Ala Pro Glu Phe Gln Gln Thr Asp Ser Gly Lys Val
            300                 305                 310

Leu Ser Lys Leu Gln Ala Arg Leu Asp Asp Leu Trp Glu Asp Ile Thr
    315                 320                 325

His Ser Leu His Asp Gln Gly His Ser His Leu Gly Asp Pro
330                 335                 340
```

<210> SEQ ID NO 90
<211> LENGTH: 150
<212> TYPE: PRT
<213> ORGANISM: Homo Sapiens
<220> FEATURE:
<221> NAME/KEY: SIGNAL
<222> LOCATION: -45..-1

<400> SEQUENCE: 90

```
Met Val Leu Met Trp Thr Ser Gly Asp Ala Phe Lys Thr Ala Tyr Phe
-45                 -40                 -35                 -30

Leu Leu Lys Gly Ala Pro Leu Gln Phe Ser Val Cys Gly Leu Leu Gln
                -25                 -20                 -15

Val Leu Val Asp Leu Ala Ile Leu Gly Gln Ala Tyr Ala Phe Ala Pro
            -10                 -5                  1

Pro Pro Glu Ala Gly Ala Pro Arg Arg Ala Pro His Trp His Gln Gly
    5                   10                  15

Pro Leu Thr Val Gly Arg Thr Arg Met Trp Asp Arg Gln Pro Arg Ala
20                  25                  30                  35

Leu Val Gly Pro Asp Leu Pro Ala Gly Arg Val Gly Ala Val Ala Pro
                40                  45                  50

Ala Gly Val Ala Glu Met Gly His Gly His Trp Gly Leu His Gln Pro
            55                  60                  65

Leu Trp Gly Val Ser Gly Trp Ala Val Gly Val Gly Leu Gly Arg Cys
        70                  75                  80

Leu Cys Ser Ala Gly Thr Ala Arg Val Asp Leu Ala Pro Arg Val Leu
    85                  90                  95

Asp Val Phe Arg Met Thr
100                 105
```

<210> SEQ ID NO 91
<211> LENGTH: 308
<212> TYPE: PRT
<213> ORGANISM: Homo Sapiens
<220> FEATURE:
<221> NAME/KEY: SIGNAL
<222> LOCATION: -68..-1

<400> SEQUENCE: 91

```
Met Asp Phe Val Ala Gly Ala Ile Gly Gly Val Cys Gly Val Ala Val
                -65                 -60                 -55

Gly Tyr Pro Leu Asp Thr Val Lys Val Arg Ile Gln Thr Glu Pro Lys
            -50                 -45                 -40
```

```
Tyr Thr Gly Ile Trp His Cys Val Arg Asp Thr Tyr His Arg Glu Arg
    -35             -30                 -25

Val Trp Gly Phe Tyr Arg Gly Leu Ser Leu Pro Val Cys Thr Val Ser
-20             -15                 -10                     -5

Leu Val Ser Ser Val Ser Phe Gly Thr Tyr Arg His Cys Leu Ala His
                 1           5                      10

Ile Cys Arg Leu Arg Tyr Gly Asn Pro Asp Ala Lys Pro Thr Lys Ala
         15              20                  25

Asp Ile Thr Leu Ser Gly Cys Ala Ser Gly Leu Val Arg Val Phe Leu
     30              35                  40

Thr Ser Pro Thr Glu Val Ala Lys Val Arg Leu Gln Thr Gln Thr Gln
45               50              55                       60

Ala Gln Lys Gln Gln Arg Leu Leu Ser Ala Ser Gly Pro Leu Ala Val
             65              70                  75

Pro Pro Met Cys Pro Val Pro Pro Ala Cys Pro Glu Pro Lys Tyr Arg
         80                  85              90

Gly Pro Leu His Cys Leu Ala Thr Val Ala Arg Glu Glu Gly Leu Cys
         95                 100             105

Gly Leu Tyr Lys Gly Ser Ser Ala Leu Val Leu Arg Asp Gly His Ser
        110             115             120

Phe Ala Thr Tyr Phe Leu Ser Tyr Ala Val Leu Cys Glu Trp Leu Ser
125             130             135                     140

Pro Ala Gly His Ser Arg Pro Asp Val Pro Gly Val Leu Val Ala Gly
             145             150                 155

Gly Cys Ala Gly Val Leu Ala Trp Ala Val Ala Thr Pro Met Asp Val
            160             165             170

Ile Lys Ser Arg Leu Gln Ala Asp Gly Gln Gly Gln Arg Tyr Arg
        175             180             185

Gly Leu Leu His Cys Met Val Thr Ser Val Arg Glu Glu Gly Pro Arg
        190             195             200

Val Leu Phe Lys Gly Leu Val Leu Asn Cys Cys Arg Ala Phe Pro Val
205             210             215                     220

Asn Met Val Val Phe Val Ala Tyr Glu Ala Val Leu Arg Leu Ala Arg
            225             230             235

Gly Leu Leu Thr
            240

<210> SEQ ID NO 92
<211> LENGTH: 114
<212> TYPE: PRT
<213> ORGANISM: Homo Sapiens
<220> FEATURE:
<221> NAME/KEY: SIGNAL
<222> LOCATION: -49..-1

<400> SEQUENCE: 92

Met Glu Lys Pro Leu Phe Pro Leu Val Pro Leu His Trp Phe Gly Phe
                -45                 -40                 -35

Gly Tyr Thr Ala Leu Val Val Ser Gly Ile Val Gly Tyr Val Lys
            -30             -25                 -20

Thr Gly Ser Val Pro Ser Leu Ala Ala Gly Leu Leu Phe Gly Ser Leu
        -15                 -10                 -5

Ala Gly Leu Gly Ala Tyr Gln Leu Tyr Gln Asp Pro Arg Asn Val Trp
 1               5                  10                  15

Gly Phe Leu Ala Ala Thr Ser Val Thr Phe Val Gly Val Met Gly Met
```

-continued

```
                    20                  25                  30
Arg Ser Tyr Tyr Tyr Gly Lys Phe Met Pro Val Gly Leu Ile Ala Gly
            35                  40                  45

Ala Ser Leu Leu Met Ala Ala Lys Val Gly Val Arg Met Leu Met Thr
        50                  55                  60

Ser Asp
    65

<210> SEQ ID NO 93
<211> LENGTH: 382
<212> TYPE: PRT
<213> ORGANISM: Homo Sapiens
<220> FEATURE:
<221> NAME/KEY: SIGNAL
<222> LOCATION: -15..-1

<400> SEQUENCE: 93

Met Gly Leu Leu Leu Pro Leu Ala Leu Cys Ile Leu Val Leu Cys Cys
-15                 -10                  -5                   1

Gly Ala Met Ser Pro Pro Gln Leu Ala Leu Asn Pro Ser Ala Leu Leu
            5                   10                  15

Ser Arg Gly Cys Asn Asp Ser Asp Val Leu Ala Val Ala Gly Phe Ala
        20                  25                  30

Leu Arg Asp Ile Asn Lys Asp Arg Lys Asp Gly Tyr Val Leu Arg Leu
    35                  40                  45

Asn Arg Val Asn Asp Ala Gln Glu Tyr Arg Arg Gly Leu Gly Ser
50                  55                  60                  65

Leu Phe Tyr Leu Thr Leu Asp Val Leu Glu Thr Asp Cys His Val Leu
            70                  75                  80

Arg Lys Lys Ala Trp Gln Asp Cys Gly Met Arg Ile Phe Phe Glu Ser
        85                  90                  95

Val Tyr Gly Gln Cys Lys Ala Ile Phe Tyr Met Asn Asn Pro Ser Arg
    100                 105                 110

Val Leu Tyr Leu Ala Ala Tyr Asn Cys Thr Leu Arg Pro Val Ser Lys
    115                 120                 125

Lys Lys Ile Tyr Met Thr Cys Pro Asp Cys Pro Ser Ser Ile Pro Thr
130                 135                 140                 145

Asp Ser Ser Asn His Gln Val Leu Glu Ala Thr Glu Ser Leu Ala
            150                 155                 160

Lys Tyr Asn Asn Glu Asn Thr Ser Lys Gln Tyr Ser Leu Phe Lys Val
        165                 170                 175

Thr Arg Ala Ser Ser Gln Trp Val Val Gly Pro Ser Tyr Phe Val Glu
    180                 185                 190

Tyr Leu Ile Lys Glu Ser Pro Cys Thr Lys Ser Gln Ala Ser Ser Cys
    195                 200                 205

Ser Leu Gln Ser Ser Asp Ser Val Pro Val Gly Leu Cys Lys Gly Ser
210                 215                 220                 225

Leu Thr Arg Thr His Trp Glu Lys Phe Val Ser Val Thr Cys Asp Phe
            230                 235                 240

Phe Glu Ser Gln Ala Pro Ala Thr Gly Ser Glu Asn Ser Ala Val Asn
        245                 250                 255

Gln Lys Pro Thr Asn Leu Pro Lys Val Glu Glu Ser Gln Gln Lys Asn
    260                 265                 270

Thr Pro Pro Thr Asp Ser Pro Ser Lys Ala Gly Pro Arg Gly Ser Val
    275                 280                 285
```

```
Gln Tyr Leu Pro Asp Leu Asp Asp Lys Asn Ser Gln Glu Lys Gly Pro
290                 295                 300                 305

Gln Glu Ala Phe Pro Val His Leu Asp Leu Thr Thr Asn Pro Gln Gly
            310                 315                 320

Glu Thr Leu Asp Ile Ser Phe Leu Phe Leu Pro Met Glu Glu Lys
                325                 330                 335

Leu Val Val Leu Pro Phe Pro Lys Glu Lys Ala Arg Thr Ala Glu Cys
            340                 345                 350

Pro Gly Pro Ala Gln Asn Ala Ser Pro Leu Val Leu Pro Pro
            355                 360                 365

<210> SEQ ID NO 94
<211> LENGTH: 212
<212> TYPE: PRT
<213> ORGANISM: Homo Sapiens
<220> FEATURE:
<221> NAME/KEY: SIGNAL
<222> LOCATION: -197..-1
<220> FEATURE:
<221> NAME/KEY: UNSURE
<222> LOCATION: -88
<223> OTHER INFORMATION: Xaa = Ala,Asp,Gly,Val
<220> FEATURE:
<221> NAME/KEY: UNSURE
<222> LOCATION: -109
<223> OTHER INFORMATION: Xaa = Asp,Glu

<400> SEQUENCE: 94

Met Ala Thr Pro Asn Asn Leu Thr Pro Thr Asn Cys Ser Trp Trp Pro
        -195                -190                -185

Ile Ser Ala Leu Glu Ser Asp Ala Ala Lys Pro Ala Glu Ala Pro Asp
        -180                -175                -170

Ala Pro Glu Ala Ala Ser Pro Ala His Trp Pro Arg Glu Ser Leu Val
-165                -160                -155                -150

Leu Tyr His Trp Thr Gln Ser Phe Ser Ser Gln Lys Ala Lys Ile Leu
            -145                -140                -135

Glu His Asp Asp Val Ser Tyr Leu Lys Lys Ile Leu Gly Glu Leu Ala
            -130                -125                -120

Met Val Leu Asp Gln Ile Glu Ala Xaa Leu Glu Lys Arg Lys Leu Glu
            -115                -110                -105

Asn Glu Gly Gln Lys Cys Glu Leu Trp Leu Cys Gly Cys Xaa Phe Thr
        -100                -95                 -90

Leu Ala Asp Val Leu Leu Gly Ala Thr Leu His Arg Leu Lys Phe Leu
-85                 -80                 -75                 -70

Gly Leu Ser Lys Lys Tyr Trp Glu Asp Gly Ser Arg Pro Asn Leu Gln
            -65                 -60                 -55

Ser Phe Phe Glu Arg Val Gln Arg Arg Phe Ala Phe Arg Lys Val Leu
        -50                 -45                 -40

Gly Asp Ile His Thr Thr Leu Leu Ser Ala Val Ile Pro Asn Ala Phe
        -35                 -30                 -25

Arg Leu Val Lys Arg Lys Pro Pro Ser Phe Phe Gly Ala Ser Phe Leu
        -20                 -15                 -10

Met Gly Ser Leu Gly Gly Met Gly Tyr Phe Ala Tyr Trp Tyr Leu Lys
-5                  1                   5                   10

Lys Lys Tyr Ile
        15

<210> SEQ ID NO 95
<211> LENGTH: 287
```

```
<212> TYPE: PRT
<213> ORGANISM: Homo Sapiens
<220> FEATURE:
<221> NAME/KEY: SIGNAL
<222> LOCATION: -26..-1

<400> SEQUENCE: 95

Met Gly Ile Gln Thr Ser Pro Val Leu Leu Ala Ser Leu Gly Val Gly
    -25                 -20                 -15

Leu Val Thr Leu Leu Gly Leu Ala Val Gly Ser Tyr Leu Val Arg Arg
-10                  -5                  1                   5

Ser Arg Arg Pro Gln Val Thr Leu Leu Asp Pro Asn Glu Lys Tyr Leu
                10                  15                  20

Leu Arg Leu Leu Asp Lys Thr Leu Ser Ala Arg Ser Pro Gly Lys His
                25                  30                  35

Ile Tyr Leu Ser Thr Arg Ile Asp Gly Ser Leu Val Ile Arg Pro Tyr
                40                  45                  50

Thr Pro Val Thr Ser Asp Glu Asp Gln Gly Tyr Val Asp Leu Val Ile
55                  60                  65                  70

Lys Val Tyr Leu Lys Gly Val His Pro Lys Phe Pro Glu Gly Gly Lys
                75                  80                  85

Met Ser Gln Tyr Leu Asp Ser Leu Lys Val Gly Asp Val Val Glu Phe
                90                  95                  100

Arg Gly Pro Ser Gly Leu Leu Thr Tyr Thr Gly Lys Gly His Phe Asn
                105                 110                 115

Ile Gln Pro Asn Lys Lys Ser Pro Pro Glu Pro Arg Val Ala Lys Lys
                120                 125                 130

Leu Gly Met Ile Ala Gly Gly Thr Gly Ile Thr Pro Met Leu Gln Leu
135                 140                 145                 150

Ile Arg Ala Ile Leu Lys Val Pro Glu Asp Pro Thr Gln Cys Phe Leu
                155                 160                 165

Leu Phe Ala Asn Gln Thr Glu Lys Asp Ile Ile Leu Arg Glu Asp Leu
                170                 175                 180

Glu Glu Leu Gln Ala Arg Tyr Pro Asn Arg Phe Lys Leu Trp Phe Thr
                185                 190                 195

Leu Asp His Pro Pro Lys Asp Trp Ala Tyr Ser Lys Gly Phe Val Thr
                200                 205                 210

Ala Asp Met Ile Arg Glu His Leu Pro Ala Pro Gly Asp Asp Val Leu
215                 220                 225                 230

Val Leu Leu Cys Gly Pro Pro Pro Met Val Gln Leu Ala Cys His Pro
                235                 240                 245

Asn Leu Asp Lys Leu Gly Tyr Ser Gln Lys Met Arg Phe Thr Tyr
                250                 255                 260

<210> SEQ ID NO 96
<211> LENGTH: 312
<212> TYPE: PRT
<213> ORGANISM: Homo Sapiens
<220> FEATURE:
<221> NAME/KEY: SIGNAL
<222> LOCATION: -25..-1

<400> SEQUENCE: 96

Met Ser Asp Leu Leu Leu Gly Leu Ile Gly Gly Leu Thr Leu Leu
    -25                 -20                 -15                 -10

Leu Leu Leu Thr Leu Leu Ala Phe Ala Gly Tyr Ser Gly Leu Leu Ala
                -5                  1                   5
```

```
Gly Val Glu Val Ser Ala Gly Ser Pro Pro Ile Arg Asn Val Thr Val
        10                  15                  20

Ala Tyr Lys Phe His Met Gly Leu Tyr Gly Glu Thr Gly Arg Leu Phe
    25                  30                  35

Thr Glu Ser Cys Ile Ser Pro Lys Leu Arg Ser Ile Ala Val Tyr Tyr
40                  45                  50                  55

Asp Asn Pro His Met Val Pro Pro Asp Lys Cys Arg Cys Ala Val Gly
                60                  65                  70

Ser Ile Leu Ser Glu Gly Glu Ser Pro Ser Pro Glu Leu Ile Asp
            75                  80                  85

Leu Tyr Gln Lys Phe Gly Phe Lys Val Phe Ser Phe Pro Ala Pro Ser
        90                  95                 100

His Val Val Thr Ala Thr Phe Pro Tyr Thr Thr Ile Leu Ser Ile Trp
       105                 110                 115

Leu Ala Thr Arg Arg Val His Pro Ala Leu Asp Thr Tyr Ile Lys Glu
120                 125                 130                 135

Arg Lys Leu Cys Ala Tyr Pro Arg Leu Glu Ile Tyr Gln Glu Asp Gln
                140                 145                 150

Ile His Phe Met Cys Pro Leu Ala Arg Gln Gly Asp Phe Tyr Val Pro
            155                 160                 165

Glu Met Lys Glu Thr Glu Trp Lys Trp Arg Gly Leu Val Glu Ala Ile
        170                 175                 180

Asp Thr Gln Val Asp Gly Thr Gly Ala Asp Thr Met Ser Asp Thr Ser
        185                 190                 195

Ser Val Ser Leu Glu Val Ser Pro Gly Ser Arg Glu Thr Ser Ala Ala
200                 205                 210                 215

Thr Leu Ser Pro Gly Ala Ser Ser Arg Gly Trp Asp Asp Gly Asp Thr
                220                 225                 230

Arg Ser Glu His Ser Tyr Ser Glu Ser Gly Ala Ser Gly Ser Ser Phe
            235                 240                 245

Glu Glu Leu Asp Leu Glu Gly Glu Gly Pro Leu Gly Glu Ser Arg Leu
        250                 255                 260

Asp Pro Gly Thr Glu Pro Leu Gly Thr Thr Lys Trp Leu Trp Glu Pro
    265                 270                 275

Thr Ala Pro Glu Lys Gly Lys Glu
280                 285

<210> SEQ ID NO 97
<211> LENGTH: 226
<212> TYPE: PRT
<213> ORGANISM: Homo Sapiens
<220> FEATURE:
<221> NAME/KEY: SIGNAL
<222> LOCATION: -29..-1

<400> SEQUENCE: 97

Met Glu Thr Val Val Ile Val Ala Ile Gly Val Leu Ala Thr Ile Phe
                -25                 -20                 -15

Leu Ala Ser Phe Ala Ala Leu Val Leu Val Cys Arg Gln Arg Tyr Cys
        -10                  -5                   1

Arg Pro Arg Asp Leu Leu Gln Arg Tyr Asp Ser Lys Pro Ile Val Asp
    5                   10                  15

Leu Ile Gly Ala Met Glu Thr Gln Ser Glu Pro Ser Glu Leu Glu Leu
20                  25                  30                  35

Asp Asp Val Val Ile Thr Asn Pro His Ile Glu Ala Ile Leu Glu Asn
            40                  45                  50
```

-continued

```
Glu Asp Trp Ile Glu Asp Ala Ser Gly Leu Met Ser His Cys Ile Ala
             55                  60                  65

Ile Leu Lys Ile Cys His Thr Leu Thr Glu Lys Leu Val Ala Met Thr
         70                  75                  80

Met Gly Ser Gly Ala Lys Met Lys Thr Ser Ala Ser Val Ser Asp Ile
 85                  90                  95

Ile Val Val Ala Lys Arg Ile Ser Pro Arg Val Asp Asp Val Val Lys
100                 105                 110                 115

Ser Met Tyr Pro Pro Leu Asp Pro Lys Leu Leu Asp Ala Arg Thr Thr
                120                 125                 130

Ala Leu Leu Leu Ser Val Ser His Leu Val Leu Val Thr Arg Asn Ala
            135                 140                 145

Cys His Leu Thr Gly Gly Leu Asp Trp Ile Asp Gln Ser Leu Ser Ala
                150                 155                 160

Ala Glu Glu His Leu Glu Val Leu Arg Glu Ala Ala Leu Ala Ser Glu
            165                 170                 175

Pro Asp Lys Gly Leu Pro Gly Pro Glu Gly Phe Leu Gln Glu Gln Ser
180                 185                 190                 195

Ala Ile

<210> SEQ ID NO 98
<211> LENGTH: 406
<212> TYPE: PRT
<213> ORGANISM: Homo Sapiens
<220> FEATURE:
<221> NAME/KEY: SIGNAL
<222> LOCATION: -35..-1

<400> SEQUENCE: 98

Met Arg Gly Ser Val Glu Cys Thr Trp Gly Trp Gly His Cys Ala Pro
-35                 -30                 -25                 -20

Ser Pro Leu Leu Leu Trp Thr Leu Leu Phe Ala Ala Pro Phe Gly
                -15                 -10                 -5

Leu Leu Gly Glu Lys Thr Arg Gln Val Ser Leu Glu Val Ile Pro Asn
  1                   5                  10

Trp Leu Gly Pro Leu Gln Asn Leu Leu His Ile Arg Ala Val Gly Thr
         15                  20                  25

Asn Ser Thr Leu His Tyr Val Trp Ser Ser Leu Gly Pro Leu Ala Val
 30                  35                  40                  45

Val Met Val Ala Thr Asn Thr Pro His Ser Thr Leu Ser Val Asn Trp
             50                  55                  60

Ser Leu Leu Leu Ser Pro Glu Pro Asp Gly Gly Leu Met Val Leu Pro
            65                  70                  75

Lys Asp Ser Ile Gln Phe Ser Ser Ala Leu Val Phe Thr Arg Leu Leu
         80                  85                  90

Glu Phe Asp Ser Thr Asn Val Ser Asp Thr Ala Ala Lys Pro Leu Gly
     95                 100                 105

Arg Pro Tyr Pro Pro Tyr Ser Leu Ala Asp Phe Ser Trp Asn Asn Ile
110                 115                 120                 125

Thr Asp Ser Leu Asp Pro Ala Thr Leu Ser Ala Thr Phe Gln Gly His
                130                 135                 140

Pro Met Asn Asp Pro Thr Arg Thr Phe Ala Asn Gly Ser Leu Ala Phe
            145                 150                 155

Arg Val Gln Ala Phe Ser Arg Ser Ser Arg Pro Ala Gln Pro Pro Arg
                160                 165                 170
```

-continued

```
Leu Leu His Thr Ala Asp Thr Cys Gln Leu Glu Val Ala Leu Ile Gly
    175                 180                 185

Ala Ser Pro Arg Gly Asn Arg Ser Leu Phe Gly Leu Glu Val Ala Thr
190                 195                 200                 205

Leu Gly Gln Gly Pro Asp Cys Pro Ser Met Gln Glu Gln His Ser Ile
                    210                 215                 220

Asp Asp Glu Tyr Ala Pro Ala Val Phe Gln Leu Asp Gln Leu Leu Trp
                225                 230                 235

Gly Ser Leu Pro Ser Gly Phe Ala Gln Trp Arg Pro Val Ala Tyr Ser
                240                 245                 250

Gln Lys Pro Gly Gly Arg Glu Ser Ala Leu Pro Cys Gln Ala Ser Pro
                255                 260                 265

Leu His Pro Ala Leu Ala Tyr Ser Leu Pro Gln Ser Pro Ile Val Arg
270                 275                 280                 285

Ala Phe Phe Gly Ser Gln Asn Asn Phe Cys Ala Phe Asn Leu Thr Phe
                    290                 295                 300

Gly Ala Ser Thr Gly Pro Gly Tyr Trp Asp Gln His Tyr Leu Ser Trp
                305                 310                 315

Ser Met Leu Leu Gly Val Gly Phe Pro Pro Val Asp Gly Leu Ser Pro
                320                 325                 330

Leu Val Leu Gly Ile Met Ala Val Ala Leu Gly Ala Pro Gly Leu Met
                335                 340                 345

Leu Leu Gly Gly Gly Leu Val Leu Leu Leu His His Lys Lys Tyr Ser
350                 355                 360                 365

Glu Tyr Gln Ser Ile Asn
                370

<210> SEQ ID NO 99
<211> LENGTH: 120
<212> TYPE: PRT
<213> ORGANISM: Homo Sapiens
<220> FEATURE:
<221> NAME/KEY: SIGNAL
<222> LOCATION: -57..-1

<400> SEQUENCE: 99

Met Met Pro Ser Arg Thr Asn Leu Ala Thr Gly Ile Pro Ser Ser Lys
        -55                 -50                 -45

Val Lys Tyr Ser Arg Leu Ser Ser Thr Asp Asp Gly Tyr Ile Asp Leu
    -40                 -35                 -30

Gln Phe Lys Lys Thr Pro Pro Lys Ile Pro Tyr Lys Ala Ile Ala Leu
-25                 -20                 -15                 -10

Ala Thr Val Leu Phe Leu Ile Gly Ala Phe Leu Ile Ile Ile Gly Ser
                -5                   1                   5

Leu Leu Leu Ser Gly Tyr Ile Ser Lys Gly Gly Ala Asp Arg Ala Val
                10                  15                  20

Pro Val Leu Ile Ile Gly Ile Leu Val Phe Leu Pro Gly Phe Tyr His
                25                  30                  35

Leu Arg Ile Ala Tyr Tyr Ala Ser Lys Gly Tyr Arg Gly Tyr Ser Tyr
40                  45                  50                  55

Asp Asp Ile Pro Asp Phe Asp Asp
                60

<210> SEQ ID NO 100
<211> LENGTH: 210
<212> TYPE: PRT
```

```
<213> ORGANISM: Homo Sapiens
<220> FEATURE:
<221> NAME/KEY: SIGNAL
<222> LOCATION: -36..-1

<400> SEQUENCE: 100

Met Ala Leu Pro Gln Met Cys Asp Gly Ser His Leu Ala Ser Thr Leu
    -35                 -30                 -25
Arg Tyr Cys Met Thr Val Ser Gly Thr Val Val Leu Val Ala Gly Thr
-20                 -15                 -10                  -5
Leu Cys Phe Ala Trp Trp Ser Glu Gly Asp Ala Thr Ala Gln Pro Gly
                  1               5                  10
Gln Leu Ala Pro Pro Thr Glu Tyr Pro Val Pro Glu Gly Pro Ser Pro
             15                  20                  25
Leu Leu Arg Ser Val Ser Phe Val Cys Cys Gly Ala Gly Gly Leu Leu
        30                  35                  40
Leu Leu Ile Gly Leu Leu Trp Ser Val Lys Ala Ser Ile Pro Gly Pro
45                  50                  55                  60
Pro Arg Trp Asp Pro Tyr His Leu Ser Arg Asp Leu Tyr Tyr Leu Thr
                65                  70                  75
Val Glu Ser Ser Glu Lys Glu Ser Cys Arg Thr Pro Lys Val Val Asp
                 80                  85                  90
Ile Pro Thr Tyr Glu Glu Ala Val Ser Phe Pro Val Ala Glu Gly Pro
             95                 100                 105
Pro Thr Pro Pro Ala Tyr Pro Thr Glu Glu Ala Leu Glu Pro Ser Gly
         110                 115                 120
Ser Arg Asp Ala Leu Leu Ser Thr Gln Pro Ala Trp Pro Pro Pro Ser
125                 130                 135                 140
Tyr Glu Ser Ile Ser Leu Ala Leu Asp Ala Val Ser Ala Glu Thr Thr
                145                 150                 155
Pro Ser Ala Thr Arg Ser Cys Ser Gly Leu Val Gln Thr Ala Arg Gly
            160                 165                 170
Gly Ser

<210> SEQ ID NO 101
<211> LENGTH: 251
<212> TYPE: PRT
<213> ORGANISM: Homo Sapiens
<220> FEATURE:
<221> NAME/KEY: SIGNAL
<222> LOCATION: -243..-1

<400> SEQUENCE: 101

Met Ala His Arg Leu Gln Ile Arg Leu Leu Thr Trp Asp Val Lys Asp
            -240                -235                -230
Thr Leu Leu Arg Leu Arg His Pro Leu Gly Glu Ala Tyr Ala Thr Lys
        -225                -220                -215
Ala Arg Ala His Gly Leu Glu Val Glu Pro Ser Ala Leu Glu Gln Gly
    -210                -205                -200
Phe Arg Gln Ala Tyr Arg Ala Gln Ser His Ser Phe Pro Asn Tyr Gly
-195                -190                -185                -180
Leu Ser His Gly Leu Thr Ser Arg Gln Trp Trp Leu Asp Val Val Leu
                -175                -170                -165
Gln Thr Phe His Leu Ala Gly Val Gln Asp Ala Gln Ala Val Ala Pro
            -160                -155                -150
Ile Ala Glu Gln Leu Tyr Lys Asp Phe Ser His Pro Cys Thr Trp Gln
        -145                -140                -135
```

```
Val Leu Asp Gly Ala Glu Asp Thr Leu Arg Glu Cys Arg Thr Arg Gly
    -130             -125                 -120

Leu Arg Leu Ala Val Ile Ser Asn Phe Asp Arg Arg Leu Glu Gly Ile
-115             -110             -105                 -100

Leu Glu Gly Leu Gly Leu Arg Glu His Phe Asp Phe Val Leu Thr Ser
             -95                  -90                  -85

Glu Ala Ala Gly Trp Pro Lys Pro Asp Pro Arg Ile Phe Gln Glu Ala
             -80                  -75                  -70

Leu Arg Leu Ala His Met Glu Pro Val Val Ala Ala His Val Gly Asp
            -65                  -60                  -55

Asn Tyr Leu Cys Asp Tyr Gln Gly Pro Arg Ala Val Gly Met His Ser
    -50              -45                 -40

Phe Leu Val Val Gly Pro Gln Ala Leu Asp Pro Val Val Arg Asp Ser
-35              -30                  -25                  -20

Val Pro Lys Glu His Ile Leu Pro Ser Leu Ala His Leu Leu Pro Ala
             -15                  -10                  -5

Leu Asp Cys Leu Glu Gly Ser Thr Pro Gly Leu
  1                  5

<210> SEQ ID NO 102
<211> LENGTH: 126
<212> TYPE: PRT
<213> ORGANISM: Homo Sapiens
<220> FEATURE:
<221> NAME/KEY: SIGNAL
<222> LOCATION: -24..-1

<400> SEQUENCE: 102

Met Asp Lys Ser Leu Leu Glu Leu Pro Ile Leu Leu Cys Cys Phe
             -20                  -15                  -10

Arg Ala Leu Ser Gly Ser Leu Ser Met Arg Asn Asp Ala Val Asn Glu
            -5                    1                   5

Ile Val Ala Val Lys Asn Asn Phe Pro Val Ile Glu Ile Ile Gln Cys
 10              15                  20

Arg Met Cys His Leu Gln Phe Pro Gly Glu Lys Cys Ser Arg Gly Arg
 25              30                  35                      40

Gly Ile Cys Thr Ala Thr Thr Glu Glu Ala Cys Met Val Gly Arg Met
             45                  50                      55

Phe Lys Arg Asp Gly Asn Pro Trp Leu Thr Phe Met Gly Cys Leu Lys
             60                  65                  70

Asn Cys Ala Asp Val Lys Gly Ile Arg Trp Ser Val Tyr Leu Val Asn
             75                  80                  85

Phe Arg Cys Cys Arg Ser His Asp Leu Cys Asn Glu Asp Leu
 90              95                  100

<210> SEQ ID NO 103
<211> LENGTH: 133
<212> TYPE: PRT
<213> ORGANISM: Homo Sapiens
<220> FEATURE:
<221> NAME/KEY: SIGNAL
<222> LOCATION: -44..-1

<400> SEQUENCE: 103

Met Asp Arg Arg Ala Thr Ser Phe Pro Pro Leu Pro Ala Lys Glu Arg
             -40                  -35                  -30

Arg Ala Gly Ile Ser Ser Ala Leu Pro Cys Pro Pro Thr Met Ser Leu
         -25                  -20                  -15
```

-continued

Ser Asp Ser Leu Trp Ser Pro His Cys Ser Trp Ser Glu Arg Pro His
        -10              -5                    1

Ser Phe Ser His Trp Arg Gln Pro Arg Met Gly Ser Ser Gly Gly Ser
 5               10              15                      20

Leu Asp Tyr Val Ser Phe Lys His Trp Ile His Ser Ser Arg Ser Lys
                25              30                  35

Gly Lys Ile Ala Ala Leu Glu Ala Gly Leu Phe Ile Ser Cys Leu Gly
            40              45              50

Asp Ala Pro Arg Gly Leu Asn Ala Ser Gln Gly Asn Gln Arg Lys Asn
            55              60              65

Met Val Cys Phe Arg Gly Val Ala Ser Leu Ala Leu Pro Ser Leu
 70              75              80

Thr Pro Ser Cys Leu
 85

<210> SEQ ID NO 104
<211> LENGTH: 221
<212> TYPE: PRT
<213> ORGANISM: Homo Sapiens
<220> FEATURE:
<221> NAME/KEY: SIGNAL
<222> LOCATION: -28..-1

<400> SEQUENCE: 104

Met Glu Ala Gly Gly Phe Leu Asp Ser Leu Ile Tyr Gly Ala Cys Val
                -25             -20             -15

Val Phe Thr Leu Gly Met Phe Ser Ala Gly Leu Ser Asp Leu Arg His
        -10              -5                    1

Met Arg Met Thr Arg Ser Val Asp Asn Val Gln Phe Leu Pro Phe Leu
 5               10              15                      20

Thr Thr Glu Val Asn Asn Leu Gly Trp Leu Ser Tyr Gly Ala Leu Lys
                25              30                  35

Gly Asp Gly Ile Leu Ile Val Val Asn Thr Val Gly Ala Ala Leu Gln
            40              45              50

Thr Leu Tyr Ile Leu Ala Tyr Leu His Tyr Cys Pro Arg Lys Arg Val
            55              60              65

Val Leu Leu Gln Thr Ala Thr Leu Leu Gly Val Leu Leu Leu Gly Tyr
 70              75              80

Gly Tyr Phe Trp Leu Leu Val Pro Asn Pro Glu Ala Arg Leu Gln Gln
 85              90              95                      100

Leu Gly Leu Phe Cys Ser Val Phe Thr Ile Ser Met Tyr Leu Ser Pro
                105             110                 115

Leu Ala Asp Leu Ala Lys Val Ile Gln Thr Lys Ser Thr Gln Cys Leu
            120             125             130

Ser Tyr Pro Leu Thr Ile Ala Thr Leu Leu Thr Ser Ala Ser Trp Cys
            135             140             145

Leu Tyr Gly Phe Arg Leu Arg Asp Pro Tyr Ile Met Val Ser Asn Phe
 150             155             160

Pro Gly Ile Val Thr Ser Phe Ile Arg Phe Trp Leu Phe Trp Lys Tyr
 165             170             175                     180

Pro Gln Glu Gln Asp Arg Asn Tyr Trp Leu Leu Gln Thr
                185             190

<210> SEQ ID NO 105
<211> LENGTH: 352
<212> TYPE: PRT

```
<213> ORGANISM: Homo Sapiens
<220> FEATURE:
<221> NAME/KEY: SIGNAL
<222> LOCATION: -23..-1

<400> SEQUENCE: 105

Met Glu Ser Gly Gly Arg Pro Ser Leu Cys Gln Phe Ile Leu Leu Gly
            -20                 -15                 -10

Thr Thr Ser Val Val Thr Ala Ala Leu Tyr Ser Val Tyr Arg Gln Lys
         -5                   1               5

Ala Arg Val Ser Gln Glu Leu Lys Gly Ala Lys Lys Val His Leu Gly
 10                 15                  20                  25

Glu Asp Leu Lys Ser Ile Leu Ser Glu Ala Pro Gly Lys Cys Val Pro
                 30                  35                  40

Tyr Ala Val Ile Glu Gly Ala Val Arg Ser Val Lys Glu Thr Leu Asn
                 45                  50                  55

Ser Gln Phe Val Glu Asn Cys Lys Gly Val Ile Gln Arg Leu Thr Leu
             60                  65                  70

Gln Glu His Lys Met Val Trp Asn Arg Thr Thr His Leu Trp Asn Asp
 75                  80                  85

Cys Ser Lys Ile Ile His Gln Arg Thr Asn Thr Val Pro Phe Asp Leu
 90                  95                 100                 105

Val Pro His Glu Asp Gly Val Asp Val Ala Val Arg Val Leu Lys Pro
                110                 115                 120

Leu Asp Ser Val Asp Leu Gly Leu Glu Thr Val Tyr Glu Lys Phe His
                125                 130                 135

Pro Ser Ile Gln Ser Phe Thr Asp Val Ile Gly His Tyr Ile Ser Gly
                140                 145                 150

Glu Arg Pro Lys Gly Ile Gln Glu Thr Glu Glu Met Leu Lys Val Gly
    155                 160                 165

Ala Thr Leu Thr Gly Val Gly Glu Leu Val Leu Asp Asn Asn Ser Val
170                 175                 180                 185

Arg Leu Gln Pro Pro Lys Gln Gly Met Gln Tyr Tyr Leu Ser Ser Gln
                190                 195                 200

Asp Phe Asp Ser Leu Leu Gln Arg Gln Glu Ser Ser Val Arg Leu Trp
                205                 210                 215

Lys Val Leu Ala Leu Val Phe Gly Phe Ala Thr Cys Ala Thr Leu Phe
                220                 225                 230

Phe Ile Leu Arg Lys Gln Tyr Leu Gln Arg Gln Glu Arg Leu Arg Leu
235                 240                 245

Lys Gln Met Gln Glu Glu Phe Gln Glu His Glu Ala Gln Leu Leu Ser
250                 255                 260                 265

Arg Ala Lys Pro Glu Asp Arg Glu Ser Leu Lys Ser Ala Cys Val Val
                270                 275                 280

Cys Leu Ser Ser Phe Lys Ser Cys Val Phe Leu Glu Cys Gly His Val
                285                 290                 295

Cys Ser Cys Thr Glu Cys Tyr Arg Ala Leu Pro Glu Pro Lys Lys Cys
            300                 305                 310

Pro Ile Cys Arg Gln Ala Ile Thr Arg Val Ile Pro Leu Tyr Asn Ser
            315                 320                 325

<210> SEQ ID NO 106
<211> LENGTH: 385
<212> TYPE: PRT
<213> ORGANISM: Homo Sapiens
<220> FEATURE:
```

```
<221> NAME/KEY: SIGNAL
<222> LOCATION: -184..-1

<400> SEQUENCE: 106

Met Trp Thr Phe Ser Tyr Ile Gly Phe Pro Val Glu Leu Asn Thr Val
            -180                -175                -170

Tyr Phe Ile Gly Ala His Lys Ile Pro Asn Ala Asn Met Asn Glu Asp
            -165                -160                -155

Gly Pro Ser Met Ser Val Asn Phe Thr Ser Pro Gly Cys Leu Asp His
            -150                -145                -140

Ile Met Lys Tyr Lys Lys Cys Val Lys Ala Gly Ser Leu Trp Asp
            -135                -130                -125

Pro Asn Ile Thr Ala Cys Lys Lys Asn Glu Glu Thr Val Glu Val Asn
-120                -115                -110                -105

Phe Thr Thr Thr Pro Leu Gly Asn Arg Tyr Met Ala Leu Ile Gln His
                -100                 -95                 -90

Ser Thr Ile Ile Gly Phe Ser Gln Val Phe Glu Pro His Gln Lys Lys
                 -85                 -80                 -75

Gln Thr Arg Ala Ser Val Val Ile Pro Val Thr Gly Asp Ser Glu Gly
             -70                 -65                 -60

Ala Thr Val Gln Leu Thr Pro Tyr Phe Pro Thr Cys Gly Ser Asp Cys
             -55                 -50                 -45

Ile Arg His Lys Gly Thr Val Val Leu Cys Pro Gln Thr Gly Val Pro
-40                  -35                 -30                 -25

Phe Pro Leu Asp Asn Asn Lys Ser Lys Pro Gly Gly Trp Leu Pro Leu
                 -20                 -15                 -10

Leu Leu Leu Ser Leu Leu Val Ala Thr Trp Val Leu Val Ala Gly Ile
                  -5                   1                   5

Tyr Leu Met Trp Arg His Glu Arg Ile Lys Lys Thr Ser Phe Ser Thr
 10                  15                  20

Thr Thr Leu Leu Pro Pro Ile Lys Val Leu Val Val Tyr Pro Ser Glu
 25                  30                  35                  40

Ile Cys Phe His His Thr Ile Cys Tyr Phe Thr Glu Phe Leu Gln Asn
                  45                  50                  55

His Cys Arg Ser Glu Val Ile Leu Glu Lys Trp Gln Lys Lys Lys Ile
                  60                  65                  70

Ala Glu Met Gly Pro Val Gln Trp Leu Ala Thr Gln Lys Lys Ala Ala
                  75                  80                  85

Asp Lys Val Val Phe Leu Leu Ser Asn Asp Val Asn Ser Val Cys Asp
 90                  95                 100

Gly Thr Cys Gly Lys Ser Glu Gly Ser Pro Ser Glu Asn Ser Gln Asp
105                 110                 115                 120

Leu Phe Pro Leu Ala Phe Asn Leu Phe Cys Ser Asp Leu Arg Ser Gln
                 125                 130                 135

Ile His Leu His Lys Tyr Val Val Tyr Phe Arg Glu Ile Asp Thr
                 140                 145                 150

Lys Asp Asp Tyr Asn Ala Leu Ser Val Cys Pro Lys Tyr His Leu Met
                 155                 160                 165

Lys Asp Ala Thr Ala Phe Cys Ala Glu Leu Leu His Val Lys Gln Gln
                 170                 175                 180

Val Ser Ala Gly Lys Arg Ser Gln Ala Cys His Asp Gly Cys Cys Ser
185                 190                 195                 200

Leu
```

<210> SEQ ID NO 107
<211> LENGTH: 69
<212> TYPE: PRT
<213> ORGANISM: Homo Sapiens
<220> FEATURE:
<221> NAME/KEY: SIGNAL
<222> LOCATION: -23..-1

<400> SEQUENCE: 107

Met Asn Leu Met Trp Thr Leu Leu Phe Leu Leu Leu Asp Val Thr
            -20             -15                 -10

Val Phe Ile Pro Ala Leu Pro Phe Ser Thr Arg His Ile Asp Asn Pro
        -5              1               5

Arg Ser Trp Val Pro Arg Gly His His Arg Tyr Cys Asp Val Met Met
10              15              20              25

Arg Arg Arg Trp Leu Ile Tyr Arg Gly Lys Cys Glu Gln Ile His Thr
            30              35              40

Phe Ile His Arg Ile
            45

<210> SEQ ID NO 108
<211> LENGTH: 108
<212> TYPE: PRT
<213> ORGANISM: Homo Sapiens
<220> FEATURE:
<221> NAME/KEY: SIGNAL
<222> LOCATION: -49..-1

<400> SEQUENCE: 108

Met Asn Lys Thr His Lys Asp Cys Ser Ser Pro Gln Tyr Ser Ile Tyr
            -45             -40             -35

Asn Ile Leu Asn Glu Leu Pro Thr Arg Pro Ile Ile Leu Ser Cys Ser
            -30             -25             -20

Gln Ile Ser Cys Leu Leu Leu Val Ser Thr Trp Ser Ala Asp Leu Met
            -15             -10             -5

Ser Tyr Arg Pro Val Thr Lys Pro Ser Gln Arg Cys Thr Ser Pro Ala
1               5               10              15

Gln Ser Met Thr Val Asn Leu Thr Lys Asp Val Gly Phe Tyr Glu Asp
            20              25              30

Thr Gln Ser Ile Arg Ile Thr Leu Ser Glu Ile Ser Gln Ala Gln Lys
            35              40              45

Asp Thr Tyr Phe Ile Ile Ser Cys Ile Cys Gly Ile
            50              55

<210> SEQ ID NO 109
<211> LENGTH: 108
<212> TYPE: PRT
<213> ORGANISM: Homo Sapiens
<220> FEATURE:
<221> NAME/KEY: SIGNAL
<222> LOCATION: -28..-1

<400> SEQUENCE: 109

Met Tyr Phe His Phe Leu Gly Ala Gly Ala Ile Leu Ile Pro Arg Leu
            -25             -20             -15

Asp Ile Val Ile Ser Phe Val Gly Ala Val Ser Ser Ser Thr Leu Ala
            -10             -5              1

Leu Ile Leu Pro Pro Leu Val Glu Ile Leu Thr Phe Ser Lys Glu His
5               10              15              20

Tyr Asn Ile Trp Met Val Leu Lys Asn Ile Ser Ile Ala Phe Thr Gly

```
                    25                  30                  35
Val Val Gly Phe Leu Leu Gly Thr Tyr Ile Thr Val Glu Glu Ile Ile
                40                  45                  50

Tyr Pro Thr Pro Lys Val Val Ala Gly Thr Pro Gln Ser Pro Phe Leu
            55                  60                  65

Asn Leu Asn Ser Thr Cys Leu Thr Ser Gly Leu Lys
        70                  75                  80

<210> SEQ ID NO 110
<211> LENGTH: 125
<212> TYPE: PRT
<213> ORGANISM: Homo Sapiens
<220> FEATURE:
<221> NAME/KEY: SIGNAL
<222> LOCATION: -37..-1

<400> SEQUENCE: 110

Met Val Cys Glu Asp Ala Pro Ser Phe Gln Met Ala Trp Glu Ser Gln
        -35                 -30                 -25

Met Ala Trp Glu Arg Gly Pro Ala Leu Leu Cys Cys Val Leu Ser Ala
    -20                 -15                 -10

Ser Gln Leu Ser Ser Gln Asp Gln Asp Pro Leu Gly His Ile Lys Ser
-5                   1                   5                   10

Leu Leu Tyr Pro Phe Gly Phe Pro Val Glu Leu Pro Arg Pro Gly Pro
            15                  20                  25

Thr Gly Ala Tyr Lys Lys Val Lys Asn Gln Asn Gln Thr Thr Ser Ser
        30                  35                  40

Glu Leu Leu Arg Lys Gln Thr Ser His Phe Asn Gln Arg Gly His Arg
    45                  50                  55

Ala Arg Ser Lys Leu Leu Ala Ser Arg Gln Ile Pro Asp Arg Thr Phe
60                  65                  70                  75

Lys Cys Gly Lys Trp Leu Pro Gln Val Pro Ser Pro Val
                80                  85

<210> SEQ ID NO 111
<211> LENGTH: 169
<212> TYPE: PRT
<213> ORGANISM: Homo Sapiens
<220> FEATURE:
<221> NAME/KEY: SIGNAL
<222> LOCATION: -88..-1

<400> SEQUENCE: 111

Met Lys Gly Gly Ile Ser Asn Val Trp Phe Asp Arg Phe Lys Ile Thr
            -85                 -80                 -75

Asn Asp Cys Pro Glu His Leu Glu Ser Ile Asp Val Met Cys Gln Val
        -70                 -65                 -60

Leu Thr Asp Leu Ile Asp Glu Glu Val Lys Ser Gly Ile Lys Lys Asn
    -55                 -50                 -45

Arg Ile Leu Ile Gly Gly Phe Ser Met Gly Gly Cys Met Ala Met His
-40                 -35                 -30                 -25

Leu Ala Tyr Arg Asn His Gln Asp Val Ala Gly Val Phe Ala Leu Ser
                -20                 -15                 -10

Ser Phe Leu Asn Lys Ala Ser Ala Val Tyr Gln Ala Leu Gln Lys Ser
            -5                  1                   5

Asn Gly Val Leu Pro Glu Leu Phe Gln Cys His Gly Thr Ala Asp Glu
        10                  15                  20

Leu Val Leu His Ser Trp Ala Glu Glu Thr Asn Ser Met Leu Lys Ser
```

-continued

```
                25                  30                  35                  40
Leu Gly Val Thr Thr Lys Phe His Ser Phe Pro Asn Val Tyr His Glu
                    45                  50                  55

Leu Ser Lys Thr Glu Leu Asp Ile Leu Lys Leu Trp Ile Leu Thr Lys
            60                  65                  70

Leu Pro Gly Glu Met Glu Lys Gln Lys
        75                  80

<210> SEQ ID NO 112
<211> LENGTH: 82
<212> TYPE: PRT
<213> ORGANISM: Homo Sapiens
<220> FEATURE:
<221> NAME/KEY: SIGNAL
<222> LOCATION: -56..-1

<400> SEQUENCE: 112

Met Lys Ala Val Trp His Phe Cys Leu Ser His Lys Ser Ser Leu Val
    -55                 -50                 -45

Ile Val Leu Lys Thr Ala Gly Trp Ile Pro Gln Ala Gly Thr Leu Ile
-40                 -35                 -30                 -25

Pro Gly Ser Arg Glu Glu Ser Arg Ser Asp Ser Gln Met Ile Met Leu
                -20                 -15                 -10

Val Cys Phe Asn Leu Ser Arg Gly Cys Leu Lys Val Phe Ile Ile
                -5                  1                   5

Ser Val Leu Pro Asp Pro Glu Thr Ile Leu Leu Gly Lys Thr Val Gly
        10                  15                  20

Ile Ala
25

<210> SEQ ID NO 113
<211> LENGTH: 251
<212> TYPE: PRT
<213> ORGANISM: Homo Sapiens
<220> FEATURE:
<221> NAME/KEY: SIGNAL
<222> LOCATION: -20..-1

<400> SEQUENCE: 113

Met Asp Lys Val Gln Ser Gly Phe Leu Ile Leu Phe Leu Phe Leu Met
-20                 -15                 -10                 -5

Glu Cys Gln Leu His Leu Cys Leu Pro Tyr Ala Asp Gly Leu His Pro
                    1                   5                   10

Thr Gly Asn Ile Thr Gly Leu Pro Gly Ser Phe Asn His Trp Phe Tyr
            15                  20                  25

Val Thr Gln Gly Glu Leu Lys Ser Cys Phe Arg Gly Asp Lys Lys Lys
        30                  35                  40

Val Ile Thr Phe His Arg Lys Lys Phe Ser Phe Gln Gly Ser Lys Arg
45                  50                  55                  60

Ser Gln Pro Pro Arg Asn Ile Thr Lys Glu Pro Lys Val Phe His
                65                  70                  75

Lys Thr Gln Leu Pro Gly Ile Gln Gly Ala Ala Ser Arg Ser Thr Ala
            80                  85                  90

Ala Ser Pro Thr Asn Pro Met Lys Phe Leu Arg Asn Lys Ala Ile Ile
        95                  100                 105

Arg His Arg Pro Ala Leu Val Lys Val Ile Leu Ile Ser Ser Val Ala
    110                 115                 120

Phe Ser Ile Ala Leu Ile Cys Gly Met Ala Ile Ser Tyr Met Ile Tyr
```

-continued

```
                125                 130                 135                 140
Arg Leu Ala Gln Ala Glu Glu Arg Gln Gln Leu Glu Ser Leu Tyr Lys
                145                 150                 155
Asn Leu Arg Ile Pro Leu Leu Gly Asp Glu Glu Gly Ser Glu Asp
                160                 165                 170
Glu Gly Glu Ser Thr His Leu Leu Pro Lys Asn Glu Asn Glu Leu Glu
            175                 180                 185
Lys Phe Ile His Ser Val Ile Ile Ser Lys Arg Ser Lys Asn Ile Lys
            190                 195                 200
Lys Lys Leu Lys Glu Glu Gln Asn Ser Val Thr Glu Asn Lys Thr Lys
205                 210                 215                 220
Asn Ala Ser His Asn Gly Lys Met Glu Asp Leu
                225                 230
```

<210> SEQ ID NO 114
<211> LENGTH: 305
<212> TYPE: PRT
<213> ORGANISM: Homo Sapiens
<220> FEATURE:
<221> NAME/KEY: SIGNAL
<222> LOCATION: -34..-1

<400> SEQUENCE: 114

```
Met Ser Phe Leu Arg Ile Thr Pro Ser Thr His Ser Ser Val Ser Ser
                -30                 -25                 -20
Gly Leu Leu Arg Leu Ser Ile Phe Leu Leu Leu Ser Phe Pro Asp Ser
            -15                 -10                 -5
Asn Gly Lys Ala Ile Trp Thr Ala His Leu Asn Ile Thr Phe Gln Val
        1                   5                   10
Gly Asn Glu Ile Thr Ser Glu Leu Gly Glu Ser Gly Val Phe Gly Asn
15                  20                  25                  30
His Ser Pro Leu Glu Arg Val Ser Gly Val Ala Leu Pro Glu Glu
                35                  40                  45
Trp Asn Gln Asn Ala Cys His Pro Leu Thr Asn Phe Ser Arg Pro Lys
                50                  55                  60
Gln Ala Asp Ser Trp Leu Ala Leu Ile Glu Arg Gly Gly Cys Thr Phe
            65                  70                  75
Thr His Lys Ile Asn Val Ala Ala Glu Lys Gly Ala Asn Gly Val Ile
        80                  85                  90
Ile Tyr Asn Tyr Gln Gly Thr Gly Ser Lys Val Phe Pro Met Ser His
95                  100                 105                 110
Gln Gly Thr Glu Asn Ile Val Ala Val Met Ile Ser Asn Leu Lys Gly
                115                 120                 125
Met Glu Ile Leu His Ser Ile Gln Lys Gly Val Tyr Val Thr Val Ile
                130                 135                 140
Ile Glu Val Gly Arg Met His Met Gln Trp Val Ser His Tyr Ile Met
            145                 150                 155
Tyr Leu Phe Thr Phe Leu Ala Ala Thr Ile Ala Tyr Phe Tyr Leu Asp
            160                 165                 170
Cys Val Trp Arg Leu Thr Pro Arg Val Pro Asn Ser Phe Thr Arg Arg
175                 180                 185                 190
Arg Ser Gln Ile Lys Thr Asp Val Lys Lys Ala Ile Asp Gln Leu Gln
                195                 200                 205
Leu Arg Val Leu Lys Glu Gly Asp Glu Glu Leu Asp Leu Asn Glu Asp
            210                 215                 220
```

-continued

```
Asn Cys Val Val Cys Phe Asp Thr Tyr Lys Pro Gln Asp Val Val Arg
        225                 230                 235

Ile Leu Thr Cys Lys His Phe Phe His Lys Ala Cys Ile Asp Pro Trp
        240                 245                 250

Leu Leu Ala His Arg Thr Cys Pro Met Cys Lys Cys Asp Ile Leu Lys
255                 260                 265                 270

Thr

<210> SEQ ID NO 115
<211> LENGTH: 61
<212> TYPE: PRT
<213> ORGANISM: Homo Sapiens
<220> FEATURE:
<221> NAME/KEY: SIGNAL
<222> LOCATION: -42..-1

<400> SEQUENCE: 115

Met Thr Asp Leu Asp Leu Met Ile Asn Phe Thr Phe Pro Ile Gln Trp
        -40                 -35                 -30

Val Asn Gln Asn Arg Met Ala Tyr Tyr Ser Leu Lys Pro Leu Leu Pro
        -25                 -20                 -15

Cys Ser Ser Val Leu Thr Cys Gly Gln Ala Ser Gln Asp Leu Leu Thr
-10                  -5                  1                   5

Ser Ala Thr Ser Val Thr Gly Met Glu Lys Ile Glu Ala
                10                  15

<210> SEQ ID NO 116
<211> LENGTH: 113
<212> TYPE: PRT
<213> ORGANISM: Homo Sapiens
<220> FEATURE:
<221> NAME/KEY: SIGNAL
<222> LOCATION: -15..-1

<400> SEQUENCE: 116

Met Asn Phe Tyr Leu Leu Leu Ala Ser Ser Ile Leu Cys Ala Leu Ile
-15                 -10                  -5                  1

Val Phe Trp Lys Tyr Arg Arg Phe Gln Arg Asn Thr Gly Glu Met Ser
         5                  10                  15

Ser Asn Ser Thr Ala Leu Ala Leu Val Arg Pro Ser Ser Ser Gly Leu
        20                  25                  30

Ile Asn Ser Asn Thr Asp Asn Asn Leu Ala Val Tyr Asp Leu Ser Arg
        35                  40                  45

Asp Ile Leu Asn Asn Phe Pro His Ser Ile Ala Arg Gln Lys Arg Ile
50                  55                  60                  65

Leu Val Asn Leu Ser Met Val Glu Asn Lys Leu Val Glu Leu Glu His
                70                  75                  80

Thr Leu Leu Ser Lys Gly Phe Arg Gly Ala Ser Pro His Arg Lys Ser
                85                  90                  95

Thr

<210> SEQ ID NO 117
<211> LENGTH: 101
<212> TYPE: PRT
<213> ORGANISM: Homo Sapiens
<220> FEATURE:
<221> NAME/KEY: SIGNAL
<222> LOCATION: -30..-1

<400> SEQUENCE: 117
```

```
Met Glu Arg Pro Arg Ser Pro Gln Cys Ser Ala Pro Ala Ser Ala Ser
-30                 -25                 -20                 -15

Ala Ser Val Thr Leu Ala Gln Leu Leu Gln Leu Val Gln Gln Gly Gln
            -10                  -5                       1

Glu Leu Pro Gly Leu Glu Lys Arg His Ile Ala Ala Ile His Gly Glu
             5                  10                  15

Pro Thr Ala Ser Arg Leu Pro Arg Arg Pro Lys Pro Trp Glu Ala Ala
        20                  25                  30

Ala Leu Ala Glu Ser Leu Pro Pro Thr Leu Arg Ile Gly Thr Ala
35                  40                  45                  50

Pro Ala Glu Pro Gly Leu Val Glu Ala Ala Thr Ala Pro Ser Ser Trp
                55                  60                  65

His Thr Val Gly Pro
                70

<210> SEQ ID NO 118
<211> LENGTH: 97
<212> TYPE: PRT
<213> ORGANISM: Homo Sapiens
<220> FEATURE:
<221> NAME/KEY: SIGNAL
<222> LOCATION: -90..-1
<220> FEATURE:
<221> NAME/KEY: UNSURE
<222> LOCATION: -39
<223> OTHER INFORMATION: Xaa = His,Gln

<400> SEQUENCE: 118

Met Asn Gln Glu Asn Pro Pro Tyr Pro Gly Pro Gly Pro Thr Ala
-90                 -85                 -80                 -75

Pro Tyr Pro Pro Tyr Pro Pro Gln Pro Met Gly Pro Gly Pro Met Gly
                -70                 -65                 -60

Gly Pro Tyr Pro Pro Pro Gln Gly Tyr Pro Tyr Gln Gly Tyr Leu Gln
                -55                 -50                 -45

Tyr Gly Trp Xaa Gly Gly Pro Gln Glu Pro Pro Lys Thr Thr Val Tyr
        -40                 -35                 -30

Val Val Glu Asp Gln Arg Arg Asp Glu Leu Gly Pro Ser Thr Cys Leu
        -25                 -20                 -15

Thr Ala Cys Trp Thr Ala Leu Cys Cys Cys Cys Leu Trp Asp Met Leu
-10                 -5                   1                   5

Thr

<210> SEQ ID NO 119
<211> LENGTH: 101
<212> TYPE: PRT
<213> ORGANISM: Homo Sapiens
<220> FEATURE:
<221> NAME/KEY: SIGNAL
<222> LOCATION: -25..-1

<400> SEQUENCE: 119

Met Val Asp Arg Glu Leu Ala Asp Ile His Glu Asp Ala Lys Thr Cys
-25                 -20                 -15                 -10

Leu Val Leu Cys Ser Arg Val Leu Ser Val Ile Ser Val Lys Glu Ile
            -5                   1                   5

Lys Thr Gln Leu Ser Leu Gly Arg His Pro Ile Ile Ser Asn Trp Phe
            10                  15                  20

Asp Tyr Ile Pro Ser Thr Arg Tyr Lys Asp Pro Cys Glu Leu Leu His
        25                  30                  35
```

```
Leu Cys Arg Leu Thr Ile Arg Asn Gln Leu Leu Thr Asn Asn Met Leu
 40              45                  50                  55

Pro Asp Gly Ile Phe Ser Leu Leu Ile Pro Ala Arg Leu Gln Asn Tyr
                 60                  65                  70

Leu Asn Leu Glu Ile
             75

<210> SEQ ID NO 120
<211> LENGTH: 152
<212> TYPE: PRT
<213> ORGANISM: Homo Sapiens
<220> FEATURE:
<221> NAME/KEY: SIGNAL
<222> LOCATION: -101..-1

<400> SEQUENCE: 120

Met Asp Asn Val Gln Pro Lys Ile Lys His Arg Pro Phe Cys Phe Ser
    -100                -95                 -90

Val Lys Gly His Val Lys Met Leu Arg Leu Ala Leu Thr Val Thr Ser
-85                 -80                 -75                 -70

Met Thr Phe Phe Ile Ile Ala Gln Ala Pro Glu Pro Tyr Ile Val Ile
                -65                 -60                 -55

Thr Gly Phe Glu Val Thr Val Ile Leu Phe Phe Ile Leu Leu Tyr Val
            -50                 -45                 -40

Leu Arg Leu Asp Arg Leu Met Lys Trp Leu Phe Trp Pro Leu Leu Asp
        -35                 -30                 -25

Ile Ile Asn Ser Leu Val Thr Thr Val Phe Met Leu Ile Val Ser Val
    -20                 -15                 -10

Leu Ala Leu Ile Pro Glu Thr Thr Thr Leu Thr Val Gly Gly Gly Val
-5                   1                   5                  10

Phe Ala Leu Val Thr Ala Val Cys Cys Leu Ala Asp Gly Ala Leu Ile
                15                  20                  25

Tyr Arg Lys Leu Leu Phe Asn Pro Ser Gly Pro Tyr Gln Lys Lys Pro
            30                  35                  40

Val His Glu Lys Lys Glu Val Leu
     45                  50

<210> SEQ ID NO 121
<211> LENGTH: 209
<212> TYPE: PRT
<213> ORGANISM: Homo Sapiens
<220> FEATURE:
<221> NAME/KEY: SIGNAL
<222> LOCATION: -86..-1

<400> SEQUENCE: 121

Met Leu Ser Pro Thr Phe Val Leu Trp Asp Val Gly Tyr Pro Leu Tyr
    -85                 -80                 -75

Thr Tyr Gly Ser Ile Cys Ile Ile Ala Leu Ile Ile Trp Gln Val Lys
-70                 -65                 -60                 -55

Lys Ser Cys Gln Lys Leu Ser Leu Val Pro Asn Arg Ser Cys Cys Arg
                -50                 -45                 -40

Cys His Arg Arg Val Gln Gln Lys Ser Gly Asp Arg Thr Ser Arg Ala
            -35                 -30                 -25

Arg Arg Thr Ser Gln Glu Glu Ala Glu Lys Leu Trp Lys Leu Leu Phe
        -20                 -15                 -10

Leu Met Lys Ser Gln Gly Trp Ile Pro Gln Glu Gly Ser Val Arg Arg
-5                   1                   5                  10
```

-continued

```
Ile Leu Cys Ala Asp Pro Cys Gln Ile Cys Asn Val Met Ala Leu
            15                  20                  25

Glu Ile Lys Gln Leu Leu Ala Glu Ala Pro Glu Val Gly Leu Asp Asn
            30                  35                  40

Lys Met Lys Leu Phe Leu His Trp Ile Asn Pro Glu Met Lys Asp Arg
            45                  50                  55

Arg His Glu Glu Ser Ile Leu Leu Ser Lys Ala Glu Thr Val Thr Gln
 60                  65                  70

Asp Arg Thr Lys Asn Ile Glu Lys Ser Pro Thr Val Thr Lys Asp His
 75                  80                  85                  90

Val Trp Gly Ala Thr Thr Gln Lys Thr Thr Glu Asp Pro Glu Ala Gln
                    95                  100                 105

Pro Pro Ser Thr Glu Glu Glu Gly Leu Ile Phe Cys Asp Ala Pro Ser
                110                 115                 120

Ala

<210> SEQ ID NO 122
<211> LENGTH: 89
<212> TYPE: PRT
<213> ORGANISM: Homo Sapiens
<220> FEATURE:
<221> NAME/KEY: SIGNAL
<222> LOCATION: -21..-1

<400> SEQUENCE: 122

Met Gly Ser Cys Ser Gly Arg Cys Ala Leu Val Val Leu Cys Ala Phe
       -20                 -15                 -10

Gln Leu Val Ala Ala Leu Glu Arg Gln Val Phe Asp Phe Leu Gly Tyr
-5                    1                   5                  10

Gln Trp Ala Pro Ile Leu Ala Asn Phe Val His Ile Ile Val Ile
                15                  20                  25

Leu Gly Leu Phe Gly Thr Ile Gln Tyr Arg Leu Arg Tyr Val Met Cys
            30                  35                  40

Thr Arg Cys Gly Gln Pro Ser Gly Ser Pro Gly Thr Ser Ser Ser Ser
            45                  50                  55

Ala Ser Thr Trp Lys Ser Val Ala Ser
60                  65

<210> SEQ ID NO 123
<211> LENGTH: 66
<212> TYPE: PRT
<213> ORGANISM: Homo Sapiens
<220> FEATURE:
<221> NAME/KEY: SIGNAL
<222> LOCATION: -19..-1

<400> SEQUENCE: 123

Met Lys Pro Leu Leu Val Val Phe Val Phe Leu Phe Leu Trp Asp Pro
                -15                 -10                 -5

Val Leu Ala Gly Ile Asn Ser Leu Ser Ser Glu Met His Lys Lys Cys
            1                   5                   10

Tyr Lys Asn Gly Ile Cys Arg Leu Glu Cys Tyr Glu Ser Glu Met Leu
       15                   20                  25

Val Ala Tyr Cys Met Phe Gln Leu Glu Cys Cys Val Lys Gly Asn Pro
30                  35                  40                  45

Ala Pro
```